(12) United States Patent
Movassaghi et al.

(10) Patent No.: US 12,180,228 B2
(45) Date of Patent: Dec. 31, 2024

(54) COMPOUNDS, CONJUGATES, AND COMPOSITIONS OF EPIPOLYTHIODIKETOPIPERAZINES AND POLYTHIODIKETOPIPERAZINES AND USES THEREOF

(71) Applicant: Massachusetts Institute of Technology, Cambridge, MA (US)

(72) Inventors: Mohammad Movassaghi, Lincoln, MA (US); Chase Robert Olsson, La Jolla, CA (US); Tony Z. Scott, Cambridge, MA (US); Jaime Cheah, Medford, MA (US); Joshua Nathaniel Payette, Hollis, NH (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/146,294

(22) Filed: Dec. 23, 2022

(65) Prior Publication Data
US 2023/0212195 A1    Jul. 6, 2023

Related U.S. Application Data

(62) Division of application No. 16/839,064, filed on Apr. 2, 2020, now Pat. No. 11,535,634.

(60) Provisional application No. 62/857,716, filed on Jun. 5, 2019.

(51) Int. Cl.
C07D 519/00 (2006.01)

(52) U.S. Cl.
CPC .................. C07D 519/00 (2013.01)

(58) Field of Classification Search
CPC .................................. C07D 519/00
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,906,562 A | 3/1990 | Hellström et al. |
| 4,935,495 A | 6/1990 | Hellström et al. |
| 4,940,726 A | 7/1990 | Pettit et al. |
| 4,946,778 A | 8/1990 | Ladner et al. |
| 4,996,237 A | 2/1991 | Pettit et al. |
| 5,225,539 A | 7/1993 | Winter |
| 5,242,824 A | 9/1993 | Hellström et al. |
| 5,338,845 A | 8/1994 | Barrow et al. |
| 5,409,953 A | 4/1995 | Pettit et al. |
| 5,423,753 A | 6/1995 | Fowles et al. |
| 5,430,062 A | 7/1995 | Cushman et al. |
| 5,475,092 A | 12/1995 | Chari et al. |
| 5,504,074 A | 4/1996 | D'Amato et al. |
| 5,525,632 A | 6/1996 | Obsumi et al. |
| 5,545,806 A | 8/1996 | Lonberg et al. |
| 5,561,122 A | 10/1996 | Pettit |
| 5,569,786 A | 10/1996 | Pettit et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,646,176 A | 7/1997 | Golik et al. |
| 5,661,016 A | 8/1997 | Lonberg et al. |
| 5,661,143 A | 8/1997 | D'Amato et al. |
| 5,674,906 A | 10/1997 | Hatanaka et al. |
| 5,731,353 A | 3/1998 | Ohsumi et al. |
| 5,821,337 A | 10/1998 | Carter et al. |
| 5,877,158 A | 3/1999 | Bosslet et al. |
| 5,886,025 A | 3/1999 | Pinney |
| 5,892,069 A | 4/1999 | D'Amato et al. |
| 5,929,211 A | 7/1999 | Ashkenazi et al. |
| 5,985,837 A | 11/1999 | Ritter et al. |
| 6,054,297 A | 4/2000 | Carter et al. |
| 6,103,236 A | 8/2000 | Suzawa et al. |
| 6,147,076 A | 11/2000 | Danishefsky et al. |
| 6,150,407 A | 11/2000 | Tuséet al. |
| 6,162,810 A | 12/2000 | Carson et al. |
| 6,162,930 A | 12/2000 | Pinney et al. |
| 6,169,104 B1 | 1/2001 | Tuséet al. |
| 6,201,001 B1 | 3/2001 | Wang et al. |
| 6,214,345 B1 | 4/2001 | Firestone et al. |
| 6,232,327 B1 | 5/2001 | Nickel et al. |
| 6,262,094 B1 | 7/2001 | Hoefle et al. |
| 6,268,488 B1 | 7/2001 | Barbas, III et al. |
| 6,271,220 B1 | 8/2001 | Garst |
| 6,329,420 B1 | 12/2001 | Uckun et al. |
| 6,335,364 B1 | 1/2002 | Uckun et al. |
| 6,350,777 B2 | 2/2002 | Pinney et al. |
| 6,358,957 B1 | 3/2002 | Fukumoto et al. |

(Continued)

FOREIGN PATENT DOCUMENTS

| | | |
|---|---|---|
| CN | 105198885 A | 12/2015 |
| CN | 104447755 B | 6/2016 |

(Continued)

OTHER PUBLICATIONS

U.S. Appl. No. 14/096,158, filed Dec. 4, 2013, Movassaghi et al.
U.S. Appl. No. 15/150,786, filed May 10, 2016, Movassaghi et al.
U.S. Appl. No. 16/293,443, filed Mar. 5, 2019, Movassaghi et al.
U.S. Appl. No. 14/490,146, filed Sep. 18, 2014, Movassaghi et al.
U.S. Appl. No. 15/255,224, filed Sep. 2, 2016, Movassaghi et al.
U.S. Appl. No. 15/951,689, filed Apr. 12, 2017, Movassaghi et al.
U.S. Appl. No. 15/592,090, filed May 10, 2017, Movassaghi et al.
U.S. Appl. No. 15/604,508, filed May 24, 2017, Movassaghi et al.
U.S. Appl. No. 16/612,468, filed Nov. 11, 2019, Movassaghi et al.
U.S. Appl. No. 16/161,036, filed Oct. 15, 2018, Movassaghi et al.
U.S. Appl. No. 16/863,015, filed Apr. 30, 2020, Movassaghi et al.

(Continued)

*Primary Examiner* — Paul V Ward
(74) *Attorney, Agent, or Firm* — Wolf, Greenfield & Sacks, P.C.

(57) ABSTRACT

The present disclosure provides, e.g., compounds, compositions, kits, methods of synthesis, and methods of use, involving epipolythiodiketopiperazines and polythiodiketopiperazines.

21 Claims, 5 Drawing Sheets

(56) References Cited

U.S. PATENT DOCUMENTS

| | | |
|---|---|---|
| 6,407,213 B1 | 6/2002 | Carter et al. |
| 6,423,753 B1 | 7/2002 | Dougherty |
| 6,433,012 B1 | 8/2002 | Tuséet al. |
| 6,528,676 B1 | 3/2003 | D'Amato et al. |
| 6,582,928 B1 | 6/2003 | Ashkenazi et al. |
| 6,620,976 B2 | 9/2003 | Sakanoue et al. |
| 6,639,055 B1 | 10/2003 | Carter et al. |
| 6,677,435 B2 | 1/2004 | Barbas, III et al. |
| 6,759,509 B1 | 7/2004 | King et al. |
| 6,815,530 B2 | 11/2004 | Ekwuribe et al. |
| 6,835,802 B2 | 12/2004 | Ekwuribe et al. |
| 6,855,689 B2 | 2/2005 | Firestone et al. |
| 6,858,580 B2 | 2/2005 | Ekwuribe et al. |
| 6,870,033 B1 | 3/2005 | Hsei et al. |
| 6,897,034 B2 | 5/2005 | Bebbington et al. |
| 7,018,809 B1 | 3/2006 | Carter |
| 7,030,082 B2 | 4/2006 | Soltero et al. |
| 7,087,840 B2 | 8/2006 | Herring et al. |
| 7,091,186 B2 | 8/2006 | Senter et al. |
| 7,115,573 B2 | 10/2006 | Pickford et al. |
| 7,119,162 B2 | 10/2006 | Ekwuribe et al. |
| 7,122,636 B1 | 10/2006 | Hsei et al. |
| 7,183,076 B2 | 2/2007 | Arathoon et al. |
| 7,214,663 B2 | 5/2007 | Bebbington et al. |
| 7,214,776 B2 | 5/2007 | Hsei et al. |
| 7,223,837 B2 | 5/2007 | de Groot et al. |
| 7,256,257 B2 | 8/2007 | Doronina et al. |
| 7,304,032 B2 | 12/2007 | Bebbington et al. |
| 7,319,139 B2 | 1/2008 | Brasalawsky et al. |
| 7,375,078 B2 | 5/2008 | Feng |
| 7,427,399 B2 | 9/2008 | Jakobovits et al. |
| 7,479,544 B2 | 1/2009 | Clark et al. |
| 7,494,646 B2 | 2/2009 | Jakobovits et al. |
| 7,507,405 B2 | 3/2009 | Hsei et al. |
| 7,521,541 B2 | 4/2009 | Eigenbrot et al. |
| 7,541,442 B2 | 6/2009 | Gudas et al. |
| 7,547,768 B2 | 6/2009 | Dowd et al. |
| 7,553,816 B2 | 6/2009 | Senter et al. |
| 7,585,834 B2 | 9/2009 | Wender et al. |
| 7,595,379 B2 | 9/2009 | Gudas et al. |
| 7,659,241 B2 | 2/2010 | Senter et al. |
| 7,662,936 B2 | 2/2010 | Kadkhodayan et al. |
| 7,691,962 B2 | 4/2010 | Boyd et al. |
| 7,696,313 B2 | 4/2010 | Pickford et al. |
| 7,705,045 B2 | 4/2010 | de Groot et al. |
| 7,714,016 B2 | 5/2010 | Gangwar et al. |
| 7,723,485 B2 | 5/2010 | Junutula et al. |
| 7,745,394 B2 | 6/2010 | Doronina et al. |
| 7,749,504 B2 | 7/2010 | Cairns et al. |
| 7,750,116 B1 | 7/2010 | Doronina et al. |
| 7,754,441 B2 | 7/2010 | de Sauvage et al. |
| 7,754,681 B2 | 7/2010 | Feng |
| 7,803,915 B2 | 9/2010 | Cairns et al. |
| 7,811,565 B2 | 10/2010 | Jakobovits et al. |
| 7,816,317 B2 | 10/2010 | Bebbington et al. |
| 7,829,531 B2 | 11/2010 | Senter et al. |
| 7,834,154 B2 | 11/2010 | Koch et al. |
| 7,842,789 B2 | 11/2010 | Hsei et al. |
| 7,846,893 B2 | 12/2010 | Sinko et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,888,536 B2 | 2/2011 | Davis et al. |
| 7,893,023 B2 | 2/2011 | Trouet et al. |
| 7,964,566 B2 | 6/2011 | Doronina et al. |
| 7,964,567 B2 | 6/2011 | Doronina et al. |
| 7,968,090 B2 | 6/2011 | Raitano et al. |
| 7,989,434 B2 | 8/2011 | Feng |
| 7,989,595 B2 | 8/2011 | Dennis et al. |
| 8,012,978 B2 | 9/2011 | Zhao et al. |
| 8,158,590 B2 | 4/2012 | Beusker et al. |
| 8,337,856 B2 | 12/2012 | Blättler et al. |
| 9,353,150 B2 | 5/2016 | Movassaghi et al. |
| 9,434,736 B2 | 9/2016 | Movassaghi et al. |
| 9,464,093 B2 | 10/2016 | Tun et al. |
| 9,962,383 B2 | 5/2018 | Movassaghi et al. |
| 10,220,099 B2 | 3/2019 | Movassaghi et al. |
| 10,640,508 B2 | 5/2020 | Movassaghi et al. |
| 10,918,627 B2 | 2/2021 | Movassaghi et al. |
| 10,918,735 B2 | 2/2021 | Movassaghi et al. |
| 11,535,634 B2 * | 12/2022 | Movassaghi ......... C07D 519/00 |
| 11,932,650 B2 | 3/2024 | Movassaghi et al. |
| 2003/0096743 A1 | 5/2003 | Senter et al. |
| 2003/0130189 A1 | 7/2003 | Senter et al. |
| 2003/0149003 A1 | 8/2003 | Chaplin et al. |
| 2005/0143429 A1 | 6/2005 | Danishefsky et al. |
| 2008/0050310 A1 | 2/2008 | Ebens et al. |
| 2008/0267981 A1 | 10/2008 | Janda et al. |
| 2009/0068202 A1 | 3/2009 | Chen et al. |
| 2009/0203584 A1 | 8/2009 | Cuthbertson et al. |
| 2009/0280056 A1 | 11/2009 | Dennis et al. |
| 2010/0125065 A1 | 5/2010 | Moon et al. |
| 2010/0210543 A1 | 8/2010 | Rabuka et al. |
| 2010/0215669 A1 | 8/2010 | Chen et al. |
| 2011/0118480 A1 | 5/2011 | Vijayaraghavan et al. |
| 2011/0124844 A1 | 5/2011 | Davis et al. |
| 2011/0135667 A1 | 6/2011 | Chen et al. |
| 2011/0137017 A1 | 6/2011 | Eigenbrot et al. |
| 2011/0142859 A1 | 6/2011 | Ebens, Jr. et al. |
| 2011/0195021 A1 | 8/2011 | Deckert et al. |
| 2011/0195022 A1 | 8/2011 | Deckert et al. |
| 2011/0269972 A1 | 11/2011 | Loh et al. |
| 2012/0183566 A1 | 7/2012 | Barfield et al. |
| 2014/0187500 A1 | 7/2014 | Movassaghi et al. |
| 2015/0080405 A1 | 3/2015 | Movassaghi et al. |
| 2015/0274742 A1 | 10/2015 | Tun et al. |
| 2016/0354483 A1 | 12/2016 | Movassaghi et al. |
| 2017/0143708 A1 | 5/2017 | Movassaghi et al. |
| 2017/0333405 A1 | 11/2017 | Movassaghi et al. |
| 2017/0342077 A1 | 11/2017 | Movassaghi et al. |
| 2018/0360830 A1 | 12/2018 | Movassaghi et al. |
| 2019/0119286 A1 | 4/2019 | Movassaghi et al. |
| 2019/0252623 A1 | 8/2019 | Layek et al. |
| 2019/0255187 A1 | 8/2019 | Movassaghi et al. |
| 2020/0062771 A1 | 2/2020 | Movassaghi et al. |
| 2020/0385407 A1 | 12/2020 | Movassaghi et al. |
| 2021/0329919 A9 | 10/2021 | Movassaghi et al. |
| 2022/0289750 A1 | 9/2022 | Movassaghi et al. |

FOREIGN PATENT DOCUMENTS

| | | |
|---|---|---|
| CN | 109021080 A | 12/2018 |
| EP | 0217577 A | 4/1987 |
| FR | 2438034 A1 | 4/1980 |
| JP | 2019-85484 A | 6/2019 |
| WO | WO 92/016486 A1 | 10/1992 |
| WO | WO 94/14787 A1 | 7/1994 |
| WO | WO 95/04535 A1 | 2/1995 |
| WO | WO 98/039323 A1 | 9/1998 |
| WO | WO 99/02166 A1 | 1/1999 |
| WO | WO 99/02514 A2 | 1/1999 |
| WO | WO 99/034788 A1 | 7/1999 |
| WO | WO 99/035150 A1 | 7/1999 |
| WO | WO 99/35164 A1 | 7/1999 |
| WO | WO 99/048495 A1 | 9/1999 |
| WO | WO 99/051224 A1 | 10/1999 |
| WO | WO 99/051246 A1 | 10/1999 |
| WO | WO 2000/000514 A2 | 1/2000 |
| WO | WO 2000/006556 A1 | 2/2000 |
| WO | WO 2000/026229 A1 | 5/2000 |
| WO | WO 2000/035865 A2 | 6/2000 |
| WO | WO 2000/040529 A1 | 7/2000 |
| WO | WO 2000/041669 A2 | 7/2000 |
| WO | WO 2000/048590 A1 | 8/2000 |
| WO | WO 2000/073264 A1 | 12/2000 |
| WO | WO 2001/009103 A2 | 2/2001 |
| WO | WO 2001/012579 A2 | 2/2001 |
| WO | WO 2001/019794 A2 | 3/2001 |
| WO | WO 2001/022954 A2 | 4/2001 |
| WO | WO 2001/024763 A2 | 4/2001 |
| WO | WO 2001/030803 A1 | 5/2001 |
| WO | WO 2001/040268 A2 | 6/2001 |
| WO | WO 2001/068654 A2 | 9/2001 |
| WO | WO 2001/081288 A1 | 11/2001 |

(56) References Cited

FOREIGN PATENT DOCUMENTS

| | | |
|---|---|---|
| WO | WO 2001/081355 A1 | 11/2001 |
| WO | WO 2001/082909 A2 | 11/2001 |
| WO | WO 2001/084929 A1 | 11/2001 |
| WO | WO 2001/092224 A2 | 12/2001 |
| WO | WO 2002/004434 A1 | 1/2002 |
| WO | WO 2002/006267 A2 | 1/2002 |
| WO | WO 2002/008213 A1 | 1/2002 |
| WO | WO 2002/012228 A1 | 2/2002 |
| WO | WO 2002/014329 A1 | 2/2002 |
| WO | WO 2002/022576 A2 | 3/2002 |
| WO | WO 2002/022626 A1 | 3/2002 |
| WO | WO 2002/042319 A2 | 5/2002 |
| WO | WO 2002/047604 A2 | 6/2002 |
| WO | WO 2002/050007 A2 | 6/2002 |
| WO | WO 2002/060872 A1 | 8/2002 |
| WO | WO 2002/088172 A2 | 11/2002 |
| WO | WO 2002/098883 A1 | 12/2002 |
| WO | WO 2003/026577 A2 | 4/2003 |
| WO | WO 2003/043583 A2 | 5/2003 |
| WO | WO 2003/068144 A2 | 8/2003 |
| WO | WO 2004/010957 A2 | 2/2004 |
| WO | WO 2004/013093 A2 | 2/2004 |
| WO | WO 2004/016801 A2 | 2/2004 |
| WO | WO 2004/032828 A2 | 4/2004 |
| WO | WO 2004/043344 A2 | 5/2004 |
| WO | WO 2004/043493 A1 | 5/2004 |
| WO | WO 2004/106343 A2 | 12/2004 |
| WO | WO 2005/001038 A2 | 1/2005 |
| WO | WO 2005/009369 A2 | 2/2005 |
| WO | WO 2005/037992 A2 | 4/2005 |
| WO | WO 2005/081711 A2 | 9/2005 |
| WO | WO 2005/082023 A2 | 9/2005 |
| WO | WO 2005/084390 A2 | 9/2005 |
| WO | WO 2006/055578 A2 | 5/2006 |
| WO | WO 2006/065533 A2 | 6/2006 |
| WO | WO 2006/086733 A2 | 8/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/011968 A2 | 1/2007 |
| WO | WO 2007/019232 A2 | 2/2007 |
| WO | WO 2007/024222 A1 | 3/2007 |
| WO | WO 2007/024536 A2 | 3/2007 |
| WO | WO 2007/030642 A2 | 3/2007 |
| WO | WO 2007/062138 A2 | 5/2007 |
| WO | WO 2007/089149 A2 | 8/2007 |
| WO | WO 2007/103288 A2 | 9/2007 |
| WO | WO 2007/137170 A2 | 11/2007 |
| WO | WO 2008/070593 A2 | 6/2008 |
| WO | WO 2008/078109 A2 | 7/2008 |
| WO | WO 2009/017394 A2 | 2/2009 |
| WO | WO 2009/048967 A1 | 4/2009 |
| WO | WO 2009/052431 A2 | 4/2009 |
| WO | WO 2009/080830 A1 | 7/2009 |
| WO | WO 2009/080831 A1 | 7/2009 |
| WO | WO 2009/080832 A1 | 7/2009 |
| WO | WO 2009/117531 A1 | 9/2009 |
| WO | WO 2009/134870 A1 | 11/2009 |
| WO | WO 2009/134952 A2 | 11/2009 |
| WO | WO 2009/134976 A1 | 11/2009 |
| WO | WO 2009/134977 A1 | 11/2009 |
| WO | WO 2009/135181 A2 | 11/2009 |
| WO | WO 2010/008726 A1 | 1/2010 |
| WO | WO 2010/025272 A1 | 3/2010 |
| WO | WO 2010/062171 A2 | 6/2010 |
| WO | WO 2010/081004 A1 | 7/2010 |
| WO | WO 2010/111018 A1 | 9/2010 |
| WO | WO 2010/126551 A1 | 11/2010 |
| WO | WO 2010/126552 A1 | 11/2010 |
| WO | WO 2010/128087 A2 | 11/2010 |
| WO | WO 2010/141566 A1 | 12/2010 |
| WO | WO 2011/038159 A2 | 3/2011 |
| WO | WO 2011/050180 A1 | 4/2011 |
| WO | WO 2011/091286 A1 | 7/2011 |
| WO | WO 2011/100398 A1 | 8/2011 |
| WO | WO 2011/100403 A1 | 8/2011 |
| WO | WO 2011/106528 A1 | 9/2011 |
| WO | WO 2011/112978 A1 | 9/2011 |
| WO | WO 2011/130613 A1 | 10/2011 |
| WO | WO 2011/133039 A2 | 10/2011 |
| WO | WO 2011/162933 A1 | 12/2011 |
| WO | WO 2012/019024 A2 | 2/2012 |
| WO | WO 2012/047724 A1 | 4/2012 |
| WO | WO 2012/054748 A2 | 4/2012 |
| WO | WO 2012/058592 A2 | 5/2012 |
| WO | WO 2012/061590 A1 | 5/2012 |
| WO | WO 2012/078688 A2 | 6/2012 |
| WO | WO 2012/112687 A1 | 8/2012 |
| WO | WO 2012/112708 A1 | 8/2012 |
| WO | WO 2012/128868 A2 | 9/2012 |
| WO | WO 2012/135517 A2 | 10/2012 |
| WO | WO 2012/135522 A2 | 10/2012 |
| WO | WO 2012/135740 A2 | 10/2012 |
| WO | WO 2012/138537 A2 | 10/2012 |
| WO | WO 2012/138749 A2 | 10/2012 |
| WO | WO 2012/145112 A2 | 10/2012 |
| WO | WO 2012/149412 A2 | 11/2012 |
| WO | WO 2012/177837 A2 | 12/2012 |
| WO | WO 2013/055990 A1 | 4/2013 |
| WO | WO 2013/055993 A1 | 4/2013 |
| WO | WO 2014/059314 A1 | 4/2014 |
| WO | WO 2014/089177 A2 | 6/2014 |

OTHER PUBLICATIONS

U.S. Appl. No. 16/839,064, filed Apr. 2, 2020, Movassaghi et al.
U.S. Appl. No. 18/146,294, filed Dec. 23, 2022, Movassaghi et al.
U.S. Appl. No. 17/561,680, filed Dec. 23, 2021, Movassaghi et al.
PCT/US2013/073062, May 20, 2014, International Search Report and Written Opinion.
PCT/US2013/073062, Jun. 18, 2015, International Preliminary Report on Patentability.
PCT/US2014/056263, Dec. 4, 2014, International Search Report and Written Opinion.
PCT/US2014/056263, Mar. 31, 2016, International Preliminary Report on Patentability.
PCT/US2017/032040, Aug. 11, 2017, International Search Report and Written Opinion.
PCT/US2017/032040, Nov. 22, 2018, International Preliminary Report on Patentability.
PCT/US2017/034327, Sep. 1, 2017, International Search Report and Written Opinion.
PCT/US2017/034327, Dec. 6, 2018, International Preliminary Report on Patentability.
PCT/US2018/032327, Jul. 23, 2018, Invitation to Pay Additional Fees.
PCT/US2018/032327, Sep. 21, 2018, International Search Report and Written Opinion.
PCT/US2018/032327, Nov. 21, 2019, International Preliminary Report on Patentability.
PCT/US2020/026415, Jul. 1, 2020, Invitation to Pay Additional Fees.
PCT/US2020/026415, Sep. 7, 2020, International Search Report and Written Opinion.
PCT/US2020/026415, Dec. 16, 2021, International Preliminary Report on Patentability.
PCT/US2021/065161, Sep. 7, 2023, International Preliminary Report on Patentability.
International Preliminary Report on Patentability for PCT/US2021/065161, mailed Sep. 7, 2023.
Antropow et al., Synthesis and Evaluation of Agelastatin Derivatives as Potent Modulators for Cancer Invasion and Metastasis. J Org Chem. Aug. 4, 2017;82(15):7720-7731. doi: 10.1021/acs.joc.7b01162. Epub Jul. 25, 2017.
Erra-Balsells, R., Photodimereization of deacetylaspidospermine. Phytochem. 1988;27(12):3945-7.
Leet et al., Himastatin, a New Antitumor Antibiotic from Streptomyces hygroscopicus. J Antibiotics. Mar. 1996;49(3):299-311.
Rehse et al., Identifizierung von Ajmalin und anderen Indolinderivaten en mit Hilfe con Farbreaktionen. Deutsche Apotheker Zeitung. 1973;113(40):1568-71.

(56) References Cited

OTHER PUBLICATIONS

Rosenkranz et al., Oxidative coupling of indolines and 1,2,3,4-tetrahydroquinolines with potassium permanganate. Helvetica Chimica Acta. 1974;57(3):887-916.
Weiner et al., Synthesis of Indole Derivatives Attached to Poly(ethylene Oxides). J Macromol Sci Chem. 1977;A11(6):1191-200.
International Search Report and Written Opinion for PCT/US2021/065161, mailed Apr. 25, 2022.
Abouelhassan et al., Discovery of quinoline small molecules with potent dispersal activity against methicillin-resistant *Staphylococcus aureus* and *Staphylococcus epidermidis* biofilms using a scaffold hopping strategy. Bioorg Med Chem Lett. Nov. 1, 2014;24(21):5076-80. doi: 10.1016/j.bmcl.2014.09.009. Epub Sep. 15, 2014.
Albin et al., Efficient flow synthesis of human antimicrobial peptides. Aust J Chem. Apr. 2020;73(4):380-388. doi: 10.1071/CH20043. Epub Apr. 8, 2020.
Benco et al., Synthesis of an ammonium ionophore and its application in a planar ion-selective electrode. Anal Chem. Jan. 1, 2003;75(1):152-6. doi: 10.1021/ac0257851.
Bhattacharyya et al., Rapid identification and phylogenetic classification of diverse bacterial pathogens in a multiplexed hybridization assay targeting ribosomal RNA. Sci Rep. Mar. 14, 2019;9(1):4516. doi: 10.1038/s41598-019-40792-3.
Boucher et al., Bad bugs, no drugs: no ESKAPE! An update from the Infectious Diseases Society of America. Clin Infect Dis. Jan. 1, 2009;48(1):1-12. doi: 10.1086/595011.
Choi et al., Lights, Camera, Action! Antimicrobial Peptide Mechanisms Imaged in Space and Time. Trends Microbiol. Feb. 2016;24(2):111-122. doi: 10.1016/j.tim.2015.11.004. Epub Dec. 13, 2015.
Ciufolini et al., Synthesis, Chemistry and Conformational Properties of Piperazic Acids. Chem Soc Rev. 1998(27):437-45. doi: 10.1039/A827437Z.
Connelly et al., Chemical Redox Agents for Organometallic Chemistry. Chem Rev. Mar. 28, 1996;96(2):877-910. doi: 10.1021/cr940053x.
Crich et al., 2,4,6-Tri-tert-butylpyrimidine (TTBP): A Cost Effective, Readily Available Alternative to the Hindered Base 2,6-Di-tert-butylpyridine and its 4-Substituted Derivatives in Glycosylation and Other Reactions. Synthesis. 2001;2001(2):0323-6. doi: 10.1055/s-2001-10798.
D'Angelo et al., Concise Total Synthesis of (−)-Himastatin via a Bioinspired Final-Stage Dimerization. Feb. 17, 2021. 8 pages.
D'Costa et al. Inactivation of the lipopeptide antibiotic daptomycin by hydrolytic mechanisms. Antimicrob Agents Chemother. Feb. 2012;56(2):757-64. doi: 10.1128/AAC.05441-11. Epub Nov. 14, 2011.
Dalsgaard et al., Communesins G and H, new alkaloids from the psychrotolerant fungus Penicillium rivulum. J Nat Prod. Feb. 2005;68(2):258-61. doi: 10.1021/np0496461.
Davis et al., Formation of raloxifene homo-dimer in CYP3A4, evidence for multi-substrate binding in a single catalytically competent P450 active site. Arch Biochem Biophys. Sep. 15, 2011;513(2):110-8. doi: 10.1016/j.abb.2011.06.016. Epub Jul. 13, 2011.
Fernandez-Lopez et al., Antibacterial agents based on the cyclic D,L-alpha-peptide architecture. Nature. Jul. 26, 2001;412(6845):452-5. doi: 10.1038/35086601. Erratum in: Nature Nov. 15, 2001;414(6861):329.
Funes-Ardoiz et al., Oxidative Coupling Mechanisms: Current State of Understanding. ACS Catal. Dec. 22, 2017;8(2):1161-72. doi: 10.1021/acscatal.7b02974.
Gassman et al., Chemistry of Nitrenium Ions. XXI. Nucleophilic Aromatic Substitution of Anilines via Aryl Nitrenium Ions (Anilenium Ions). J Am Chem Soc. 1972;94:3884-91.
Grandner et al., Mechanism of the P450-Catalyzed Oxidative Cyclization in the Biosynthesis of Griseofulvin. ACS Catal. Jul. 1, 2016;6(7):4506-4511. doi: 10.1021/acscatal.6b01068. Epub May 31, 2016.
Greenman et al., Synthesis of phakellistatin 13 and oxidation to phakellistatin 3 and isophakellistatin 3. Org Lett. May 27, 2004;6(11):1713-6. doi: 10.1021/ol049614p.
Grzybowski et al., Synthetic Applications of Oxidative Aromatic Coupling-From Biphenols to Nanographenes. Angew Chem Int Ed Engl. Feb. 17, 2020;59(8):2998-3027. doi: 10.1002/anie.201904934. Epub Dec. 3, 2019.
Guo et al., Design and Biosynthesis of Dimeric Alboflavusins with Biaryl Linkages via Regiospecific C-C Bond Coupling. J Am Chem Soc. Dec. 26, 2018;140(51):18009-18015. doi: 10.1021/jacs.8b10136. Epub Dec. 14, 2018.
Guo et al., NW-G01, a novel cyclic hexadepsipeptide antibiotic, produced by Streptomyces alboflavus 313: I. Taxonomy, fermentation, isolation, physicochemical properties and antibacterial activities. J Antibiot (Tokyo). Apr. 2009;62(4):201-5. doi: 10.1038/ja.2009.15. Epub Mar. 6, 2009.
Guo et al., NW-G01, a novel cyclic hexapeptide antibiotic, produced by Streptomyces alboflavus 313: II. Structural elucidation. J Antibiot (Tokyo). May 2010;63(5):231-5. doi: 10.1038/ja.2010.24. Epub Apr. 9, 2010. Erratum in: J Antibiot (Tokyo). Dec. 2010;63(12):733.
Hand et al., Anodic Oxidation Pathways of N-Alkylanilines. J Am Chem Soc. Feb. 6, 1974;96(3): 850-60.
Hong et al., Bidirectional synthesis of the central amino acid of chloptosin. Org Lett. Oct. 12, 2006;8(21):4919-22. doi: 10.1021/ol0620139.
Ivashenko et al., Oxidative electrochemical aryl C-C coupling of spiropyrans. Chem Commun (Camb). Aug. 4, 2013;49(60):6737-9. doi: 10.1039/c3cc42396d.
Jadulco et al., New communesin derivatives from the fungus *Penicillium* sp. derived from the Mediterranean sponge *Axinella verrucosa*. J Nat Prod. Jan. 2004;67(1):78-81. doi: 10.1021/np030271y.
Kamenecka et al., Discovery through total synthesis: a retrospective on the himastatin problem. Chemistry. Jan. 5, 2001;7(1):41-63. doi: 10.1002/1521-3765(20010105)7:1<41:: aid-chem41>3.0.co;2-d.
Kamenecka et al., Studies in the Total Synthesis of Himastatin: A Revision of the Stereochemical Assignment. Angew Chem Int Ed Engl. Nov. 16, 1998;37(21):2993-2995. doi: 10.1002/(SICI)1521-3773(19981116)37:21<2993::AID-ANIE2993>3.0.CO;2-I.
Kirchgessner et al., Understanding reactivity patterns of the dialkylaniline radical cation. J Org Chem. Dec. 22, 2006;71(26):9849-52. doi: 10.1021/jo061809i.
Lam et al., Himastatin, a new antitumor antibiotic from Streptomyces hygroscopicus. I. Taxonomy of producing organism, fermentation and biological activity. J Antibiot (Tokyo). Aug. 1990;43(8):956-60. doi: 10.7164/antibiotics.43.956.
Larumbe et al., Anodic Oxidation of Some Tertiary Amines. J Electroanal Chem. 1991;304:241-7.
Lathrop et al., Convergent and Biomimetic Enantioselective Total Synthesis of (−)- Communesin F. J Am Chem Soc. Jun. 22, 2016;138(24):7763-9. doi: 10.1021/jacs.6b04072. Epub Jun. 14, 2016.
Leet et al., Himastatin, a new antitumor antibiotic from Streptomyces hygroscopicus. II. Isolation and characterization. J Antibiot (Tokyo). Aug. 1990;43(8):961-6. doi: 10.7164/antibiotics.43.961.
Leet et al., Himastatin, a new antitumor antibiotic from Streptomyces hygroscopicus. III. Structural elucidation. J Antibiot (Tokyo). Mar. 1996;49(3):299-311. doi: 10.7164/antibiotics.49.299.
Li et al., Consequences of Depsipeptide Substitution on the ClpP Activation Activity of Antibacterial Acyldepsipeptides. ACS Med Chem Lett. Oct. 19, 2017;8(11):1171-1176. doi: 10.1021/acsmedchemlett.7b00320.
Ling et al., A new antibiotic kills pathogens without detectable resistance. Nature. Jan. 22, 2015;517(7535):455-9. doi: 10.1038/nature14098. Epub Jan. 7, 2015. Erratum in: Nature. Apr. 16, 2015;520(7547):388.
Ling et al., Synthesis of benzidine derivatives via $FeCl_3 \cdot 6H_2O$-promoted oxidative coupling of anilines. J Org Chem. Jun. 7, 2013;78(11):5218-26. doi: 10.1021/jo4002504. Epub May 28, 2013.
Lopez et al., Mechanistic insights into the stereocontrolled synthesis of hexahydropyrrolo[2,3-b]indoles by electrophilic activation of

(56) References Cited

OTHER PUBLICATIONS tryptophan derivatives. Org Lett. Jan. 3, 2008;10(1):77-80. doi: 10.1021/ol702732j. Epub Dec. 11, 2007.

Ma et al., Biosynthesis of himastatin: assembly line and characterization of three cytochrome P450 enzymes involved in the post-tailoring oxidative steps. Angew Chem Int Ed Engl. Aug. 16, 2011;50(34):7797-802. doi: 10.1002/anie.201102305. Epub Jul. 1, 2011.

Mamber et al., Inhibition of antibacterial activity of himastatin, a new antitumor antibiotic from Streptomyces hygroscopicus, by fatty acid sodium salts. Antimicrob Agents Chemother. Nov. 1994;38(11):2633-42. doi: 10.1128/AAC.38.11.2633.

Matsumoto et al., Catalytic and Aerobic Oxidative Biaryl Coupling of Anilines Using a Recyclable Heterogeneous Catalyst for Synthesis of Benzidines and Bicarbazoles. J Org Chem. Dec. 4, 2020;85(23):15154-15166. doi: 10.1021/acs.joc.0c02020. Epub Nov. 23, 2020.

Miranda et al., Alkaloids of Aspidosperma melanocalyx Muell-Arg. Experientia. Jun. 15, 1969;25(6):575-6. doi: 10.1007/BF01896517.

Natali et al., Interaction studies between photochromic spiropyrans and transition metal cations: the curious case of copper. Org Biomol Chem. Feb. 14, 2012;10(6):1162-71. doi: 10.1039/c1ob06375h. Epub Dec. 7, 2011.

Nelson et al., Concise total synthesis of (+)-asperazine A and (+)-pestalazine B. Org Biomol Chem. Jan. 3, 2018;16(2):202-207. doi: 10.1039/c7ob02985c.

Nguyen et al., A general solid phase method for the synthesis of depsipeptides. Org Biomol Chem. Feb. 21, 2013;11(7):1167-70. doi: 10.1039/c2ob26893k.

Numata et al., Communesins, cytotoxic metabolites of a fungus isolated from a marine alga. Tetrahedron Lett. Apr. 2, 1993;34(14):2355-8. doi: 10.1016/S0040-4039(00)77612-X.

Oelke et al., Total synthesis of chloptosin. Angew Chem Int Ed Engl. Aug. 16, 2010;49(35):6139-42. doi: 10.1002/anie.201002880.

Oelke et al., Total synthesis of chloptosin: a dimeric cyclohexapeptide. Chemistry. Apr. 4, 2011;17(15):4183-94. doi: 10.1002/chem.201003216. Epub Mar. 15, 2011.

Ooi et al., XF-73, a novel antistaphylococcal membrane-active agent with rapid bactericidal activity. J Antimicrob Chemother. Oct. 2009;64(4):735-40. doi: 10.1093/jac/dkp299. Epub Aug. 18, 2009.

Palmisano et al., Aspidosperma Alkaloids. A New Didehydrodimerization Mode of β-Anilinoacrylic Alkaloids by Anodic Oxidation. Helv Chim Acta. 1992;75:813-24. doi: 10.1002/hlca.19920750316.

Peterson et al., Antibiotic Resistance Mechanisms in Bacteria: Relationships Between Resistance Determinants of Antibiotic Producers, Environmental Bacteria, and Clinical Pathogens. Front Microbiol. Nov. 30, 2018;9:2928. doi: 10.3389/fmicb.2018.02928.

Pogliano et al., Daptomycin-mediated reorganization of membrane architecture causes mislocalization of essential cell division proteins. J Bacteriol. Sep. 2012;194(17):4494-504. doi: 10.1128/JB.00011-12. Epub Jun. 1, 2012.

Pompeo et al., Total Synthesis and Anti-Cancer Activity of All Known Communesin Alkaloids and Related Derivatives. J Am Chem Soc. Sep. 11, 2019;141(36):14411-14420. doi: 10.1021/jacs.9b07397. Epub Aug. 30, 2019.

Qian et al., Rhodium(II)- and copper(II)-catalyzed reactions of enol diazoacetates with nitrones: metal carbene versus Lewis acid directed pathways. Angew Chem Int Ed Engl. Jun. 11, 2012;51(24):5900-3. doi: 10.1002/anie.201202525. Epub May 4, 2012.

Roch et al., Daptomycin Resistance in Clinical MRSA Strains Is Associated with a High Biological Fitness Cost. Front Microbiol. Dec. 5, 2017;8:2303. doi: 10.3389/fmicb.2017.02303.

Rodriguez-Vazquez et al., Membrane-targeted self-assembling cyclic peptide nanotubes. Curr Top Med Chem. 2014;14(23):2647-61. doi: 10.2174/1568026614666141215143431.

Ruiz-Sanchis et al., Orthogonal Protecting Groups in the Synthesis of Tryptophanyl-Hexahydropyrroloindoles. Eur J Org Chem. Jan. 2012;1:67-73. doi: 10.1002/ejoc.201101057.

Sakaitani et al., Syntheses and Reactions of Silyl Carbamates. 1. Chemoselective Transformation of Amino Protecting Groups via Tert-Butyldimethylsilyl Carbamates. J Org Chem. Feb. 1, 1990;55(3):870-6. doi: 10.1021/jo00290a015.

Saruwatari et al., Cytochrome P450 as dimerization catalyst in diketopiperazine alkaloid biosynthesis. Chembiochem. Mar. 21, 2014;15(5):656-9. doi: 10.1002/cbic.201300751.

Shende et al., Structure and Function of NzeB, a Versatile C—C and C—N Bond-Forming Diketopiperazine Dimerase. J Am Chem Soc. Oct. 14, 2020;142(41):17413-17424. doi: 10.1021/jacs.0c06312. Epub Sep. 30, 2020.

Steinbuch et al., Mechanisms of Resistance to Membrane-Disrupting Antibiotics in Gram-Positive and Gram-Negative Bacteria. Med Chem Commun. Nov. 19, 2015;7:86-102. doi: 10.1039/C5MD00389J.

Tabakovic et al., One pot electrochemical synthesis of 10,10'-bisvindoline by an oxidation-reduction sequence. Tetrahedron Lett. May 20, 1996;37(21):3659-62. doi: 10.1016/0040-4039(96)00655-7.

Takahashi et al., Novel Homodimer Metabolites of GDC-0994 via Cytochrome P450- Catalyzed Radical Coupling. Drug Metab Dispos. Jun. 2020;48(6):521-527. doi: 10.1124/dmd.119.090019. Epub Mar. 31, 2020.

Tomasic et al., Some cyclic oligopeptides with S2n symmetry. Helv Chim Acta. Jul. 8, 1987;70(4):1012-6. doi: 10.1002/hlca.19870700413.

Umezawa et al., Chloptosin, an apoptosis-inducing dimeric cyclohexapeptide produced by Streptomyces. J Org Chem. Jan. 28, 2000;65(2):459-63. doi: 10.1021/jo991314b.

Ventola, C.L., The antibiotic resistance crisis: part 1: causes and threats. P T. Apr. 2015;40(4):277-83.

Wade et al., All-D amino acid-containing channel-forming antibiotic peptides. Proc Natl Acad Sci U S A. Jun. 1990;87(12):4761-5. doi: 10.1073/pnas.87.12.4761.

Wang et al., Mirror Images of Antimicrobial Peptides Provide Reflections on Their Functions and Amyloidogenic Properties. J Am Chem Soc. May 4, 2016;138(17):5706-13. doi: 10.1021/jacs.6b02575. Epub Apr. 26, 2016.

Wiegand et al., Agar and broth dilution methods to determine the minimal inhibitory concentration (MIC) of antimicrobial substances. Nat Protoc. 2008;3(2):163-75. doi: 10.1038/nprot.2007.521.

Wilen et al., Strategies in optical resolutions. Tetrahedron. 1977;33(21):2725-2736. doi: 10.1016/0040-4020(77)80264-0.

Wright, G.D., Bacterial resistance to antibiotics: enzymatic degradation and modification. Adv Drug Deliv Rev. Jul. 29, 2005;57(10):1451-70. doi: 10.1016/j.addr.2005.04.002.

Wright, G.D., Something old, something new: revisiting natural products in antibiotic drug discovery. Can J Microbiol. Mar. 2014;60(3):147-54. doi: 10.1139/cjm-2014-0063. Epub Jan. 22, 2014.

Xi et al., Elevated Conformational Rigidity in Dipeptides Incorporating Piperazic Acid Derivatives. J Am Chem Soc. Jan. 14, 1998;120(1):80-6.

Yang et al., Application of Rapid Scan Cyclic Voltammetry to a Study of the Oxidation and Dimerization of N,N-Dimethylaniline in Acetonitrile. J Electroanal Chem. 1992;331:913-24.

Yang et al., Oxidative C—H/C—H Coupling Reactions between Two (Hetero)arenes. Chem Rev. Jul. 12, 2017;117(13):8787-8863. doi: 10.1021/acs.chemrev.6b00567. Epub Jan. 13, 2017.

Yasir et al., Mode of action of the antimicrobial peptide Me14 is independent of *Staphylococcus aureus* cell membrane permeability. PLoS One. Jul. 29, 2019;14(7):e0215703. doi: 10.1371/journal.pone.0215703.

Yu et al., Total synthesis of chloptosin, a potent apoptosis-inducing cyclopeptide. Org Lett. Mar. 5, 2010;12(5):1124-7. doi: 10.1021/ol100135a.

Zhang et al., Riboflavin Is Directly Involved in N-Dealkylation Catalyzed by Bacterial Cytochrome P450 Monooxygenases. Chembiochem. Aug. 17, 2020;21(16):2297-2305. doi: 10.1002/cbic.202000071. Epub Apr. 30, 2020.

Zhao et al., Binding of two flaviolin substrate molecules, oxidative coupling, and crystal structure of Streptomyces coelicolor A3(2) cytochrome P450 158A2. J Biol Chem. Mar. 25, 2005;280(12):11599-607. doi: 10.1074/jbc.M410933200. Epub Jan. 19, 2005.

(56) References Cited

OTHER PUBLICATIONS

International Search Report and Written Opinion for PCT/US2013/073062, mailed on May 20, 2014.
International Preliminary Report on Patentability for PCT/US2013/073062, mailed on Jun. 18, 2015.
International Search Report and Written Opinion for PCT/US2014/056263, mailed on Dec. 4, 2014.
International Preliminary Report on Patentability for PCT/US2014/056263, mailed on Mar. 31, 2016.
International Search Report and Written Opinion for PCT/US2017/032040, mailed on Aug. 11, 2017.
International Preliminary Report on Patentability for PCT/US2017/032040, mailed on Nov. 22, 2018.
International Search Report and Written Opinion for PCT/US2017/034327, mailed on Sep. 1, 2017.
International Preliminary Report on Patentability for PCT/US2017/034327, mailed on Dec. 6, 2018.
Invitation to Pay Additional Fees for PCT/US2018/032327, mailed on Jul. 23, 2018.
International Search Report and Written Opinion for PCT/US2018/032327, mailed on Sep. 21, 2018.
International Preliminary Report on Patentability for PCT/US2018/032327, mailed on Nov. 21, 2019.
Invitation to Pay Additional Fees for PCT/US2020/026415, mailed on Jul. 1, 2020.
International Search Report and Written Opinion for PCT/US2020/026415, mailed on Sep. 7, 2020.
International Preliminary Report on Patentability for PCT/US2020/026415, mailed Dec. 16, 2021.
Adam et al., Photochemistry of the Azoalkanes 2,3-Diazabicyclo[2.2.1]hept-2-ene and Spiro[cyclopropane-1, 7-[2,3]diazabicyclo[2.2.1]hept-2-ene]: On the Questions of One-Bond vs. Two-Bond Cleavage during the Denitrogenation, Cyclization vs. Rearrangement of the 1,3-Diradicals, and Double Inversion, J. Org. Chem. 1985, 50, pp. 3303-3312.
Adams et al., Concise Total Synthesis of (+)-Luteoalbusins A and B. Organic Letters Aug. 2015;17(17):4268-4271. DOI: 10.1021/acs.orglett.5b02059.
Adjibade et al., In Vitro Cytotoxicity of Polyindolenine Alkaloids on Rat Hepatoma Cell Lines. Structure Activity Relationships, Journal of Ethnopharmacology 1990, 29, pp. 127-136.
Aleksandrzak et al., Antimitotic activity of diaryl compounds with structural features resembling combretastatin A-4. Anticancer Drugs. Jul. 1998; 9(6):545-50.
Aliev et al., A concise approach to the epidithiodiketopiperazine (ETP) core. Tetrahedron Lett. 2006; 47(14):2387-2390.
Amador et al., Antinociceptive Profile of Hodgkinsine, Planta Med 2000, 66, pp. 770-772.
Amir et al., Self-immolative dendrimers. Angew Chem Int Ed Engl. Sep. 29, 2003; 42(37):4494-9.
Amsberry et al., The lactonization of 2'-hydroxyhydrocinnamic acid amides: a potential prodrug for amines. J. Org. Chem. 1990; 55(23):5867-5877.
Andersen et al., Penicillium expansum: consistent production of patulin, chaetoglobosins, and other secondary metabolites in culture and their natural occurrence in fruit products. J Agric Food Chem. Apr. 21, 2004;52(8):2421-8.
Anderson et al., Studies on Total Synthesis of the Cytotoxic Marine Alkaloid Agelastatin A, J. Org. Chem., 63:7594-7595 (1998).
Andres et al., "Combretatropones"—hybrids of combretastatin and colchicine. Synthesis and biochemical evaluation Bioorganic. Med. Chem. Lett. 1993; 3(4):571-576.
Anet et al., Hodgkinsine, the Alkaloid of Hodgkinsonia Frutescens F. Muell, J. Chem. 1961, 14, pp. 173-174.
Anthon I, U. et al., Naturally Occurring Cyclotryptophans and Cyclotryptamines, Alkaloids: Chemical and Biological Perspectives, Pelletier, S. W., Ed .; Pergamon: London, 1999; vol. 13, pp. 163-236.
Aoyagi et al., Mild and Efficient One-Step Synthesis of Trithiocarbonates Using Minimum Amount of CS2. Synlett. 2006;636-638.

Bacher et al., D-24851, a novel synthetic microtubule inhibitor, exerts curative antitumoral activity in vivo, shows efficacy toward multidrug-resistant tumor cells, and lacks neurotoxicity. Cancer Res. Jan. 1, 2001; 61(1):392-9.
Bai et al., Interaction of dolastatin 10 with tubulin: induction of aggregation and binding and dissociation reactions. Molecular Pharmacology May 1995; 47(5):965-976.
Baldwin et al., Azo Anions in Synthesis. Use of Trityl- and Diphenyl-4-Pyridylmenthylhydrazones for Reductive C—C Bond Formation, Tetrahedron 1986, vol. 42, No. 15, pp. 4235-4246.
Banwell et al., Synthesis, X-Ray Crystal Structure and Tubulin-Binding Properties of a Benzofuran Analogue of the Potent Cytotoxic Agent Combretastatin A4. Australian Journal of Chemistry 1999; 52(8):767-774.
Barrow et al., WIN 64821, a new competitive antagonist to substance P, isolated from an *Aspergillus* species: structure determination and solution conformation. J. Org. Chem. 1993; 58(22):6016-6021.
Beck et al., Mild Aerobic Oxidative Palladium (II) Catalyzed C—H Bond Functionalization: Regioselective and Switchable C—H Alkenylation and Annulation of Pyrroles. J. Am. Chem. Soc. 2006; 128(8):2528-2529.
Bedford et al., Synthesis of water-soluble prodrugs of the cytotoxic agent Combretastatin A4. Bioorganic. Med. Chem. Lett. 1996; 6(2):157-160.
Behenna et al., Confirmation of the absolute configuration of (−)-aurantioclavine. Tetrahedron Letters Apr. 2011;52(17):2152-2154.
Belmar et al., Total Synthesis of (±)-Communesin F via a Cycloaddition with Indol-2-one. J. Am. Chem. Soc., 2012;134(41):16941-16943. DOI: 10.1021/ja307277w.
Belmar et al., Total Synthesis of (±)-isophellibiline and (±)-communesin F, and Design, Synthesis and Pharmacological Evaluation of Dihydro-β-erythroidine (DHβE) Analogs. Pennsylvania State University Dissertation 2012.
Benkovics et al., Oxaziridine-mediated oxyamination of indoles: an approach to 3-aminoindoles and enantiomerically enriched 3-aminopyrroloindolines. Angew Chem Int Ed Engl. Nov. 22, 2010;49(48):9153-7. doi: 10.1002/anie.201004635.
Beretz et al., Polyindolinic Alkaloids from Psychotria forsteriana. Potent Inhibitors of the Aggregation of Human Platelets, Planta Med. 1985, 51, pp. 300-303.
Bernardo et al., A Novel Redox Mechanism for the Glutathione-dependent Reversible Uptake of a Fungal Toxin in Cells. J Biol. Chem. 2003; 278(47):46549-46555.
Bertling et al., Candida albicans and its metabolite gliotoxin inhibit platelet function via interaction with thiols. Thromb Haemost. Aug. 2010;104(2):270-8.
Blokhin et al., Characterization of the interaction of the marine cyanobacterial natural product curacin A with the colchicine site of tubulin and initial structure-activity studies with analogues. Molecular Pharmacology Sep. 1995; 48(3):523-531.
Boger et al., Synthesis of the lower subunit of rhizoxin. J. Org. Chem. 1992; 57(8):2235-2244.
Boyer et al., Concise Total Synthesis of (+)-Gliocladins B and C. Chem Sci. Jan. 1, 2012;3(6):1798-1803. Epub Mar. 30, 2012.
Boyer et al., Synthesis and Anticancer Activity of Epipolythiodiketopiperazine Alkaloids. Chem Sci. 2013;4(4):1646-1657. doi:10.1039/C3SC50174D.
Brak et al., Total Synthesis of (−)-Aurantioclavine. Org. Lett., 2010;12(9):2004-2007. DOI: 10.1021/ol100470g.
Brown et al., Investigation of various N-heterocyclic substituted piperazine versions of 5/7-{[2-(4-aryl-piperazin-1-yl)-ethyl]-propyl-amino }-5,6,7,8-tetrahydro-naphthalen-2-ol: effect on affinity and selectivity for dopamine D3 receptor. Bioorg Med Chem. Jun. 1, 2009;17(11):3923-33.
Bundgaard, H., (C) Means to enhance penetration: (1) Prodrugs as a means to improve the delivery of peptide drugs. Advanced Drug Delivery Revieivs. 1992; 8(1):1-38.
Canham et al., Stereocontrolled enantioselective total synthesis of the [2+2] quadrigeminealkaloids, Tetrahedron 2015, 71, pp. 6424-6436.

(56) References Cited

OTHER PUBLICATIONS

Chaib et al., Anti-leukemia activity of chaetocin via death receptor-dependent apoptosis and dual modulation of the histone methyltransferase SUV39H1. Leukemia. Apr. 2012;26(4):662-74.
Chang et al., Heterocyclic Compounds. Part 15. NN'-Di-t-Butylthiadiaziridine 1, 1-Dioxide:Synthesis and Reactions, J. Chem. Soc., Perkin Trans. 1, 1977, pp. 1601-1605.
Chen et al., Ecology-based screen identifies new metabolites from a Cordyceps-colonizing fungus as cancer cell proliferation inhibitors and apoptosis inducers. Cell Prolif. Dec. 2009;42(6):838-47.
Cherblanc et al., On the Determination of the Stereochemistry of Semisynthetic Natural Product Analogues using Chiroptical Spectroscopy: Desulfurization of Epidithiodioxopiperazine Fungal Metabolites. Chem.-Eur. J. 2011; 17(42):11868-11875.
Choi et al., Agelastatin A (AgA), a Marine Sponge Derived Alkaloid, Inhibits Wnt/Beta-Catenin Signaling and Selectively Induces Apoptosis in Chronic Lymphocytic Leukemia Independently of p53, Blood (ASH Annual Meeting Abstracts), 118:Abstract1786, 2 (2011).
Chou et al., Therapeutic Cure against Human Tumor Xenografts inNude Mice by a Microtubule Stabilization Agent,Fludelone, via Parenteral or Oral Route. Cancer Res. 2005; 65(20):9445-9454.
Codelli et al., Enantioselective Total Synthesis of (−)-Acetylaranotin, a Dihydrooxepine Epidithiodiketopiperazine. J. Am. Chem. Soc. 2012; 134(4):1930-1933.
Coffen et al., A short synthesis of aromatic analogues of the aranotins. J. Org. Chem. Mar. 18, 1977;42(6):948-52.
Cogan et al., Asymmetric synthesis of chiral amines by highly diastereoselective 1,2-additions of organometallic reagents to N-tert-butanesulfinyl imines. Tetrahedron Jul. 1999;55(29):8883-8904.
Coleman et al., Antifungal activity of microbial secondary metabolites. PLoS One. 2011;6(9):e25321.
Collet et al., Catalytic C—H amination: recent progress and future directions, Chem. Commun. 2009, pp. 5061-5074.
Combeau et al., RPR112378 and RPR115781: Two Representatives of a New Family of Microtubule Assembly Inhibitors. Molecular Pharmacology Mar. 2000; 57(3):553-563.
Cook et al., Epidithiodiketopiperazines Block the Interaction between Hypoxia-inducible Factor-1α(HIF-1α) and p300 by a Zinc Ejection Mechanism. J Biol. Chem. 2009; 284:26831-26838.
Cordell et al., Bisindole Alkaloids, The Alkaloids: Chemistry and Physiology, Manske R. H. F., Rodrigo, R. G. A., Ed .; Academic Press: New York, 1981; vol. 20, pp. 3-295.
Coretese et al., Podophyllotoxin as a probe for the colchicine binding site of tubulin. J Biol Chem. Feb. 25, 1977;252(4):1134-40.
Corey et al., Enantioselective Total Synthesis of Ecteinascidin 743, J. Am. Chem. Soc. 1996, 118, pp. 9202-9203.
Coste et al., Concise Total Synthesis of (+)-Bionectins A and C. Chem Sci. 2013;4(8):3191-3197. doi:10.1039/C3SC51150B.
Crawley et al., A Synthetic Approach to Nomofungin/Communesin B. Org. Lett., 2003, 5(18), pp. 3169-3171. DOI: 10.1021/o1034407v.
Crich et al., Chemistry of the Hexahydropyrrolo[2,3-b]indoles: Configuration, Conformation, Reactivity, and Applications in Synthesis, Acc. Chem. Res. 2007, 40, pp. 151-161.
Crich et al., Expedient Synthesis of threo-β-Hydroxy-α-amino Acid Derivatives: Phenylalanine, Tyrosine, Histidine, and Tryptophan. J. Org. Chem. 2006; 71(18):7106-7109.
Cushman et al., Synthesis and evaluation of stilbene and dihydrostilbene derivatives as potential anticancer agents that inhibit tubulin polymerization. J. Med. Chem. 1991; 34(8):2579-2588.
Cushman et al., Synthesis of Analogs of 2-Methoxyestradiol with Enhanced Inhibitory Effects on Tubulin Polymerization and Cancer Cell Growth. J. Med. Chem. 1997; 40(15):2323-2334.
D'Ambrosia et al., Agelastatin A, a New Skeleton Cytotoxic Alkaloid of the Oroidin Family. Isolation from the Axinellid Sponge Agelas dendromorpha of the Coral Sea, J. Chem. Soc., Chem. Commun., pp. 1305-1306 (1993).
D'Aambrosio et al., The Active Centres of Agelastatin A, a Strongly Cytotoxic Alkaloid of the Coral Sea Axinellid Sponge Agelas dendromorpha, as Determined by Comparative Bioassays with Semisynthetic Derivatives, Helv. Chem. Acta, 79:727-735(1996).
Davis et al., Adventures in Sulfur-Nitrogen Chemistry, J. Org. Chem. 2006, 71, pp. 8993-9003.
Davis et al., Asymmetric synthesis of amino acids using sulfinimines (thiooxime S-oxides), Chem. Soc. Rev. 1998, 27, pp. 13-18.
De Groot et al., Cascade-release dendrimers liberate all end groups upon a single triggering event in the dendritic core. Angew Chem Int Ed Engl. Sep. 29, 2003; 42(37):4490-4.
De Groot et al., Design, Synthesis, and Biological Evaluation of a Dual Tumor-specific Motive Containing Integrin-targeted Plasmin-cleavable Doxorubicin Prodrug. Molecular Cancer Therapeutics 2002; 1(11):901-911.
De Groot et al., Synthesis and Biological Evaluation of Novel Prodrugs of Anthracyclines for Selective Activation by the Tumor-Associated Protease Plasmin. J. Med. Chem. 1999; 42(25):5277-5283.
De Loera et al., Efficient Aziridine Synthesis in Metastable Crystalline Phases by Photoinduced Denitrogenation of Crystalline Triazolines, Org. Lett. 2012, vol. 14, No. 15, pp. 3874-3877.
De Loera et al., Photoinduced and Thermal Denitrogenation of Bulky Triazoline Crystals: Insights into Solid-to-Solid Transformation, J. Am. Chem. Soc. 2013, 135, pp. 6626-6632.
Delfourne, Marine natural products and other derivatives as potent indoleamine 2,3-dioxygenase inhibitors. Mini Rev Med Chem. 2012;12(10):988-996. doi:10.2174/138955712802762374.
Delorbe et al., Enantioselective Total Synthesis of (+)-Gliocladine C: Convergent Construction of Cyclotryptamine-Fused Polyoxopiperazines and a General Approach for Preparing Epidithiodioxopiperazines from Trioxopiperazine Precursors. J Am Chem Soc. Apr. 7, 2011;133(17):6549-52.
DeLorbe et al., General Approach for Preparing Epidithiodioxopiperazines from Trioxopiperazine Precursors: Enantioselective Total Syntheses of (+)- and (−)-Gliocladine C, (+)-Leptosin D, (+)-T988C, (+)-Bionectin A, and (+)-Gliocladin A. J. Am. Chem. Soc. 2013; 135(10):4117-4128.
Denmark et al., Palladium-Catalyzed Cross-Coupling Reactions of 2-Indolyldimethylsilanols with Substituted Aryl Halides. Org. Lett. 2004; 6(20):3649-3652.
Depew et al., Total Synthesis of 5-N-Acetylardeemin and Amauromine: Practical Routes to Potential MDR Reversal Agents. J. Am. Chem. Soc.1999; 121(51):11953-11963.
DePorter et al., N-Nosyl oxaziridines as terminal oxidants in copper(II)-catalyzed olefinoxyaminations, Tetrahedron 2010, 51, pp. 5223-5225.
Dong et al., Nematicidal epipolysulfanyldioxopiperazines from Gliocladium roseum. J Nat Prod. Oct. 2005;68(10):1510-3.
Dorr et al., Antitumor activity of combretastatin-A4 phosphate, a natural product tubulin inhibitor. Invest. New Drugs Jun. 1996; 14(2):131-137.
Du Bois, J., Rhodium-Catalyzed C—H Amination. An Enabling Method for Chemical Synthesis, Org. Process Res. Dev. 2011, 15, pp. 758-762.
Dubey et al., Direct organocatalytic coupling of carboxylated piperazine-2,5-diones with indoles through conjugate addition of carbon nucleophiles to indolenine intermediates. Tetrahedron Lett. 2010;51(4):609-612. doi:10.1016/j.tetlet.2009.11.068.
Dubowchik et al., Monomethoxytrityl (MMT) as a versatile amino protecting group for complex prodrugs of anticancer compounds sensitive to strong acids, bases and nucleophiles. Tetrahedron Letters 1997; 38(30):5257-60.
Dubs et al., Eine neue Methode zur Herstellung gemischter Disulfide. Vorläufige Mitteilung Helv. Chim. Acta 1976; 59(4):1307-1311.
Ducki et al., Potent antimitotic and cell growth inhibitory properties of substituted chalcones. Bioorg Med Chem Lett. May 5, 1998; 8(9):1051-6.
Dörwald, F.Z., Preface. In: Side Reactions in Organic Synthesis. 2005, Wiley-VCH Verlag GmbH & Co. KGaA, Weinheim, p. IX.
Engel et al., Thermolysis of Free-Radical Initiators: tert-Butylazocumene and Its 1,3- and 1,4- Bisazo and 1,3,5-Trisazo Analogues, J. Am. Chem. Soc. 2001, 123, pp. 3706-3715.

(56) References Cited

OTHER PUBLICATIONS

Engel, P. S., Mechanism of the Thermal and Photochemical Decomposition of Azoalkanes, Chemical Reviews Apr. 1980, vol. 80, No. 2, 52.
Engel, P. S., Photochemistry of Aliphatic Azo Compounds in Solution, Accounts of Chemical Research 1973, vol. 6, pp. 275-281.
Erkel et al., Induction of differentiation in acute promyelocytic leukemia cells (HL-60) by the verticillin derivative Sch 52900. Z Naturforsch C J Biosci. Jul.-Aug. 2002;57(7-8):759-67. doi: 10.1515/znc-2002-7-834.
Espino et al., A Rh-Catalyzed C—H Insertion Reaction for the Oxidative Conversion of Carbamates to Oxazolidinones, Angew. Chem. Int. Ed. 2001, 40:3, pp. 598-600.
Espino et al., Expanding the Scope of C—H Amination through Catalyst Design, J. Am. Chem. Soc. 2004, 126, pp. 15378-15379.
Eto et al., Conformation of aromatic rings in isolable atropisomers of 2-arylindoline derivatives and kinetic evidences for π-π interaction. Tetrahedron Lett. Jan. 23, 2010;66(4):898-903.
Fan et al., Alkaloids with Cardiovascular Effects from the Marine-Derived Fungus Penicillium expansum Y32. Mar Drugs. Oct. 22, 2015;13(10):6489-504. doi: 10.3390/md13106489.
Fang et al., Dimerization of a 3-Substituted Oxindole at C-3 and Its Application to the Synthesis of (±)-Folicanthine, J. Am. Chem. Soc. 1994, 116, pp. 9480-9486.
Fink et al., Mercaptoacyl Dipeptides as Orally Active Dual Inhibitors of Angiotensin-Converting Enzyme and Neutral Endopeptidase. J. Med. Chem.1996; 39(16):3158-3168.
Fiori et al., A mechanistic analysis of the Rh-catalyzed intramolecular C—H amination reaction, Tetrahedron 2009, 65, pp. 3042-3051.
Fiori et al., Catalytic Intermolecular Amination of C—H Bonds: Method Development and Mechanistic Insights, J. Am. Chem. Soc. 2007, 129, pp. 562-568.
Firouzabadi et al., Bispyridinesilver permanganate[Ag(C5H5N)2]MnO4: an efficient oxidizing reagent for organic substrates. Tetrahedron Lett. 1982; 23(17): 1847-1850.
Flynn et al., The synthesis and tubulin binding activity of thiophene-based analogues of combretastatin A-4. Bioorg Med Chem Lett. Sep. 3, 2001; 11(17):2341-3.
Foo et al., Total Synthesis-Guided Structure Elucidation of (+)-Psychotetramine, Angew. Chem. Int. Ed. Engl. 2011, 50(12), pp. 2716-2719.
Fotsis et al., The endogenous oestrogen metabolite 2-methoxyoestradiol inhibits angiogenesis and suppresses tumour growth. Nature. Mar. 17, 1994; 368(6468):237-9.
Frisch et al., Synthesis of Short Polyoxyethylene-Based Heterobifunctional Cross-Linking Reagents. Application to the Coupling of Peptides to Liposomes. Bioconjugate Chem., 1996, 7(2), pp. 180-186.
Fuchs et al., Total Synthesis of (±)-Perophoramidine, J. Am. Chem. Soc. 2004, 126, pp. 5068-5069.
Fukuyama et al., A total synthesis of gliotoxin. J. Am. Chem. Soc. 1976; 98(21):6723-6724.
Furst, L. et al., Total Synthesis of (+)-Gliocladin C Enabled by Visible-Light Photoredox Catalysis, Angew. Chem. Int. Ed. 2011, 50, pp. 9655-9659.
Gardiner et al., The epipolythiodioxopiperazine (ETP) class of fungal toxins: distribution, mode of action, functions and biosynthesis. Microbiology. Apr. 2005; 151(Pt 4):1021-32.
Gardner et al., Understanding C—H bond oxidations: H. and H-transfer in the oxidation of toluene by permanganate. Science. Sep. 29, 1995; 269(5232):1849-51.
Gastpar et al., Methoxy-Substituted 3-Formyl-2-phenylindoles Inhibit Tubulin Polymerization. J. Med. Chem. 1998; 41(25):4965-4972.
Gerwick et al., Structure of Curacin A, a Novel Antimitotic, Antiproliferative and Brine Shrimp Toxic Natural Product from the Marine Cyanobacterium Lyngbya majuscula. J. Org. Chem.1994; 59(6):1243-1245.
Getahun et al., Synthesis of alkoxy-substituted diaryl compounds and correlation of ring separation with inhibition of tubulin polymerization: differential enhancement of inhibitory effects under suboptimal polymerization reaction conditions. J. Med. Chem. 1992; 35(6):1058-1067.
Gilow et al., Sulfenylation of some pyrroles and indoles. J Heterocyclic Chem. 1991, 28(4):1025-1034.
Golitz et al., A New Method for the Introduction of Trifluoromethyl Groups, Angew. Chem. Int. Ed. Engl. 1977, 16, No. 12, pp. 854-855.
Govek et al., Total Synthesis of (+)-asperazine, Tetrahedron 2007, 63, pp. 8499-8513.
Greene et al., Greene's Protective Groups in Organic Synthesis, Fifth Edition, Wiley, New York, NY 2014, Chapter 7, Protection for the Amino Group, 299 (Parts 1 & 2).
Greiner et al., Identification of a specific inhibitor of the histone methyltransferase SU(VAR)3-9. Nat Chem Biol. Aug. 2005;1(3):143-5.
Gueritte-Voegelein et al., Alkaloids From Psychotria Oleoides with Activity on Growth Hormone Release, J. Nat. Prod. 1992, 55, pp. 923-930.
Gwaltney et al., Novel sulfonate derivatives: potent antimitotic agents. Bioorg Med Chem Lett. Jul. 9, 2001; 11(13):1671-3.
Hadimani et al., Synthesis, in vitro, and in vivo evaluation of phosphate ester derivatives of combretastatin A-4. Bioorg. Med. Chem. Lett. 2003; 13(9):1505-1508.
Hale et al., Enantiospecific Formal Total Synthesis of the Tumor and GSK-3b Inhibiting Alkaloid, (−)-Agelastatin A, Org. Lett., 5(16):2927-2930 (2003).
Hall et al., Biogenetic-Type Synthesis of the Calycanthaceous Alkaloids, Tetrahedron 1967, 23, pp. 4131-4141.
Hamada et al., Selective removal of electron-accepting p-toluene- and naphthalenesulfonyl protecting groups for amino function via photoinduced donor acceptor ion pairs with electron-donating aromatics. J. Am. Chem. Soc. 1986; 108(1):140-145.
Hammonds et al., Studies to show that with podophyllotoxin the early replicative stages of herpes simplex virus type 1 depend upon functional cytoplasmic microtubules. J Med Microbiol. Sep. 1996; 45(3):167-72.
Han et al., A Diastereodivergent Synthetic Strategy for the Syntheses of Communesin F and Perophoramidine, Org. Lett. 2014, 16, pp. 3316-3319.
Han et al., Evolution of a Unified, Sterodivergent Approach to the Synthesis of Communesin F and Perophoramidine, J. Org. Chem. 2015, 80, pp. 528-547.
Han et al., Synthesis and Anticancer Activity of All Known (−)-Agelastatin Alkaloids, The Journal of Organic Chemistry, 78, p. 11970-11984 (2013).
Hansen et al., A stereoselective synthetic approach to (2S,3R)-N-(1',1'-dimethyl-2',3'-epoxypropyl)-3-hydroxytryptophan, a component of cyclomarin A. Tetrahedron: Asymmetry 2006; 17(1):15-21.
Hatanaka et al., Novel B-ring modified combretastatin analogues: syntheses and antineoplastic activity. Bioorg Med Chem Lett. Dec. 1, 1998; 8(23):3371-4.
Hay et al., A 2-nitroimidazole carbate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT. Bioorg. Med. Chem. Lett. 1999; 9:2237-2242.
Hayashi et al., New insecticidal compounds, communesins C, D and E, from Penicillium expansum link MK-57. Biosci Biotechnol Biochem. Mar. 2004;68(3):753-6. doi: 10.1271/bbb.68.753.
He et al., Total Syntheses of (−)-Asperlicin and (−)-Asperlicin C. J Am Chem Soc. Jun. 11, 1998;120(25):6417-8.
Hegedus et al., Palladium-Catalyzed Reactions in the Synthesis of 3- and 4-Substituted Indoles. 3. Total Synthesis of(±)-Aurantioclavine, J. Org. Chem. 1987, 52, pp. 3319-3322.
Hendrickson et al., Total Synthesis of the Calycanthaceous Alkaloids, Tetrahedron 1964, vol. 20, pp. 565-579.
Hendrickson et al., Total Synthesis of the Calycanthaceous Alkaloids. Chimonanthine, R. Proc. Chem. Soc. 1962, pp. 383-384.
Herscheid et al., Biosynthesis of gliotoxin. Synthesis of sulfur-bridged dioxopiperazines from N-hydroxyamino acids. J. Org. Chem. 1980; 45(10):1885-1888.
Herzon et al., Enantioselective Synthesis of Stephacidin B, J. Am. Chem. Soc. 2005, 127, pp. 5342-5344.

(56) References Cited

OTHER PUBLICATIONS

Higuchi et al., First Total Synthesis of Hinckdentine A. Org Lett. 2009;11(1):197-9.

Higuchi et al., Preparation of 2,2-disubstituted 1,2-dihydro-3H-indol-3-ones via oxidation of 2-substituted indoles and Mannich-type reaction. Tetrahedron Lett. Feb. 6, 2010;66(6):1236-43.

Hino et al., Chemistry and Reactions of Cyclic Tautomers of Tryptamines and Tryptophans, The Alkaloids: Chemistry and Pharmacology, Brossi, A., Ed .; Academic Press: New York, 1989; vol. 34, pp. 1-75.

Hino et al., Oxidative Dimerization of Nb-Methoxycarbonyltryptamines by Dye-Sensitized Photooxygenation in Formic Acid. Synthesis of (±)-Folicanthine and (±)-Chimonanthine, Tetrahedron Letters 1978, 49, pp. 4913-4916.

Hino et al., Synthesis of 3,6-diethoxycarbonyl-3,6-epipolythia-2,5-piperazinedione derivatives. Tetrahedron Lett. 1971; 12(33):3127-3129.

Hino et al., Total Synthesis of (±)-Folicanthine, Tetrahedron Letters 1963, 25, pp. 1757-1760.

Hoffmann et al., A Powerful Br0nsted Acid Catalyst for the Organocatalytic Asymmetric Transfer Hydrogenation of Imines, Angew. Chem. Int. Ed. 2005, 44, pp. 7424-7427.

Hoijemberg et al., Photolysis of an asymmetrically substituted diazene in solution and in the crystalline state, Photochem. Photobiol. Sci. 2009, 8, pp. 961-969.

Holwell et al., Anti-vascular effects of vinflunine in the MAC 15A transplantable adenocarcinoma model. Br. J. Cancer., 2001; 84:290-295.

Hossain, T. Md. et al., Synthesis of Bisbicyclo[1.1.1]pentyldiazene. The Smallest Brigehead Diazene, J. Org. Chem. 2001, 66, pp. 6282-6285.

Hsieh et al., Structure-activity and crystallographic analysis of benzophenone derivatives—the potential anticancer agents. Bioorg Med Chem Lett. 2002; 13(1):101-105.

Huang et al., Diketopiperazines from Marine Organisms. Chem. Biodiv. 2010; 7(12):2809-2829.

Huard et al., N-Tosyloxycarbamates as Reagents in Rhodium-Catalyzed C—H Amination Reactions, Chem. Eur. J. 2008, 14, pp. 6222-6230.

Ikeda et al., Evidence for Significant Through-Space and Through-Bond Electronic Coupling in the 1,4-Diphenylcyclohexane-1,4-diyl Radical Cation Gained by Absorption Spectroscopy and OFT Calculations, Chem. Eur. J. 2007, 13, DD. 9207-9215.

Isham et al., Chaetocin: a promising new antimyeloma agent with in vitro and in vivo activity mediated via imposition of oxidative stress. Blood. Mar. 15, 2007;109(6):2579-88.

Isham et al., The anticancer effects of chaetocin are independent of programmed cell death and hypoxia, and are associated with inhibition of endothelial cell proliferation. Br J Cancer. Jan. 17, 2012;106(2):314-23.

Ishikawa et al., Dimerization of indole derivatives with hypervalent iodines(III): a new entry for the concise total synthesis of rac- and meso-chimonanthines, Tetrahedron Lett. 2002, 43, pp. 5637-5639.

Iwasa et al., Total Synthesis of (+)-Chaetocin and its Analogues: Their Histone Methyltransferase G9a Inhibitory Activity. J. Am. Chem. Soc. 2010; 132(12):4078-4079.

Iwasa, et al., Epipolythiodiketopiperazine Alkaloids: Total Syntheses and Biological Activities. Isr. J Chem. 2011; 51(3-4):420-433.

Jabri et al., Enantioselective Total Synthesis of Plectosphaeroic Acid B and C. J. Org. Chem. Aug. 27, 2013;78(17):8766-8788. doi: 10.1021/jo4015479.

Jadulco et al., New Communesin Derivatives from the Fungus *Penicillium* sp. Derived from theMediterranean Sponge *Axinella verrucosa*, J. Nat. Prod. 2004, 67, pp. 78-81.

Jadulco, Isolation and Structure Elucidation of Bioactive Secondary Metabolites from Marine Sponges and Sponge-derived Fungi, 2002, 88.

Jamison et al., Enantioselective Synthesis of Polypyrrolo-indolines by Controlled Oligomerization, Nat. Chem. 2017, doi: 10.1038/nchem.2825, 1 page.

Janik et al., Synthesis and antimicrobtubule activity of combretatropone derivatives. Bioorg. Med. Chem. Lett. 2002; 10:1895-1903.

Jannic et al., Pyrrolidinoindoline alkaloids from Psychotria oleoides and Psychotria lyciiflora. J Nat Prod. Jun. 1999;62(6):838-43.

Jiang et al., Disulfide- and Multisulfide-Containing Metabolites from Marine Organisms. Chem. Rev. 2012; 112(4):2179-2207.

Jiang et al., Epipolythiodioxopiperazines from fungi: chemistry and bioactivities. Mini Rev Med Chem. Aug. 2011;11(9):728-45.

Jiang et al., Synthesis and biological evaluation of 2-styrylquinazolin-4(3H)-ones, a new class of antimitotic anticancer agents which inhibit tubulin polymerization. J. Med. Chem.1990; 33(6):1721-1728.

Jordan et al., Fungal epipolythiodioxopiperazine toxins have therapeutic potential and roles in disease. Trends Pharmacol. Sci. 8, 144-149.

Jouanneau et al., Derivatization of agelastatin A leading to bioactive analogs and a trifunctional probe, Bioorganic & Medicinal Chemistry Letters, 26, p. 2092-2097 (2016).

Kakeya, et al., Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid. Chem. Pharm. Bull. 1984 32(2):692-698.

Kaneko et al., New hydrazone derivatives of Adriamycin and their immunoconjugates—a correlation between acid stability and cytotoxicity. Bioconjugate Chem. 1991; 2(3):133-141.

Kanoh et al., (−)-Phenylahistin arrests cells in mitosis by inhibiting tubulin polymerization. J Antibiot (Tokyo). Feb. 1999; 52(2):134-41.

Karaman et al., Preparation and properties of quaternary ammonium and phosphonium permanganates. J. Org. Chem.1984; 49(23):4509-4516.

Kerzaon et al., Structural investigation and elucidation of new communesins from a marine-derived Penicillium expansum Link by liquid chromatography/electrospray ionization mass spectrometry. Rapid Commun Mass Spectrom. Dec. 2009;23(24):3928-38. doi: 10.1002/rcm.4330.

Kieffer et al., Copper-Catalyzed Diastereoselective Arylation of Tryptophan Derivatives: Total Synthesis of (+)-Naseseazines A and B, J. Am. Chem. Soc. 2013, 135(15), pp. 5557-5560.

Kim et al., Alkylthiolation of allylic sulfides. [2,3] Sigmatropic rearrangement of thiosulfonium ions. J. Org. Chem. 1979; 44(12): 1897-1904.

Kim et al., Biogenetically inspired syntheses of alkaloid natural products. Chem Soc Rev. Nov. 2009;38(11):3035-50. doi: 10.1039/b819925f. Epub Sep. 23, 2009.

Kim et al., Biogenetically-Inspired Total Synthesis of Epidithiodiketopiperazines, Acc. Chem. Res. 2015, 48, pp. 1159-1171.

Kim et al., Concise Total Synthesis and Stereochemical Revision of (+)-Naseseazines A and B: Regioselective Arylative Dimerization of Diketopiperazine Alkaloids. J. Am. Chem. Soc. 2011; 133(38):14940-14943.

Kim et al., General approach to epipolythiodiketopiperazine alkaloids: total synthesis of (+)- chaetocins A and C and (+)-12,12'-dideoxychetracin A. J Am Chem Soc. Oct. 20, 2010;132(41):14376-8. doi: 10.1021/ja106869s.

Kim et al., Total synthesis of (+)-11,11'-dideoxyverticillin A. Science. Apr. 10, 2009;324(5924):238-41. doi: 10.1126/science.1170777.

Kim et al., Transition-Metal-Mediated Direct C—H Amination of Hydrocarbons with Amine Reactants: The Most Desirable but Challenging C—N Bond-Formation Approach, ACS Cata/. 2016, 6, pp. 2341-2351.

King et al., Facile synthesis of maleimide bifuntional linkers, Tetrahedron Lett. 2002; 43:1987-1990.

Kingsbury et al., A novel peptide delivery system involving peptidase activated prodrugs as antimicrobial agents. Synthesis and biological activity of peptidyl derivatives of 5-fluorouracil. J. Med. Chem. 1984; 27:1447-1451.

Kingston et al., The Chemistry of Taxol, a Clinically Useful Anticancer Agent. J. Nat. Prod. 1990; 53(1):1-12.

(56) References Cited

OTHER PUBLICATIONS

Kishi et al., Total synthesis of dehydrogliotoxin. J. Am. Chem. Soc. 1973; 95(19):6492-6493.

Kitir et al., Total synthesis and structural validation of cyclodepsipeptides solonamide A and B, Tetrahedron 2014, 70, pp. 7721-7732.

Kobayashi et al., Synthetic study on an antitumor antibiotic rhizoxin by using an enzymatic process on prochiral β-substituted glutarates. Pure Appl. Chem. 1992; 64(8):1121-1124.

Kodanko et al., Enantioselective Total Syntheses of the Cyclotryptamine Alkaloids Hodgkinsine and Hodgkinsine B, Angew. Chem. Int. Ed. 2003, 42, pp. 2528-2531.

Kodanko et al., Synthesis of All Low-energy Stereoisomers of the Tris(pyrrolidinoindoline) Alkaloid Hodgkinsine and Preliminary Assessment of Their Antinociceptive Activity, J. Org. Chem. 2007, 72, pp. 7909-7914.

Kosower, E. M., Monosubstituted Diazenes (Diimides). Suprising Intermediates, Accounts ofChemical Research 1971, vol. 1, No. 6, pp. 193-198.

Kricheldorf, H.R. Synthese von Isothiocyanatocarbonsäurechloriden aus Lactamen. Angew. Chem. 1975; 87(14):517.

Krishnan et al., Pd-Catalyzed Enantioselective Aerobic Oxidation of Secondary Alcohols:Applications to the Total Synthesis of Alkaloids, J. Am. Chem. Soc. 2008, 130, pp. 137 45-13754.

Kroutil et al., First preparative biocatalytic hydrolysis and S-methylation of cyclic trithiocarbonates. Tetrahedron 2002; 58(13):2589-2592.

Ksander et al., Chemie der α-Aminonitrile 1. Mitteilung Einleitung und Wege zu Uroporphyrinogen-octanitrilen. Helv Chim Acta. Jul. 8, 1987;70(4):1115-72.

Kung et al., Small molecule blockade of transcriptional coactivation of the hypoxia-inducible factor pathway. Cancer Cell. Jul. 2004;6(1):33-43.

Kurokawa et al., Synthesis of 1,3-Diamines Through Rhodium-Catalyzed C—H Insertion, Angew. Chem. Int. Ed. 2009, 48, pp. 2777-2779.

Laguzza et al., New antitumor monoclonal antibody-vinca conjugates LY203725 and related compounds: design, preparation, and representative in vivo activity. J. Med. Chem. 1989; 32(3):548-555.

Lathrop et al., Application of diazene-directed fragment assembly to the total synthesis and stereochemical assignment of (+)-desmethyl-meso-chimonanthine and related heterodimeric alkaloids, Chem. Sci. 2014, 5, DD. 333-340.

Lathrop et al., Radical-mediated dimerization and oxidation reactions for the synthesis of complex alkaloids. Chimia (Aarau). 2012;66(6):389-93. doi: 10.2533/chimia.2012.389.

Lavielle et al., New .alpha.-amino phosphonic acid derivatives of vinblastine: chemistry and antitumor activity. J. Med. Chem. 1991; 34(7):1998-2003.

Lawrence et al., The interaction of chalcones with tubulin. Anticancer Drug Des. Apr. 2000; 15(2):135-41.

Lebsack et al., Enantioselective Total Synthesis of Quadrigemine C and Psycholeine, J. Am. Chem. Soc. 2002, 124, pp. 9008-9009.

Lee et al., Antihepatoma activity of chaetocin due to deregulated splicing of hypoxia-inducible factor 1α pre-mRNA in mice and in vitro. Hepatology. Jan. 2011;53(1):171-80.

Leoni et al., Indanocine, a microtubule-binding indanone and a selective inducer of apoptosis in multidrug-resistant cancer cells. J Natl Cancer Inst. Feb. 2, 2000;92(3):217-24.

Li et al., An integrated approach to the discovery of potent agelastatin A analogues for brain tumors: chemical synthesis and biological, physicochemical and CNS pharmacokinetic analyses, Med. Chem. Commun., 4, p. 1093-1098 (2013).

Li et al., Cytotoxic metabolites from the antarctic psychrophilic fungus Oidiodendron truncatum. J Nat Prod. May 25, 2012;75(5):920-7. doi: 10.1021/np3000443. Epub May 14, 2012.

Li et al., General Approach for the Synthesis of Ajmaline/Sarpagine Indole Alkaloids: Enantiospecific Total Synthesis of (+)-Ajmaline, Alkaloid G, and Norsuaveoline via the Asymmetric Pictet-Spengler Reaction. J Am Chem Soc. Jul. 16, 1999;121(30):6998-7010.

Li et al., Ligand-based targeted therapy: a novel strategy for hepatocellular carcinoma. Int J Nanomedicine. Oct. 31, 2016;11:5645-5669. eCollection 2016.

Li et al., Pharmacokinetics of Agelastatin A in the central nervous system. Med. Chem. Commun. 2012;3:233-237.

Liang et al., Organocatalytic stereoselective conjugate addition of 3-substituted oxindoles with in situ generated ortho-quinone methides. Tetrahedron Lett. May 2, 2018;59(18):1742-7.

Libot et al., Biomimetic Transformation of Hodgkinsine, a Pyrrolidinoindoline Alkaloids, Heterocycles 1988, 27, pp. 2381-2386.

Libot et al., Rubiacees D'Oceanie: Alcalo'ldes de Psychotria Oleoides de Nouvelle-Caledonie et de Calycodendron Milnei du Vanuatu (Nouvelles-Hebrides), Journal of Natural Products 1987, vol. 50, No. 3, pp. 468-473.

Lim et al., Novel Route to Azobenzenes via Pd-Catalyzed Coupling Reactions of Aryl Hydrazides with Aryl Halides, Followed by Direct Oxidations, Org. Lett. 2003, vol. 5, No. 7, pp. 979-982.

Lin et al., Antimitotic natural products combretastatin A-4 and combretastatin A-2: studies on the mechanism of their inhibition of the binding of colchicine to tubulin. Biochemistry 1989; 28(17):6984-6991.

Lin et al., Elucidation of the Concise Biosynthetic Pathway of the Communesin Indole Alkaloids, Angew. Chem. Int. Ed. 2015, 54, pp. 3004-3007.

Lin et al., P450-Mediated Coupling of Indole Fragments To Forge Communesin and Unnatural Isomers. J Am Chem Soc. Mar. 30, 2016;138(12):4002-5. doi: 10.1021/jacs.6b01413. Epub Mar. 18, 2016.

Lindovska et al., Concise Synthesis of (−)-Hodgkinsine, (−)-Calycosidine, (−)-Hodgkinsine B, (−)- Quadrigemine C, and (−)-Psycholeine via Convergent and Directed Modular Assembly of Cyclotryptamines, https://www.ncbi.nlm.nih.gov/m/pubmed/29058431, 2017, 7 pages.

Link et al., Stereocontrolled Total Syntheses of meso-Chimonanthine and meso-Calycanthine via a Novel Samarium Mediated Reductive Dialkylation, J. Am. Chem. Soc. 1996, 118, pp. 8166-8167.

Little et al., Total Synthesis of the Marine Natural Product il9(121-Capnellene. Reversal ofRegiochemistry in the Intramolecular 1,3-Diyl Trapping Reaction, J. Am. Chem. Soc. 1983, 105, pp. 928-932.

Little, R. D., Diyl Trapping and Electroreductive Cyclization Reactions, Chem. Rev. 1996, 96, pp. 93-114.

Liu et al., Total Synthesis of the Polycyclic Fungal Metabolite (±)-Communesin F, Angew. Chem. Int. Ed. 2010, 49, pp. 2000-2003.

Liu et al., Verticillin A overcomes apoptosis resistance in human colon carcinoma through DNA methylation-dependent upregulation of BNIP3. Cancer Res. Nov. 1, 2011;71(21):6807-16.

Loach et al., Concise Total Synthesis of (+)-Asperazine, (+)-Pestalazine A, and (+)-iso-Pestalazine A. Structure Revision of (+)-Pestalazine A. J Am Chem Soc. Jan. 27, 2016;138(3):1057-64. doi: 10.1021/jacs.5b12392. Epub Jan. 19, 2016.

Mahboobi et al., Synthetic 2-Aroylindole Derivatives as a New Class of Potent Tubulin-Inhibitory, Antimitotic Agents. J. Med. Chem. 2001; 44(26):4535-4553.

Mannila et al., Combretastatin Analogs via Hydration of Stilbene Derivatives. Liebigs. Ann. Chem. 1993; 1993(9):1037-1039.

Mascitti et al., Total Synthesis of (±)-Pentacycloanammoxic Acid, J. Am. Chem. Soc. 2004, 126, pp. 15664-15665.

Mason et al., Agelastatin A: a novel inhibitor of osteopontin-mediated adhesion, invasion, and colony formation, Mol. Cancer Ther., 7:548-558 (2008).

Matano et al., Synthesis and Charge-Carrier Transport Properties of Poly(phosphole P-alkanesulfonylimide)s, Org. Lett., 2013, 15 (4), pp. 932-935.

Matsuda et al., Total Synthesis and Structure Reinvestigation of So-Called Isochimonanthine, Heterocycles 2005, 65, pp. 1031-1033.

May, J. A. et al., Biomimetic approach to communesin B (a.k.a. nomofungin), Tetrahedron Letters 2003, 44, pp. 1203-1205.

May, J. A. et al., The structural and synthetic implications of the biosynthesis of the calycanthaceous alkaloids, the communesins, and nomofungin, Tetrahedron 2006, 62, pp. 5262-5271.

(56) References Cited

OTHER PUBLICATIONS

Mcmahon, VEGF receptor signaling in tumor angiogenesis. Oncologist. 2000;5 Suppl 1:3-10. doi: 10.1634/theoncologist.5-suppl_1-3. PMID: 10804084.

Medarde et al., Synthesis and antineoplastic activity of combretastatin analogues: Heterocombretastatins. Eur. J. Med. Chem., 1998; 33(1)71-77.

Medarde et al., Synthesis and pharmacological activity of combretastatin analogues. Naphthylcombretastatins and related compounds. Bioorganic. Med. Chem. Lett. 1995; 5(3):229-232.

Medarde et al., Synthesis and pharmacological activity of diarylindole derivatives. Cytotoxic agents based on combretastatins. Bioorg Med Chem Lett. Aug. 1, 1999; 9(16):2303-2308.

Medina et al., Novel antineoplastic agents with efficacy against multidrug resistant tumor cells. Bioorg Med Chem Lett. Oct. 6, 1998; 8(19):2653-6.

Michaelis, D. J. et al., Oxaziridine-mediated enantioselective aminohydroxylation of styrenes catalyzed by copper(II) bis(oxazoline) complexes, Tetrahedron 2009, 65, pp. 5118-5124.

Miknis et al., Total synthesis of (.+-.)-aspirochlorine. J. Am. Chem. Soc. 1993; 115(2):536-547.

Miller et al., Specific Inhibition of Viral Ribonucleic Acid Replication by Gliotoxin. Science Jan. 26, 1968; 159(3813):431-432.

Moody et al., Dirhodium(II) tetraacetate catalysed reactions of diazo thioamides: isolation and cycloaddition of anhydro-4-hydroxy-1,3-thiazolium hydroxides (thioisomünchnones), an approach to analogues of dehydrogliotoxin. Org. Biomol. Chem. 2003;1(15):2716-2722.

Morton, D. et al., Chiral non-racemic sulfinimines: versatile reagents for asymmetric synthesis, Tetrahedron 2006, 62, pp. 8869-8905.

Movassaghi et al., Concise total synthesis of (+)-WIN 64821 and (−)-ditryptophenaline. Angew Chem Int Ed Engl. 2008;47(8):1485-7. doi: 10.1002/anie.200704960.

Movassaghi et al., Concise total synthesis of (−)-calycanthine, (+)-chimonanthine, and (+)-folicanthine. Angew Chem Int Ed Engl. 2007;46(20):3725-8. doi: 10.1002/anie.200700705.

Movassaghi et al., Directed heterodimerization: stereocontrolled assembly via solvent-caged unsymmetrical diazene fragmentation. J Am Chem Soc. Aug. 24, 2011;133(33):13002-5. doi: 10.1021/ja2057852. Epub Aug. 1, 2011.

Movassaghi et al., Total Synthesis of All (−)-Agelastatin Alkaloids Asymmetric Synthesis Ii: More Methods and Applications. 2013;391-396. DOI: 10.1002/9783527652235.ch49.

Movassaghi et al., Total synthesis of all (−)-agelastatin alkaloids. Chem. Sci. 2010;1:561-66.

Mu et al, Synthesis, anticancer activity, and inhibition of tubulin polymerization by conformationally restricted analogues of lavendustin A. J Med Chem. Apr. 24, 2003; 46(9):1670-82.

Myers et al., A Concise, Stereocontrolled Synthesis of (−)-Saframycin A by the Directed Condensation of α-Amino Aldehyde Precursors. J Am Chem Soc. Nov. 5, 1999;121(46):10828-29.

Müllbacher et al., Structural relationship of epipolythiodioxopiperazines and their immunomodulating activity. Molec. Immunol. Feb. 1986; 23(2):231-235.

Nakada et al., The first total synthesis of the antitumor macrolide, rhizoxin. Tetrahedron Lett., 1993; 34(6):1039-1042.

Nakagawa et al., Oxidative Dimerization of Nb-Acyltryptophans Total Synthesis and Absolute Configuration of Ditryptophenaline, Tetrahedron Letters 1981, vol. 22, No. 52, pp. 5323-5326.

Nam et al., Combretastatin A-4 analogues as antimitotic antitumor agents. Curr Med Chem. Sep. 2003; 10(17):1697-722.

Nam et al., Synthesis and anti-tumor activity of novel combretastatins: combretocyclopentenones and related analogues. Bioorg Med Chem Lett. 2002; 12(15):1955-1958.

Nascimento et al., New Alkaloids from Margaritopsis carrascoana (Rubiaceae), J. Braz. Chem. Soc. 2015, vol. 26, No. 6, pp. 1152-1159.

Nelsen et al., Azocumene. I. Preparation and Decomposition of Azocumene. Unsymmetrical Coupling Products of the Cumyl Radical, Journal of the American Chemical Society, Jan. 5, 1966, 88:1, pp. 137-143.

Nelson et al., Chiral Anion Phase Transfer of Aryldiazonium Cations: An EnantioselectiveSynthesis of C3-Diazenated Pyrroloindolines, Angew. Chem. Int. Ed. 2014, 53, pp. 5600-5603.

Neuman et al., cis-Diazenes. Viscosity Effects, One-Bond Scission, and Cis-Trans Isomerization, J. Org. Chem. 1990, 55, pp. 2682-2688.

Nguyen-Hai et al., Combretoxazolones: synthesis, cytotoxicity and antitumor activity. Bioorg. Med. Chem. Lett. 2001; 11(23):3073-3076.

Nicolaou et al., A Practical Sulfenylation of 2,5-Diketopiperazines. Angem. Chem. Int. Ed. 2012; 51(3):728-732.

Nicolaou et al., Synthesis of epothilones A and B in solid and solution phase. Nature. May 15, 1997;387(6630):268-72.

Nicolaou et al., Total Synthesis of Epicoccin G. J. Am. Chem. Soc. 2011; 133(21):8150-8153.

Nielsen et al., Glycolamide Esters as Biolabile Prodrugs of Carboxylic Acid Agents: Synthesis, Stability, Bioconversion, and Physicochemical Properties. J. Pharma. Sciences. 1988; 77(4):285-298.

Nishida et al., Fungal metabolite gliotoxin targets flavocytochrome b558 in the activation of the human neutrophil NADPH oxidase. Infect Immun. Jan. 2005;73(1):235-44.

Numata, A. et al., Communesins, Cytotoxic Metabolites of a Fungus Isolated from a Marine Alga, Tetrahedron Lett. 1993, 34, pp. 2355-2358.

Oguri et al., Amino Acids and Peptides. XXIX. A New Efficient Asymmetric Synthesis of α-Amino Acid Derivatives with Recycle of a Chiral Reagent-Asymmetric Alkylation of a Chiral Schiff Base from Glycine. Chem. Pharm. Bull. 1978; 26(3):803-808.

Ohme, R. et al., Preparation of Azo Compounds from N,N'-Dialkylsulfamides, Angew. Chem. Internat. Edit. 1965, vol. 4, No. 5, p. 433.

Ohsumi et al., Novel Combretastatin Analogues Effective against Murine Solid Tumors: Design and Structure-Activity Relationships. J. Med. Chem. 1998; 41(16):3022-3032.

Ohsumi et al., Syntheses and antitumor activity of cis-restricted combretastatins: 5-membered heterocyclic analogues. Bioorg Med Chem Lett. Nov. 17, 1998; 8(22):3153-8.

Okoth et al., End-labeled amino terminated monotelechelic glycopolymers generated by ROMP and Cu(I)-catalyzed azide-alkyne cycloaddition, Beilstein J. Org. Chem. 2013, 9, 608-612.

Olsson et al., Synthesis of Potent Cytotoxic Epidithiodiketopiperazines Designed for Derivatization. J Org Chem. Apr. 3, 2020;85(7):4648-4662. doi: 10.1021/acs.joc.9b03371. Epub Mar. 19, 2020. PMID: 32126173; PMCID: PMC7127967.

Ottenheijm et al., Approaches to analogs of dehydrogliotoxin. 6. An efficient synthesis of a gliotoxin analog with anti-reverse transcriptase activity. J. Org. Chem. 1976: 41(21):3433-3438.

Overman et al., Construction of Epidithiodioxopiperazines by Directed Oxidation of Hydroxyproline-Derived Dioxopiperazines. Org. Lett. 2007; 9(25):5267-5270.

Overman et al., Direct Stereo- and Enantiocontrolled Synthesis of Vicinal Stereogenic Quaternary Carbon Centers. Total Synthesis of meso- and (−)-Chimonanthine and (+)- Calycanthine, J. Am. Chem. Soc. 1999, 121, pp. 7702-7703.

Overman et al., Enantioselective Construction of Vicinal Stereogenic Quaternary Centers by Dialkylation: Practical Total Syntheses of(+)- and meso-Chimonanthine, Angew. Chem. Int. Ed. 2000, vol. 39, No. 1, pp. 213-215.

Overman et al., Enantioselective synthesis of (−)-idiospermuline, Tetrahedron 2003, 59, pp. 6905-6919.

Overman et al., Enantioselective Total Synthesis of (+)-Gliocladin C, Org. Lett. 2007, 9(2), pp. 339-341.

Overman et al., Enantioselective Total Synthesis of the Cyclotryptamine Alkaloid Idiospermuline, Angew. Chem. Int. Ed. 2003, 42, pp. 2525-2528.

Overman et al., The cyanomethyl group for nitrogen protection and iminium ion generation in ring-enlarging pyrrolidine annulation. A

(56) References Cited

OTHER PUBLICATIONS short synthesis of the amaryllidaceae alkaloid d, 1-crinine. Tetrahedron Lett. 1982;23(27):2741-4.
Owellen et al., Inhibition of tubulin-microtubule polymerization by drugs of the Vinca alkaloid class. Cancer Res. Apr. 1976; 36(4):1499-502.
Pahl et al., The immunosuppressive fungal metabolite gliotoxin specifically inhibits transcription factor NF-kappaB. J Exp Med. Apr. 1, 1996; 183(4): 1829-1840.
Patel et al., Straightforward access to protected syn alpha-amino-beta-hydroxy acid derivatives. Angew Chem Int Ed Engl. 2008; 47(22):4224-7.
Patron et al., Origin and distribution of epipolythiodioxopiperazine (ETP) gene clusters in filamentous ascomycetes. BMC Evolutionary Biology 2007; 7:174.
Perez-Balado et al., Expedient Total Synthesis of WIN 64745 and WIN 64821, Org. Lett. 2008, vol. 10, No. 17, pp. 3701-3704.
Perez-Balado et al., Stereocontrolled and Versatile Total Synthesis of Bispyrrolidinoindoline Diketopiperazine Alkaloids: Structural Revision of the Fungal Isolate (+)-Asperdimin, Chem. Eur. J. 2009, 15, pp. 9928-9937.
Pettit et al., Antineoplastic agents 365. Dolastatin 10 SAR probes. Anticancer Drug Des. Jun. 1998; 13(4):243-77.
Pettit et al., Antineoplastic Agents, 122. Constituents of Combretum caffrum. J. Nat. Prod. 1987; 50(3):386-391.
Pettit et al., Antineoplastic agents. 113. Synthesis of natural (−)-combretastatin. J. Org. Chem. 1985; 50(18):3404-3406.
Pettit et al., Antineoplastic agents. 257. Isolation and structure of spongistatin 1. J. Org. Chem.1993; 58(6): 1302-1304.
Pettit et al., Antineoplastic Agents. 291. Isolation and Synthesis of Combretastatins A-4, A-5, and A-6. J. Med. Chem. 1995; 38(10):1666-1672.
Pettit et al., Antineoplastic Agents. 443. Synthesis of the Cancer Cell Growth Inhibitor Hydroxyphenstatin and Its Sodium Diphosphate Prodrug. J. Med. Chem. 2000; 43(14):2731- 2737.
Pettit et al., Antineoplastic agents. 487. Synthesis and biological evaluation of the antineoplastic agent 3,4-methylenedioxy-5,4'-dimethoxy-3'-amino-Z-stilbene and derived amino acid amides. J Med Chem. Feb. 13, 2003; 46(4):525-31.
Pettit et al., cation salts, combretastatin A-3, diphosphate, prodrugs. Anti-Cancer Drug Design 2000: 15(6):397-403.
Pettit et al., Isolation and structure of combretastatin. Canadian Journal of Chemistry, 1982, 60(11): 1374-137.
Pettit et al., The isolation and structure of a remarkable marine animal antineoplastic constituent: dolastatin 10. J. Am. Chem. Soc.1987; 109(22):6883-6885.
Pinedo et al., Translational Research: the role of VEGF in tumor angiogenesis. Oncologist. Jan. 2000;5:1-2.
Pinney et al., A new anti-tubulin agent containing the benzo[b]thiophene ring system. Bioorg Med Chem Lett. Apr. 19, 1999; 9(8):1081-6.
Pinney et al., Synthesis and biological evaluation of aryl azide derivatives of combretastatin A-4 as molecular probes for tubulin. Bioorg Med Chem. Oct. 2000; 8(10):2417-25.
Poisel et al., Syntheseversuche in der Reihe der 3.6-Epidithio-2.5-dioxo-piperazin-Antibiotika Gliotoxin, Sporidesmin, Aranotin und Chaetocin, II. Chem. Ber., 1971; 104(6):17141721.
Polaske et al., Enantioselective organocatalytic α-sulfenylation of substituted diketopiperazines. Tetrahedron: Asym. 2009; 20(23):2742-2750.
Porter et al., Diazenyl Radicals: A 15N CIDNP and Radical Trapping Study of Unsymmetric Diazenes, Journal of the American Chemical Society Feb. 1, 1978, 100:3, pp. 920-925.
Porter et al., Photolysis of Unsymmetric Azo Compounds. Cis Azo Compound Intermediates, Journal of the American Chemical Society Jun. 27, 1973, 95:13, pp. 4361-4367.
Pubchem CID 161244 deposited on Mar. 27, 2005, pp. 1-15.
Pubchem CID 18624123 deposited on Dec. 4, 2007, pp. 1-12.
Pubchem CID 69829071 deposited on Dec. 1, 2012, pp. 1-12.
Rao et al., Radical mediated enantioselective construction of C-1 to C-9 segment of rhizoxin. Tetrahedron Lett. 1992; 33(27):3907-3910.
Rao et al., Studies directed towards the total synthesis of rhizoxin: Stereoselective synthesis of C-12 to C-18 segment. Tetrahedron Lett. 1993; 34(4):707-710.
Rasolonjanahary et al., Psycholeine, a natural alkaloid extracted from Psychotria oleoides, acts as a weak antagonist of somatostatin, European Journal of Pharmacology 1995, 285, pp. 19-23.
Reece et al., Epidithiodiketopiperazines (ETPs) exhibit in vitro antiangiogenic and in vivo antitumor activity by disrupting the HIF-1α/p300 complex in a preclinical model of prostate cancer. Mol Cancer. Apr. 28, 2014;13:91. doi: 10.1186/1476-4598-13-91.
Rezanka et al., Pharmacologically Active Sulfur-Containing Compounds. Anti-Infect. Agents Med. Chem., 2006; 5(2):187-224.
Ried et al., Uber Synthese und Reaktionen neuer vinyloger Chlorformamidine. Liebigs Ann Chem. 1986:389-394.
Rightsel et al., Antiviral Activity of Gliotoxin and Gliotoxin Acetate. Nature. Dec. 26, 1964;204:1333-4.
Robak et al., Synthesis and Applications of tert-Butanesulfinamide, Chem. Rev. 2010, 110, pp. 3600-3637 40 (Parts 1 & 2).
Robinson et al., Calcycanthine and Calycanthidine, Chem. Ind. 1954, 27, pp. 783-784.
Rodrigues et al., Synthesis and beta-lactamase-mediated activation of a cephalosporin-taxol prodrug. Chem Biol. Apr. 1995; 2(4):223-7.
Roizen et al., Metal Catalyzed Nitrogen-Atom Transfer methods for the Oxidation of Aliphatic C—H Bonds, Accounts of Chemical Research, Jan. 10, 2012, vol. 45, No. 6, pp. 911-922.
Roizen et al., Selective Intermolecular Amination of C—H Bonds at Tertiary Carbon Centers, Angew. Chem. Int. Ed. 2013, 52, pp. 11343-11346.
Ross et al., The Chemistry of Methyl Vinyl Ketone. II. Reactions with Esters, β-Keto Esters, Malonic Ester, Amines, Tar Bases, and Inorganic Salts. J. Org. Chem. 1964; 29(8):2346-2350.
Ruff et al., Thiolation of symmetrical and unsymmetrical diketopiperazines. Org. Biomol. Chem. 2012; 10(5):935-940.
Saad et al., Biological Activities of Pyrrolidinoindoline Alkaloids from Calycodendron milnei, Planta Med. 1995, 61, pp. 313-316.
Sala et al., Tetrabutylammonium permanganate: an efficient oxidant for organic substrates. J. Chem. Soc., Chem. Commun. 1978; 253-254.
Salayova et al., Stereoselective synthesis of 1-methoxyspiroindoline phytoalexins and their amino analogues. Tetrahedron: Asymmetry. Sep. 15, 2014;24(16-17):1221-33.
Schammel et al., Exploration of the interrupted Fischer indolization reaction, Tetrahedron 2010, 66, pp. 4687-4695.
Schiff et al., Promotion of microtubule assembly in vitro by taxol. Nature. 1979; 277:665-667.
Schmidt et al., New Strategies for the Synthesis of Hexahydropyrroloindole Alkaloids Inspired by Biosynthetic Hypotheses, Synlett 2008, 3, pp. 0313-0324.
Schumacher et al., Potent Antitumor Activity of 2-Methoxyestradiol in Human Pancreatic Cancer Cell Lines. Clin. Cancer Res. 1999; 5(3):493-499.
Scott et al., Reaction Pathways in the Photochemical Conversion of Diphenylamines toCarbazoles, J. Am. Chem. Soc. 1964, 86, pp. 302-303.
Senanayake et al., Enantiopure Sulfoxides and Sulfinamides: Recent Developments in Their Stereoselective Synthesis and Applications to Asymmetric Synthesis, Aldrichim. Acta 2005, 38, pp. 93-104.
Seo, J. H. et al., Synthetic Studies on Perophoramidine and the Communesins: Construction of the Vicinal Quaternary Stereocenters, J. Org. Chem. 2006, 71, pp. 8891-8900
Sevier et al., Formation and transfer of disulphide bonds in living cells. Nat Rev Mol Cell Biol. Nov. 2002;3(11):836-47.
Shamis et al., Bioactivation of Self-Immolative Dendritic Prodrugs by Catalytic Antibody 38C2, J. Am. Chem. Soc. 2004; 126 (6):1726-1731.
Shan et al., Selective, covalent modification of B-tubulin residue Cys-239 by T138067, an antitumor agent with in vivo efficacy against multidrug-resistant tumors. Proc. Nat. Acad. Sci. USA May 11, 1999; 96(10):5686-5691.

(56) References Cited

OTHER PUBLICATIONS

Shi et al., Distinct reactivity differences of metal oxo and its corresponding hydroxo moieties in oxidations: implications from a manganese(IV) complex having dihydroxide ligand. Angew Chem Int Ed Engl. Aug. 1, 2011; 50(32):7321-4.
Shi et al., Synthesis and Reactions of 2-(Alkylthio)-4,4-dimenthyl-1,3-thiazole-5(4H)-thiones. Helvetica Chemica Acta. 1994;77:1903-1920.
Shin et al., Transition-Metal-Catalyzed C—N Bond Forming Reactions Using Organic Azides as the Nitrogen Source: A Journey for the Mild and Versatile C—H Amination. Acc. Chem. Res. 2015;48:1040-1052.
Shirai et al., Asymmetric synthesis of antimitotic combretadioxolane with potent antitumor activity against multi-drug resistant cells. Bioorg Med Chem Lett. Aug. 4, 1998; 8(15):1997-2000.
Shirai et al., Synthesis and nti-tubulin activity of aza-combretastatins. Bioorganic. Med. Chem. Lett. 1994; 4(5):699-704.
Shiraki et al., Solid-state photochemistry of crystalline pyrazolines: reliable generation and reactivity control of 1,3-biradicals and their potential for the green chemistry sysnthesis of substitutedcyclopropanes, Photochem. Photobiol. Sci. 2012, 11, pp. 1929-1937.
Shiraki et al., The synthesis and stereospecific solid-state photodecarbonylation of hexasubstituted mesa- and d,/-ketones. Photochem. Photobiol. Sci. 2011;10:1480-1487.
Singh et al., Antineoplastic agents. 166. Isolation, structure, and synthesis of combretastatin C-1. J. Org. Chem. 1989; 54(17):4105-4114.
Singh et al., Recent trends in targeted anticancer prodrug and conjugate design. Curr Med Chem. 2008;15(18):1802-26.
Snell et al., Catalytic Enantioselective Total Synthesis of Hodgkinsine B. Angew. Chem. Int. Ed. 2011;50:9116-9119.
Soledade et al., Minor phytotoxins from the blackleg fungus Phoma lingam. Phytochem. 1990; 29(3):777-782.
Solladie-Cavallo et al., A Four-Step Diastereoselective Synthesis of D-erythro-Sphingosine by an Enantioselective Aldol Reaction Using a Titanium Enolate Derived from a Chiral Iminoglycinate. J. Org. Chem. 1994; 59(11):3240-3242.
Solladie-Cavallo et al., A four-step synthesis of erythro-m-chloro-3-hydroxytyrosine ethyl ester enantiomerically pure. Tetrahedron Lett., 1998; 39(15):2191-2194.
Solladie-Cavallo et al., Diastereoselective monoalkylation of lithium and potassium enolates of a chiral imine of ethyl glycinate: the role of added salts. Organometallics1993; 12(9):3743-3747.
Solladie-Cavallo et al., Enantioselective synthesis of optically pure natural S(+) or unnatural R(-) DABA. Tetrahedron Lett. 1989;30(44):6011-6014.
Somei et al., A novel reductive amino-cyclization method and its application for the total syntheses of (±)-aurantio-clavine and (±)-lophocerine, Heterocycles 2007, 7 4, pp. 943-950.
Somei et al., Preparations of melatonin and 1-hydroxymelatonin, and its novel nucleophilicdimerization to (±)-3a,3a'-bispyrrolo[2,3-b]indoles. Heterocycles. 1999;51(6):1237-1242.
Speth et al., Gliotoxin as putative virulence factor and immunotherapeutic target in a cell culture model of cerebral aspergillosis. Mol Immunol. Sep. 2011;48(15-16):2122-9.
Springer et al., The structure of ditryptophenaline—a new metabolite of aspergillusflavus. Tetrahedron Lett. 1977: 18(28):2403-2406.
Steininger, Synthesis of 5-Chloromethyl-2,dinitrotetrahydrofuran. Angew. Chem. Internat. Edit.1965;4(5):433.
Stephens et al., Straightforward Access to Hexahydropyrrolo[2,3-b]indole Core by aRegioselective C3-Azo Coupling Reaction of Arenediazonium Compounds with Tryptamines, Eur. J. Org. Chem. 2014, pp. 3662-3670.
Steven et al., Total Synthesis of Complex Cyclotryptamine Alkaloids: Stereocontrolled Construction of Quaternary Carbon Stereocenters, Angew. Chem. Int. Ed. 2007, 46, pp. 5488-5508.
Stork, The stereospecific synthesis of reserpine. Pure Appl Chem. 1989;61(3):439-42.
Storm et al., Effect of small changes in orientation on reaction rate. J. Am. Chem. Soc. 1972; 94(16):5815-5825.
Stout et al., Potent Fluorinated Agelastatin Analogues for Chronic Lymphocytic Leukemia: Design, Synthesis, and Pharmacokinetic Studies, J. Med. Chem., 57, p. 5085-5093 (2014).
Strassner et al., Mechanism of Permanganate Oxidation of Alkanes: Hydrogen Abstraction and Oxygen "Rebound" J. Am. Chem. Soc. 2000; 122(32):7821-7822.
Stueber et al., Carbonates, Thiocarbonates, and the Corresponding Monoalkyl Derivatives. 1. Their Preparation and Isotropic 13C NMR Chemical Shifts. Inorg. Chem. 2001; 40(8):1902-1911.
Suetsugu et al., Asymmetric Synthesis of (−)-Aurantioclavine via Palladium-CatalyzedIntramolecular Allylic Amination, Org. Lett. 2014, 16, pp. 996-999.
Sugiyama et al., Syntheses of four unusual amino acids, constituents of cyclomarin A. Tetrahedron Lett. 2002: 43(19):3489-2492.
Sumiyoshi et al., Laser Flash Photolysis of Azocumenes. Direct Observation of StepwiseDecomposition, Bull. Chem. Soc. Jpn. 1987, 60, pp. 77-81.
Sun et al., Construction of 3-oxyindoles via hypervalent iodine mediated tandem cyclization-acctoxylation of o-acyl anilines. Chem Commun. 2010;46(36):6834-6.
Sun et al., Enabling ScFvs as multi-drug carriers: A dendritic approach, Bioorganic & Medicinal Chemistry Letters 2003; 11:1761-1768.
Sun et al., Syntheses of Dendritic Linkers Containing Chlorambucil Residues for the Preparation of Antibody-Multidrug Immunoconjugates, Bioorganic & Medicinal Chemistry Letters 2002; 12:2213-2215.
Szalai et al., Geometric disassembly of dendrimers: dendritic amplification. J Am Chem Soc. Dec. 24, 2003;125(51):15688-9.
Tadano et al., Bio-Inspired Dimerization Reaction of Tryptophan Derivatives in Aqueous AcidicMedia: Three-Step Syntheses of (+)-WIN 64821, (−)-Ditryptophenaline, and (+)-Naseseazine B. Angew. Chem. Int. Ed. 2013;52:7990-7994.
Takahashi et al., Inhibition of histone H3K9 methyltransferases by gliotoxin and related epipolythiodioxopiperazines. J Antibiot (Tokyo). May 2012;65(5):263-5.
Teng et al., Unnatural enantiomer of chaetocin shows strong apoptosis-inducing activity through caspase-8/caspase-3 activation. Bioorg. Med. Chem. Lett. 2010; 20(17):5085-5088.
Teniou et al., (+)(1R,2R,5R) 2-Hydroxy-3-pinanone as Chiral Auxiliary in Erythro-selective Aldol Reactions. Asian J Chem. 2006; 18:2487-2490.
Tibodeau et al., The anticancer agent chaetocin is a competitive substrate and inhibitor of thioredoxin reductase. Antioxid Redox Signal. May 2009; 11(5):1097-106.
Tilvi et al., Agelastatin E, Agelastatin F, and Benzosceptrin C from the Marine Sponge Agelas dendromorpha, J. Nat. Prod., 73, p. 720-723 (2010).
Timberlake et al., Thiadiaziridine 1, 1-Dioxides: Synthesis and Chemistry. J. Org. Chem. 1981;46:2082-2089.
Toki et al., Protease-Mediated Fragmentation of p-Amidobenzyl Ethers: A New Strategy for the Activation of Anticancer Prodrugs. J. Org. Chem. 2002; 67(6):1866-1872.
Trail et al., Cure of xenografted human carcinomas by BR96-doxorubicin immunoconjugates. Science Jul. 9, 1993; 261(5118):212-215.
Trail et al., Effect of Linker Variation on the Stability, Potency, and Efficacy of Carcinoma-reactive BR64-Doxornbicin Immunoconjugates. Cancer Research 1997; 57:100-105.
Traunecker et al., Bispecific single chain molecules (Janusins) target cytotoxic lymphocytes on HIV infected cells. EMBO J. Dec. 1991; 10(12): 3655-3659.
Trost et al., Recent Advances on the Total Syntheses of Communesin Alkaloids andPerophoramidine, Chem. Eur. J. 2015, 21, pp. 16318-16343.
Trown, P.W, Antiviral activity of N, N'-dimethyl-epidithiapiperazinedione, a synthetic compound related to the gliotoxins, LL-S88alpha and beta, chetomin and the sporidesmins. Biochem Biophys Res Commun. Nov. 8, 1968;33(3):402-7.
Tsuji et al., Diazenes. VI. Alkyldizenes, Journal of the American Chemical Society 1971, 93(8), pp. 1992-1999.
Uckun et al., Structure-based design of a novel synthetic spiroketal pyran as a pharmacophore for the marine natural product spongistatin 1. Bioorg Med Chem Lett. Mar. 20, 2000; 10(6):541-5.

(56) References Cited

OTHER PUBLICATIONS

Uraguchi et al., Catalytic Asymmetric Oxidation of N-Sulfonyl I mines with HydrogenPeroxide-Trichloroacetonitrile System, J. Am. Chem. Soc. 2013, 135, pp. 8161-8164.
Usami et al., Gliocladins A-C and Glioperazine; Cytotoxic Dioxo- or Trioxopiperazine Metabolites from a *Gliocladium* Sp. Separated from a Sea Hare. Heterocycles 2004; 63(5):2004:1123-1129.
Verbitski et al., Isolation, Structure Determination, and Biological Activity of a Novel Alkaloid, Perophoramidine, from the Philippine Ascidian Perophora namei, J. Org. Chem. 2002, 67, pp. 7124-7126.
Verdier-Pinard et al., A Steroid Derivative with Paclitaxel-Like Effects on Tubulin Polymerization. Molecular Pharmacology Mar. 2000: 57(3):568-575.
Verdier-Pinard et al., Biosynthesis of radiolabeled curacin A and its rapid and apparently irreversible binding to the colchicine site of tubulin. Arch Biochem Biophys. Oct. 1, 1999; 370(1):51-8.
Verotta et al., Pyrrolidinoindoline Alkaloids from Psychotria colorata, J. Nat. Prod. 1998, 61, pp. 392-396.
Verotta et al., Synthesis and Antinociceptive Activity of Chimonanthines and Pyrrolidinoindoline-Type Alkaloids, Bioorganic & Medicinal Chemistry 2002, 10, pp. 2133-2142.
Vingushin et al., Gliotoxin is a dual inhibitor of farnesyltransferase and geranylgeranyltransferase I with antitumor activity against breast cancer in vivo. Med Oncol. 2004;21(1):21-30.
Walker et al., A High Yielding Synthesis of N-Alkyl Maleimides Using a Novel Modification of the Mitsunobu Reaction. J. Org. Chem., 1995; 60(16):5352-5355.
Wang et al., Potent, Orally Active Heterocycle-Based Combretastatin A-4 Analogues: Synthesis, Structure-Activity Relationship, Pharmacokinetics, and In Vivo Antitumor Activity Evaluation. J. Med. Chem. 2002; 45(8):1697-1711.
Wang et al., Synthesis of B-ring homologated estradiol analogues that modulate tubulin polymerization and microtubule stability. J Med Chem. Jun. 15, 2000; 43(12):2419-29.
Wantanabe et al., Reaction of 1-Acyl and Aroyl-2-hydroxy-3,3-dimethylindolines with Arylamines Catalyzed by BF3. Etherate. Formation of Dihydroindolo[1,2-c]quinazoline. Heterocycles. 2007;71(2):343-59.
Waring et al., Gliotoxin and related epipolythiodioxopiperazines. Gen Pharmacol. Dec. 1996;27(8):1311-6.
Waring et al., The chemistry and biology of the immunomodulating agent gliotoxin and related epipolythiodioxopiperazines. Med Res Rev. Oct.-Dec. 1988;8(4):499-524.
Wen et al., Synthesis of a fully protected (2S,3R)-N-(1',1'-dimethyl-2'-propenyl)-3-hydroxytryptophan from tryptophan. Tetrahedron Lett. 2002: 43(30):5291-5294.
Wen et al., Total Synthesis of Cyclomarin C. Org. Lett. 2004; 6(16):2721-2724.
Wender et al., Practical Synthesis of Prostratin, OPP, and Their Analogs, Adjuvant Leads Against Latent HIV, Science May 8, 2008, 320(5876), pp. 649-652.
Wenkert et al., Five-membered aromatic heterocycles as dienophiles in Diels-Alder reactions. Furan, pyrrole, and indole. J. Am. Chem. Soc. 1988; 110(21):7188-7194.
White et al., Concise Total Syntheses of (+)-Haplocidine and (+)-Haplocine Via Late-StageOxidation of (+)-Fendleridine Derivatives, J. Am. Chem. Soc. 2016, 138(35), pp. 11383-11389.
Wigley, L. J. et al., Natural and directed biosynthesis of communesin alkaloids, Phytochemistry 2006, 67, pp. 561-569.
Williams et al., Divergent, generalized synthesis of unsymmetrically substituted 2,5-piperazinediones. J. Am. Chem. Soc. 1985; 107(11):3246-3253.
Williams et al., Syntheses of the fungal metabolites (.+−.)-gliovictin and (.+−−.)-hyalodendrin. J. Org. Chem. 1980; 45(13):2625-2631.
Williamson et al., Iron Catalyzed Asymmetric Oxyamination of Olefins, J. Am. Chem. Soc. 2012, 134, pp. 12370-12373.
Williamson et al., Iron-Catalyzed Aminohydroxylation of Olefins, J. Am. Chem. Soc. 2010, 132, pp. 4570-4571.
Woods et al., The interaction with tubulin of a series of stilbenes based on combretastatin A-4. Br J Cancer. Apr. 1995; 71(4):705-11.
Woodward et al., Calycanthine: The Structure of the Alkaloid and its Degradation Product, Calycanine, Proc. Chem. Soc. 1960, pp. 76-78.
Wu-Wong et al., Identification and Characterization of A-105972, an Antineoplastic Agent. Cancer Res. 2001; 61:1486-1492.
Xie et al., Highly Enantioselective Bromocyclization of Tryptamines and Its Application in theSynthesis of(−)-Chimonanthine, Angew. Chem. Int. Ed. 2013, 52, pp. 12924-12927.
Xu et al., Iridium(III)-Catalyzed Regioselective C7-Amination of N-Pivaloylindoles with Sulfonoazides, J. Org. Chem. 2016, 81, pp. 10476-10483.
Xu et al., Studies on the Alkaloids of the Calycanthaceae and Their Syntheses, Molecules 2015, 20, pp. 6715-6738.
Xu et al., Total Synthesis of Clavicipitic Acid and Aurantioclavine: Stereochemistry of Clavicipitic Acid Revisited, J. Org. Chem. 2010, 75, pp. 7626-7635.
Yamada et al., A Total and Practical Synthesis of Ergot Alkaloid, (±)-Aurantioclavine, Chem. Pharm. Bull. 1985, 33, pp. 2162-2163.
Yamada et al., Concise Synthesis of (±)-Aurantioclavine through a Base-Promoted Pictet-Spengler Reaction, Eur. J. Org. Chem. 2009, pp. 5752-5759.
Yanagihara et al., Leptosins isolated from marine fungus Leptoshaeria species inhibit DNA topoisomerases I and/or II and induce apoptosis by inactivation of Akt/protein kinase B. Cancer Sci. Nov. 2005;96(11):816-24.
Yang et al., Total Synthesis of (±)-Communesin F, J. Am. Chem. Soc. 2007, 129, pp. 13794-13795.
Yano et al., Chetomin induces degradation of XIAP and enhances TRAIL sensitivity in urogenital cancer cells. Int J Oncol. Feb. 2011;38(2):365-74.
Yu et al., A General Strategy for the Synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinoll. J Org Chem. Apr. 19, 2005;70(10):3963-79.
Yu et al., A new epipolythiodioxopiperazine with antibacterial and cytotoxic activities from the endophytic fungus *Chaetomium* sp. M336. Nat Prod Res. 2018;32(6):689-694. doi:10.1080/14786419.2017.1338285.
Yu et al., Stereocontrolled Total Synthesis of (−)-Vincamajinine and (−)-11-Methoxy-17-epivincamajine. J Am Chem Soc. Jan. 21, 2004;126(5):1358-9.
Zalatan et al., Metal-Catalyzed Oxidations of C—H to C—N Bonds, Top. Curr. Chem. 2010, 292, pp. 347-378.
Zalatan et al., Understanding the Differential Performance of Rh2(esp)2 as a Catalyst for C—H Amination, J. Am. Chem. Soc. 2009, 131, pp. 7558-7559.
Zhang et al., Microtubule effects of welwistatin, a cyanobacterial indolinone that circumvents multiple drug resistance. Molecular Pharmacology Feb. 1996; 49(2):288-294.
Zheng et al., Bionectins A-C, Epidithiodioxopiperazines with Anti-MRSA Activity, from Bionectra byssicola F120, J. Nat. Prod., 2006, 69 (12), pp. 1816-1819.
Zhou et al., Recent advances in asymmetric reactions using sulfinimines (N-sulfinyl imines), Tetrahedron 2004, 60, pp. 8003-8030.
Zhu et al., Aptamer-Drug Conjugates. Bioconjug Chem. Nov. 18, 2015;26(11):2186-97. doi: 10.1021/acs.bioconjchem.5b00291. Epub Jul. 14, 2015.
Zuo, Z. et al., Enantioselective Total Syntheses of Communesins A and B, Angew. Chem. Int. Ed. 2011, 50, pp. 12008-12011.
Zuo, Z. et al., Total Synthesis and Absolute Stereochemical Assignment of (−)-Communesin F, J. Am. Chem. Soc. 2010, 132, pp. 13226-13228.

* cited by examiner

COMPOUNDS, CONJUGATES, AND COMPOSITIONS OF EPIPOLYTHIODIKETOPIPERAZINES AND POLYTHIODIKETOPIPERAZINES AND USES THEREOF

RELATED APPLICATIONS

The present application is a division of U.S. patent application U.S. Ser. No. 16/839,064, filed Apr. 2, 2020, which claims priority under 35 U.S.C. § 119(e) to U.S. provisional application, U.S. Ser. No. 62/857,716, filed Jun. 5, 2019, each of which is incorporated herein by reference.

GOVERNMENT SUPPORT

This invention was made with Government support under Grant No. R01 GM089732 awarded by the National Institutes of Health (NIH). The Government has certain rights in the invention.

BACKGROUND

Epipolythiodiketopiperazine (ETP) alkaloids comprise a structurally diverse and biologically active family of fungal metabolites characterized by a polysulfide bridged 2,5-diketopiperazine moiety.[1,2] These natural products have demonstrated potent biological activities including anticancer, antibacterial, and antiviral properties,[3] and thus have attracted considerable interest from synthetic chemists.[4,5] While the mode of action of these compounds is still not precisely understood, several studies have unequivocally demonstrated the central role of the polysulfide bridge for bioactivity.[3h,i] Recently, an extensive SAR study of 60 structurally diverse natural and synthetic pyrroloindoline-containing ETP derivatives for cytotoxic activity against multiple human cancer cell lines was reported.[3p] These experiments identified several subsets of natural and unnatural monomeric and dimeric ETPs exhibiting $IC_{50}$ values in the low to (sub)nanomolar range (FIG. 1).[3p] To further enable exploration of the translational potential of ETPs, it was sought to gain access to functionalized ETPs containing conjugatable chemical handles. A robust means to derivatize ETPs through conjugation chemistry would for the first time permit evaluation of these biologically potent compounds in many new contexts.

SUMMARY

In one aspect, the present disclosure provides derivatized ETP compounds. These compounds may be biologically active and used to treat and prevent diseases. In some aspects, the derivative ETP compounds may improve the delivery of the compound, or a fragment thereof, to a subject, cell, tissue, or biological sample. The compounds may be advantageous over known ETP compounds for treating or preventing diseases. In another aspect, the present disclosure provides compositions, kits, methods of preparation, and methods of treating or preventing a disease.

In some aspects, the present disclosure describes the design and synthesis of derivatized ETPs possessing a chemical handle for conjugation to a desired coupling partner.[6] Copper(I)-catalyzed azide-alkyne cycloaddition (CuAAC) reactions of azido ETPs proceed smoothly even in the presence of the highly sensitive epidisulfide functionality. Furthermore, the disclosure details the nanomolar cytotoxic activities of derivatized ETPs across human cancer cell lines.

A first aspect of the disclosure is directed to compounds of the formula:

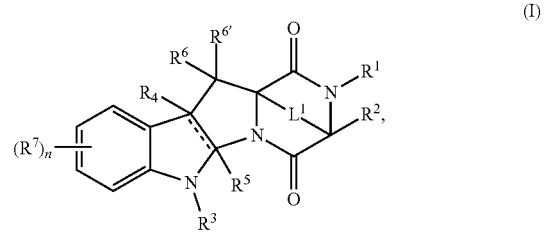

(I)

or a salt thereof, wherein at least one instance of $R^1$, $R^3$, and $R^4$ comprises R wherein R is -$L^2$-$R^H$-$L^3$-D. $R^1$, $R^2$, $R^3$, $R^4$, $R^5$, $R^6$, $R^{6'}$, $R^7$, R, $R^H$, $L^1$, $L^2$, L, D, ═, and n are as described herein.

In some aspects of the present disclosure is directed to compounds of the formula:

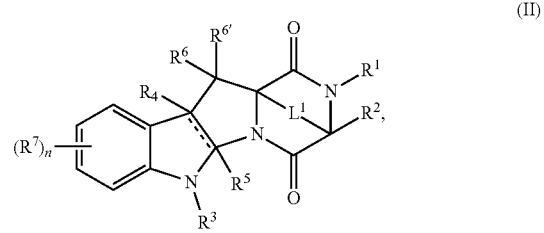

(II)

or a salt thereof, wherein at least one instance of $R^1$, $R^3$, and $R^4$ comprises R wherein R is -$L^2$-$R^{H1}$. $R^1$, $R^2$, $R^3$, $R^4$, $R^5$, $R^6$, $R^{6'}$, $R^7$, $R^{H1}$, $L^1$, $L^2$, ═, and n are as described herein.

Also provided herein, are methods of making a compound of Formula (I) comprising reacting a compound of Formula (II), or a salt thereof, with a compound of Formula (III):

$R^{H2}$-$L^3$-D (III), or a salt thereof, wherein $R^{H2}$, $L^3$, and D are as described herein.

In another aspect, the disclosure is directed to compounds of the formula:

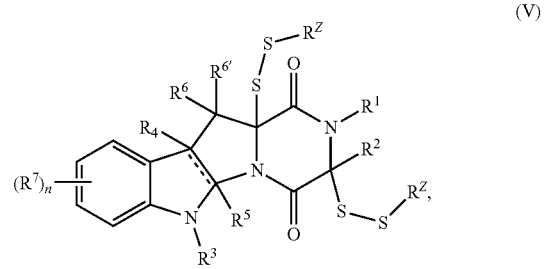

(V)

or a salt thereof, wherein $R^1$, $R^2$, $R^3$, $R^4$, $R^5$, $R^6$, $R^{6'}$, $R^7$, $R^Z$, ═, and n are as described herein.

Exemplary compounds of Formula (I) are of the formula:

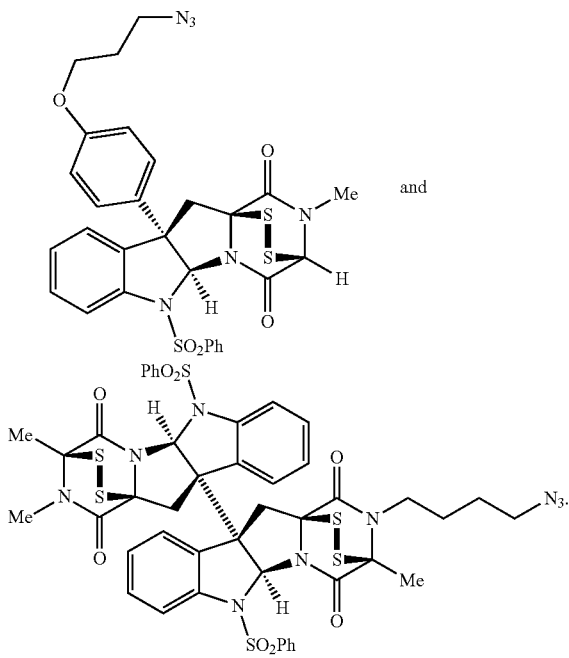

and

In certain aspects, the disclosure provides compositions comprising a compound as described herein, or a salt thereof, and optionally an excipient.

Further provided are kits comprising a compound as described herein, or a salt thereof, or composition as described herein; and instructions for using the compound, or a salt thereof, or the composition.

The present disclosure further provides methods of treating a disease in a subject in need thereof, the method comprising administering to the subject in need thereof a therapeutically effective amount of a compound as described herein, or a salt thereof, or a composition as described herein. In some embodiments, a disease is a cancer, autoimmune disease or infectious disease. In some embodiments, a disease is cancer. In some embodiments, a disease is an autoimmune disease. In some embodiments, a disease is an infectious disease. In some embodiments, a provided compound is a compound of formula I. In some embodiments, a provided compound is a compound of formula II. In some embodiments, a provided compound is a compound of formula V.

In some embodiments, the present disclosure provides methods for inducing apoptosis of a cell, a cell in a subject, a cell in a tissue, or a cell in biological sample. In some embodiments, the present disclosure provides methods for inhibiting proliferation of a cell, a cell in a subject, a cell in a tissue, or a cell in biological sample. In some embodiments, the present disclosure provides methods for generating reactive oxygen species in a subject, cell, tissue, or biological sample. In some embodiments, the present disclosure provides methods for inhibiting a protein in a subject, cell, tissue, or biological sample. In some embodiments, the present disclosure provides methods for disrupting structures of proteins containing a $Zn^{2+}$ in a subject, cell, tissue, or biological sample. In some embodiments, a provided compound is a compound of formula I. In some embodiments, a provided compound is a compound of formula II. In some embodiments, a provided compound is a compound of formula V.

In another aspect, the present disclosure provides compounds of Formula (X):

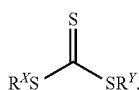

(X)

or salt thereof, wherein $R^X$ and $R^Y$ are defined herein. Also provided herein are methods of cyclization using compounds of Formula (X), which may be employed in the synthesis of derivatized ETPs.

Further provided herein are methods of generating a substituted or unsubstituted dihydroxypiperazinedione, or salt thereof, comprising reacting a substituted or unsubstituted piperazinedione, or salt thereof, with bis(2,2'-bipyridyl)copper(II) permanganate, which may be used in the synthesis of derivatized ETPs.

The details of certain embodiments of the disclosure are set forth in the Detailed Description of Certain Embodiments, as described below. Other features, objects, and advantages of the disclosure will be apparent from the Definitions, Figures, Examples, and Claims. It should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Definitions

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 93$^{rd}$ Ed. Additionally, general principles of organic chemistry are described in "Organic Chemistry", 2$^{nd}$ Ed, Thomas N. Sorrell, University Science Books, Sausalito: 2005, and "March's Advanced Organic Chemistry", 6$^{th}$ Ed., Smith, M. B. and March, J., John Wiley & Sons, New York: 2007, the entire contents of which are hereby incorporated by reference.

For convenience, certain terms employed herein, in the specification, examples and appended claims are collected herein.

Unless otherwise required by context, singular terms shall include pluralities, and plural terms shall include the singular.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, Some Modern Methods of Organic Synthesis, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation, but which is not aromatic (also referred to herein as "carbocycle," "cycloaliphatic" or "cycloalkyl"), that has, unless otherwise specified, a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The term "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_5$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_3$-$C_{20}$ for branched chain), and alternatively, about 1-10. In some embodiments, a cycloalkyl ring has from about 3-10 carbon atoms in their ring structure where such rings are monocyclic, bicyclic or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls). The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

As used herein, the term "alkenyl" refers to an alkyl group, as defined herein, having one or more double bonds. The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$, 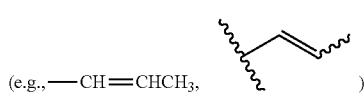)

may be in the (E)- or (Z)-configuration.

As used herein, the term "alkynyl" refers to an alkyl group, as defined herein, having one or more triple bonds. The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" is given its ordinary meaning in the art and refers to alkyl groups as described herein in which at least one carbon atom, optionally with one or more attached hydrogen atoms, is replaced with a heteroatom (e.g., oxygen, nitrogen, sulfur, phosphorus, selenium, boron and the like). Examples of heteroalkyl groups include, but are not limited to, alkoxy, poly(ethylene glycol)-, alkyl-substituted amino, tetrahydrofuranyl, piperidinyl, morpholinyl, etc. In some embodiments, a heteroatom may be oxidized (e.g., —S(O)—, —S(O)$_2$—, —N(O)—, —P(O)— and the like). The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and 1 or more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and 1 or more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, and sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("heteroC$_1$-C$_{1000}$ alkenyl"), 1 to 900 carbon atoms and 1 or more heteroatoms within the parent chain ("heteroC$_1$-C$_{900}$ alkenyl"), 1 to 800 carbon atoms and 1 or more heteroatoms within the parent chain ("heteroC$_1$-C$_{800}$ alkenyl"), 1 to 700 carbon atoms and 1 or more heteroatoms within the parent chain ("heteroC$_1$-C$_{700}$ alkenyl"), 1 to 600 carbon atoms and 1 or more heteroatoms within the parent chain ("heteroC$_1$-C$_{600}$ alkenyl"), 1 to 500 carbon atoms and 1 or more heteroatoms within the parent chain ("heteroC$_1$-C$_{500}$ alkenyl"), 1 to 400 carbon atoms and 1 or more heteroatoms within the parent chain ("heteroC$_1$-C$_{400}$ alkenyl"), 1 to 300 carbon atoms and 1 or more heteroatoms within the parent chain ("heteroC$_1$-C$_{300}$ alkenyl"), 1 to 200 carbon atoms and 1 or more heteroatoms within the parent chain ("heteroC$_1$-C$_{200}$ alkenyl"), or 1 to 100 carbon atoms and 1 or more heteroatoms within the parent chain ("heteroC$_1$-C$_{100}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl" refers to an alkynyl group, which further includes at least one heteroatom (e.g., 1, 2, 3, or 4 heteroatoms) selected from oxygen, nitrogen, and sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("heteroC$_1$-C$_{1000}$ alkynyl"), 1 to 900 carbon atoms and 1 or more heteroatoms within the parent chain ("heteroC$_1$-C$_{900}$ alkynyl"), 1 to 800 carbon atoms and 1 or more heteroatoms within the parent chain ("heteroC$_1$-C$_{800}$ alkynyl"), 1 to 700 carbon atoms and 1 or more heteroatoms within the parent chain ("heteroC$_1$-C$_{700}$ alkynyl), 1 to 600 carbon atoms and 1 or more heteroatoms within the parent chain ("heteroC$_1$-C$_{600}$ alkynyl"), 1 to 500 carbon atoms and 1 or more heteroatoms within the parent chain ("heteroC$_1$-C$_{500}$ alkynyl"), 1 to 400 carbon atoms and 1 or more heteroatoms within the parent chain ("heteroC$_1$-C$_{400}$ alkynyl"), 1 to 300 carbon atoms and 1 or more heteroatoms within the parent chain ("heteroC$_1$-C$_{300}$ alkynyl"), 1 to 200 carbon atoms and 1 or more heteroatoms within the parent chain ("heteroC$_1$-C$_{200}$ alkynyl"), or 1 to 100 carbon atoms and 1 or more heteroatoms within the parent chain ("heteroC$_1$-C$_{100}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted. The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" and "triazolylene" refer to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of boron, oxygen, sulfur, selenium, nitrogen, phosphorus, or silicon (including, any oxidized form of nitrogen, sulfur, selenium, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety (e.g., carbocyclene refers to a carbocyclic ring which is bivalent (e.g., $C_6$ alkyl-carbocyclyl-$C_6$ alkyl)).

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —NH$_2$.

As described herein, compounds of the disclosure may contain "optionally substituted" moieties. In general, the term "substituted," whether preceded by the term "optionally" or not, means that one or more hydrogen atoms of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —(CH$_2$)$_{0-4}$SR$^\circ$; —(CH$_2$)$_{0-4}$S(O)R$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR; —SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —P(O)(OR$^\circ$)R$^\circ$; —P(O)(OR$^\circ$)$_2$; —OP(O)R$^\circ$$_2$; —OP(O)(OR$^\circ$)R$^\circ$; —OP(O)(OR$^\circ$)$_2$; —PR$^\circ$$_2$; —P(OR$^\circ$)R$^\circ$; —P(OR$^\circ$)$_2$; —OPR$^\circ$$_2$; —OP(OR$^\circ$)R$^\circ$; —OP(OR$^\circ$)$_2$; —SiR$^\circ$$_3$; —OSiR$^\circ$$_3$; —SeR$^\circ$; —(CH$_2$)$_{0-4}$SeSeR$^\circ$; —B(R$^\circ$)$_2$, —B(OR$^\circ$)$_2$, —(C$_{1-4}$ straight or branched alkylene)O—N(R$^\circ$)$_2$; or —(C$_{1-4}$ straight or branched alkylene)C(O)O—N(R$^\circ$)$_2$; wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R$^\circ$, taken together with their intervening atom(s), form a 3-12-membered saturated, partially unsaturated, or aryl mono- or bicyclic ring having 0-6 heteroatoms independently selected from nitrogen, oxygen, and sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a suitable carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the carbon atom substituents are independently halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, or 5-14 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$. Each instance of R$^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{dd}$ groups;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, or two R$^{ff}$ groups are joined to form a 3-10 membered heterocyclyl or 5-10 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC (=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP (=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, or 5-10 membered heteroaryl; or two geminal R$^{gg}$ substituents can be joined to form =O or =S;

each instance of X$^-$ is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted C$_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC (CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, P$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "chiral" is given its ordinary meaning in the art and refers to a molecule that is not superimposable with its mirror image, wherein the resulting non-superimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, the term "electron-withdrawing group" is given its ordinary meaning in the art and refers to an atom or group that draws electron density from a neighboring atom or group, usually by resonance and/or inductive effects. In some embodiments, an electron-withdrawing group withdraws electron density from an aromatic ring system by resonance and/or inductive effects. In some embodiments, an electron-withdrawing group withdraws electron density from an aromatic ring system by resonance and inductive effects. In some embodiments, an electron-withdrawing group lowers the electron density of an aromatic ring system such as phenyl. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —NO$_2$, —S(O)— moieties, —P(O)— moieties and —S(O)$_2$— moieties. In some embodiments, an electron-withdrawing group comprises one or more —C(O)—, —C(=N—)-, —C(S)—, —S(O)—, —S(O)$_2$— or —P(O)— groups, and is connected to the rest of a molecule via one or more —C(O)—, —C(=N—)—, —C(S)—, —S(O)—, —S(O)$_2$— or —P(O)— groups. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I. In some embodiments, hydrogen is used as reference and regarded as having no effect.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N—[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, 0-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyl-oxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

"Click chemistry" refers to a chemical approach to conjugation introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition reactions); and Diels-Alder reactions (e.g., tetrazine [4+2] cycloaddition). Examples of click chemistry reactions and click-chemistry handles can be found in, e.g., Kolb, H. C.; Finn, M. G. and Sharpless, K. B. *Angew. Chem. Int. Ed.* 2001, 40, 2004-2021. Kolb, H. C. and Sharless, K. B. *Drug Disc. Today*, 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al., *J. Am. Chem. Soc.* 2003, 125, 3192-3193; Lee, L. V. et al., *J. Am. Chem. Soc.* 2003

125, 9588-9589; Lewis, W. G. et al., *Angew. Chem. Int. Ed.* 2002, 41, 1053-41057; Manetsch, R. et al., *J. Am. Chem. Soc.* 2004, 126, 12809-12818; Mocharla, V. P. et al., *Angew. Chem., Int. Ed.* 2005, 44, 116-120.

Any methods known in the art of bioconjugation can be used (e.g., click chemistry reactions) to generate a compound of Formula (I). In certain embodiments, a compound of Formula (I) comprises a polymeric moiety, dendrimeric moiety, antibody, particle, bead, nanostructure, liposome, micelle, or vesicle. The polymeric moiety, dendrimeric moiety, antibody, particle, bead, nanostructure, liposome, micelle, or vesicle may aid in the delivery of therapeutically effective ETPs. For example, a polymeric moiety, dendrimeric moiety, antibody, particle, bead, nanostructure, liposome, micelle, or vesicle may comprise a click chemistry handle, which can react with an orthogonal click chemistry handle on a functionalized ETP (e.g., a compound of Formula (II)), thereby covalently linking the two fragments. In certain embodiments, one or more instances of a polymeric moiety, dendrimeric moiety, antibody, particle, bead, nanostructure, liposome, micelle, or vesicle are conjugated to the targeting agent via click chemistry. In certain embodiments, the linker comprises a moiety derived from a click chemistry reaction (e.g., triazole, diazole, diazine, sulfide bond, maleimide ring, succinimide ring, ester, amide). In certain embodiments, click-chemistry may be useful for introducing a reaction handle (e.g., a reaction handle that is not azide, alkenyl, and/or alkynyl) for subsequent reactions (e.g., conjugation or functionalization). In certain embodiments, click-chemistry may be useful for introducing —$NH_2$, mono-substituted amino, —OH, carboxyl, aldehyde, thiol, O-alkyl hydroxyl amino, alkenyl, or alkynyl for subsequent reactions. In certain embodiments, click-chemistry may be useful for introducing —$NH_2$ for subsequent reactions.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this disclosure. Such compounds are useful, for example, as analytical tools or probes in biological assays.

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

The term "administer," "administering," or "administration" refers to implanting, absorbing, ingesting, injecting, inhaling, or otherwise introducing a compound described herein, or a composition thereof, in or on a subject.

The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The terms "composition" and "formulation" are used interchangeably.

As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+($C_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N+($C_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A general, a "prodrug," as that term is used herein and as is understood in the art, is an entity that, when administered to an organism, is metabolized in the body to deliver an active (e.g., therapeutic or diagnostic) agent of interest. Typically, such metabolism involves removal of at least one "prodrug moiety" so that the active agent is formed. Various forms of "prodrugs" are known in the art. For examples of such prodrug moieties, see:

a) *Design of Prodrugs*, edited by H. Bundgaard, (Elsevier, 1985) and *Methods in Enzymology*, 42:309-396, edited by K. Widder, et al. (Academic Press, 1985);
b) *Prodrugs and Targeted Delivery*, edited by by J. Rautio (Wiley, 2011);
c) *Prodrugs and Targeted Delivery*, edited by by J. Rautio (Wiley, 2011);
d) A Textbook of Drug Design and Development, edited by Krogsgaard-Larsen;
e) Bundgaard, Chapter 5 "Design and Application of Prodrugs", by H. Bundgaard, p. 113-191 (1991);
f) Bundgaard, *Advanced Drug Delivery Reviews*, 8:1-38 (1992);
g) Bundgaard, et al., *Journal of Pharmaceutical Sciences*, 77:285 (1988); and
h) Kakeya, et al., *Chem. Pharm. Bull.*, 32:692 (1984).

As with other compounds described herein, prodrugs may be provided in any of a variety of forms, e.g., crystal forms, salt forms etc. In some embodiments, prodrugs are provided as pharmaceutically acceptable salts thereof.

As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain l-amino acids, d-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition. In some embodiments, a subject is human. A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

An individual who is "suffering from" a disease, disorder, and/or condition has been diagnosed with and/or displays one or more symptoms of a disease, disorder, and/or condition An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The phrases "systemic administration," "administered systemically," "peripheral administration," and "administered peripherally" as used herein have their art-understood meaning referring to administration of a compound or composition such that it enters the recipient's system.

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compounds, conjugates, or particles disclosed herein comprise an agent(s), e.g., a first therapeutic agent (e.g., at least one (including, e.g., at least two, at least three). In some embodiments, the compositions (e.g., compounds, conjugates, or particles) can further comprise a second therapeutic agent, a targeting moiety, a diagnostic moiety, e.g., as described herein. The agent(s) can be coupled to the conjugate or particle. In other embodiments, the agent(s) can be associated with a conjugate or particle. In some embodiments, a first agent can be coupled to the conjugate or particle, and a second agent, targeting moiety, and/or diagnostic moiety can be non-covalently associated with the conjugate or particle. Any of the agents disclosed herein can be used in the compounds, conjugates, particles and other compositions and methods disclosed herein.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition. As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refers to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs. In certain embodiments, a prodrug is a bisdisulfide. In certain embodiments, a prodrug is an ETP bisdisulfide. In some embodiments, a prodrug is a compound of Formula (V). In certain embodiments, a prodrug is able to be cleaved in vivo (e.g., under physiological conditions (e.g., with a half-life of between 1 hours and 6 hours, between 6 hours and 1 day, between 1 day and 3 days, or between 3 days and 1 week) to release its corresponding pharmaceutically active ingredient (API, e.g., epidisulfide). In certain embodiments, the prodrug, as compared with the corresponding API, increases the activity (e.g., potency and/or efficacy), increases bioavailability, reduces toxicity, increases safety, increases therapeutic window, reduces drug resistance, reduces and/or modifies metabolism, inhibits excretion, modifies distribution, and/or increases the compliance of the subject. In certain embodiments, the prodrug is advantageous (e.g., for the reasons provided immediately above) over the corresponding API in inhibiting the proliferation and/or killing aggressive cell lines (e.g., cancer cell lines) with higher extracellular thiol concentrations (e.g., higher extracellular thiol concentrations than the extracellular thiol concentrations in noncancerous cells). In certain embodiments, extracellular thiol concentrations are concentrations of extracellular thiol-containing compounds. In certain embodiments, the prodrug changes (e.g., increases) the uptakes ability of the corresponding API into aggressive cell lines.

In some embodiments, the agent, e.g., a therapeutic agent, a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents, e.g., a therapeutic agents, include, but are not limited to, those found in *Harrison's Principles of Internal Medicine,* 13th Edition, Eds. T. R. Harrison et al., McGraw-Hill N.Y., NY; *Physicians' Desk Reference,* 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index,* the complete contents of all of which are incorporated herein by reference.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the agent is a diagnostic agent. A diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition. The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the terms "effective amount" and "effective dose" refer to any amount or dose of a compound or composition that is sufficient to fulfill its intended purpose (s), i.e., a desired biological or medicinal response in a tissue or subject at an acceptable benefit/risk ratio. The relevant intended purpose may be objective (i.e., measurable by some test or marker) or subjective (i.e., subject gives an indication of or feels an effect). An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In some embodiments, a therapeutically effective amount is an amount that, when administered to a population of subjects that meet certain clinical criteria for a disease or disorder (for example, as determined by symptoms manifested, disease progression/stage, genetic profile, etc.), a statistically significant therapeutic response is obtained among the population. A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts. Those of ordinary skill in the art will appreciate that in some embodiments of the disclosure, a unit dosage may be considered to contain an effective amount if it contains an amount appropriate for administration in the context of a dosage regimen correlated with a positive outcome.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, "epipolythiodiketopiperazine," "epipolythiodioxopiperazine," and "ETP" are used interchangeably. Epipolythiodiketopiperazines may include epidithiodiketopiperazines, a subset of epipolythiodiketopiperazines. In some embodiments, epipolythiodiketopiperazine (ETP) alkaloids are characterized by a polysulfide bridged 2,5-diketopiperazine moiety. In some aspects, epipolythiodiketopiperazine alkaloids constitute a large (ca. 120 members) and diverse family of biologically active secondary metabolites produced by a number of filamentous fungi including those from the *Chaetomium, Leptosphaeria, Aspergillus, Verticillium, Penicillium*, and Pithomyces genera. In certain aspects, ETPs are characterized by the incorporation of an intramolecular polysulfide bridge at the α,α'-positions of a cyclo-dipeptide

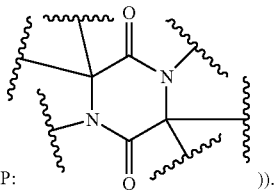

(or diketopiperazine-DKP (e.g., 2,5-DKP: ))

Although mono-, di-, tri-, and tetrasulfide members are naturally occurring, the disulfides are most prevalent.

The disclosure is not intended to be limited in any manner by the above exemplary listing of substituents. Additional terms may be defined in other sections of this disclosure.

DETAILED DESCRIPTION OF CERTAIN EMBODIMENTS

Figure 1:
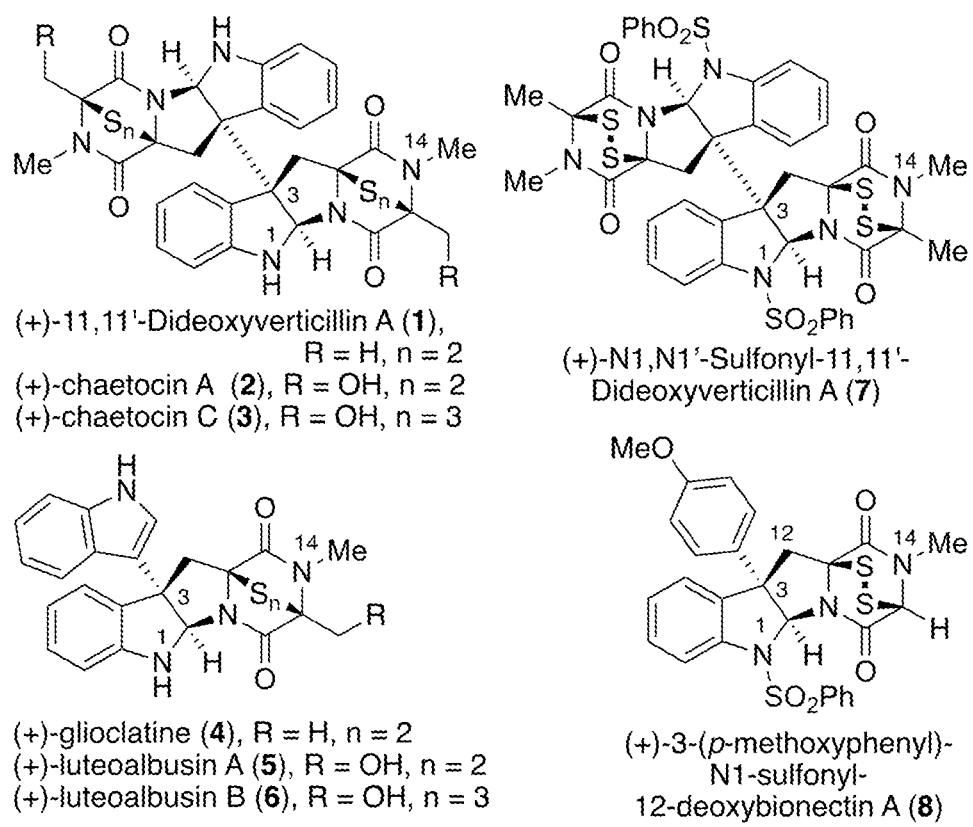
FIG. 1 shows exemplary epithiodiketopiperazines.

Recent studies describe the potent cytotoxic activities of a structurally diverse collection of ETPs and demonstrated the potential of this class of compounds as anti-cancer therapeutics.[3p] Synthetic access to ETPs containing a conjugatable chemical handle would provide a powerful tool to further evaluate the biological activity of these compounds. In recent studies, bioactive small molecules were structurally modified and used as photoaffinity labels for target identification[7], in situ small molecule clickable imaging probes[8], polymer-drug conjugates for improved pharmacokinetics[9], and antibody-drug conjugates for targeted drug delivery[10]. Based on these precedents, efforts to attach an alkyl azide handle to ETPs were undertaken to provide a robust and general method for coupling various chemical groups using CuAAC for utilization in biological applications such as those described above (e.g., drug delivery). Compounds In some embodiments, the present disclosure provides a compound having the structure of Formula (I):

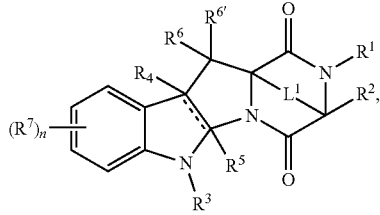

(I)

or a salt thereof, wherein
each --- is independently a single bond or a double bond, as valency permits;

each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;

each R is independently hydrogen, -L$^2$-R$^H$-L$^3$-D, or an optionally substituted group selected from C$_{1-20}$ alkyl, C$_{1-20}$ heteroalkyl, phenyl, a 3-7 membered saturated or partially unsaturated, carbocyclic ring, an 8-14 membered bicyclic or polycyclic, saturated carbocyclic ring, partially unsaturated carbocyclic ring, or aryl ring, a 5-6 membered monocyclic heteroaryl ring having 1-4 heteroatoms independently selected from nitrogen, oxygen, and sulfur, a 3-7 membered saturated or partially unsaturated, heterocyclic ring having 1-3 heteroatoms independently selected from nitrogen, oxygen, and sulfur, a 7-14 membered bicyclic or polycyclic, saturated or partially unsaturated, heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or:

two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;

each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—S(=O)$_2$R, or —[C(R)$_2$]$_q$—OP(OR)$_2$; or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur;

each q is independently 0, 1, 2, 3, or 4;
each $R^3$ is independently —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$;
$R^4$ is absent when === is a double bond or is selected from R, halogen, and

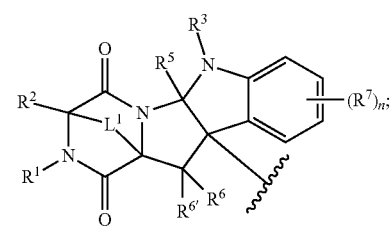

wherein
at least one instance of $R^1$, $R^3$, and $R^4$ comprises R wherein R is -L$^2$-R$^H$-L$^3$-D;
each L$^2$ is independently substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein:

optionally one or more backbone carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, and $C_{2-20}$ heteroalkynylene are independently replaced with —C(=O)—, substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, $C_{1-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each $R^H$ is independently substituted or unsubstituted triazolylene, —O—, —S—, —$NR^A$—, —C(=O)O—, —C(=$NR^A$)O—, —S(=O)O—, —S(=O)$_2$O—, —C(=O)$NR^A$—, —C(=$NR^A$)$NR^A$—, —S(=O)$NR^A$—, —S(=O)$_2NR^A$—, —OC(=O)—, —OC(=$NR^A$)—, —OS(=O)—, —OS(=O)$_2$—, —$NR^A$C(=O)—, —$NR^A$C(=$NR^A$)—, —$NR^A$S(=O)—, —$NR^A$S(=O)$_2$—, —OC(=O)O—, —OC(=$NR^A$)O—, —OS(=O)O—, —OS(=O)$_2$O—, —$NR^A$C(=O)O—, —$NR^A$C(=$NR^A$)O—, —$NR^A$S(=O)O—, —$NR^A$S(=O)$_2$O—, —OC(=O)$NR^A$—, —OC(=$NR^A$)$NR^A$—, —OS(=O)$NR^A$—, —OS(=O)$_2NR^A$—, —$NR^A$C(=O)$NR^A$—, —$NR^A$C(=$NR^A$)$NR^A$—, —$NR^A$S(=O)$NR^A$—, —$NR^A$S(=O)$_2NR^A$—, —C(=O)—, —C(=$NR^A$)—, —S(=O)—, —S(=O)$_2$—, substituted or unsubstituted carbocyclylene, substituted or unsubstituted heterocyclylene, substituted or unsubstituted arylene, or substituted or unsubstituted heteroarylene;

each $R^A$ is independently hydrogen, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, substituted or unsubstituted heteroaryl, or a nitrogen protecting group;

each $L^3$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein:

optionally one or more backbone carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, and $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, $C_{1-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each D is independently absent, polymeric moiety, dendrimeric moiety, antibody, particle, bead, nanostructure, liposome, micelle, or vesicle;

each $R^5$ is absent when $=\!=\!=$ is a double bond or is independently hydrogen or an optionally substituted $C_{1-6}$ aliphatic group;

each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$ or =NR;

each n is independently 0, 1, 2, 3, or 4;

each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]2, —B(R)$_2$, —B(OR)$_2$, or —Si(R)$_3$; or:

two $R^7$ are taken together with their intervening atoms to form an optionally substituted 4-7 membered ring having 0-2 heteroatoms independently selected from nitrogen, oxygen, and sulfur;

each $L^1$ independently is —S—, —(S)$_m$—[C(R)$_2$]$_q$—(S)$_p$—, —(S)$_m$(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—;

each m is independently 1, 2, or 3; and each p is independently 1, 2, or 3.

In the compounds and formulae disclosed herein, wherein more than one instance of a particular variable (e.g., $R^1$, $R^2$, $R^3$, $R^4$, $R^5$, $R^6$, $R^{6'}$, $R^7$, R, $R^H$, $R^{H1}$, $R^{H2}$, $R^A$, $R^P$, $R^S$, $R^X$, $R^Y$, $R^Z$, $L^1$, $L^2$, $L^{2'}$, $L^3$, $M^X$, $M^Y$, D, Ring A, $=\!=\!=$, h, g, m, n, p, and q) is present, each instance of the variable is independent from one another (i.e., each instance of the variable is independently selected from the definition of the variable as described herein). In certain embodiments, at least two instances of a variable are different from each other. In certain embodiments, all instances of a variable are different from each other. In certain embodiments, all instances of a variable are the same.

In certain embodiments, a compound of Formula (I) is of the formula:

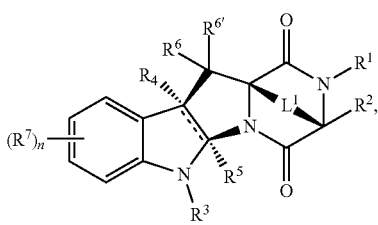

or stereoisomer thereof.

As generally defined, ⚌ is a single bond or a double bond, as valency permits. In some embodiments, ⚌ is a single bond. In some embodiments, ⚌ is a double bond. In some embodiments, there are two or more ⚌ in a provided compound, and at least one ⚌ is a single bond, and at least one ⚌ is a double bond. In some other embodiments, there are two or more ⚌ in a provided compound, and each ⚌ is a single bond. In some other embodiments, there are two or more ⚌ in a provided compound, and each ⚌ is a double bond. In some embodiments, ⚌ is a single bond, $R^4$ is R or halogen, and $R^5$ is hydrogen or an optionally substituted $C_{1-6}$ aliphatic. In some embodiments, ⚌ is a double bond, $R^4$ is absent and $R^5$ is absent.

As generally defined above, each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur. In some embodiments, each $R^1$ is independently R, —C(O)R, —C(O)N(R)$_2$, —S(O)R, —S(O)$_2$R, —S(O)$_2$OR, —CH$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur. In some embodiments, each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur. In some embodiments, $R^1$ is R, —C(O)R, —C(O)N(R)$_2$, —S(O)R, —S(O)$_2$R, —S(O)$_2$OR, or —S(O)$_2$N(R)$_2$. In some embodiments, $R^1$ is R. In some embodiments, $R^1$ is —C(O)R. In some embodiments, $R^1$ is —C(O)N(R)$_2$. In some embodiments, $R^1$ is —S(O)R. In some embodiments, $R^1$ is —S(O)$_2$R. In some embodiments, $R^1$ is —S(O)$_2$OR. In some embodiments, $R^1$ is —C(R)$_2$OR. In some embodiments, $R^1$ is —CH$_2$OR. In some embodiments, $R^1$ is —S(O)$_2$ N(R)$_2$. In some embodiments, a provided compound has more than one $R^1$ groups. In some embodiments, each $R^1$ of a provided compound is the same. In some embodiments, at least one $R^1$ is different from the other $R^1$.

In some embodiments, $R^1$ is R. In some embodiments, $R^1$ is hydrogen. In some embodiments, $R^1$ is optionally substituted $C_{1-20}$ alkyl. In some embodiments, $R^1$ is optionally substituted $C_{1-10}$ alkyl. In some embodiments, $R^1$ is optionally substituted $C_{1-6}$ alkyl. In some embodiments, $R^1$ is optionally substituted $C_{1-6}$ alkyl. In some embodiments, $R^1$ is optionally substituted hexyl, pentyl, butyl, propyl, ethyl or methyl. In some embodiments, $R^1$ is optionally substituted hexyl. In some embodiments, $R^1$ is optionally substituted pentyl. In some embodiments, $R^1$ is optionally substituted butyl. In some embodiments, $R^1$ is optionally substituted propyl. In some embodiments, $R^1$ is optionally substituted ethyl. In some embodiments, $R^1$ is optionally substituted methyl. In some embodiments, $R^1$ is hexyl. In some embodiments, $R^1$ is pentyl. In some embodiments, $R^1$ is butyl. In some embodiments, $R^1$ is propyl. In some embodiments, $R^1$ is ethyl. In some embodiments, $R^1$ is methyl. In some embodiments, $R^1$ is isopropyl. In some embodiments, $R^1$ is n-propyl. In some embodiments, $R^1$ is tert-butyl. In some embodiments, $R^1$ is sec-butyl. In some embodiments, $R^1$ is n-butyl. In some embodiments, $R^1$ is benzyloxymethyl. In some embodiments, $R^1$ is benzyl. In some embodiments, $R^1$ is allyl. In some embodiments, $R^1$ comprises an —OH, —NHR or —SH.

In some embodiments, $R^1$ is methyl, $R^3$ is not Boc (tert-butyloxycarbonyl) and CF$_3$C(O)—. In some embodiments, $R^1$ is methyl, $R^3$ is not CF$_3$C(O)—. In some embodiments, $R^1$ is methyl, $R^3$ is not Boc (tert-butyloxycarbonyl) and CF$_3$C(O)—. In some embodiments, $R^1$ is other than methyl. In some embodiments, $R^1$ is methyl, $R^3$ is Boc (tert-butyloxycarbonyl) or CF$_3$C(O)—In some embodiments, $R^1$ is methyl, $R^3$ is CF$_3$C(O)—. In some embodiments, $R^1$ is methyl, $R^3$ is Boc (tert-butyloxycarbonyl) or CF$_3$C(O)—. In some embodiments, $R^1$ is methyl.

Exemplary $R^1$ groups are depicted below.

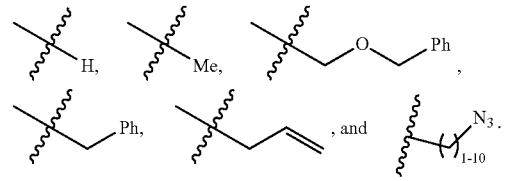

In certain embodiments, $R^1$ is

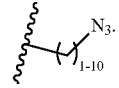

In certain embodiments, $R^1$ is

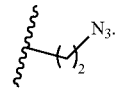

In certain embodiments, $R^1$ is

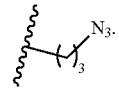

In some embodiments, each R is independently optionally substituted group selected from $C_{1-20}$ alkyl, $C_{1-20}$ heteroalkyl, phenyl, a 3-7 membered saturated or partially unsaturated, carbocyclic ring, an 8-14 membered bicyclic or polycyclic, saturated carbocyclic ring, partially unsaturated carbocyclic ring, or aryl ring, a 5-6 membered monocyclic heteroaryl ring having 1-4 heteroatoms independently selected from nitrogen, oxygen, and sulfur, a 3-7 membered saturated or partially unsaturated, heterocyclic ring having 1-3 heteroatoms independently selected from nitrogen, oxygen, and sulfur, a 7-14 membered bicyclic or polycyclic, saturated or partially unsaturated, heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur. In certain embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur.

In some embodiments, R is optionally substituted $C_{1-20}$ alkyl. In some embodiments, R is optionally substituted $C_{1-15}$ alkyl. In some embodiments, R is optionally substituted $C_{1-10}$ alkyl. In some embodiments, R is optionally substituted $C_{1-6}$ alkyl. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is halogen substituted methyl. In some embodiments, R is —$CF_3$. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is benzyloxymethyl. In some embodiments, R is benzyl. In some embodiments, R is allyl. In some embodiments, R is not hydrogen. In some embodiments, R is not alkyl.

In some embodiments, R is optionally substituted $C_{1-20}$ heteroalkyl. In some embodiments, R is optionally substituted $C_{1-20}$ heteroalkyl comprising 1-6 heteroatoms independently selected from nitrogen, sulfur, phosphorus selenium, silicon and boron within the $C_{1-20}$ heteroalkyl backbone. In some embodiments, R is optionally substituted $C_{1-20}$ heteroalkyl comprising 1-6 heteroatoms independently selected from nitrogen, sulfur, phosphorus, selenium, silicon and boron within the $C_{1-20}$ heteroalkyl backbone, optionally including one or more oxidized forms of nitrogen, sulfur, phosphorus, selenium, silicon or boron within the $C_{1-20}$ heteroalkyl backbone. In some embodiments, R is optionally substituted $C_{1-20}$ heteroalkyl comprising 1-6 groups independently selected from

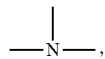

—N═, ≡N, —S—, —S(O)—, —S(O)$_2$—, —O—, ═O,

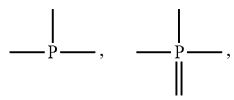

—Se—, —Se(O)—, and

within the $C_{1-20}$ heteroalkyl backbone. In some embodiments, R is not heteroalkyl. In some embodiments, R is methoxymethyl. In some embodiments, R is benzyloxymethyl.

In some embodiments, R is optionally substituted phenyl. In some embodiments, R is optionally substituted phenyl wherein one or more substituents are halogen. In some embodiments, R is optionally substituted phenyl wherein one or more substituents are —F. In some embodiments, R is optionally substituted phenyl wherein one or more substituents are —Cl. In some embodiments, R is optionally substituted phenyl wherein one or more substituents are —Br. In some embodiments, R is optionally substituted phenyl wherein one or more substituents are —I. In some embodiments, R is phenyl.

In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 8-14 membered bicyclic or polycyclic saturated, partially unsaturated or aryl ring. In some embodiments, R is an optionally substituted 8-14 membered bicyclic or polycyclic saturated ring. In some embodiments, R is an optionally substituted 8-14 membered bicyclic or polycyclic partially saturated ring. In some embodiments, R is an optionally substituted 8-14 membered bicyclic or polycyclic aryl ring. In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl. In some embodiments, R is optionally substituted anthracenyl. In some embodiments, R is optionally substituted 9-anthracenyl.

In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, or sulfur. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is optionally substituted phenyl. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 5-6 membered monocyclic heteroaryl ring having 1-4 heteroatoms independently selected from nitrogen, oxygen, or sulfur. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 8-10 membered bicyclic aryl ring. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is optionally substituted naphthyl. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 8-10 membered bicyclic heteroaryl ring having 1-5 heteroatoms independently selected from nitrogen, oxygen, and sulfur. In some embodiments, R is optionally substituted biaryl wherein each aryl group is independently optionally substituted phenyl. In some embodiments, R is optionally substituted biaryl wherein each aryl group is independently optionally substituted phenyl, or an optionally substituted 5-6 membered monocyclic heteroaryl ring having 1-4 heteroatoms independently selected from nitrogen, oxygen. In some embodiments, R is optionally substituted biaryl wherein each aryl group is independently an optionally substituted 8-10 membered bicyclic aryl ring. In some embodiments, R is optionally substituted biaryl wherein one aryl group is optionally substituted naphthyl, and the other aryl group is independently an optionally substituted 8-10 membered bicyclic aryl ring. In some embodiments, R is optionally substituted biaryl wherein each aryl group is optionally substituted naphthyl. In some embodiments, R is optionally substituted biaryl wherein one aryl group is optionally substituted naphthyl, and the other aryl group is an optionally substituted 8-10 membered bicyclic heteroaryl ring having 1-5 heteroatoms independently selected from nitrogen, oxygen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Exemplary R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur.

In some embodiments, R is optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is optionally substituted 4-membered heterocyclic ring having 1-3 heteroatoms independently selected from nitrogen, oxygen, and sulfur. Exemplary R groups include but are not limited to optionally substituted azetidinyl, oxetanyl, thietanyl, oxazetidinyl, thiazetidinyl, or diazetidinyl. In some embodiments, R is optionally substituted 5-membered heterocyclic ring having 1-3 heteroatoms independently selected from nitrogen, oxygen, and sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, R is optionally substituted 6-membered heterocyclic ring having 1-3 heteroatoms independently selected from nitrogen, oxygen, and sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, R is optionally substituted 7-membered heterocyclic ring having 1-3 heteroatoms independently selected from nitrogen, oxygen, and sulfur. Exemplary R groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated monocyclic ring having 1-3 heteroatoms independently selected from nitrogen, oxygen, and sulfur. Exemplary R groups include but are not limited to optionally substituted dihydropyridinyl, tetrahydropyridinyl, dihydropyrimidinyl, tetrahydropyrimidinyl, dihydropyrazinyl, tetrohydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated monocyclic ring having 1-3 heteroatoms independently selected from nitrogen, oxygen, and sulfur. Exemplary R groups include but are not limited to optionally substituted azepiyl, oxepinyl, thiepinyl, diazepinyl, oxazepinyl, thiazepinyl, triazepinyl, oxadiazepinyl, thiadiazepinyl, dihydroazepiyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepiyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, R is an optionally substituted 7-14 membered bicyclic or polycyclic saturated or partially unsaturated heterocyclic ring having 1-5 heteroatoms independently selected from nitrogen, oxygen, and sulfur. In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-14 membered bicyclic or polycyclic heteroaryl ring having 1-5 heteroatoms independently selected from nitrogen, oxygen, and sulfur. In some embodiments, R is an optionally substituted 8-14 membered bicyclic or tricyclic heteroaryl ring having 1-5 heteroatoms independently selected from nitrogen, oxygen, and sulfur. In some embodiments, R is an 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted heterobiaryl wherein each heteroaryl group is independently an optionally substituted group selected from a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, R is optionally substituted heterobiaryl wherein each aryl group is an optionally substituted 8-10 membered bicyclic heteroaryl ring having 1-5 heteroatoms independently selected from nitrogen, oxygen, and sulfur.

In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur. In some embodiments, two R groups on the same atom are optionally taken together with the atom to which they are attached to form an optionally substituted 3-14 membered, saturated, partially unsaturated, or aryl ring having 0-4 heteroatoms independently selected from nitrogen, oxygen, and sulfur. In some embodiments, two R groups on the same carbon atom are optionally taken together with the carbon atom to form an optionally substituted 3-14 membered, saturated, partially unsaturated, or aryl ring having 0-4 heteroatoms independently selected from nitrogen, oxygen, and sulfur. In some embodiments, two R groups on the same nitrogen atom are optionally taken together with the nitrogen atom to form an optionally substituted 3-14 membered, saturated, partially unsaturated, or aryl ring having 1-5 heteroatoms independently selected from nitrogen, oxygen, and sulfur. In some embodiments, two R groups on the same sulfur atom are optionally taken together with the sulfur atom to form an optionally substituted 3-14 membered, saturated, partially unsaturated, or aryl ring having 1-5 heteroatoms independently selected from nitrogen, oxygen, and sulfur. In some embodiments, two R groups on the same oxygen atom are optionally taken together with the oxygen atom to form an optionally substituted 3-14 membered, saturated, partially unsaturated, or aryl ring having 1-5 heteroatoms independently selected from nitrogen, oxygen, and sulfur. In some embodiments, two R groups on the same phosphorus atom are optionally taken together with the phosphorus atom to form an optionally substituted 3-14 membered, monocyclic or bicyclic, saturated, partially unsaturated, or aryl ring having, in addition to the phosphorus atom, 0-4 heteroatoms independently selected from nitrogen, oxygen, and sulfur. In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur, wherein the two R groups are attached to two different atoms.

In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur. In some embodiments, two R groups are taken together to form an optionally substituted saturated ring. In some embodiments, two R groups are taken together to form an optionally substituted partially unsaturated ring. In some embodiments, two R groups are taken together to form an optionally substituted carbocyclic ring. In some embodiments, two R groups are taken together to form an optionally substituted aryl ring. In some embodiments, two R groups are taken together to form an optionally substituted phenyl ring. In some embodiments, two R groups are taken together to form an optionally substituted heterocyclic ring. In some embodiments, two R groups are taken together to form an optionally substituted heteroaryl ring.

In some embodiments, a ring formed by taking two R groups together is monocyclic, bicyclic or tricyclic. In some embodiments, a ring formed by taking two R groups together is monocyclic. In some embodiments, a ring formed by taking two R groups together is bicyclic. In some embodiments, a ring formed by taking two R groups together is monocyclic or bicyclic. In some embodiments, a ring formed by taking two R groups together is tricyclic. In some embodiments, a ring formed by taking two R groups together is monocyclic, bicyclic or tricyclic.

In some embodiments, R is -$L^2$-$R^H$-$L^3$-D. In some embodiments, each instance of R is -$L^2$-$R^H$-$L^3$-D. In certain embodiments, two of $R^1$, $R^2$, $R^3$, $R^4$, $R^6$, $R^{6'}$, $R^7$ comprise -$L^2$-$R^H$-$L^3$-D. In certain embodiments, only one of $R^1$, $R^2$, $R^3$, $R^4$, $R^6$, $R^{6'}$, $R^7$ comprise -$L^2$-$R^H$-$L^3$-D. In certain embodiments, at least one instance of $R^1$, $R^3$, and $R^4$ comprise R wherein R is -$L^2$-$R^H$-$L^3$-D. In certain embodiments, at least one instance of $R^1$ comprises R wherein R is -$L^2$-$R^H$-$L^3$-D. In some embodiments, at least one instance of $R^1$ is -$L^2$-$R^H$-$L^3$-D. In certain embodiments, at least one instance of $R^3$ comprises R wherein R is -$L^2$-$R^H$-$L^3$-D. In certain embodiments, at least one instance of $R^3$ is —$S(O)_2R$ wherein R is -$L^2$-$R^H$-$L^3$-D. In certain embodiments, at least one instance of $R^3$ is —C(O)R wherein R is -$L^2$-$R^H$-$L^3$-D. In certain embodiments, $R^4$ comprises R wherein R is -$L^2$-$R^H$-$L^3$-D. In some embodiments, $R^4$ is -$L^2$-$R^H$-$L^3$-D.

In some embodiments, each $L^2$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein optionally one or more backbone carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, and $C_{2-20}$ heteroalkynylene are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, each $L^2$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein optionally one or more backbone heteroatoms in each instance of the substituted or unsubstituted, $C_{1-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene.

In some embodiments, $L^2$ is substituted or unsubstituted, $C_{1-20}$ alkylene. In some embodiments, $L^2$ is substituted or unsubstituted, $C_{1-20}$ alkylene, wherein optionally 1, 2, or 3 backbone carbons in each instance of the substituted or unsubstituted, $C_{1-20}$ alkylene are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, $L^2$ is substituted or unsubstituted, $C_{1-20}$ alkylene wherein one or more backbone carbon atoms are replaced with substituted or unsubstituted arylene.

In some embodiments, $L^2$ is substituted or unsubstituted, $C_{1-20}$ heteroalkylene. In some embodiments, $L^2$ is substituted or unsubstituted, $C_{1-20}$ heteroalkylene, wherein optionally 1, 2, or 3 backbone carbons in each instance of the substituted or unsubstituted, $C_{1-20}$ heteroalkylene are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, $L^2$ is substituted or unsubstituted, $C_{1-20}$ heteroalkylene, wherein optionally 1, 2, or 3 backbone carbons in each instance of the substituted or unsubstituted, $C_{1-20}$ heteroalkylene are independently replaced with substituted or unsubstituted carbocyclylene, substituted or unsubstituted heterocyclylene, substituted or unsubstituted arylene, or substituted or unsubstituted heteroarylene. In some embodiments, $L^2$ is substituted or unsubstituted, $C_{1-20}$ heteroarylene wherein one or more backbone carbon atoms are replaced with substituted or unsubstituted arylene.

In certain embodiments, $L^2$ comprises

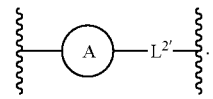

In certain embodiments, each instance of $L^{2'}$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene. In some embodiments, $L^{2'}$ is substituted or unsubstituted, $C_{1-20}$ alkylene. In certain embodiments, $L^{2'}$ is substituted or unsubstituted, $C_{1-20}$ heteroalkylene. In some embodiments, $L^{2'}$ is substituted or unsubstituted, $C_{1-20}$ heteroalkylene comprising one or more backbone oxygen atoms. In certain embodiments, $L^{2'}$ is

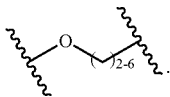

In certain embodiments, L$^{2'}$ is

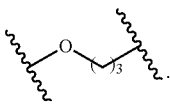

In some embodiments, L$^{2'}$ is

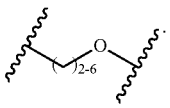

In some embodiments, L$^{2'}$ is

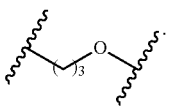

In some embodiments, each instance of Ring A is independently selected from the group consisting of substituted or unsubstituted phenylene, substituted or unsubstituted indolylene, substituted or unsubstituted pyrrolylene, substituted or unsubstituted imidazolylene, substituted or unsubstituted pyridinylene, substituted or unsubstituted quinolinylene, substituted or unsubstituted oxazolylene, substituted or unsubstituted isooxazolylene, substituted or unsubstituted thiazolylene, substituted or unsubstituted isothiazolylene, substituted or unsubstituted benzimidazolylene, substituted or unsubstituted thiadiazolylene, and substituted or unsubstituted quinazolylene. In certain embodiments, Ring A is substituted or unsubstituted phenylene, substituted or unsubstituted indolylene, or substituted or unsubstituted pyrrolylene. In some embodiments, Ring A is substituted or unsubstituted indolylene. In some embodiments, Ring A is indolylene substituted with 1-4 substituents each independently selected from —F, —Br, —OH, —OCH$_3$, —NO$_2$, —SCH$_3$, and —Boc. In certain embodiments, Ring A is substituted or unsubstituted pyrrolylene. In certain embodiments, Ring A is pyrrolylene substituted with 1-3 substituents each independently selected from —F, —Br, —OH, —OCH$_3$, —NO$_2$, —SCH$_3$, and —Boc. In certain embodiments, Ring A is substituted or unsubstituted phenylene. In certain embodiments, Ring A is phenylene substituted with 1-4 substituents each independently selected from —F, —Br, —OH, —OCH$_3$, —NO$_2$, and —SCH$_3$.

In some embodiments, each instance of R$^H$ is independently selected from substituted or unsubstituted triazolylene, —O—, —S—, —NR$^A$—, —C(=O)O—, —C(=NR$^A$)O—, —S(=O)O—, —S(=O)$_{20}$—, —C(=O)NR$^A$—, —C(=NR$^A$)NR$^A$—, —S(=O)NR$^A$—, —S(=O)$_2$NR$^A$—, —OC(=O)—, —OC(=NR$^A$)—, —OS(=O)—, —OS(=O)$_2$—, —NR$^A$C(=O)—, —NR$^A$C(=NR$^A$)—, —NR$^A$S(=O)—, —NR$^A$S(=O)$_2$—, —OC(=O)O—, —OC(=NR$^A$)O—, —OS(=O)O—, —OS(=O)$_2$O—, —NR$^A$C(=O)O—, —NR$^A$C(=NR$^A$)O—, —NR$^A$S(=O)O—, —NR$^A$S(=O)$_2$O—, —OC(=O)NR$^A$—, —OC(=NR$^A$)NR$^A$—, —OS(=O)NR$^A$—, —OS(=O)$_2$NR$^A$—, —NR$^A$C(=O)NR$^A$—, —NR$^A$C(=NR$^A$)NR$^A$—, —NR$^A$S(=O)NR$^A$—, —NR$^A$S(=O)$_2$NR$^A$—, —C(=O)—, —C(=NR$^A$)—, —S(=O)—, —S(=O)$_2$—, substituted or unsubstituted carbocyclylene, substituted or unsubstituted heterocyclylene, substituted or unsubstituted arylene, and substituted or unsubstituted heteroarylene. In certain embodiments, R$^H$ is substituted or unsubstituted triazolylene. In certain embodiments, R$^H$ is substituted or unsubstituted 1,5-triazolylene. In certain embodiments, R$^H$ is substituted or unsubstituted 1,4-triazolylene. In some embodiments, R$^H$ is unsubstituted triazolylene. In some embodiments, R$^H$ is unsubstituted 1,4-triazolylene. In some embodiments, R$^H$ is —C(=O)NR$^A$—. In certain embodiments, R$^H$ is-NR$^A$C(=O)—. In certain embodiments, R$^H$ is —NR$^A$—.

In some embodiments, each instance of R$^A$ is independently hydrogen, substituted or unsubstituted C$_{1-6}$ alkyl, substituted or unsubstituted C$_{1-6}$ heteroalkyl, substituted or unsubstituted C$_{2-6}$ alkenyl, substituted or unsubstituted C$_{2-6}$ alkynyl, substituted or unsubstituted carbocyclyl, substituted or unsubstituted heterocyclyl, substituted or unsubstituted aryl, substituted or unsubstituted heteroaryl, or a nitrogen protecting group. In certain embodiments, R$^A$ is hydrogen. In certain embodiments, R$^A$ is methyl, ethyl, or propyl.

In certain embodiments, each instance of L$^3$ is independently selected from substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{1-20}$ heteroalkylene, substituted or unsubstituted, C$_{2-20}$ heteroalkenylene, or C$_{2-20}$ heteroalkynylene, wherein optionally one or more backbone carbons in each instance of the substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{1-20}$ heteroalkylene, substituted or unsubstituted, C$_{2-20}$ heteroalkenylene, and C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene. In certain embodiments, each instance of L$^3$ is independently selected from substituted or unsubstituted, C$_{1-20}$ heteroalkylene, substituted or unsubstituted, C$_{2-20}$ heteroalkenylene, or C$_{2-20}$ heteroalkynylene, wherein optionally one or more backbone heteroatoms in each instance of the substituted or unsubstituted, C$_{1-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene.

In some embodiments, L$^3$ is substituted or unsubstituted, C$_{1-20}$ alkylene. In some embodiments, L$^3$ is substituted or unsubstituted, C$_{1-20}$ alkylene, wherein optionally 1, 2, or 3 backbone carbons in each instance of the substituted or unsubstituted, C$_{1-20}$ alkylene are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, L$^3$ is substituted or unsubstituted, C$_{1-20}$ alkylene wherein one or more backbone carbon atoms are replaced with substituted or unsubstituted arylene. In some embodiments, L$^3$ is substituted or unsubstituted, $C_{1-20}$ alkylene. In certain embodiments, $L^3$ is substituted $C_{1-20}$ alkylene. In certain embodiments, $L^3$ is substituted $C_{1-20}$ alkylene wherein at least one substituent on the $C_{1-20}$ alkylene is —NHBoc. In certain embodiments, $L^3$ is substituted $C_{1-20}$ alkylene wherein at least one substituent on the $C_{1-20}$ alkylene is —NH$_2$.

In some embodiments, $L^3$ is substituted or unsubstituted, $C_{1-20}$ heteroalkylene. In some embodiments, $L^3$ is substituted or unsubstituted, $C_{1-20}$ heteroalkylene, wherein optionally 1, 2, or 3 backbone carbons in each instance of the substituted or unsubstituted, $C_{1-20}$ heteroalkylene are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, $L^3$ is substituted or unsubstituted, $C_{1-20}$ heteroalkylene, wherein optionally 1, 2, or 3 backbone carbons in each instance of the substituted or unsubstituted, $C_{1-20}$ heteroalkylene are independently replaced with substituted or unsubstituted carbocyclylene, substituted or unsubstituted heterocyclylene, substituted or unsubstituted arylene, or substituted or unsubstituted heteroarylene. In some embodiments, $L^3$ is substituted or unsubstituted, $C_{1-20}$ heteroarylene wherein one or more backbone carbon atoms are replaced with substituted or unsubstituted arylene. In some embodiments, $L^3$ is substituted or unsubstituted, $C_{1-20}$ heteroalkylene with one or more backbone atoms selected from oxygen and nitrogen. In some embodiments, $L^3$ is substituted or unsubstituted, $C_{1-20}$ heteroalkylene comprising at least one backbone carbon atom and at least one backbone nitrogen atom. In certain embodiments, $L^3$ is

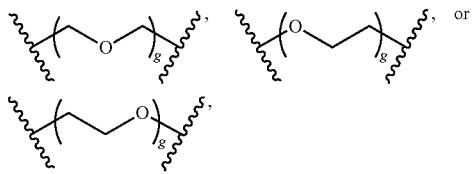

wherein g is an integer from 1 to 10, inclusive. In certain embodiments, $L^3$ is

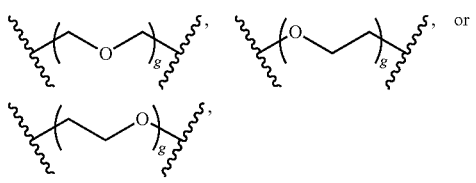

wherein g is 1, 2, or 3. In certain embodiments, $L^3$ is

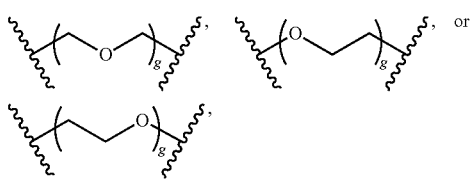

wherein g is 1. In certain embodiments, $L^3$ is

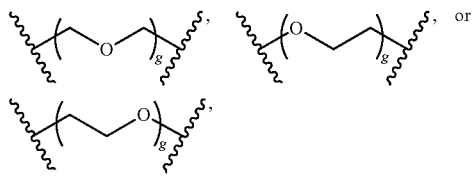

wherein g is 3.

In some embodiments, $L^3$ comprises phenylene. In certain embodiments, $L^3$ comprises substituted or unsubstituted,

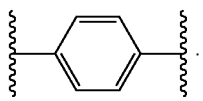

In some embodiments, $L^3$ comprises substituted or unsubstituted,

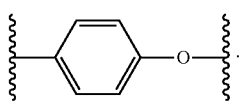

In certain embodiments, $L^3$ is a substituted $C_{1-20}$ heteroalkylene with one or more backbone atoms selected from oxygen and nitrogen and a backbone substituted or unsubstituted phenylene. In some embodiments, $L^3$ is a substituted $C_{1-20}$ heteroalkylene wherein at least one substituent on the $C_{1-20}$ heteroalkylene is —NHBoc. In certain embodiments, $L^3$ is a substituted $C_{1-20}$ heteroalkylene with one or more backbone atoms selected from oxygen and nitrogen and a backbone substituted or unsubstituted phenylene, wherein at least one substituent on the $C_{1-20}$ heteroalkylene is —NHBoc. In some embodiments, $L^3$ is a substituted $C_{1-20}$ heteroalkylene wherein at least one substituent on the $C_{1-20}$ heteroalkylene is —NH$_2$. In certain embodiments, $L^3$ is a substituted $C_{1-20}$ heteroalkylene with one or more backbone atoms selected from oxygen and nitrogen and a backbone substituted or unsubstituted phenylene, wherein at least one substituent on the $C_{1-20}$ heteroalkylene is —NH$_2$.

In certain embodiments, g is 1. In some embodiments, g is 2. In certain embodiments, g is 3. In some embodiments, g is 4, 5, or 6. In certain embodiments, g is 7, 8, or 9.

In some embodiments, D is a polymeric moiety, dendrimeric moiety, antibody, nanostructure, liposome, micelle, or vesicle. In certain embodiments, D is a polymeric moiety. In some embodiments, D is a brush polymeric moiety. In certain embodiments D is a brush-arm star polymeric moiety. In some embodiments, D is a dendrimeric moiety In some embodiments, D is a particle or bead. In certain embodiments, D is nanostructure (e.g., nanoparticle, nanoflake). In some embodiments, D is a microparticle. In certain embodiments, D is a supraparticle. In some embodiments, D is liposome, micelle, or vesicle. In some embodiments, D is an antibody. In certain embodiments, D is not an antibody. In some embodiments, D facilitates endocytosis delivery of an derivatized ETP, improves bioavailability, or/and reduces cell toxicity by lowering the concentration of ETP needed for treatment.

In certain embodiments, D is absent, and $L^3$ is substituted or unsubstituted, $C_{1-20}$ alkyl, substituted or unsubstituted, $C_{2-20}$ alkenyl, substituted or unsubstituted, $C_{2-20}$ alkynyl, substituted or unsubstituted, $C_{1-20}$ heteroalkyl, substituted or unsubstituted, $C_{2-20}$ heteroalkenyl, or $C_{2-20}$ heteroalkynyl, wherein: optionally one or more backbone carbons in each instance of the substituted or unsubstituted, $C_{1-20}$ alkyl, substituted or unsubstituted, $C_{2-20}$ alkenyl, substituted or unsubstituted, $C_{2-20}$ alkynyl, substituted or unsubstituted, $C_{1-20}$ heteroalkyl, substituted or unsubstituted, $C_{2-20}$ heteroalkenyl, and $C_{2-20}$ heteroalkynyl are independently replaced with substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, $C_{1-20}$ heteroalkyl, substituted or unsubstituted, $C_{2-20}$ heteroalkenyl, and substituted or unsubstituted, $C_{2-20}$ heteroalkynyl are independently replaced with substituted or unsubstituted carbocyclylene, substituted or unsubstituted heterocyclylene, substituted or unsubstituted arylene, or substituted or unsubstituted heteroarylene. In certain embodiments, D is absent, and $L^3$ is substituted or unsubstituted, $C_{1-20}$ alkyl, substituted or unsubstituted, $C_{2-20}$ alkenyl, substituted or unsubstituted, $C_{2-20}$ alkynyl, substituted or unsubstituted, $C_{1-20}$ heteroalkyl, substituted or unsubstituted, $C_{2-20}$ heteroalkenyl, or $C_{2-20}$ heteroalkynyl.

In certain embodiments, D is absent, and $L^3$ is substituted or unsubstituted, $C_{1-20}$ alkyl. In some embodiments, D is absent, and $L^3$ is substituted or unsubstituted, $C_{1-20}$ alkyl, wherein optionally 1, 2, or 3 backbone carbons in each instance of the substituted or unsubstituted, $C_{1-20}$ alkyl are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, D is absent, and $L^3$ is substituted or unsubstituted, $C_{1-20}$ alkyl wherein one or more backbone carbon atoms are replaced with substituted or unsubstituted arylene. In certain embodiments, D is absent, and $L^3$ is substituted $C_{1-20}$ alkyl. In certain embodiments, D is absent, and $L^3$ is substituted $C_{1-20}$ alkyl wherein at least one substituent on the $C_{1-20}$ alkylene is —NHBoc. In certain embodiments, D is absent, and $L^3$ is substituted $C_{1-20}$ alkyl wherein at least one substituent on the $C_{1-20}$ alkylene is —NH$_2$.

In some embodiments, D is absent, and $L^3$ is substituted or unsubstituted, $C_{1-20}$ heteroalkyl. In some embodiments, D is absent, and $L^3$ is substituted or unsubstituted, $C_{1-20}$ heteroalkyl, wherein optionally 1, 2, or 3 backbone carbons in each instance of the substituted or unsubstituted, $C_{1-20}$ heteroalkyl are independently replaced with —C(=O)—, substituted or unsubstituted carbocyclylene, substituted or unsubstituted heterocyclylene, substituted or unsubstituted arylene, or substituted or unsubstituted heteroarylene. In some embodiments, D is absent, and $L^3$ is substituted or unsubstituted, $C_{1-20}$ heteroalkyl, wherein optionally 1, 2, or 3 backbone carbons in each instance of the substituted or unsubstituted, $C_{1-20}$ heteroalkyl are independently replaced with substituted or unsubstituted carbocyclylene, substituted or unsubstituted heterocyclylene, substituted or unsubstituted arylene, or substituted or unsubstituted heteroarylene. In some embodiments, D is absent, and $L^3$ is substituted or unsubstituted, $C_{1-20}$ heteroaryl wherein one or more backbone carbon atoms are replaced with substituted or unsubstituted arylene. In some embodiments, D is absent, and $L^3$ is substituted or unsubstituted, $C_{1-20}$ heteroalkyl with one or more backbone atoms selected from oxygen and nitrogen. In some embodiments, D is absent, and $L^3$ is substituted or unsubstituted, $C_{1-20}$ heteroalkyl comprising at least one backbone carbon atom and at least one backbone nitrogen atom.

In certain embodiments, D is absent, and $L^3$ is substituted or unsubstituted, $C_{1-20}$ heteroalkyl comprising substituted or unsubstituted phenylene. In some embodiments, D is absent, and $L^3$ comprises a phenylene. In certain embodiments, D is absent, and $L^3$ comprises substituted or unsubstituted,

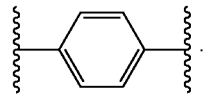

In some embodiments, D is absent, and $L^3$ comprises substituted or unsubstituted,

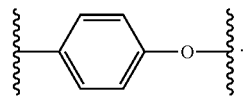

As generally defined above, each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur. In some embodiments, $R^2$ is R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$. In some embodiments, $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur.

In some embodiments, $R^2$ is R. In some embodiments, $R^2$ is hydrogen. In some embodiments, $R^2$ is optionally substituted $C_{1-20}$ alkyl. In some embodiments, $R^2$ is optionally substituted $C_{1-15}$ alkyl. In some embodiments, $R^2$ is optionally substituted $C_{1-10}$ alkyl. In some embodiments, $R^2$ is optionally substituted $C_{1-6}$ alkyl. In some embodiments, $R^2$ is optionally substituted $C_{1-6}$ alkyl. In some embodiments, $R^2$ is optionally substituted hexyl, pentyl, butyl, propyl, ethyl or methyl. In some embodiments, $R^2$ is optionally substituted hexyl. In some embodiments, $R^2$ is optionally substituted pentyl. In some embodiments, $R^2$ is optionally substituted butyl. In some embodiments, $R^2$ is optionally substituted propyl. In some embodiments, $R^2$ is optionally substituted ethyl. In some embodiments, $R^2$ is optionally substituted methyl. In some embodiments, $R^2$ is hexyl. In some embodiments, $R^2$ is pentyl. In some embodiments, $R^2$ is butyl. In some embodiments, $R^2$ is propyl. In some embodiments, $R^2$ is ethyl. In some embodiments, $R^2$ is methyl. In some embodiments, $R^2$ is isopropyl. In some embodiments, $R^2$ is n-propyl. In some embodiments, $R^2$ is tert-butyl. In some embodiments, $R^2$ is sec-butyl. In some embodiments, $R^2$ is n-butyl. In some embodiments, $R^2$ is benzyloxymethyl. In some embodiments, $R^2$ is benzyl.

In some embodiments, $R^2$ is optionally substituted $C_{1-20}$ heteroalkyl. In some embodiments, $R^2$ is optionally substituted $C_{1-20}$ heteroalkyl having 1-6 heteroatoms independently selected from nitrogen, sulfur, phosphorus selenium, silicon or boron. In some embodiments, $R^2$ is optionally substituted $C_{1-20}$ heteroalkyl having 1-6 heteroatoms independently selected from nitrogen, sulfur, phosphorus, selenium, silicon or boron, optionally including one or more oxidized forms of nitrogen, sulfur, phosphorus, selenium, silicon or boron.

In some embodiments, $R^2$ is $-[C(R)_2]_q-OR$. In some embodiments, $R^2$ is $-OR$. In some embodiments, $R^2$ is $-OH$. In some embodiments, $R^2$ is $-CH_2OR$. In some embodiments, $R^2$ is $-[C(R)_2]_q-N(R)_2$. In some embodiments, $R^2$ is $-CH_2N(R)_2$. In some embodiments, $R^2$ is $-CH_2NHR$. In some embodiments, $R^2$ is $-[C(R)_2]_q-SR$. In some embodiments, $R^2$ is $-CH_2SR$. In some embodiments, $R^2$ is $-[C(R)_2]_q-OSi(R)_3$. In some embodiments, $R^2$ is $-CH_2OSi(R)_3$. In some embodiments, $R^2$ is $-[C(R)_2]_q-OC(O)R$. In some embodiments, $R^2$ is $-CH_2OC(O)R$. In some embodiments, $R^2$ is $-[C(R)_2]_q-OC(O)OR$. In some embodiments, $R^2$ is $-CH_2OC(O)OR$. In some embodiments, $R^2$ is $-[C(R)_2]_q-OC(O)N(R)_2$. In some embodiments, $R^2$ is $-CH_2OC(O)N(R)_2$. In some embodiments, $R^2$ is $-CH_2OC(O)NHR$. In some embodiments, $R^2$ is $-[C(R)_2]_q-OC(O)N(R)-SO_2R$. In some embodiments, $R^2$ is $-CH_2OC(O)N(R)-SO_2R$. In some embodiments, $R^2$ is $-CH_2OC(O)NHSO_2R$. In some embodiments, $R^2$ is $-[C(R)_2]_q-OP(OR)_2$. In some embodiments, $R^2$ is $-CH_2OP(OR)_2$. In some embodiments, $R^2$ comprises an $-OH$, $-NHR$ or $-SH$ group.

Exemplary $R^2$ groups are depicted below:

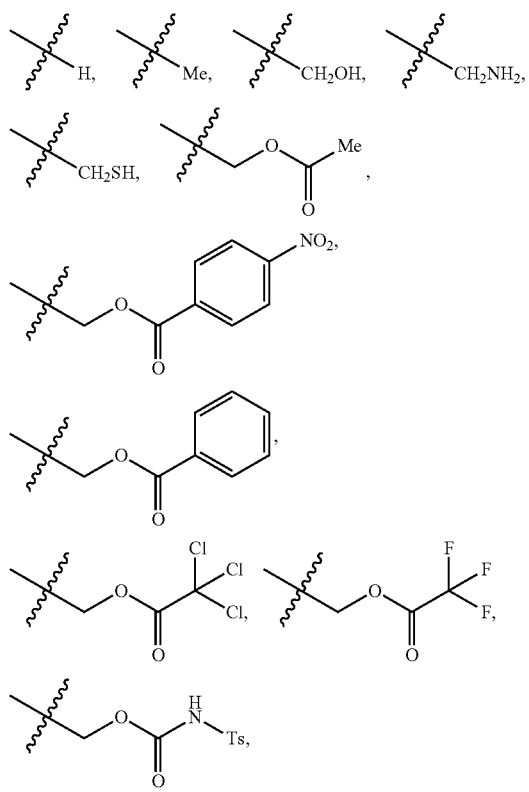

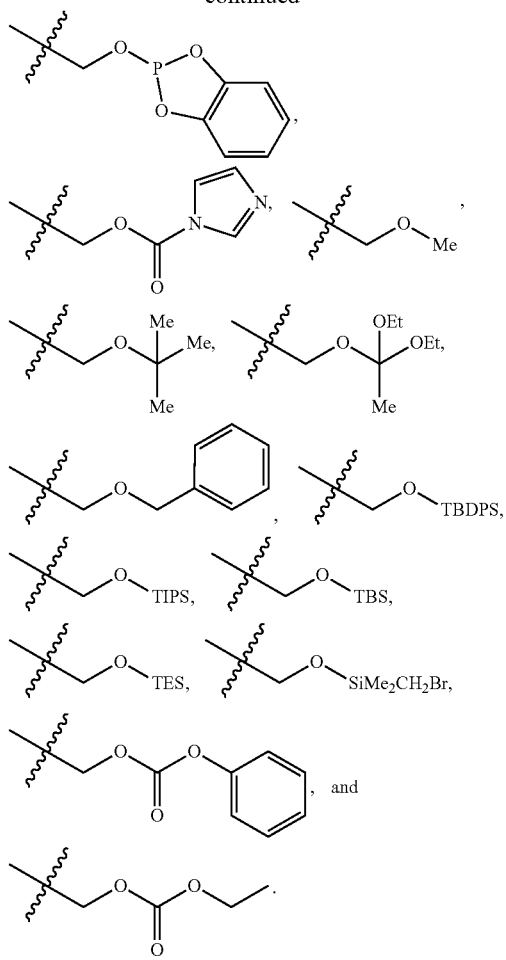

In some embodiments, $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur. In some embodiments, $R^1$ and $R^2$ are taken together with their intervening atoms to form an optionally substituted 4-membered heterocyclic ring having, in addition to the nitrogen atom to which $R^1$ is attached, 0-2 heteroatoms independently selected from oxygen, nitrogen, and sulfur. In some embodiments, $R^1$ and $R^2$ are taken together with their intervening atoms to form an optionally substituted 5-membered heterocyclic ring having, in addition to the nitrogen atom to which $R^1$ is attached, 0-2 heteroatoms independently selected from oxygen, nitrogen, and sulfur. In some embodiments, $R^1$ and $R^2$ are taken together with their intervening atoms to form an optionally substituted 6-membered heterocyclic ring having, in addition to the nitrogen atom to which $R^1$ is attached, 0-2 heteroatoms independently selected from oxygen, nitrogen, and sulfur. In some embodiments, $R^1$ and $R^2$ are taken together with their intervening atoms to form an optionally substituted 7-membered heterocyclic ring having, in addition to the nitrogen atom to which $R^1$ is attached, 0-2 heteroatoms independently selected from oxygen, nitrogen, and sulfur. In some embodiments, $R^1$ and $R^2$ are taken together with their intervening atoms to form

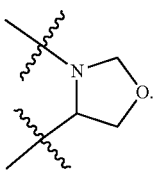 [SMILES: *C1COCN1*]

In some embodiments, $R^1$ and $R^2$ are taken together with their intervening atoms to form substituted or unsubstituted

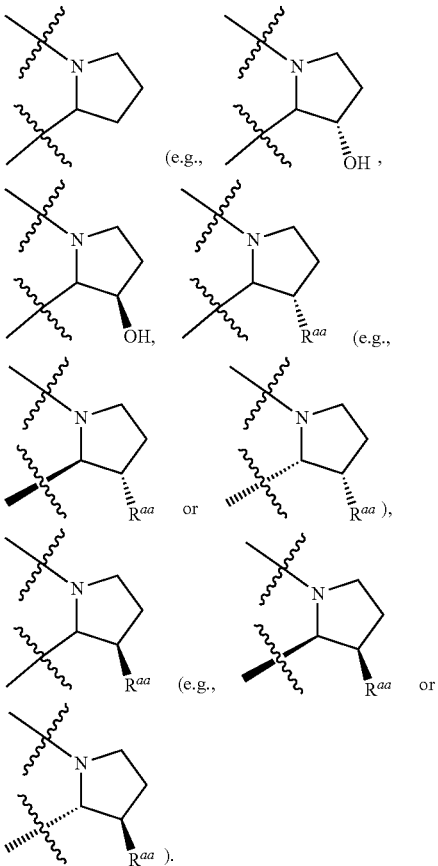

As generally defined above, each q is independently 0, 1, 2, 3 or 4. In some embodiments, q is 0. In some embodiments, q is 1. In some embodiments, q is 2. In some embodiments, q is 3. In some embodiments, q is 4.

In certain embodiments, at least one instance of $R^3$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]2. In certain embodiments, at least one instance of $R^3$ is —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, or —S(O)R. In certain embodiments, at least one instance of $R^3$ is —S(O)$_2$R. In certain embodiments, at least one instance of $R^3$ is —S(O)$_2$ (substituted phenyl). In certain embodiments, at least one instance of $R^3$ is —S(O)$_2$ (unsubstituted phenyl). In certain embodiments, at least one instance of $R^3$ is —C(O)OR, —C(O)N(R)$_2$, or —C(O)N(R)—OR. In certain embodiments, at least one instance of $R^3$ is —C(O)R. In certain embodiments, at least one instance of $R^3$ is —C(O)(substituted phenyl). In certain embodiments, at least one instance of $R^3$ is —C(O)(unsubstituted phenyl). In certain embodiments, at least one instance of $R^3$ is —P(O)(R)$_2$, —P(O)(OR)$_2$, or —P(O)[N(R)$_2$]2. Exemplary $R^3$ groups include:

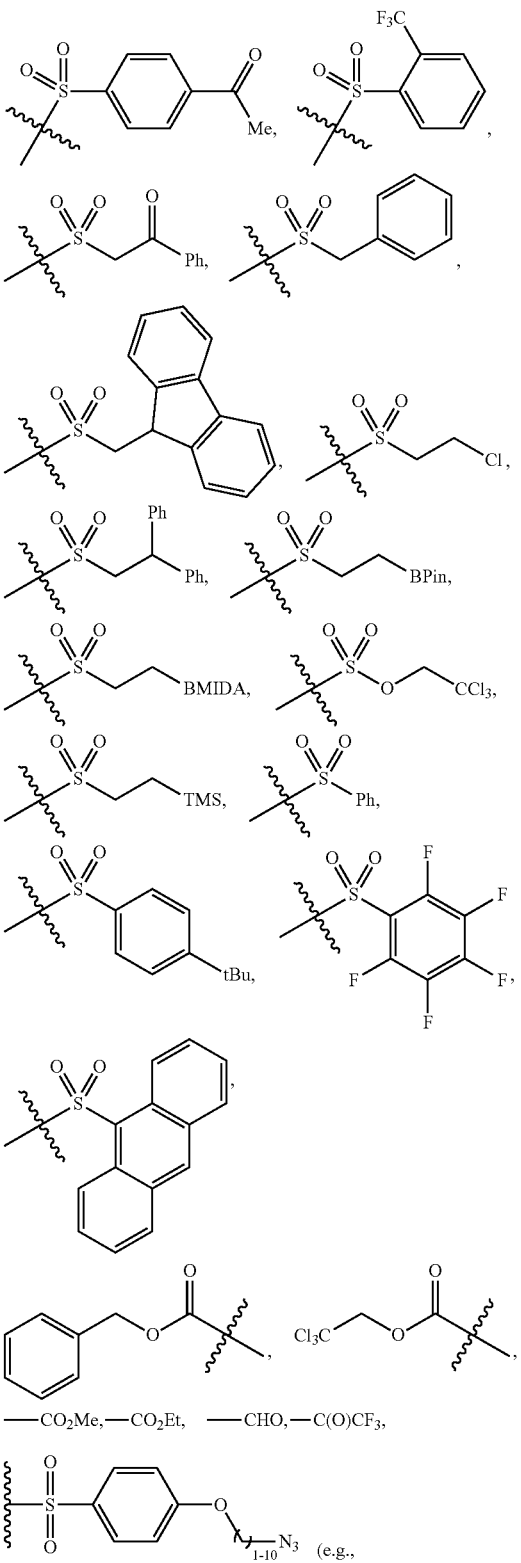

—CO$_2$Me, —CO$_2$Et, —CHO, —C(O)CF$_3$,

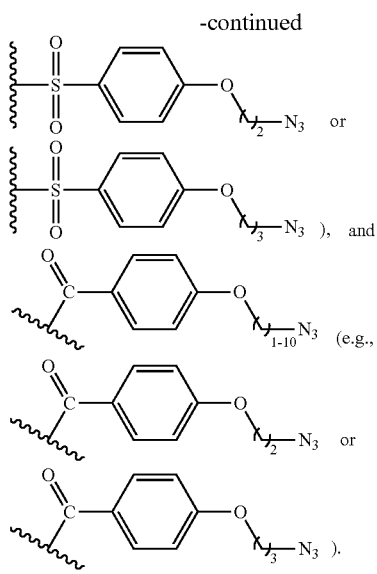

In some embodiments, $R^4$ is absent when ═ is a double bond. In some other embodiments, ═ is a single bond and $R^4$ is R or halogen.

In some embodiments, $R^4$ is R. In some embodiments, $R^4$ is hydrogen. In some embodiments, $R^4$ is an optionally substituted group selected from $C_{1-20}$ alkyl, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, or an 8-14 membered bicyclic or polycyclic heteroaryl ring having 1-5 heteroatoms independently selected from nitrogen, oxygen, and sulfur.

In some embodiments, $R^4$ is an optionally substituted $C_{1-20}$ alkyl. In some embodiments, $R^4$ is an optionally substituted $C_{1-10}$ alkyl. In some embodiments, $R^4$ is an optionally substituted $C_{1-6}$ alkyl. In some embodiments, $R^4$ is optionally substituted $C_{1-6}$ alkyl. In some embodiments, $R^4$ is optionally substituted hexyl, pentyl, butyl, propyl, ethyl or methyl. In some embodiments, $R^4$ is optionally substituted hexyl. In some embodiments, $R^4$ is optionally substituted pentyl. In some embodiments, $R^4$ is optionally substituted butyl. In some embodiments, $R^4$ is optionally substituted propyl. In some embodiments, $R^4$ is optionally substituted ethyl. In some embodiments, $R^4$ is optionally substituted methyl. In some embodiments, $R^4$ is hexyl. In some embodiments, $R^4$ is pentyl. In some embodiments, $R^4$ is butyl. In some embodiments, $R^4$ is propyl. In some embodiments, $R^4$ is ethyl. In some embodiments, $R^4$ is methyl. In some embodiments, $R^4$ is isopropyl. In some embodiments, $R^4$ is n-propyl. In some embodiments, $R^4$ is tert-butyl. In some embodiments, $R^4$ is sec-butyl. In some embodiments, $R^4$ is n-butyl. In some embodiments, $R^4$ is benzyloxymethyl. In some embodiments, $R^4$ is benzyl. In some embodiments, $R^4$ is an optionally substituted $C_{1-6}$ alkyl. In some embodiments, $R^4$ is optionally substituted allyl. In some embodiments, $R^4$ is ally. In some embodiments, $R^4$ is styrenyl. In some embodiments, $R^4$ is other than hydrogen.

In some embodiments, $R^4$ is optionally substituted $C_{1-20}$ heteroalkyl. In some embodiments, $R^4$ is optionally substituted $C_{1-10}$ heteroalkyl. In some embodiments, $R^4$ is optionally substituted $C_{1-6}$ heteroalkyl.

In some embodiments, $R^4$ is optionally substituted phenyl. In some embodiments, $R^4$ is substituted phenyl. In some embodiments, $R^4$ is unsubstituted phenyl. In some embodiments, $R^4$ is p-MeOPh.

In some embodiments, $R^4$ is an optionally substituted 3-7 membered saturated or partially unsaturated carbocyclic ring. In some embodiments, $R^4$ is an optionally substituted 3-membered saturated ring. In some embodiments, $R^4$ is an optionally substituted 4-membered saturated or partially unsaturated carbocyclic ring. In some embodiments, $R^4$ is an optionally substituted 5-membered saturated or partially unsaturated carbocyclic ring. In some embodiments, $R^4$ is an optionally substituted 6-membered saturated or partially unsaturated carbocyclic ring. In some embodiments, $R^4$ is an optionally substituted 7-membered saturated or partially unsaturated carbocyclic ring.

In some embodiments, $R^4$ is an optionally substituted 8-14 membered bicyclic or polycyclic saturated, partially unsaturated or aryl ring. In some embodiments, $R^4$ is an optionally substituted an 8-14 membered bicyclic or polycyclic saturated ring. In some embodiments, $R^4$ is an optionally substituted 8-14 membered bicyclic or polycyclic partially unsaturated ring. In some embodiments, $R^4$ is an optionally substituted 8-14 membered bicyclic or polycyclic aryl ring. In some embodiments, $R^4$ is an optionally substituted 10-membered bicyclic aryl ring. In some embodiments, $R^4$ is an optionally substituted 14-membered tricyclic aryl ring.

In some embodiments, $R^4$ is an optionally substituted 5-6 membered monocyclic heteroaryl ring having 1-4 heteroatoms independently selected from nitrogen, oxygen, and sulfur. In some embodiments, $R^4$ is optionally substituted pyrrolyl. In some embodiments, $R^4$ is optionally substituted pyrrol-3-yl. In some embodiments, $R^4$ is N-TIPS-pyrrol-3-yl. In some embodiments, $R^4$ is pyrrol-3-yl.

In some embodiments, $R^4$ is an optionally substituted 3-7 membered saturated or partially unsaturated heterocyclic ring having 1-3 heteroatoms independently selected from nitrogen, oxygen, and sulfur. In some embodiments, $R^4$ is an optionally substituted 3-7 membered saturated heterocyclic ring having 1-3 heteroatoms independently selected from nitrogen, oxygen, and sulfur. In some embodiments, $R^4$ is an optionally substituted 3-7 membered partially unsaturated heterocyclic ring having 1-3 heteroatoms independently selected from nitrogen, oxygen, and sulfur.

In some embodiments, $R^4$ is an optionally substituted 8-14 membered bicyclic or polycyclic heteroaryl ring having 1-5 heteroatoms independently selected from nitrogen, oxygen, and sulfur. In some embodiments, $R^4$ is an optionally substituted 8-membered bicyclic or polycyclic heteroaryl ring having 1-5 heteroatoms independently selected from nitrogen, oxygen, and sulfur. In some embodiments, $R^4$ is an optionally substituted 8-membered bicyclic heteroaryl ring having 1-5 heteroatoms independently selected from nitrogen, oxygen, and sulfur. In some embodiments, $R^4$ is an optionally substituted 9-membered bicyclic or polycyclic heteroaryl ring having 1-5 heteroatoms independently selected from nitrogen, oxygen, and sulfur. In some embodiments, $R^4$ is an optionally substituted 9-membered bicyclic heteroaryl ring having 1-5 heteroatoms independently selected from nitrogen, oxygen, and sulfur. In some embodiments, R⁴ is an optionally substituted 10-membered bicyclic or polycyclic heteroaryl ring having 1-5 heteroatoms independently selected from nitrogen, oxygen, and sulfur. In some embodiments, R⁴ is an optionally substituted 10-membered bicyclic heteroaryl ring having 1-5 heteroatoms independently selected from nitrogen, oxygen, and sulfur. In some embodiments, R⁴ is an optionally substituted 11-membered bicyclic or polycyclic heteroaryl ring having 1-5 heteroatoms independently selected from nitrogen, oxygen, and sulfur. In some embodiments, R⁴ is an optionally substituted 11-membered tricyclic heteroaryl ring having 1-5 heteroatoms independently selected from nitrogen, oxygen, and sulfur. In some embodiments, R⁴ is an optionally substituted 12-membered bicyclic or polycyclic heteroaryl ring having 1-5 heteroatoms independently selected from nitrogen, oxygen, and sulfur. In some embodiments, R⁴ is an optionally substituted 12-membered tricyclic heteroaryl ring having 1-5 heteroatoms independently selected from nitrogen, oxygen, and sulfur. In some embodiments, R⁴ is an optionally substituted 13-membered bicyclic or polycyclic heteroaryl ring having 1-5 heteroatoms independently selected from nitrogen, oxygen, and sulfur. In some embodiments, R⁴ is an optionally substituted 13-membered tricyclic heteroaryl ring having 1-5 heteroatoms independently selected from nitrogen, oxygen, and sulfur. In some embodiments, R⁴ is an optionally substituted 14-membered bicyclic or polycyclic heteroaryl ring having 1-5 heteroatoms independently selected from nitrogen, oxygen, and sulfur. In some embodiments, R⁴ is an optionally substituted 14-membered tricyclic heteroaryl ring having 1-5 heteroatoms independently selected from nitrogen, oxygen, and sulfur. In some embodiments, R⁴ is optionally substituted indolyl. In some embodiments, R⁴ is optionally substituted indol-3-yl. In some embodiments, R⁴ is indol-3-yl. In some embodiments, R⁴ is

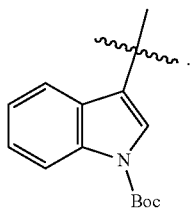 [SMILES: *c1cn(C(=O)OC(C)(C)C)c2ccccc12]

In some embodiments, R⁴ is

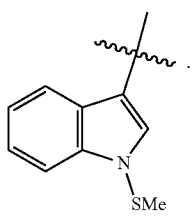 [SMILES: *c1cn(SC)c2ccccc12]

In some embodiments, R⁴ is an optionally substituted group selected from phenyl, a 8-14 membered bicyclic or tricyclic aryl ring, a 5-6 membered monocyclic heteroaryl ring having 1-4 heteroatoms independently selected from nitrogen, oxygen, and sulfur, or an 8-14 membered bicyclic or tricyclic heteroaryl ring having 1-5 heteroatoms independently selected from nitrogen, oxygen, and sulfur. Exemplary R⁴ substituents include

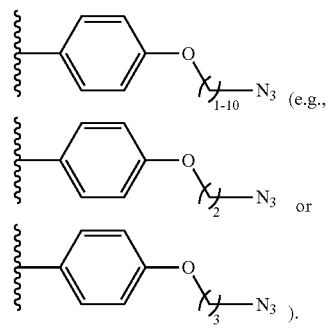

In some embodiments, R⁴ is halogen. In some embodiments, R⁴ is —F. In some embodiments, R⁴ is —Cl. In some embodiments, R⁴ is —Br. In some embodiments, R⁴ is —I. In some embodiments, R⁴ comprises an —OH, —NHR or —SH group.

In certain embodiments, R⁴ is

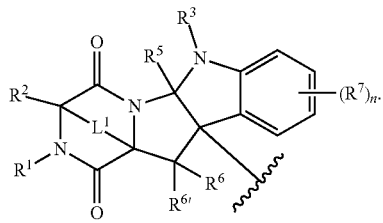

In certain embodiments, R⁴ is

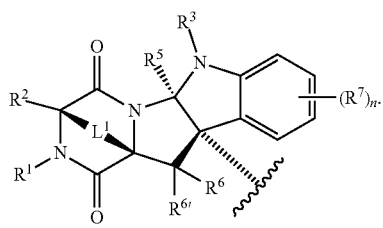

In some embodiments, a compound of Formula (I) is of the formula:

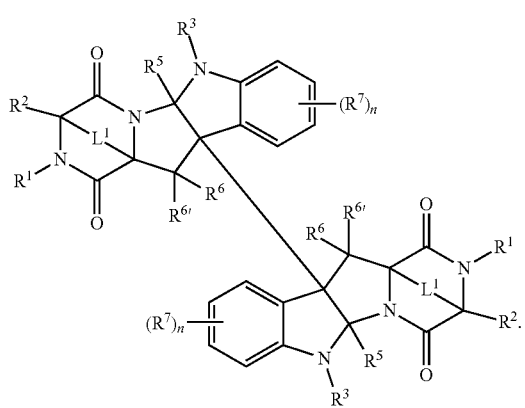

In some embodiments, a compound of Formula (I) is of the formula:

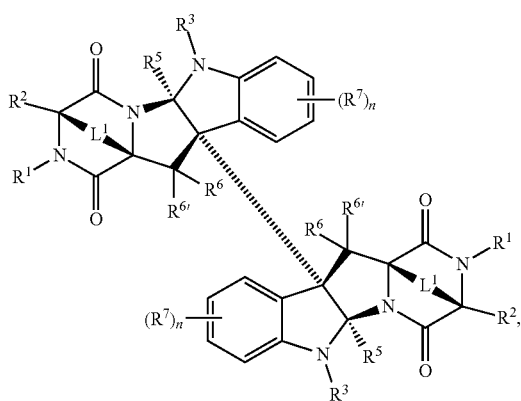

or stereoisomer thereof.

In some embodiments, $R^5$ is absent when ═══ is a double bond. In some embodiments, each $R^5$ is independently hydrogen or an optionally substituted $C_{1-6}$ aliphatic. In some embodiments, $R^5$ is hydrogen. In some embodiments, $R^5$ optionally substituted $C_{1-6}$ aliphatic. In some embodiments, $R^5$ is a substituted $C_{16}$ aliphatic comprising an —OH, —NHR or —SH group.

As generally defined above, each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form ═O, ═C(R)$_2$ or ═NR.

In some embodiments, each of $R^6$ and $R^{6'}$ is hydrogen. In some embodiments, each of $R^6$ and $R^{6'}$ is independently R. In some embodiments, one of $R^6$ and $R^{6'}$ is hydrogen, and the other is R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$. In some embodiments, one of $R^6$ and $R^{6'}$ is hydrogen, and the other is R. In some embodiments, one of $R^6$ and $R^{6'}$ is hydrogen, and the other is halogen. In some embodiments, one of $R^6$ and $R^{6'}$ is hydrogen, and the other is —CN. In some embodiments, one of $R^6$ and $R^{6'}$ is hydrogen, and the other is —NO$_2$. In some embodiments, one of $R^6$ and $R^{6'}$ is hydrogen, and the other is —OR. In some embodiments, one of $R^6$ and $R^{6'}$ is hydrogen, and the other is —SR. In some embodiments, one of $R^6$ and $R^{6'}$ is hydrogen, and the other is —N(R)$_2$. In some embodiments, one of $R^6$ and $R^{6'}$ is hydrogen, and the other is —S(O)$_2$R. In some embodiments, one of $R^6$ and $R^{6'}$ is hydrogen, and the other is —S(O)$_2$N(R)$_2$. In some embodiments, one of $R^6$ and $R^{6'}$ is hydrogen, and the other is —S(O)R. In some embodiments, one of $R^6$ and $R^{6'}$ is hydrogen, and the other is —C(O)R. In some embodiments, one of $R^6$ and $R^{6'}$ is hydrogen, and the other is —C(O)OR. In some embodiments, one of $R^6$ and $R^{6'}$ is hydrogen, and the other is —C(O)N(R)$_2$. In some embodiments, one of $R^6$ and $R^{6'}$ is hydrogen, and the other is —C(O)N(R)—OR. In some embodiments, one of $R^6$ and $R^{6'}$ is hydrogen, and the other is —N(R)C(O)OR. In some embodiments, one of $R^6$ and $R^{6'}$ is hydrogen, and the other is —N(R)C(O)N(R)$_2$. In some embodiments, one of $R^6$ and $R^{6'}$ is hydrogen, and the other is —N(R)S(O)$_2$R. In some embodiments, one of $R^6$ and $R^{6'}$ is hydrogen, and the other is —OSi(R)$_3$. In some embodiments, one of $R^6$ and $R^{6'}$ is hydrogen, and the other is —OSi(R)$_3$, wherein one R is optionally substituted indolyl. In some embodiments, one of $R^6$ and $R^{6'}$ is hydrogen, and the other is —OSi(R)$_3$, wherein one R is optionally substituted indol-2-yl. In some embodiments, one of $R^6$ and $R^{6'}$ is hydrogen, and the other is —OSi(R)$_3$, wherein one R is optionally substituted

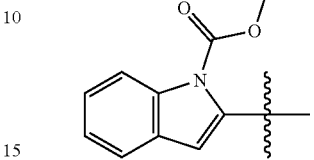

In some embodiments, one of $R^6$ and $R^{6'}$ is hydrogen, and the other is

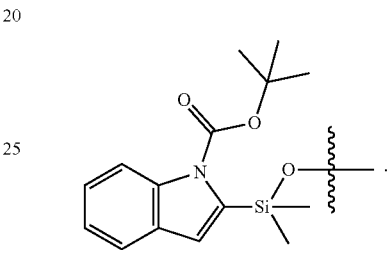

In some embodiments, $R^6$ and $R^{6'}$ are taken together to form ═O, ═C(R)$_2$ or ═NR. In some embodiments, $R^6$ and $R^{6'}$ are taken together to form ═O. In some embodiments, $R^6$ and $R^{6'}$ are taken together to form ═C(R)$_2$. In some embodiments, $R^6$ and $R^{6'}$ are taken together to form ═NR.

In some embodiments, $R^6$ is R. In some embodiments, $R^6$ is hydrogen. In some embodiments, $R^6$ is an optionally substituted group selected from $C_{1-20}$ alkyl, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, or an 8-14 membered bicyclic or polycyclic heteroaryl ring having 1-5 heteroatoms independently selected from nitrogen, oxygen, and sulfur.

In some embodiments, $R^6$ is halogen. In some embodiments, $R^6$ is —F. In some embodiments, $R^6$ is —Cl. In some embodiments, $R^6$ is —Br. In some embodiments, $R^6$ is —I.

In some embodiments, $R^6$ is —CN. In some embodiments, $R^6$ comprises an —OH, —NHR or —SH group. In some embodiments, $R^6$ is —N$_{02}$. In some embodiments, $R^6$ is —OR. In some embodiments, $R^6$ is —SR. In some embodiments, $R^6$ is —N(R)$_2$. In some embodiments, $R^6$ is —S(O)$_2$R. In some embodiments, $R^6$ is —S(O)$_2$N(R)$_2$. In some embodiments, $R^6$ is —S(O)R. In some embodiments, $R^6$ is —C(O)R. In some embodiments, $R^6$ is —C(O)OR. In some embodiments, $R^6$ is —C(O)N(R)$_2$. In some embodiments, $R^6$ is —C(O)N(R)—OR. In some embodiments, $R^6$ is —N(R)C(O)OR. In some embodiments, $R^6$ is —N(R)C(O)N(R)$_2$. In some embodiments, $R^6$ is —N(R)S(O)$_2$R. In some embodiments, $R^6$ is —OSi(R)$_3$. In some embodiments, $R^6$ is —OSi(R)$_3$, wherein one R is optionally substituted indolyl. In some embodiments, $R^6$ is —OSi(R)$_3$, wherein one R is optionally substituted indol-2-yl. In some embodiments, $R^6$ is —OSi(R)$_3$, wherein one R is

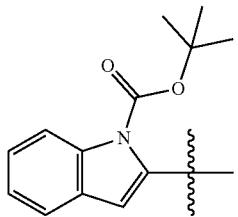

In some embodiments, $R^6$ is

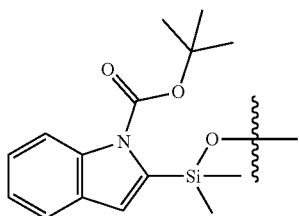

In some embodiments, $R^6$ is hydrogen, and $R^{6'}$ is R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$.

In some embodiments, $R^{6'}$ is R. In some embodiments, $R^{6'}$ is hydrogen. In some embodiments, $R^{6'}$ is an optionally substituted group selected from C$_{1-20}$ alkyl, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, or an 8-14 membered bicyclic or polycyclic heteroaryl ring having 1-5 heteroatoms independently selected from nitrogen, oxygen, and sulfur.

In some embodiments, $R^{6'}$ is halogen. In some embodiments, $R^{6'}$ is —F. In some embodiments, $R^{6'}$ is —C$_1$. In some embodiments, $R^{6'}$ is —Br. In some embodiments, $R^{6'}$ is —I.

In some embodiments, $R^{6'}$ is —CN. In some embodiments, $R^{6'}$ comprises an —OH, —NHR or —SH group. In some embodiments, $R^{6'}$ is —N$_{02}$. In some embodiments, $R^{6'}$ is —OR. In some embodiments, $R^{6'}$ is —SR. In some embodiments, $R^{6'}$ is —N(R)$_2$. In some embodiments, $R^{6'}$ is —S(O)$_2$R. In some embodiments, $R^{6'}$ is —S(O)$_2$N(R)$_2$. In some embodiments, $R^{6'}$ is —S(O)R. In some embodiments, $R^{6'}$ is —C(O)R. In some embodiments, $R^{6'}$ is —C(O)OR. In some embodiments, $R^{6'}$ is —C(O)N(R)$_2$. In some embodiments, $R^{6'}$ is —C(O)N(R)—OR. In some embodiments, $R^{6'}$ is —N(R)C(O)OR. In some embodiments, $R^{6'}$ is —N(R)C(O)N(R)$_2$. In some embodiments, $R^{6'}$ is —N(R)S(O)$_2$R. In some embodiments, $R^{6'}$ is —OSi(R)$_3$. In some embodiments, $R^{6'}$ is —OSi(R)$_3$, wherein one R is optionally substituted indolyl. In some embodiments, $R^{6'}$ is —OSi(R)$_3$, wherein one R is optionally substituted indol-2-yl. In some embodiments, $R^{6'}$ is —OSi(R)$_3$, wherein one R is

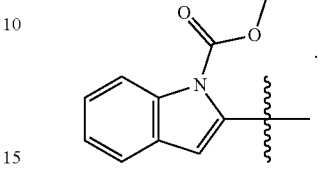

In some embodiments, $R^{6'}$ is

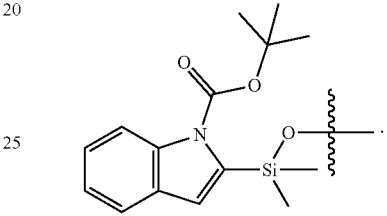

In some embodiments, n is 0, 1, 2, 3 or 4. In some embodiments, n is 0. In some embodiments, n is 1-4. In some embodiments, n is 1. In some embodiments, n is 2. In some embodiments, n is 3. In some embodiments, n is 4.

As generally defined above, each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]2, —B(R)$_2$, —B(OR)$_2$, or —Si(R)$_3$; or two $R^7$ are taken together with their intervening atoms to form an optionally substituted 4-7 membered ring having 0-2 heteroatoms independently selected from nitrogen, oxygen, and sulfur. In some embodiments, each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$. In some embodiments, two $R^7$ are taken together with their intervening atoms to form an optionally substituted 4-7 membered ring having 0-2 heteroatoms independently selected from nitrogen, oxygen, and sulfur.

In some embodiments, $R^7$ is R. In some embodiments, $R^7$ is hydrogen. In some embodiments, $R^7$ is independently hydrogen or an optionally substituted group selected from C$_{1-20}$ alkyl, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, or an 8-14 membered bicyclic or polycyclic heteroaryl ring having 1-5 heteroatoms independently selected from nitrogen, oxygen, and sulfur.

In some embodiments, $R^7$ is halogen. In some embodiments, $R^7$ is —F. In some embodiments, $R^7$ is —Cl. In some embodiments, $R^7$ is —Br. In some embodiments, $R^7$ is —I.

In some embodiments, $R^7$ is —CN. In some embodiments, $R^7$ comprises an —OH, —NHR, or —SH group. In some embodiments, $R^7$ is —NO$_2$. In some embodiments, $R^7$ is —OR. In some embodiments, $R^7$ is —OSi(R)$_3$. In some embodiments, $R^7$ is —SR. In some embodiments, $R^7$ is —N(R)$_2$. In some embodiments, $R^7$ is —S(O)$_2$R. In some embodiments, $R^7$ is —S(O)$_2$OR. In some embodiments, $R^7$ is —S(O)$_2$N(R)$_2$. In some embodiments, $R^7$ is —S(O)R. In some embodiments, $R^7$ is —C(O)R. In some embodiments, $R^7$ is —C(O)OR. In some embodiments, $R^7$ is —C(O)N(R)$_2$. In some embodiments, $R^7$ is —C(O)N(R)—OR. In some embodiments, $R^7$ is —N(R)C(O)OR. In some embodiments, $R^7$ is —N(R)C(O)N(R)$_2$. In some embodiments, $R^7$ is —N(R)S(O)$_2$R. In some embodiments, $R^7$ is —P(R)$_2$. In some embodiments, $R^7$ is —P(OR)$_2$. In some embodiments, $R^7$ is —P(O)(R)$_2$. In some embodiments, $R^7$ is —P(O)(OR)$_2$. In some embodiments, $R^7$ is —P(O)[N(R)$_2$]$_2$. In some embodiments, $R^7$ is —B(R)$_2$. In some embodiments, $R^7$ is —B(OR)$_2$. In some embodiments, $R^7$ is —Si(R)$_3$.

In some embodiments, $R^7$ is an electron-withdrawing group. In some embodiments, $R^7$ is an electron-donating group.

In some embodiments, n is 1, 2, 3 or 4, and at least one $R^7$ is not hydrogen.

As generally defined above, each $L^1$ is independently —S—, —(S)$_m$—[C(R)$_2$]$_q$—(S)$_p$—, —(S)$_m$(S)$_p$—, —(S)$_m$C(O)—(S)$_p$—, —(S)$_m$C(S)—(S)$_p$—, —(S)$_m$S(O)—(S)$_p$—, or —(S)$_m$S(O)$_2$—(S)$_p$—. In some embodiments, each $L^1$ is independently —S—, —(S)$_m$—[C(R)$_2$]$_q$—(S)$_p$—, —(S)$_m$(S)$_p$—, —(S)$_m$C(O)—(S)$_p$—, —(S)$_m$C(S)—(S)$_p$—, —(S)$_m$S(O)—(S)$_p$—, or —(S)$_m$S(O)$_2$—(S)$_p$—. In some embodiments, each $L^1$ is independently —S—, —(S)$_m$C(R)$_2$—(S)$_p$—, —(S)$_m$(S)$_p$—, —(S)$_m$C(O)—(S)$_p$—, —(S)$_m$—C(S)—(S)$_p$—, —(S)$_m$S(O)—(S)$_p$—, or —(S)$_m$S(O)$_2$—(S)$_p$—. In some embodiments, each $L^1$ is independently —(S)$_m$(S)$_p$—, —(S)$_m$C(O)—(S)$_p$—, —(S)$_m$—C(S)—(S)$_p$—, —(S)$_m$—S(O)—(S)$_p$—, or —(S)$_m$—S(O)$_2$—(S)$_p$—. In some embodiments, each $L^1$ is independently —S—. In some embodiments, each $L^1$ is independently —S—S—. In some embodiments, each $L^1$ is independently —(S)$_m$—[C(R)$_2$]$_q$—(S)$_p$—. In some embodiments, each $L^1$ is independently —(S)$_m$C(R)$_2$—(S)$_p$—. In some embodiments, each $L^1$ is independently —(S)$_m$—CH$_2$—(S)$_p$—. In some embodiments, each $L^1$ is independently —S—CH$_2$—S—. In some embodiments, each $L^1$ is independently —(S)$_m$—(S)$_p$—. In some embodiments, each $L^1$ is independently —S—S—. In some embodiments, each $L^1$ is independently —S—S—S—. In some embodiments, each $L^1$ is independently —S—S—S—S—. In some embodiments, each $L^1$ is independently —(S)$_m$C(O)—(S)$_p$—. In some embodiments, each $L^1$ is independently —S—C(O)—S—. In some embodiments, each $L^1$ is independently —(S)$_m$C(S)—(S)$_p$—. In some embodiments, each $L^1$ is independently —S—C(S)—S—. In some embodiments, each $L^1$ is independently —(S)$_m$—S(O)—(S)$_p$—. In some embodiments, each $L^1$ is independently —S—S(O)—S—. In some embodiments, each $L^1$ is independently —(S)$_m$S(O)$_2$—(S)$_p$—. In some embodiments, each $L^1$ is independently —S—S(O)$_2$—S—. In certain embodiments, each $L^1$ can be cleaved. In some embodiments, each $L^1$ can be cleaved when administered to a subject.

In some embodiments, m is 1. In some embodiments, m is 2-3. In some embodiments, m is 2. In some embodiments, m is 3.

In some embodiments, p is 1. In some embodiments, p is 2-3. In some embodiments, p is 2. In some embodiments, p is 3.

In some embodiments, $R^1$ is R, wherein R is -$L^2$-$R^H$-$L^3$-D. In certain embodiments, a compound of Formula (I) is of the formula:

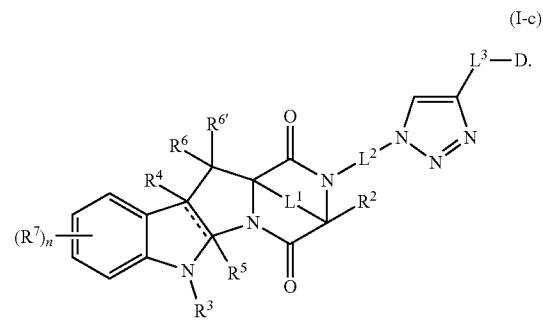

(I-c)

In certain embodiments, a compound of Formula (I) is of the formula:

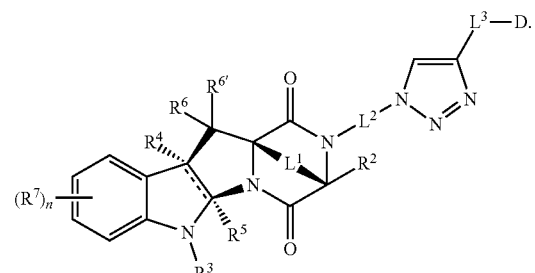

In certain embodiments of a compound of formula (I-c), $L^2$ is substituted or unsubstituted $C_{1-20}$ heteroalkylene comprising one or more backbone oxygen atoms. In certain embodiments of a compound of formula (I-c), $L^2$ is substituted or unsubstituted $C_{1-20}$ alkylene. In certain embodiments of a compound of formula (I-c), $L^2$ is

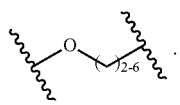

In certain embodiments of a compound of formula (I-c), $L^2$ is

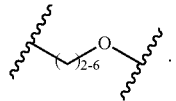

In certain embodiments, a compound of Formula (I) is of the formula:

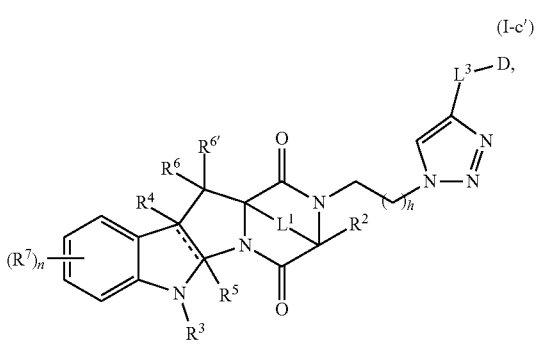

(I-c')

wherein h is an integer 0 to 10, inclusive. In certain embodiments, a compound of Formula (I) is of the formula:

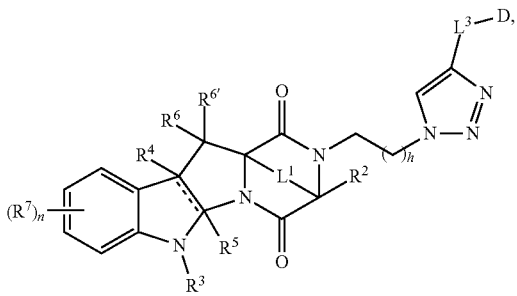

wherein h is 3. In certain embodiments, a compound of Formula (I) is of the formula:

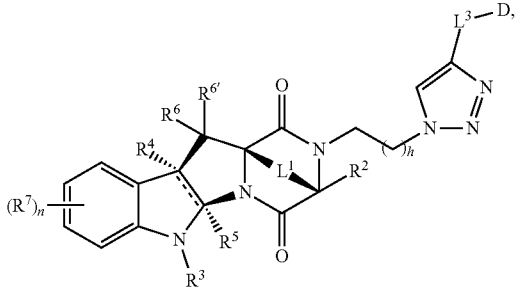

wherein h is an integer 0 to 10, inclusive. In certain embodiments, a compound of Formula (I) is of the formula:

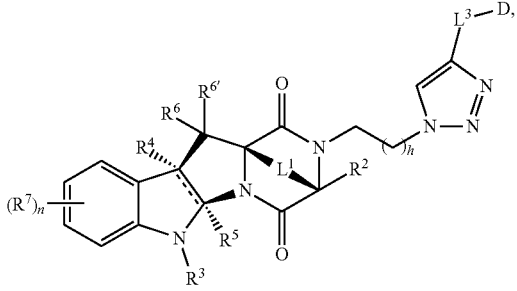

wherein h is 3.

In certain embodiments of a compound of formula (I-c) or (I-c'), $L^3$ comprises phenylene. In certain embodiments of a compound of formula (I-c) or (I-c'), $L^3$ comprises substituted or unsubstituted,

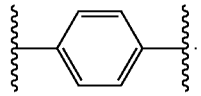

In some embodiments of a compound of formula (I-c) or (I-c'), $L^3$ comprises substituted or unsubstituted,

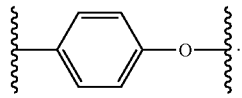

In certain embodiments of a compound of formula (I-c) or (I-c'), $L^3$ comprises a $C_{1-20}$ heteroalkylene. In certain embodiments of a compound of formula (I-c) or (I-c'), $L^3$ comprises substituted or unsubstituted, $C_{1-20}$ heteroalkylene with one or more backbone atoms selected from oxygen and nitrogen. In certain embodiments of a compound of formula (I-c) or (I-c'), $L^3$ comprises

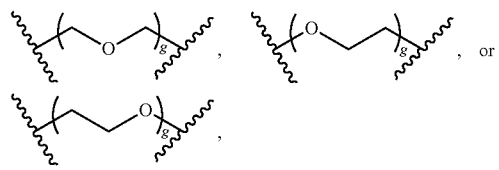

wherein g is 1, 2, or 3. In certain embodiments of a compound of formula (I-c) or (I-c'), $L^3$ comprises substituted or unsubstituted phenylene. In certain embodiments of a compound of formula (I-c) or (I-c'), $L^3$ comprises a substituted $C_{1-20}$ heteroalkylene with one or more backbone atoms selected from oxygen and nitrogen and a backbone substituted or unsubstituted phenylene.

In certain embodiments of a compound of formula (I-c) or (I-c'), D is absent, and $L^3$ comprises phenylene. In certain embodiments of a compound of formula (I-c) or (I-c'), D is absent, and $L^3$ comprises a $C_{1-20}$ heteroalkyl. In certain embodiments of a compound of formula (I-c) or (I-c'), D is absent, and $L^3$ comprises substituted or unsubstituted, $C_{1-20}$ heteroalkyl with one or more backbone atoms selected from oxygen and nitrogen. In certain embodiments of a compound of formula (I-c) or (I-c'), D is absent, and $L^3$ comprises

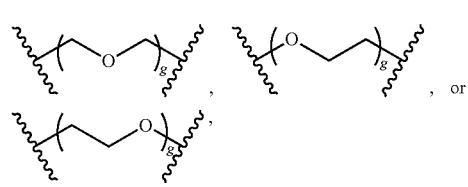

wherein g is 1, 2, or 3. In certain embodiments of a compound of formula (I-c) or (I-c'), D is absent, and $L^3$ comprises a substituted $C_{1-20}$ heteroalkyl with one or more backbone atoms selected from oxygen and nitrogen and a backbone substituted or unsubstituted phenylene. In certain embodiments of a compound of formula (I-c) or (I-c'), D is absent, and $L^3$ is para-methoxyphenyl.

In certain embodiments, h is 1. In some embodiments, h is 2. In certain embodiments, h is 3. In some embodiments, h is 4, 5, or 6. In certain embodiments, h is 7, 8, or 9.

In some embodiments, $R^3$ comprises R, wherein R is -$L^2$-$R^H$-$L^3$-D. In certain embodiments, $R^3$ is —S(O)$_2$R, wherein R is -$L^2$-$R^H$-$L^3$-D. In some embodiments, $R^3$ is —C(=O)R, wherein R is -$L^2$-$R^H$-$L^3$-D. In certain embodiments, a compound of Formula (I) is of the formula:

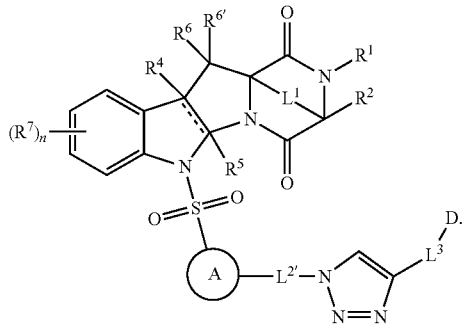

(I-b)

In some embodiments, a compound of Formula (I) is of the formula:

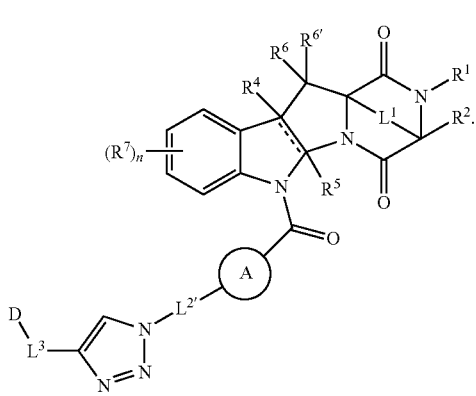

(I-b-i)

In certain embodiments, a compound of Formula (I) is of the formula:

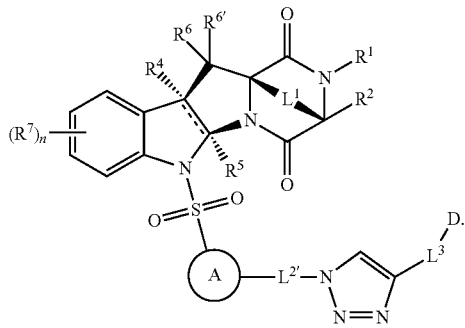

In some embodiments, a compound of Formula (I) is of the formula:

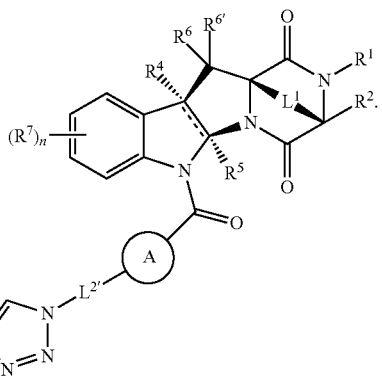

In certain embodiments of a compound of formula (I-b) or (I-b-i), Ring A is substituted or unsubstituted phenylene, substituted or unsubstituted indolylene, or substituted or unsubstituted pyrrolylene. In certain embodiments of a compound of formula (I-b) or (I-b-i), Ring A is substituted or unsubstituted phenylene. In certain embodiments of a compound of formula (I-b) or (I-b-i), $L^{2'}$ is substituted or unsubstituted $C_{1-20}$ heteroalkylene comprising one or more backbone oxygen atoms. In certain embodiments of a compound of formula (I-b) or (I-b-i), $L^{2'}$ is substituted or unsubstituted $C_{1-20}$ alkylene. In certain embodiments of a compound of formula (I-b) or (I-b-i), $L^{2'}$ is

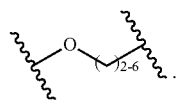

In certain embodiments of a compound of formula (I-b) or (I-b-i), $L^{2'}$ is

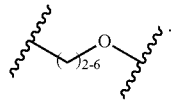

In certain embodiments, a compound of Formula (I) is of the formula:

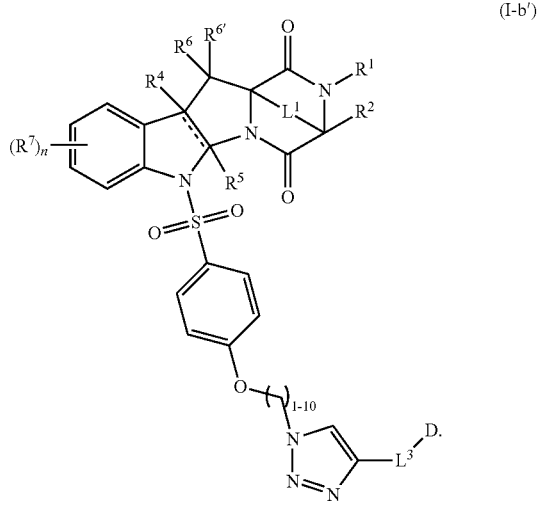

(I-b')

In some embodiments, a compound of Formula (I) is of the formula:

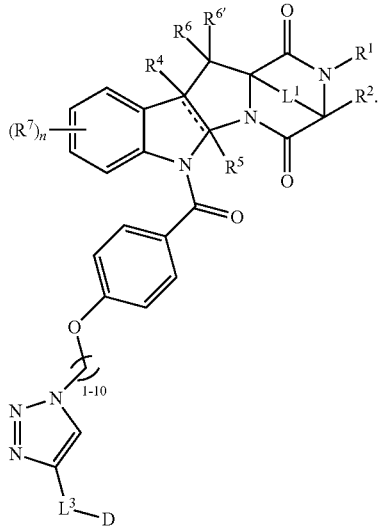

(I-b-i')

In certain embodiments, a compound of Formula (I) is of the formula:

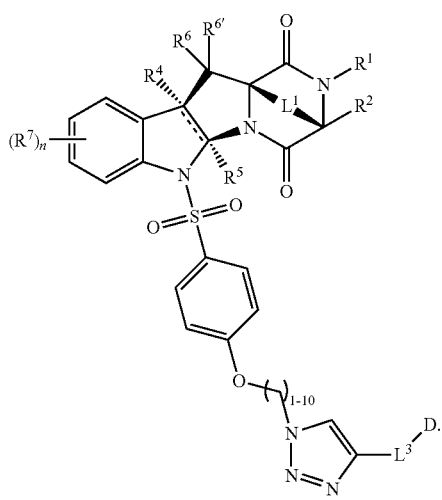

In some embodiments, a compound of Formula (I) is of the formula:

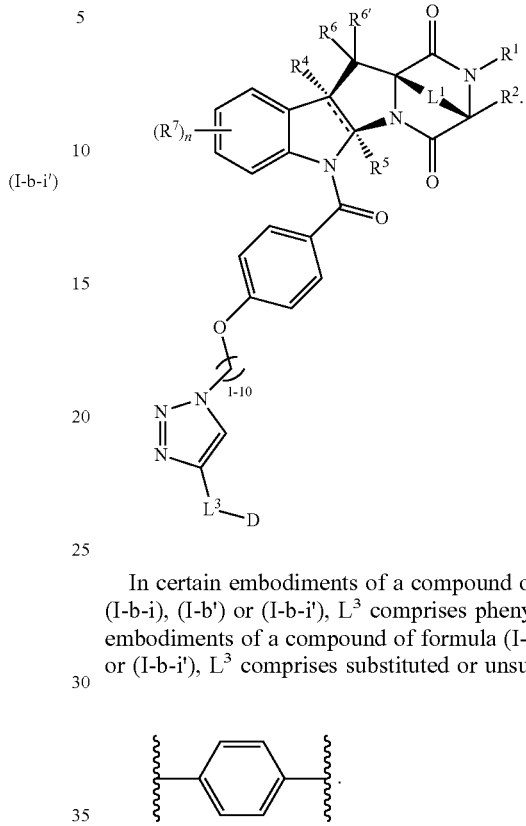

In certain embodiments of a compound of formula (I-b), (I-b-i), (I-b') or (I-b-i'), $L^3$ comprises phenylene. In certain embodiments of a compound of formula (I-b), (I-b-i), (I-b') or (I-b-i'), $L^3$ comprises substituted or unsubstituted, $$\text{(phenylene)}$$

In some embodiments of a compound of formula (I-b), (I-b-i), (I-b') or (I-b-i'), $L^3$ comprises substituted or unsubstituted, $$\text{(phenylene-O-)}$$

In certain embodiments of a compound of formula (I-b), (I-b-i), (I-b') or (I-b-i'), $L^3$ comprises a $C_{1-20}$ heteroalkylene. In certain embodiments of a compound of formula (I-b), (I-b-i), (I-b') or (I-b-i'), $L^3$ comprises substituted or unsubstituted, $C_{1-20}$ heteroalkylene with one or more backbone atoms selected from oxygen and nitrogen. In certain embodiments of a compound of formula (I-b), (I-b-i), (I-b') or (I-b-i'), $L^3$ comprises

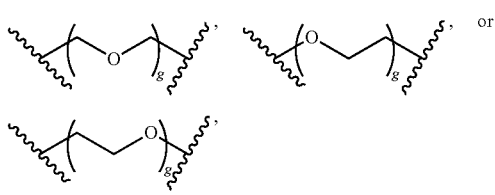

wherein g is 1, 2, or 3. In certain embodiments of a compound of formula (I-b), (I-b-i), (I-b') or (I-b-i'), $L^3$ comprises substituted or unsubstituted phenylene. In certain embodiments of a compound of formula (I-b), (I-b-i), (I-b') or (I-b-i'), $L^3$ comprises a substituted $C_{1-20}$ heteroalkylene with one or more backbone atoms selected from oxygen and nitrogen and a backbone substituted or unsubstituted phenylene.

In certain embodiments of a compound of formula (I-b), (I-b-i), (I-b') or (I-b-i'), D is absent, and $L^3$ comprises phenylene. In certain embodiments of a compound of formula (I-b), (I-b-i), (I-b') or (I-b-i'), D is absent, and $L^3$ comprises a $C_{1-20}$ heteroalkyl. In certain embodiments of a compound of formula (I-b), (I-b-i), (I-b') or (I-b-i'), D is absent, and $L^3$ comprises substituted or unsubstituted, $C_{1-20}$ heteroalkyl with one or more backbone atoms selected from oxygen and nitrogen. In certain embodiments of a compound of formula (I-b), (I-b-i), (I-b') or (I-b-i'), D is absent, and $L^3$ comprises a substituted $C_{1-20}$ heteroalkyl with one or more backbone atoms selected from oxygen and nitrogen and a backbone substituted or unsubstituted phenylene. In certain embodiments of a compound of formula (I-b), (I-b-i), (I-b') or (I-b-i'), D is absent, and $L^3$ is para-methoxyphenyl.

In some embodiments, $R^4$ is R, wherein R is $-L^2-R^H-L^3-$D. In certain embodiments, a compound of Formula (I) is of the formula:

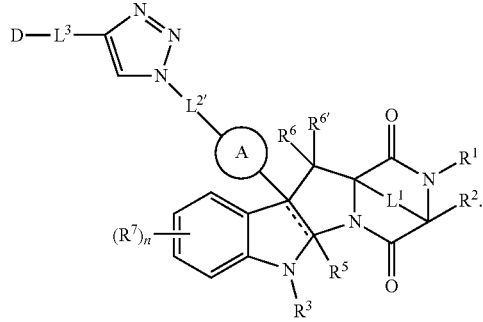

(I-a)

In certain embodiments, a compound of Formula (I) is of the formula:

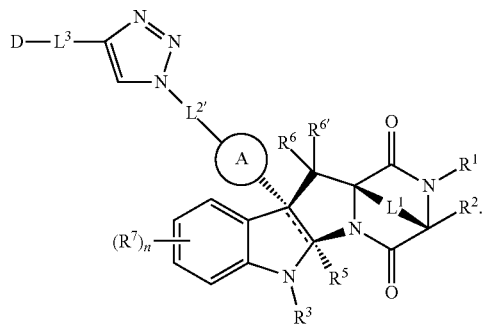

In certain embodiments of a compound of formula (I-a), Ring A is substituted or unsubstituted phenylene, substituted or unsubstituted indolylene, or substituted or unsubstituted pyrrolylene. In certain embodiments of a compound of formula (I-a), Ring A is substituted or unsubstituted phenylene. In certain embodiments of a compound of formula (I-a), $L^{2'}$ is substituted or unsubstituted $C_{1-20}$ heteroalkylene comprising one or more backbone oxygen atoms. In certain embodiments of a compound of formula (I-a), $L^{2'}$ is substituted or unsubstituted $C_{1-20}$ alkylene. In certain embodiments of a compound of formula (I-a), $L^{2'}$ is

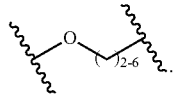

In certain embodiments of a compound of formula (I-a), $L^{2'}$ is

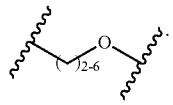

In certain embodiments, a compound of Formula (I) is of the formula:

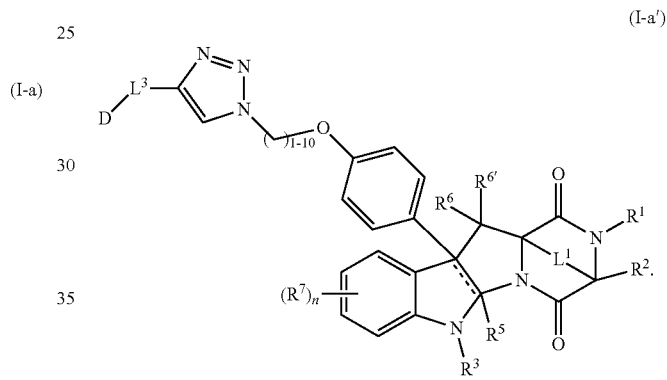

In certain embodiments, a compound of Formula (I) is of the formula:

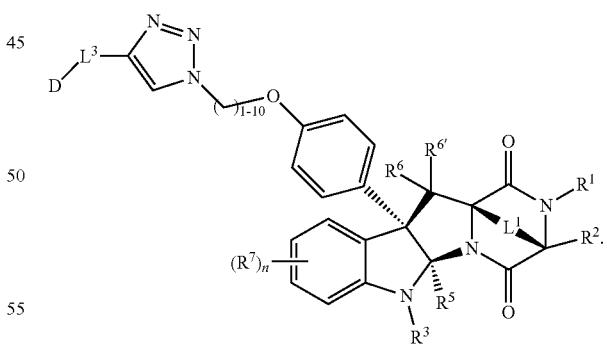

In certain embodiments of a compound of formula (I-a) or (I-a'), $L^3$ comprises phenylene. In embodiments of a compound of formula (I-a) or (I-a'), $L^3$ comprises a $C_{1-20}$ heteroalkylene. In certain embodiments of a compound of formula (I-a) or (I-a'), $L^3$ comprises substituted or unsubstituted, $C_{1-20}$ heteroalkylene with one or more backbone atoms selected from oxygen and nitrogen. In certain embodiments of a compound of formula (I-a) or (I-a'), $L^3$ comprises

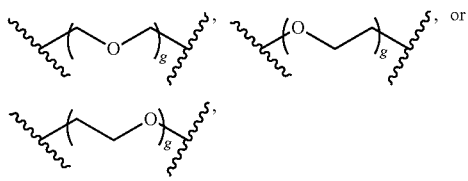

wherein g is 1, 2, or 3. In certain embodiments of a compound of formula (I-a) or (I-a'), $L^3$ comprises substituted or unsubstituted phenylene. In certain embodiments of a compound of formula (I-a) or (I-a'), $L^3$ comprises a substituted $C_{1-20}$ heteroalkylene with one or more backbone atoms selected from oxygen and nitrogen and a backbone substituted or unsubstituted phenylene. In certain embodiments of a compound of formula (I-a) or (I-a'), $L^3$ comprises substituted or unsubstituted,

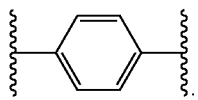

In some embodiments of a compound of formula (I-a) or (I-a'), $L^3$ comprises substituted or unsubstituted,

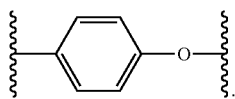

In some embodiments of a compound of formula (I-a) or (I-a'), $L^3$ is a substituted $C_{1-20}$ alkylene, wherein at least one substituent on the $C_{1-20}$ alkylene is —NHBoc. In some embodiments of a compound of formula (I-a) or (I-a'), $L^3$ is a substituted $C_{1-20}$ heteroalkyl wherein at least one substituent on the $C_{1-20}$ heteroalkylene is —NHBoc. In certain embodiments of a compound of formula (I-a) or (I-a'), $L^3$ is a substituted $C_{1-20}$ heteroalkylene with one or more backbone atoms selected from oxygen and nitrogen and a backbone substituted or unsubstituted phenylene, wherein at least one substituent on the $C_{1-20}$ heteroalkylene is —NHBoc. In some embodiments of a compound of formula (I-a) or (I-a'), $L^3$ is a substituted $C_{1-20}$ alkylene, wherein at least one substituent on the $C_{1-20}$ alkylene is —NH$_2$. In some embodiments of a compound of formula (I-a) or (I-a'), $L^3$ is a substituted $C_{1-20}$ heteroalkyl wherein at least one substituent on the $C_{1-20}$ heteroalkylene is —NH$_2$. In certain embodiments of a compound of formula (I-a) or (I-a'), $L^3$ is a substituted $C_{1-20}$ heteroalkylene with one or more backbone atoms selected from oxygen and nitrogen and a backbone substituted or unsubstituted phenylene, wherein at least one substituent on the $C_{1-20}$ heteroalkylene is —NH$_2$.

In certain embodiments of a compound of formula (I-a) or (I-a'), D is absent, and $L^3$ comprises phenylene. In certain embodiments of a compound of formula (I-a) or (I-a'), D is absent, and $L^3$ comprises a $C_{1-20}$ heteroalkyl. In certain embodiments of a compound of formula (I-a) or (I-a'), D is absent, and $L^3$ comprises substituted or unsubstituted, $C_{1-20}$ heteroalkyl with one or more backbone atoms selected from oxygen and nitrogen. In certain embodiments of a compound of formula (I-a) or (I-a'), D is absent, and $L^3$ comprises

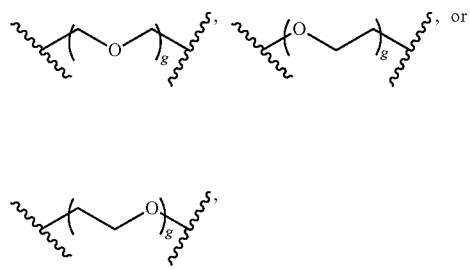

wherein g is 1, 2, or 3. In certain embodiments of a compound of formula (I-a) or (I-a'), D is absent, and $L^3$ comprises a substituted $C_{1-20}$ heteroalkyl with one or more backbone atoms selected from oxygen and nitrogen and a backbone substituted or unsubstituted phenylene. In certain embodiments of a compound of formula (I-aa) or (I-a'), D is absent, and $L^3$ comprises substituted or unsubstituted,

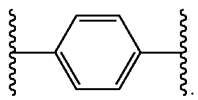

In some embodiments of a compound of formula (I-a) or (I-a'), D is absent, and $L^3$ comprises substituted or unsubstituted,

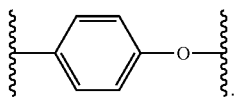

In some embodiments of a compound of formula (I-a) or (I-a'), D is absent, and $L^3$ is a substituted $C_{1-20}$ alkyl wherein at least one substituent on the $C_{1-20}$ alkyl is —NHBoc. In some embodiments of a compound of formula (I-a) or (I-a'), D is absent, and $L^3$ is a substituted $C_{1-20}$ heteroalkyl wherein at least one substituent on the $C_{1-20}$ heteroalkyl is —NHBoc. In certain embodiments of a compound of formula (I-a) or (I-a'), D is absent, and $L^3$ is a substituted $C_{1-20}$ heteroalkyl with one or more backbone atoms selected from oxygen and nitrogen and a backbone substituted or unsubstituted phenylene, wherein at least one substituent on the $C_{1-20}$ heteroalkyl is —NHBoc. In some embodiments of a compound of formula (I-a) or (I-a'), D is absent, and $L^3$ is a substituted $C_{1-20}$ alkyl wherein at least one substituent on the $C_{1-20}$ alkyl is —NH$_2$. In some embodiments of a compound of formula (I-a) or (I-a'), D is absent, and $L^3$ is a substituted $C_{1-20}$ heteroalkyl wherein at least one substituent on the $C_{1-20}$ heteroalkyl is —NH$_2$. In certain embodiments of a compound of formula (I-a) or (I-a'), D is absent, and $L^3$ is a substituted $C_{1-20}$ heteroalkyl with one or more backbone atoms selected from oxygen and nitrogen and a backbone substituted or unsubstituted phenylene, wherein at least one substituent on the $C_{1-20}$ heteroalkyl is —NH$_2$. In certain embodiments of a compound of formula (I-a) or (I-a'), D is absent, and $L^3$ is para-methoxyphenyl.

In certain embodiments, a compound of Formula (I) is of the formula:

83
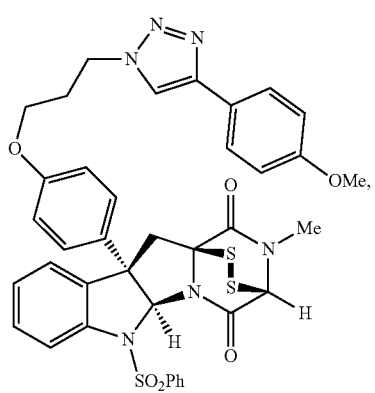
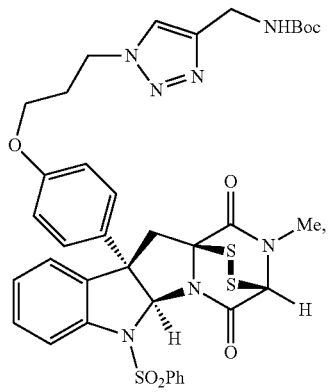
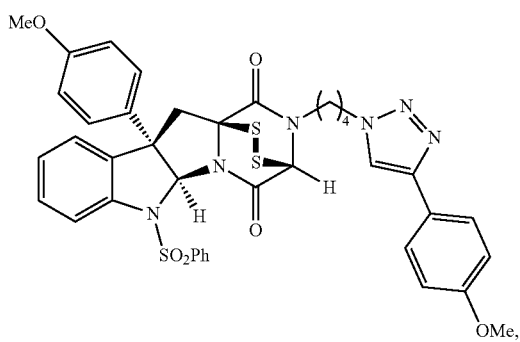
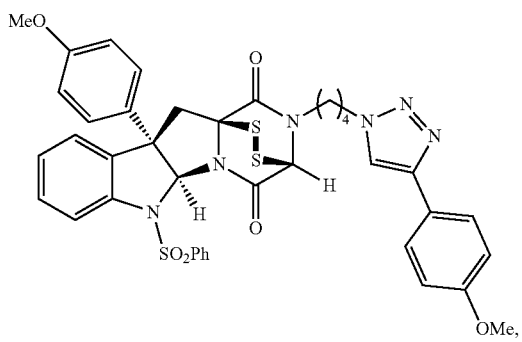
84
-continued
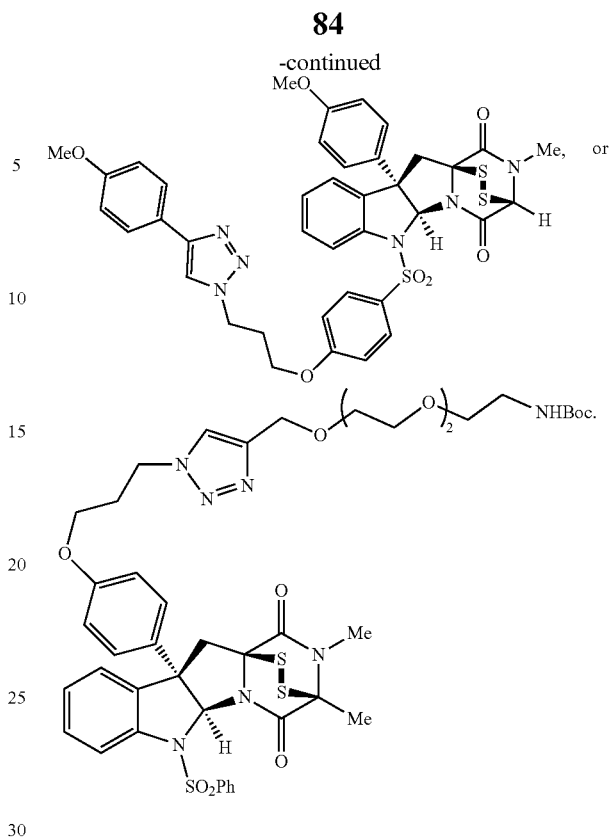
In some embodiments, a compound of Formula (I) is of the formula:
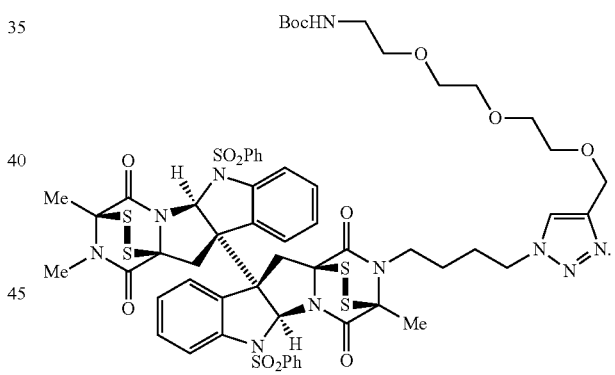
In some embodiments, the present disclosure provides a compound having the structure of Formula (II):
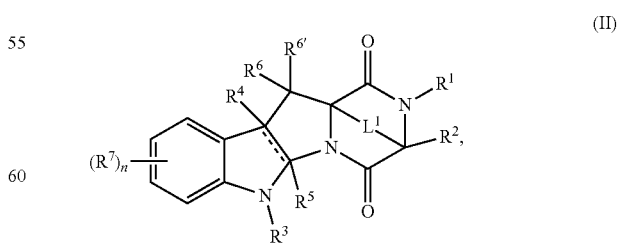
(II)
or a salt thereof, wherein:
each ═ is independently a single bond or a double bond, as valency permits;

each R¹ is independently R, —C(O)R, —C(O)N(R)₂, —S(O)R, —S(O)₂R, —S(O)₂OR, —C(R)₂OR, or —S(O)₂N(R)₂;

each R is independently hydrogen, -L²-R^H1, or an optionally substituted group selected from C₁₋₂₀ alkyl, C₁₋₂₀ heteroalkyl, phenyl, a 3-7 membered saturated or partially unsaturated, carbocyclic ring, an 8-14 membered bicyclic or polycyclic, saturated carbocyclic ring, partially unsaturated carbocyclic ring, or aryl ring, a 5-6 membered monocyclic heteroaryl ring having 1-4 heteroatoms independently selected from nitrogen, oxygen, and sulfur, a 3-7 membered saturated or partially unsaturated, heterocyclic ring having 1-3 heteroatoms independently selected from nitrogen, oxygen, and sulfur, a 7-14 membered bicyclic or polycyclic, saturated or partially unsaturated, heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or:

two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;

each R² is independently R, —[C(R)₂]_q—OR, —[C(R)₂]_q—N(R)₂, —[C(R)₂]_q—SR, —[C(R)₂]_q—OSi(R)₃, —[C(R)₂]_q—OC(O)R, —[C(R)₂]_q—OC(O)OR, —[C(R)₂]_q—OC(O)N(R)₂, —[C(R)₂]_q—OC(O)N(R)—S(=O)₂R or —[C(R)₂]_q—OP(OR)₂; or R¹ and R² are taken together with their intervening atoms to form an optionally substituted 4-7 membered heterocyclic ring having, in addition to the nitrogen atom to which R¹ is attached, 0-2 heteroatoms independently selected from oxygen, nitrogen, and sulfur;

each q is independently 0, 1, 2, 3, or 4;

each R³ is independently —S(O)₂R, —S(O)₂—[C(R)₂]_q—R, —S(O)₂—[C(R)₂]_q—B(OR)₂, —S(O)₂—[C(R)₂]_q—Si(R)₃, —S(O)₂OR, —S(O)₂N(R)₂, —S(O)R, —C(O)R, —C(O)OR, —C(O)N(R)₂, —C(O)N(R)—OR, —P(O)(R)₂, —P(O)(OR)₂, or —P(O)[N(R)₂]₂;

each R⁴ is absent when ═ is a double bond or is independently R, halogen, or

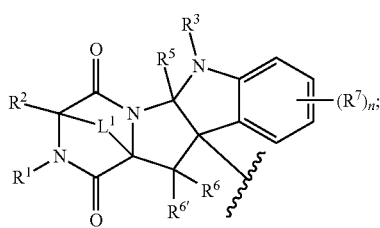

at least one instance of R¹, R³, and R⁴ comprises R wherein R is -L²-R^H1.

each L² is independently substituted or unsubstituted, C₁₋₂₀ alkylene, substituted or unsubstituted, C₂₋₂₀ alkenylene, substituted or unsubstituted, C₂₋₂₀ alkynylene, substituted or unsubstituted, C₁₋₂₀ heteroalkylene, substituted or unsubstituted, C₂₋₂₀ heteroalkenylene, or C₂₋₂₀ heteroalkynylene, wherein:

optionally one or more backbone carbons in each instance of the substituted or unsubstituted, C₁₋₂₀ alkylene, substituted or unsubstituted, C₂₋₂₀ alkenylene, substituted or unsubstituted, C₂₋₂₀ alkynylene, substituted or unsubstituted, C₁₋₂₀ heteroalkylene, substituted or unsubstituted, C₂₋₂₀ heteroalkenylene, and C₂₋₂₀ heteroalkynylene are independently replaced with —C(═O)—, substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, C₁₋₂₀ heteroalkylene, substituted or unsubstituted, C₂₋₂₀ heteroalkenylene, and substituted or unsubstituted, C₂₋₂₀ heteroalkynylene are independently replaced with substituted or unsubstituted carbocyclylene, substituted or unsubstituted heterocyclylene, substituted or unsubstituted arylene, or substituted or unsubstituted heteroarylene;

each R^H1 is independently a first click-chemistry handle, a nucleophile, an electrophile, a leaving group, substituted or unsubstituted alkenyl, substituted or unsubstituted alkynyl, halogen, —OH, —SH, —NHR^A, —N₃, —C(═O)OH, —C(═NR^A)OH, —S(═O)OH, —S(═O)₂OH, —C(═O)— (a leaving group), —C(═NR^A)— (a leaving group), —S(═O)— (a leaving group), or —S(═O)₂— (a leaving group), provided that each R^H1 is not —OCH₃ or —NR^AC(═O)R^A;

each R^A is independently hydrogen, substituted or unsubstituted C₁₋₆ alkyl, substituted or unsubstituted C₁₋₆ heteroalkyl, substituted or unsubstituted C₂₋₆ alkenyl, substituted or unsubstituted C₂₋₆ alkynyl, substituted or unsubstituted carbocyclyl, substituted or unsubstituted heterocyclyl, substituted or unsubstituted aryl, substituted or unsubstituted heteroaryl, or a nitrogen protecting group;

each R⁵ is absent when ═ is a double bond or is independently hydrogen or an optionally substituted C₁₋₆ aliphatic group;

each of R⁶ and R⁶' is independently R, halogen, —CN, —NO₂, —OR, —SR, —N(R)₂, —S(O)₂R, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, or —OSi(R)₃; or R⁶ and R⁶' are taken together to form ═O, ═C(R)₂ or ═NR;

each n is independently 0, 1, 2, 3, or 4;

each R⁷ is independently R, halogen, —CN, —NO₂, —OR, —OSi(R)₃, —SR, —N(R)₂, —S(O)₂R, —S(O)₂OR, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, —P(R)₂, —P(OR)₂, —P(O)(R)₂, —P(O)(OR)₂, —P(O)[N(R)₂]₂, —B(R)₂, —B(OR)₂, or —Si(R)₃; or:

two R⁷ are taken together with their intervening atoms to form an optionally substituted 4-7 membered ring having 0-2 heteroatoms independently selected from nitrogen, oxygen, and sulfur;

each L¹ is independently —S—, —(S)_m—[C(R)₂]_q—(S)_p—, —(S)_m(S)_p—, —(S)_mC(O)—(S)_p—, —(S)_mC(S)—(S)_p—, —(S)_mS(O)—(S)_p—, or —(S)_m—S(O)₂—(S)_p—;

each m is independently 1, 2, or 3; and each p is independently 1, 2, or 3.

In certain embodiments, a compound of Formula (II) is of the formula:

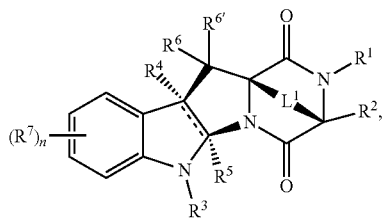

or stereoisomer thereof.

In certain embodiments, a compound of Formula (II) is of the formula:

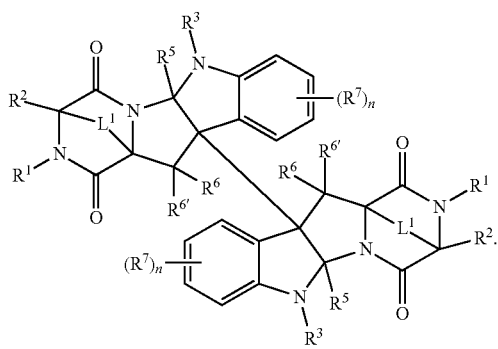

In certain embodiments, a compound of Formula (II) is of the formula:

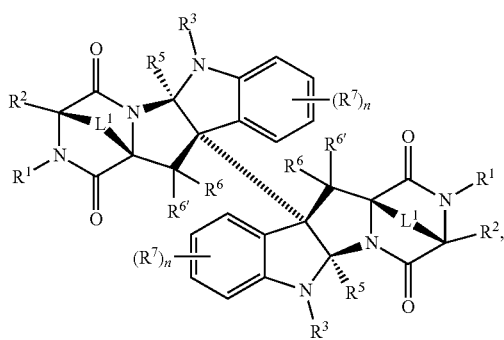

or stereoisomer thereof.

In some embodiments, R is -L$^2$-R$^{H1}$. In some embodiments, each instance of R is -L$^2$-R$^{H1}$. In certain embodiments, two of R$^1$, R$^2$, R$^3$, R$^4$, R$^6$, R$^{6'}$, and R$^7$ comprise -L$^2$-R$^{H1}$. In certain embodiments, only one of R$^1$, R$^2$, R$^3$, R$^4$, R$^6$, R$^{6'}$, and R$^7$ comprise -L$^2$-R$^{H1}$. In certain embodiments, at least one instance of R$^1$, R$^3$, and R$^4$ comprise R wherein R is -L$^2$-R$^{H1}$. In certain embodiments, at least one instance of R$^1$ comprises R wherein R is -L$^2$-R$^{H1}$. In some embodiments, at least one instance of R$^1$ is -L$^2$-R$^{H1}$. In certain embodiments, at least one instance of R$^3$ comprises R wherein R is -L$^2$-R$^{H1}$. In certain embodiments, at least one instance of R$^3$ is —S(O)$_2$R wherein R is -L$^2$-R$^{H1}$. In certain embodiments, at least one instance of R$^3$ is —C(O)R wherein R is -L$^2$-R$^{H1}$. In certain embodiments, R$^4$ comprises R wherein R is -L$^2$-R$^{H1}$. In some embodiments, R$^4$ is -L$^2$-R$^{H1}$.

In certain embodiments, each R$^{H1}$ is independently selected from a first click-chemistry handle, a nucleophile, an electrophile, a leaving group, substituted or unsubstituted alkenyl, substituted or unsubstituted alkynyl, halogen, —OH, —SH, —NHR$^A$, —N$_3$, —C(=O)OH, —C(=NR$^A$)OH, —S(=O)OH, —S(=O)$_2$OH, —C(=O)— (a leaving group), —C(=NR$^A$)— (a leaving group), —S(=O)— (a leaving group), and —S(=O)$_2$— (a leaving group). In certain embodiments, R$^{H1}$ is not —OCH$_3$. In some embodiments, R$^{H1}$ is not —NR$^A$C(=O)R$^A$. In certain embodiments, R$^{H1}$ is a first click-chemistry handle. In certain embodiments, R$^{H1}$ is —N$_3$. In certain embodiments, R$^{H1}$ is —C≡CH. In certain embodiments, at least one instance of R$^{H1}$ is a first click-chemistry handle. In certain embodiments, at least one instance of R$^{H1}$ is —N$_3$. In certain embodiments, at least one instance of R$^{H1}$ is —C≡CH. In certain embodiments, R$^{H1}$ is a leaving group. In certain embodiments, R$^{H1}$ is a metathesis handle.

In some embodiments, a compound of Formula (II) is of the formula:

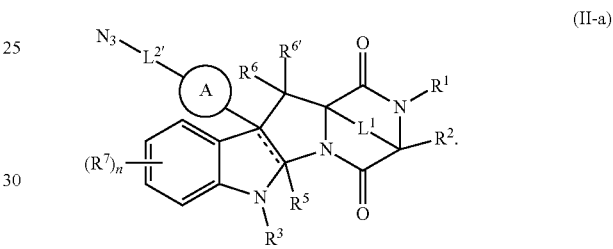

(II-a)

In some embodiments, a compound of Formula (II) is of the formula:

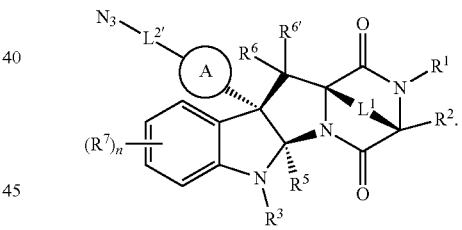

In certain embodiments of a compound of formula (II-a), Ring A is substituted or unsubstituted phenylene, substituted or unsubstituted indolylene, or substituted or unsubstituted pyrrolylene. In certain embodiments of a compound of formula (II-a), Ring A is substituted or unsubstituted phenylene. In certain embodiments of a compound of formula (II-a), L$^{2'}$ is substituted or unsubstituted C$_{1-20}$ heteroalkylene comprising one or more backbone oxygen atoms. In certain embodiments of a compound of formula (II-a), L$^{2'}$ is substituted or unsubstituted C$_{1-20}$ alkylene. In certain embodiments of a compound of formula (II-a), L$^{2'}$ is

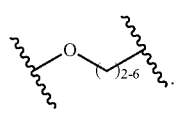

In certain embodiments of a compound of formula (II-a), $L^{2'}$ is

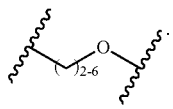

In some embodiments, a compound of Formula (II) is of the formula:

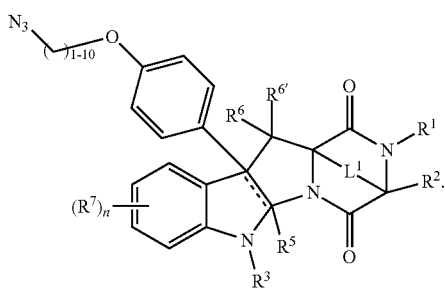

(II-a')

In some embodiments, a compound of Formula (II) is of the formula:

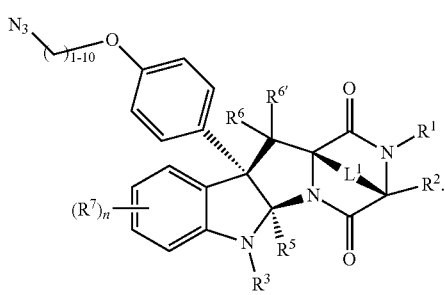

In some embodiments, a compound of Formula (II) is of the formula:

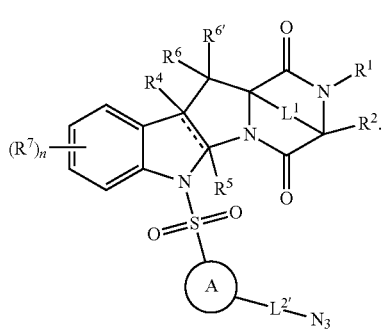

(II-b)

In some embodiments, a compound of Formula (II) is of the formula:

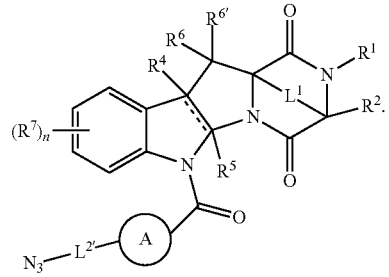

(II-b-i)

In some embodiments, a compound of Formula (II) is of the formula:

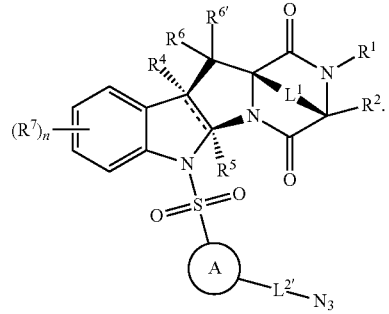

In some embodiments, a compound of Formula (II) is of the formula:

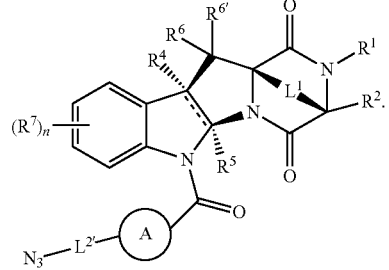

In certain embodiments of a compound of formula (II-b) or (II-b-i), Ring A is substituted or unsubstituted phenylene, substituted or unsubstituted indolylene, or substituted or unsubstituted pyrrolylene. In certain embodiments of a compound of formula (II-b) or (II-b-i), Ring A is substituted or unsubstituted phenylene. In certain embodiments of a compound of formula (II-b) or (II-b-i), $L^{2'}$ is substituted or unsubstituted $C_{1-20}$ heteroalkylene comprising one or more backbone oxygen atoms. In certain embodiments of a compound of formula (II-b) or (II-b-i), $L^{2'}$ is substituted or unsubstituted $C_1$-20 alkylene. In certain embodiments of a compound of formula (II-b) or (II-b-i), $L^{2'}$ is

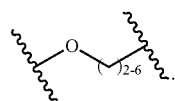

In certain embodiments of a compound of formula (II-b) or (II-b-i), $L^{2'}$ is

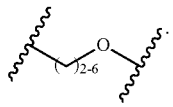

In certain embodiments, a compound of Formula (II) is of the formula:

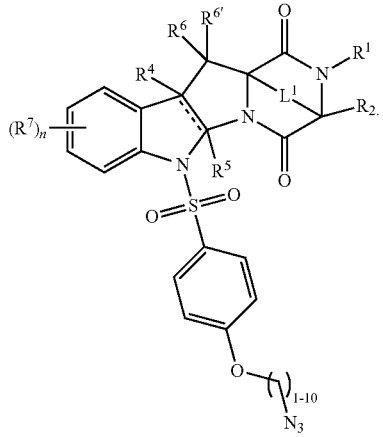

(II-b')

In certain embodiments, a compound of Formula (II) is of the formula:

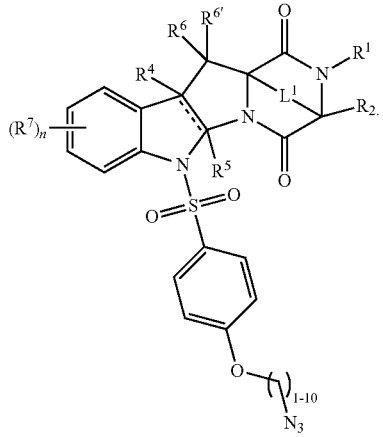

In certain embodiments, a compound of Formula (II) is of the formula:

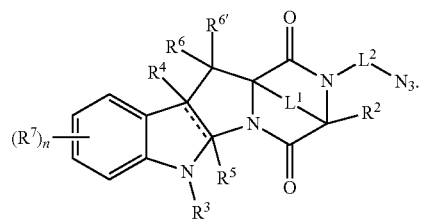

(II-c)

In certain embodiments, a compound of Formula (II) is of the formula:

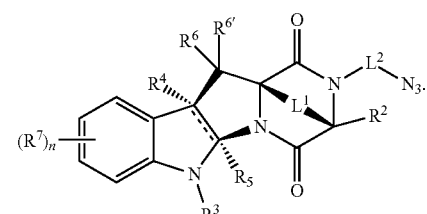

In certain embodiments of a compound of formula (II-c), $L^{2'}$ is substituted or unsubstituted $C_{1-20}$ heteroalkylene comprising one or more backbone oxygen atoms. In certain embodiments of a compound of formula (II-c), $L^{2'}$ is substituted or unsubstituted $C_{1-20}$ alkylene. In certain embodiments of a compound of formula (II-c), $L^{2'}$ is

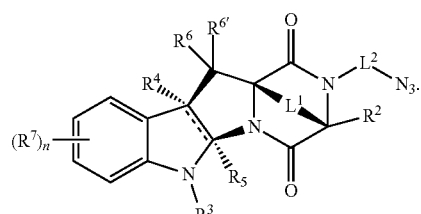

In certain embodiments of a compound of formula (II-c), $L^{2'}$ is

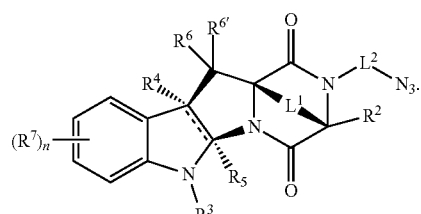

In certain embodiments, a compound of Formula (II) is of the formula:

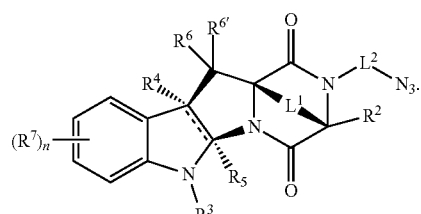

(II-c')

wherein h is an integer from 0 to 10, inclusive. In certain embodiments, a compound of Formula (II) is of the formula:

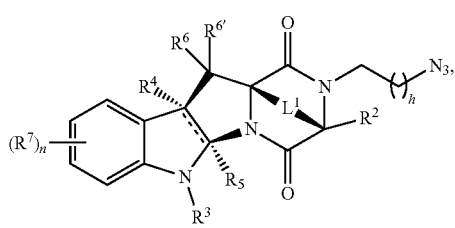

wherein h is an integer from 0 to 10, inclusive. In certain embodiments of a compound of formula (II-c'), h is 1. in certain embodiments of a compound of formula (II-c'), h is 2. in certain embodiments of a compound of formula (II-c'), h is 3.

In certain embodiments, a compound of Formula (II) is of the formula:

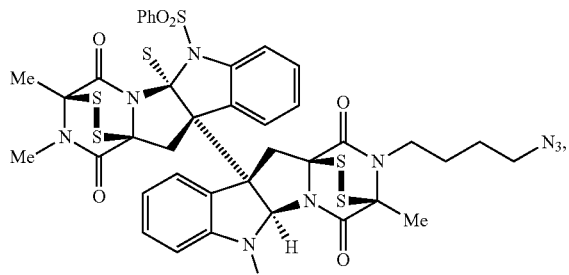

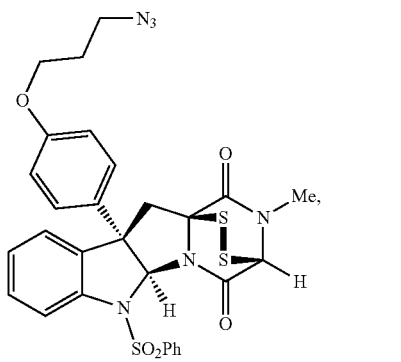

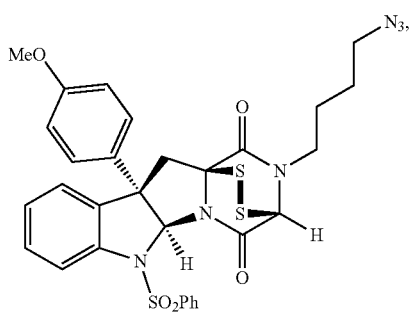

-continued

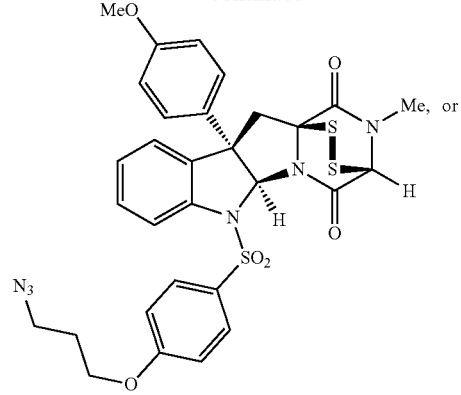

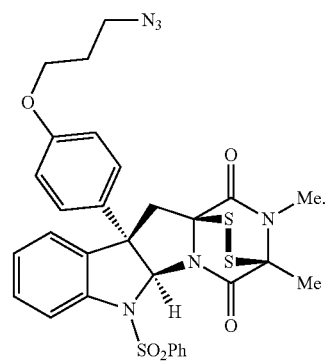

Also provided herein are compounds of Formula (III):

$$R^{H2}\text{-}L^3\text{-}D \tag{III}$$

or a salt thereof, wherein $R^{H2}$ is a reaction handle, wherein the reaction handle is able to react with $R^{H1}$ to form $R^H$.

In certain embodiments, $R^{H2}$ is a second click-chemistry handle, a nucleophile, an electrophile, a leaving group, substituted or unsubstituted alkenyl, substituted or unsubstituted alkynyl, halogen, —OH, —SH, —NHR$^A$, —N$_3$, —C(=O)OH, —C(=NR$^A$)OH, —S(=O)OH, —S(=O)$_2$OH, —C(=O)—(a leaving group), —C(=NR$^A$)—(a leaving group), —S(=O)—(a leaving group), or —S(=O)$_2$-(a leaving group). In certain embodiments, $R^{H2}$ is —C≡CH. In some embodiments, $R^{H2}$ is —N$_3$. In certain embodiments, $R^{H2}$ is a nucleophile. In certain embodiments, $R^{H2}$ is a leaving group. In some embodiments, $R^{H2}$ is —C(=O)—(a leaving group).

In certain embodiments, $R^{H1}$ is —N$_3$, and $R^{H2}$ is —C≡CH. In some embodiments, $R^{H1}$ is —C≡CH, and $R^{H2}$ is —N$_3$. In certain embodiments, $R^{H1}$ is a leaving group, and $R^{H2}$ is —N$_3$. In some embodiments, $R^{H1}$ is a leaving group, and $R^{H2}$ is a nucleophile. In certain embodiments, $R^{H1}$ is a nucleophile, and $R^{H2}$ is a leaving group. In some embodiments, $R^{H1}$ is —NH$_2$, and $R^{H2}$ is —C(=O)—(a leaving group).

In aspects of the disclosure, provided herein are compounds of Formula (V):

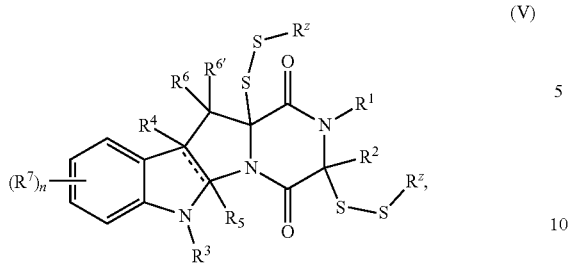 (V)

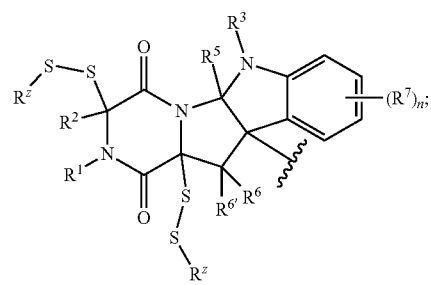

or salt thereof, wherein:

each === is independently a single bond or a double bond, as valency permits;

each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;

each R is independently hydrogen or an optionally substituted group selected from $C_{1-20}$ alkyl, $C_{1-20}$ heteroalkyl, phenyl, a 3-7 membered saturated or partially unsaturated, carbocyclic ring, an 8-14 membered bicyclic or polycyclic, saturated carbocyclic ring, partially unsaturated carbocyclic ring, or aryl ring, a 5-6 membered monocyclic heteroaryl ring having 1-4 heteroatoms independently selected from nitrogen, oxygen, and sulfur, a 3-7 membered saturated or partially unsaturated, heterocyclic ring having 1-3 heteroatoms independently selected from nitrogen, oxygen, and sulfur, a 7-14 membered bicyclic or polycyclic, saturated or partially unsaturated, heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or:

two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;

each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—S(=O)$_2$R, or —[C(R)$_2$]$_q$—OP(OR)$_2$; or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur;

each q is independently 0, 1, 2, 3, or 4;

each $R^3$ is independently —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$;

$R^4$ is absent when === is a double bond or is selected from R, halogen, and each $R^5$ is absent when === is a double bond or is independently hydrogen or an optionally substituted $C_{1-6}$ aliphatic group;

each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$, or =NR;

each n is independently 0, 1, 2, 3, or 4;

each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]2, —B(R)$_2$, —B(OR)$_2$, or —Si(R)$_3$; or:

two $R^7$ are taken together with their intervening atoms to form an optionally substituted 4-7 membered ring having 0-2 heteroatoms independently selected from nitrogen, oxygen, and sulfur;

each $R^Z$ is independently hydrogen, -$L^2$-$R^{H1}$, -$L^2$-$R^H$-$L^3$-D, -($L^2$)$_{0-1}$-$R^P$, substituted methyl, or an optionally substituted group selected from $C_{2-20}$ alkyl, $C_{1-20}$ heteroalkyl, phenyl, a 3-7 membered saturated or partially unsaturated, carbocyclic ring, an 8-14 membered bicyclic or polycyclic, saturated carbocyclic ring, partially unsaturated carbocyclic ring, or aryl ring, a 5-6 membered monocyclic heteroaryl ring having 1-4 heteroatoms independently selected from nitrogen, oxygen, and sulfur, a 3-7 membered saturated or partially unsaturated, heterocyclic ring having 1-3 heteroatoms independently selected from nitrogen, oxygen, and sulfur, a 7-14 membered bicyclic or polycyclic, saturated or partially unsaturated, heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur;

wherein at least one instance of $R^Z$ is not hydrogen;

each $L^2$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein:

optionally one or more backbone carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, and $C_{2-20}$ heteroalkynylene are independently replaced with —C(=O)—, substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, $C_{1-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each $R^{H1}$ is independently a first click-chemistry handle, a nucleophile, an electrophile, a leaving group, substituted or unsubstituted alkenyl, substituted or unsubstituted alkynyl, halogen, —OH, —SH, —NHR$^A$, —N$_3$, —C(=O)OH, —C(=NR$^A$)OH, —S(=O)OH, —S(=O)$_2$OH, —C(=O)— (a leaving group), —C(=NR$^A$)— (a leaving group), —S(=O)— (a leaving group), or —S(=O)$_2$— (a leaving group);

each $R^H$ is independently substituted or unsubstituted triazolylene, —O—, —S—, —NR$^A$—, —C(=O)O—, —C(=NR$^A$)O—, —S(=O)O—, —S(=O)$_2$O—, —C(=O)NR$^A$—, —C(=NR$^A$)NR$^A$—, —S(=O)NR$^A$—, —S(=O)$_2$NR$^A$—, —OC(=O)—, —OC(=NR$^A$)—, —OS(=O)—, —OS(=O)$_2$—, —NR$^A$C(=O)—, —NR$^A$C(=NR$^A$)—, —NR$^A$S(=O)—, —NR$^A$S(=O)$_2$—, —OC(=O)O—, —OC(=NR$^A$)O—, —OS(=O)O—, —OS(=O)$_2$O—, —NR$^A$C(=O)O—, —NR$^A$C(=NR$^A$)O—, —NR$^A$S(=O)O—, —NR$^A$S(=O)$_2$O—, —OC(=O)NR$^A$—, —OC(=NR$^A$)NR$^A$—, —OS(=O)NR$^A$—, —OS(=O)$_2$NR$^A$—, —NR$^A$C(=O)NR$^A$—, —NR$^A$C(=NR$^A$)NR$^A$—, —NR$^A$S(=O)NR$^A$—, —NR$^A$S(=O)$_2$NR$^A$—, —C(=O)—, —C(=NR$^A$)—, —S(=O)—, —S(=O)$_2$—, substituted or unsubstituted carbocyclylene, substituted or unsubstituted heterocyclylene, substituted or unsubstituted arylene, or substituted or unsubstituted heteroarylene;

each $R^A$ is independently hydrogen, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, substituted or unsubstituted heteroaryl, or a nitrogen protecting group;

each $L^3$ is independently substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, or $C_{2-20}$ heteroalkynylene, wherein:

optionally one or more backbone carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{1-20}$ heteroalkylene, substituted or unsubstituted, $C_{2-20}$ heteroalkenylene, and $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more backbone heteroatoms in each instance of the substituted or unsubstituted, $C_{1-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each D is independently absent, polymeric moiety, dendrimeric moiety, antibody, particle, bead, nanostructure, liposome, micelle, or vesicle; and $R^P$ is an amino acid, a peptide, or a polypeptide.

In certain embodiments, a compound of Formula (V) is of the formula:

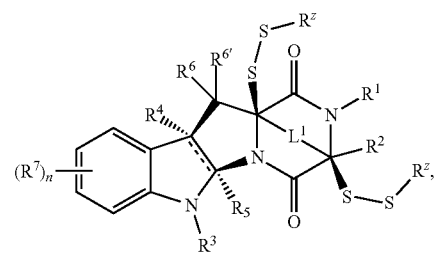

or stereoisomer thereof. In certain embodiments, a compound of Formula (V) is of the formula:

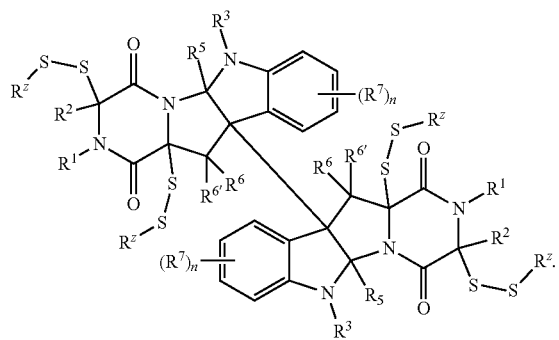

In certain embodiments, a compound of Formula (V) is of the formula:

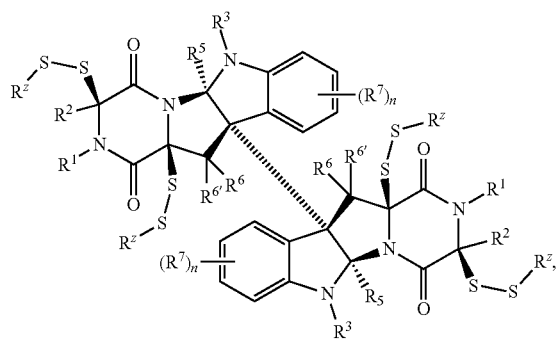

or stereoisomer thereof.

In certain embodiments, each instance of $R^Z$ is the same. In certain embodiments, each instance of $R^Z$ is different.

In certain embodiments, at least one $R^Z$ is not hydrogen. In certain embodiments, $R^Z$ is hydrogen. In some embodiments, $R^Z$ is a substituted methyl. In certain embodiments, $R^Z$ is —$CH_2F$, —$CHF_2$, —$CF_3$, or benzyl. In some embodiments, $R^Z$ is -$L^2$-$R^{H1}$. In some embodiments, $R^Z$ is -$L^2$-$R^H$, and $L^2$ comprises a substituted or unsubstituted,

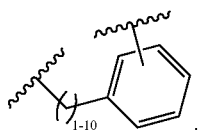

In some embodiments, $R^Z$ is -$L^2$-$R^H$, and $L^2$ comprises

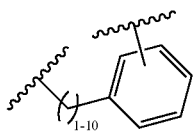

substituted with halogen. In some embodiments, -$L^2$-$R^{H1}$ comprises

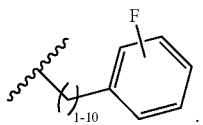

In certain embodiments, $R^Z$ is -$L^2$-$R^H$-$L^3$-D. In certain embodiments, $R^Z$ is -$(L^2)_1$-$R^P$. In certain embodiments, $R^Z$ is —$R^P$.

In some embodiments, $R^Z$ is optionally substituted $C_{2-20}$ alkyl. In some embodiments, $R^Z$ is optionally substituted $C_{2-15}$ alkyl. In some embodiments, $R^Z$ is optionally substituted $C_{2-10}$ alkyl. In some embodiments, $R^Z$ is optionally substituted $C_{2-6}$ alkyl. In some embodiments, $R^Z$ is optionally substituted $C_{2-6}$ alkyl. In some embodiments, $R^Z$ is optionally substituted hexyl, pentyl, butyl, propyl, ethyl or methyl. In some embodiments, $R^Z$ is optionally substituted hexyl. In some embodiments, $R^Z$ is optionally substituted pentyl. In some embodiments, $R^Z$ is optionally substituted butyl. In some embodiments, $R^Z$ is optionally substituted propyl. In some embodiments, $R^Z$ is optionally substituted ethyl. In some embodiments, $R^Z$ is hexyl. In some embodiments, $R^Z$ is pentyl. In some embodiments, $R^Z$ is butyl. In some embodiments, $R^Z$ is propyl. In some embodiments, $R^Z$ is ethyl. In some embodiments, $R^Z$ is methyl. In some embodiments, $R^Z$ is isopropyl. In some embodiments, $R^Z$ is n-propyl. In some embodiments, $R^Z$ is tert-butyl. In some embodiments, $R^Z$ is sec-butyl. In some embodiments, $R^Z$ is n-butyl. In some embodiments, $R^Z$ is benzyloxymethyl. In some embodiments, $R^Z$ is benzyl. In some embodiments, $R^Z$ is allyl. In some embodiments, $R^Z$ is not hydrogen. In some embodiments, $R^Z$ is not alkyl.

In some embodiments, $R^Z$ is optionally substituted $C_{1-20}$ heteroalkyl. In some embodiments, $R^Z$ is optionally substituted $C_{1-20}$ heteroalkyl comprising 1-6 heteroatoms independently selected from nitrogen, sulfur, phosphorus selenium, silicon and boron within the $C_{1-20}$ heteroalkyl backbone. In some embodiments, $R^Z$ is optionally substituted $C_{1-20}$ heteroalkyl comprising 1-6 heteroatoms independently selected from nitrogen, sulfur, phosphorus, selenium, silicon and boron within the $C_{1-20}$ heteroalkyl backbone, optionally including one or more oxidized forms of nitrogen, sulfur, phosphorus, selenium, silicon or boron within the $C_{1-20}$ heteroalkyl backbone. In some embodiments, $R^Z$ is optionally substituted $C_{1-20}$ heteroalkyl comprising 1-6 groups independently selected from

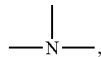

—N=, ≡N, —S—, —S(O)—, —S(O)$_2$—, —O—, =O,

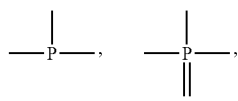

—Se—, —Se(O)—, and

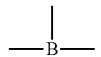

within the $C_{1-20}$ heteroalkyl backbone. In some embodiments, $R^Z$ is not heteroalkyl. In some embodiments, $R^Z$ is methoxymethyl. In some embodiments, $R^Z$ is benzyloxymethyl.

In some embodiments, $R^Z$ is optionally substituted phenyl. In some embodiments, $R^Z$ is optionally substituted phenyl wherein one or more substituents are halogen. In some embodiments, $R^Z$ is optionally substituted phenyl wherein one or more substituents are —F. In some embodiments, $R^Z$ is optionally substituted phenyl wherein one or more substituents are —C$_1$. In some embodiments, $R^Z$ is optionally substituted phenyl wherein one or more substituents are —Br. In some embodiments, $R^Z$ is optionally substituted phenyl wherein one or more substituents are —I. In some embodiments, $R^Z$ is phenyl.

In some embodiments, $R^Z$ is an optionally substituted 3-7 membered saturated or partially unsaturated carbocyclic ring. In some embodiments, $R^Z$ is an optionally substituted 3-membered saturated or partially unsaturated carbocyclic ring. In some embodiments, $R^Z$ is an optionally substituted 4-membered saturated or partially unsaturated carbocyclic ring. In some embodiments, $R^Z$ is an optionally substituted 5-membered saturated or partially unsaturated carbocyclic ring. In some embodiments, $R^Z$ is an optionally substituted 6-membered saturated or partially unsaturated carbocyclic ring. In some embodiments, $R^Z$ is an optionally substituted 7-membered saturated or partially unsaturated carbocyclic ring. In some embodiments, $R^Z$ is optionally substituted cycloheptyl. In some embodiments, $R^Z$ is cycloheptyl. In some embodiments, $R^Z$ is optionally substituted cyclohexyl. In some embodiments, $R^Z$ is cyclohexyl. In some embodiments, $R^Z$ is optionally substituted cyclopentyl. In some embodiments, $R^Z$ is cyclopentyl. In some embodiments, $R^Z$ is optionally substituted cyclobutyl. In some embodiments, $R^Z$ is cyclobutyl. In some embodiments, $R^Z$ is optionally substituted cyclopropyl. In some embodiments, $R^Z$ is cyclopropyl.

In some embodiments, $R^Z$ is an optionally substituted 8-14 membered bicyclic or polycyclic saturated, partially unsaturated or aryl ring. In some embodiments, $R^Z$ is an optionally substituted 8-14 membered bicyclic or polycyclic saturated ring. In some embodiments, $R^Z$ is an optionally substituted 8-14 membered bicyclic or polycyclic partially saturated ring. In some embodiments, $R^Z$ is an optionally substituted 8-14 membered bicyclic or polycyclic aryl ring. In some embodiments, $R^Z$ is an optionally substituted 8-10 membered bicyclic saturated, partially unsaturated or aryl ring. In some embodiments, $R^Z$ is an optionally substituted 8-10 membered bicyclic saturated ring. In some embodiments, $R^Z$ is an optionally substituted 8-10 membered bicyclic partially unsaturated ring. In some embodiments, $R^Z$ is an optionally substituted 8-10 membered bicyclic aryl ring. In some embodiments, $R^Z$ is optionally substituted naphthyl. In some embodiments, $R^Z$ is optionally substituted anthracenyl. In some embodiments, $R^Z$ is optionally substituted 9-anthracenyl.

In some embodiments, $R^Z$ is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, or sulfur. In some embodiments, $R^Z$ is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is optionally substituted phenyl. In some embodiments, $R^Z$ is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 5-6 membered monocyclic heteroaryl ring having 1-4 heteroatoms independently selected from nitrogen, oxygen, or sulfur. In some embodiments, $R^Z$ is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 8-10 membered bicyclic aryl ring. In some embodiments, $R^Z$ is optionally substituted biaryl wherein each aryl group is independently an optionally substituted group selected from phenyl, 5-6 membered monocyclic heteroaryl ring having 1-4 heteroatoms independently selected from nitrogen, oxygen, and sulfur, an 8-10 membered bicyclic aryl ring, or an 8-10 membered bicyclic heteroaryl ring having 1-5 heteroatoms independently selected from nitrogen, oxygen, and sulfur, and wherein at least one aryl group is an optionally substituted 8-10 membered bicyclic heteroaryl ring having 1-5 heteroatoms independently selected from nitrogen, oxygen, and sulfur. In some embodiments, $R^Z$ is optionally substituted biaryl wherein each aryl group is independently optionally substituted phenyl. In some embodiments, $R^Z$ is optionally substituted biaryl wherein each aryl group is independently optionally substituted phenyl, or an optionally substituted 5-6 membered monocyclic heteroaryl ring having 1-4 heteroatoms independently selected from nitrogen, oxygen. In some embodiments, $R^Z$ is optionally substituted biaryl wherein each aryl group is independently an optionally substituted 8-10 membered bicyclic aryl ring. In some embodiments, $R^Z$ is optionally substituted biaryl wherein one aryl group is optionally substituted naphthyl, and the other aryl group is independently an optionally substituted 8-10 membered bicyclic aryl ring. In some embodiments, $R^Z$ is optionally substituted biaryl wherein each aryl group is optionally substituted naphthyl. In some embodiments, $R^Z$ is optionally substituted biaryl wherein one aryl group is optionally substituted naphthyl, and the other aryl group is an optionally substituted 8-10 membered bicyclic heteroaryl ring having 1-5 heteroatoms independently selected from nitrogen, oxygen, and sulfur.

In some embodiments, $R^Z$ is an optionally substituted 5-6 membered monocyclic heteroaryl ring having 1-4 heteroatoms independently selected from nitrogen, oxygen, and sulfur. In some embodiments, $R^Z$ is a substituted 5-6 membered monocyclic heteroaryl ring having 1-4 heteroatoms independently selected from nitrogen, oxygen, and sulfur. In some embodiments, $R^Z$ is an unsubstituted 5-6 membered monocyclic heteroaryl ring having 1-4 heteroatoms independently selected from nitrogen, oxygen, and sulfur.

In some embodiments, $R^Z$ is an optionally substituted 5-membered monocyclic heteroaryl ring having 1-4 heteroatoms independently selected from nitrogen, oxygen or sulfur. In some embodiments, $R^Z$ is an optionally substituted 6-membered monocyclic heteroaryl ring having 1-4 heteroatoms independently selected from nitrogen, oxygen, and sulfur.

In some embodiments, $R^Z$ is an optionally substituted 5-membered monocyclic heteroaryl ring having one heteroatom selected from nitrogen, oxygen, and sulfur. In some embodiments, $R^Z$ is selected from optionally substituted pyrrolyl, furanyl, or thienyl.

In some embodiments, $R^Z$ is an optionally substituted 5-membered heteroaryl ring having two heteroatoms independently selected from nitrogen, oxygen, and sulfur. In certain embodiments, $R^Z$ is an optionally substituted 5-membered heteroaryl ring having one nitrogen atom, and an additional heteroatom selected from sulfur or oxygen. Exemplary $R^Z$ groups include but are not limited to optionally substituted pyrazolyl, imidazolyl, thiazolyl, isothiazolyl, oxazolyl or isoxazolyl.

In some embodiments, $R^Z$ is an optionally substituted 5-membered heteroaryl ring having three heteroatoms independently selected from nitrogen, oxygen, and sulfur. Exemplary $R^Z$ groups include but are not limited to optionally substituted triazolyl, oxadiazolyl or thiadiazolyl.

In some embodiments, $R^Z$ is an optionally substituted 5-membered heteroaryl ring having four heteroatoms independently selected from nitrogen, oxygen, and sulfur. Exemplary $R^Z$ groups include but are not limited to optionally substituted tetrazolyl, oxatriazolyl and thiatriazolyl.

In some embodiments, $R^Z$ is an optionally substituted 6-membered heteroaryl ring having 1-4 nitrogen atoms. In some embodiments, $R^Z$ is an optionally substituted 6-membered heteroaryl ring having 1-3 nitrogen atoms. In other embodiments, $R^Z$ is an optionally substituted 6-membered heteroaryl ring having 1-2 nitrogen atoms. In some embodiments, $R^Z$ is an optionally substituted 6-membered heteroaryl ring having four nitrogen atoms. In some embodiments, $R^Z$ is an optionally substituted 6-membered heteroaryl ring having three nitrogen atoms. In some embodiments, $R^Z$ is an optionally substituted 6-membered heteroaryl ring having two nitrogen atoms. In certain embodiments, $R^Z$ is an optionally substituted 6-membered heteroaryl ring having one nitrogen atom. Exemplary $R^Z$ groups include but are not limited to optionally substituted pyridinyl, pyrimidinyl, pyrazinyl, pyridazinyl, triazinyl, or tetrazinyl.

In some embodiments, $R^Z$ is an optionally substituted 3-7 membered saturated or partially unsaturated heterocyclic ring having 1-3 heteroatoms independently selected from nitrogen, oxygen, and sulfur. In some embodiments, $R^Z$ is a substituted 3-7 membered saturated or partially unsaturated heterocyclic ring having 1-3 heteroatoms independently selected from nitrogen, oxygen, and sulfur. In some embodiments, $R^Z$ is an unsubstituted 3-7 membered saturated or partially unsaturated heterocyclic ring having 1-3 heteroatoms independently selected from nitrogen, oxygen, and sulfur.

In some embodiments, $R^Z$ is optionally substituted 3-membered heterocyclic ring having one heteroatom selected from nitrogen, oxygen or sulfur. Exemplary $R^Z$ groups include but are not limited to optionally substituted aziridinyl, thiiranyl or oxiranyl. In some embodiments, $R^Z$ is optionally substituted 4-membered heterocyclic ring having 1-3 heteroatoms independently selected from nitrogen, oxygen, and sulfur. Exemplary $R^Z$ groups include but are not limited to optionally substituted azetidinyl, oxetanyl, thietanyl, oxazetidinyl, thiazetidinyl, or diazetidinyl. In some embodiments, $R^Z$ is optionally substituted 5-membered heterocyclic ring having 1-3 heteroatoms independently selected from nitrogen, oxygen, and sulfur. Exemplary $R^Z$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, $R^Z$ is optionally substituted 6-membered heterocyclic ring having 1-3 heteroatoms independently selected from nitrogen, oxygen, and sulfur. Exemplary $R^Z$ groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, $R^Z$ is optionally substituted 7-membered heterocyclic ring having 1-3 heteroatoms independently selected from nitrogen, oxygen, and sulfur. Exemplary $R^Z$ groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, $R^Z$ is an optionally substituted 5-7 membered partially unsaturated monocyclic ring having 1-3 heteroatoms independently selected from nitrogen, oxygen, and sulfur. In certain embodiments, $R^Z$ is an optionally substituted 5-6 membered partially unsaturated monocyclic ring having 1-3 heteroatoms independently selected from nitrogen, oxygen, and sulfur. In certain embodiments, $R^Z$ is an optionally substituted 5-membered partially unsaturated monocyclic ring having 1-3 heteroatoms independently selected from nitrogen, oxygen, and sulfur. Exemplary $R^Z$ groups include but are not limited to optionally substituted dihydroimidazolyl, dihydrothiazolyl, dihydrooxazolyl, or oxazolinyl. In certain embodiments, $R^Z$ is an optionally substituted 6-membered partially unsaturated monocyclic ring having 1-3 heteroatoms independently selected from nitrogen, oxygen, and sulfur. Exemplary $R^Z$ groups include but are not limited to optionally substituted dihydropyridinyl, tetrahydropyridinyl, dihydropyrimidinyl, tetrahydropyrimidinyl, dihydropyrazinyl, tetrohydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^Z$ is an optionally substituted 7-membered partially unsaturated monocyclic ring having 1-3 heteroatoms independently selected from nitrogen, oxygen, and sulfur. Exemplary $R^Z$ groups include but are not limited to optionally substituted azepiyl, oxepinyl, thiepinyl, diazepinyl, oxazepinyl, thiazepinyl, triazepinyl, oxadiazepinyl, thiadiazepinyl, dihydroazepiyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepiyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In certain embodiments, $R^Z$ is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, $R^Z$ is an optionally substituted 7-14 membered bicyclic or polycyclic saturated or partially unsaturated heterocyclic ring having 1-5 heteroatoms independently selected from nitrogen, oxygen, and sulfur. In some embodiments, $R^Z$ is an optionally substituted 7-10 membered bicyclic saturated or partially unsaturated heterocyclic ring having 1-5 heteroatoms independently selected from nitrogen, oxygen, and sulfur. In some embodiments, $R^Z$ is optionally substituted indolinyl. In some embodiments, $R^Z$ is optionally substituted isoindolinyl. In some embodiments, $R^Z$ is optionally substituted 1, 2, 3, 4-tetrahydroquinolinyl. In some embodiments, $R^Z$ is optionally substituted 1, 2, 3, 4-tetrahydroisoquinolinyl. In some embodiments, $R^Z$ is an optionally substituted azabicyclo[3.2.1]octanyl.

In some embodiments, $R^Z$ is an optionally substituted 8-14 membered bicyclic or polycyclic heteroaryl ring having 1-5 heteroatoms independently selected from nitrogen, oxygen, and sulfur. In some embodiments, $R^Z$ is an optionally substituted 8-14 membered bicyclic or tricyclic heteroaryl ring having 1-5 heteroatoms independently selected from nitrogen, oxygen, and sulfur. In some embodiments, $R^Z$ is an 8-10 membered bicyclic heteroaryl ring having 1-5 heteroatoms independently selected from nitrogen, oxygen, and sulfur.

In some embodiments, $R^Z$ is an optionally substituted 5,6-fused heteroaryl ring having 1-5 heteroatoms independently selected from nitrogen, oxygen, and sulfur. In some embodiments, $R^Z$ is an optionally substituted 5,6-fused heteroaryl ring having 1-4 heteroatoms independently selected from nitrogen, oxygen, and sulfur. In some embodiments, $R^Z$ is an optionally substituted 5,6-fused heteroaryl ring having 1-3 heteroatoms independently selected from nitrogen, oxygen, and sulfur. In some embodiments, $R^Z$ is an optionally substituted 5,6-fused heteroaryl ring having two heteroatoms independently selected from nitrogen, oxygen, and sulfur. In some embodiments, $R^Z$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^Z$ is an optionally substituted 5,6-fused heteroaryl ring having three heteroatoms independently selected from nitrogen, oxygen, and sulfur. In some embodiments, $R^Z$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^Z$ is an optionally substituted 5,6-fused heteroaryl ring having four heteroatoms independently selected from nitrogen, oxygen, and sulfur. In some embodiments, $R^Z$ is an optionally substituted 5,6-fused heteroaryl ring having five heteroatoms independently selected from nitrogen, oxygen, and sulfur.

In some embodiments, $R^Z$ is an optionally substituted 5,6-fused heteroaryl ring having 1-5 heteroatoms independently selected from nitrogen, oxygen, and sulfur. In other embodiments, $R^Z$ is an optionally substituted 5,6-fused heteroaryl ring having 1-2 heteroatoms independently selected from nitrogen, oxygen, and sulfur. In certain embodiments, $R^Z$ is an optionally substituted 5,6-fused heteroaryl ring having one heteroatom independently selected from nitrogen, oxygen, and sulfur. In some embodiments, $R^Z$ is optionally substituted indolyl. In some embodiments, $R^Z$ is optionally substituted benzofuranyl. In some embodiments, $R^Z$ is optionally substituted benzo[b]thienyl. In certain embodiments, $R^Z$ is an optionally substituted 5,6-fused heteroaryl ring having two heteroatoms independently selected from nitrogen, oxygen, and sulfur. In some embodiments, $R^Z$ is optionally substituted azaindolyl. In some embodiments, $R^Z$ is optionally substituted benzimidazolyl. In some embodiments, $R^Z$ is optionally substituted benzothiazolyl. In some embodiments, $R^Z$ is optionally substituted benzoxazolyl. In some embodiments, $R^Z$ is an optionally substituted indazolyl. In certain embodiments, $R^Z$ is an optionally substituted 5,6-fused heteroaryl ring having three heteroatoms independently selected from nitrogen, oxygen, and sulfur. In some embodiments, $R^Z$ is optionally substituted oxazolopyridiyl, thiazolopyridinyl or imidazopyridinyl. In certain embodiments, $R^Z$ is an optionally substituted 5,6-fused heteroaryl ring having four heteroatoms independently selected from nitrogen, oxygen, and sulfur. In some embodiments, $R^Z$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^Z$ is an optionally substituted 5,6-fused heteroaryl ring having five heteroatoms independently selected from nitrogen, oxygen, and sulfur.

In certain embodiments, $R^Z$ is an optionally substituted 6,6-fused heteroaryl ring having 1-5 heteroatoms independently selected from nitrogen, oxygen, and sulfur. In some embodiments, $R^Z$ is an optionally substituted 6,6-fused heteroaryl ring having 1-2 heteroatoms independently selected from nitrogen, oxygen, and sulfur. In other embodiments, $R^Z$ is an optionally substituted 6,6-fused heteroaryl ring having one heteroatom selected from nitrogen, oxygen, and sulfur. In some embodiments, $R^Z$ is optionally substituted quinolinyl. In some embodiments, $R^Z$ is optionally substituted isoquinolinyl. In some embodiments, $R^Z$ is an optionally substituted 6,6-fused heteroaryl ring having two heteroatoms independently selected from nitrogen, oxygen, and sulfur. In some embodiments, $R^Z$ is optionally substituted quinazolinyl, phthalazinyl, quinoxalinyl or naphthyridinyl. In some embodiments, $R^Z$ is an optionally substituted 6,6-fused heteroaryl ring having three heteroatoms independently selected from nitrogen, oxygen, and sulfur. In some embodiments, $R^Z$ is optionally substituted pyridopyrimidinyl, pyridopyridazinyl, pyridopyrazinyl, or benzotriazinyl. In some embodiments, $R^Z$ is an optionally substituted 6,6-fused heteroaryl ring having four heteroatoms independently selected from nitrogen, oxygen, and sulfur. In some embodiments, $R^Z$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^Z$ is an optionally substituted 6,6-fused heteroaryl ring having five heteroatoms independently selected from nitrogen, oxygen, and sulfur.

In some embodiments, $R^Z$ is optionally substituted heterobiaryl wherein each heteroaryl group is independently an optionally substituted group selected from a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, $R^Z$ is optionally substituted heterobiaryl wherein each aryl group is an optionally substituted 8-10 membered bicyclic heteroaryl ring having 1-5 heteroatoms independently selected from nitrogen, oxygen, and sulfur.

In some embodiments, two $R^Z$ groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur. In some embodiments, two $R^Z$ groups on the same atom are optionally taken together with the atom to which they are attached to form an optionally substituted 3-14 membered, saturated, partially unsaturated, or aryl ring having 0-4 heteroatoms independently selected from nitrogen, oxygen, and sulfur. In some embodiments, two $R^Z$ groups on the same carbon atom are optionally taken together with the carbon atom to form an optionally substituted 3-14 membered, saturated, partially unsaturated, or aryl ring having 0-4 heteroatoms independently selected from nitrogen, oxygen, and sulfur. In some embodiments, two $R^Z$ groups on the same nitrogen atom are optionally taken together with the nitrogen atom to form an optionally substituted 3-14 membered, saturated, partially unsaturated, or aryl ring having 1-5 heteroatoms independently selected from nitrogen, oxygen, and sulfur. In some embodiments, two $R^Z$ groups on the same sulfur atom are optionally taken together with the sulfur atom to form an optionally substituted 3-14 membered, saturated, partially unsaturated, or aryl ring having 1-5 heteroatoms independently selected from nitrogen, oxygen, and sulfur. In some embodiments, two $R^Z$ groups on the same oxygen atom are optionally taken together with the oxygen atom to form an optionally substituted 3-14 membered, saturated, partially unsaturated, or aryl ring having 1-5 heteroatoms independently selected from nitrogen, oxygen, and sulfur. In some embodiments, two $R^Z$ groups on the same phosphorus atom are optionally taken together with the phosphorus atom to form an optionally substituted 3-14 membered, monocyclic or bicyclic, saturated, partially unsaturated, or aryl ring having, in addition to the phosphorus atom, 0-4 heteroatoms independently selected from nitrogen, oxygen, and sulfur. In some embodiments, two $R^Z$ groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur, wherein the two $R^Z$ groups are attached to two different atoms.

In some embodiments, two $R^Z$ groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur. In some embodiments, two $R^Z$ groups are taken together to form an optionally substituted saturated ring. In some embodiments, two $R^Z$ groups are taken together to form an optionally substituted partially unsaturated ring. In some embodiments, two $R^Z$ groups are taken together to form an optionally substituted carbocyclic ring. In some embodiments, two $R^Z$ groups are taken together to form an optionally substituted aryl ring. In some embodiments, two $R^Z$ groups are taken together to form an optionally substituted phenyl ring. In some embodiments, two $R^Z$ groups are taken together to form an optionally substituted heterocyclic ring. In some embodiments, two $R^Z$ groups are taken together to form an optionally substituted heteroaryl ring.

In some embodiments, a ring formed by taking two $R^Z$ groups together is monocyclic, bicyclic or tricyclic. In some embodiments, a ring formed by taking two $R^Z$ groups together is monocyclic. In some embodiments, a ring formed by taking two $R^Z$ groups together is bicyclic. In some embodiments, a ring formed by taking two $R^Z$ groups together is monocyclic or bicyclic. In some embodiments, a ring formed by taking two $R^Z$ groups together is tricyclic. In some embodiments, a ring formed by taking two $R^Z$ groups together is monocyclic, bicyclic or tricyclic.

In certain embodiments, $R^P$ is an amino acid. In certain embodiments, $R^P$ is a peptide. In some embodiments, $R^P$ is a peptide comprising 2 to 10 amino acids. In some embodiments, $R^P$ is a peptide comprising 2 to 5 amino acids. In some embodiments, $R^P$ is a peptide comprising glutamic acid, cysteine, and glycine. In certain embodiments, an amino acid is selected from the group consisting alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In certain embodiments, $R^P$ is a peptide bound through the N-terminus. In certain embodiments, $R^P$ is a peptide bound through the C-terminus. In certain embodiments, $R^P$ is a peptide bound through a side chain.

In certain embodiments, a compound of Formula (V) is of the formula:

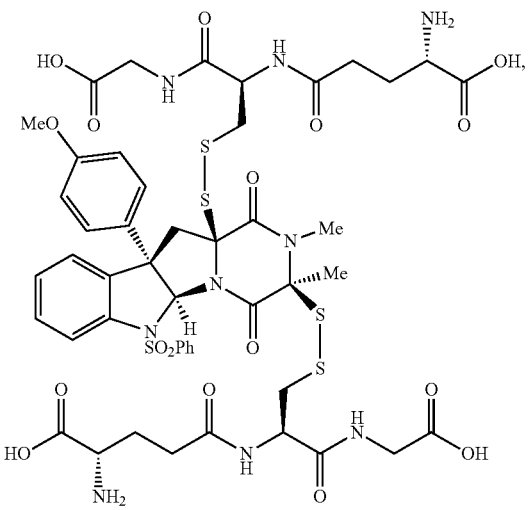

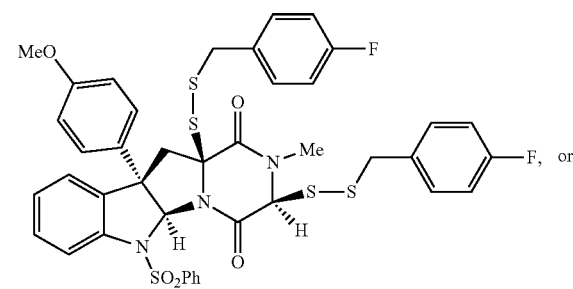

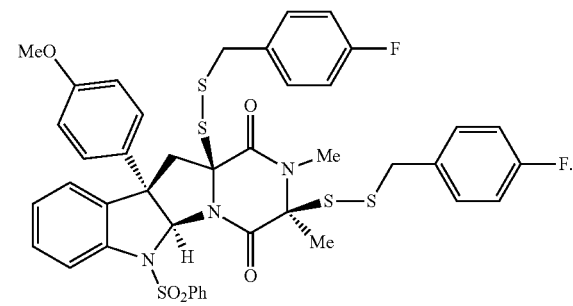

In some embodiments, a compound of Formula I, II, or V is deprotected. In certain embodiments, a compound of Formula I, II, or V is a free base. In certain embodiments, a compound of Formula I, II, or V is a salt. In some embodiments, a compound of Formula I is of the formula:

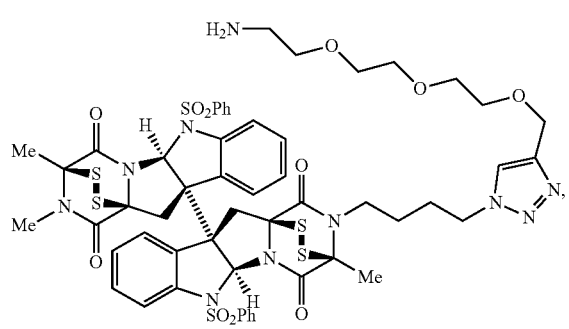
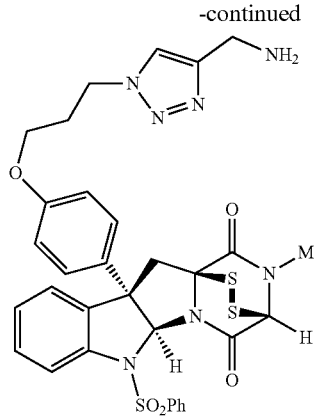
-continued
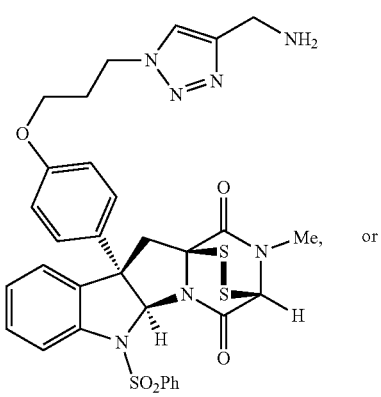
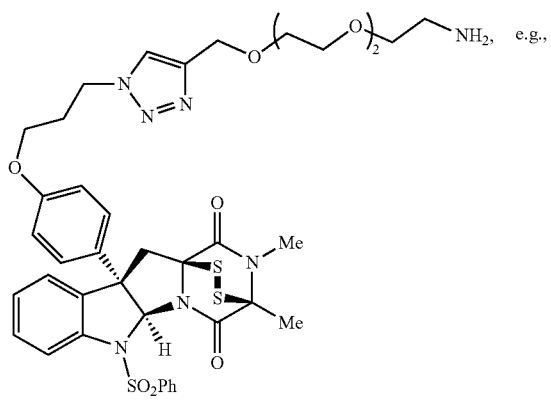
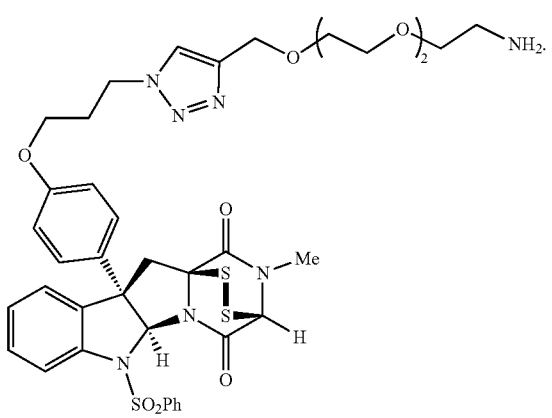
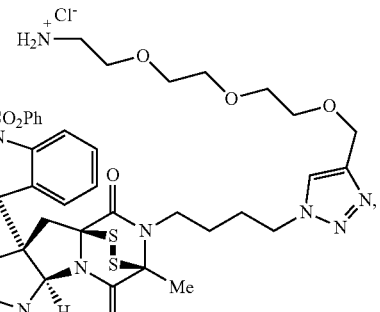
In some embodiments, a compound of Formula I is a salt of
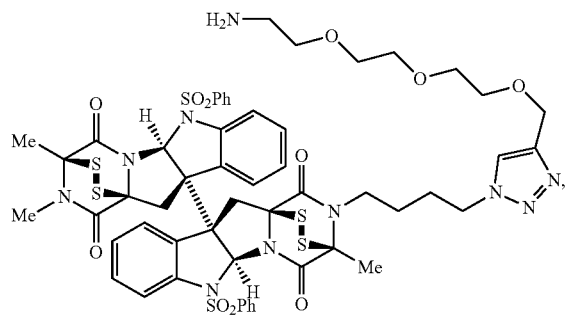
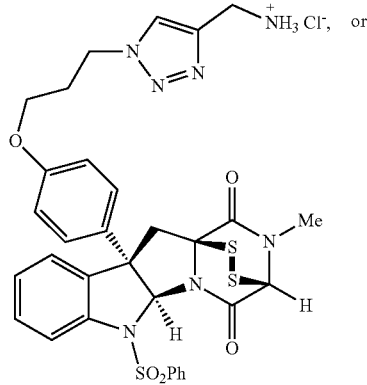

-continued

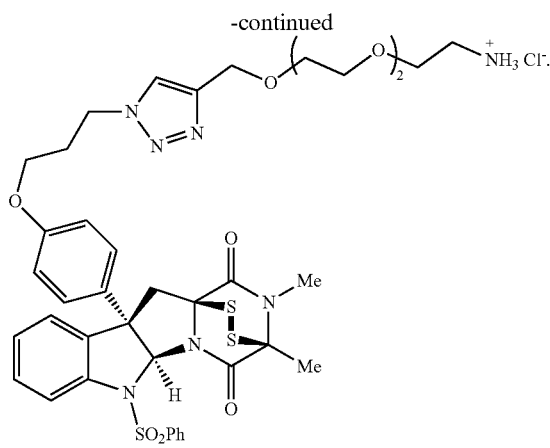

In certain aspects, the scope of this disclosure also includes the in vivo metabolic products of compounds described herein, e.g., compounds of Formula I, II, or V. Such products may result for example from the oxidation, reduction, hydrolysis, amidation, esterification, enzymatic cleavage, and the like, of the administered compound. Accordingly, the disclosure includes compounds produced by a process comprising contacting a provided compound, e.g., a compound of Formula I, II, or V, with a subject for a period of time sufficient to yield a metabolic product thereof.

In some embodiments, a provided compound generates reactive oxygen species (ROS). Exemplary ROS includes superoxide radical anion, hydroxyl radical and hydrogen peroxide. In some embodiments, the present disclosure provides compounds capable of generating reactive oxygen species in a subject. In some embodiments, a provided compound conjugates with and/or inhibits cellular proteins by forming mixed disulfides between cysteine residues. In some embodiments, a provided compound conjugates with and/or inhibits cellular proteins by catalytic formation of intramolecular disulfide bonds between cysteine residues. In some embodiments, the present disclosure provides compounds capable of conjugating with and/or inhibiting cellular proteins. In some embodiments, a provided compound disrupts tertiary structure of proteins containing a thiol or disulfide in the active site. In certain embodiments, a provided compound disrupts the tertiary structure of proteins containing a metal (e.g., metal ion). In certain embodiments, the metal is Na, K, Mg, Ca, Fe, Mn, Co, Cu, Zn, or Mo. In certain embodiments, the metal is Fe. In certain embodiments, the metal is Cu. In certain embodiments, the metal is Zn (e.g., Zn(II)). In some embodiments, a provided compound disrupts tertiary structure of proteins containing a $Zn^{2+}$-binding cysteine-histidine rich protein domain. In some embodiments, the present disclosure provides compounds capable of disrupting tertiary structures of proteins containing a $Zn^{2+}$-binding cysteine-histidine rich protein domain In some embodiments, a provided compound ejects $Zn^{2+}$ ions from a protein. In some embodiments, the present disclosure provides compounds capable of ejecting a $Zn^{2+}$ ion from a protein. In some embodiments, a provided compound induces caspase-dependent apoptosis. In some embodiments, the present disclosure provides compounds capable of inducing apoptosis. In some embodiments, the present disclosure provides compounds capable of inducing caspase-dependent apoptosis.

In certain aspects, the disclosure provides compounds of Formula (X):

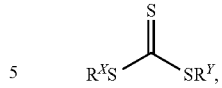

(X)

or salt thereof, wherein $R^X$ is unsubstituted alkyl, —Si($R^S$)$_3$, —Sn($R^S$)$_3$, substituted or unsubstituted benzyl, or $M^X$;

$R^Y$ is unsubstituted alkyl, —Si($R^S$)$_3$, —Sn($R^S$)$_3$, substituted or unsubstituted benzyl, hydrogen, or $M^Y$;

each $R^S$ is independently hydrogen, halogen, hydroxyl, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl;

$M^X$ is a metal selected from the group consisting of sodium, potassium, lithium, rubidium, and cesium; and $M^Y$ is a metal selected from the group consisting of sodium, potassium, lithium, rubidium, and cesium.

In some embodiments, a compound of formula (X) is not sodium benzhydryl trithiocarbonate. In some embodiments, a compound of formula (X) is not sodium p-methoxybenzhydryl trithiocarbonate.

In certain embodiments, $R^X$ is unsubstituted alkyl. In some embodiments, $R^X$ is unsubstituted methyl, ethyl, propyl, iso-propyl, butyl, tert-butyl, or pentyl. In certain embodiments, $R^X$ is —Si($R^S$)$_3$, and $R^S$ is methyl. In some embodiments, $R^X$ is —Sn($R^S$)$_3$, and $R^S$ is methyl. In some embodiments, $R^X$ is substituted benzyl. In certain embodiments, $R^X$ is unsubstituted benzyl. In some embodiments, $R^X$ is $M^X$.

In certain embodiments, $R^Y$ is unsubstituted alkyl. In some embodiments, $R^Y$ is unsubstituted methyl, ethyl, propyl, iso-propyl, butyl, tert-butyl, or pentyl. In certain embodiments, $R^Y$ is —Si($R^S$)$_3$, and $R^S$ is methyl. In some embodiments, $R^Y$ is —Sn($R^S$)$_3$, and $R^S$ is methyl. In some embodiments, $R^Y$ is substituted benzyl. In certain embodiments, $R^Y$ is unsubstituted benzyl. In some embodiments, $R^Y$ is $M^Y$.

In some embodiments, $R^S$ is hydrogen. In certain embodiments, $R^S$ is halogen. In certain embodiments, $R^S$ is hydroxyl. In certain embodiments, $R^S$ is substituted or unsubstituted $C_{1-6}$ alkyl. In certain embodiments, $R^S$ is methyl. In certain embodiments, $R^S$ is $C_{1-6}$ heteroalkyl. In certain embodiments, $R^S$ is —OCH$_3$.

In certain embodiments, $M^X$ is sodium. In some embodiments, $M^X$ is potassium. In certain embodiments, $M^X$ is lithium. In some embodiments, $M^X$ is rubidium. In certain embodiments, $M^X$ is cesium.

In certain embodiments, $M^Y$ is sodium. In certain embodiments, $M^Y$ is potassium. In certain embodiments, $M^Y$ is lithium. In certain embodiments, $M^Y$ is rubidium. In certain embodiments, $M^Y$ is cesium. In certain embodiments, $M^X$ and $M^Y$ are not both sodium and are not both potassium.

In certain embodiments, a compound of Formula (X) is of the formula:

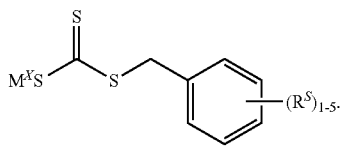

In certain embodiments, a compound of Formula (X) is of the formula:

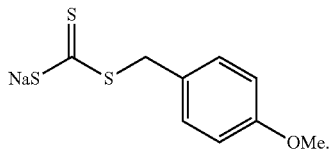

Also provided herein are compounds of Formula (XII):

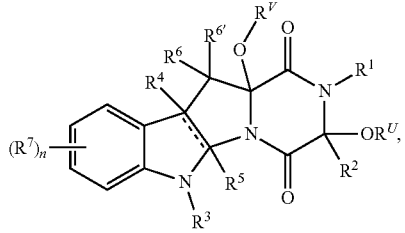

(XII)

or a salt thereof, wherein:

one of $R^U$ and $R^V$ is hydrogen, and the other one of $R^U$ and $R^V$ is an oxygen protecting group or —Si($R^S$)$_3$;

or $R^U$ and $R^V$ are each attached to the same ⁓ to form a ring; and each $R^S$ is independently hydrogen, halogen, hydroxyl, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

In certain embodiments, a compound of Formula (XII) comprises only one —OH.

In some embodiments, a compound of Formula (XII) is of the formula:

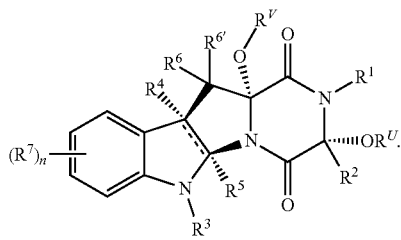

In certain embodiments, a compound of Formula (XII) is of the formula:

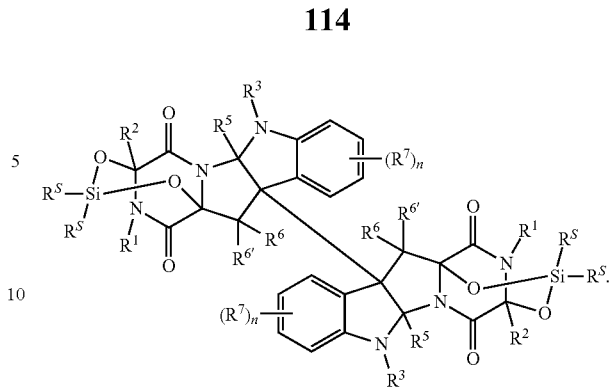

In certain embodiments, a compound of Formula (XII) is of the formula:

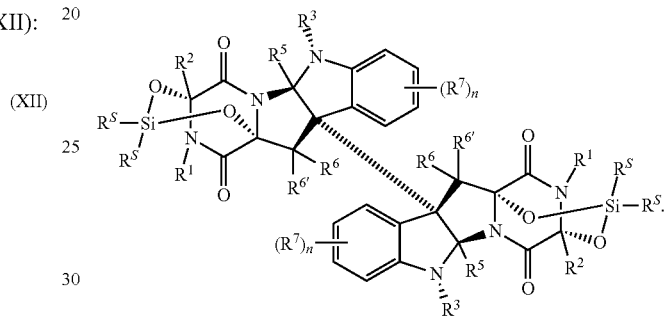

In some embodiments, $R^U$ is hydrogen. In certain embodiments, $R^U$ is an oxygen protecting group. In some embodiments, $R^U$ is an oxygen protecting group selected from the group consisting of acetyl, benzoyl, methoxymethyl ether, or pivaloyl. In some embodiments, $R^U$ is —Si($R^S$)$_3$. In some embodiments, $R^U$ is —Si(Me)$_3$, —Si(iPr)$_3$, or —Si(tBu)(Me)$_2$.

In some embodiments, $R^V$ is hydrogen. In certain embodiments, $R^V$ is an oxygen protecting group. In some embodiments, $R^V$ is an oxygen protecting group selected from the group consisting of acetyl, benzoyl, methoxymethyl ether, or pivaloyl. In some embodiments, $R^V$ is —Si($R^S$)$_3$. In some embodiments, $R^V$ is —Si(Me)$_3$, —Si(iPr)$_3$, or —Si(tBu)(Me)$_2$.

In certain embodiments, $R^U$ is hydrogen, and $R^V$ is —Si(Me)$_3$. In certain embodiments, $R^V$ is hydrogen, and $R^U$ is —Si(Me)$_3$. In certain embodiments, $R^U$ is hydrogen, and $R^V$ is —Si(tBu)(Me)$_2$. In certain embodiments, $R^V$ is hydrogen, and $R^U$ is —Si(tBu)(Me)$_2$.

In certain embodiments, $R^U$ and $R^V$ are each attached to the same

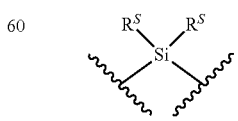

to form a ring (e.g., $R^U$ and $R^V$ are joined to form a ring that comprises

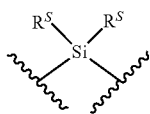

in the ring system, wherein the two attachment points of

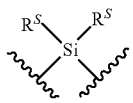

are attached to the two oxygen atoms to which $R^U$ and $R^V$ are attached, respectively).

Methods of Preparation

In certain aspects, the present disclosure provides methods of making a compound of Formula (I), or a salt thereof, comprising reacting a compound of Formula (II), or a salt thereof, with a compound of Formula (III):

$$R^{H2}\text{-}L^3\text{-}D \qquad \text{(III),}$$

or a salt thereof, wherein $R^{H2}$ is a reaction handle, wherein the reaction handle is able to react with $R^{H1}$ of Formula (II) to form $R^H$ of Formula (I). In some embodiments, the step of reacting comprises a click-chemistry reaction. In certain embodiments, the step of reacting comprises a metathesis reaction. In certain embodiments, the step of reacting comprises a condensation reaction. In certain embodiments, the step of reacting comprises a nucleophilic substitution reaction. In certain embodiments, the step of reacting comprises an addition reaction. In some embodiments, the step of reacting comprises an elimination reaction. In certain embodiments, the step of reacting comprises a substitution reaction. In certain embodiments, the step of reacting comprises a rearrangement reaction. In some embodiments, the step of reacting comprises photochemical reaction. In certain embodiments, the step of reacting comprises redox reaction.

Also provided herein are methods of synthesizing a compound of the formula:

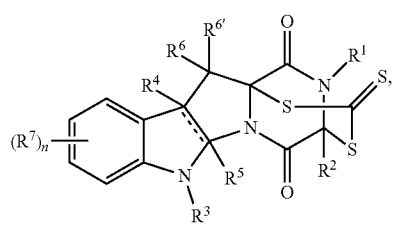

(XI)

or salt thereof, comprising reacting a compound of the formula:

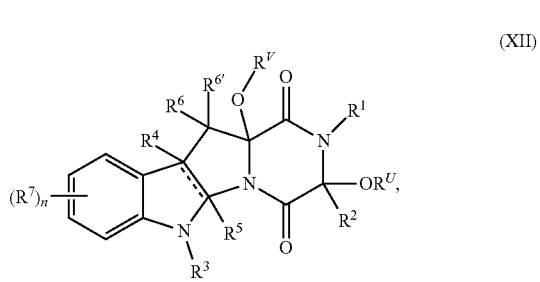

(XII)

or a salt thereof, with a compound of Formula (X), or a salt thereof, wherein: one of $R^U$ and $R^V$ is hydrogen, and the other one of $R^U$ and $R^V$ is an oxygen protecting group or —Si$(R^S)_3$; and each $R^S$ is independently hydrogen, halogen, hydroxyl, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl. In certain embodiments, $R^1$, $R^2$, $R^3$, $R^4$, $R^5$, $R^6$, $R^{6'}$, $R^7$, $R^U$, $R^V$, ---, and n are as defined herein. In some embodiments, $R^4$ is absent when --- is a double bond or is R or halogen; and R, $R^1$, $R^2$, $R^3$, $R^5$, $R^6$, $R^{6'}$, $R^7$, $R^U$, $R^V$, ---, and n are as defined herein. In certain embodiments, the compound of Formula (X) is of the formula:

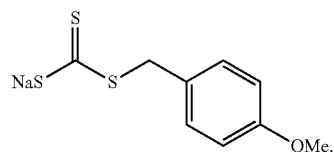

In certain embodiments, $R^U$ is hydrogen, and $R^V$ is —Si(Me)$_3$. In certain embodiments, $R^V$ is hydrogen, and $R^U$ is —Si(Me)$_3$. In certain embodiments, $R^U$ is hydrogen, and $R^V$ is —Si(tBu)(Me)$_2$. In certain embodiments, $R^V$ is hydrogen, and $R^U$ is —Si(tBu)(Me)$_2$. In certain embodiments, a compound of Formula (XII) comprises only one —OH. In some embodiments, a compound of formula (XI) is of the formula:

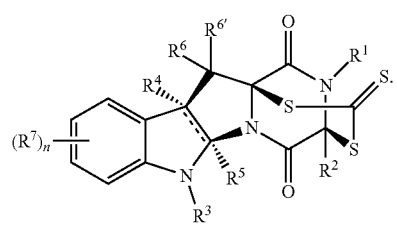

Also provided herein are methods of synthesizing a compound of the formula:

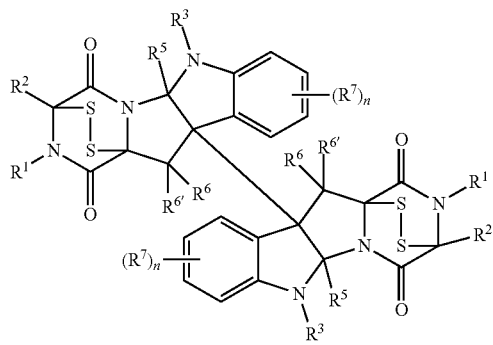

or salt thereof, comprising reacting a compound of the formula:

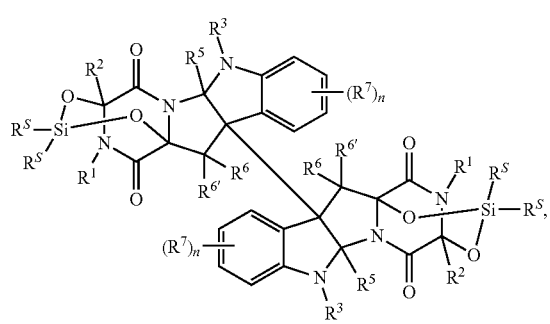

or salt thereof, with tritylhydrodisulfane. In some embodiments, a compound of the formula:

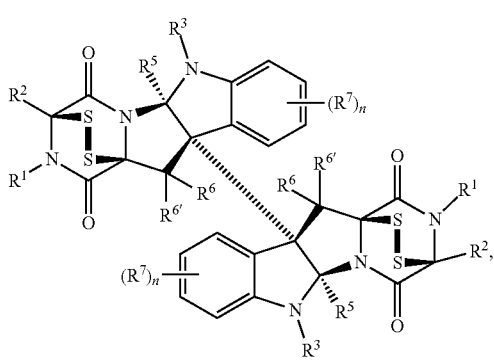

or stereoisomer or salt thereof, is formed by reacting a compound of the formula:

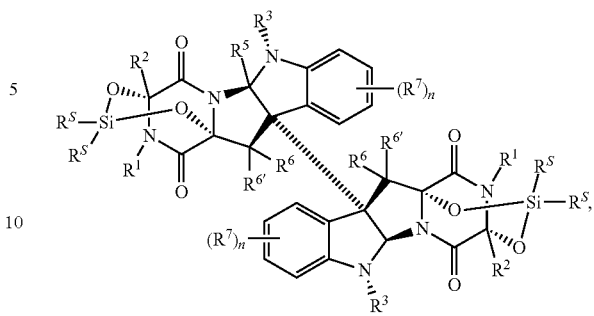

with tritylhydrodisulfane. In certain embodiments, each instance of $R^S$ is unsubstituted alkyl (e.g., isopropyl).

Also provided herein are methods of synthesizing a substituted or unsubstituted dihydroxypiperazinedione, or salt thereof, comprising reacting a substituted or unsubstituted piperazinedione, or salt thereof, with bis(2,2'-bipyridyl)copper(II) permanganate. In certain embodiments, the dihydroxypiperazinedione is a substituted or unsubstituted 3,6-dihydroxypiperazine-2,5-dione. In some embodiments, the piperazinedione is a substituted or unsubstituted piperazine-2,5-dione. In certain embodiments, the dihydroxypiperazinedione is a substituted or unsubstituted 3,6-dihydroxypiperazine-2,5-dione and the piperazinedione is a substituted or unsubstituted piperazine-2,5-dione. In certain embodiments, the piperazinedione is of the formula:

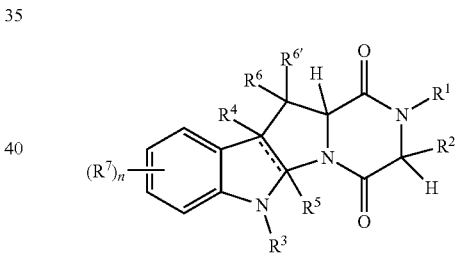

or salt thereof, wherein $R^1$, $R^2$, $R^3$, $R^4$, $R^5$, $R^6$, $R^{6'}$, $R^7$, ⚌, and n are as defined herein. In some embodiments, the dihydroxypiperazinedione is of the formula

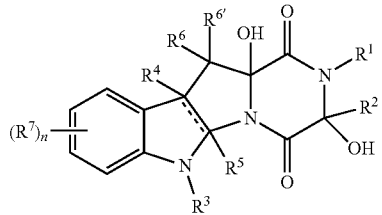

or salt thereof, wherein $R^1$, $R^2$, $R^3$, $R^4$, $R^5$, $R^6$, $R^{6'}$, $R^7$, ⚌, and n are as defined herein. In some embodiments, the piperazinedione is of the formula:

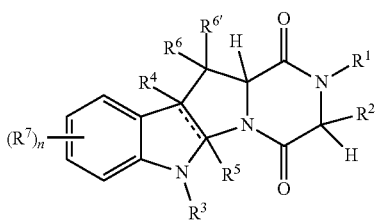

or salt thereof, and the dihydroxypiperazinedione is of the formula:

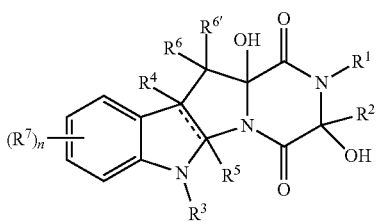

or salt thereof, wherein $R^1$, $R^2$, $R^3$, $R^4$, $R^5$, $R^6$, $R^{6'}$, $R^7$, ⚌, and n are as defined herein. In certain embodiments, provided herein are methods of synthesizing a piperazinedione of the formula:

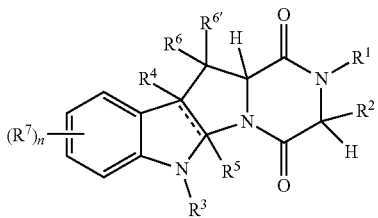

or salt thereof, by reacting a dihydroxypiperazinedione of the formula:

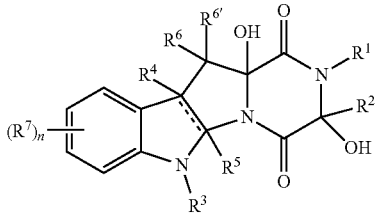

or salt thereof, wherein $R^1$, $R^2$, $R^3$, $R^4$, $R^5$, $R^6$, $R^{6'}$, $R^7$, ⚌, and n are as defined herein, with bis(2,2'-bipyridyl)copper (II) permanganate. In some embodiments, the method is useful in the synthesis of ETPs and derivatives thereof. In certain embodiments, a piperazinedione is of the formula:

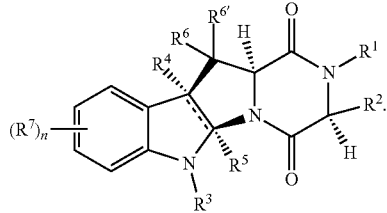

In some embodiments, a dihydroxypiperazinedione is of the formula:

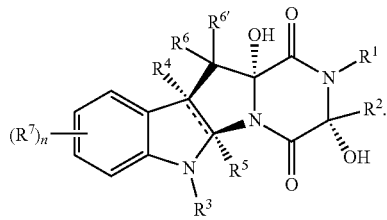

In some embodiments, the present disclosure recognizes the challenges for preparing ETP or thiodiketopiperazine alkaloids or derivatives or analogs thereof. In some embodiments, the present disclosure provides a method for preparing ETP or thiodiketopiperazine alkaloids or derivatives or analogs thereof. In some embodiments, the present disclosure provides a method for preparing a provided compound. In some embodiments, the present disclosure provides new reagents for preparing ETP or thiodiketopiperazine alkaloids or derivatives or analogs thereof. In some embodiments, the present disclosure provides new reagents for preparing a provided compound. In some embodiments, a provided method and/or reagent provides unexpectedly high synthetic efficiency, for example, in terms of product yield and/or purity.

In some embodiments, the present disclosure provides methods for flexible and scalable synthesis of ETP or thiodiketopiperazine alkaloids or derivatives or analogs thereof, for example, a provided compound of formula I, II, or V. In some embodiments, the present disclosure provides a method for scalable synthesis, e.g., >5 g, >6 g, >7 g, >8 g, >9 g, >10 g, >11 g, >12 g, >13 g, >14 g, >15 g, >16 g, >17 g, >18 g, >19 g, or >20 g, >15 g or >20 g scale, of an erythro-o-hydroxytryptophan compound, an intermediate useful for the preparation of ETP or thiodiketopiperazine compounds, or derivatives or analogs thereof.

Compositions and Kits

The present disclosure provides compositions (e.g., pharmaceutical compositions) comprising a compound or conjugate as described herein, and optionally an excipient (e.g., pharmaceutically acceptable excipient). In certain embodiments, the composition is a pharmaceutical composition. In certain embodiments, the excipient is a pharmaceutically acceptable excipient.

In certain embodiments, the pharmaceutical compositions are useful for delivering an agent (e.g., to a subject or cell). In certain embodiments, the pharmaceutical compositions are useful for treating a disease in a subject in need thereof. In certain embodiments, the pharmaceutical compositions are useful for preventing a disease in a subject. In certain embodiments, the pharmaceutical compositions are useful for diagnosing a disease in a subject.

In certain embodiments, the compound or conjugate described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a cancer in a subject in need thereof. In certain embodiments, the effective amount is an amount effective for preventing cancer in a subject in need thereof. In some embodiments, the cancer is cervical cancer, lung cancer, breast cancer, colorectal cancer, or prostate cancer. In certain embodiments, the cancer is metastatic. In certain embodiments, the cancer is characterized by higher extracellular thiol concentrations. In certain embodiments, the effective amount is an amount effective for treating an autoimmune disease in a subject in need thereof. In certain embodiments, the effective amount is an amount effective for preventing an autoimmune disease in a subject in need thereof. In certain embodiments, the effective amount is an amount effective for treating an infectious disease in a subject in need thereof. In certain embodiments, the effective amount is an amount effective for preventing an infectious disease in a subject in need thereof. In certain embodiments, the effective amount is an amount effective for generating reactive oxygen species in a subject in need thereof. In certain embodiments, the effective amount is an amount effective for generating reactive oxygen species in a cell, tissue, or biological sample. In certain embodiments, the effective amount is an amount effective for inhibiting a protein in a subject in need thereof. In certain embodiments, the effective amount is an amount effective for inhibiting a protein in a cell, tissue, or biological sample. In certain embodiments, the effective amount is an amount effective for disrupting structures of proteins containing a thiol or disulfide in the active site in a subject in need thereof. In certain embodiments, the effective amount is an amount effective for disrupting structures of proteins containing a thiol or disulfide in the active site in a cell, tissue, or biological sample. In certain embodiments, the effective amount is an amount effective for disrupting structures of proteins containing a metal (e.g., a metal ion) (e.g., Na, K, Mg, Ca, Fe, Mn, Co, Cu, Zn, or Mo (e.g., Zn, Fe, or Cu) in a subject in need thereof. In certain embodiments, the effective amount is an amount effective for disrupting structures of proteins containing a metal (e.g., Na, K, Mg, Ca, Fe, Mn, Co, Cu, Zn, or Mo (e.g., Zn, Fe, or Cu) in a cell, tissue, or biological sample. In certain embodiments, the effective amount is an amount effective for disrupting structures of proteins containing a $Zn^{2+}$ in a subject in need thereof. In certain embodiments, the effective amount is an amount effective for disrupting structures of proteins containing a $Zn^{2+}$ in a cell, tissue, or biological sample. In certain embodiments, the effective amount is an amount effective for inducing apoptosis of a cell. In certain embodiments, the effective amount is an amount effective for inducing apoptosis of a cell in a subject. In certain embodiments, the effective amount is an amount effective for inducing apoptosis of a cell in a tissue or biological sample. In certain embodiments, the effective amount is an amount effective for inhibiting proliferation of a cell. In certain embodiments, the effective amount is an amount effective for inhibiting proliferation of a cell in a subject. In certain embodiments, the effective amount is an amount effective for inhibiting proliferation of a cell in a tissue or biological sample. In certain embodiments, the effective amount is an amount effective for reducing the risk of developing a disease (e.g., proliferative disease, autoimmune disease, hematological disease, neurological disease, painful condition, psychiatric disorder, or metabolic disorder) in a subject in need thereof. In certain embodiments, the effective amount is an amount effective for preventing a disease in a subject in need thereof. In certain embodiments, the effective amount is an amount effective for diagnosing a disease in a subject in need thereof.

In certain embodiments, the effective amount is an amount effective for delivering a pharmaceutical agent to a biological sample or cell. In certain embodiments, the cell is in vitro. In certain embodiments, the cell is in vivo. In certain embodiments, the cell is a malignant cell. In some embodiments, the cell is a premalignant cell.

Pharmaceutical compositions described herein can be prepared by any method known in the art of pharmacology. In general, such preparatory methods include bringing the compound or conjugate described herein (which may include a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients, such as cocoa butter and suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip©, methylparaben, Germall© 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound or conjugate described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds and conjugates provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds, conjugates, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound, conjugate, or pharmaceutical compositions described herein is suitable for topical administration to the eye of a subject. In some embodiments, provided pharmaceutical formulations of provided compounds or conjugates are typically prepared for parenteral administration, i.e. bolus, intravenous, intratumor injection with a pharmaceutically acceptable parenteral vehicle and in a unit dosage injectable form. In some embodiments, the compounds or conjugates having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

A provided pharmaceutical composition may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The exact amount of a compound or conjugate required to achieve an effective amount will vary from subject to subject, depending, for example, on species, age, and general condition of a subject, severity of the side effects or disorder, identity of the particular compound or conjugate, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound or conjugate described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound or conjugate described herein. In certain embodiments, a dose described herein includes independently between 1 mg and 3 mg, inclusive, of a compound or conjugate described herein. In certain embodiments, a dose described herein includes independently between 3 mg and 10 mg, inclusive, of a compound or conjugate described herein. In certain embodiments, a dose described herein includes independently between 10 mg and 30 mg, inclusive, of a compound or conjugate described herein. In certain embodiments, a dose described herein includes independently between 30 mg and 100 mg, inclusive, of a compound or conjugate described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound, conjugate, or composition as described herein, can be administered in combination with one or more additional pharmaceutical agents (e.g., therapeutically and/or prophylactically active agents). The compound, conjugate, or composition can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in diagnosing a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound or conjugate described herein and an additional pharmaceutical agent shows a synergistic effect that is absent in a pharmaceutical composition including one of the compound or conjugate and the additional pharmaceutical agent, but not both.

The compound, conjugate, or compositions can be administered concurrently with, prior to, or subsequent to one or more additional pharmaceutical agents, which are different from the compound, conjugate, or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound, conjugate, or composition described herein in a single dose or administered separately in different doses. The particular combination to employ in a regimen will take into account compatibility of the compound or conjugate described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation.

In certain embodiments, the compounds or conjugates described herein or pharmaceutical compositions can be administered in combination with an anti-cancer therapy including surgery, radiation therapy, transplantation (e.g., stem cell transplantation, bone marrow transplantation), immunotherapy, and chemotherapy. In certain embodiments, the compounds or conjugates described herein or pharmaceutical compositions can be administered in combination with an additional therapy. In some embodiments, the compounds or conjugates described herein or pharmaceutical compositions can be administered in combination with radiation therapy.

Also encompassed by the disclosure are kits (e.g., pharmaceutical packs). The kits provided may comprise a pharmaceutical composition, compound, or conjugate described herein and instructions for use. The kits may further comprise a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition, compound, or conjugate described herein. In some embodiments, the pharmaceutical composition, compound, or conjugate described herein provided in the first container and the second container are combined to form one unit dosage form.

In some embodiments, the percentage of the conjugate that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the conjugate that comprise an agent is less than about 50%, e.g., less than about 40%, less than about 35%, less than about 30%, less than about 25%, less than about 20%, less than about 15%, or less than about 10%. In some embodiments, the percentage of the conjugate that comprise an agent is between about 5% and about 50%, about 5% and about 40%, about 5% and about 30%, about 5% and about 25%, or about 5% and about 20%. In some embodiments, the percentage of the conjugate that comprise an agent is between about 5% and 90%. In some embodiments, the percentage of the conjugate that comprise an agent is between about 5% and about 75%. In the some embodiments, the conjugate that comprise an agent is between about 5% and about 50%. In the some embodiments, the percentage of the conjugate that comprise an agent is between about 10% and about 25%.

In some embodiments, the total amount of the agent present in the conjugate is greater than about 5% (e.g., about 6%, about 7%, about 8%, about 9%, about 10%, about 12%, about 15%, about 20%, about 25%, about 30%, or more) of the total size or weight of the conjugate. In some embodiments, the total amount of the agent present in the conjugate is greater than about 10% (e.g., about 12%, about 15%, about 20%, about 25%, about 30%, or more) of the total size or weight of the conjugate.

Without being bound by theory, the conjugate disclosed herein may improve the efficiency of an agent by one or more of increasing the localization and/or release (e.g., preferential release) of the agent to a target cell (e.g., a cancer cell), or increasing the half-life of the agent, thus resulting in a significantly higher amount of a released agent at a target site (e.g., a tumor or liver (e.g., cirrhotic cell). According, the conjugates disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates disclosed herein can reduce the adverse effect associated with systemic administration of an agent in free form (e.g., not coupled to polymer, conjugate or particle described herein).

Without being bound by theory, due to the localized delivery of the conjugate or compositions described herein, a lower dose or amount of the agent can be administered (e.g., through local sustained delivery) compared to the agent in free form. In other embodiments, the agent-containing conjugates are administered at a dose or amount of the agent that is less than the dose or amount of said agent in free form to have a desired effect (e.g., a desired therapeutic effect).

In some embodiments, the agent is incorporated into a conjugate at a dose that is less than the dose or amount of said agent in free form to have a desired effect (e.g., a desired therapeutic effect), e.g., the standard of care dose for the intended use of the free agent. In one embodiment, the agent is incorporated into the conjugate at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a conjugate at a dose equivalent to the dose or amount of said agent in free form to have a desired effect (e.g., a desired therapeutic effect), e.g., the standard of care dose for the intended use of the free agent. In these embodiments, the conjugate produces a greater therapeutic effect and/or a less adverse effect than the free agent. In certain embodiments, the conjugate increases the amount of the agent delivered to a tissue or cell in need thereof and reduces the amount of the agent exposed to a non-target tissue or cell, as compared to the free agent.

In some embodiments, the agent is incorporated into a conjugate at a dose higher than the dose or amount of said agent in free form to have a desired effect (e.g., a desired therapeutic effect), e.g., the standard of care dose for the intended use of the free agent. In some embodiments, the agent is incorporated into a conjugate at a dose higher than the dose or amount of said agent in free form that would produce an adverse effect by systemic administration (e.g., a reduction in blood pressure). In some embodiments, since the conjugate described herein releases the agent at a target site based on pH microenvironment, other non-target sites (e.g., blood vessels) with different pH would be less likely to be exposed to the agent.

In another aspect, provided are kits including a first container comprising a compound, conjugate, or pharmaceutical composition described herein. In certain embodiments, the kits are useful for delivering an agent (e.g., to a subject, cell, biological sample). In certain embodiments, the kits are useful for treating a disease (e.g., proliferative disease, autoimmune disease, infectious disease, hematological disease, neurological disease, painful condition, psychiatric disorder, or metabolic disorder) in a subject in need thereof. In certain embodiments, the kits are useful for preventing a disease (e.g., proliferative disease, autoimmune disease, infectious disease, hematological disease, neurological disease, painful condition, psychiatric disorder, or metabolic disorder) in a subject in need thereof. In certain embodiments, the kits are useful for reducing the risk of developing a disease (e.g., proliferative disease, autoimmune disease, infectious disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein in a subject or cell, tissue, or biological sample. In certain embodiments, the kits are useful for generating a reactive oxygen species in a subject, cell, tissue or biological sample. In certain embodiments, the kits are useful for disrupting structures of proteins in a subject, cell, tissue or biological sample. In certain embodiments, the kits are useful for disrupting structures of proteins containing a $Zn^{2+}$ in a subject, cell, tissue or biological sample. In certain embodiments, the kits are useful for inducing apoptosis of a cell, a cell in a subject, or a cell in a tissue or biological sample. In certain embodiments, the kits are useful for inhibiting proliferation of a cell, a cell in a subject, or a cell in a tissue or biological sample.

In certain embodiments, a kit described herein further includes instructions for using the kit. A kit described herein may also include information as required by a regulatory agency such as the U.S. Food and Drug Administration (FDA). In some embodiments, a kit comprises a compound, conjugate, or composition as described herein and instructions for using the polymer or composition. In certain embodiments, the information included in the kits is prescribing information. In certain embodiments, the kits and instructions provide for delivering an agent. In certain embodiments, the kits and instructions provide for treating a disease (e.g., proliferative disease, autoimmune disease, infectious disease, hematological disease, neurological disease, painful condition, psychiatric disorder, or metabolic disorder) in a subject in need thereof. In certain embodiments, the kits and instructions provide for preventing a disease (e.g., proliferative disease, autoimmune disease, infectious disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, autoimmune disease, infectious disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein in a subject, cell, tissue, or biological sample. In certain embodiments, the kits are useful for generating a reactive oxygen species in a subject, cell, tissue or biological sample. In certain embodiments, the kits are useful for disrupting structures of proteins containing a $Zn^{2+}$ in a subject, cell, tissue or biological sample. In certain embodiments, the kits are useful for inducing apoptosis of a cell, a cell in a subject, or a cell in a tissue or biological sample. In certain embodiments, the kits are useful for inhibiting proliferation of a cell, a cell in a subject, or a cell in a tissue or biological sample. A kit described herein may include one or more additional pharmaceutical agents described herein as a separate composition.

In some embodiments, the present disclosure provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Methods and Uses

The compounds and compositions of the present disclosure may be used to treat various diseases or disorders. In certain embodiments, the present disclosure provides methods for treating or preventing a cancer, an autoimmune disease, or infectious disease in a subject in need thereof. In certain embodiments, the present disclosure provides methods for generating reactive oxygen species in a subject in need thereof. In certain embodiments, the present disclosure provides methods for generating reactive oxygen species in a cell, tissue, or biological sample. In certain embodiments, the present disclosure provides methods for inhibiting a protein in a subject in need thereof. In certain embodiments, the present disclosure provides methods for inhibiting a protein in a cell, tissue, or biological sample. In certain embodiments, the present disclosure provides methods for disrupting structures of proteins containing a thiol or disulfide in the active site in a subject in need thereof. In certain embodiments, the present disclosure provides methods for disrupting structures of proteins containing a thiol or disulfide in the active site in a cell, tissue, or biological sample. In certain embodiments, the present disclosure provides methods for disrupting structures of proteins containing an iron or copper in a subject in need thereof. In certain embodiments, the present disclosure provides methods for disrupting structures of proteins containing an iron or copper in a cell, tissue, or biological sample. In certain embodiments, the present disclosure provides methods for disrupting structures of proteins containing a $Zn^{2+}$ in a subject in need thereof. In certain embodiments, the present disclosure provides methods for disrupting structures of proteins containing a $Zn^{2+}$ in a cell, tissue, or biological sample. In certain embodiments, the present disclosure provides methods for inducing apoptosis of a cell. In certain embodiments, the present disclosure provides methods for inducing apoptosis of a cell in a subject. In certain embodiments, the present disclosure provides methods for inducing apoptosis of a cell in a tissue or biological sample. In certain embodiments, the present disclosure provides methods for inhibiting proliferation of a cell. In certain embodiments, the present disclosure provides methods for inhibiting proliferation of a cell in a subject. In certain embodiments, the present disclosure provides methods for inhibiting proliferation of a cell in a tissue or biological sample. In certain embodiments, the present disclosure provides methods for reducing the risk of developing a disease (e.g., proliferative disease, autoimmune disease, hematological disease, neurological disease, painful condition, psychiatric disorder, or metabolic disorder) in a subject in need thereof. In certain embodiments, the present disclosure provides methods for preventing a disease in a subject in need thereof. In certain embodiments, the present disclosure provides methods for diagnosing a disease in a subject in need thereof.

A provided compound or composition of the present disclosure may be used to treat various diseases or disorders, e.g. characterized by the overexpression of an antigen such as a cancer antigen. In some embodiments, the disease is cervical cancer, lung cancer, breast cancer, colorectal cancer, or prostate cancer. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In some embodiments, the present disclosure provides a method for killing or inhibiting proliferation of cells comprising treating the cells with an amount of a provided compound, or a pharmaceutically acceptable salt thereof, being effective to kill or inhibit proliferation of the cells. In some embodiments, the cells are tumor cells or cancer cells. In some embodiments, the present disclosure provides a method of treating a disease, comprising administering to a subject in need an effective amount of a provided compound or a pharmaceutically acceptable salt thereof. In some embodiments, the present disclosure provides a method of treating a disease, comprising administering to a subject suffering therefrom or susceptible thereto an effective amount of a provided compound or pharmaceutically salt thereof. In some embodiments, a disease is a cancer, autoimmune disease or infectious disease. In some embodiments, a disease is cancer. In some embodiments, a disease is an autoimmune disease. In some embodiments, a disease is an infectious disease. In some embodiments, a provided is a compound of formula I. In some embodiments, a provided is a compound of formula II. In some embodiments, a provided is a compound of formula V.

A provided compound of the disclosure may be combined in a pharmaceutical combination formulation, or dosing regimen as combination therapy, with a second compound having therapeutic properties. A second compound of the pharmaceutical combination formulation or dosing regimen preferably has complementary activities to a provided compound of the combination such that they do not adversely affect each other.

In some embodiments, a second compound is a chemotherapeutic agent, cytotoxic agent, cytokine, growth inhibitory agent, anti-hormonal, a drug for an autoimmune disease, a drug for an infectious disease, and/or cardioprotectant. Such molecules are suitably present in combination in amounts that are effective for the purpose intended.

A combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for co-administered agents are those presently used and may be lowered due to the combined action (synergy) of the newly identified agent and other chemotherapeutic agents or treatments.

A provided combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In some embodiments, the present disclosure provides methods of treating cancer. In some embodiments, the present disclosure provides a method of treating cancer in a subject suffering therefrom, comprising administering to the subject a therapeutically effective amount of a provided compound. In some embodiments, a provided compound has the structure of formula I. In some embodiments, a provided compound has the structure of formula II. In some embodiments, a provided compound has the structure of formula V.

Provided compounds and/or compositions are useful for inhibiting the multiplication of a tumor cell or cancer cell, causing apoptosis in a tumor or cancer cell, or for treating cancer in a subject. Provided compounds and compositions can be used in a variety of settings for the treatment of cancers. A provided conjugate compound, e.g., a compound of formula I, can be used to deliver a drug to a tumor cell or cancer cell. Without being bound by theory, in one embodiment, a portion of a conjugate o binds to or associates with a cancer-cell or a tumor-cell-associated antigen, and a provided compound can be taken up inside a tumor cell or cancer cell through receptor-mediated endocytosis. An antigen can be attached to a tumor cell or cancer cell or can be an extracellular matrix protein associated with the tumor cell or cancer cell. In some embodiments, once inside the cell, a conjugate compound is cleaved, for example, one or more specific peptide sequences within a linker unit are hydrolytically cleaved by one or more tumor-cell or cancer-cell-associated proteases, resulting in release of a drug comprising part or all of the drug unit and optionally part or all of the linker unit. A released drug is then free to migrate within the cell and induce cytotoxic or cytostatic activities. In some other embodiments, a provided conjugate compound is cleaved outside a tumor cell or cancer cell, and a drug or drug-linker compound subsequently penetrates the cell.

In some embodiments, a portion of a conjugate binds to a tumor cell or cancer cell. In some embodiments, a portion of a conjugate binds to a tumor cell or cancer cell antigen which is on the surface of the tumor cell or cancer cell. In some embodiments, a portion of a conjugate binds to a tumor cell or cancer cell antigen which is an extracellular matrix protein associated with a tumor cell or cancer cell. In some embodiments, the specificity of a portion of a conjugate for a particular tumor cell or cancer cell can be important for determining those tumors or cancers that are most effectively treated. For example, a provided conjugate compound having a BR96 Ligand unit can be useful for treating antigen positive carcinomas including those of the lung, breast, colon, ovaries, and pancreas. In some embodiments, a provided conjugate compound having an Anti-CD30 or an anti-CD40 Ligand unit can be useful for treating hematologic malignancies.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure.

In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In some embodiments, the compounds and conjugates described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Other particular types of cancers that can be treated with provided compounds and/or compositions include, but are not limited to, those listed below: Solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma ultiforme, astrocytoma, medulloblastoma, craniopharyngioma, ependymoma, pinealoma, emangioblastoma, acoustic neuroma, oligodendroglioma, meningioma, skin cancer, melanoma, neuroblastoma, retinoblastoma. Blood-borne cancers, including but not limited to: acute lymphoblastic leukemia "ALL", acute lymphoblastic B-cell leukemia, acute lymphoblastic T-cell leukemia, acute myeloblastic leukemia AML", acute promyelocytic leukemia "APL", acute monoblastic leukemia, acute erythroleukemic leukemia, acute megakaryoblastic leukemia, acute myelomonocytic leukemia, acute non-lymphocyctic leukemia, acute undifferentiated leukemia, chronic myelocytic leukemia "CML", chronic lymphocytic leukemia "CLL", hairy cell leukemia, multiple myeloma, acute and chronic leukemias, lymphoblastic, myelogenous, lymphocytic and myelocytic leukemias. Lymphomas, Hodgkin's disease, non-Hodgkin's Lymphoma, Multiple myeloma, Waldenström's macroglobulinemia, Heavy chain disease, and Polycythemia vera.

In some embodiments, the cancer is cervical cancer, lung cancer, breast cancer, colorectal cancer, or prostate cancer. In some embodiments, the cancer is leukemia or lymphoma. In some embodiments, the cancer is cervical cancer, lung cancer, breast cancer, colorectal cancer, prostate cancer, leukemia, or lymphoma.

In some embodiments, the cancer is leukemia. In certain embodiments, the cancer is chronic myelogenous leukemia (CML) (also known as chronic myeloid leukemia). In certain embodiments, the cancer is acute T cell leukemia.

In certain embodiments, the cancer is lymphoma. In certain embodiments, the cancer is non-Hodgkin's lymphoma. In certain embodiments, the cancer is non-Hodgkin's B cell lymphoma. In some embodiments, the cancer is diffuse large cell lymphoma.

In some embodiments, a cancer being treated is carcinoma, lymphoma, blastoma, sarcoma, leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In some embodiments, a provided conjugate compound provides conjugation-specific tumor or cancer targeting, thus reducing general toxicity of these compounds. In some embodiments, a linker unit stabilizes a provided compound in blood, yet are cleavable by tumor-specific proteases within the cell, liberating a drug unit optionally comprising part of the linker unit.

Cancers, including, but not limited to, a tumor, metastasis, or other disease or disorder characterized by uncontrolled cell growth, can be treated or prevented by administration of a provided compound or composition. In some embodiments, a provided compound or composition is administered with another cancer treatment. In some embodiments, the other cancer treatment (e.g., an anti-cancer agent) is an agent including, but not limited to, abiraterone acetate, ABVD, ABVE, ABVE-PC, AC, AC-T, ADE, ado-trastuzumab emtansine, afatinib dimaleate, aldesleukin, alemtuzumab, anastrozole, arsenic trioxide, asparaginase *Erwinia chrysanthemi*, axitinib, azacitidine, BEACOPP, belinostat, bendamustine hydrochloride, BEP, bevacizumab, bicalutamide, bleomycin, blinatumomab, bortezomib, bosutinib, brentuximab vedotin, busulfan, cabazitaxel, cabozantinib-s-malate, CAF, capecitabine, CAPOX, carboplatin, carboplatin-taxol, carfilzomibcarmustine, carmustine implant, ceritinib, cetuximab, chlorambucil, chlorambucil-prednisone, CHOP, cisplatin, clofarabine, CMF, COPP, COPP-ABV, crizotinib, CVP, cyclophosphamide, cytarabine, dabrafenib, dacarbazine, dactinomycin, dasatinib, daunorubicin hydrochloride, decitabine, degarelix, denileukin diftitox, denosumab, Dinutuximab, docetaxel, doxorubicin hydrochloride, doxorubicin hydrochloride liposome, enzalutamide, epirubicin hydrochloride, EPOCH, erlotinib hydrochloride, etoposide, etoposide phosphate, everolimus, exemestane, FEC, fludarabine phosphate, fluorouracil, FOLFIRI, FOLFIRI-BEVACIZUMAB, FOLFIRI-CETUXIMAB, FOLFIRINOX, FOLFOX, FU-LV, fulvestrant, gefitinib, gemcitabine hydrochloride, gemcitabine-cisplatin, gemcitabine-oxaliplatin, goserelin acetate, Hyper-CVAD, ibritumomab tiuxetan, ibrutinib, ICE, idelalisib, ifosfamide, imatinib mesylate, imiquimod, ipilimumab, irinotecan hydrochloride, ixabepilone, lanreotide acetate, lapatinib ditosylate, lenalidomide, lenvatinib, letrozole, leucovorin calcium, leuprolide acetate, liposomal cytarabine, lomustine, mechlorethamine hydrochloride, megestrol acetate, mercaptopurine, methotrexate, mitomycin c, mitoxantrone hydrochloride, MOPP, nelarabine, nilotinib, nivolumab, obinutuzumab, OEPA, ofatumumab, OFF, olaparib, omacetaxine mepesuccinate, OPPA, oxaliplatin, paclitaxel, paclitaxel albumin-stabilized nanoparticle formulation, PAD, palbociclib, pamidronate disodium, panitumumab, panobinostat, pazopanib hydrochloride, pegaspargase, peginterferon alfa-2b, peginterferon alfa-2b, pembrolizumab, pemetrexed disodium, pertuzumab, plerixafor, pomalidomide, ponatinib hydrochloride, pralatrexate, prednisone, procarbazine hydrochloride, radium 223 dichloride, raloxifene hydrochloride, ramucirumab, R-CHOP, recombinant HPV bivalent vaccine, recombinant human papillomavirus, nonavalent vaccine, recombinant human papillomavirus, quadrivalent vaccine, recombinant interferon alfa-2b, regorafenib, rituximab, romidepsin, ruxolitinib phosphate, siltuximab, sipuleucel-t, sorafenib tosylate, STANFORD V, sunitinib malate, TAC, tamoxifen citrate, temozolomide, temsirolimus, thalidomide, thiotepa, topotecan hydrochloride, toremifene, tositumomab and iodine I 131, tositumomab, TPF, trametinib, trastuzumab, VAMP, vandetanib, VEIP, vemurafenib, vinblastine sulfate, vincristine sulfate, vincristine sulfate liposome, vinorelbine tartrate, vismodegib, vorinostat, XELIRI, XELOX, ziv-aflibercept, and zoledronic acid. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g., mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS—354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™) SGX523, PF-04217903, PF-02341066, PF-299804, BMS—777607, ABT-869, MP470, BIBF 1120 (VARGATEF®), AP24534, JNJ-26483327, MGCD265, DCC-2036, BMS—690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, methods for treating or preventing cancer are provided, comprising administering to a subject in need thereof an effective amount of a provided compound or composition. In some embodiments, a provided compound is administered prior to, concurrently with, or subsequent to, a chemotherapeutic agent. In some embodiments, a chemotherapeutic agent is that with which treatment of the cancer has not been found to be refractory. In some embodiments, a chemotherapeutic agent is that with which the treatment of cancer has been found to be refractory. In some embodiments, a provided compound is administered to a patient that has also undergone surgery as treatment for the cancer.

In some embodiments, an additional method of treatment is radiation therapy. In some embodiments, a provided compound or composition is administered prior to, concurrently with or subsequent to radiation.

In some embodiments, a provided compound or composition is administered concurrently with a chemotherapeutic agent or with radiation therapy. In some embodiments, a chemotherapeutic agent or radiation therapy is administered prior or subsequent to administration of a provided compound or composition. In some embodiments, a chemotherapeutic agent or radiation therapy is administered concurrently with administration of a provided compound or composition. In some embodiments, a provided compound or composition is administered at least one hour, five hours, 12 hours, a day, a week, a month, or several months (e.g., up to three months), prior or subsequent to administration of a provided compound or composition.

A chemotherapeutic agent can be administered over a series of sessions. Any one or a combination of the chemotherapeutic agents can be administered.

Exemplary chemotherapy drugs are widely known in the art, including but not limited to tubulin-binding drugs, kinase inhibitors, alkylating agents, DNA topoisomerase inhibitors, anti-folates, pyrimidine analogs, purine analogs, DNA antimetabolites, hormonal therapies, retinoids/deltoids, photodynamic therapies, cytokines, angiogenesis inhibitors, histone modifying enzyme inhibitors, and antimitotic agents. Examples are extensively described in the art, including but not limited to those in PCT Application Publication No. WO2010/025272. In some embodiments, a "tubulin-binding drug" refers to a ligand of tubulin or to a compound capable of binding α or β-tubulin monomers or oligomers thereof, αβ-tubulin heterodimers or oligomers thereof, or polymerized microtubules. Exemplary tubulin-binding drugs include, but are not limited to: (a) Combretastatins or other stilbene analogs (e.g., described in Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992; Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacal., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacal, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Biooorg. Med. Chem. Lett., 2002; Kim et al., Bioorg Med Chem Lett., 2002; Li et al, Biooorg. Med. Chem. Lett., 2002; Nam et al, Bioorg. Med. Chem. Lett., 2002; Wang et al, J. Med. Chem. 2002; Hsieh et al, Biooorg. Med. Chem. Lett., 2003; Hadimani et al., Bioorg. Med. Chem. Lett., 2003; Mu et al, J. Med. Chem, 2003; Nam, Curr. Med. Chem., 2003; Pettit et al, J. Med. Chem., 2003; WO 02/50007, WO 02/22626, WO 02/14329, WO 01/81355, WO 01/12579, WO 01/09103, WO 01/81288, WO 01/84929, WO 00/48591, WO 00/48590, WO 00/73264, WO 00/06556, WO 00/35865, WO 00/48590, WO 99/51246, WO 99/34788, WO 99/35150, WO 99/48495, WO 92/16486, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528); (b) 2,3-substituted Benzo[b]thiophenes (e.g., described in Pinney et al, Bioorg. Med. Chem. Lett., 1999; Chen et al, J. Org. Chem., 2000; U.S. Pat. Nos. 5,886,025; 6,162,930, and 6,350,777; WO 98/39323); (c) 2,3-disubstituted Benzo[b] furans (e.g., described in WO 98/39323, WO 02/060872); (d) Disubstituted Indoles (e.g., described in Gastpar R, J. Med. Chem., 1998; Bacher et al, Cancer Res., 2001; Flynn et al, Bioorg. Med. Chem. Lett, 2001; WO 99/51224, WO 01/19794, WO 01/92224, WO 01/22954; WO 02/060872, WO 02/12228, WO 02/22576, and U.S. Pat. No. 6,232,327); (e) 2-Aroylindoles (e.g., described in Mahboobi et al, J. Med. Chem., 2001; Gastpar et al., J. Med. Chem., 1998; WO 01/82909); (f) 2,3-disubstituted Dihydronaphthalenes (e.g., described in WO 01/68654, WO 02/060872); (g) Benzamidazoles (e.g., described in WO 00/41669); (h) Chalcones (e.g., described in Lawrence et al, Anti-Cancer Drug Des, 2000; WO 02/47604); (i) Colchicine, Allocolchicine, Thiocolcichine, Halichondrin B, and Colchicine derivatives (e.g., described in WO 99/02166, WO 00/40529, WO 02/04434, WO 02/08213, U.S. Pat. Nos. 5,423,753, 6,423,753) in particular the N-acetyl colchinol prodrug, ZD-6126; (j) Curacin A and its derivatives (e.g., described in Gerwick et al, J. Org. Chem., 1994, Blokhin et al, Mol. Phamacol., 1995; Verdier-Pinard, Arch. Biochem. Biophys., 1999; WO 02/06267); (k) Dolastatins such as Dolastatin-10, Dolastatin-15, and their analogs (e.g., described in Pettit et al, J. Am. Chem. Soc., 1987; Bai et al, Mol. Pharmacal, 1995; Pettit et al, Anti-Cancer Drug Des., 1998; Poncet, Curr. Pharm. Design, 1999; WO 99/35164; WO 01/40268; U.S. Pat. No. 5,985,837); (l) Epothilones such as Epothilones A, B, C, D, and Desoxyepothilones A and B, Fludelone (e.g., described in Chou et al. Cancer Res. 65:9445-9454, 2005, the entirety of which is hereby incorporated by reference), 9,10-dehydro-desoxyepothilone B (dehydelone), iso-oxazole-dehydelone (17-isooxazole-dehydelone), fludelone, iso-oxazolefludelone (17-isooxazole-fludelone), (Danishefsky, et al., PNAS, v. 105, 35:13157-62, 2008; WO 99/02514, U.S. Pat. No. 6,262,094, Nicolau et al., Nature, 1997, Pub. No.

US2005/0143429); (m) Inadones (e.g., described in Leoni et al., J. Natl. Cancer Inst., 2000; U.S. Pat. No. 6,162,810); (n) Lavendustin A and its derivatives (Mu F et al, J. Med. Chern., 2003, the entirety of which is hereby incorporated by reference); (o) 2-Methoxyestradiol and its derivatives (e.g., described in Fotsis et al, Nature, 1994; Schumacher et al, Clin. Cancer Res., 1999; Cushman et al, J. Med. Chern., 1997; Verdier-Pinard et al, Mol. Pharmacal, 2000; Wang et al, J. Med. Chern., 2000; WO 95/04535, WO 01/30803, WO 00/26229, WO 02/42319 and U.S. Pat. Nos. 6,528,676, 6,271,220, 5,892,069, 5,661,143, and 5,504,074); (p) Monotetrahydrofurans (e.g., "COBRAs"; Uckun, Bioorg. Med. Chern. Lett., 2000; U.S. Pat. No. 6,329,420); (q) Phenylhistin and its derivatives (e.g., described in Kanoh et al, J. Antibiot., 1999; Kano et al, Bioorg. Med. Chern., 1999 and U.S. Pat. No. 6,358,957); (r) Podophyllotoxins such as Epidophyllotoxin (e.g., described in Hammonds et al, J. Med. Microbial, 1996; Coretese et al, J. Biol. Chem., 1977); (s) Rhizoxins (e.g., described in Nakada et al, Tetrahedron Lett., 1993; Boger et al, J. Org. Chern., 1992; Rao, et al, Tetrahedron Lett., 1992; Kobayashi et al, Pure Appl. Chern., 1992; Kobayashi et al, Indian J. Chern., 1993; Rao et al, Tetrahedron Lett., 1993); (t) 2-strylquinazolin-4(3H)-ones (e.g., "SQOs", Jiang et al, J. Med. Chern., 1990, the entirety of which is hereby incorporated by reference); (u) Spongistatin and Synthetic spiroketal pyrans (e.g., "SPIKETs"; Pettit et al, J. Org. Chern., 1993; Uckun et al, Bioorgn. Med. Chern. Lett., 2000; U.S. Pat. No. 6,335,364, WO00/00514); (v) Taxanes such as Paclitaxel (TAXOL®), Docetaxel (TAXOTERE®), and Paclitaxel derivatives (e.g., described in U.S. Pat. No. 5,646,176, WIPO Publication No. WO 94/14787, Kingston, J. Nat. Prod., 1990; Schiff et al, Nature, 1979; Swindell et al, J. Cell Biol., 1981); (x) Vinca Alkaloids such as Vinblastine, Vincristine, Vindesine, Vinflunine, Vinorelbine (NAVELBINE®) (e.g., described in Owellen et al, Cancer Res., 1976; Lavielle et al, J. Med. Chern., 1991; Holwell et al, Br. J. Cancer., 2001); and (y) Welwistatin (e.g., described in Zhang et al, Molecular Pharmacology, 1996, the entirety of which is hereby incorporated by reference).

Exemplary specific examples of tubulin-binding drugs include, but are not limited to, allocolchicine, amphethinile, chelidonine, colchicide, colchicine, combrestatin A1, combretastin A4, combretastain A4 phosphate, combrestatin 3, combrestatin 4, cryptophycin, curacin A, deo-dolastatin 10, desoxyepothilone A, desoxyepothilone B, dihydroxypentamethoxyflananone, docetaxel, dolastatin 10, dolastatin 15, epidophyllotoxin, epothilone A, epothilone B, epothilone C, epothilone D, etoposide, 9,10-dehydro-desoxyepothilone B (dehydelone), iso-oxazole-dehydelone (17-isooxazole-dehydelone), fludelone, iso-oxazolefludelone (17-isooxazolefludelone), griseofulvin, halichondrin B, isocolchicine, lavendustin A, methyl-3,5-diiodo-4-(4'-methoxyphenoxy) benzoate, N-acetylcolchinol, N-acetylcolchinol-O-phosphate, N—[2-[(4-hydroxyphenyl)amino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, TAXOL, teniposide, thiocolchicine, vincristine, vinblastine, welwistatin, (Z)-2-methoxy-5-[2-(3,4,5-trimethoxyphenyl) vinyl] phenylamine, (Z)-3,5,4'-trimethoxystilbene ($R^3$), 2-aryl-1,8-naphthyridin-4(1H)-one, 2-(41-methoxyphenyl)-3-(31,41,51-rimethoxybenzoyl)-6-methoxybenzo[b]thiophene, 2-methoxy estradiol, 2-strylquinazolin-4(3H)-one, 5,6-dihydroindolo(2,1-a)isoquinoline, and 10-deacetylbaccatin III.

In some other embodiments, exemplary chemotherapy drugs include but are not limited to nitrogen mustards, nitrosoureas, alkylsulphonates, triazenes, platinum complexes, epipodophyllins, mitomycins, DHFR inhibitors, IMP dehydrogenase inhibitors, ribonucleotide reductase inhibitors, uracil analogs, cytosine analogs, purine analogs, receptor antagonists (for example, anti-estrogen, LHRH agonists, anti-androgens), vitamin derivative or analogs, isoprenylation inhibitors, dopaminergic neurotoxins, cell cycle inhibitors, actinomycins, bleomycins, anthracyclines, MDR inhibitors, $Ca^{2+}$ ATPase inhibitors, and anti-metastatis agents. In some embodiments, exemplary specific examples of tubulin-binding drugs include, but are not limited to, Cyclophosphamide, Ifosfamide, Trofosfamide, Chlorambucil, Carmustine, Lomustine, Busulfan, Treosulfan, Dacarbazine, Procarbazine, Temozolomide, Cisplatin, Carboplatin, Aroplatin, Oxaliplatin, Topotecan, Irinotecan, 9-aminocamptothecin, Camptothecin, Crisnatol, Mitomycin C, Methotrexate, Trimetrexate, Mycophenolic acid, Tiazofurin, Ribavirin, 5-Ethynyl-1-beta-D-ribofuranosylimidazole-4-carboxamide (EICAR), Hydroxyurea, Deferoxamine, 5-Fluorouracil, Fluoxuridine, Doxifluridine, Ralitrexed, Cytarabine, Cytosine arabinoside, Fludarabine, Gemcitabine, Capecitabine, Mercaptopurine, Thioguanine, O—6-benzylguanine, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, Pyrazoloimidazole, Tamoxifen, Raloxifene, Megestrol, Goserelin, Leuprolide acetate, Flutamide, Bicalutamide, Cis-retinoic acid, All-trans retinoic acid (ATRA-IV), EB 1089, CB 1093, KH 1060, Vertoporfin, Phthalocyanine, Photosensitizer Pc4, Demethoxy-hypocrellin A, ABT-627, Bay 12-9566, Benefin, BMS—275291, cartilage-derived inhibitor, CAI, CEP-7055, Col 3, Halofuginone, Heparin hexasaccharide fragment, IM-862, Marimastat, Metalloproteinase inhibitors, 2-Methoxyestra diol, MMI 270, Neovastat, NM-3, Panzem, PI-88, Placental ribonuclease inhibitor, Plasminogen activator inhibitor, Prinomastat, Retinoids, Solimastat, Squalamine, SS 3304, SU 5416, SU 6668, SU 11248, Tetrahydrocortisol-S, Tetrathiomolybdate, Thalidomide, TNP-470, ZD 6126, ZD 6474, farnesyl transferase inhibitors, Bisphosphonates, trityl cysteine, 1-methyl-4-phenylpyridinium ion, Staurosporine, Actinomycin D, Dactinomycin, Bleomycin A2, Bleomycin B2, Peplomycin, Daunorubicin, Doxorubicin, Idarubicin, Epirubicin, Pirarubicin, Zorubicin, Mitoxantrone, Verapamil, Ardeemin, Ningalin, Thapsigargin, Metastatin, GLiY-SD-ME-1, Sorafenib, Imatinib, Gefinitib, Lapatinib, Dasatinib, Nilotinib, Temsirolimus, Erlotinib, Pomalidomide, Regorafenib, Paclitaxel Protein-Bound Particles For Injectable Suspension, Everolimus, Bosutinib, Cabozantinib, Cabozantinib, Ponatinib, Axitinib, Carfilzomib, Ingenol Mebutate, Regorafenib, Fentanyl, Omacetaxine Mepesuccinate, Cephalotaxine, Pazopanib, Enzalutamide, Fentanyl Citrate, Sunitinib, Vandetanib, Crizotinib, Vemurafenib, Abiraterone Acetate, Eribulin Mesylate, Cabazitaxel, Ondansetron, Pralatrexate, Romidepsin, Plerixafor, Granisetron, Bendamustine Hydrochloride, Raloxifene Hydrochloride, Topotecan, Ixabepilone, Nilotinib, Temsirolimus, Lapatinib, Nelarabine, Sorafenib, Clofarabine, Cinacalcet, Erlotinib, Palonosetron, Tositumomab, Aprepitant, Gefitinib, Abarelix, Conjugated Estrogens, Alfuzosin, Bortezomib, Leucovorin, Fulvestrant, Ibritumomab Tiuxetan, Zoledronic Acid, Triptorelin Pamoate, Arsenic Trioxide, Aromasin, Busulfan, Amifostine, Temozolomide, Odansetron, Dolasetron, Irinotecan, Gemcitabine, Porfimer Sodium, Valrubicin, Capecitabine, Zofran, Bromfenac, Letrozole, Leuprolide, Samarium ($^{153}$ sm) Lexidronam, Pamidronate, Anastrozole, Levoleucovorin, Flutamide And Goserelin.

In some embodiments, a provided compound or composition is administered prior to, concurrently with or subsequent to a polypeptide or protein. In some embodiments, a polypeptide or protein is a recombinant polypeptide or protein. Exemplary polypeptides or proteins include but are not limited to cytokines, interferon alfa-2b, interleukin 2, filgrastim, rasburicase, secretin, asparaginase *Erwinia chrysanthemi*, and ziv-aflibercept. In some embodiments, a polypeptide or protein comprises an antibody or a fragment of an antibody. In some embodiments, a polypeptide or protein is an antibody or a fragment of an antibody. Examples include but are not limited to rituximab, trastuzumab, tositumomab, alemtuzumab, bevacizumab, cetuximab, panitumumab, ofatumumab, denosumab, ipilimumab, pertuzumab. In some embodiments, a polypeptide or protein is chemically modified. In some embodiments, a polypeptide or protein is conjugated to a drug. In some embodiments, an antibody or an antibody fragment is conjugated to a payload drug, forming an antibody-drug conjugate. In some embodiments, a payload drug is cytotoxic. Exemplary antibody-drug conjugates include but are not limited to gemtuzumab ozogamicin, brentuximab vedotin, and ado-trastuzumab emtansine. In some embodiments, a cancer treatment comprises the use of a vaccine. Exemplary vaccines for cancer treatment are well known in the art, for example but not limited to sipuleucel-T.

A provided compound may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, a provided compound (and optionally other agents as described herein) may be administered to the patient. In some embodiments, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

With respect to radiation, any radiation therapy protocol can be used depending upon the type of cancer to be treated. For example, but not by way of limitation, X-ray radiation can be administered; in some embodiments, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In some embodiments, methods of treatment of cancer with a provided compound or composition are provided as an alternative to chemotherapy or radiation therapy where the chemotherapy or the radiation therapy has proven or can prove too toxic, e.g., results in unacceptable or unbearable side effects, for a subject being treated. A subject being treated can, optionally, be treated with another cancer treatment such as surgery, radiation therapy or chemotherapy, depending on which treatment is found to be acceptable or bearable.

In some embodiments, a provided compound or composition can be used in an in vitro or ex vivo fashion, such as for the treatment of certain cancers, including, but not limited to leukemias and lymphomas. In some embodiments, such a treatment involves autologous stem cell transplants. In some embodiments, this can involve a multi-step process in which a subject's autologous hematopoietic stem cells are harvested and purged of all cancer cells, a subject's remaining bone-marrow cell population is then eradicated via the administration of a high dose of a provided compound or composition with or without accompanying high dose radiation therapy, and the stem cell graft is infused back into the animal. Supportive care is then provided while bone marrow function is restored and a subject recovers.

In some embodiments, the present disclosure provides methods for treating an autoimmune disease, comprising administering to a subject suffering therefrom or susceptible thereto an effective amount of a provided compound or a pharmaceutically acceptable salt thereof. In some embodiments, a subject is suffering from an autoimmune disease. In some embodiments, a provided compound is useful for killing or inhibiting replication of a cell that produces an autoimmune disease or for treating an autoimmune disease. A provided compound or composition can be used in a variety of settings for the treatment of an autoimmune disease in a patient. A provided compound can be used to deliver a drug to a target cell. Without being bound by theory, in some embodiments, a provided conjugate compound associates with an antigen on the surface of a target cell, and a provided conjugate compound is then taken up inside a target-cell through receptor-mediated endocytosis. Once inside the cell, a provided conjugate compound can be cleaved. In some embodiments, one or more specific peptide sequences within the linker unit are enzymatically or hydrolytically cleaved, resulting in release of a drug comprising all or part of the drug unit and optionally part or all of the linker unit. A released drug is then free to migrate in the cytosol and induce cytotoxic or cytostatic activities. In an alternative embodiment, a conjugate compound is cleaved and a drug is released outside the target cell, and the drug subsequently penetrates the cell.

In some embodiments, a ligand unit binds to an autoimmune antigen. In some embodiments, an antigen is on the surface of a cell involved in an autoimmune condition. In some embodiments, a ligand unit binds to an autoimmune antigen which is on the surface of a cell. In some embodiments, a ligand binds to activated lymphocytes that are associated with the autoimmune disease state. In some embodiments, a provided compound kills or inhibits the multiplication of cells that produce an autoimmune antibody associated with a particular autoimmune disease.

Exemplary types of autoimmune diseases that can be treated with provided compounds or compositions include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those selected from the group consisting of: Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, and Wegener's Granulomatosis.

In some embodiments, an autoimmune disease being treated is selected from rheumatologic disorders (such as, for example, rheumatoid arthritis, Sjagren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease andhearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, andautoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjagren's syndrome, Graves' disease, IDDM, pernicious anemia, thyroiditis, and glomerulonephritis.

In some embodiments, the present disclosure provides methods for treating an autoimmune disease, comprising administering to a subject suffering therefrom an effective amount of a provided compound or composition. In some embodiments, a provided method comprises administering an effective amount of a provided compound or composition and another therapeutic agent known for treatment of an autoimmune disease. Exemplary therapeutic agents are widely known in the art, including but not limited to cyclosporine, cyclosporine A, mycophenylate mofetil, sirolimus, tacrolimus, enanercept, prednisone, azathioprine, methotrexate cyclophosphamide, prednisone, aminocaproic acid, chloroquine, hydroxychloroquine, hydrocortisone, dexamethasone, chlorambucil, DHEA, danazol, bromocriptine, meloxicam and infliximab.

In some embodiments, the present disclosure provides methods for treating an infectious disease, comprising administering to a subject suffering therefrom or susceptible thereto an effective amount of a provided compound or a pharmaceutically acceptable salt thereof. In some embodiments, a provided compound or composition is useful for killing or inhibiting the multiplication of a cell that produces an infectious disease or for treating an infectious disease. A provided compound can be used in a variety of settings for the treatment of an infectious disease in a subject. In some embodiments, a provided conjugate compound is used to deliver a drug to a target cell. In one embodiment, a ligand unit binds to the infectious disease cell. In one embodiment, a provided compound kills or inhibits the multiplication of cells that produce a particular infectious disease.

Exemplary types of infectious diseases that can be treated with a provided compound include, but are not limited to: Bacterial Diseases such as Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococcal, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, *Chlamydia*, Chlamydial Pneumonia, Trachoma and Inclusion Conjunctivitis; Systemic Fungal Diseases such as Histoplamosis, Coccidiodomycosis, Blastomycosis, Sporotrichosis, Cryptococcsis, Systemic Candidiasis, Aspergillosis, Mucormycosis, Mycetoma and Chromomycosis; Rickettsial Diseases such as Typhus, Rocky Mountain Spotted Fever, Ehrlichiosis, Eastern Tick-Borne Rickettsioses, Rickettsialpox, Q Fever and Bartonellosis; Parasitic Diseases such as Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease and Alveolar Hydatid Disease; Viral Diseases such as Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections and Smallpox.

In some embodiments, the present disclosure provides methods for treating an infectious disease, comprising administering to a subject suffering therefrom an effective amount of a provided compound or composition. In some embodiments, a provided method comprises administering an effective amount of a provided compound or composition and another therapeutic agent known for treatment of an infectious disease.

In some embodiments, a provided method for treating an infectious disease includes administering to a patient in need thereof a provided compound and another therapeutic agent that is an anti-infectious disease agent. Exemplary anti-infectious disease agents are widely known in the art, including but not limited to β-Lactam Antibiotics such as Penicillin G, Penicillin V, Cloxacilliin, Dicloxacillin, Methicillin, Nafcillin, Oxacillin, Ampicillin, moxicillin, Bacampicillin, Azlocillin, Carbenicillin, Mezlocillin, Piperacillin and Ticarcillin; Aminoglycosides: Amikacin, Gentamicin, Kanamycin, Neomycin, Netilmicin, Streptomycin and Tobramycin; Macrolides such as Azithromycin, Clarithromycin, Erythromycin, Lincomycinand Clindamycin; Tetracyclines such as Demeclocycline, Doxycycline, Minocycline, Oxytetracycline and Tetracycline; Quinolones such as Cinoxacin and Nalidixic Acid; Fluoroquinolones such as Ciprofloxacin, Enoxacin, Grepafloxacin, Levofloxacin, Lomefloxacin, Norfloxacin, Ofloxacin, Sparfloxacin and Trovafloxicin; Polypeptides such as Bacitracin, Colistin and Polymyxin B; Sulfonamides such as Sulfisoxazole, Sulfamethoxazole, Sulfadiazine, Sulfamethizole and Sulfacetamide; Miscellaneous Antibacterial Agents such as Trimethoprim, Sulfamethazole, Chloramphenicol, Vancomycin, Metronidazole, Quinupristin, Dalfopristin, Rifampin, Spectinomycin, Nitrofurantoin; General Antiviral Agents such as Idoxuradine, Vidarabine, Trifluridine, Acyclovir, Famcicyclovir, Pencicyclovir, Valacyclovir, Gancicyclovir, Foscarnet, Ribavirin, Amantadine, Rimantadine, Cidofovir, Antisense Oligonucleotides, Immunoglobulins and Inteferons; Drugs for HIV infection such as Tenofovir, Emtricitabine, Zidovudine, Didanosine, Zalcitabine, Stavudine, Lamivudine, Nevirapine, Delavirdine, Saquinavir, Ritonavir and Indinavir, Nelfinavir.

It will be appreciated that, in certain embodiments, each variable recited is as defined above and described in embodiments, herein, both singly and in combination.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

The present disclosure recognizes, among other things, that there is a continuing demand for compounds, compositions and methods for treating various diseases, for example, cancer. In some embodiments, the present disclosure provides such compounds, compositions and methods. In some embodiments, the present disclosure provides methods and uses for such compounds and compositions. Exemplary but non-limiting examples are described herein.

The epipolythiodiketopiperazine (ETP) alkaloids are a highly complex class of compounds. In some embodiments, the present disclosure provides methods for flexible and scalable synthesis of ETP alkaloids or thiodiketopiperazines, or derivatives and analogs thereof, for example, a provided compound of formula I, II, or V.

General Procedures

All reactions were performed in oven-dried or flame-dried round-bottom flasks, modified Schlenk (Kjeldahl shape) flasks, or glass pressure vessels. The flasks were fitted with rubber septa, and reactions were conducted under a positive pressure of argon. Cannulae or gas-tight syringes with stainless steel needles were used to transfer air- or moisture-sensitive liquids. Flash column chromatography was performed as described by Still et al.[11] using granular silica gel (60-Å pore size, 40-63 µm, 4-6% $H_2O$ content, Zeochem) or $C_{18}$-reversed-phase silica gel (90-Å pore size, 40-63 µm, Fluka). Analytical thin layer chromatography (TLC) was performed using glass plates pre-coated with 0.25 mm 230-400 mesh silica gel impregnated with a fluorescent indicator (254 nm) or basic alumina impregnated with a fluorescent indicator (254 nm). Thin layer chromatography plates were visualized by exposure to short wave ultraviolet light (254 nm) and/or irreversibly stained by treatment with an aqueous solution of ceric ammonium molybdate (CAM), an ethanolic solution of phosphomolybdic acid (PMA), an aqueous solution of silver nitrate ($AgNO_3$), Ellman's reagent (5,5'-dithiobis-(2-nitrobenzoic acid), DTNB) in dimethylformamide,[12] or an aqueous solution of potassium permanganate ($KMnO_4$), followed by heating (~1 min) on a hot plate (~250° C.). Organic solutions were concentrated at 30° C. on rotary evaporators capable of achieving a minimum pressure of ~2 Torr.

Materials

Commercial reagents and solvents were used as received with the following exceptions: dichloromethane, acetonitrile, toluene, diethyl ether, tetrahydrofuran, N,N-dimethylformamide, and methanol were purchased from J. T. Baker (Cycletainer™) or Sigma-Aldrich and were purified by the method of Grubbs et al. under positive argon pressure.[13] Benzene, N,N-diisopropylethylamine, and 1,2-dichloroethane were dried by distillation over calcium hydride under an inert nitrogen atmosphere. Acetone 1,3-dimethyl-3,4,5,6-tetrahydro-2-pyrimidinone was dried by distillation over calcium hydride under an inert nitrogen atmosphere. 1-Ethyl-3-(3-dimethylaminopropyl) carbodiimide hydrochloride and 1-[bis(dimethylamino)-methylene]-1H-1,2,3-triazolo[4,5-b]pyridinium 3-oxide hexafluorophosphate (HATU) were purchased from Oakwood Products, Inc.; N-hydroxybenzotriazole was purchased from Aroz Technologies. LLC; silver hexafluoroantimonate was purchased from Strem Chemicals Inc.; 2,6-di-tert-butyl-4-methylpyridine was further purchased from Matrix Scientific and was further purified by flash column chromatography on silica gel (eluent: hexanes). p-Methoxybenzyl thiol and carbon disulfide were purchased from Alfa Aesar. All other solvents and chemicals were purchased from Sigma-Aldrich.

Instrumentation

Proton nuclear magnetic resonance ($^1$H NMR) spectra were recorded with a Bruker AVANCE 600 spectrometer, a Bruker AVANCE NEO 500 spectrometer, a Varian inverse probe 500 INOVA spectrometer, a Bruker AVANCE III 400 spectrometer, or a JEOL ECZR 500 spectrometer. Chemical shifts are recorded in parts per million on the δ scale and are referenced from the residual protium in the NMR solvent (CHCl$_3$: δ 7.26, CD$_2$HCN: 1.94, CD$_2$HOD: 3.31, CD$_3$SOCD$_2$H: 2.50, H$_2$O: 4.79).[14] Data are reported as follows: chemical shift [multiplicity (s=singlet, d=doublet, t=triplet, q=quartet, p=pentet, m=multiplet, br=broad), coupling constant(s) in Hertz, integration, assignment]. Carbon-13 nuclear magnetic resonance ($^{13}$C NMR) spectra were recorded with a Bruker AVANCE 600 spectrometer, a Varian 500 INOVA spectrometer, a Bruker AVANCE III 400 spectrometer, or a JEOL 500 spectrometer, are recorded in parts per million on the δ scale, and are referenced from the carbon resonances of the solvent (CDCl$_3$: δ 77.16, CD$_3$CN: 118.26, CD$_3$OD: 49.00, DMSO-d$_6$: 39.52). Infrared data were obtained with a Perkin-Elmer 2000 FTIR or a Bruker Alpha II Platinum ATR and are reported as follows: [frequency of absorption (cm$^{-1}$), intensity of absorption (s=strong, m=medium, w=weak, br=broad)]. Optical Rotations were recorded on a Jasco P-1010 Polarimeter and specific rotations are reported as follows: [wavelength of light, temperature (° C.), specific rotation, concentration in grams/100 mL of solution, solvent]. High resolution mass spectra (HRMS) were recorded on a Bruker Daltonics AP EXIV 4.7 Tesla FT-ICR-MS using using electrospray (ESI) (m/z) ionization source or direct analysis in real time (DART), an Agilent 6545 Q-TOF LC/MS using electrospray (ESI) (m/z) ionization source, or a JEOL AccuTOF LC-plus 4G using direct analysis in real time (DART).

Positional Numbering System

At least three numbering systems exist for dimeric diketopiperazine alklaoids exist in the literature.[15] In assigning the $^1$H and $^{13}$C NMR data for all intermediates en route to the syntheses of monomeric ETP's (+)-9a, (+)-9b, (+)-9c, and (+)-9d, a uniform numbering scheme was empolyed. For ease of direct comparison, particularly between early intermediates, non-thiolated diketopiperazines, and advanced compounds, the numbering system used by Barrow for (+)-WIN-64821 (using positional numbers 1-17) is optimal and used throughout this report.

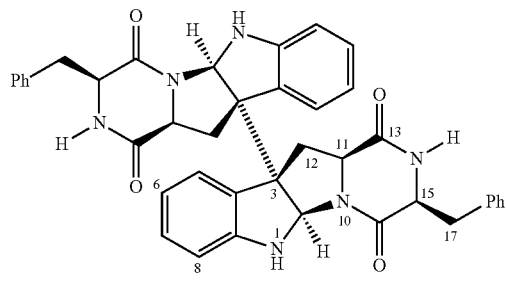

(+)-WIN-64821
Barrow's numbering for
dimeric diketopiperazines

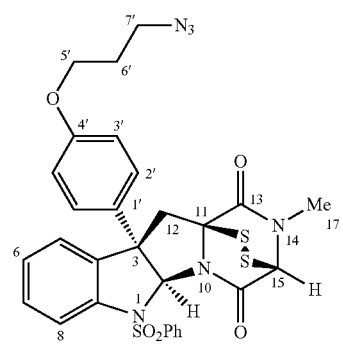

(+)-9a
This document

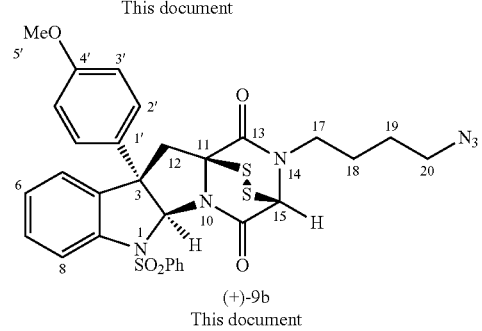

(+)-9b
This document

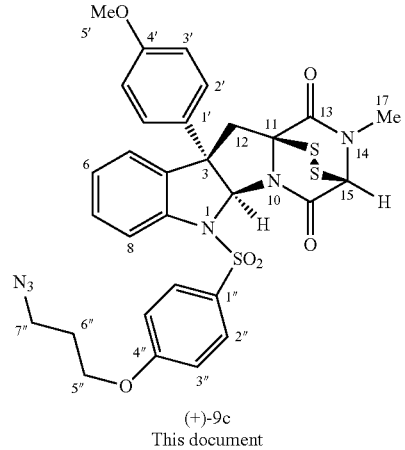

(+)-9c
This document

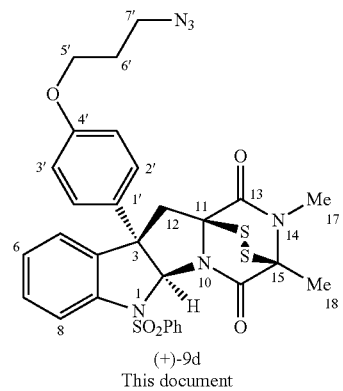

(+)-9d
This document

Cell Culture Information (HeLa, A549, HCT-116, DU-145, and MCF7)

Cells were grown in media supplemented with fetal bovine serum (FBS) and antibiotics (100 μg/mL penicillin and 100 U/mL streptomycin). Specifically, experiments were performed using the following cell lines and media compositions: HeLa (cervical adenocarcimona) and A549 (lung carcinoma) were grown in RPMI-1640+10% FBS; HCT-116 (colorectal carcinoma) was grown in DMEM+ 10% FBS; DU-145 (prostate carcinoma) and MCF7 (breast adenocarcinoma) were grown in EMEM+10% FBS. Cells were incubated at 37° C. in a 5% CO2, 95% humidity atmosphere.

Cell Viability Assays (HeLa, A549, HCT-116, DU-145, and MCF7)

Cells were plated at 250 cells/well into duplicate assay plates in 50 µL media into 384-well white, opaque, tissue-culture treated plates and allowed to adhere overnight at 37° C./5% CO2. Compounds were solubilized in DMSO as 1000× stocks and 100 nl was pin-transferred to cells (V&P pin tool mounted on Tecan Freedom Evo MCA96). Compounds were tested in 10-pt, 2-fold dilution with concentrations tested between 1 nM-20 µM for most compounds, except where indicated. DMSO (32 wells of 384-wells) was used as vehicle control. After 72 hours of incubation at 37° C./5% CO2, 10 µL Cell Titer-Glo (Promega) was added to each well and plates were incubated at room temperature for 10 minutes before the luminescence was read on a Tecan M1000 plate reader. Cell Titer-Glo measures ATP levels of cells as a surrogate for cell viability. All compound-treated wells was normalized to the DMSO control averages and expressed as a % of DMSO viability. IC50 values were determined from the dose curves using Spotfire (Perkin Elmer).

Jurkat, K-562, and Toledo Cell Culture Information and Viability Assays

Cells were grown in RPMI-1640+10% FBS+Pen/Strep and all are suspension cell lines. Each were plated at 250 cells per well in 50 µL of media in a 384 well plate and 50 nL of compounds was added via pin-tool (same as our usual procedure). Compounds were tested at 20 µM starting assay concentration in 20-pt, 2-fold dose in duplicate on the same assay plate. Cells were incubated with compound for 72 hours and viability was read out with CellTiter-Glo.

Detailed Description of Examples

Several subsets of natural and unnatural monomeric and dimeric ETPs exhibiting $IC_{50}$ values in the low to (sub) nanomolar range have been identified (FIG. 1).[3p] To further enable exploration of the translational potential of ETPs, functionalized ETPs containing conjugatable chemical handles were sought. A robust means to derivatize ETPs through conjugation chemistry would permit evaluation of these biologically potent compounds in new contexts. Herein, the design and synthesis of derivatized ETPs possessing an alkyl azide moiety for conjugation to a desired coupling partner via the copper(I)-catalyzed azide-alkyne cycloaddition (CuAAC) reaction is described.[16] The CuAAC reactions of these azido ETPs proceed smoothly even in the presence of the highly sensitive epidisulfide functionality. Furthermore, the nanomolar cytotoxic activities of these designed azido ETPs across five human cancer cell lines is reported.

A recent study describing the potent cytotoxic activities of a structurally diverse collection of ETPs demonstrated the potential of this class of compounds as anti-cancer therapeutics.[3p] Synthetic access to ETPs containing a conjugatable chemical handle may provide a powerful tool to further evaluate the biological activity of these compounds. In recent studies, bioactive small molecules have been structurally modified and used as photoaffinity labels for target identification[17], in situ small molecule clickable imaging probes[18], polymer-drug conjugates for improved pharmacokinetics[19], and antibody-drug conjugates for targeted drug delivery[20]. Based on these precedents, attachment of an alkyl azide handle to ETPs may provide a robust and general method for coupling various chemical groups using CuAAC for utilization in biological applications such as those described above.

Figure 2:
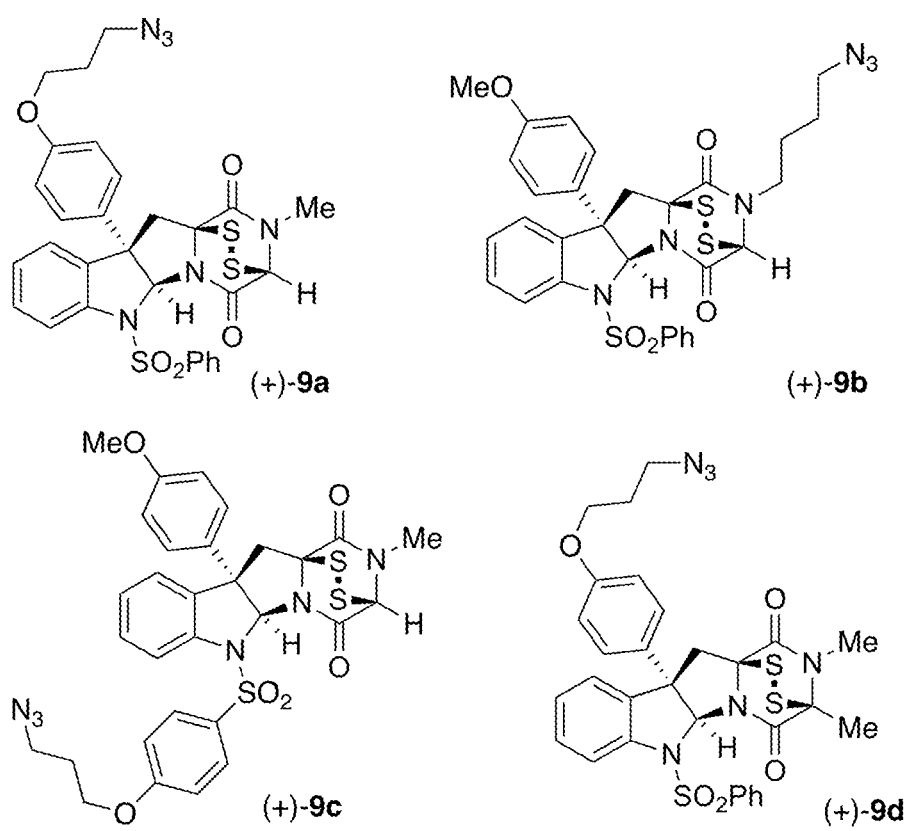
FIG. 2 shows design of structurally diverse conjugatable ETP probes.
Figure 2:
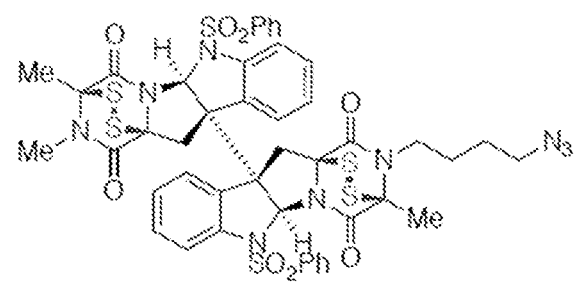

Identification of the site for attachment of an alkyl azide moiety onto the parent ETP was needed; the site should not lead to a significant loss in potency upon conjugation to a coupling partner relative to the parent compound. Previous SAR data indicated that aryl substituents at C3 were well tolerated and often led to an increase in potency relative to short chain alkyl substitutents. Additionally, it was found that N1 benzenesulfonyl substitution led to higher activities compared to the unsubstituted compounds. As such, exploration of N14 substitution beyond a methyl group was also considered. These considerations led to the design of monomeric ETP derivatives (+)-9a, (+)-9b, and (+)-9c substituted at alternative positions with an alkyl azide moiety (FIG. 2). In each case, a monomeric rather than a dimeric ETP scaffold was chosen to allow for more direct synthetic access to these compounds.[2f,3p] During the course of these studies, it was discovered that alanine-derived ETPs are less sensitive to basic conditions than glycine-derived ETPs, thus it was sought to prepare ETP derivative (+)-9d.

As shown in Scheme 1, the synthesis of ETP (+)-9a commenced with exposure of known endo-tetracyclic bromide (+)-10 to aryl ether 11 in the presence of silver hexafluoroantimonate and 2,6-di-tert-butyl-4-methylpyridine (DTBMP) as a Brønsted acid scavenger in dichloromethane to provide the desired cis-fused Friedel-Crafts adduct in 78% yield, resulting from exclusive attack of aryl ether 11 from the para position.[21] Removal of the triisopropylsilyl group with tetrabutylammonium fluoride in THF at 0° C. afforded an inseparable mixture of alcohol (+)-12 and its $C_{11}$ epimer (3:1, respectively) in 88% yield. Fortunately, epimerization of the base sensitive $C_{11}$ stereocenter could be completely suppressed by employing hydrogen fluoride in a mixture of pyridine and THF at 23° C. for 16 h to furnish alcohol (+)-12 in 90% yield as a single diastereomer. Alcohol (+)-12 was converted into azide (+)-13 in 87% yield utilizing the Bose-Mitsunobu protocol with polymer-supported triphenylphosphine.[22] Treatment of azide (+)-13 with tetra-n-butylammonium permanganate (n-Bu$_4$MnO$_4$) in 1,2-dichloroethane gave diol (−)-14 in 63% yield as a single diastereomer.[23] Installation of the epidisulfide bridge was achieved by exposure of diol (−)-14 to trifluoroacetic acid in a saturated solution of hydrogen sulfide in nitroethane followed by facile oxidation of the crude bisthiol with potassium triiodide to afford azido ETP (+)-9a in 65% yield over two steps.

Scheme 1: Synthesis of designed ETP azide (+)-9a

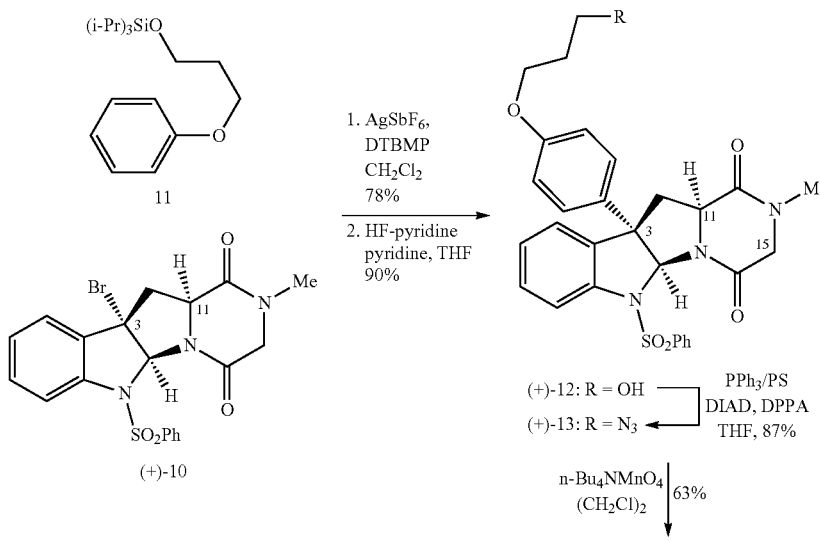

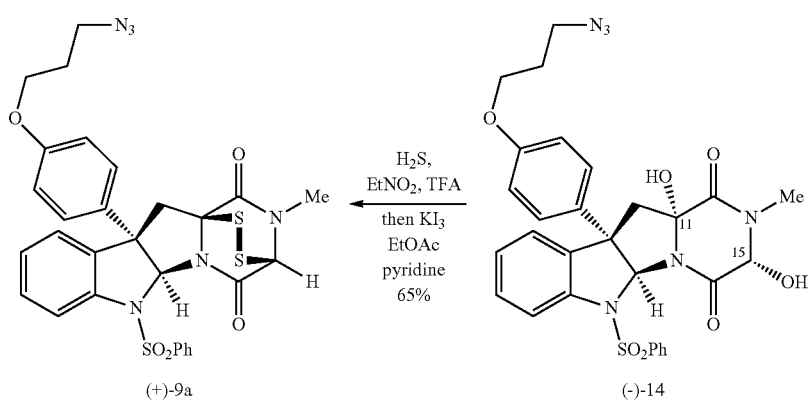

The synthetic route to ETP (+)-9b (Scheme 2) commenced with an examination of the amide alkylation of diketopiperazine (+)-15.[24] In preliminary studies it was found that treatment of diketopiperazine (+)-15 with LHMDS in DMPU-THF at −30° C. followed by addition of either alkyl iodide or 3-substituted allyl bromide derivatives resulted in no reactivity or low conversions with significant amounts of epimerization at C11, respectively. To address the issue of epimerization, it was reasoned that installation of the C3 aryl group prior to the alkylation step would potentially mitigate the inductive electron withdrawing effects of the C3 bromide and thereby reduce the propensity for epimerization at C11. Further, the larger steric dimensions of an aryl group relative to bromine might also suppress epimerization. Next, in an effort to increase the reactivity of the electrophile it was hypothesized that an alkynyl bromide electrophile might offer increased reactivity relative to an allyl bromide electrophile.[25]

Scheme 2: Synthesis of designed ETP azide (+)-9b

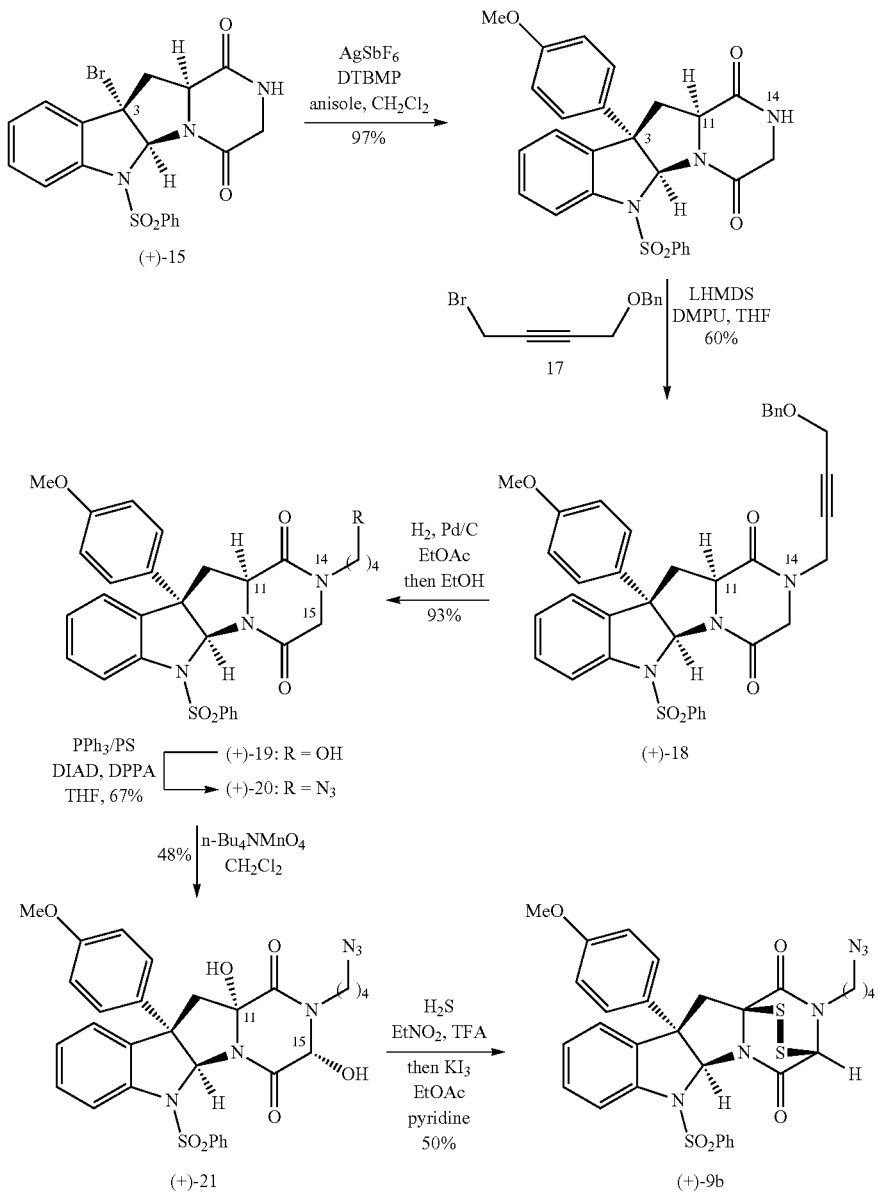

Based on these considerations, Friedel-Crafts arylation of bromide (+)-15 in the presence of silver hexafluoroantimonate and DTBMP in a mixture of anisole and dichloromethane (1:1) afforded C3-arylated diketopiperazine (+)-16 in 97% yield. Notably, treatment of diketopiperazine (+)-16 with LHMDS in a mixture of DMPU-THF (1:4) at −30° C. followed by addition of alkynyl bromide 17 afforded alkyne (+)-18 and the undesired C11 epimer in 60% and 14% yield, respectively.

Having developed a practical solution for amide alkylation, the hydrogenation of alkyne (+)-18 was explored. In initial experiments, exposure of alkyne (+)-18 to 5% Pd/C in ethyl acetate under an atmosphere of hydrogen gas at 23° C. for 24 h gave an equimolar mixture of alcohol (+)-19 and an intermediate product which had undergone complete reduction of the alkyne moiety but still possessed the benzyloxy group. Interestingly, changing the solvent to ethanol in order to increase the rate of hydrogenation provided alcohol (+)-19 in 67% yield accompanied by isolation of the N14-n-butyl derivative of alcohol (+)-19 in 18% yield which is postulated to have arisen from complete reduction of a putative allyl alcohol intermediate.[26] To exclude formation of this species, alkyne (+)-18 was subjected to 5% Pd/C in ethyl acetate over 1 atmosphere of hydrogen for 30 min which resulted in complete reduction of the alkyne moiety but preserved the benzyloxy group. Subsequently, the reaction mixture was diluted with ethanol and stirred for an additional 1 h to remove the benzyl protecting group affording alcohol (+)-19 in 93% yield. Analogous to the synthesis of ETP (+)-9a, utilization of the Bose-Mitsunobu protocol with polymer-supported triphenylphosphine transformed alcohol (+)-19 into azide (+)-20 in 67% yield. Dihydroxylation of diketopiperazine (+)-20 with n-Bu₄MnO₄ in dichloromethane furnished diol (+)-21 in 48% yield. Addition of trifluoroacetic acid to a saturated solution of hydrogen sulfide and diol (+)-21 in nitroethane resulted in bisthiolation, which upon exposure to KI₃ afforded azido ETP (+)-9b in 50% yield over two steps.

mide (+)-24 in 79% yield in >18:1 dr. Analogous to the synthesis of ETP (+)-9a, treatment of bromide (+)-24 with silver hexafluoroantimonate in the presence of anisole and DTBMP gave Friedel-Crafts adduct (+)-25 in 99% yield.

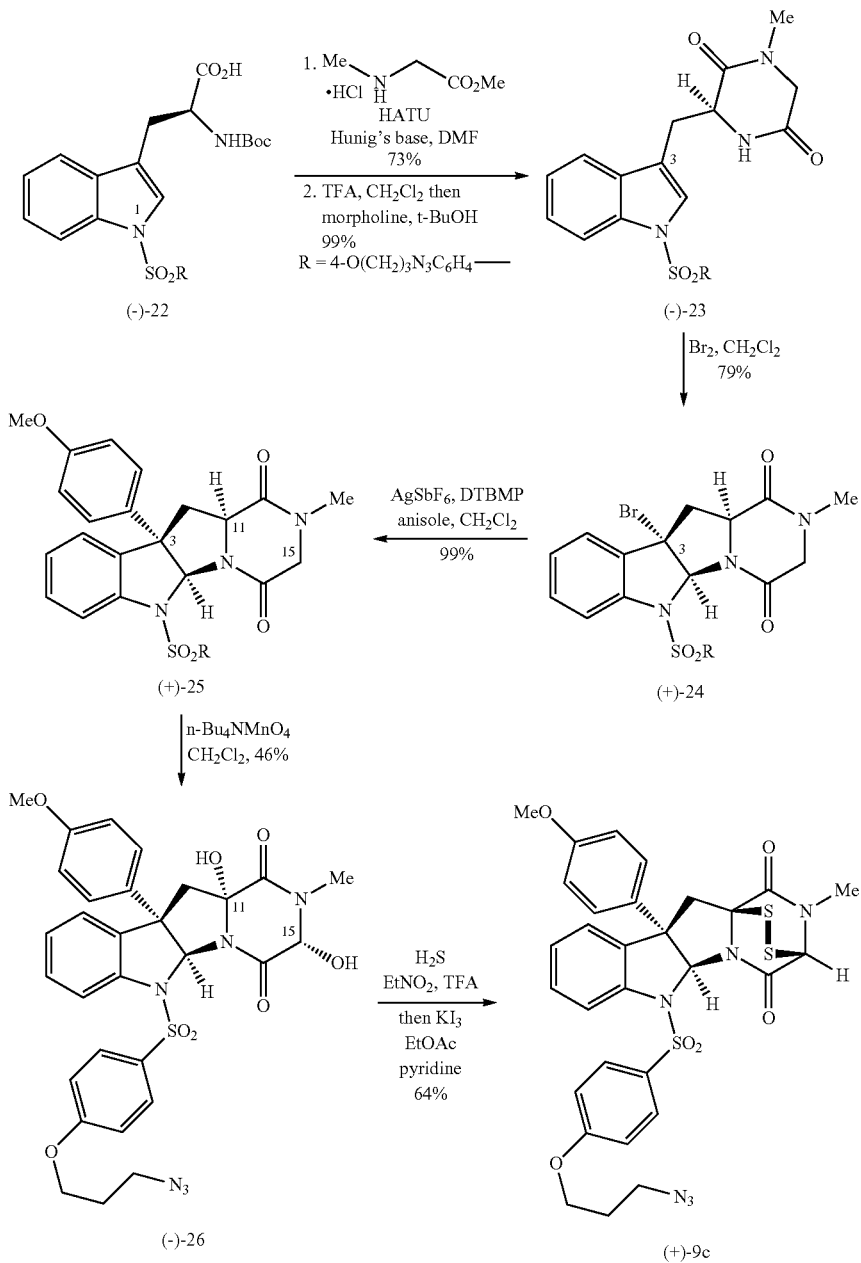

Scheme 3: Synthesis of designed ETP azide (+)-9c

Synthesis of the azido ETP (+)-9c (Scheme 3) began with HATU promoted amide coupling between acid (−)-22 and sarcosine methyl ester hydrochloride to afford the corresponding dipeptide in 73% yield. Deprotection of the tert-butoxycarbonyl group with trifluoroacetic acid in dichloromethane followed by treatment with morpholine in tert-butanol resulted in cyclization to diketopiperazine (−)-23 in 99% yield. Addition of molecular bromine to diketopiperazine (−)-23 in dichloromethane at 23° C. for 10 minutes effected bromocyclization to produce endo-tetracyclic bro- Dihydroxylation of diketopiperazine (+)-25 with n-Bu₄MnO₄ in dichloromethane furnished diol (−)-26 in 46% yield. Addition of trifluoroacetic acid to a solution of diol (−)-26 in nitroethane saturated with hydrogen sulfide followed by mild oxidation with KI₃ produced azido ETP (+)-9c in 64% yield over two steps.

With azido ETPs (+)-9a, (+)-9b, and (+)-9c synthesized, the compatibility of the epidisulfide functionality with the copper(I)-catalyzed azide-alkyne cycloaddition (CuAAC) reaction was explored. Based on previous work, epidithioketopiperazines are known to be sensitive to reductive, oxidative, basic, and strongly acidic conditions.[3,4,5] As such, 4-ethynylanisole 27 was chosen as a representative model substrate for possible conjugation partners to demonstrate the efficiency of the CuAAC coupling strategy with designed ETPs (Scheme 4). Treatment of either ETP (+)-9a, (+)-9b, or (+)-9c with 4-ethynylanisole 27 with CuI, AcOH, and Hunig's base in dichloromethane or toluene[27] at 23° C.[28] proceeded smoothly to provide the corresponding cycloadducts (+)-28a, (+)-28b, and (+)-28c in 94%, 85% and 57% yield, respectively.

Scheme 4: Conjugation of designed ETPs with model alkyne

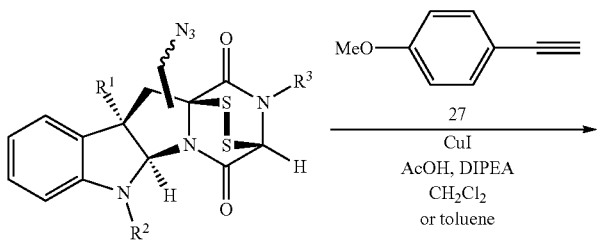

| Entry | ETP | Product | Yield |
|---|---|---|---|
| 1 | (+)-9a | 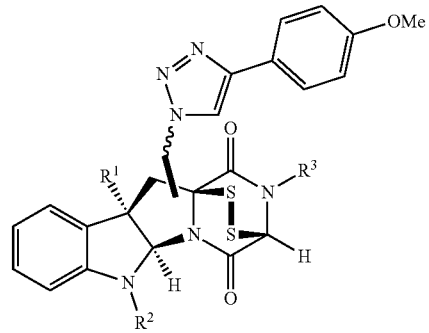 (+)-28a | 94% |

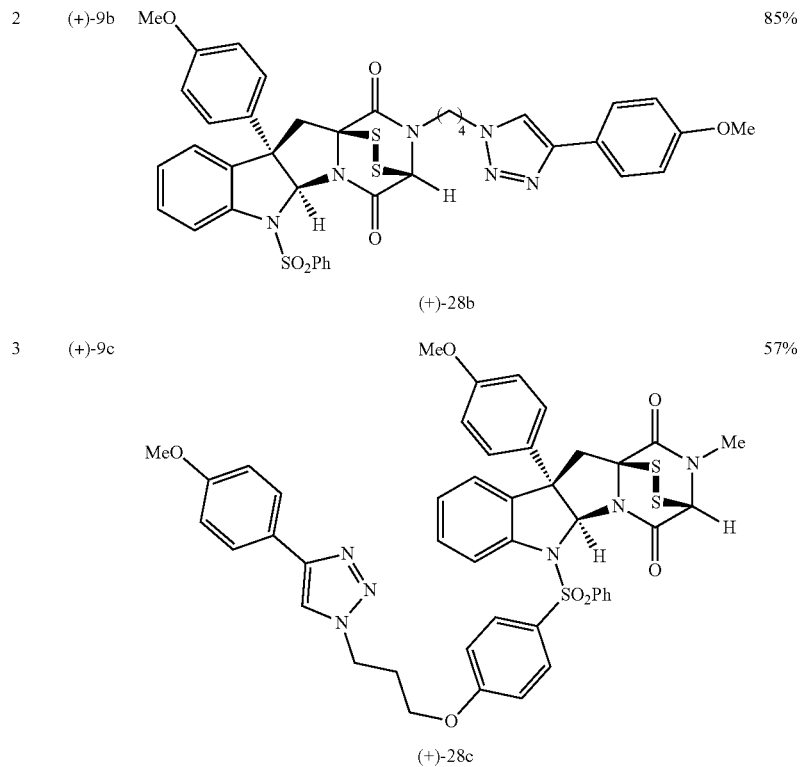

| 2 | (+)-9b | | 85% |
|---|---|---|---|

(+)-28b

| 3 | (+)-9c | | 57% |
|---|---|---|---|

(+)-28c

In certain contexts an amino functionality might be desirable for bioconjugation to activated acyl donors. To this end, N-Boc-propargylamine was coupled to ETP azide (+)-9a using the standard CuAAC reaction conditions to afford amino ETP (+)-29 in 89% yield. To demonstrate the competency of amino ETP (+)-29 as an acyl acceptor, N-Boc ETP (+)-29 was treated with anhydrous HCl in dioxane followed by addition of benzoyl chloride as a model acyl donor to afford ETP amide (+)-30 in 87% yield (Scheme 5).

Scheme 5: Click functionalization of amino-ETP for acylation chemistry

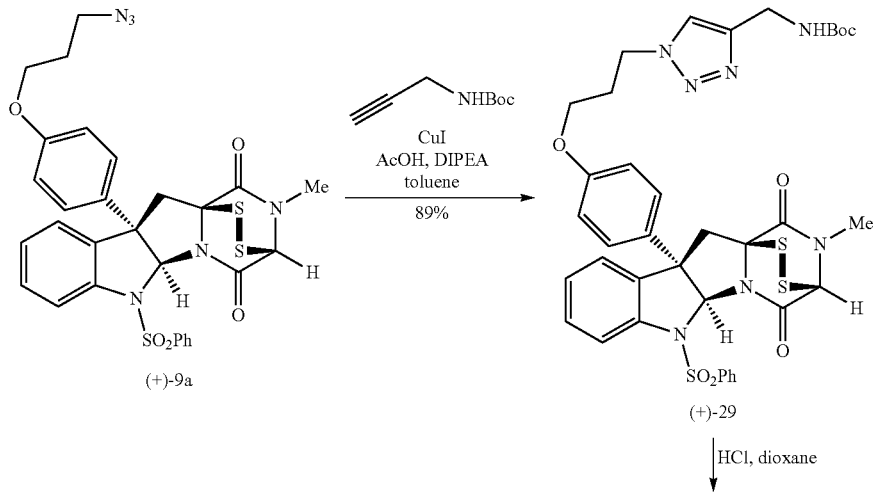

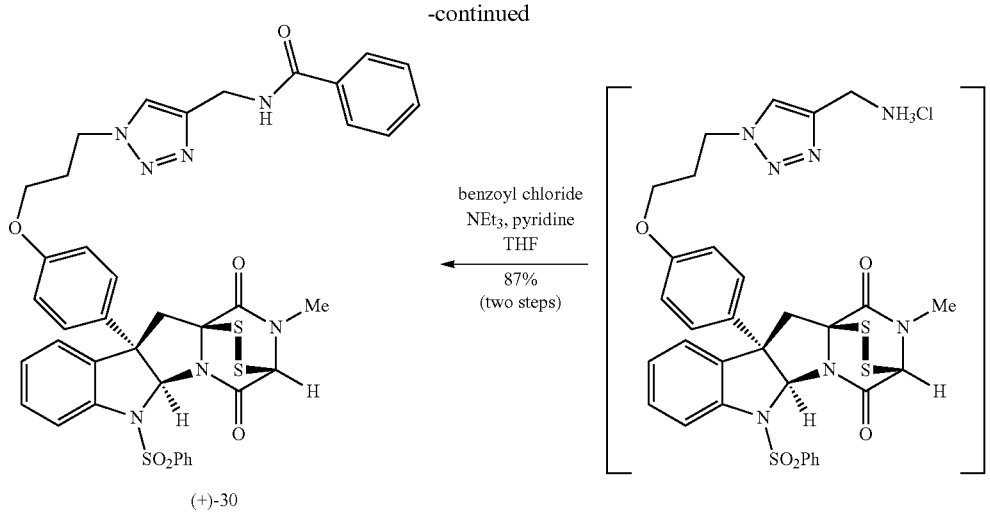

In situ monitoring of epidisulfide (+)-8 by $^1$H NMR spectroscopy revealed a sensitivity to basic conditions in organic solvents. In the absence of base, 98% of epidisulfide (+)-8 remained after 20 hours in deuterochloroform. However, subsequent exposure to triethylamine, N,N-diisopropylethyl amine (Hunig's base), or 1,4-diazabicyclo-[2.2.2]-octane (DABCO) for 20 hours resulted in the formation of 4-6% yield of epitrisulfide 31, with 84-85% of epidisulfide (+)-8 remaining. In deuteroacetonitrile, it was directly observed the complete consumption of epidisulfide (+)-8 after 2 hours, followed by the isolation of epitrisulfide 31 (16%) and epitetrasulfide 32 (24%).

Stirring epidisulfide (+)-8 in N,N-dimethylformamide alone resulted in a cascade of color changes (pink, blue, green, then yellow) characteristic of the decomposition of epidisulfide (+)-8. When (+)-8 was exposed to triethylamine in DMF, epitrisulfide 31 (8%), epitetrasulfide 32 (11%), diketopiperazinethione 34-S (3%) corresponding hydrolyzed triketopiperazine 34-O (3%), diketopiperazinethione 35-S (16%) and its corresponding hydrolyzed triketopiperazine (5%) were isolated. One hypothesis is that H15 deprotonation of epidisulfide (+)-8 formed C11-thiol-diketopiperazine-C15-thione 33 via S—S bond scission, a reactive species that could catalytically consume the starting disulfide and ultimately give rise to the higher order polysulfanes via electrophilic sulfur transfer.

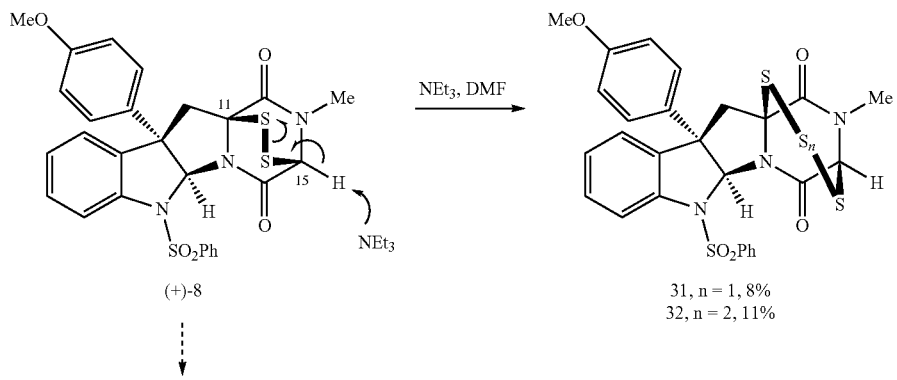

Scheme 6: Base-catalyzed sulfur transfer of model Trp-Gly ETPs

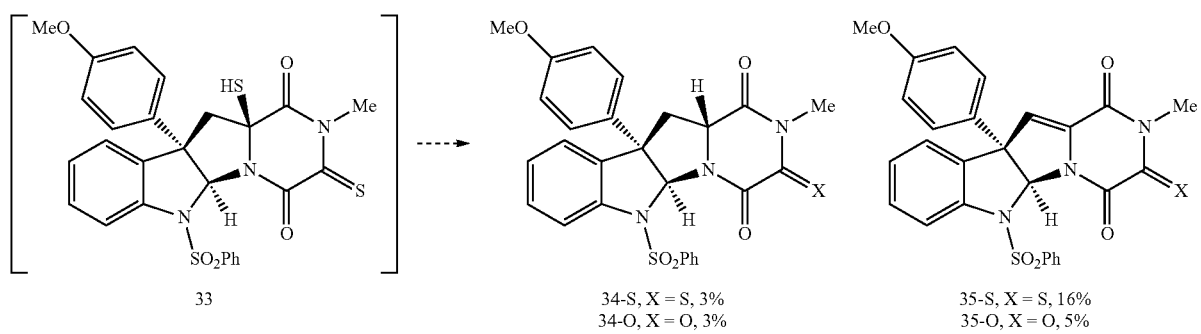

33

34-S, X = S, 3%
34-O, X = O, 3%

35-S, X = S, 16%
35-O, X = O, 5%

To address possible concerns of C15-proton acidity of glycine-derived epidisulfide (+)-8, alanine-derived C15-methyl substituted epidisulfide (+)-42 were explored to reduce the rate of E2 elimination (Scheme 7). To minimize competetive ortho-arylation, known tetracyclic bromide (+)-36 was exposed to silver trifluoromethanesulfonate in the presence of anisole and DTBMP at −25° C. to give C3-p-methoxyphenyl diketopiperazine (+)-37 in 81% yield (d.r. 40:1). The selectivity of the permanganate-mediated dihydroxylation of diketopiperazine (+)-37 depended significantly on the permanganate counter-ion. With bis(pyridine) silver(I) permanganate ($Py_2AgMnO_4$) and n-$Bu_4MnO_4$, partial (10-15%) and significant (50%) diastereomers were observed, respectively. However, oxidation with bis(2,2'-bipyridyl)copper(II) permanganate ($bipy_2Cu(MnO_4)_2$) furnished diol 38 as a single diastereomer in 74% yield.[29]

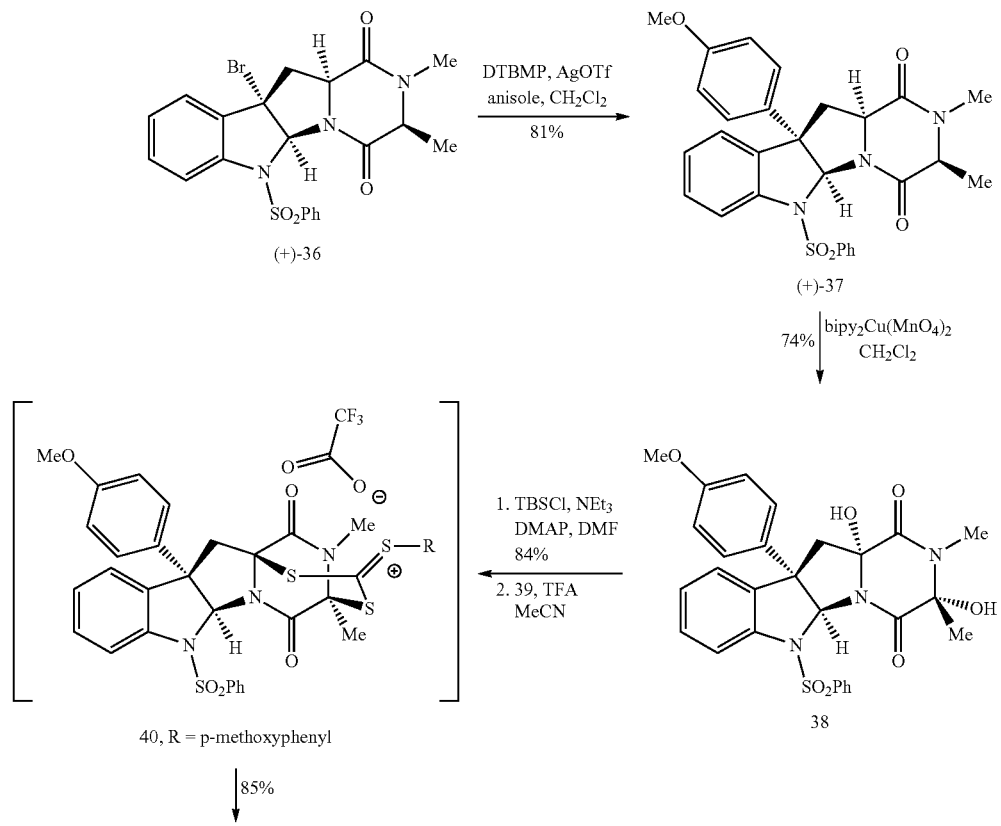

Scheme 7: Synthesis of model Trp-Ala ETPs

40, R = p-methoxyphenyl

171

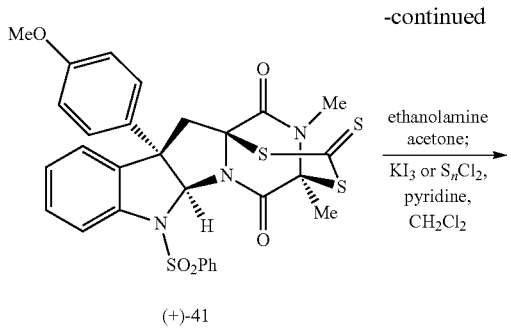

(+)-41

-continued

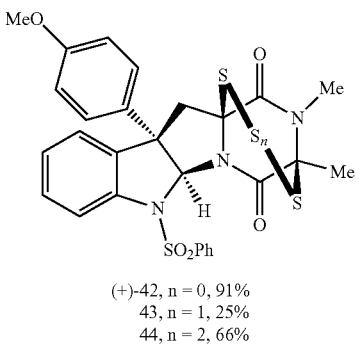

ethanolamine acetone;
$KI_3$ or $S_nCl_2$,
pyridine,
$CH_2Cl_2$ (+)-42, n = 0, 91%
43, n = 1, 25%
44, n = 2, 66%

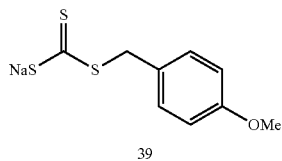

39

The tactical conversion of diol 38 to an alcohol by monosilylation (84%) resulted in a mixture of regioisomers (1:1) with improved stability and solubility parameters, setting the stage for incorporation of sulfur atoms. Dropwise addition of either regioisomer as a solution in dichloromethane to a solution of potassium trithiocarbonate ($K_2CS_3$) in trifluoroacetic acid and dichloromethane converged to the same dithiepanethione (+)-41 in 66-73% yield.[30] However, due to the challenging preparation of potassium trithiocarbonate from toxic hydrogen sulfide gas and its poor solubility prior to protonation, an alternative reagent that could obviate its use was sought.

It was hypothesized that an appropriately designed alkyl trithiocarbonate could stabilize the formation of a sulfonium ion during intramolecular cyclization onto the N-acyl-imminum ion. Drawing inspiration from Lo's synthesis[31] of Biotin Thioacid using bis(4-methoxyphenyl)-methanethiol as a protecting group, a known sodium benzhydryl trithiocarbonate was prepared.[32] Upon subjecting the mixture of regioisomers resulting from silylation of diol 38 to sodium benzhydryl trithiocarbonate and trifluoroacetic acid in dichloromethane, dithiepanethione (+)-41 was obtained in 68% yield. Monosodium trithiocarbonate 39, conveniently prepared from commercially available p-methoxybenzyl thiol, could achieve the same transformation in 60% yield under the same conditions (85% after optimization). From dithiepanethione (+)-41, access to all bioactive sulfur congeners (di-, tri-, and tetrasulfide) was obtained. Accordingly, dithiepanethione (+)-41 was deprotected via mild transcarbamation to give a bisthiol, which was oxidized to the epidisulfide (+)-42 with triiodide (91%), or converted to epitrisulfide 43 with sulfur dichloride (25%) or to epitetrasulfide 44 with disulfur dichloride (66%).

172

Scheme 8: Enhanced stability of alanine-derived epidisulfide (+)-42

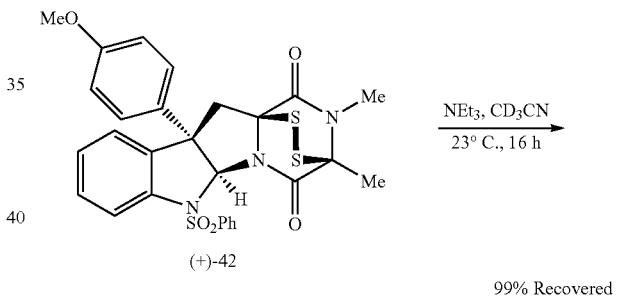

(+)-42

$NEt_3$, $CD_3CN$
23° C., 16 h

99% Recovered

Stability assays confirmed that the $C_{15}$-Me substituted epidisulfide (+)-42 (Scheme 8) did not suffer from the base-catalyzed decomposition that completely consumed epidisulfide (+)-8 (Scheme 6). Monitoring in situ by $^1$H NMR spectroscopy, 99% remaining starting material in the presence of triethylamine after 16 hours in deuteroacetonitrile was observed. These results encouraged the investigation of the thiol-disulfide exchange reactivity of model ETPs (+)-8 and (+)-42, to help gain insight into their mechanism of action.

The SAR profile of ETPs confirmed the importance of C11 and C15 sulfuration for anticancer activity, and further demonstrated that potentially labile sulfur derivatives, such as mixed bis-disulfides, also served as competent anticancer agents.[3p] It was hypothesized that these species might act as prodrugs, being converted to their corresponding epidisulfide pharmacophores under biological conditions, which are then concentrated within the cell via a glutathione-dependent mechanism.[33] Given that one of the proposed mechanisms of ETP toxicity invokes reactivity with cellular thiols,[2,34] the conversion of ETPs (+)-8 and (+)-42 into mixed bis-disulfides was studied.

Scheme 9: Thiol-disulfide exchange studies on model epidisulfides

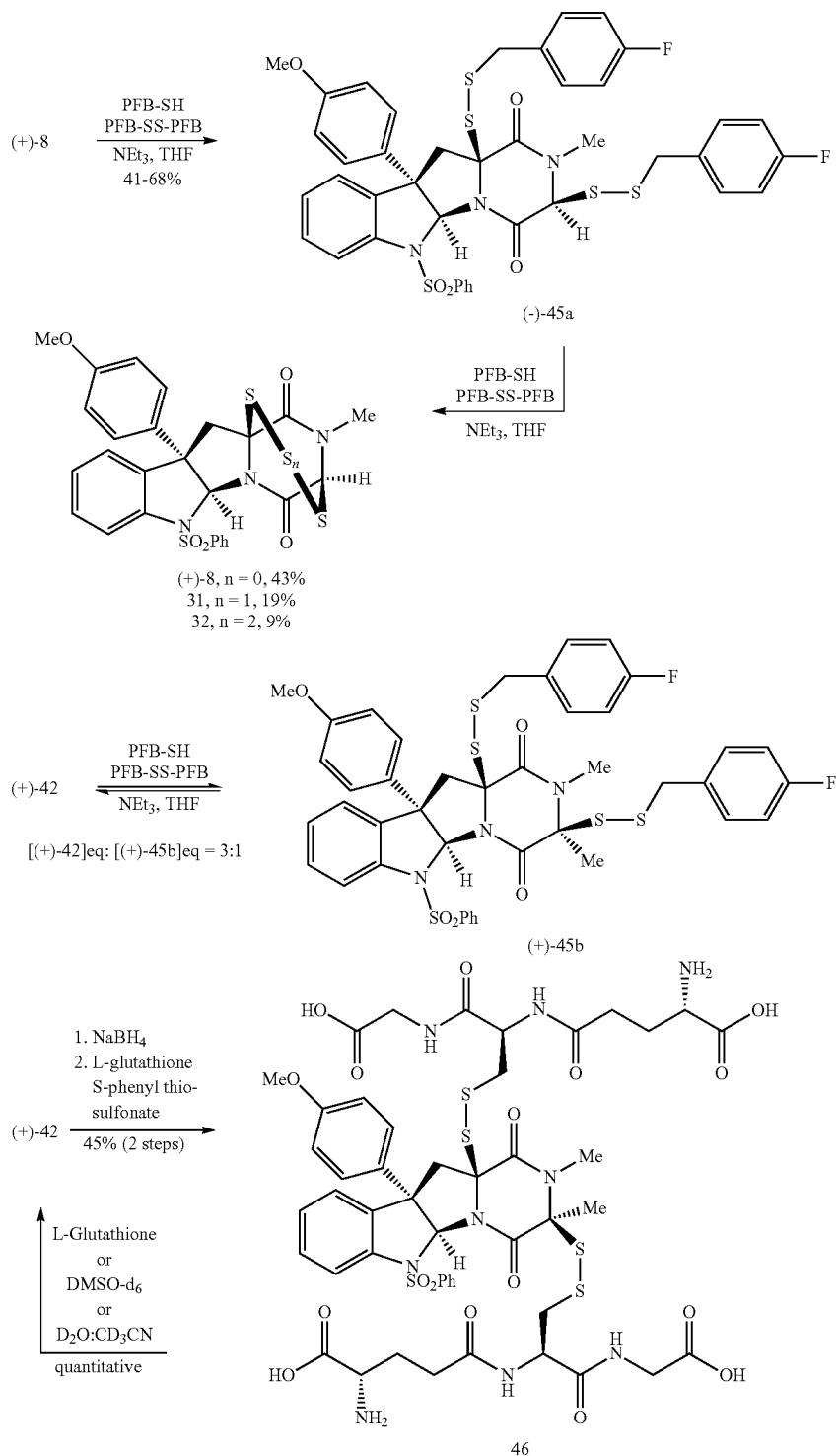

The first study involved thiol-disulfide exchange of ETPs in organic solvents using a surrogate thiol, and then transitioned to more biologically informative aqueous conditions involving glutathione (Scheme 9). Exposure of epidisulfide (+)-8 to 4-fluorobenzyl mercaptan (PFB-SH) and its corresponding disulfide (PFB-SS-PFB) indeed resulted in the formation of bisdisulfide (−)-45a. However, there were disparities between crude and isolated yields, due to continuing reactivity upon concentration in the presence of base and/or exposure to silica.[35] Furthermore, a reversion experiment of bisdisulfide (−)-45a resulted in a mixture of di-, tri-, and tetra-sulfides (Scheme 9). This result demonstrates possible challenges of establishing an equilibrium between epidisulfide (+)-8 and bisdisulfide (−)-45a.

In comparison to a glycine-derived epidisulfide (+)-8, alanine-derived epidisulfide (+)-42 permitted a more robust investigation of the thiol-disulfide exchange chemistry, as it did not decompose when exposed to basic conditions (see Scheme 9). Far slower and lower conversion (~25%) to corresponding bisdisulfide (+)-45b was observed, however the formation of trisulfide 43 or tetrasulfide 44 was not observed. By diluting aliquots of the disulfide-exchange reaction into deuterio-chloroform (Scheme 9), the equilibration between epidisulfide (+)-42 and bisdisulfide (+)-45b (3:1 in favor of epidisulfide (+)-42) was observed by $^1$H NMR spectroscopy. Furthermore, this study demonstrated that the equilibrium could be established from both directions by reverting bisdisulfide (+)-45b to epidisulfide (+)-42.[36]

In order to demonstrate that mixed disulfides could undergo reversion to their corresponding epidisulfide pharmacophores under biologically relevant conditions, the preparation of a water-soluble mixed disulfide was explored. Following hydride reduction of epidisulfide (+)-42, exposure of the crude bisthiol to glutathione S-Phenyl-thiosulfonate[37] provided the water-soluble glutathione bisdisulfide 46 in 45% yield, which was purified using reverse-phase silica chromatography. Epidisulfide (+)-42 and bisdisulfide 46 were both soluble in a mixture of $D_2O$ and $CD_3CN$, and addition of glutathione facilitated the quantitative reversion of bisdisulfide 46 to ETP (+)-42, in a matter of minutes with base or days without. In the absence of additional thiol or base, it was observed the same reversion of bisdisulfide 46 to epidisulfide (+)-46 in $d_6$-DMSO, with a 1:1 ratio after a week that progressed to >15:1 ETP after 3 weeks.

The results of these thiol-disulfide exchange studies on model epidisulfides (+)-8 and (+)-42 highlight the remarkable thermodynamic stability of the ETP substructure, as ETP-derived mixed bisdisulfides (−)-45a, (+)-45b, and 46 readily revert to their respective ETPs. The application of these bisdisulfides as ETP prodrugs may find utility in the treatments of certain types of cancer with higher glutathione (GSH)/glutathione disulfide (GSSG) ratios. For example, several studies have found that invasive and metastatic colon and prostate tumors have higher extracellular thiol concentrations than healthy tissue.[38] Thus, it may be possible to both modulate ETP toxicity in prodrug form, and to promote ETP formation only at the local tumor environment.

Given the enhanced chemical stability of model epidisulfide (+)-42 compared to epidisulfide (+)-8, epidisulfide azide (+)-9d was prepared (Scheme 10). The C3 arylation of bromide (+)-36 proceeded by silver-mediated electrophilic activation with trapping of the benzylic carbocation by aryl ether 11 (73% yield). Following silyl ether deprotection to arrive at alcohol (+)-47, the crucial alkyl azide moiety was installed in a highly efficient two-step tosylation (96%) and azidation (89%) sequence. Oxidation of propoxyazide (+)-48 using bis(pyridine)silver(I) permanganate furnished diol 49 in 64% yield, which was then subjected to monosilylation to arrive at a regioisomeric mixture of alcohols (1.1:1) in 85% yield. As with probes (+)-9a, (+)-9b, and (+)-9c, subsequent exposure to nitroethane saturated with hydrogen sulfide gas resulted in bis-sulfidation, which gave epidisulfide (+)-9d in 42% yield upon oxidation with triiodide. To highlight the flexibility in linkers that may be attached to these ETP probes, epidisulfide probe (+)-9d was conjugated with ethylene glycol-derived alkyne 50 using an CuAAC coupling strategy to give triazolyl ETP 51 in 92% yield, which can be subjected to downstream acylation as demonstrated in Scheme 5.

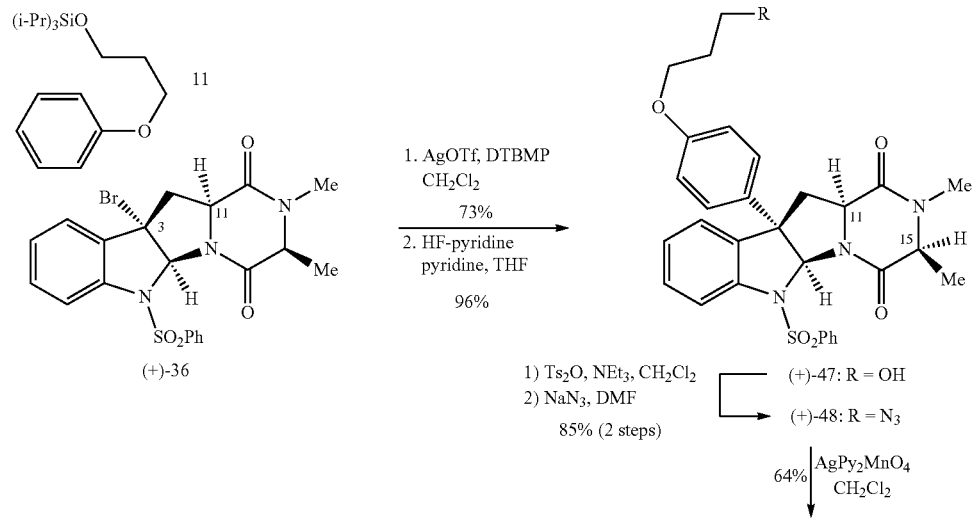

Scheme 10: Synthesis and conjugation of designed ETP azide (+)-9d

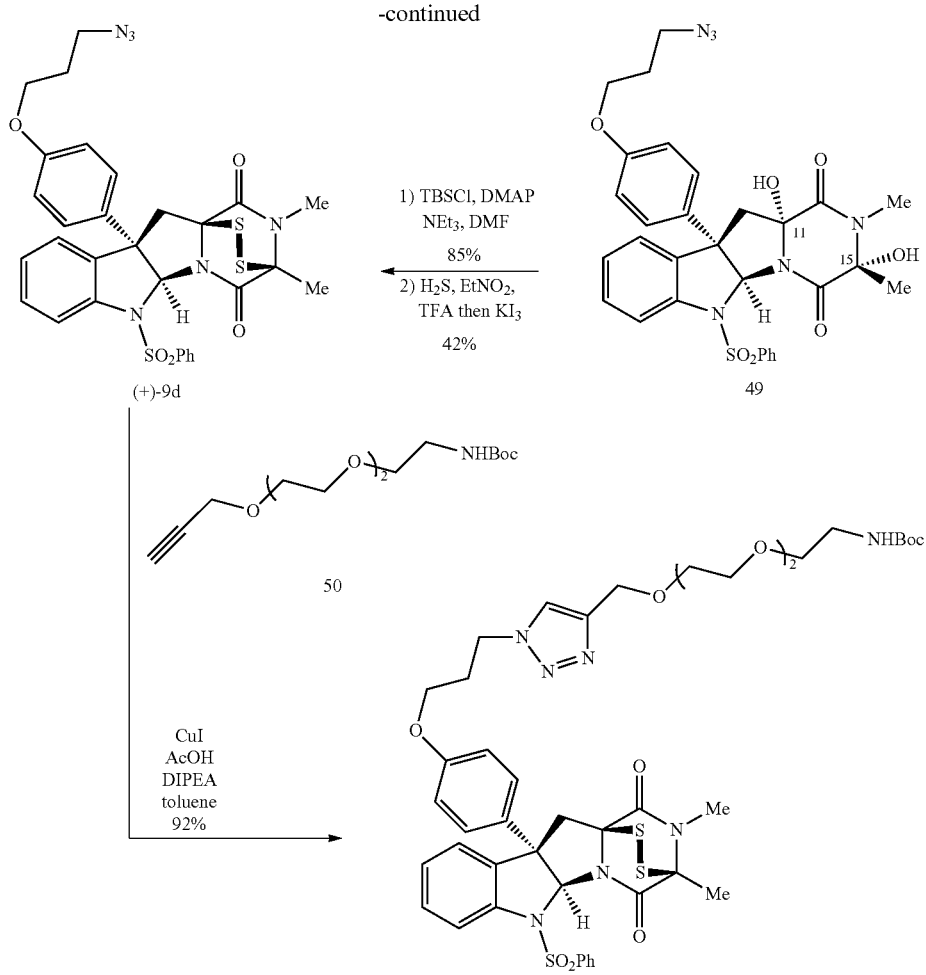

To evaluate the model and functionalized ETP probes as anticancer agents, fifteen derivatives were tested in culture against a panel of five human cancer cell lines (Table 1). Model monomeric and dimeric ETPs (+)-8, (+)-42, and (+)-7, designed azido ETPs (+)-9a-d, the ETP triazolyl cycloadducts (+)-28a-c, (+)-29, and 51, and bisdisulfides (−)-45a, (+)-45b, and 46 were evaluated for cytotoxic activity against cervical (HeLa), lung (A549), breast (MCF7), colorectal (HCT116), and prostate (DU-145) carcinoma cell lines. Across all five cell lines, the model and designed ETPs displayed similar patterns of potency in the form of low nanomolar cytotoxicity (Table 1).

While it was demonstrated that alanine-derived ETP (+)-42 is chemically more stable than glycine-derived ETP (+)-8 (Scheme 6 vs. 8), it was also observed that the glycine-derived ETPs were more active against the same cell lines (3.4-16 nM vs. 32-374 nM). Whereas the p-fluorobenzyl bisdisulfides (−)-45a and (+)-45b to have approximately the same activities as their parent ETPs (+)-8 and (+)-42, respectively, the water-soluble glutathione bisdisulfide 46 derived from ETP (+)-42 was significantly less active against the same cell lines.

These results indicate that ETPs possessing conjugatable chemical handles about either the C3, N14, or N1 positions retain potency, even after conjugation with several different coupling partners. In comparing model ETP (+)-8 to its functionalized derivatives azido ETPs (+)-9a-c, it was found the activity of ETP (+)-9a to be unaffected (<2-fold difference), (+)-9c to be slightly impaired (2.7- to 13.0-fold decrease), and (+)-9b to be most affected (3.2- to 18.6-fold decrease). Similarly, functionalization of model ETP (+)-42 as azido ETP (+)-9d did not impact the activity against HCT116 or MCF7 cell and gave only slightly reduced activities against A549, HeLa, and DU-145 cells (2.7-, 4.3-, and 8.6-fold decreases, respectively). Further derivatization of azide (+)-9a to triazole (+)-28a resulted in minimal (1.5- to 2.8-fold) loss of activity, whereas derivatization of azides (+)-9b-c to triazoles (+)-28b-c resulted in slight (1.9- to 4.3-fold) gain in activity. For the alanine-derived ETP (+)-42, the functionalization as azido ETP (+)-9d was unaffected for MCF7 and HCT116 cell lines, and resulted in slightly lower (2.7- to 8.6-fold) activities against A549, HeLa, and DU145 cell lines. The derivatization of azido ETP (+)-9d as triazole 51 recovered some of the lost activity, resulting in activities comparable to parent ETP (+)-42.

Detailed herein is the development of a concise synthetic route to alkyl azide functionalized ETP derivatives. Important features of this approach include stereocontrolled construction of the C3 quaternary center and stereo- and chemoselective late-stage hydroxylation and thiolation reactions. Notably, CuAAC reactions of these azido ETPs are tolerant of the sensitive epidisulfide moiety, cleanly affording the corresponding 1,2,3-triazole cycloadducts in high yields. In vitro cytotoxicity assays of ETP azide and triazole cycloadducts demonstrate that these derivatives retain high potency as anticancer agents against five human cancer cell lines. The ability to append virtually any chemical group to ETPs via CuAAC chemistry should facilitate diversification of these compounds with a wide array of chemical groups for various biological applications.

TABLE 1

Assessment of designed ETPs for cytotoxicity in five human cancer cell lines {HeLa (cervical carcinoma), A549 (alveolar adenocarcinoma), IMF7 (breast adenocarcinoma), HCT116 (colorectal carcinoma), and DU-145 (prostate carcinoma)}.[a]

| | HeLa | A549 | MCF7 | HCT116 | DU-145 |
|---|---|---|---|---|---|
| *Alanine-derived dimer with epipolystilfide bridge* | | | | | |
| (+)-7 | 0.11 ± 0.14 | 0.46 ± 0.45 | 0.30 ± 0.44 | 0.24 ± 0.29 | 0.18 ± 0.18 |
| 60 | 6.2 | 19 | 10.9 | 14.6 | 10 |
| *Glycine-derived monomers with epipolysulfide bridges* | | | | | |
| (+)-8 | 5.5 ± 1.7 | 16 ± 9.8 | 9.2 ± 3.1 | 6.9 ± 2.9 | 3.4 ± 4.2 |
| (+)-9a | 5.3 ± 0.2 | 8.8 ± 2.6 | 7.8 ± 3.6 | 5.7 ± 0.2 | 6.9 ± 2.1 |
| (+)-28a | 7.9 ± 3.7 | 25 ± 7.7 | 7.8 ± 5.9 | 11 ± 6.3 | 15 ± 5.6 |
| (+)-29 | 61 ± 46 | 753 ± 13 | 148 ± 58 | 119 ± 30 | 80 ± 25 |
| (+)-9b | 44 ± 25 | 143 ± 16 | 51 ± 7.1 | 101 ± 7.5 | 63 ± 22 |
| (+)-28b | 14 ± 11 | 78 ± 15 | 14 ± 3.3 | 23 ± 1.9 | 22 ± 3.5 |
| (+)-9c | 15 ± 12 | 76 ± 35 | 53 ± 48 | 37 ± 21 | 44 ± 46 |
| (+)-28c | 6.3 ± 5.9 | 39 ± 12 | 19 ± 15 | 20 ± 8.6 | 16 ± 14 |
| *Glycine-derived monomer with bisdisulfide* | | | | | |
| (−)-45a | 4.0 ± 0.1 | 21 ± 1.1 | 5.0 ± 2.3 | 6.9 ± 1.6 | 5.4 ± 1.9 |
| *Alanine-derived monomers with epipolysulfide bridges* | | | | | |
| (+)-42 | 32 ± 37 | 92 ± 87 | 81 ± 64 | 374 ± 83 | 36 ± 43 |
| (+)-9d | 136 ± 84 | 251 ± 307 | 86 ± 113 | 348 ± 442 | 306 ± 385 |
| 51 | 24 ± 29 | 116 ± 102 | 82 ± 105 | 148 ± 148 | 62 ± 75 |
| *Alanine-derived monomers with bisdisulfides* | | | | | |
| (+)-45b | 81 ± 26 | 141 ± 68 | 90 ± 23 | 141 ± 20 | 88 ± 50 |
| 46 | 508 ± 75 | 910 ± 324 | 500 ± 152 | 1096 ± 540 | 580 ± 216 |

[a] Cytoxicity $IC_{50}$ values (in nM) aller 72 h of compound treatment as determined by Cell Titer-Glo (Promega) which measures ATP levels as a surrogate for cell viability. Error is standard deviation of the mean, n ≥ 2; $IC_{50}$ = half maximal inhibitory concentration.

Having achieved the synthesis of ETP probes (+)-9a-d and demonstrated that they retain potency against human cancer cell lines (Table 1) in comparison to their non-functionalized analogs, the design and synthesis of a heterodimeric ETP probe based on lead compound dimeric ETP (+)-7 was next sought.[3p] Functionalization of N14 en route to heterodimeric probe 60, allowed for a divergent synthesis from known intermediates (+)-52 and (+)-36.[5a] As shown in Scheme 11, the latent functional handle was introduced by N-alkylation of known tetracyclic bromide 52 with propargylic iodide 53 using trisdimethylaminosulfonium trimethylsilyldifluoride (TASF) as a source of anhydrous fluoride to give alkyne 54 in 84% yield. Under these mild conditions no C11-epimerization was observed, a notable improvement over the analogous alkylation of monomeric diketopiperazine (+)-16 (Scheme 2). Hydrogenation of alkyne 54 with 5% Pd/C in ethyl acetate followed by benzyl ether cleavage with boron trichloride afforded alcohol 55 in 81% yield over two steps. Previously the $C_3$-$C_{3'}$ bond in related, homodimeric natural products was synthesized,[39] reductive dimerization of alcohol 55 and reported N-methyl bromide using Co(I) $C_1(PPh)_3$ furnished heterodimeric alcohol 56 in 26% yield. Conversion of the primary alcohol to the methanesulfonate followed by $S_{N2}$ displacement with sodium azide secured the alkyl azide in 81% yield over two steps. Oxidation with bispyridyl silver permanganate provided tetraol 58 in 60% yield. This sensitive intermediate was tethered with dichlorodiisopropylsilane to give dioxasilane 59, which exhibited more controlled reactivity in the key thiolation step by reducing the rate of competitive elimination. Finally, bis-sulfidation using tritylhydrodisulfane provided direct access to functionalized heterodimeric ETP probe 60 in 39% yield. Heterodimeric ETP probe 60 retains low nanomolar activity against five human cancer cell lines (Table 1), making it a promising candidate for further investigations including protein target identification and antibody-drug conjugation.

Scheme 11: Synthesis of designed heterodimeric ETP azide 60

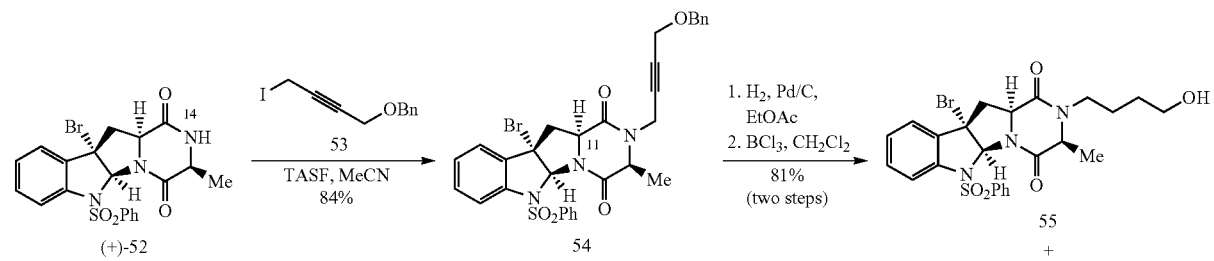

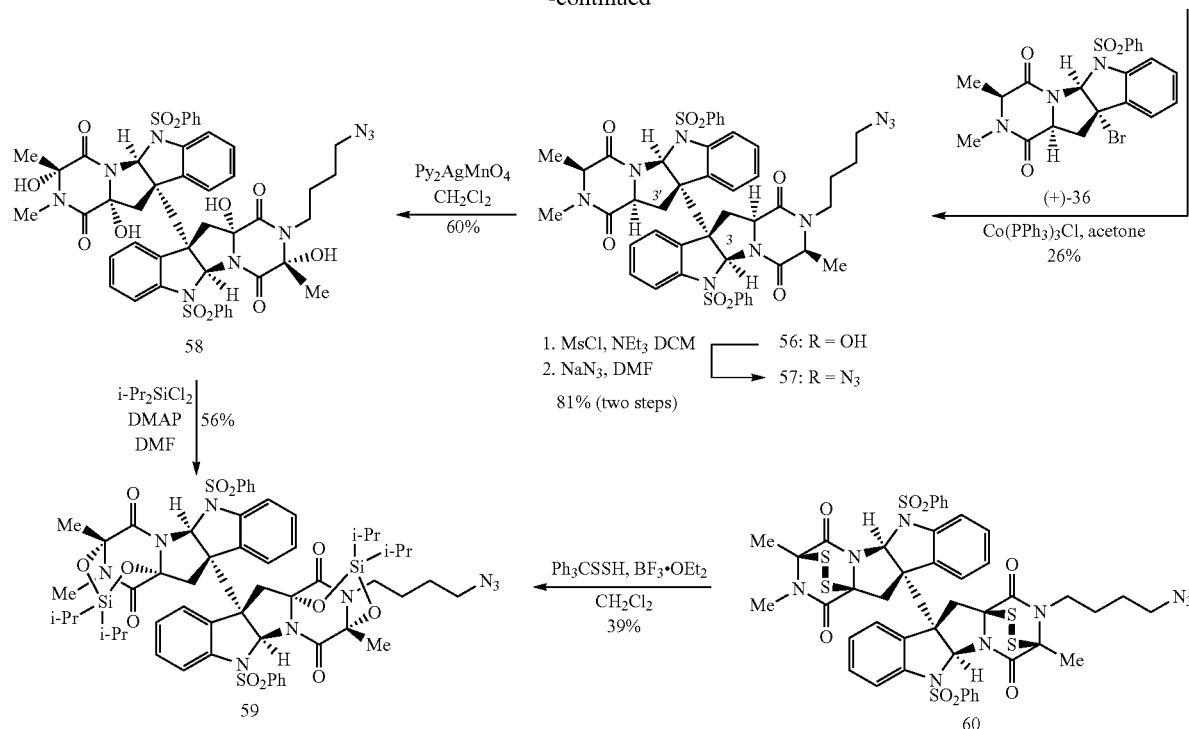
Additional cell viability assays were carried out with Jurkat cell lines (acute T cell leukemia), K-562 cell lines (chronic myelogenous leukemia (CML)), and Toledo cell lines (diffuse large cell lymphoma; non-Hodgkin's B cell lymphoma). Exemplary results are shown in Table 2.
TABLE 2
| Compound | Cell Line | IC$_{50}$ (μM) |
|---|---|---|
| 60 | Jurkat | 0.00647 |
|  | K-562 | 0.01971 |
|  | Toledo | 0.00829 |
| (+)-9d | Jurkat | 0.41937 |
|  | K-562 | 1.28054 |
|  | Toledo | 1.81121 |

Synthesis of Exemplary Compounds

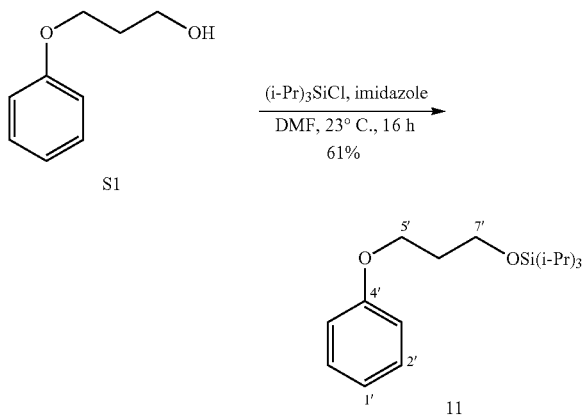

Example 1: (3-Phenoxypropoxy)triisopropylsilane 11

Triisopropylsilyl chloride (5.84 mL, 27.3 mmol, 1.00 equiv) was added via syringe to a solution of 3-phenoxypropan-1-ol[40] (4.16 g, 27.3 mmol, 1 equiv) and imidazole (2.42 g, 62.3 mmol, 2.30 equiv) in N,N-dimethylformamide (45 mL) at 23° C. After 18 h, the reaction mixture was diluted with ethyl acetate (300 mL) and was slowly poured into saturated aqueous sodium bicarbonate solution (100 mL). The organic layer was washed sequentially with a saturated aqueous sodium bicarbonate solution (2×50 mL), with water (3×50 mL), and with a saturated aqueous sodium chloride solution (40 mL). The organic layer was dried over anhydrous sodium sulfate, was filtered, and was concentrated under reduced pressure. The resulting residue was purified by flash column chromatography on silica gel (eluent: 0-10% ethyl acetate in hexanes) to afford (3-phenoxypropoxy)triisopropylsilane 11 (4.90 g, 61.4%) as a colorless oil. $^1$H NMR (600 MHz, CDCl$_3$, 25° C.): δ 7.26 (app-t, J=7.9 Hz, 2H, C$_2$·H), 6.92-6.89 (m, 3H, C$_1$·H, C$_3$·H), 4.08 (t, J=6.3 Hz, 2H, C$_5$H), 3.87 (t, J=6.0 Hz, 2H, C$_2$H), 1.99 (p, J=6.1 Hz, 2H, C$_6$H), 1.10-1.03 (m, 21H, SiCH(CH$_3$)$_2$, SiCH(CH$_3$)$_2$). $^{13}$C NMR (150 MHz, CDCl$_3$, 25° C.): δ 159.3 (C$_4$·), 129.6 (C$_2$·), 120.7 (C$_1$·), 114.7 (C$_3$·) 64.7 (C$_5$·), 60.1 (C$_7$·), 32.9 (C$_6$·), 18.2 (SiCH(CH$_3$)$_2$), 12.2 (SiCH(CH$_3$)$_2$). FTIR (thin film) cm$^{-1}$: 2941 (s), 2865 (s), 1497 (s), 1244 (s), 1103 (s), 881 (s), 751 (s). HRMS (ESI) (m/z): calc'd for C$_{18}$H$_{33}$O$_2$Si [M+H]+: 309.2244, found: 309.2266. TLC (10% ethyl acetate in hexanes), Rf: 0.39 (UV, CAM).

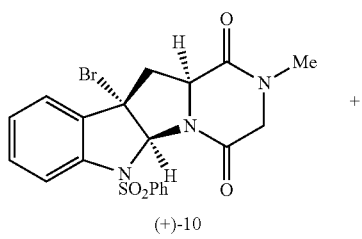

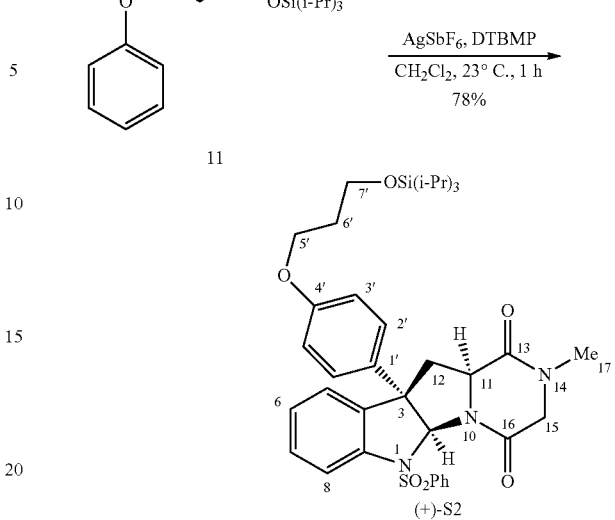

Example 2: C$_3$-Friedel-Crafts Adduct (+)—S2

Endo-tetracyclic bromide (+)-10[41] (1.67 g, 3.50 mmol, 1 equiv), 2,6-di-tert-butyl-4-methylpyridine (DTBMP, 1.81 g, 8.80 mmol, 2.51 equiv), and (3-phenoxypropoxy)triisopropylsilane 11 (2.16 g, 6.99 mmol, 2.00 equiv) were azeotropically dried by concentration from anhydrous benzene (30 mL) under reduced pressure. Dichloromethane (35 mL) was added via syringe, and silver hexafluoroantimonate (2.40 g, 6.99 mmol, 2.00 equiv) was added as a solid in one portion to the solution at 23° C. After 1 h, the reaction mixture was diluted with dichloromethane (100 mL) and was filtered through a pad of Celite. The filter cake was washed with dichloromethane (3×50 mL), and the filtrate was concentrated under reduced pressure. The resulting residue was purified by flash column chromatography on silica gel (eluent: 0→20% acetone in dichloromethane) to afford Friedel-Crafts adduct (+)—S2 (1.93 g, 78.4%) as a white solid. Structural assignments were made with additional information from gCOSY, gHSQC, and gHMBC experiments. $^1$H NMR (400 MHz, CDCl$_3$, 25° C.): δ 7.58 (d, J=8.1 Hz, 1H, C$_8$H), 7.46 (app-d, J=8.5 Hz, 2H, SO$_2$Ph-o-H), 7.30 (app-t, J=7.5 Hz, 1H, SO$_2$Ph-p-H), 7.28-7.24 (m, 1H, C$_7$H), 7.10 (m, 4H, SO$_2$Ph-o-H, C$_5$H, C$_6$H), 6.68-6.61 (m, 4H, C$_2$·H, C$_3$·H), 6.13 (s, 1H, C$_2$H), 4.39 (app-t, J=8.3 Hz, 1H, C$_{11}$H), 4.10 (d, J=17.4 Hz, 1H, C$_{15}$H$_a$), 4.04 (t, J=6.3 Hz, 2H, C$_5$·H), 3.86 (t, J=6.1 Hz, 2H, C$_7$·H), 3.82 (d, J=17.4 Hz, 1H, C$_{15}$H$_b$), 3.06 (dd, J=7.0, 14.1 Hz, 1H, C$_{12}$H$_a$), 2.89-2.83 (m, 4H, C$_{12}$H$_b$, C$_{17}$H), 1.98 (p, J=6.1 Hz, 2H, C$_6$·H)), 1.11-1.03 (m, 21H, SiCH(CH$_3$)$_2$, SiCH(CH$_3$)$_2$). $^{13}$C NMR (100 MHz, CDCl$_3$, 25° C.): δ 167.1 (C$_{13}$), 165.2 (C$_{16}$), 158.4 (C$_4$·), 139.9, (C$_9$) 138.2 (SO$_2$Ph-ipso-C), 135.8 (C$_4$), 133.0 (SO$_2$Ph-p-C), 132.5 (C$_1$·), 129.2 (C$_7$), 128.7 (SO$_2$Ph-m-C), 128.1 (C$_2$·), 128.0 (SO$_2$Ph-o-C), 126.0 (C$_6$), 125.4 (C$_5$), 117.2 (C$_8$), 115.0 (C$_3$·), 87.2 (C$_2$), 64.9 (C$_5$·), 59.8 (C$_7$·), 59.4 (C$_3$), 58.6 (C$_{11}$), 54.5 (C$_{15}$), 39.1 (C$_{12}$), 33.7 (C$_{17}$), 32.7 (C$_6$·), 18.2 (SiCH(CH$_3$)$_2$), 12.1 (SiCH(CH$_3$)$_2$). FTIR (thin film) cm$^{-1}$: 3065 (m), 2943 (s), 2868 (s), 1684 (s), 1610 (m), 1512 (m), 1253 (m), 1171 (m), 883 (m), 686 (w). HRMS (DART) (m/z): calc'd for C$_{38}$H$_{50}$N$_3$O$_6$SSi [M+H]+: 704.3184, found: 704.3195. [α]$_D^{23}$: +19 (c=0.24, CHCl$_3$). TLC (30% acetone in dichloromethane), Rf: 0.63 (UV, CAM).

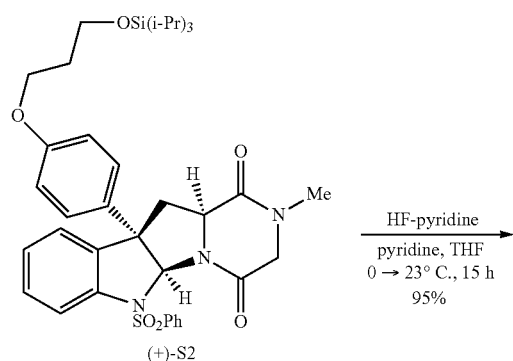

(+)-S2

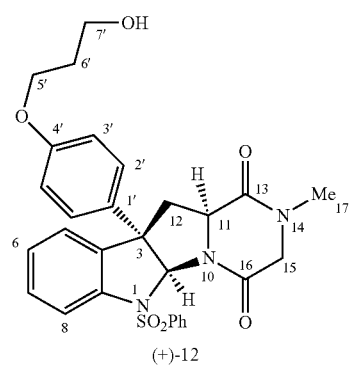

(+)-12

Example 3: Alcohol (+)-12

A freshly prepared solution of hydrogen fluoride-pyridine (70% HF, 9 mL), pyridine (18 mL), and tetrahydrofuran (72 mL) at 0° C. was poured into a solution of Friedel-Crafts adduct (+)—S2 (1.894 g, 2.691 mmol, 1 equiv) in tetrahydrofuran (90 mL) at 0° C. contained in a 1-L polypropylene vessel. After 5 min, the ice-water bath was removed and the solution was allowed to stir and warm to 23° C. After 20 h, the reaction mixture was cooled to 0° C. and was diluted with a saturated aqueous sodium bicarbonate solution (500 mL) in portions (50 mL) over 15 min. The resulting mixture was extracted with ethyl acetate (300 mL), the layers were separated, and the aqueous layer was extracted with ethyl acetate (2×75 mL). The combined organic extracts were washed sequentially with a saturated aqueous copper(II) sulfate solution (3×100 mL), with a saturated aqueous ammonium chloride solution (3×100 mL), and with a saturated aqueous sodium chloride solution (75 mL). The organic layer was dried over anhydrous sodium sulfate, was filtered, and was concentrated under reduced pressure. The resulting residue was purified by flash column chromatography on silica gel (eluent: 0→60% acetone in dichloromethane) to afford alcohol (+)-12 (1.33 g, 90.0%) as a white solid. Structural assignments were made with additional information from gCOSY, gHSQC, and gHMBC experiments. $^1$H NMR (400 MHz, CDCl$_3$, 25° C.): δ 7.57 (d, J=8.1 Hz, 1H, C$_8$H), 7.45 (app-d, J=9.7 Hz, 2H, SO$_2$Ph-o-H), 7.33 (app-t, J=7.5 Hz, 1H, SO$_2$Ph-p-H), 7.28-7.23 (m, 1H, C$_7$H), 7.12-7.08 (m, 4H, SO$_2$Ph-m-H, C$_5$H, C$_6$H), 6.65 (app-d, J=9.0 Hz, 2H, C$_2$·H) 6.60 (app-d, J=9.0 Hz, 2H, C$_3$·H), 6.13 (s, 1H, C$_2$H), 4.41 (app-t, J=8.3 Hz, 1H, C$_{11}$H), 4.10 (d, J=17.3 Hz, 1H, C$_{15}$H$_a$), 4.05 (t, J=6.0 Hz, 2H, C$_5$·H), 3.84 (t, J=6.0 Hz, 2H, C$_7$·H), 3.81 (d, J=17.7 Hz, 1H, C$_{15}$H$_b$), 3.06 (dd, J=7.0, 14.1 Hz, 1H, C$_{12}$H$_a$), 2.88-2.82 (m, 4H, C$_{12}$H$_b$, C$_{17}$H), 2.02 (p, J=5.9 Hz, 2H, C$_6$·H), 1.88 (br-s, 1H, OH). $^{13}$C NMR (100 MHz, CDCl$_3$, 25° C.): δ 167.1 (C$_{13}$), 165.3 (C$_{16}$), 158.1 (C$_{4'}$), 139.9 (C$_9$), 138.2 (SO$_2$Ph-ipso-C), 135.9 (C$_4$), 133.1 (SO$_2$Ph-p-C), 132.9 (C$_{1'}$), 129.3 (C$_7$), 128.8 (SO$_2$Ph-m-C), 128.2 (C$_{2'}$), 127.6 (SO$_2$Ph-o-C), 126.0 (C$_6$), 125.5 (C$_5$), 117.2 (C$_8$), 115.0 (C$_{3'}$), 87.2 (C$_2$), 65.8 (C$_{5'}$), 60.2 (C$_{7'}$), 59.4 (C$_3$), 58.6 (C$_{11}$), 54.4 (C$_{15}$), 39.0 (C$_{12}$), 33.7 (C$_{17}$), 32.1 (C$_{6'}$). FTIR (thin film) cm$^{-1}$: 2954 (w), 1700 (s), 1684 (s), 1507 (m), 1362 (m), 1169 (m), 832 (w), 668 (m). HRMS (DART) (m/z): calc'd for C$_{29}$H$_{30}$N$_3$O$_6$S [M+H]$^+$: 548.1850, found: 548.1872. [α]$_D^{23}$: +26 (c=0.12, CHCl$_3$). TLC (30% acetone in dichloromethane), Rf: 0.21 (UV, CAM).

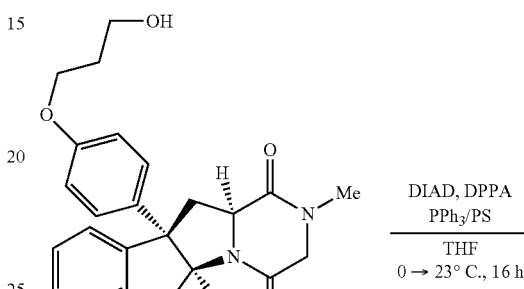

(+)-12

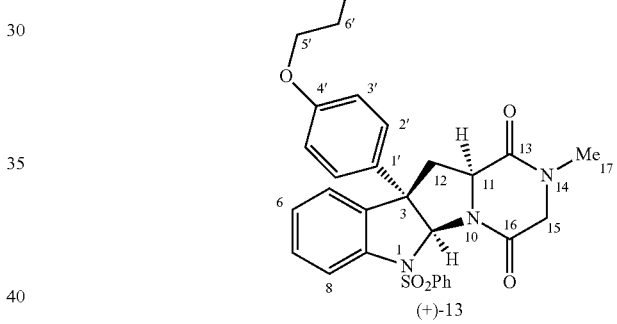

(+)-13

Example 4: Azide (+)-13

Diisopropyl azodicarboxylate (DIAD, 256 μL, 1.28 mmol, 1.50 equiv) and diphenylphosphoryl azide (DPPA, 276 μL, 1.28 mmol, 1.50 equiv) were added dropwise via syringe to a suspension of alcohol (+)-12 (466 mg, 851 μmol, 1 equiv) and resin-bound triphenylphosphine (1.31 mmol/g on 100-200 mesh polystyrene cross-linked with 1% divinylbenzene, 973 mg, 1.28 mmol, 1.50 equiv) in tetrahydrofuran (20 mL) at 0° C. After 5 min, the ice-water bath was removed and the reaction mixture was allowed to stir and warm to 23° C. After 16 h, the reaction mixture was filtered through a 1 cm pad of Celite in a 60-mL medium-porosity fritted-glass funnel. The filter cake was washed with dichloromethane (100 mL), and the filtrate was concentrated under reduced pressure. The resulting residue was purified by flash column chromatography on silica gel (eluent: 30% acetone in dichloromethane) to afford azide (+)-13 (425 mg, 87.2%) as a white solid. Structural assignments were made with additional information from gCOSY, gHSQC, and gHMBC experiments. $^1$H NMR (400 MHz, CDCl$_3$, 25° C.): δ 7.58 (d, J=8.1 Hz, 1H, C$_8$H), 7.49 (app-d, J=8.4 Hz, 2H, SO$_2$Ph-o-H), 7.34 (app-t, J=7.5 Hz, 1H, SO$_2$Ph-p-H), 7.28-7.23 (m, 1H, C$_7$H), 7.14-7.09 (m, 4H, SO$_2$Ph-o-H, C$_5$H, C$_6$H), 6.68 (app-d, J=9.0 Hz, 2H, C$_2$H) 6.62 (app-d, J=9.0 Hz, 2H, C$_3$'H), 6.13 (s, 1H, C$_2$'H), 4.39 (app-t, J=8.2 Hz, 1H, C$_{11}$H), 4.10 (d, J=17.4 Hz, 1H, C$_{15}$H$_a$), 3.99 (t, J=5.9 Hz, 2H, C$_5$'H), 3.82 (d, J=17.4 Hz, 1H, C$_{15}$H$_b$), 3.51 (t, J=6.5 Hz, 2H, C$_7$'H), 3.06 (dd, J=7.1, 14.2 Hz, 1H, C$_{12}$H$_a$), 2.89-2.83 (m, 4H, C$_{12}$H$_b$, C$_{17}$H), 2.04 (p, J=6.2 Hz, 2H, C$_6$'H). $^{13}$C NMR (100 MHz, CDCl$_3$, 25° C.): δ 167.1 (C$_{13}$), 165.3 (C$_{16}$), 157.9 (C$_4$'), 139.9 (C$_9$), 138.2 (SO$_2$Ph-ipso-C), 135.8 (C$_4$), 133.1 (SO$_2$Ph-p-C), 133.0 (C$_1$'), 129.3 (C$_7$), 128.7 (SO$_2$Ph-m-C), 128.2 (C$_2$'), 127.7 (SO$_2$Ph-o-C), 126.0 (C$_6$), 125.4 (C$_5$), 117.2 (C$_8$), 115.0 (C$_3$'), 87.1 (C$_2$), 64.7 (C$_5$'), 59.4 (C$_3$), 58.6 (C$_{11}$), 54.4 (C$_{15}$), 48.3 (C$_7$'), 39.0 (C$_{12}$), 33.7 (C$_{17}$), 28.9 (C$_6$'). FTIR (thin film) cm$^{-1}$: 2929 (w), 2099 (s), 1700 (s), 1684 (s), 1512 (m), 1362 (m), 1252 (m), 1169 (m), 1091 (w), 832 (w), 668 (m). HRMS (DART) (m/z): calc'd for C$_{29}$H$_{29}$N$_6$O$_5$S [M+H]$^+$: 573.1915, found: 573.1921. [α]$_D^{23}$: +21.8 (c=0.22, CHCl$_3$). TLC (30% acetone in dichloromethane), Rf: 0.55 (UV, CAM).

under reduced pressure. The resulting residue was purified by flash column chromatography on silica gel (eluent: 0→40% acetone in dichloromethane) to afford diol (−)-14 (169 mg, 63.2%) as a white solid. Structural assignments were made with additional information from gCOSY, gHSQC, and gHMBC experiments. $^1$H NMR (400 MHz, DMSO-d$_6$, 25° C.): δ 7.43 (app-t, J=7.4 Hz, 1H, SO$_2$Ph-p-H), 7.39-7.32 (m, 4H, SO$_2$Ph-o-H, C$_7$H, C$_8$H), 7.26-7.19 (m, 3H, C$_{11}$OH, C$_5$H, C$_6$H), 7.13 (app-t, J=7.5 Hz, 2H, SO$_2$Ph-m-H), 7.01 (d, J=7.2 Hz, 1H, C$_{15}$OH), 6.75 (app-d, J=8.9 Hz, 2H, C$_2$'H), 6.66 (app-d, J=8.9 Hz, 2H, C$_3$'H), 6.21 (s, 1H, C$_2$H), 5.00 (d, J=6.8 Hz, 1H, C$_{15}$H), 4.02 (t, J=6.0 Hz, 2H, C$_5$'H), 3.54 (t, J=6.7 Hz, 2H, C$_7$'H), 3.19 (d, J=14.9 Hz, 1H, C$_{12}$H$_a$), 2.77 (s, 3H, C$_{17}$H), 2.66 (d, J=14.9 Hz, 1H, C$_{12}$H$_b$), 1.99 (p, J=6.3 Hz, 2H, C$_6$'H). $^{13}$C NMR (100 MHz, DMSO-d$_6$, 25° C.): δ 166.6 (C$_{13}$), 165.8 (C$_{16}$), 157.1 (C$_4$'), 139.3 (C$_9$), 138.0 (SO$_2$Ph-ipso-C), 137.7 (C$_4$), 133.6 (C$_1$'), 133.2 (SO$_2$Ph-p-C), 128.9 (C$_7$), 128.7 (SO$_2$Ph-m-C), 128.0 (C$_2$'), 126.7 (SO$_2$Ph-o-C), 126.6 (C$_6$), 125.7 (C$_5$), 117.0 (C$_8$), 114.5 (C$_3$), 87.3 (C$_2$), 86.0 (C$_{11}$), 80.9 (C$_{15}$), 64.6 (C$_5$'), 57.4 (C$_3$), 49.7 (C$_{12}$), 47.7 (C$_7$'), 30.5 (C$_{17}$), 28.1 (C$_6$'). FTIR (thin film) cm$^{-1}$: 2095 (m), 1844 (m), 1734 (m), 1700 (s), 1685 (s), 1653 (s), 1559 (s), 1540 (m), 1507 (m), 1457 (m), 1055 (w), 668 (m). [α]$_D^{23}$: −6 (c=0.16, DMSO). HRMS (DART) (m/z): calc'd for C$_{29}$H$_{29}$N$_6$O$_7$S [M+H]$^+$: 605.1813, found: 605.1814. TLC (30% acetone in dichloromethane), Rf: 0.40 (UV, CAM).

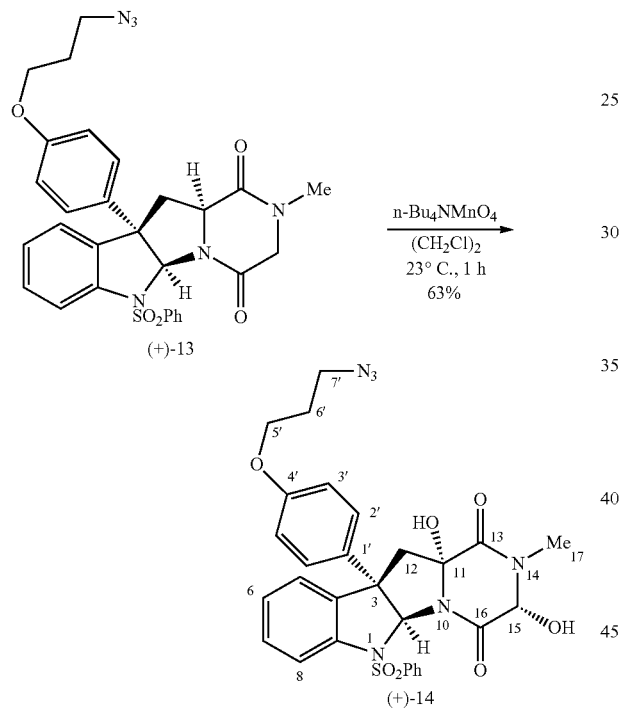

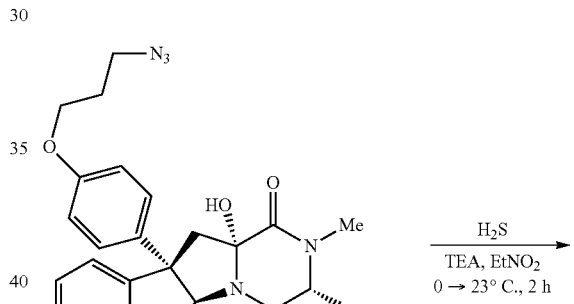

Example 5: Diol (−)-14

Tetra-n-butylammonium permanganate$^{42}$ (807 mg, 2.23 mmol, 5.05 equiv) was added as a solid to a solution of azide (+)-13 (253 mg, 442 μmol, 1 equiv) in 1,2-dichloroethane (16 mL) at 23° C. After 1 h, the reaction mixture was diluted with a saturated aqueous sodium sulfite solution (50 mL) and with ethyl acetate-hexanes (9:1, 200 mL). The resulting mixture was washed with a saturated aqueous sodium bicarbonate solution (50 mL), the layers were separated, and the organic layer was washed sequentially with a saturated aqueous sodium bicarbonate solution (50 mL), with deionized water (50 mL), and with a saturated aqueous sodium chloride solution (25 mL). The combined aqueous layers were extracted with ethyl acetate-hexanes (9:1, 2×50 mL), and the combined organic extracts were dried over anhydrous sodium sulfate, were filtered, and were concentrated

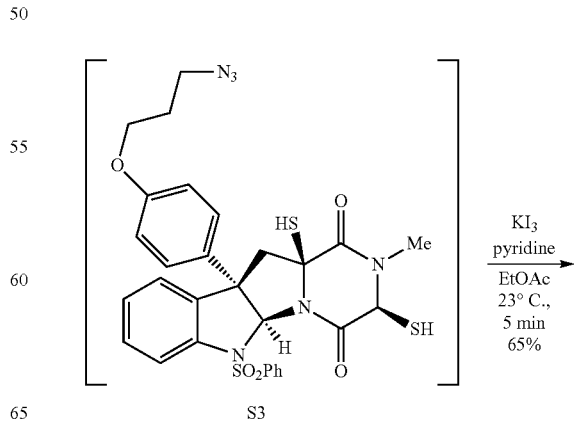

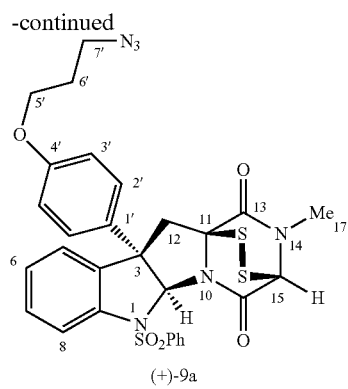

(+)-9a

Example 6: Epidithiodiketopiperazine Azide (+)-9a

A solution of diol (−)-14 (190 mg, 314 μmol, 1 equiv) in anhydrous nitroethane (13 mL) at 0° C. was sparged with hydrogen sulfide gas for 20 min by discharge of a balloon equipped with a needle extending into the reaction mixture, providing a saturated hydrogen sulfide solution. Trifluoroacetic acid (TFA, 9.8 mL) was added via syringe over 20 seconds, and the sparging with hydrogen sulfide gas was maintained for another 20 min. The ice-water bath was removed and the solution was allowed to stir and warm to 23° C. under an atmosphere of hydrogen sulfide. After 2 h, the reaction mixture was diluted with ethyl acetate (125 mL), was slowly poured into a stirring saturated aqueous sodium bicarbonate solution (50 mL), and the organic layer was washed with a saturated aqueous sodium chloride solution (35 mL). A stock solution of potassium triiodide in pyridine[43] was added dropwise into the organic layer containing crude bisthiol S3 until a persistent yellow color was observed. The resulting mixture was washed with an aqueous hydrogen chloride solution (1 M, 2×35 mL), was washed with a saturated aqueous sodium chloride solution (35 mL), was dried over anhydrous sodium sulfate, was filtered, and was concentrated under reduced pressure. The resulting residue was purified by flash column chromatography on silica gel (eluent: 10→20% ethyl acetate in dichloromethane) to afford epidithiodiketopiperazine azide (+)-9a (129 mg, 65.4%) as a beige solid. Structural assignments were made with additional information from gCOSY, gHSQC, and gHMBC experiments.[44] $^1$H NMR (400 MHz, CDCl$_3$, 25° C.): δ 7.59 (d, J=8.0 Hz, 1H, C$_8$H), 7.40-7.34 (m, 3H, C$_7$H, SO$_2$Ph-o-H), 7.29 (app-t, J=7.5 Hz, 1H, SO$_2$Ph-p-H), 7.25-7.21 (m, 2H, C$_5$H, C$_6$H), 7.03 (t, J=7.9 Hz, 2H, SO$_2$Ph-m-H), 6.75 (app-d, J=8.9 Hz, 2H, C$_{2'}$H), 6.61 (app-d, J=8.9 Hz, 2H C$_{3'}$H), 6.38 (s, 1H, C$_2$H), 5.24 (s, 1H, C$_{15}$H), 3.99 (t, J=6.0 Hz, 2H, C$_{5'}$H), 3.62 (d, J=15.5 Hz, 1H, C$_{12}$H$_a$), 3.51 (t, J=6.5 Hz, 2H, C$_{7'}$H), 3.11 (s, 3H, C$_{17}$H), 2.84 (d, J=15.5 Hz, 1H, C$_{12}$H$_b$), 2.03 (p, J=6.1 Hz, 2H, C$_{6'}$H). $^{13}$C NMR (100 MHz, CDCl$_3$, 25° C.): δ 165.2 (C$_{13}$), 160.2 (C$_{16}$), 158.1 (C$_{4'}$), 141.3 (C$_9$), 138.5 (SO$_2$Ph-ipso-C), 135.9 (C$_4$), 133.1 (SO$_2$Ph-p-C), 131.6 (C$_{1'}$), 129.9 (C$_7$), 128.7 (SO$_2$Ph-m-C), 128.1 (C$_{2'}$), 127.3 (SO$_2$Ph-o-C), 126.2 (C$_6$), 125.7 (C$_5$), 119.0 (C$_8$), 115.1 (C$_{3'}$), 87.7 (C$_2$), 74.6 (C$_{11}$), 68.5 (C$_{15}$), 64.7 (C$_{5'}$), 59.6 (C$_3$), 48.3 (C$_{7'}$), 45.5 (C$_{12}$), 32.2 (C$_{17}$), 28.9 (C$_{6'}$). FTIR (thin film) cm$^{-1}$: 2926 (w), 2098 (m), 1717 (s), 1700 (s), 1685 (s), 1559 (m), 1507 (m), 1473 (w), 972 (w), 668 (m). HRMS (DART) (m/z): calc'd for C$_{29}$H$_{30}$N$_7$O$_5$S$_3$[M+NH$_4$]$^+$: 652.1465, found: 652.1454. [α]$_D^{23}$: +236 (c=0.10, CHCl$_3$). TLC (20% ethyl acetate in CH$_2$Cl$_2$), Rf: 0.32 (UV, CAM).

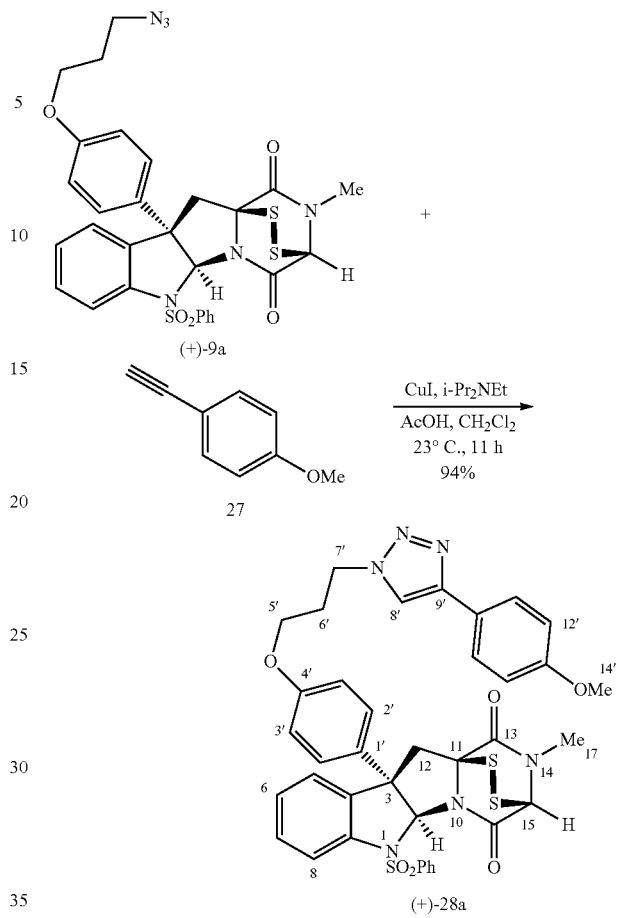

Example 7: Triazole (+)-28a

Copper (I) iodide (45.7 mg, 0.240 mmol, 1.50 equiv) was added as a solid to a solution of epidithiodiketopiperazine azide (+)-9a (102 mg, 0.160 mmol, 1 equiv), 4-ethynylanisole 27 (104 μL, 0.800 mmol, 5.00 equiv), acetic acid (28 μL, 0.48 mmol, 3.0 equiv), and N,N-diisopropylethylamine (84 μL, 0.48 mmol, 3.0 equiv) in dichloromethane (1.6 mL) at 23° C. After 11 h, the reaction mixture was directly purified by flash column chromatography on silica gel (eluent: 20% ethyl acetate in dichloromethane→100% ethyl acetate) to afford triazole (+)-28a (116 mg, 94.3%) as a yellow solid. Structural assignments were made with additional information from gCOSY, gHSQC, and gHMBC experiments. $^1$H NMR (400 MHz, CDCl$_3$, 25° C.): δ 7.70 (app-d, J=8.8 Hz, 2H, C$_{11'}$H), 7.68 (s, 1H, C$_{8'}$H), 7.57 (d, J=8.0 Hz, 1H, C$_8$H), 7.39-7.35 (m, 3H, C$_7$H, SO$_2$Ph-o-H), 7.30-7.19 (m, 3H, C$_5$H, C$_6$H, SO$_2$Ph-p-H), 7.03 (t, J=7.9 Hz, 2H, SO$_2$Ph-m-H), 6.92 (app-d, J=8.8 Hz, 2H, C$_{12'}$H), 6.76 (app-d, J=8.8 Hz, 2H, C$_{2'}$H), 6.60 (app-d, J=8.8 Hz, 2H, C$_{3'}$H), 6.38 (s, 1H, C$_2$H), 5.21 (s, 1H, C$_{15}$H), 4.61 (t, J=6.7 Hz, 2H, C$_{7'}$H), 3.94-3.91 (m, 2H, C$_{5'}$H), 3.81 (s, 3H, C$_{14'}$H), 3.62 (d, J=15.5 Hz, 1H, C$_{12}$H$_a$), 3.10 (s, 3H, C$_{17}$H), 2.83 (d, J=15.5 Hz, 1H, C$_{12}$H$_b$), 2.42 (p, J=6.3 Hz, 2H, C$_6$H). $^{13}$C NMR (100 MHz, CDCl$_3$, 25° C.): δ 165.1 (C$_{13}$), 160.1 (C$_{16}$), 159.7 (C$_{14'}$), 157.8 (C$_{4'}$), 147.8 (C$_{9'}$), 141.3 (C$_9$), 138.3 (SO$_2$Ph-ipso-C), 135.8 (C$_4$), 133.1 (SO$_2$Ph-p-C), 131.7 (C$_{1'}$), 129.8 (C$_7$), 128.6 (SO$_2$Ph-m-C), 128.0 (C$_{2'}$), 127.2 (SO$_2$Ph-o-C), 127.1 (C$_{11'}$), 126.2 (C$_6$), 125.6 (C$_5$), 123.3 ($C_{10'}$), 119.3 ($C_{8'}$), 118.9 ($C_8$), 115.0 ($C_{3'}$), 114.4 ($C_{12'}$), 87.6 ($C_2$), 74.6 ($C_{11}$), 68.4 ($C_{15}$), 64.3 ($C_{5'}$), 59.5 ($C_3$), 55.4 ($C_{14'}$), 47.1 ($C_7$), 45.4 ($C_{12}$), 32.1 ($C_{17}$), 30.0 ($C_{6'}$). FTIR (thin film) cm$^{-1}$: 3058 (m), 2958 (w), 1700 (s), 1646 (s), 1559 (m), 1512 (s), 1458 (m), 1250 (w), 1171 (s), 1032 (w), 836 (m). HRMS (ESI) (m/z): calc'd for $C_{38}H_{35}N_6O_6S_3$ [M+H]$^+$: 767.1775, found: 767.1796. $[\alpha]_D^{23}$: +315 (c=0.10, CHCl$_3$). TLC (100% ethyl acetate), Rf: 0.38 (UV, CAM).

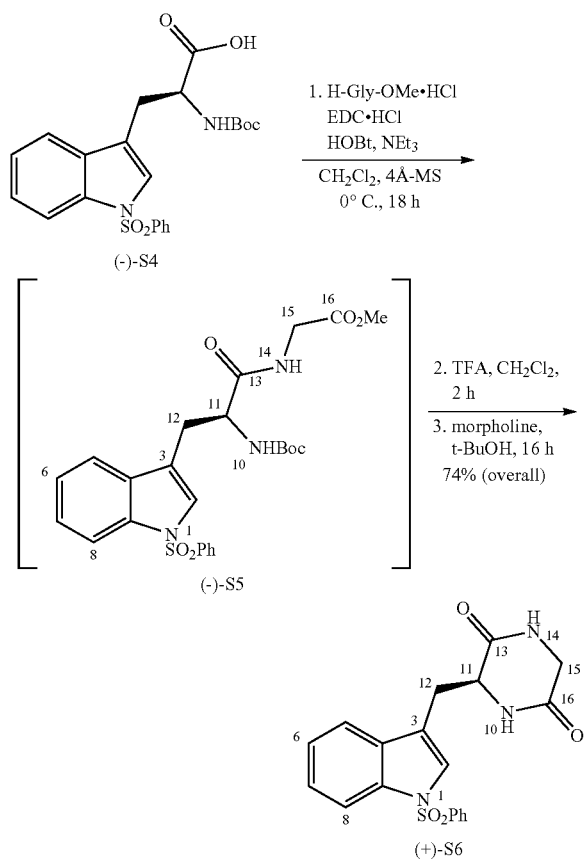

Example 8: Diketopiperazine (+)—S6

Triethylamine (47.0 mL, 337 mmol, 7.00 equiv) was added via cannula to a solution of L-tryptophan derivative (−)—S4[45] (21.4 g, 48.1 mmol, 1 equiv), glycine methyl ester hydrochloride (7.86 g, 62.6 mmol, 1.30 equiv), 1-ethyl-3-(3-dimethylaminopropyl) carbodiimide hydrogen chloride (EDC·HCl, 21.2 g, 111 mmol, 2.30 equiv), N-hydroxybenzotriazole (HOBt, 9.76 g, 72.2 mmol, 1.20 equiv), and powdered 4 Å molecular sieves (25.0 g) in dichloromethane (500 mL) at 0° C. The ice-water bath was removed and the solution was allowed to stir and warm to 23° C. After 18 h, the reaction mixture was washed with an aqueous hydrogen chloride solution (1 M, 150 mL), the layers were separated, and the organic layer was washed sequentially with a saturated aqueous sodium bicarbonate solution (150 mL) and with a saturated aqueous sodium chloride solution (100 mL). The organic layer was dried over anhydrous sodium sulfate, was filtered, and was concentrated under reduced pressure to afford dipeptide (−)—S5 as an orange foam that was used in the next step without further purification.[46] Trifluoroacetic acid (TFA, 73 mL) was added to a solution of crude dipeptide (−)—S5 (22.8 g) in dichloromethane (365 mL) at 23° C. After 2 h, the reaction mixture was concentrated under reduced pressure, and the resulting residue was dissolved in tert-butanol (335 mL) and stirred vigorously at 23° C. as morpholine (125 mL) was added via cannula. After 16 h, the reaction mixture was concentrated under reduced pressure, and the resulting orange oil was dissolved in diethyl ether (225 mL) and ethyl acetate (75 mL). The resulting solution was stirred vigorously and was diluted with an aqueous hydrogen chloride solution (1 M, 225 mL), resulting in the formation of a white precipitate. After 1 h, the solids were collected by filtration and were washed sequentially with diethyl ether (3×100 mL) and with deionized water (4×100 mL), and were dried under reduced pressure at 50° C. for 12 h to afford diketopiperazine (+)—S6 (13.6 g, 73.7% overall) as a white solid. Structural assignments were made with additional information from gCOSY, gHSQC, and gHMBC experiments. $^1$H NMR (400 MHz, DMSO-d$_6$, 25° C.): δ 8.26 (d, J=2.1 Hz, 1H, NH), 7.92 (s, 1H, NH), 7.92-7.89 (m, 2H, SO$_2$Ph-o-H), 7.85 (d, J=8.2 Hz, 1H, C$_8$H), 7.68 (app-t, J=7.4 Hz, 1H, SO$_2$Ph-p-H), 7.63 (d, J=7.6 Hz, 1H, C$_5$H), 7.59-7.56 (m, 3H, C$_2$H, SO$_2$Ph-m-H), 7.32 (app-t, J=7.7 Hz, 1H, C$_7$H), 7.24 (app-t, J=7.5 Hz, 1H, C$_6$H), 4.18-4.12 (m, 1H, C$_{11}$H), 3.42 (dd, J=1.9, 17.6 Hz, 1H, C$_{15}$H$_a$), 3.21 (dd, J=4.6, 14.7 Hz, 1H, C$_{12}$H$_a$), 3.01 (dd, J=4.7, 14.4 Hz, 1H, C$_{12}$H$_b$), 2.86 (app-d, J=16.5 Hz, 1H, C$_{15}$H$_b$). $^{13}$C NMR (100 MHz, DMSO-d$_6$, 25° C.): δ 167.2 (C$_{13}$), 165.4 (C$_{16}$), 136.9 (SO$_2$Ph-ipso-C), 134.6 (SO$_2$Ph-p-C), 134.0 (C$_9$), 130.8 (C$_4$), 129.8 (SO$_2$Ph-m-C), 126.6 (SO$_2$Ph-o-C), 125.4 (C$_2$), 124.8 (C$_7$), 123.3 (C$_6$), 120.3 (C$_5$), 117.4 (C$_3$), 112.9 (C$_8$), 54.3 (C$_{11}$), 43.9 (C$_{15}$), 28.0 (C$_{12}$). FTIR (thin film) cm$^{-1}$: 3048 (m), 1664 (s), 1457 (m), 1364 (m), 1326 (m), 1274 (m), 1169 (s), 1118 (s), 976 (w), 826 (w). HRMS (DART) (m/z): calc'd for $C_{19}H_{18}N_3O_4S$ [M+H]$^+$: 384.1013, found: 384.1014. $[\alpha]_D^{23}$: +13 (c=0.20, DMSO). TLC (30% acetone in dichloromethane), Rf: 0.11 (UV, CAM).

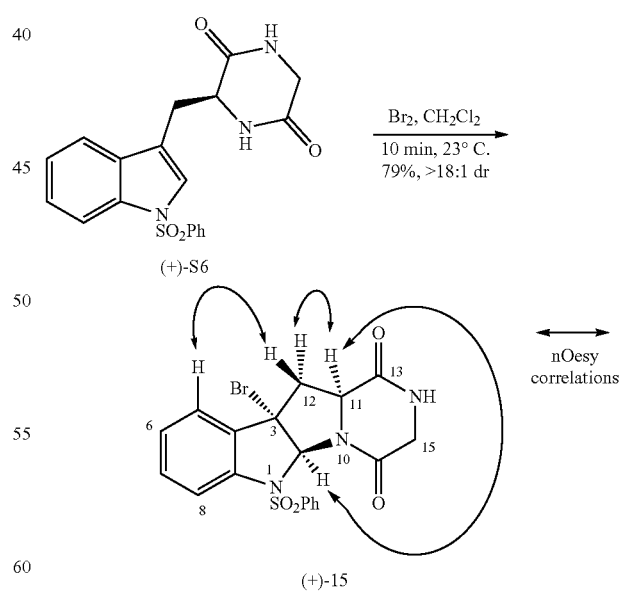

Example 9: Endo-Tetracyclic Bromide (+)-15

A solution of bromine (1.0 M, 26 mL, 26 mmol, 5.0 equiv) in dichloromethane was slowly poured into a solution of diketopiperazine (+)—S6 (2.00 g, 5.22 mmol, 1 equiv) in dichloromethane (105 mL) at 23° C. After 10 min, the reaction mixture was diluted with a saturated aqueous sodium thiosulfate solution (65 mL) and was extracted with ethyl acetate (350 mL). The organic layer was washed with a saturated aqueous sodium bicarbonate solution (2×80 mL) and with a saturated aqueous sodium chloride solution (80 mL), was dried over anhydrous sodium sulfate, was filtered, and was concentrated under reduced pressure. The resulting solid was suspended in diethyl ether (200 mL), was collected by filtration, and was washed with diethyl ether (3×50 mL) to afford a mixture of the endo-tetracyclic bromide (+)-15 and its minor exo-diastereomer (1.91 g, 79.2%, >18:1 dr) as a white solid. Structural assignments were made with additional information from gCOSY, gHSQC, gHMBC, and gNOESY experiments. $^1$H NMR (400 MHz, DMSO-$d_6$, 25° C.): δ 8.01 (app-d, J=4.8 Hz, 1H, $N_{14}H$), 7.91 (app-d, J=8.4 Hz, 2H, $SO_2Ph$-o-H), 7.65-7.61 (app-t, J=7.4 Hz, 1H, $SO_2Ph$-p-H), 7.55-7.51 (m, 2H, $SO_2Ph$-m-H), 7.47 (d, J=7.6 Hz, 1H, $C_5H$), 7.34-7.32 (m, 2H, $C_7H$, $C_8H$), 7.17-7.13 (m, 1H, $C_6H$), 6.28 (s, 1H, $C_2H$), 4.54 (dd, J=4.2, 10.0 Hz, 1H, $C_{11}H$), 3.98 (d, J=17.1 Hz, 1H, $C_{15}H_a$), 3.48 (dd, J=5.0, 17.1 Hz, 1H $C_{15}H_b$), 3.38-3.33 (m, 1H, $C_{12}H_β$), 2.97 (dd, J=10.2, 14.0 Hz, 1H, $C_{12}H_α$). $^{13}$C NMR (100 MHz, DMSO-$d_6$, 25° C.): δ 168.0 ($C_{13}$), 165.9 ($C_{16}$), 138.3 ($C_9$), 138.0 ($SO_2Ph$-ipso-C), 134.7 ($C_4$), 134.0 ($SO_2Ph$-p-C), 130.71 ($C_7$), 129.1 ($SO_2Ph$-m-C), 128.0 ($SO_2Ph$-o-C), 125.9 ($C_6$), 125.4 ($C_5$), 116.5 ($C_8$), 86.0 ($C_2$), 61.6 ($C_3$), 57.1 ($C_{11}$), 46.3 ($C_{15}$), 37.2 ($C_{12}$). FTIR (thin film) cm$^{-1}$: 1684 (s), 1653 (s), 1559 (m), 1540 (m), 1473 (m), 1457 (m), 1165 (s), 1090 (m), 971 (w), 948 (w), 731 (m), 683 (w), 667 (m). HRMS (DART) (m/z) calc'd for $C_{19}H_{17}BrN_3O_4S$ [M+H]$^+$: 462.0118, found: 462.0154. $[α]_D^{23}$: +143 (c=0.29, CHCl$_3$). TLC (30% acetone in dichloromethane), Rf: 0.37 (UV, CAM).

was diluted with dichloromethane (50 mL) and was filtered through a pad of Celite. The filter cake was washed with dichloromethane (3×50 mL), and the filtrate was concentrated under reduced pressure. The resulting residue was purified by flash column chromatography on silica gel (eluent: 0→70% acetone in dichloromethane) to afford anisole adduct (+)-16 (2.03 g, 96.6%) as a white solid. Structural assignments were made with additional information from gCOSY, gHSQC, and gHMBC experiments. $^1$H NMR (400 MHz, CDCl$_3$, 25° C.): δ 7.56 (d, J=8.0 Hz, 1H, $C_8H$), 7.41 (app-d, J=8.4 Hz, 2H, $SO_2Ph$-o-H), 7.31-7.26 (m, 2H, $C_7H$, $SO_2Ph$-p-H), 7.14-7.10 (m, 2H, $C_5H$, $C_6H$), 7.06 (app-t, J=7.9 Hz, 2H, $SO_2Ph$-m-H) 6.67 (app-d, J=8.9 Hz, 2H, $C_2'H$), 6.59 (app-d, J=8.9 Hz, 2H, $C_3'H$), 6.50 (d, J=4.5 Hz, 1H, $N_{14}H$), 6.16 (s, 1H, $C_2H$), 4.42 (dd, J=5.6, 9.4 Hz, 1H, $C_{11}H$), 3.95 (d, J=17.3 Hz, 1H, $C_{15}H_a$), 3.88-3.82 (m, 1H, $C_{15}H_b$), 3.75 (s, 3H, $C_{5'}H$), 3.10 (dd, J=5.6, 14.1 Hz, 1H, $C_{12}H_a$), 2.79 (dd, J=9.4, 14.1 Hz, 1H, $C_{12}H_b$). $^{13}$C NMR (100 MHz, CDCl$_3$, 25° C.): δ 169.6 ($C_{13}$), 166.1 ($C_{16}$), 158.8 ($C_{4'}$), 139.8 ($SO_2Ph$-ipso-C), 138.2 ($C_9$), 135.2 ($C_4$), 132.9 ($SO_2Ph$-p-C), 132.4 ($C_{1'}$), 129.5 ($C_7$), 128.7 ($SO_2Ph$-m-C), 128.3 ($C_{2'}$), 127.5 ($SO_2Ph$-o-C), 126.3 ($C_6$), 125.3 ($C_5$), 117.3 ($C_8$), 114.5 ($C_{3'}$), 87.3 ($C_2$), 59.5 ($C_3$), 58.4 ($C_{11}$), 55.5 ($C_{5'}$), 47.5 ($C_{15}$), 37.8 ($C_{12}$). FTIR (thin film) cm$^{-1}$: 3254 (m), 3064 (w), 2929 (w), 1700 (s), 1654 (m), 1610 (m), 1514 (s), 1458 (m), 1362 (m), 1254 (s), 1170 (s), 1090 (m), 1033 (m), 975 (m), 833 (m), 687 (m). HRMS (DART) (m/z): calc'd for $C_{26}H_{24}N_3O_5S$ [M+H]$^+$: 490.1431, found: 490.1453. $[α]_D^{23}$: +56 (c=0.14, CHCl$_3$). TLC (50% acetone in dichloromethane), Rf: 0.30 (UV, CAM).

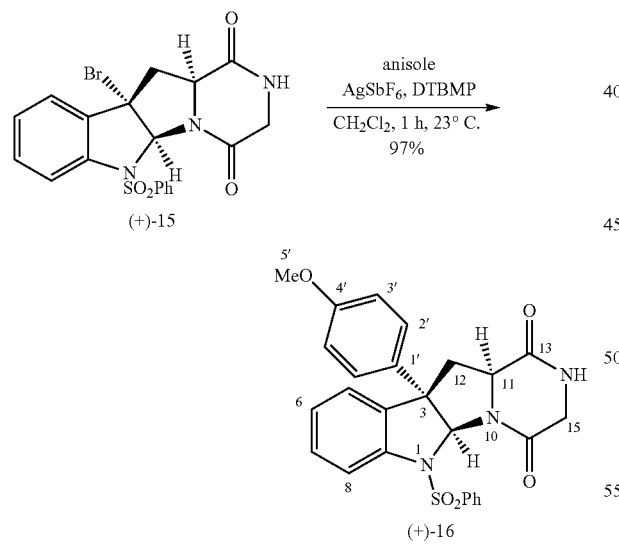

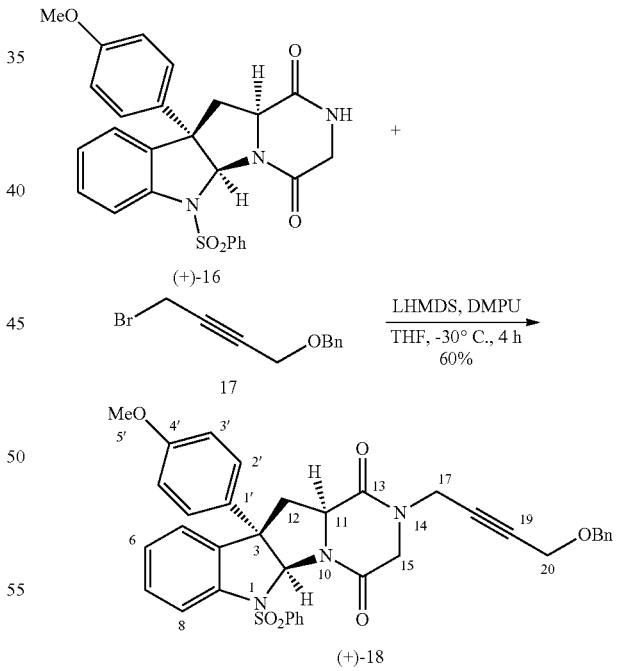

Example 10: Anisole Adduct (+)-16

Silver hexafluoroantimonate (2.95 g, 8.58 mmol, 2.00 equiv) was added as a solid in one portion to a solution of endo-tetracyclic bromide (+)-15 (2.00 g, 4.29 mmol, 1 equiv), 2,6-di-tert-butyl-4-methylpyridine (DTBMP, 1.94 g, 9.44 mmol, 2.20 equiv), and anisole (22 mL) in dichloromethane (22 mL) at 23° C. After 1 h, the reaction mixture Example 11: Alkyne (+)-18

Anisole adduct (+)-16 (1.94 g, 3.96 mmol, 1 equiv) was azeotropically dried by concentration from anhydrous benzene (3×50 mL) under reduced pressure. Tetrahydrofuran (70 mL) and anhydrous 1,3-dimethyl-3,4,5,6-tetrahydro-2 (1H)-pyrimidinone (DMPU, 25 mL) were introduced sequentially via cannula, and the solution was cooled to −78° C. A solution of lithium bis(trimethylsilyl)amide (LHMDS, 861 mg, 5.15 mmol, 1.30 equiv) in tetrahydrofuran (28 mL) was then added via cannula, and the reaction mixture was warmed to −30° C. After 20 min, a solution of bromide 17[47] (2.37 g, 9.90 mmol, 2.50 equiv, azeotropically dried by concentration from anhydrous benzene (3×10 mL) under reduced pressure) in tetrahydrofuran (2.0 mL) was added via syringe. After 4 h, the reaction mixture was diluted with a saturated aqueous ammonium chloride solution (75 mL) and with ethyl acetate (350 mL). The organic layer was washed with a saturated aqueous ammonium chloride solution (3×100 mL), was dried over anhydrous sodium sulfate, was filtered, and was concentrated under reduced pressure. The resulting residue was purified by flash column chromatography on silica gel (eluent: 5-10% acetone in dichloromethane) to afford alkyne (+)-18 (1.53 g, 59.6%) as a white foam. Structural assignments were made with additional information from gCOSY, gHSQC, and gHMBC experiments. $^1$H NMR (400 MHz, CDCl$_3$, 25° C.): δ 7.57 (d, J=8.0 Hz, 1H, C$_8$H), 7.45 (app-d, J=7.4 Hz, 2H, SO$_2$Ph-o-H), 7.33-7.29 (m, 5H, OCH$_2$Ph), 7.28-7.27 (m, 2H, C$_7$H, SO$_2$Ph-p-H), 7.11-7.07 (m, 4H, C$_5$H, C$_6$H, SO$_2$Ph-m-H), 6.67 (app-d, J=8.9 Hz, 2H, C$_2$H), 6.60 (app-d, J=8.9 Hz, 2H, C$_3$H), 6.15 (s, 1H, C$_2$H), 4.52 (s, 2H, OCH$_2$Ph), 4.43 (dd, J=6.8, 8.8 Hz, 1H, C$_{11}$H), 4.36 (dt, J=1.7, 17.4 Hz, 1H, C$_{15}$H$_a$), 4.13 (d, J=17.2 Hz, 1H, C$_{17}$H$_a$), 4.13 (app-t, J=1.8 Hz, 2H, C$_{20}$H) 3.98 (d, J=17.3 Hz, 1H, C$_{17}$H$_b$), 3.93 (dt, J=1.8, 17.4 Hz, 1H, C$_{15}$H$_b$), 3.74 (s, 3H, C$_{5'}$H), 3.07 (dd, J=6.7, 14.2 Hz, 1H, C$_{12}$H$_a$), 2.85 (dd, J=9.1, 14.1 Hz, 1H, C$_{12}$H$_b$). $^{13}$C NMR (100 MHz, CDCl$_3$, 25° C.): δ 166.7 (C$_{13}$), 165.3 (C$_{16}$), 158.8 (C$_{4'}$), 139.8 (C$_9$), 138.2 (SO$_2$Ph-ipso-C), 137.4 (OCH$_2$Ph-ipso-C), 135.6 (C$_4$), 132.9 (SO$_2$Ph-p-C), 132.5 (C$_{1'}$), 129.2 (C$_7$), 128.7 (SO$_2$Ph-m-C), 128.6 (OCH$_2$Ph-m-C), 128.2 (OCH$_2$Ph-o-C), 128.1 (C$_{2'}$), 128.0 (OCH$_2$Ph-p-C), 127.6 (SO$_2$Ph-o-C), 126.0 (C$_6$), 125.4 (C$_5$), 117.2 (C$_8$), 114.4 (C$_{3'}$), 87.1 (C$_2$), 81.2 (C$_{19}$), 79.6 (C$_{18}$), 72.0 (OCH$_2$Ph), 59.4 (C$_3$), 58.6 (C$_{11}$), 57.5 (C$_{20}$), 55.4 (C$_{5'}$), 51.7 (C$_{17}$), 38.7 (C$_{12}$), 35.3 (C$_{15}$). FTIR (thin film) cm$^{-1}$: 3063 (w), 2932 (w), 1685 (s), 1609 (m), 1513 (m), 1409 (m), 1254 (m), 1171 (s), 1090 (m), 977 (w), 832 (m), 737 (m). HRMS (DART) (m/z): calc'd for 37H$_{34}$N$_3$O$_6$S [M+H]$^+$: 648.2163, found: 648.2180. [α]$_D^{23}$:+46 (c=0.14, CHCl$_3$). TLC (10% acetone in dichloromethane), Rf: 0.65 (UV, CAM).

Example 12: Alcohol (+)-19

A suspension of alkyne (+)-18 (787 mg, 1.21 mmol, 1 equiv) and palladium on activated charcoal (5% w/w, 185 mg, 84.7 μmol, 0.0700 equiv) in ethyl acetate (45 mL) at 23° C. was sparged with hydrogen gas for 10 min by discharge of a balloon equipped with a needle extending into the reaction mixture, and was then allowed to stir under an atmosphere of hydrogen gas. After 30 min, ethanol (100 mL) was added via cannula to the reaction mixture, the reaction mixture was sparged with hydrogen gas for 10 min by discharge of a balloon equipped with a needle extending into the reaction mixture, and the reaction mixture was allowed to stir under an atmosphere of hydrogen gas. After 1 h, the reaction mixture was filtered through a pad of Celite, the filter cake was washed with ethyl acetate (3×50 mL), and the filtrate was concentrated under reduced pressure. The resulting residue was purified by flash column chromatography on silica gel (eluent: 90% acetone in dichloromethane) to afford alcohol (+)-19 (634 mg, 93.2%) as a white solid. Structural assignments were made with additional information from gCOSY, gHSQC, and gHMBC experiments. $^1$H NMR (400 MHz, CDCl$_3$, 25° C.): 67.52 (d, J=7.5 Hz, 1H, C$_8$H), 7.36 (app-d, J=7.5 Hz, 2H, SO$_2$Ph-o-H), 7.29-7.21 (m, 2H, C$_7$H, SO$_2$Ph-p-H), 7.14 (app-d, J=7.5 Hz, 1H, C$_5$H) 7.08 (app-t, J=7.4 Hz, 1H, C$_6$H), 7.02 (app-t, J=8.1 Hz, 2H, SO$_2$Ph-m-H), 6.65 (app-d, J=8.9 Hz, 2H, C$_2$H), 6.55 (app-d, J=8.9 Hz, 2H, C$_3$H), 6.14 (s, 1H, C$_2$H), 4.44 (dd, J=5.1, 9.1 Hz, 1H, C$_{11}$H), 4.09 (d, J=17.1 Hz, 1H, C$_{15}$H$_a$), 3.79 (d, J=17.1 Hz, 1H, C$_{15}$H$_b$), 3.71 (s, 3H, C$_{5'}$H), 3.47 (t, J=6.2 Hz, 2H, C$_{20}$H), 3.41-3.34 (m, 1H, C$_{17}$H$_a$), 3.19-3.10 (m, 2H, C$_{17}$H$_b$, C$_{12}$H$_a$), 2.79 (dd, J=9.4, 14.1 Hz, 1H, C$_{12}$H$_b$), 2.50 (br-s, 1H, OH), 1.41 (app-p, J=7.2 Hz, 2H, C$_{19}$H), 1.22-1.14 (m, 2H, C$_{18}$H). $^{13}$C NMR (100 MHz, CDCl$_3$, 25° C.): δ 167.4 (C$_{13}$), 165.8 (C$_{16}$), 158.7 (C$_{4'}$), 139.7 (C$_9$), 138.1 (SO$_2$Ph-ipso-C), 135.1 (C$_4$), 132.8 (SO$_2$Ph-p-C), 132.2 (C$_{1'}$), 129.2 (C$_7$), 128.6 (SO$_2$Ph-m-C), 128.2 (C$_{2'}$), 127.3 (SO$_2$Ph-o-C), 126.4 (C$_6$), 125.2 (C$_5$), 116.9 (C$_8$), 114.3 (C$_{3'}$), 87.2 (C$_2$), 62.1 (C$_{20}$), 59.7 (C$_3$), 58.8 (C$_{11}$), 55.4 (C$_{5'}$), 52.4 (C$_{15}$), 45.8 (C$_{17}$), 37.8 (C$_{12}$), 29.0 (C$_{18}$), 23.8 (C$_{19}$). FTIR (thin film) cm$^{-1}$: 3440 (w), 2936 (w), 1675 (s), 1653 (m), 1559 (m), 1514 (m), 1419 (m), 1362 (s), 1255 (s), 1169 (s), 1090 (w), 981 (w), 734 (m), 686 (m), 668 (m). HRMS (DART) (m/z): calc'd for C$_{30}$H$_{32}$N$_3$O$_6$S [M+H]$^+$: 562.2006, found: 562.1997. [α]$_D^{23}$: +40 (c 0.17, CHCl$_3$). TLC (30% acetone in dichloromethane), Rf: 0.13 (UV, CAM).

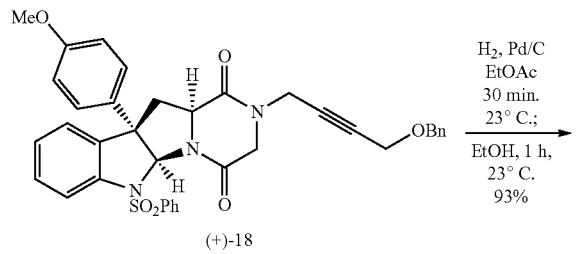

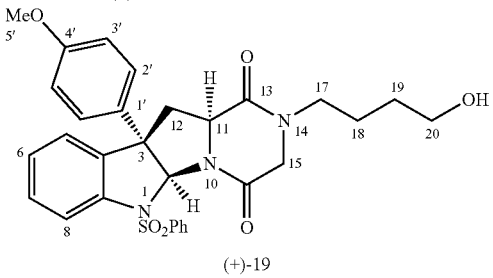

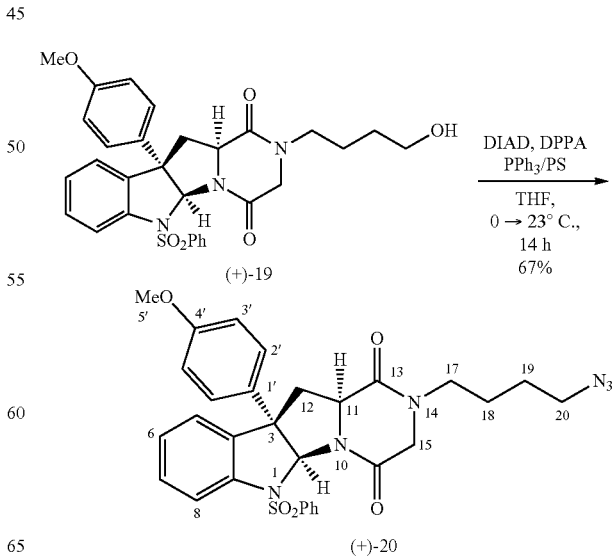

Example 13: Azide (+)-20

Diisopropyl azodicarboxylate (DIAD, 526 μL, 2.67 mmol, 1.50 equiv) and diphenylphosphoryl azide (DPPA, 575 μL, 2.67 mmol, 1.50 equiv) were added dropwise via syringe to a suspension of alcohol (+)-19 (1.00 g, 1.78 mmol, 1 equiv) and resin-bound triphenylphosphine (1.31 mmol/g on 100-200 mesh polystyrene cross-linked with 1% divinylbenzene, 1.90 g, 2.49 mmol, 1.40 equiv) in tetrahydrofuran (43 mL) at 0° C. After 5 min, the ice-water bath was removed and the reaction mixture was allowed to stir and warm to 23° C. After 14 h, the reaction mixture was filtered through a 1 cm pad of Celite in a 60-mL medium-porosity fritted-glass funnel. The filter cake was washed with dichloromethane (100 mL), and the filtrate was concentrated under reduced pressure. The resulting residue was purified by flash column chromatography on silica gel (eluent: 10→15% acetone in dichloromethane) to afford azide (+)-20 (697 mg, 66.7%) as a clear oil. Structural assignments were made with additional information from gCOSY, gHSQC, and gHMBC experiments. $^1$H NMR (400 MHz, CDCl$_3$, 25° C.): δ 7.56 (d, J=7.5 Hz, 1H, C$_8$H), 7.41 (app-d, J=7.9 Hz, 2H, SO$_2$Ph-o-H), 7.32-7.24 (m, 2H, C$_7$H, SO$_2$Ph-p-H), 7.15 (d, J=7.5 Hz, 1H, C$_5$H) 7.12-7.04 (m, 3H, C$_6$H, SO$_2$Ph-m-H), 6.68 (app-d, J=8.9 Hz, 2H, C$_2$·H), 6.59 (app-d, J=8.9 Hz, 2H, C$_3$·H), 6.15 (s, 1H, C$_2$H), 4.39 (dd, J=5.2, 9.2 Hz, 1H, C$_{11}$H), 4.07 (d, J=17.0 Hz, 1H, C$_{15}$H$_a$), 3.76 (d, J=16.9 Hz, 1H, C$_{15}$H$_b$), 3.75 (s, 3H, C$_5$·H), 3.39 (dt, J=7.2, 14.0 Hz, 1H, C$_{17}$H$_a$) 3.22-3.06 (m, 4H, C$_{17}$H$_b$, C$_{20}$H, C$_{12}$H$_a$), 2.82 (dd, J=9.4, 14.1 Hz, 1H, C$_{12}$H$_b$), 1.47-1.37 (m, 2H, C$_{18}$H), 1.26-1.20 (m, 2H, C$_{19}$H). $^{13}$C NMR (100 MHz, CDCl$_3$, 25° C.): δ 167.3 (C$_{13}$), 165.4 (C$_{16}$), 158.8 (C$_4$·), 139.9 (C$_9$), 138.3 (SO$_2$Ph-ipso-C), 135.1 (C$_4$), 132.9 (SO$_2$Ph-p-C), 132.2 (C$_1$·), 129.3 (C$_7$), 128.7 (SO$_2$Ph-m-C), 128.2 (C$_2$·), 127.5 (SO$_2$Ph-o-C), 126.4 (C$_6$), 125.2 (C$_5$), 117.0 (C$_8$), 114.4 (C$_3$·), 87.2 (C$_2$), 59.8 (C$_3$), 58.9 (C$_{11}$), 55.5 (C$_5$·), 52.5 (C$_{15}$), 51.0 (C$_{20}$), 45.5 (C$_{17}$), 37.9 (C$_{12}$), 25.7 (C$_{19}$), 24.5 (C$_{18}$). FTIR (thin film) cm$^{-1}$: 3063 (w), 2932 (m), 2098 (s), 1700 (s), 1684 (s), 1514 (m), 1458 (m), 1362 (m), 1255 (m), 1169 (m), 1091 (m), 756 (s), 668 (s). HRMS (DART) (m/z): calc'd for C$_{30}$H$_{31}$N$_6$O$_5$S [M+H]$^+$: 587.2071, found: 587.2073. [α]$_D^{23}$: +32 (c=0.17, CHCl$_3$). TLC (10% acetone in dichloromethane), Rf: 0.43 (UV, CAM).

Example 14: Diol (+)-21

Tetra-n-butylammonium permanganate$^{42}$ (2.13 g, 5.90 mmol, 5.00 equiv) was added as a solid to a solution of azide (+)-20 (692 mg, 1.18 mmol, 1 equiv) in dichloromethane (43 mL) at 23° C. After 2 h, the reaction mixture was diluted with a saturated aqueous sodium sulfite solution (50 mL) and with ethyl acetate (150 mL). The resulting mixture was washed with a saturated aqueous sodium bicarbonate solution (50 mL), the layers were separated, and the organic layer was washed with a saturated aqueous sodium chloride solution (50 mL). The combined aqueous layers were extracted with ethyl acetate (2×50 mL), and the combined organic extracts were dried over anhydrous sodium sulfate, were filtered, and were concentrated under reduced pressure. The resulting residue was purified by flash column chromatography on silica gel (eluent: 20% acetone in dichloromethane) to afford diol (+)-21 (340 mg, 47.6%) as a white solid. Structural assignments were made with additional information from gCOSY, gHSQC, and gHMBC experiments. $^1$H NMR (400 MHz, CDCl$_3$, 25° C.): δ 7.53 (d, J=8.0 Hz, 1H, C$_8$H), 7.30-7.14 (m, 6H, C$_5$H, C$_6$H, C$_7$H, SO$_2$Ph-o-H, SO$_2$Ph-p-H), 6.99 (app-t, J=7.6 Hz, 2H, SO$_2$Ph-m-H), 6.77 (app-d, J=8.8 Hz, 2H, C$_2$·H), 6.54 (app-d, J=8.9 Hz, 2H, C$_3$·H), 6.43 (s, 1H, C$_2$H), 6.06 (d, J=6.4 Hz, 1H, C$_{15}$OH), 5.67 (s, 1H, C$_{11}$OH), 5.23 (d, J=6.4 Hz, 1H, C$_{15}$H), 3.74 (s, 3H, C$_5$·H), 3.57 (d, J=15.1 Hz, 1H, C$_{12}$H$_a$), 3.44-3.39 (m, 2H, C$_{17}$H) 3.18 (t, J=6.8 Hz, 2H, C$_{20}$H), 2.87 (d, J=15.0 Hz, 1H, C$_{12}$H$_b$), 1.66-1.48 (m, 2H, C$_{18}$H), 1.40-1.28 (m, 2H, C$_{19}$H). $^{13}$C NMR (100 MHz, CDCl$_3$, 25° C.): δ 167.3 (C$_{13}$), 166.4 (C$_{16}$), 158.7 (C$_4$·), 139.5 (C$_9$), 138.0 (SO$_2$Ph-ipso-C), 136.3 (C$_4$), 133.1 (SO$_2$Ph-p-C), 133.0 (C$_1$·), 129.3 (C$_7$), 128.7 (C$_2$·), 128.7 (SO$_2$Ph-m-C), 127.4 (SO$_2$Ph-o-C), 126.9 (C$_6$), 125.9 (C$_5$), 117.3 (C$_8$), 114.3 (C$_3$·), 88.3 (C$_{11}$), 88.3 (C$_2$), 82.0 (C$_{15}$), 58.9 (C$_3$), 55.5 (C$_5$·), 51.1 (C$_{20}$), 47.8 (C$_{12}$), 44.9 (C$_{17}$), 26.0 (C$_{19}$), 25.5 (C$_{18}$). FTIR (thin film) cm$^{-1}$: 2936 (w), 2097 (s), 1700 (s), 1684 (s), 1513 (m), 1474 (m), 1458 (m), 1362 (m), 1254 (s), 1169 (s), 1091 (w), 832 (m), 668 (m). HRMS (DART) (m/z): calc'd for C$_{30}$H$_{31}$N$_6$O$_7$S [M+H]$^+$: 619.1969, found: 619.1991. [α]$_D^{23}$: +26 (c=0.20, CHCl$_3$). TLC (30% acetone in dichloromethane), Rf: 0.55 (UV, CAM).

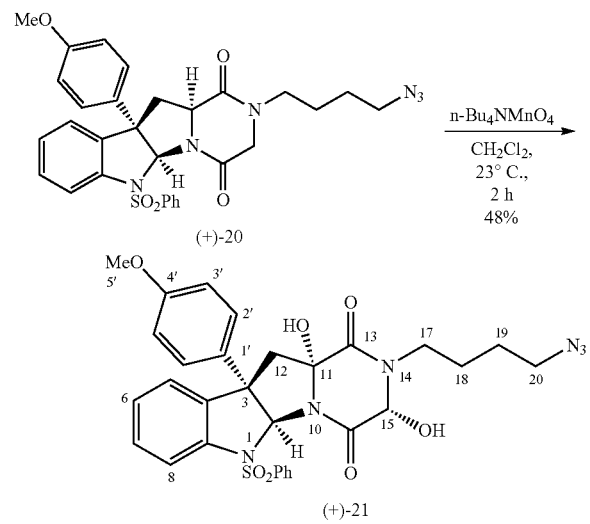

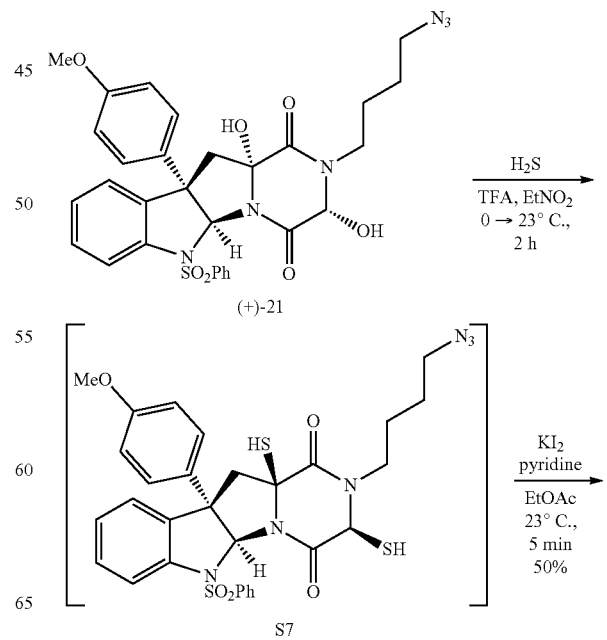

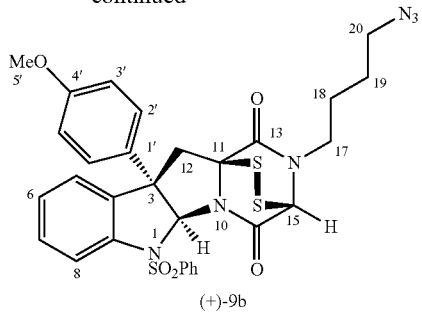

(+)-9b

Example 15: Epidithiodiketopiperazine Azide (+)-9b

A solution of diol (+)-21 (259 mg, 419 μmol, 1 equiv) in anhydrous nitroethane (18 mL) at 0° C. was sparged with hydrogen sulfide gas for 20 min by discharge of a balloon equipped with a needle extending into the reaction mixture, providing a saturated hydrogen sulfide solution. Trifluoroacetic acid (TFA, 13.5 mL) was added via syringe over 20 seconds, and the sparging with hydrogen sulfide gas was maintained for another 20 min. The ice-water bath was removed, and the solution was allowed to stir and warm to 23° C. under an atmosphere of hydrogen sulfide. After 2 h, the reaction mixture was diluted with ethyl acetate (150 mL) and was slowly poured into a saturated aqueous sodium bicarbonate solution (70 mL). The organic layer was washed with a saturated aqueous sodium chloride solution (40 mL). A stock solution of potassium triiodide in pyridine[43] was added dropwise into the organic layer containing crude bisthiol S7 until a persistent yellow color was observed. The resulting mixture was washed with an aqueous hydrogen chloride solution (1 M, 2×40 mL), was washed with a saturated aqueous sodium chloride solution (40 mL), was dried over anhydrous sodium sulfate, was filtered, and was concentrated under reduced pressure. The resulting residue was purified by flash column chromatography on silica gel (eluent: 10→15% ethyl acetate in dichloromethane) to afford epidithiodiketopiperazine azide (+)-9b (136 mg, 50.0%) as a beige solid. Structural assignments were made with additional information from gCOSY, gHSQC, and gHMBC experiments.[48] $^1$H NMR (400 MHz, CDCl$_3$, 25° C.): δ 7.61 (d, J=8.0 Hz, 1H, C$_8$H), 7.40-7.37 (m, 1H, C$_7$H), 7.35 (app-d, J=5.5 Hz, 2H, SO$_2$Ph-o-H), 7.30-7.21 (m, 3H, C$_5$H, C$_6$H, SO$_2$Ph-p-H), 7.02 (app-t, J=8.0 Hz, 2H, SO$_2$Ph-m-H), 6.75 (app-d, J=6.7 Hz, 2H, C$_2$·H), 6.61 (app-d, J=6.8 Hz, 2H, C$_3$·H), 6.39 (s, 1H, C$_2$H), 5.32 (s, 1H, C$_{15}$H), 3.76 (s, 3H, C$_5$·H), 3.63 (d, J=15.5 Hz, 1H, C$_{12}$H$_a$), 3.56 (t, J=6.9 Hz, 2H, C$_{17}$H), 3.30 (t, J=6.6 Hz, 2H, C$_{20}$H), 2.84 (d, J=15.5 Hz, 1H, C$_{12}$H$_b$), 1.85-1.67 (m, 2H, C$_{18}$H), 1.65-1.58 (m, 2H, C$_{19}$H). $^{13}$C NMR (100 MHz, CDCl$_3$, 25° C.): δ 165.0 (C$_{13}$), 160.3 (C$_{16}$), 159.0 (C$_{4'}$), 141.3 (C$_9$), 138.5 (SO$_2$Ph-ipso-C), 135.9 (C$_4$), 133.1 (SO$_2$Ph-p-C), 131.3 (C$_{1'}$), 129.9 (C$_7$), 128.7 (SO$_2$Ph-m-C), 128.1 (C$_{2'}$), 127.3 (SO$_2$Ph-o-C), 126.2 (C$_6$), 125.7 (C$_5$), 119.0 (C$_8$), 114.6 (C$_{3'}$), 87.7 (C$_2$), 74.9 (C$_{11}$), 66.6 (C$_{15}$), 59.6 (C$_3$), 55.5 (C$_{5'}$), 51.1 (C$_{20}$), 45.5 (C$_{12}$), 45.4 (C$_{17}$), 26.2 (C$_{19}$), 25.4 (C$_{18}$). FTIR (thin film) cm$^{-1}$: 3063 (w), 2932 (s), 2098 (s), 1717 (s), 1700 (s), 1685 (s), 1609 (m), 1514 (s), 1458 (m), 1363 (m), 1256 (s), 1171 (s), 1090 (m), 972 (m), 737 (m). HRMS (DART) (m/z): calc'd for C$_{30}$H$_{32}$N$_7$O$_5$S$_3$[M+NH$_4$]$^+$: 666.1622, found: 666.1630. [α]$_D^{23}$: +245 (c=0.22, CHCl$_3$). TLC (20% ethyl acetate in dichloromethane), Rf: 0.61 (UV, CAM).

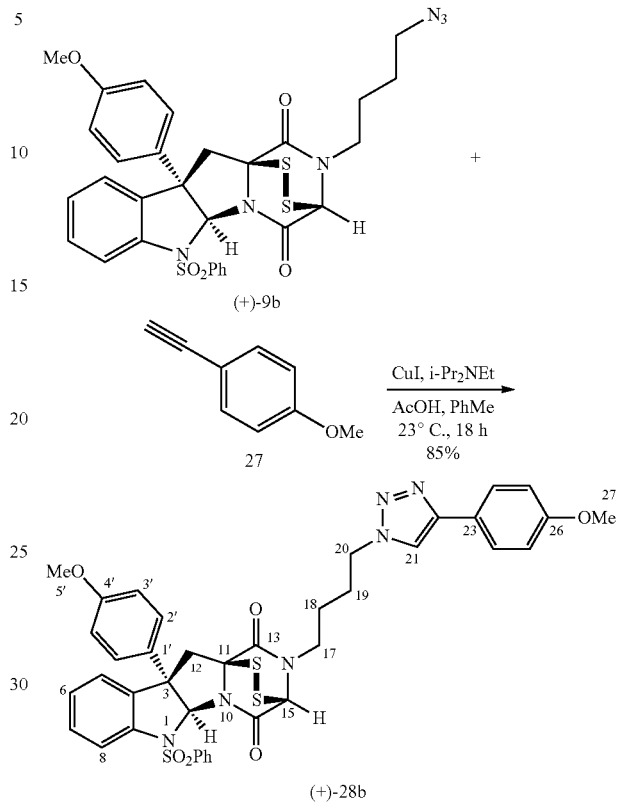

(+)-28b

Example 16: Triazole (+)-28b

A suspension of copper(I) iodide (5.5 mg, 29 μmol, 0.51 equiv), acetic acid (3.3 μL, 57 μmol, 1.0 equiv) and N—N-diisopropylethylamine (9.9 μL, 57 μmol, 1.0 equiv) in toluene (0.50 mL) was added via syringe to a solution of epidithiodiketopiperazine (+)-9b (37.0 mg, 57.0 mol, 1 equiv) and 4-ethynylanisole 27 (38 μL, 290 μmol, 5.1 equiv) in toluene (0.30 mL) at 23° C. After 18 h, the reaction mixture was diluted with dichloromethane (1.6 mL) and was purified by flash column chromatography on silica gel (eluent: 20% ethyl acetate in dichloromethane→100% ethyl acetate) to afford triazole (+)-28b (37.6 mg, 84.5%) as a yellow solid. Structural assignments were made with additional information from gCOSY, gHSQC, and gHMBC experiments. $^1$H NMR (400 MHz, CDCl$_3$, 25° C.): δ 7.71 (app-d, J=8.8 Hz, 2H, C$_{24}$H), 7.69 (s, 1H, C$_{21}$H), 7.60 (d, J=8.0 Hz, 1H, C$_8$H), 7.38 (td, J=1.8, 8.6 Hz, 1H, C$_7$H), 7.32 (app-d, J=7.9 Hz, 2H, SO$_2$Ph-o-H), 7.29-7.21 (m, 3H, C$_5$H, C$_6$H, SO$_2$Ph-p-H), 7.01 (app-t, J=7.6 Hz, 2H, SO$_2$Ph-m-H), 6.91 (app-d, J=8.8 Hz, 2H, C$_{25}$H), 6.75 (app-d, J=6.8 Hz, 2H, C$_{2'}$H), 6.61 (app-d, J=6.9 Hz, 2H, C$_{3'}$H), 6.39 (s, 1H, C$_2$H), 5.37 (s, 1H, C$_{15}$H), 4.40 (t, J=6.9 Hz, 2H, C$_{20}$H), 3.81 (s, 3H, C$_{27}$H), 3.76 (s, 3H, C$_{5'}$H), 3.66-3.51 (m, 2H, C$_{17}$H), 3.63 (d, J=15.4 Hz, 1H, C$_{12}$H$_a$), 2.83 (d, J=15.5 Hz, 1H, C$_{12}$H$_b$), 1.97 (p, J=7.3 Hz, 2H, C$_{19}$H), 1.84-1.67 (m, 2H, C$_{18}$H). $^{13}$C NMR (100 MHz, CDCl$_3$, 25° C.): δ 164.9 (C$_{13}$), 160.2 (C$_{16}$), 159.6 (C$_{26}$), 158.8 (C$_{4'}$), 147.7 (C$_{22}$), 141.1 (C$_9$), 138.2 (SO$_2$Ph-ipso-C), 135.7 (C$_4$), 132.9 (SO$_2$Ph-p-C), 131.0 (C$_{1'}$), 129.7 (C$_7$), 128.5 (SO$_2$Ph-m-C), 127.9 (C$_{2'}$), 127.1 (SO$_2$Ph-o-C), 127.1 (C$_{24}$), 126.1 (C$_6$), 125.6 (C$_5$), 123.4 (C$_{23}$), 119.0 (C$_{21}$), 118.8 (C$_8$), 114.4 (C$_{3'}$), 114.2 (C$_{25}$), 87.7 (C$_2$), 74.7 (C$_{11}$), 66.3 (C$_{15}$), 59.4 (C$_3$), 55.4 (C$_{5'}$), 55.3 (C$_{27}$), 49.6 (C$_{20}$), 45.3 (C$_{12}$), 44.9 (C$_{17}$), 27.3 (C$_{19}$), 24.9 (C$_{18}$). FTIR (thin film) cm$^{-1}$: 2926 (m), 1717 (s), 1700 (s), 1685 (s), 1653 (m), 1559 (m), 1457 (m), 1362 (m), 1252 (s), 1172 (m), 1032 (m), 737 (m), 668 (m). HRMS (ESI) (m/z): calc'd for C$_{39}$H$_{37}$N$_6$O$_6$S$_3$ [M+H]$^+$: 781.1931, found: 781.1947. [α]$_D^{23}$: +484 (c=0.06, CHCl$_3$). TLC (100% ethyl acetate), Rf: 0.41 (UV, CAM).

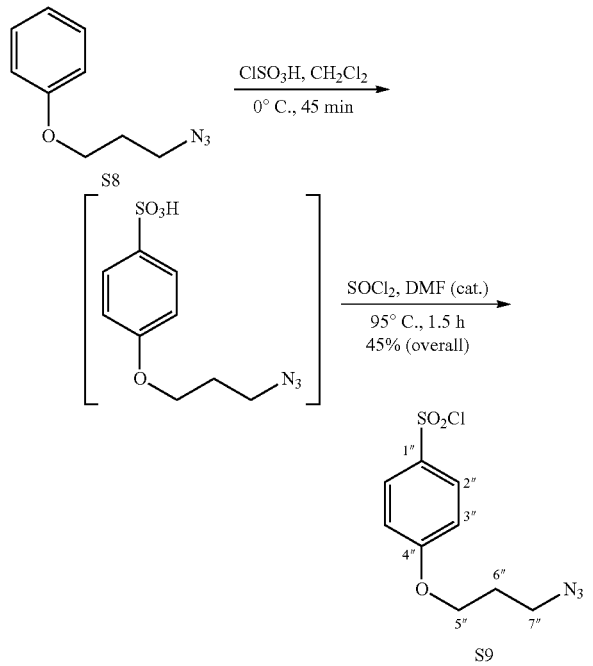

Example 17: Sulfonyl Chloride S9

Chlorosulfonic acid (5.20 mL, 77.9 mmol, 1.00 equiv) was added via syringe to a solution of (3-azidopropoxy)benzene[49] (S7, 13.8 g, 77.9 mmol, 1 equiv) in dichloromethane (165 mL) at 0° C. After 45 min, the reaction mixture was concentrated under reduced pressure, and the resulting colorless residue was dissolved in thionyl chloride (100 mL). N,N-Dimethylformamide (250 µL, 3.2 mmol, 0.041 equiv) was added via syringe, and the reaction mixture was heated to reflux in an oil bath at 95° C. After 1.5 h, the brown solution was concentrated under reduced pressure. The resulting residue was dissolved in dichloromethane (600 mL) and was washed with an aqueous sodium hydroxide solution (1.25 M, 2×100 mL) and with a saturated aqueous sodium chloride solution (150 mL). The organic layer was dried over anhydrous sodium sulfate, was filtered, and was concentrated under reduced pressure. The resulting residue was purified by flash column chromatography on silica gel (eluent: 25% ethyl acetate in hexanes) to afford sulfonyl chloride S9 (9.58 g, 44.6%) as a yellow oil. $^1$H NMR (600 MHz, CDCl$_3$, 25° C.): δ 7.95 (d, J=9.0 Hz, 2H, C$_{2''}$H), 7.03 (d, J=9.0 Hz, 2H, C$_{3''}$H), 4.14 (t, J=5.9 Hz, 2H, C$_{5''}$H), 3.52 (t, J=6.5 Hz, 2H, C$_{7''}$H), 2.08 (p, J=6.2 Hz, 2H, C$_{6''}$H). $^{13}$C NMR (150 MHz, CDCl$_3$, 25° C.): δ 164.1 (C$_{4''}$), 136.5 (C$_{1''}$), 129.8 (C$_{2''}$), 115.3 (C$_{3''}$) 65.6 (C$_{5''}$), 48.1 (C$_{7''}$), 28.6 (C$_{6''}$). FTIR (thin film) cm$^{-1}$: 3101 (w), 2948 (m), 2098 (s), 1594 (s), 1374 (m), 1085 (m), 833 (m). HRMS (ESI) (m/z): calc'd for C$_9$H$_{10}$ClN$_3$NaO$_3$S [M+Na]$^+$: 298.0024, found: 298.0040. TLC (25% ethyl acetate in hexanes), Rf: 0.44 (UV, CAM).

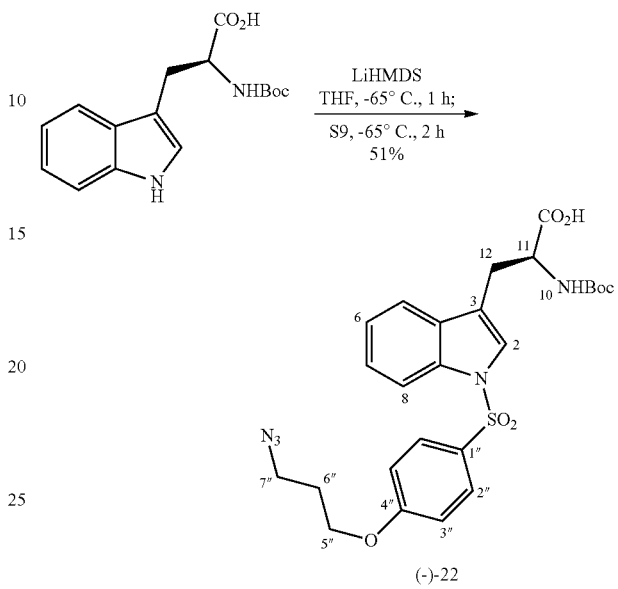

Example 18: N-Sulfonylated Tryptophan (−)-22

N-Boc-L-tryptophan (2.76 g, 9.07 mmol, 2.00 equiv) was azeotropically dried by concentration from anhydrous benzene (3×15 mL) under reduced pressure. The resulting residue was dissolved in tetrahydrofuran (20 mL) and cooled to −65° C. A solution of lithium hexamethyldisilazide (LHMDS, 4.55 g, 47.2 mmol, 6.00 equiv) in tetrahydrofuran (20 mL) was added via cannula over 5 min. After 1 h, sulfonyl chloride S9 (1.25 g, 4.53 mmol, 1 equiv) was added via syringe in one portion and the reaction mixture was stirred for an additional 2 h at −65° C. Excess base was quenched at this temperature by addition of a solution of acetic acid in ethyl acetate (1:1 v/v, 5 mL), then the ice-water bath was removed and the resulting mixture was allowed to stir and warm to room temperature. The mixture was then diluted with an aqueous hydrogen chloride solution (1 M, 100 mL) and was extracted with ethyl acetate (3×100 mL). The combined organic extracts were dried over anhydrous sodium sulfate, were filtered, and were concentrated. The resulting residue was purified by flash column chromatography on silica gel (eluent: 5% acetic acid, 45% hexanes, 50% dichloromethane)[50] to afford N-sulfonylated tryptophan (−)-22 (1.22 g, 50.8%) as a white solid. Structural assignments were made with additional information from gCOSY, gHSQC, and gHMBC experiments. $^1$H NMR (400 MHz, DMSO-d$_6$, 25° C.): δ 12.7 (br-s, 1H, CO$_2$H), 7.88 (d, J=8.2 Hz, 1H, C$_8$H), 7.84 (app-d, J=9.0 Hz, 2H, C$_{2''}$H), 7.60-7.58 (m, 2H, C$_2$H, C$_5$H), 7.35 (t, J=7.7 Hz, 1H, C$_7$H), 7.26 (t, J=7.3 Hz, 1H, C$_6$H), 7.17 (d, J=8.2 Hz, 1H, N—H), 7.05 (app-d, J=9.0 Hz, 2H, C$_{3''}$H), 4.21-4.16 (m, 1H, C$_{11}$H), 4.05 (t, J=6.0 Hz, 2H, C$_{5''}$H), 3.44 (t, J=6.7 Hz, 2H, C$_{7''}$H), 3.11 (dd, J=4.3, 14.8 Hz, 1H, C$_{12}$H$_a$), 2.95 (dd, J=10.1, 14.8 Hz, 1H, C$_{12}$H$_b$), 1.93 (p, J=6.4 Hz, 2H, C$_{6''}$H), 1.32 (s, 9H, C(CH$_3$)$_3$). $^{13}$C NMR (100 MHz, DMSO-d$_6$, 25° C.): δ 173.3 (C$_{13}$), 162.7 (C$_{4''}$), 155.4 (CO$_2$t-Bu), 134.2 (C$_9$), 130.5 (C$_4$), 129.0 (C$_{2''}$), 128.6 (C$_{1''}$), 124.7 (C$_7$), 124.6 (C$_2$), 123.2 (C$_6$), 119.6 (C$_5$), 118.7 (C$_3$), 115.3 (C$_{3''}$), 113.2 (C$_8$), 78.2 (C(CH$_3$)$_3$), 65.4 (C$_{5''}$), 53.3 (C$_{11}$), 47.5 (C$_{7''}$), 28.1 (C(CH$_3$)$_3$) 28.1 (C$_{6''}$), 27.8 (C$_{12}$). FTIR (thin film) cm$^{-1}$: 2931 (w), 2100 (s), 1717 (s), 1653 (m), 1595 (m), 1497 (m), 1368 (s), 1261 (s), 1167 (s), 834 (m), 746 (w), 667 (m). HRMS (DART) (m/z): calc'd for C$_{25}$H$_{33}$N$_6$O$_7$S [M+NH$_4$]$^+$: 561.2126, found: 561.2131. [α]$_D^{23}$: −18 (c=0.14, DMSO). TLC (5% AcOH, 5% CH$_3$OH, 40% hexanes, 50% CH$_2$Cl$_2$), Rf: 0.47 (UV, CAM).

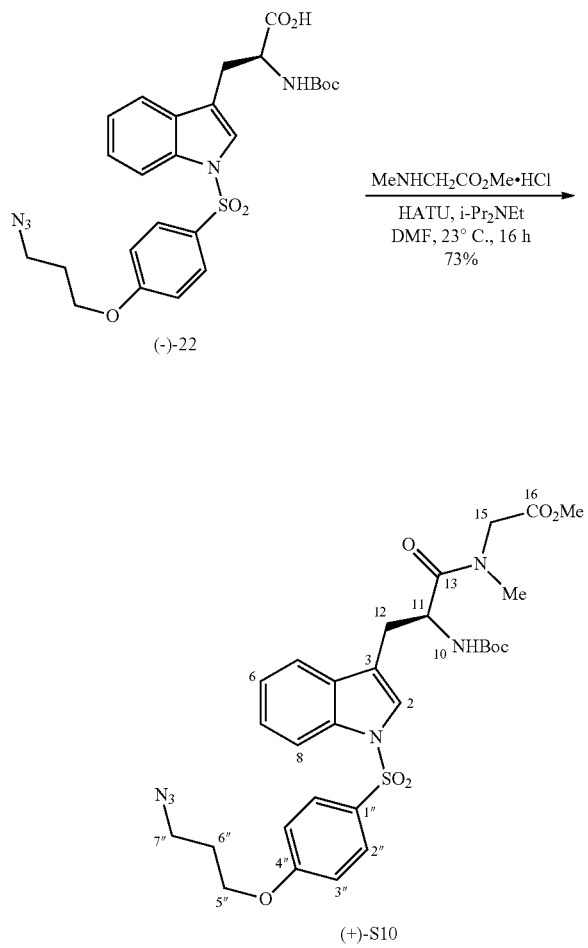

Example 19: Dipeptide (+)—S10

N—N-Diisopropylethylamine (3.00 mL, 17.0 mmol, 6.00 equiv) was added via syringe to a solution of carboxylic acid (−)-22 (1.50 g, 2.83 mmol, 1 equiv), sarcosine methyl ester hydrochloride (791 mg, 5.66 mmol, 2.00 equiv), and N-[(Dimethylamino)-1H-1,2,3-triazolo-[4,5-b]pyridin-1-ylmethylene]-N-methyl-methanaminium hexafluorophosphate N-oxide (HATU, 2.59 g, 6.80 mmol, 2.40 equiv) in N,N-dimethylformamide (25 mL) at 23° C. After 16 h, the reaction mixture was diluted with ethyl acetate (150 mL) and was washed with a saturated aqueous sodium bicarbonate solution (50 mL) and with a saturated aqueous sodium chloride solution (50 mL). The combined aqueous layers were extracted with ethyl acetate (2×50 mL), and the combined organic extracts were dried over anhydrous sodium sulfate, were filtered, and were concentrated under reduced pressure. The resulting residue was purified by flash column chromatography on silica gel (eluent: 60% ethyl acetate in hexanes) to afford dipeptide (+)—S10 (1.30 g, 73.3%) as a white solid. Structural assignments were made with additional information from gCOSY, gHSQC, and gHMBC experiments. Based on the $^1$H NMR analysis at 25° C. in CDCl$_3$, the product exists as a 5:1 mixture of major:minor conformers. $^1$H NMR (400 MHz, CDCl$_3$, 25° C.): Major conformer: δ 7.92 (d, J=8.1 Hz, 1H, C$_8$H), 7.77 (app-d, J=8.9 Hz, 2H, C$_{2''}$H), 7.54 (d, J=7.7 Hz, 1H, C$_5$H), 7.44 (s, 1H, C$_2$H), 7.27 (app-t, J=7.3 Hz, 1H, C$_7$H), 7.23-7.18 (m, 1H, C$_6$H), 6.83 (d, J=9.0 Hz, 2H, C$_{3''}$H), 5.38 (d, J=8.4 Hz, 1H, N$_{10}$H), 4.93 (dd, J=6.2, 13.8 Hz, 1H, C$_{11}$H), 4.00 (d, J=17.2 Hz, 1H, C$_{15}$H$_a$), 3.99 (t, J=5.9 Hz, 2H, C$_{5''}$H), 3.92 (d, J=17.2 Hz, 1H, C$_{15}$H$_b$), 3.71 (s, 3H, N$_{14}$CH$_3$), 3.43 (t, J=6.5 Hz, 2H, C$_{7''}$H), 3.15-3.08 (m, 1H, C$_{12}$H$_a$), 3.05-2.95 (m, 1H, C$_{12}$H$_b$), 2.77 (s, 3H, C$_{14}$H), 1.98 (p, J=6.2 Hz, 2H, C$_{6''}$H), 1.38 (s, 9H, C(CH$_3$)$_3$). Minor conformer: δ 7.92 (d, J=8.1 Hz, 2H, C$_8$H), 7.77 (app-d, J=8.9 Hz, 2H, C$_{2''}$H), 7.51 (d, J=7.8 Hz, 1H, C$_5$H), 7.39 (s, 1H, C$_2$H), 7.27 (app-t, J=7.3 Hz, 1H, C$_7$H), 7.23-7.18 (m, 1H, C$_6$H), 6.83 (d, J=9.0 Hz, 2H, C$_{3''}$H), 5.28 (d, J=8.8 Hz, 1H, N$_{10}$H), 4.69 (dd, J=6.9, 15.1 Hz, 1H, C$_{11}$H), 3.99 (t, J=5.9 Hz, 2H, C$_{5''}$H), 3.87 (d, J=18.4 Hz, 1H, C$_{15}$H$_a$), 3.79 (d, J=18.3 Hz, 1H, C$_{15}$H$_b$), 3.59 (s, 3H, N$_{14}$CH$_3$), 3.43 (t, J=6.5 Hz, 2H, C$_{7''}$H), 3.15-3.08 (m, 1H, C$_{12}$H$_a$), 3.05-2.95 (m, 1H, C$_{12}$H$_b$), 2.85 (s, 3H, C$_{14}$H), 1.98 (p, J=6.2 Hz, 2H, C$_{6''}$H), 1.37 (s, 9H, C(CH$_3$)$_3$). $^{13}$C NMR (100 MHz, CDCl$_3$, 25° C.): Major conformer: δ 172.2 (C$_{13}$), 169.4 (C$_{16}$), 162.9 (C$_{4''}$), 155.2 (N$_{10}$CO$_2$t-Bu), 135.1 (C$_9$), 131.2 (C$_4$), 130.2 (C$_{1''}$), 129.3 (C$_{2''}$), 125.0 (C$_2$), 124.9 (C$_7$), 123.3 (C$_6$), 119.6 (C$_5$), 117.3 (C$_3$), 114.9 (C$_{3''}$), 113.8 (C$_8$), 80.0 (C(CH$_3$)$_3$), 65.1 (C$_{15}$), 52.4 (N$_{14}$CH$_3$), 50.3 (C$_{11}$), 49.7 (C$_{5''}$), 48.0 (C$_{7''}$), 36.5 (C$_{14}$), 29.0 (C$_{12}$), 28.6 (C$_{6''}$), 28.4 (C(CH$_3$)$_3$). Minor conformer: δ 172.1 (C$_{13}$), 169.1 (C$_{16}$), 162.9 (C$_{4''}$), 155.2 (N$_{10}$CO$_2$t-Bu), 135.1 (C$_9$), 131.0 (C$_4$), 130.2 (C$_{1''}$), 129.2 (C$_{2''}$), 125.0 (C$_2$), 124.8 (C$_7$), 123.3 (C$_6$), 119.6 (C$_5$), 117.6 (C$_3$), 114.9 (C$_{3''}$), 113.8 (C$_8$), 80.1 (C(CH$_3$)$_3$), 65.1 (C$_{15}$), 52.6 (N$_{14}$CH$_3$), 51.1 (C$_{5''}$), 50.1 (C$_{11}$), 48.0 (C$_{7''}$), 36.5 35.3 (C$_{14}$), 29.1 (C$_{12}$), 28.6 (C$_{6''}$), 28.4 (C(CH$_3$)$_3$). FTIR (thin film) cm$^{-1}$: 3318 (w), 2933 (w), 2100 (s), 1750 (s), 1700 (s), 1653 (s), 1594 (m), 1497 (w), 1365 (s), 1260 (s), 1168 (s), 977 (w), 834 (m), 668 (m). HRMS (ESI) (m/z): calc'd for C$_{29}$H$_{36}$N$_6$NaO$_8$S [M+Na]$^+$: 651.2208, found: 651.2212. [α]$_D^{23}$: +31 (c=0.12, CHCl$_3$). TLC (60% ethyl acetate in hexanes), Rf: 0.56 (UV, CAM).

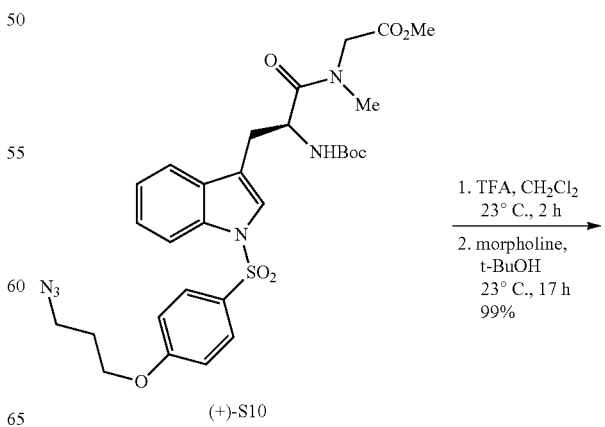

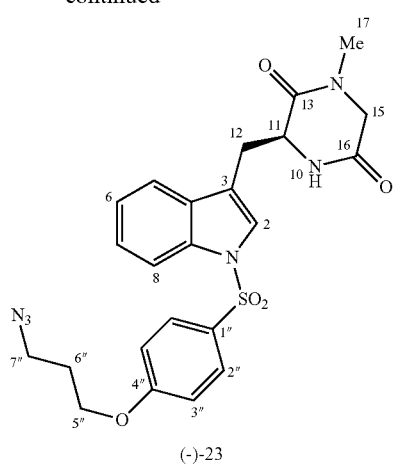

(−)-23

Example 20: Diketopiperazine (−)-23

Trifluoroacetic acid (TFA, 3.5 mL) was added via syringe to a solution of dipeptide (+)—S10 (951 mg, 1.51 mmol, 1 equiv) in dichloromethane (17.5 mL) at 23° C. After 2 h, the reaction mixture was concentrated under reduced pressure and the resulting residue was dissolved in t-butanol (15 mL). The reaction mixture was stirred vigorously at 23° C. as morpholine (5.6 mL) was added via syringe. After 17 h, the reaction mixture was concentrated under reduced pressure. The resulting residue was dissolved in ethyl acetate (200 mL) and was washed with an aqueous hydrogen chloride solution (1 M, 3×50 mL) and with a saturated aqueous sodium chloride solution (50 mL). The organic layer was dried over anhydrous sodium sulfate, was filtered, and was concentrated under reduced pressure. The resulting residue was purified by flash column chromatography on silica gel (eluent: 75% acetone in dichloromethane) to afford diketopiperazine (−)-23 (741 mg, 98.8%) as a colorless oil. Structural assignments were made with additional information from gCOSY, gHSQC, and gHMBC experiments. $^1$H NMR (400 MHz, CDCl$_3$, 25° C.): δ 7.90 (d, J=8.3 Hz, 1H, C$_8$H), 7.78 (app-d, J=8.9 Hz, 2H, C$_{2''}$H), 7.55-7.45 (m, 3H, C$_2$H, C$_5$H, N$_{10}$H), 7.27 (app-t, J=6.7 Hz, 1H, C$_7$H), 7.19 (app-t, J=7.6 Hz, 1H, C$_6$H), 6.85 (app-d, J=9.0 Hz, 2H, C$_{3''}$H), 4.28 (br-s, 1H, C$_{11}$H), 3.98 (t, J=5.9 Hz, 2H, C$_{5''}$H), 3.48-3.40 (m, 1H, C$_{15}$H$_a$), 3.42 (t, J=6.5 Hz, 2H, C$_{7''}$H), 3.29 (dd, J=5.6, 14.6 Hz, 1H, C$_{12}$H$_a$), 3.19 (dd, J=3.4, 14.4 Hz, 1H, C$_{12}$H$_b$), 2.93 (d, J=17.3 Hz, 1H, C$_{15}$H$_b$), 2.59 (s, 3H, C$_{17}$H), 1.97 (p, J=6.1 Hz, 2H, C$_{6''}$H). $^{13}$C NMR (100 MHz, CDCl$_3$, 25° C.): δ 166.3 (C$_{13}$), 165.7 (C$_{16}$), 163.1 (C$_{4''}$), 135.0 (C$_9$), 130.3 (C$_4$), 129.7 (C$_{1''}$), 129.4 (C$_{2''}$), 126.0 (C$_2$), 125.2 (C$_7$), 123.5 (C$_6$), 120.0 (C$_5$), 116.1 (C$_3$), 115.2 (C$_{3''}$), 113.6 (C$_8$), 65.2 (C$_{5''}$), 55.2 (C$_{11}$), 51.1 (C$_{15}$), 48.0 (C$_{7''}$), 33.8 (C$_{17}$), 30.6 (C$_{12}$), 28.6 (C$_{6''}$). FTIR (thin film) cm$^{-1}$: 3235 (w), 3103 (w), 2934 (w), 2100 (s), 1685 (s), 1653 (s), 1594 (m), 1364 (m), 1263 (s), 1167 (s), 1122 (m), 1096 (m), 978 (m), 835 (m), 694 (m). HRMS (DART) (m/z): calc'd for C$_{23}$H$_{25}$N$_6$O$_5$S [M+H]$^+$: 497.1602, found: 497.1616. [α]$_D^{23}$: −71 (c=0.11, CHCl$_3$). TLC (50% acetone in dichloromethane), Rf: 0.43 (UV, CAM).

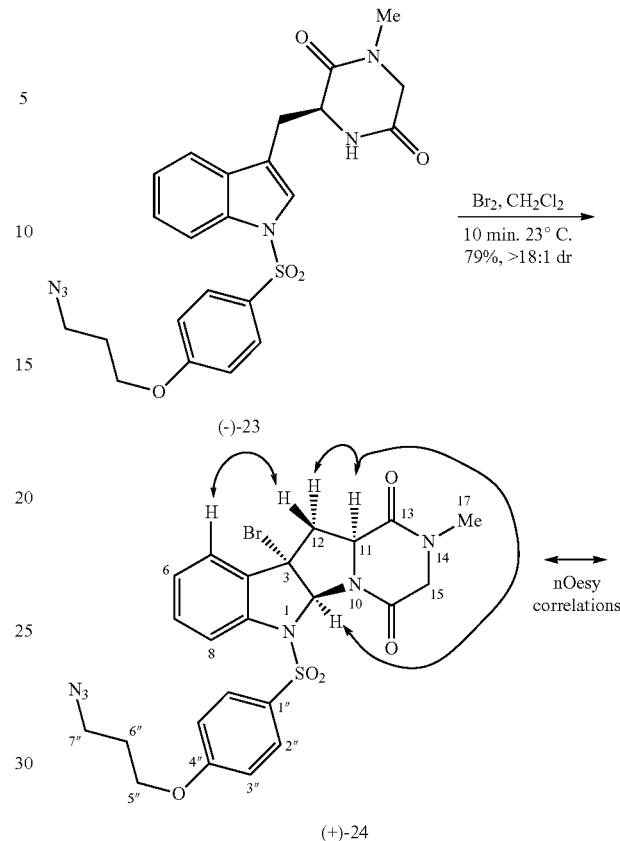

(+)-24

Example 21: Endo-Tetracyclic Bromide (+)-24

A solution of bromine (1.0 M, 6.1 mL, 6.1 mmol, 5.0 equiv) in dichloromethane was slowly poured into a solution of diketopiperazine (−)-23 (606 mg, 1.22 mmol, 1 equiv) in dichloromethane (25 mL) at 23° C. After 10 min, the solution was diluted with a saturated aqueous sodium thiosulfate solution (40 mL) and was extracted with ethyl acetate (120 mL). The organic layer was washed with a saturated aqueous sodium bicarbonate solution (2×40 mL), was washed with a saturated aqueous sodium chloride solution (25 mL), was dried over anhydrous sodium sulfate, was filtered, and was concentrated under reduced pressure. The resulting solid was suspended in diethyl ether (120 mL), was collected by filtration, and was washed with diethyl ether (3×50 mL) to afford endo-tetracyclic bromide (+)-24 and its minor exo-diastereomer (556 mg, 79.2%, >18:1 dr) as a white solid. Structural assignments were made with additional information from gCOSY, gHSQC, gHMBC, and gNOESY experiments. $^1$H NMR (400 MHz, DMSO, 25° C.): δ 7.84 (app-d, J=9.0 Hz, 2H, C$_{2''}$H), 7.48 (d, J=7.5 Hz, 1H, C$_5$H), 7.35-7.28 (m, 2H, C$_7$H, C$_8$H), 7.16 (app-t, J=7.0 Hz, 1H, C$_6$H), 7.04 (app-d, J=9.0 Hz, 2H, C$_{3''}$H), 6.27 (s, 1H, C$_2$H), 4.61 (dd, J=5.6, 9.7 Hz, 1H, C$_{11}$H), 4.19 (d, J=17.1 Hz, 1H, C$_{15}$H$_a$), 4.07 (t, J=6.1 Hz, 2H, C$_{5''}$H), 3.77 (d, J=17.2 Hz, 1H, C$_{15}$H$_b$), 3.47 (t, J=6.1 Hz, 2H, C$_{7''}$H), 3.28 (dd, J=5.6, 14.2 Hz, 1H, C$_{12}$H□), 3.01 (dd, J=10.0, 14.2 Hz, 1H, C$_{12}$H□), 2.70 (s, 3H, C$_{17}$H), 1.94 (p, J=6.4 Hz, 2H, C$_{6''}$H). $^{13}$C NMR (100 MHz, DMSO, 25° C.): δ 166.3 (C$_{13}$), 165.0 (C$_{16}$), 162.4 (C$_{4''}$), 138.5 (C$_9$), 135.1 (C$_4$), 130.6 (C$_7$), 130.4 (C$_{2''}$), 129.6 (C$_{1''}$), 125.9 (C$_6$), 125.2 (C$_5$), 116.5

($C_8$), 114.6 ($C_{3''}$), 86.1 ($C_2$), 65.3 ($C_{5''}$), 61.5 ($C_3$), 56.8 ($C_{11}$), 53.3 ($C_{15}$), 47.5 ($C_{7''}$), 38.6 ($C_{12}$), 32.7 ($C_{17}$), 27.9 ($C_{6''}$). FTIR (thin film) cm$^{-1}$: 2097 (s), 1685 (s), 1653 (m), 1594 (m), 1497 (m), 1259 (m), 1073 (m), 668 (m). HRMS (DART) (m/z): calc'd for $C_{23}H_{24}BrN_6O_5S$ [M+H]$^+$: 575.0707, found: 575.0713. $[\alpha]_D^{23}$: +92 (c=0.26, DMSO). TLC (50% acetone in dichloromethane), Rf: 0.65 (UV, CAM).

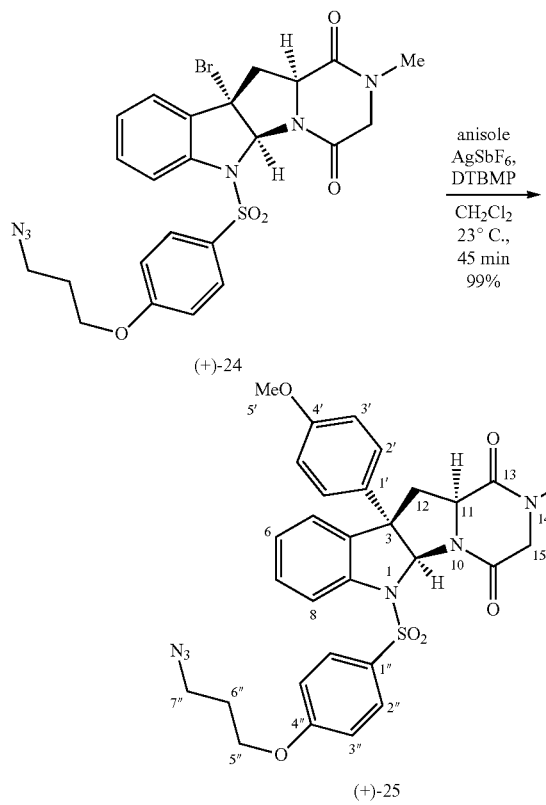

(+)-24

(+)-25

Example 22: Anisole Adduct (+)-25

Silver hexafluoroantimonate (708 mg, 8.58 mmol, 2.00 equiv) was added as a solid in one portion to a solution of bromide (+)-24 (590 mg, 1.03 mmol, 1 equiv), 2,6-di-tert-butyl-4-methylpyridine (DTBMP, 463 mg, 2.26 mmol, 2.20 equiv), and anisole (2.0 mL, 18 mmol, 17 equiv) in dichloromethane (8.0 mL) at 23° C. After 45 min, the suspension was diluted with dichloromethane (50 mL) and was filtered through a pad of Celite. The filter cake was washed with dichloromethane (3×50 mL) and the filtrate was concentrated under reduced pressure. The resulting residue was purified by flash column chromatography on silica gel (eluent: 10→30% acetone in dichloromethane) to afford anisole adduct (+)-25 (613 mg, 98.7%) as a white solid. Structural assignments were made with additional information from gCOSY, gHSQC, and gHMBC experiments. $^1$H NMR (400 MHz, CDCl$_3$, 25° C.): δ 7.57 (d, J=8.0 Hz, 1H, $C_8H$), 7.32 (app-d, J=9.0 Hz, 2H, $C_2H$), 7.28-7.24 (m, 1H, $C_7H$), 7.14-7.09 (m, 2H, $C_5H$, $C_6H$), 6.64 (app-d, J=8.9 Hz, 2H, $C_{2''}H$), 6.57 (app-d, J=9.0 Hz, 2H, $C_{3'}H$), 6.49 (app-d, J=9.0 Hz, 2H, $C_{3''}H$), 6.10 (s, 1H, $C_2H$), 4.42 (dd, J=6.9, 8.9 Hz, 1H, $C_{11}H$), 4.09 (d, J=17.4 Hz, 1H, $C_{15}H_a$), 3.95 (t, J=6.2 Hz, 2H, $C_{5''}H$), 3.79 (d, J=17.5 Hz, 1H, $C_{15}H_b$), 3.74 (s, 3H, $C_{5'}H$), 3.46 (t, J=6.6 Hz, 2H, $C_{7''}H$), 3.07 (dd, J=6.7, 14.1 Hz, 1H, $C_{12}H_a$), 2.86-2.77 (m, 1H, $C_{12}H_b$), 2.83 (s, 3H, $C_{17}H$), 1.99 (p, J=6.2 Hz, 2H, $C_{6''}H$). $^{13}$C NMR (100 MHz, CDCl$_3$, 25° C.): δ 167.1 ($C_{13}$), 165.4 ($C_{16}$), 162.2 ($C_{4''}$), 158.6 ($C_{4'}$), 140.1 ($C_9$), 136.0 ($C_4$), 133.1 ($C_{1'}$), 130.0 ($C_{1''}$), 129.6 ($C_{2''}$), 129.2 ($C_7$), 128.1 ($C_{2'}$), 126.2 ($C_5$), 125.5 ($C_6$), 117.5 ($C_8$), 114.3 ($C_{3''}$), 114.2 ($C_{3'}$), 87.2 ($C_2$), 64.9 ($C_{5''}$), 59.4 ($C_3$), 58.4 ($C_{11}$), 55.4 ($C_{5'}$), 54.4 ($C_{15}$), 48.1 ($C_{7''}$), 39.2 ($C_{12}$), 33.6 ($C_{17}$), 28.6 ($C_{6''}$). FTIR (thin film) cm$^{-1}$: 2936 (w), 2100 (s), 1684 (s), 1654 (m), 1457 (m), 1261 (s), 1159 (s), 830 (m), 667 (s). HRMS (DART) (m/z): calc'd for $C_{30}H_{31}N_6O_6S$ [M+H]$^+$: 603.2020, found: 603.2012. $[\alpha]_D^{23}$+23 (c=0.24, CHCl$_3$). TLC (30% acetone in dichloromethane), Rf: 0.48 (UV, CAM).

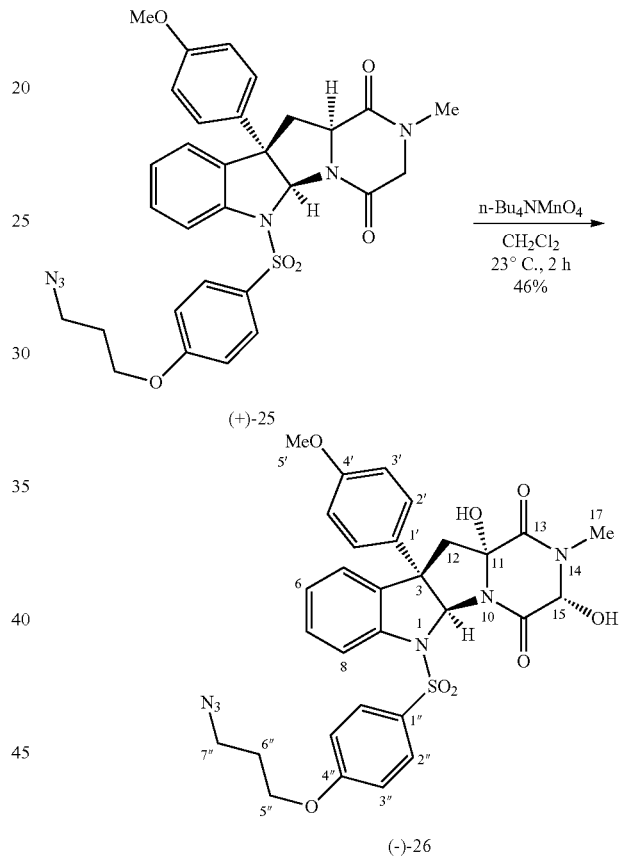

(+)-25

(−)-26

Example 23: Diol (−)-26

Tetra-n-butylammonium permanganate[42] (900 mg, 2.49 mmol, 5.00 equiv) was added as a solid in one portion to a solution of anisole adduct (+)-25 (300 mg, 486 μmol, 1 equiv) in dichloromethane (20 mL) at 23° C. After 2 h, the dark purple reaction mixture was diluted with a saturated aqueous sodium sulfite solution (30 mL) and with ethyl acetate (125 mL). The resulting mixture was washed with a saturated aqueous sodium bicarbonate solution (40 mL), the layers were separated, and the organic layer was washed with a saturated aqueous sodium chloride solution (40 mL). The combined aqueous layers were extracted with ethyl acetate (2×50 mL) and the combined organic extracts were dried over anhydrous sodium sulfate, were filtered, and were concentrated under reduced pressure. The resulting residue was purified by flash column chromatography on silica gel (eluent: 10→25% acetone in dichloromethane) to afford diol (−)-26 (146 mg, 46.0%) as a white solid. Structural assignments were made with additional information from gCOSY, gHSQC, and gHMBC experiments. $^1$H NMR (400 MHz, CDCl$_3$, 25° C.): δ 7.57 (d, J=8.0 Hz, 1H, C$_8$H), 7.32-7.27 (m, 1H, C$_7$H), 7.19-7.15 (m, 4H, C$_{2''}$H, C$_5$H, C$_6$H), 6.78 (app-d, J=8.7 Hz, 2H, C$_{2'}$H), 6.56 (app-d, J=8.7 Hz, 2H, C$_{3'}$H), 6.41 (app-d, J=8.8 Hz, 2H, C$_{3''}$H), 6.33 (s, 1H, C$_2$H), 6.07 (br-s, 1H, C$_{15}$OH), 5.48 (br-s, 1H, C$_{11}$OH), 5.19 (d, J=5.7 Hz, 1H, C$_{15}$H), 3.96-3.92 (m, 2H, C$_{5''}$H), 3.75 (s, 3H, C$_{5'}$H), 3.48 (t, J=6.5 Hz, 2H, C$_{7''}$H), 3.44 (m, 1H, C$_{12}$H$_a$), 3.00 (s, 3H, C$_{17}$H), 2.87 (d, J=15.1 Hz, 1H, C$_{12}$H$_b$), 2.01 (p, J=6.1 Hz, 2H, C$_{6''}$H). $^{13}$C NMR (150 MHz, CDCl$_3$, 25° C.): δ 167.5 (C$_{13}$), 166.3 (C$_{16}$), 162.3 (C$_{4''}$), 158.5 (C$_{4'}$), 140.0 (C$_9$), 137.2 (C$_4$), 133.9 (C$_{1'}$), 129.8 (C$_{1''}$), 129.5 (C$_{2''}$), 129.3 (C$_7$), 128.7 (C$_{2'}$), 126.7 (C$_5$), 126.2 (C$_6$), 118.0 (C$_8$), 114.2 (C$_{3''}$), 114.1 (C$_{3'}$), 88.3 (C$_{11}$), 87.9 (C$_2$), 83.1 (C$_{15}$), 64.9 (C$_{5''}$), 58.7 (C$_3$), 55.4 (C$_{5'}$), 49.0 (C$_{12}$), 48.1 (C$_{7''}$), 32.4 (C$_{17}$), 28.7 (C$_{6''}$). FTIR (thin film) cm$^{-1}$: 3385 (m), 2936 (w), 2099 (s), 1700 (s), 1685 (s), 1595 (m), 1513 (m), 1362 (m), 1258 (s), 1163 (s), 832 (m), 667 (m). HRMS (DART) (m/z): calc'd for C$_{30}$H$_{31}$N$_6$O$_8$S [M+H]$^+$: 635.1919, found: 635.1906. [α]$_D^{23}$: −11 (c=0.10, CHCl$_3$). TLC (30% acetone in dichloromethane), Rf: 0.36 (UV, CAM).

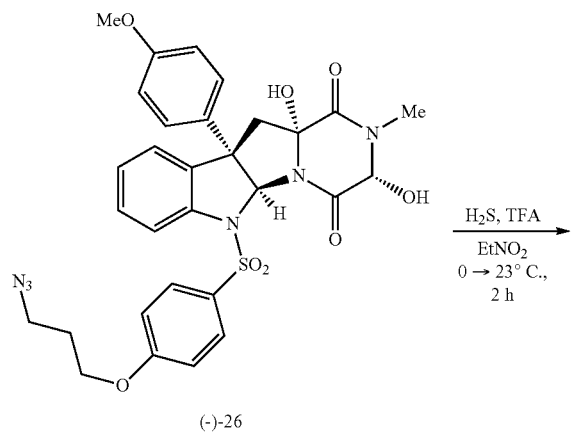

(−)-26

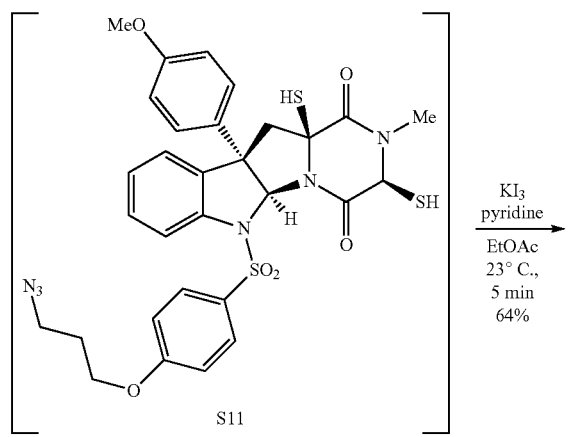

S11

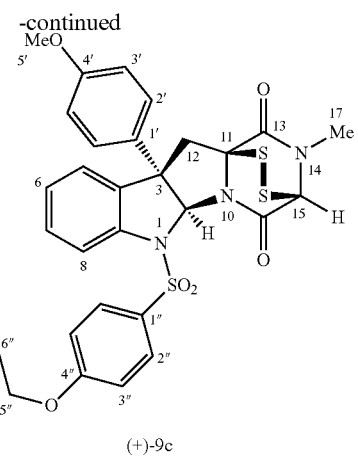

(+)-9c

Example 24: Epidithiodiketopiperazine Azide (+)-9c

A solution of diol (−)-26 (142 mg, 224 μmol, 1 equiv) in anhydrous nitroethane (9.5 mL) at 0° C. was sparged with hydrogen sulfide gas for 20 min by discharge of a balloon equipped with a needle extending into the reaction mixture, providing a saturated hydrogen sulfide solution. Trifluoroacetic acid (TFA, 7.1 mL) was added via syringe over 20 seconds, and the sparging with hydrogen sulfide was maintained for another 20 min. The ice-water bath was removed, and the solution was allowed to stir and warm to 23° C. under an atmosphere of hydrogen sulfide. After 2 h, the reaction mixture was diluted with ethyl acetate (110 mL) and was slowly poured into a saturated aqueous sodium bicarbonate solution (50 mL). The organic layer was washed with a saturated aqueous sodium chloride solution (30 mL). A stock solution of potassium triiodide in pyridine[43] was added dropwise into the organic layer containing crude bisthiol S11 until a persistent yellow color was observed. The resulting mixture was washed with an aqueous hydrogen chloride solution (1 M, 2×30 mL), was washed with a saturated aqueous sodium chloride solution (30 mL), was dried over anhydrous sodium sulfate, was filtered, and was concentrated under reduced pressure. The resulting residue was purified by flash column chromatography on silica gel (eluent: 0→20% ethyl acetate in dichloromethane) to afford epidithiodiketopiperazine azide (+)-9c (93.9 mg, 64.2%) as a beige solid. Structural assignments were made with additional information from gCOSY, gHSQC, and gHMBC experiments.[51] $^1$H NMR (400 MHz, CDCl$_3$, 25° C.): δ 7.64 (d, J=8.0 Hz, 1H, C$_8$H), 7.39 (td, J=1.6, 7.0 Hz, 1H, C$_7$H), 7.28-7.22 (m, 2H, C$_6$H, C$_5$H), 7.20 (app-d, J=8.9 Hz, 2H, C$_{2''}$H), 6.73 (app-d, J=8.8 Hz, 2H, C$_{2'}$H), 6.61 (app-d, J=8.8 Hz, 2H, C$_{3'}$H), 6.40 (app-d, J=8.9 Hz, 2H, C$_{3''}$H), 6.32 (s, 1H, C$_2$H), 5.25 (s, 1H, C$_{15}$H), 3.95-3.90 (m, 2H, C$_{5''}$H), 3.76 (s, 3H, C$_{5'}$H), 3.58 (d, J=15.5 Hz, 1H, C$_{12}$H$_a$), 3.48 (t, J=6.5 Hz, 2H, C$_{7''}$H), 3.10 (s, 3H, C$_{17}$H), 2.82 (d, J=15.5 Hz, 1H, C$_{12}$H$_b$), 2.00 (p, J=6.2 Hz, 2H, C$_{6''}$H). $^{13}$C NMR (100 MHz, CDCl$_3$, 25° C.): δ 165.1 (C$_{13}$), 162.1 (C$_{4''}$), 160.0 (C$_{16}$), 158.6 (C$_{4'}$), 141.5 (C$_9$), 135.8 (C$_4$), 131.3 (C$_{1'}$), 129.9 (C$_{1''}$), 129.7 (C$_7$), 129.2 (C$_{2''}$), 127.9 (C$_{2'}$), 126.1 (C$_5$), 125.6 (C$_6$), 119.3 (C$_8$), 114.3 (C$_{3'}$), 114.0 (C$_{3''}$), 87.7 (C$_2$), 74.5 (C$_{11}$), 68.3 (C$_{15}$), 64.7 (C$_{5''}$), 59.4 (C$_3$), 55.4 (C$_{5'}$), 48.0 (C$_{7''}$), 45.8 (C$_{12}$), 32.0 (C$_{17}$), 28.5 (C$_{6''}$). FTIR (thin film) cm$^{-1}$: 2930 (w), 2098 (s), 1718 (s), 1700 (s), 1685 (s), 1653 (m), 1559 (m), 1507 (m), 1457 (m), 1362 (m), 1259 (s), 1162 (s), 831

(m), 667 (m). HRMS (DART) (m/z): calc'd for $C_{30}H_{32}N_7O_6S_3[M+NH_4]^+$: 682.1571, found: 682.1559. $[\alpha]_D^{23}$: +222 (c=0.08, CHCl$_3$). TLC (20% ethyl acetate in dichloromethane), Rf: 0.35 (UV, CAM).

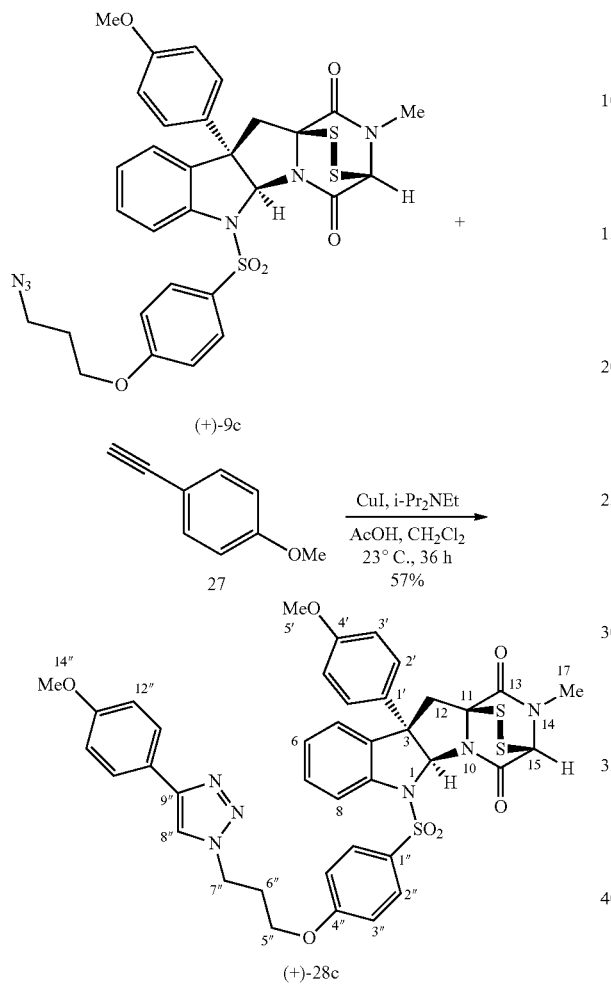

Example 25: Triazole (+)-28c

A suspension of copper(I) iodide (3.05 mg, 15.4 μmol, 0.500 equiv), acetic acid (1.77 μL, 30.8 μmol, 1.00 equiv), and N,N-diisopropylethylamine (5.40 μL, 30.8 μmol, 1.00 equiv) in dichloromethane (0.50 mL) was added via syringe to a solution of epidithiodiketopiperazine (+)-9c (20.5 mg, 30.8 μmol, 1 equiv) and 4-ethynylanisole (27, 20.8 μL, 0.160 mmol, 5.00 equiv) in dichloromethane (0.50 mL) at 23° C. After 36 h, the reaction mixture was directly purified by flash column chromatography on silica gel (eluent: 20% ethyl acetate in dichloromethane→100% ethyl acetate) to afford triazole (+)-28c (14.2 mg, 56.8%) as a yellow solid. Structural assignments were made with additional information from gCOSY, gHSQC, and gHMBC experiments. $^1$H NMR (400 MHz, CDCl$_3$, 25° C.): δ 7.70-7.68 (m, 3H, C$_{8''}$H, C$_{11''}$H), 7.61, (d, J=8.0 Hz, 1H, C$_8$H), 7.38 (app-t, J=7.7 Hz, 1H, C$_7$H), 7.28-7.23 (m, 2H, C$_6$H, C$_5$H), 7.19 (app-d, J=8.9 Hz, 2H, C$_{2''}$H), 6.91 (app-d, J=8.4 Hz, 2H, C$_{12''}$H), 6.72 (app-d, J=8.8 Hz, 2H, C$_{2'}$H), 6.59 (app-d, J=8.6 Hz, 2H, C$_{3'}$H), 6.38 (app-d, J=8.8 Hz, 2H, C$_{3''}$H), 6.31 (s, 1H, C$_2$H), 5.22 (s, 1H, C$_{15}$H), 4.57 (t, J=6.6 Hz, 2H, C$_{7''}$H), 3.92-3.88 (m, 2H, C$_{5''}$H), 3.81 (s, 3H, C$_{14''}$H), 3.73 (s, 3H, C$_{5'}$H), 3.57 (d, J=15.6 Hz, 1H, C$_{12}$H$_a$), 3.09 (s, 3H, C$_{17}$H), 2.81 (d, J=15.5 Hz, 1H, C$_{12}$H$_b$), 2.40 (p, J=6.2 Hz, 2H, C$_{6''}$H). $^{13}$C NMR (100 MHz, CDCl$_3$, 25° C.): δ 165.2 (C$_{13}$), 162.0 (C$_{4''}$), 160.2 (C$_{16}$), 159.8 (C$_{13''}$), 158.8 (C$_{4'}$), 147.9 (C$_{9''}$), 141.6 (C$_9$), 135.9 (C$_4$), 131.5 (C$_{1'}$), 130.3 (C$_{1''}$), 129.9 (C$_7$), 129.4 (C$_{2''}$), 128.1 (C$_{2'}$), 127.2 (C$_{11''}$), 126.3 (C$_5$), 125.8 (C$_6$), 123.3 (C$_{10''}$), 119.5 (C$_{8''}$), 119.4 (C$_8$), 114.5 (C$_{3'}$), 114.5 (C$_{12''}$), 114.2 (C$_{3''}$), 87.9 (C$_2$), 74.6 (C$_{11}$), 68.5 (C$_{15}$), 64.6 (C$_{5''}$), 59.6 (C$_3$), 55.6 (C$_{5'}$), 55.5 (C$_{14''}$), 47.1 (C$_{7''}$), 45.9 (C$_{12}$), 32.2 (C$_{17}$), 30.0 (C$_{16'}$). FTIR (thin film) cm$^{-1}$: 2924 (w), 1717 (s), 1700 (s), 1685 (s), 1653 (m), 1559 (s), 1457 (m), 1362 (m), 1259 (s), 1162 (s), 1031 (m), 668 (m). HRMS (ESI) (m/z): calc'd for $C_{39}H_{37}N_6O_7S_3$ [M+H]$^+$: 797.1880, found: 797.1880. $[\alpha]_D^{23}$: +150 (c=0.11, CHCl$_3$). TLC (100% ethyl acetate), Rf: 0.38 (UV, CAM).

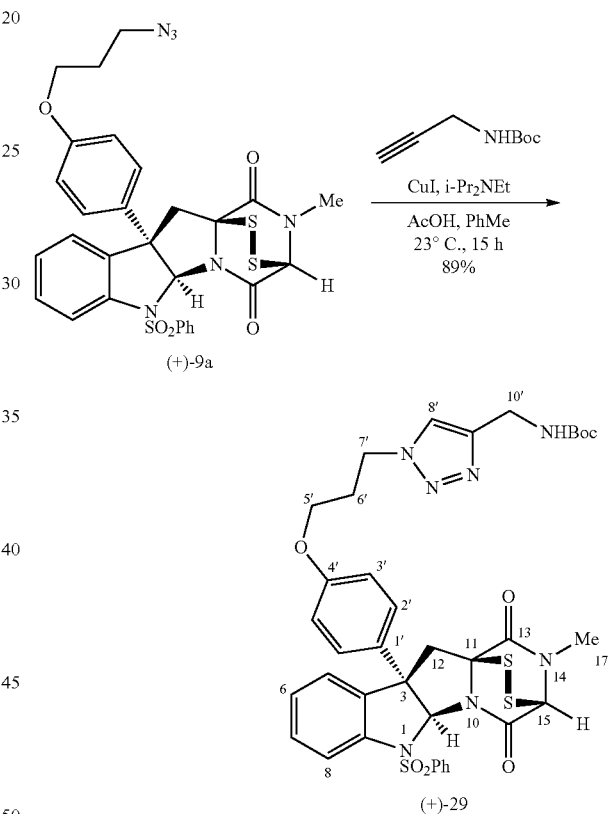

Example 26: Triazole (+)-29

A suspension of copper(I) iodide (24.8 mg, 128 μmol. 0.750 equiv), acetic acid (15 μL, 260 μmol, 1.5 equiv), and DIPEA (45 μL, 260 μmol, 1.5 equiv) in toluene (1.5 mL) was introduced via syringe to a solution of epidithiodiketopiperazine (+)-9a (108 mg, 170 μmol, 1 equiv) and N-Boc-propargylamine (132 mg, 850 μmol, 5.00 equiv) in toluene (0.3 mL) at 23° C. After 15 h, the reaction mixture was diluted with dichloromethane (3 mL) and was directly purified by flash column chromatography on silica gel (eluent: 0.8%→2.5% methanol in dichloromethane) to afford triazole (+)-29 (119 mg, 88.8%) as a white solid. Structural assignments were made with additional information from gCOSY, gHSQC, and gHMBC experiments. $^1$H NMR (400 MHz, CDCl$_3$, 25° C.): δ 7.68-7.50 (m, 2H, C$_8$H, C$_{8'}$H), 7.40-7.16 (m, 6H, C$_7$H, SO$_2$Ph-o-H, SO$_2$Ph-p-H, C$_5$H, C$_6$H), 7.00 (app-t, J=7.1 Hz, 2H, SO$_2$Ph-m-H), 6.73 (app-d, J=7.8 Hz, 2H, C$_{2'}$H), 6.56 (app-d, J=6.8 Hz, 2H, C$_{3'}$H), 6.37 (s, 1H, C$_2$H), 5.30 (br-s, 2H, C$_{15}$H, NH), 4.54 (br-s, 2H, C$_{7'}$H), 4.36 (br-s, 2H, C$_{10'}$H), 3.89 (br-s, 2H, C$_{5'}$H), 3.60 (d, J=15.4 Hz, 1H, C$_{12}$H$_a$), 3.09 (s, 3H, C$_{17}$H), 2.84 (d, J=15.4 Hz, 1H, C$_{12}$H$_b$), 2.34 (br-s, 2H, C$_{6'}$H), 1.38 (s, 9H, C(CH$_3$)$_3$). $^{13}$C NMR (150 MHz, CDCl$_3$, 25° C.): δ 165.1 (C$_{13}$), 160.2 (C$_{16}$), 157.7 (C$_{4'}$), 156.0 (NCO$_2$C(CH$_3$)$_3$), 145.8 (C$_{9'}$), 141.2 (C$_9$), 138.3 (SO$_2$Ph-ipso-C), 135.8 (C$_4$), 133.2 (SO$_2$Ph-p-C), 131.7 (C$_{1'}$), 129.9 (C$_7$), 128.7 (SO$_2$Ph-m-C), 128.1 (C$_{2'}$), 127.2 (SO$_2$Ph-o-C), 126.2 (C$_6$), 125.7 (C$_5$), 122.7 (C$_8$), 118.9 (C$_{8'}$), 115.0 (C$_{3'}$), 87.7 (C$_2$), 79.8 (C(CH$_3$)$_3$), 74.6 (C$_{11}$), 68.3 (C$_{15}$), 64.3 (C$_{5'}$), 59.5 (C$_3$), 47.2 (C$_7$), 45.4 (C$_{12}$), 36.1 (C$_{10'}$), 32.1 (C$_{17}$), 30.0 (C$_{6'}$), 28.5 (C(CH$_3$)$_3$). FTIR (thin film) cm$^{-1}$: 3391 (w), 2977 (w), 1695 (s), 1512 (m), 1363 (m), 1251 (m), 1168 (s). HRMS (ESI) (m/z): calc'd for C$_{37}$H$_{39}$N$_7$NaO$_7$S$_3$ [M+Na]$^+$: 812.1965, found: 812.1969. [α]$_D^{23}$: +185 (c=0.20, CHCl$_3$). TLC (5% methanol in dichloromethane), Rf: 0.44 (UV, CAM).

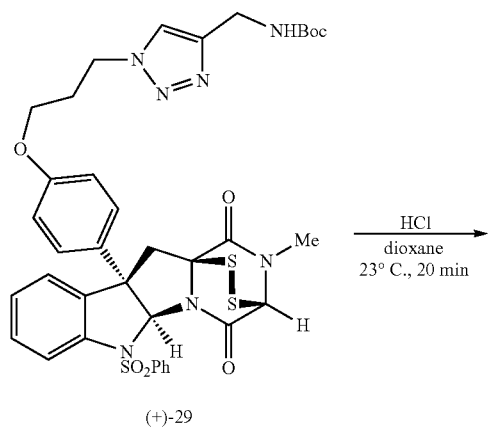

(+)-29

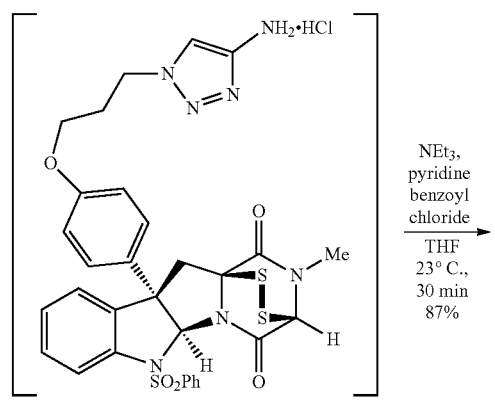

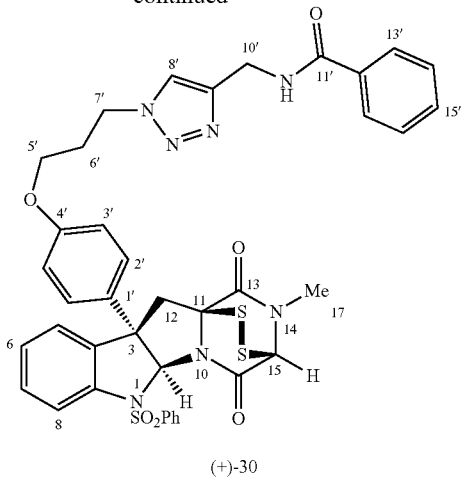

(+)-30

Example 27: Benzamide (+)-30

A solution of hydrogen chloride in 1,4-dioxane (4.0 M, 1.0 mL) was added via syringe to a solution of triazole (+)-29 (15.0 mg, 19.0 μmol, 1 equiv) in 1,4-dioxane (0.5 mL) at 23° C. After 20 min, the reaction mixture was concentrated under reduced pressure, and the resulting yellow solid was dissolved in pyridine (240 μL). A solution of benzoyl chloride (48 mM, 0.60 mL, 29 μmol, 1.5 equiv) in tetrahydrofuran was added via syringe, followed by the addition of triethylamine (40 μL, 290 μmol, 15 equiv) via syringe. After 30 min, the reaction mixture was diluted with ethyl acetate (30 mL) and was slowly poured into an aqueous hydrogen chloride solution (1 M, 5 mL). The organic layer was washed sequentially with an aqueous hydrogen chloride solution (1 M, 5 mL), with a saturated aqueous sodium bicarbonate solution (5 mL), and with a saturated aqueous sodium chloride solution (5 mL). The organic layer was dried over anhydrous sodium sulfate, was filtered, and was concentrated under reduced pressure. The resulting residue was purified by flash column chromatography on silica gel (eluent: 1→2% methanol in dichloromethane) to afford benzamide (+)-30 (13.1 mg, 86.8%) as a beige solid. Structural assignments were made with additional information from gCOSY, gHSQC, and gHMBC experiments. $^1$H NMR (400 MHz, CDCl$_3$, 25° C.): δ 7.77 (app-d, J=7.3 Hz, 2H, C$_{13'}$H), 7.71 (br-s, 1H, C$_{8'}$H), 7.57 (d, J=8.0 Hz, 1H, C$_8$H), 7.46 (app-t, J=7.4 Hz, 1H, C$_{15'}$H), 7.40-7.32 (m, 5H, SO$_2$Ph-o-H, C$_{14'}$H, C$_7$H), 7.28-7.20 (m, 3H, SO$_2$Ph-o-H, C$_5$H, C$_6$H), 7.16 (br-s, 1H, NH), 7.01 (app-t, J=7.8 Hz, 2H, SO$_2$Ph-m-H), 6.71 (app-d, J=8.8 Hz, 2H, C$_{2'}$H), 6.56 (app-d, J=8.8 Hz, 2H, C$_{3'}$H), 6.36 (s, 1H, C$_2$H), 5.27 (s, 1H, C$_{15}$H), 4.68 (br-s, 2H, C$_{10'}$H), 4.55 (t, J=6.3 Hz, 2H, C$_{7'}$H), 3.95-3.84 (m, 2H, C$_{5'}$H), 3.60 (d, J=15.5 Hz, 1H, C$_{12}$H$_a$), 3.10 (s, 3H, C$_{17}$H), 2.83 (d, J=15.5 Hz, 1H, C$_{12}$H$_b$), 2.37 (p, J=5.9 Hz, 2H, C$_{6'}$H). $^{13}$C NMR (150 MHz, CDCl$_3$, 25° C.): δ 167.6 (C$_{11'}$), 165.2 (C$_{13}$), 160.2 (C$_{16}$), 157.8 (C$_{4'}$), 145.0 (C$_{9'}$), 141.3 (C$_9$), 138.4 (SO$_2$Ph-ipso-C), 135.9 (C$_4$), 134.0 (C$_{12'}$), 133.2 (SO$_2$Ph-p-C), 131.9 (C$_{15'}$), 131.8 (C$_{1'}$), 129.9 (C$_7$), 128.8 (C$_{14'}$), 128.7 (SO$_2$Ph-m-C), 128.1 (C$_{2'}$), 127.3 (SO$_2$Ph-o-C), 127.2 (C$_{13'}$), 126.3 (C$_6$), 125.7 (C$_5$), 123.3 (C$_{8'}$), 119.0 (C$_8$), 115.1 (C$_{3'}$), 87.2 (C$_2$), 74.6 (C$_{11}$), 68.5 (C$_{15}$), 64.4 (C$_{5'}$), 59.6 (C$_3$), 47.4 (C$_7$), 45.5 (C$_{12}$), 35.5 (C$_{10'}$), 32.2 (C$_{17}$), 30.0 (C$_{6'}$). FTIR (thin film) cm$^{-1}$: 3345 (w), 3001 (w), 1695 (s), 1512 (m), 1461 (m), 1169 (m), 755 (m). HRMS (ESI) (m/z): calc'd for $C_{39}H_{36}N_7O_6S_3[M+H]^+$: 794.1884, found: 794.1890. $[\alpha]_D^{23}$: +175 (c=0.11, CHCl$_3$). TLC (10% methanol in dichloromethane), Rf: 0.52 (UV, CAM).

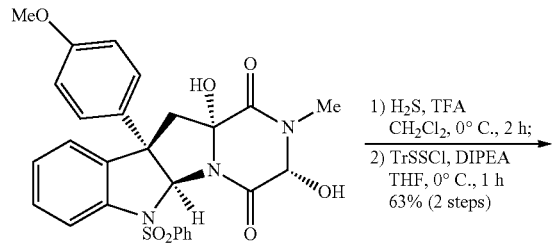

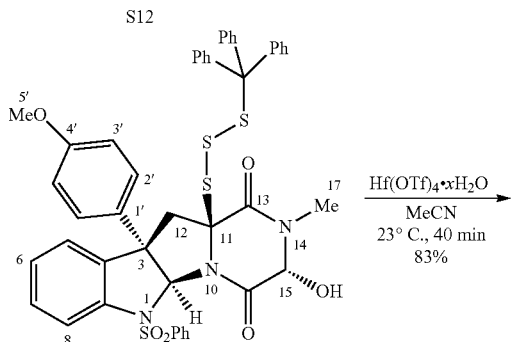

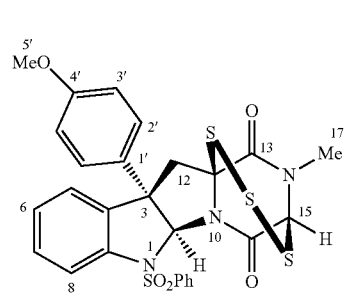

Example 28: Epitrithiodiketopiperazine 31

This compound was prepared in three steps starting from diol S12[52] using the methodology developed to access corresponding C3-(indol-3'-yl) epitrithiodiketopiperazine. First, the corresponding C11-thiohemiaminal was prepared from diol S12 (57.2 mg, 107 µmol) and was purified by flash column chromatography on silica gel (eluent: 10→80% acetone in dichloromethane) to afford the C11-thiohemiaminal (49.2 mg, 83.5%)[53] as a white foam. Next, the C11-triphenylmethanetrisulfide S13 was prepared from C11-thiohemiaminal (26.4 mg, 47.9 µmol) and was purified by flash column chromatography on silica gel (eluent: 0→30% ethyl acetate in dichloromethane) to afford C11-triphenylmethanetrisulfide S13 (31.2 mg, 76.0%)[54] as a white solid. Finally, epitrithiodiketopiperazine 31 was prepared from the C11-triphenylmethanetrisulfide S13 (29.5 mg, 34.4 µmol) and was purified by flash column chromatography on silica gel (eluent: 5-15% ethyl acetate in dichloromethane) to afford epitrithiodiketopiperazine 31 (17.0 mg, 82.7%) as a white solid. Structural assignments were made with additional information from gCOSY, gHSQC, and gHMBC experiments. Based on $^1$H NMR analysis at 25° C. degrees in CDCl$_3$, epitrithiodiketopiperazine 31 exists as a 2.6:1 mixture of major:minor conformers. $^1$H NMR (500 MHz, CDCl$_3$, 25° C.): Major conformer: δ 7.65 (app-d, J=7.4 Hz, 2H, SO$_2$Ph-o-H), 7.57 (d, J=8.1 Hz, 1H, C$_8$H), 7.44-7.37 (m, 2H, C$_7$H, SO$_2$Ph-p-H), 7.23 (app-t, J=7.9 Hz, 2H, SO$_2$Ph-m-H), 7.21-7.09 (m, 2H, C$_5$H, C$_6$H), 6.86 (app-d, J=8.8 Hz, 2H, C$_{2'}$H), 6.69 (app-d, J=8.8 Hz, 2H, C$_{3'}$H), 4.84 (s, 1H, C$_{15}$H), 3.77 (s, 3H, C$_{5'}$H), 3.44 (d, J=14.8 Hz, 1H, C$_{12}$H$_a$), 3.16 (s, 3H, C$_{17}$H), 3.08 (d, J=14.8 Hz, 1H, C$_{12}$H$_b$). Minor conformer: δ 7.51 (m, 3H, C$_8$H, SO$_2$Ph-o-H), 7.34 (app-t, J=7.4, 1H, SO$_2$Ph-p-H), 7.30 (app-t, J=8.1 Hz, C$_7$H), 7.21-7.09 (m, 4H, SO$_2$Ph-m-H, C$_5$H, C$_6$H), 6.83 (app-d, J=8.8 Hz, 2H, C$_{2'}$H), 6.72 (s, 1H, C$_2$H), 6.66 (app-d, J=8.9 Hz, 2H, C$_{3'}$H), 5.18 (s, 1H, C$_{15}$H), 3.78 (s, 3H, C$_{5'}$H), 3.29 (d, J=14.9 Hz, 1H, C$_{12}$H$_a$), 2.98 (s, 3H, C$_{17}$H), 2.98 (d, J=14.9 Hz, 1H, C$_{12}$H$_b$). $^{13}$C NMR (125 MHz, CDCl$_3$, 25° C.): Major conformer: δ 168.0 (C$_{13}$), 162.1 (C$_{16}$), 159.0 (C$_{5'}$), 142.9 (C$_9$), 139.5 (SO$_2$Ph-ipso-C), 135.0 (C$_4$), 133.0 (SO$_2$Ph-p-C), 131.5 (C$_{1'}$), 130.2 (C$_7$), 128.8 (SO$_2$Ph-m-C), 127.5 (C$_{2'}$), 127.1 (SO$_2$Ph-o-C), 125.8 (C$_5$/C$_6$), 125.7 (C$_5$/C$_6$), 118.7 (C$_8$), 114.6 (C$_{3'}$), 86.2 (C$_2$), 79.6 (C$_{11}$), 67.2 (C$_{15}$), 57.7 (C$_3$), 55.5 (C$_{5'}$), 50.8 (C$_{12}$), 32.5 (C$_{17}$). Minor conformer: δ 166.9 (C$_{13}$), 161.3 (C$_{16}$), 158.9 (C$_{5'}$), 141.5 (C$_9$), 138.9 (SO$_2$Ph-ipso-C), 135.8 (C$_4$), 133.0 (SO$_2$Ph-p-C), 131.4 (C$_{1'}$), 129.6 (C$_7$), 128.6 (SO$_2$Ph-m-C), 127.8 (C$_{2'}$/SO$_2$Ph-o-C), 127.5 (C$_{2'}$/SO$_2$Ph-o-C), 126.3 (C$_5$/C$_6$), 125.7 (C$_5$/C$_6$), 118.6 (C$_8$), 114.6 (C$_{3'}$), 88.1 (C$_2$), 75.0 (C$_{11}$), 71.1 (C$_{15}$), 57.8 (C$_3$), 55.5 (C$_{5'}$), 48.9 (C$_{12}$), 33.1 (C$_{17}$). FTIR (thin film) cm$^{-1}$: 3063 (w), 2837 (w), 1686 (br-s), 1609 (w), 1513 (m), 1364 (m), 1254 (m), 1168 (s), 1090 (w), 1033 (m), 832 (w), 797 (w), 736 (m), 600 (m), 575 (m). HRMS (ESI) (m/z): calc'd for $C_{27}H_{23}N_3O_5S_4$ $[M+H]^+$: 598.0593, found: 598.0585. TLC (20% ethyl acetate in dichloromethane), Rf: 0.51 (UV, CAM).

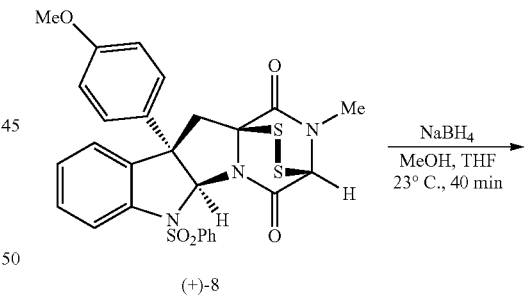

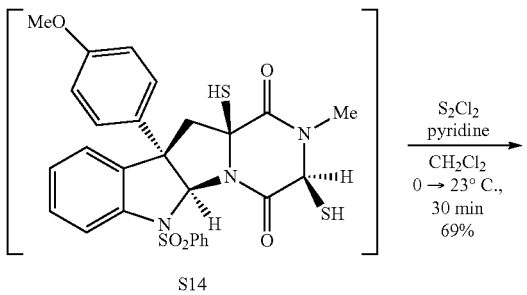

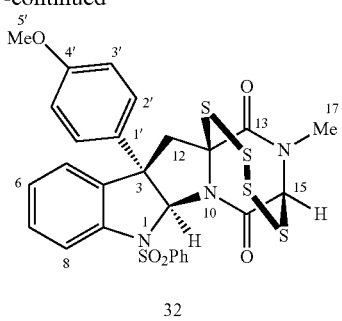

32

Example 29: Epitetrathiodiketopiperazine 32

Sodium borohydride (2.4 mg, 63 µmol, 5.0 equiv) was added as a solid in one portion to a solution of epidithiodiketopiperazine (+)-8 (17.5 mg, 30.9 µmol, 1 equiv) in tetrahydrofuran (7.7 mL) and methanol (77 µL). After 40 min, the reaction mixture was diluted with dichloromethane (75 mL) and was washed with a saturated aqueous ammonium chloride solution (2×35 mL). The aqueous layer was extracted with dichloromethane (35 mL). The combined organic extracts were dried over anhydrous sodium sulfate, were filtered, and were sparged with argon for 15 min by discharge of a balloon equipped with a needle extending into the stirring reaction mixture. The reaction mixture was then concentrated under reduced pressure to approximately 15 mL and was cooled to 0° C. Pyridine (25 µL, 0.31 mmol, 10 equiv) was added via syringe to the solution of bisthiol $S_{14}$, followed by the dropwise addition of a solution of disulfur dichloride (0.50 M, 0.10 mL, 50 µmol, 1.6 equiv) in dichloromethane via syringe. The reaction mixture was removed from the ice-water bath and allowed to stir and warm to 23° C. After 30 min, the reaction was diluted with dichloromethane (35 mL) and was washed sequentially with a saturated aqueous ammonium chloride solution (2×30 mL), with deionized water (30 mL), and with a saturated aqueous sodium chloride solution (30 mL). The combined aqueous layers were extracted with a single portion of dichloromethane (50 mL), and the combined organic extracts were dried over anhydrous sodium sulfate, were filtered, and were concentrated under reduced pressure. The resulting residue was purified by flash column chromatography on silica gel (eluent: 0→10% ethyl acetate in dichloromethane) to afford the epitetrathiodiketopiperazine 32 (13.5 mg, 69.2%) as a white solid. Structural assignments were made with additional information from gCOSY, gHSQC, and gHMBC experiments. $^1$H NMR (600 MHz, CDCl$_3$, 25° C.): δ 7.94 (app-d, J=7.8 Hz, 2H, SO$_2$Ph-o-H), 7.53 (td, J=7.6, 1.3 Hz, 1H, SO$_2$Ph-p-H), 7.45 (d, J=8.2 Hz, 1H, C$_8$H), 7.42 (app-t, J=7.7 Hz, 2H, SO$_2$Ph-m-H), 7.29-7.23 (m, 1H, C$_7$H), 7.08 (app-t, J=7.4 Hz, 1H, C$_6$H), 7.03 (d, J=7.6 Hz, 1H, C$_5$H), 6.89 (app-d, J=8.3 Hz, 2H, C$_{2'}$H), 6.83 (s, 1H, C$_2$H), 6.71 (app-d, J=8.7 Hz, 1H, C$_{3'}$H), 5.12 (s, 1H, C$_{15}$H), 3.27 (d, J=14.5 Hz, 1H, C$_{12}$H$_a$), 3.10 (d, J=14.5 Hz, 1H, C$_{12}$H$_b$), 3.01 (s, 3H, C$_{17}$H). $^{13}$C NMR (150 MHz, CDCl$_3$, 25° C.): δ 167.9 (C$_{13}$), 162.7 (C$_{16}$), 159.0 (C$_{4'}$), 141.7 (C$_9$), 139.2 (SO$_2$Ph-ipso-C), 136.6 (C$_4$), 133.5 (C$_{1'}$), 133.3 (SO$_2$Ph-p-C), 129.5 (C$_7$), 129.1 (SO$_2$Ph-m-C), 127.8 (SO$_2$Ph-o-C), 127.0 (C$_{2'}$), 125.5 (C$_6$), 124.8 (C$_5$), 116.6 (C$_8$), 114.6 (C$_{3'}$), 86.6 (C$_2$), 76.0 (C$_{11}$), 68.3 (C$_{15}$), 57.2 (C$_3$), 55.5 (C$_{5'}$), 49.7 (C$_{12}$), 32.3 (C$_{17}$). FTIR (thin film) cm$^{-1}$: 3064 (w), 2836 (w), 1692 (s), 1674 (s), 1610 (w), 1513 (m), 1383 (m), 1254 (m), 1169 (s), 1090 (w), 1032 (m), 832 (w), 796 (w), 737 (m), 597 (m), 565 (m). HRMS (ESI) (m/z): calc'd for C$_{27}$H$_{23}$N$_3$O$_5$S$_5$ [2M+H]$^+$: 1281.0375, found: 1281.0376. TLC (20% ethyl acetate in dichloromethane), Rf: 0.53 (UV, CAM).

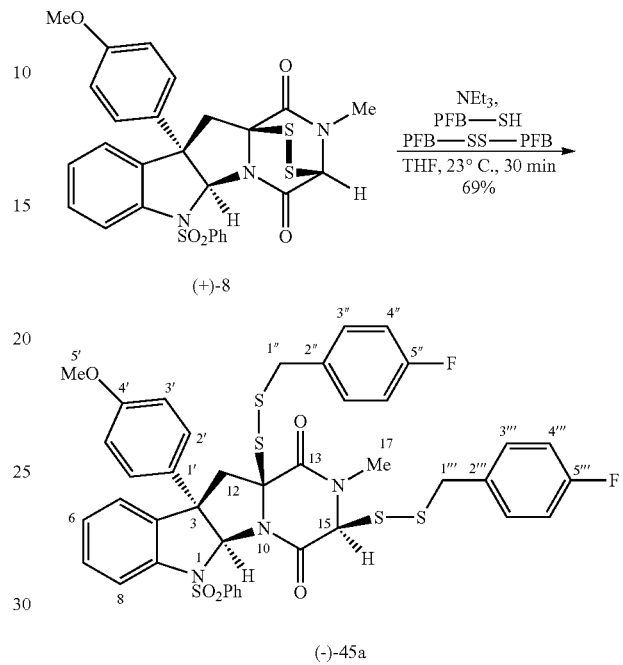

Example 30: Bis(p-fluorobenzyl)disulfide (−)-45a

A solution of triethylamine (0.72 M, 54 µL, 39 µmol, 2.2 equiv) in tetrahydrofuran and a solution of (p-fluorophenyl)methanethiol (PFB-SH, 0.41 M, 22 µL, 9.0 mol, 0.51 equiv) in tetrahydrofuran were added dropwise via syringe to a solution of epidithiodiketopiperazine (+)-8 (10.0 mg, 17.7 µmol, 1 equiv) and 1,2-bis(p-fluorobenzyl)disulfane (PFB-SS-PFB, 15.2 mg, 54.0 mmol, 3.05 equiv) in tetrahydrofuran (0.9 mL). After 30 min, the reaction mixture was concentrated under reduced pressure. The resulting residue was purified by flash column chromatography on silica gel (eluent: 2→50% ethyl acetate in dichloromethane) to afford bisdisulfide (−)-45a (10.3 mg, 68.6%) as a white solid, epitrithiodiketopiperazine 31 (0.2 mg, 2%) as a white solid, and unreacted epidithiodiketopiperazine (+)-8 (1.7 mg, 17%) as a white solid. Structural assignments were made with additional information from gCOSY, gHSQC, and gHMBC experiments. $^1$H NMR (500 MHz, CDCl$_3$, 25° C.): δ 7.64 (d, J=8.1 Hz, 1H, C$_8$H), 7.59 (app-d, J=7.4 Hz, 2H, SO$_2$Ph-o-H), 7.42-7.31 (m, 4H, C$_{3''/3'''}$H, SO$_2$Ph-p-H, C$_7$H), 7.19-7.13 (m, 4H, SO$_2$Ph-m-H, C$_5$H, C$_6$H), 7.08 (dd, J=8.6, 5.4 Hz, 2H, C$_{3''/3'''}$H), 7.04 (d, J=8.7 Hz, 2H, C$_{4''/4'''}$H), 6.91 (t, J=8.7 Hz, 2H, C$_{4''/4'''}$H), 6.74 (app-d, J=8.8 Hz, 2H, C$_{2'}$H), 6.63 (app-d, J=8.9 Hz, 2H, C$_{3'}$H), 6.59 (s, 1H, C$_2$H), 4.91 (s, 1H, C$_{15}$H), 4.21 (d, J=12.8 Hz, 1H, C$_{1''/1'''}$H), 4.01 (d, J=12.8 Hz, 1H, C$_{1''/1'''}$H), 3.83 (d, J=12.3 Hz, 1H, C$_{1''/1'''}$H), 3.79 (d, J=12.6 Hz, 1H, C$_{1''/1'''}$H), 3.77 (s, 3H, C$_{5'}$H), 3.55 (d, J=14.8 Hz, 1H, C$_{12}$H$_a$), 3.12 (s, 3H, C$_{17}$H), 3.06 (d, J=14.9 Hz, 1H, C$_{12}$H$_b$). $^{13}$C NMR (100 MHz, CDCl$_3$, 25° C.): δ 165.7 (C$_{13}$), 162.5 (C$_{16}$), 162.4 (d, J=246 Hz, Cs$_{5''/5'''}$), 162.3 (d, J=246 Hz, C$_{5''/5'''}$), 158.7 (C$_{5'}$), 142.1 (C$_9$), 138.5 (SO$_2$Ph-ipso-C), 135.8 (C$_4$), 133.1 (SO$_2$Ph-p-C), 133.1 (C$_{1'}$), 132.4 (d, J=3.3 Hz, C$_{2''/2'''}$), 132.1 (d, J=3.1 Hz, C$_{2''/2'''}$), 131.8 (d, J=8.2 Hz, C$_{3''/3'''}$), 131.2 (d, J=8.1 Hz, C$_{3''/3'''}$), 129.5 (C$_7$), 128.9 (SO$_2$Ph-m-C), 127.4 (C$_{2'}$), 127.4 (SO$_2$Ph-o-C), 125.8 (C$_{5/6}$), 125.4 (C$_{5/6}$), 118.1 (C$_8$), 115.6 (d, J=21.6 Hz, C$_{4''/4'''}$), 115.5 (d, J=21.5 Hz, C$_{4''/4'''}$), 114.4 (C$_{3'}$), 87.4 (C$_2$), 77.7 (C$_{15}$), 73.9 (C$_{11}$), 57.4 (C$_3$), 55.5 (C$_{5'}$), 47.1 (C$_{12}$), 42.5 (C$_{1''/1'''}$), 42.1 (C$_{1''/1'''}$), 32.6 (C$_{17}$). FTIR (thin film) cm$^{-1}$: 2937 (w), 1695 (m), 1672 (m), 1509 (s), 1384 (m), 1222 (m), 1033 (w), 833 (w), 597 (w). HRMS (ESI) (m/z): calc'd for C$_{41}$H$_{36}$N$_3$O$_5$S$_5$F$_2$ [M+H]$^+$: 848.1221, found: 848.1223. [α]$_D^{23}$: −49 (c=0.24, CHCl$_3$). TLC (10% ethyl acetate in dichloromethane), Rf: 0.53 (UV, CAM).

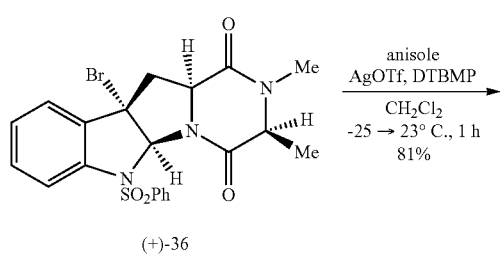

(+)-36

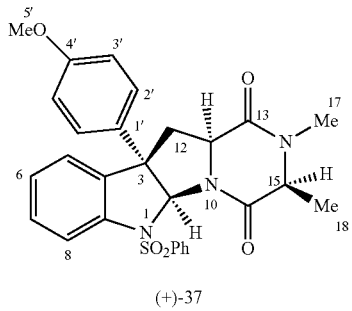

(+)-37

Example 31: Anisole Adduct (+)-37

Endo-tetracyclic bromide[55] (+)-36 (2.01 g, 4.10 mmol, 1 equiv) and 2,6-di-tert-butyl-4-methylpyridine (DTBMP, 2.11 g, 10.3 mmol, 2.51 equiv) were azeotropically dried by concentration from anhydrous benzene (2×10 mL) under reduced pressure. Dichloromethane (40 mL) and anisole (8.9 mL, 82 mmol, 20 equiv) were added sequentially, and the resulting colorless solution was cooled to −25° C. Silver trifluoromethanesulfonate (AgOTf, 2.11 g, 8.21 mmol, 2.00 equiv) was added as a solid in one portion, the reaction mixture was stirred at −25° C. for 30 min, then the cold bath was removed and the resulting mixture was allowed to stir and warm to room temperature. After 30 min, the suspension was diluted with dichloromethane (200 mL) and was washed with a mixture of deionized water, saturated aqueous sodium thiosulfate solution, and saturated aqueous sodium bicarbonate solution (2:1:1, 2×300 mL). The aqueous layers were extracted with dichloromethane (2×100 mL), and the combined organic extracts were washed sequentially with deionized water (250 mL) and with a saturated aqueous sodium chloride solution (150 mL). The combined aqueous layers were extracted with dichloromethane (100 mL), and the combined organic extracts were dried over anhydrous sodium sulfate, were filtered, and were concentrated under reduced pressure. The resulting foam was purified by flash column chromatography on silica gel (eluent: 0→50% acetone in chloroform) to afford anisole adduct (+)-37 (1.72 g, 81.2%) as a white foam. Structural assignments were made with additional information from gCOSY, gHSQC, and gHMBC experiments. $^1$H NMR (400 MHz, CDCl$_3$, 25° C.): δ 7.61 (d, J=8.1 Hz, 1H, C$_8$H), 7.45 (app-d, J=8.4 Hz, 2H, SO$_2$Ph-o-H), 7.32 (app-t, J=7.5 Hz, 1H, SO$_2$Ph-p-H), 7.30-7.26 (m, 1H, C$_7$H) 7.14-7.11 (m, 2H, C$_5$H, C$_6$H), 7.09 (app-t, J=7.9 Hz, 2H, SO$_2$Ph-m-H), 6.67 (app-d, J=8.8 Hz, 2H, C$_2$·H), 6.61 (app-d, J=8.9 Hz, 2H, C$_3$·H), 6.15 (s, 1H, C$_2$H), 4.39 (dd, J=5.6, 9.0 Hz, 1H, C$_{11}$H), 4.04 (q, J=7.0 Hz, 1H, C$_{15}$H), 3.77 (s, 3H, C$_5$·H), 3.14 (dd, J=6.5, 14.1 Hz, 1H, C$_{12}$H$_a$), 2.87 (dd, J=8.9, 14.0 Hz, 1H, C$_{12}$H$_b$), 2.85 (s, 3H, C$_{17}$H), 1.58 (d, J=7.1 Hz, 3H, C$_{18}$H). $^{13}$C NMR (100 MHz, CDCl$_3$, 25° C.): δ 168.4 (C$_{13}$), 167.9 (C$_{16}$), 158.7 (C$_{4'}$), 139.9 (C$_9$), 138.3 (SO$_2$Ph-ipso-C), 135.7 (C$_4$), 132.8 (SO$_2$Ph-p-C, C$_{1'}$), 129.2 (C$_7$), 128.6 (SO$_2$Ph-m-C), 128.1 (C$_{2'}$), 127.5 (SO$_2$Ph-o-C), 126.0 (C$_5$), 125.3 (C$_6$), 117.2 (C$_8$), 114.4 (C$_{3'}$), 87.3 (C$_2$), 59.4 (C$_3$), 58.8 (C$_{11}$), 57.1 (C$_{15}$), 55.4 (C$_{5'}$), 39.0 (C$_{12}$), 29.6 (C$_{17}$), 14.5 (C$_{18}$). FTIR (thin film) cm$^{-1}$: 2994 (w), 1677 (s), 1513 (m), 1253 (m), 1169 (s), 1031 (w), 832 (w), 757 (w), 602 (m). HRMS (ESI) (m/z): calc'd for C$_{28}$H$_{28}$N$_3$O$_5$S [M+H]$^+$: 519.1775, found: 519.1775. [α]$_D^{23}$: +58 (c=0.30, CHCl$_3$). TLC (20% acetone in chloroform), Rf: 0.26 (UV, CAM).

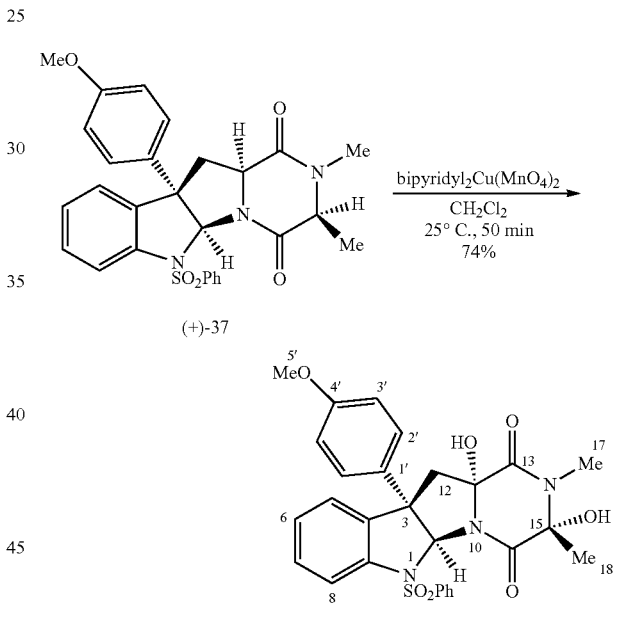

(+)-37

38

Example 32: Diol 38

Bis(2,2'-bipyridyl)copper(II) permanganate[56] (1.61 g, 2.62 mmol, 2.70 equiv) was added as a solid to solution of anisole adduct (+)-37 (502 mg, 0.970 mmol, 1 equiv) in dichloromethane (10 mL) at 23° C. After 50 min, the reaction mixture was diluted with dichloromethane (100 mL) and was poured into an aqueous sodium bisulfite solution (1 M, 200 mL). The layers were separated, and the organic layer was washed sequentially with an aqueous sodium bisulfite solution (1 M, 75 mL), with a mixture of a saturated aqueous copper(II) sulfate solution and deionized water (1:1, 100 mL), with a saturated aqueous ammonium chloride solution (100 mL), and with a saturated aqueous sodium chloride solution (100 mL). The aqueous layers were separately extracted with dichloromethane (2×75 mL). The combined organic extracts were dried over anhydrous sodium sulfate, were filtered, and were concentrated under reduced pressure. The resulting light blue foam was purified by flash column chromatography on silica gel (eluent: 0→30% acetone in dichloromethane) to afford diol 38 (393 mg, 74%) as a white foam. Structural assignments were made with additional information from gCOSY, gHSQC, and gHMBC experiments. $^1$H NMR (400 MHz, CDCl$_3$, 25° C.): δ7.61 (d, J=8.1 Hz, 1H, C$_8$H), 7.34-7.26 (m, 4H, C$_7$H, SO$_2$Ph-p-H, SO$_2$Ph-o-H), 7.22-7.15 (m, 2H, C$_5$H, C$_6$H), 7.02 (app-t, J=7.9 Hz, 2H, SO$_2$Ph-m-H), 6.78 (app-d, J=8.9 Hz, 2H, C$_2$H), 6.55 (app-d, J=8.9 Hz, 2H, C$_3$H), 6.35, (s, 1H, C$_2$H), 5.62 (br-s, 1H, OH), 5.24 (br-s, 1H, OH), 3.76 (s, 3H, C$_5$H), 3.38 (d, J=15.1 Hz, 1H, C$_{12a}$H), 2.99 (s, 3H, C$_{17}$H), 2.92 (d, J=15.1 Hz, 1H, C$_{12b}$H), 1.81 (s, 3H, C$_{18}$H). $^{13}$C NMR (100 MHz, CDCl$_3$, 25° C.): δ 168.2 (C$_{13}$), 166.8 (C$_{16}$), 158.4 (C$_{4'}$), 140.0 (C$_9$), 138.2 (SO$_2$Ph-ipso-C), 137.7 (C$_4$), 133.9 (C$_{1'}$), 132.9 (SO$_2$Ph-p-C), 129.1 (C$_7$), 128.6 (SO$_2$Ph-m-C/C$_{2'}$), 128.5 (SO$_2$Ph-m-C/C$_{2'}$), 127.5 (SO$_2$Ph-o-C), 126.5 (C$_5$), 126.1 (C$_6$), 118.0 (C$_8$), 114.3 (C$_{3'}$), 88.7 (C$_2$), 87.4 (C$_{11}$), 85.8 (C$_{15}$), 58.1 (C$_3$), 55.4 (C$_{5'}$), 49.6 (C$_{12}$), 28.2 (C$_{17}$), 22.8 (C$_{18}$). FTIR (thin film) cm$^{-1}$: 3375 (br), 3067 (w), 1687 (m), 1512 (m), 1361 (m), 1252 (m), 1169 (s), 832 (m), 737 (w), 600 (m), HRMS (ESI) (m/z): calc'd for C$_{48}$H$_{59}$N$_9$O$_{17}$S$_5$ [M+H]$^+$: 550.1642, found: 550.1640. TLC (20% acetone in dichloromethane), Rf: 0.22 (UV, CAM).

chloride solution (100 mL). The aqueous layer was extracted with ethyl acetate-hexanes (4:1, 2×60 mL), and the combined organic extracts were washed sequentially with deionized water (3×100 mL) and with a saturated aqueous sodium chloride solution (100 mL). The combined aqueous layers were extracted with a single portion of ethyl acetate-hexanes (3:1, 100 mL), and the organic extract was washed sequentially with deionized water (3×50 mL) and with a saturated aqueous sodium chloride solution (50 mL). The combined organic extracts were dried over anhydrous sodium sulfate, were filtered, and were concentrated under reduced pressure. The resulting white foam was purified by flash column chromatography on silica gel (eluent: 0→30% acetone in hexanes) to afford a mixture of regioisomeric O-TBS protected monoalcohols S$_{15}$ and S$_{16}$ (1.01 g, 84%, 1.1:1) as a white foam. Analytical samples of O-TBS protected monoalcohols S$_{15}$ and S$_{16}$ were obtained by flash column chromatography on silica gel (eluent: 0→10% diethyl ether in dichloromethane). Structural assignments were made with additional information from gCOSY, gHSQC, and gHMBC experiments.

Example 34: Monoalcohol S15

$^1$H NMR (400 MHz, CDCl$_3$, 25° C.): δ 7.60 (d, J=8.0 Hz, 1H, C$_8$H), 7.33-7.23 (m, 4H, C$_7$H, SO$_2$Ph-p-H, SO$_2$Ph-o-H), 7.20-7.15 (m, 2H, C$_5$H, C$_6$H), 6.99 (app-t, J=7.9 Hz, 2H,

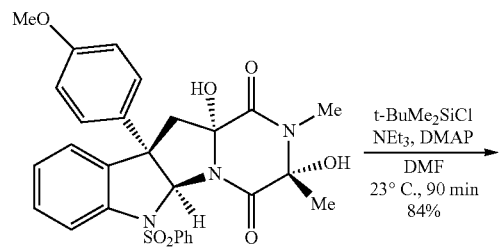

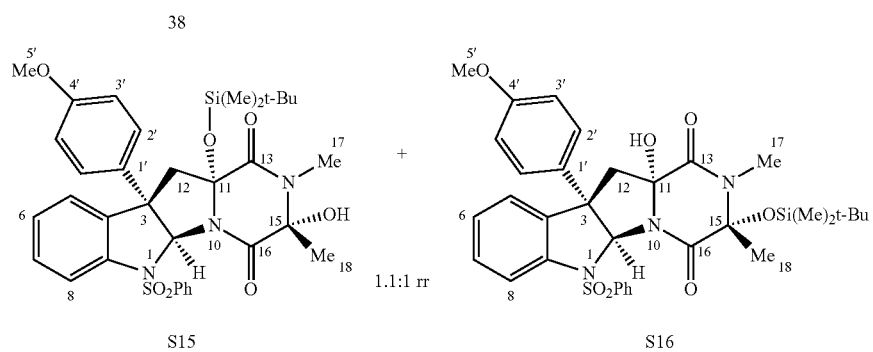

Example 33: O-TBS Protected Monoalcohols S$_{15}$ and S$_{16}$

Diol 38 (1.00 g, 1.82 mmol, 1 equiv) was azeotropically dried by concentration from anhydrous dichloromethane (2.5 mL) and anhydrous benzene (9.0 mL) under reduced pressure. The flask was charged with 4-(dimethylamino) pyridine (DMAP, 10.2 mg, 83.5 μmol, 0.0459 equiv), and the solids were dissolved in N,N-dimethylformamide (18 mL). Triethylamine (0.76 mL, 5.45 mmol, 3.00 equiv) was then added via syringe followed immediately by tert-butyldimethylsilyl chloride (352 mg, 2.34 mmol, 1.29 equiv) as a solid in one portion. After 90 min, the white suspension was diluted with ethyl acetate-hexanes (4:1, 125 mL) and was washed with a saturated aqueous ammonium SO$_2$Ph-m-H), 6.71 (app-d, J=8.9 Hz, 2H, C$_{2'}$H), 6.56 (app-d, J=8.9 Hz, 2H, C$_{3'}$H), 6.42 (s, 1H, C$_2$H), 3.82 (s, 1H, C$_{15}$OH), 3.78 (s, 3H, C$_5$H$_3$), 3.53 (d, J=15.0 Hz, 1H, C$_{12}$H$_a$), 2.93 (s, 3H, C$_{17}$H), 2.78 (d, J=15.1 Hz, 1H, C$_{12}$H$_b$), 1.65 (s, 3H, C$_{18}$H), 0.97 (s, 9H, SiC(CH$_3$)$_3$), 0.23 (s, 3H, SiCH$_3$), 0.09 (s, 3H, SiCH$_3$). $^{13}$C NMR (100 MHz, CDCl$_3$, 25° C.): δ 167.3 (C$_{16}$), 166.3 (C$_{13}$), 158.6 (C$_{4'}$), 139.9 (C$_9$), 138.6 (SO$_2$Ph-ipso-C), 136.9 (C$_4$), 133.4 (C$_{1'}$), 132.7 (SO$_2$Ph-p-C), 129.2 (C$_7$), 128.5 (SO$_2$Ph-m-C), 128.3 (C$_{2'}$), 127.3 (SO$_2$Ph-o-C), 126.4 (C$_5$), 125.9 (C$_6$), 118.0 (C$_8$), 114.3 (C$_{3'}$), 89.2 (C$_{11}$), 88.2 (C$_2$), 85.2 (C$_{15}$), 58.3 (C$_3$), 55.5 (C$_{5'}$), 50.7 (C$_{12}$), 27.9 (C$_{17}$), 25.8 (SiC(CH$_3$)$_3$) 24.2 (C$_{18}$), 18.4 (SiC(CH$_3$)$_3$), −3.3 (SiCH$_3$), −4.6 (SiCH$_3$). FTIR (thin film) cm$^{-1}$: 3450 (br-w), 2956 (w), 2931 (w), 1677 (m), 1513 (m), 1254 (s), 1170 (s), 829 (m), 687 (w), 601 (m).

HRMS (ESI) (m/z): calc'd for $C_{34}H_{42}N_3O_7SSi$ [M+H]$^+$: 664.2507, found: 665.2508. TLC (40% acetone in hexanes), Rf: 0.43 (UV, CAM). TLC (7% diethyl ether in dichloromethane), Rf: 0.26 (UV, CAM).

Example 35: Monoalcohol S16

$^1$H NMR (400 MHz, CDCl$_3$, 25° C.): δ 7.61 (d, J=8.1 Hz, 1H, C$_8$H), 7.31-7.25 (m, 4H, C$_7$H, SO$_2$Ph-p-H, SO$_2$Ph-o-H), 7.17-7.14 (m, 2H, C$_5$H, C$_6$H), 7.00 (app-t, J=7.9 Hz, 2H, SO$_2$Ph-m-H), 6.74 (app-d, J=8.8 Hz, 2H, C$_2$,H), 6.58 (app-d, J=8.9 Hz, 2H, C$_3$,H), 6.30 (s, 1H, C$_2$H), 4.84 (s, 1H, C$_{11}$OH), 3.78 (s, 3H, C$_5$,H$_3$), 3.37 (d, J=15.1 Hz, 1H, C$_{12}$H$_a$), 2.97 (s, 3H, C$_{17}$H), 2.84 (d, J=15.1 Hz, 1H, C$_{12}$H$_b$), 1.83 (s, 3H, C$_{18}$H), 0.92 (s, 9H, SiC(CH$_3$)$_3$), 0.33 (s, 3H, SiCH$_3$), 0.32 (s, 3H, SiCH$_3$). $^{13}$C NMR (100 MHz, CDCl$_3$, 25° C.): δ 167.9 (C$_{13}$), 164.8 (C$_{16}$), 158.4 (C$_4$,), 140.1 (C$_9$), 138.4 (SO$_2$Ph-ipso-C), 137.7 (C$_4$), 134.1 (C$_1$,), 132.8 (SO$_2$Ph-p-C), 129.0 (C$_7$), 128.5 (SO$_2$Ph-m-C, C$_2$,), 127.5 (SO$_2$Ph-o-C), 126.4 (C$_5$), 125.9 (C$_6$), 117.9 (C$_8$), 114.2 (C$_3$,), 88.9 (C$_2$), 87.9 (C$_{15}$), 87.3 (C$_{11}$), 58.0 (C$_3$), 55.4 (C$_5$,), 49.2 (C$_{12}$), 28.1 (C$_{17}$), 25.7 (SiC(CH$_3$)$_3$), 23.5 (C$_{18}$), 18.2 (SiC(CH$_3$)$_3$), −2.3 (SiCH$_3$), −3.4 (SiCH$_3$). FTIR (thin film) cm$^{-1}$: 3415 (br-w), 2930 (w), 2859 (w), 2102 (w), 1714 (w), 1513 (w), 1365 (m), 1253 (s), 1171 (s), 833 (m), 601 (w). HRMS (ESI) (m/z): calc'd for $C_{34}H_{42}N_3O_7SSiNa$ [M+H]$^+$: 664.2507, found: 664.2499. TLC (40% acetone in hexanes), Rf: 0.43 (UV, CAM). TLC (7% diethyl ether in dichloromethane), Rf: 0.53 (UV, CAM).

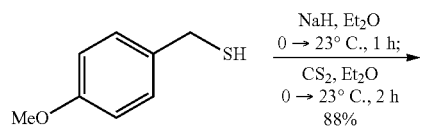

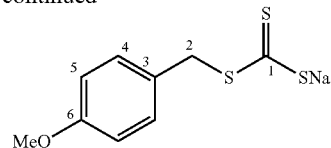

Example 36: Sodium p-methoxybenzyl trithiocarbonate 39

A suspension of sodium hydride (60% dispersion, 1.03 g, 25.8 mmol, 1 equiv) in diethyl ether (125 mL) at 0° C. was sparged with argon for 20 min by discharge of a balloon equipped with a needle extending into the reaction mixture. p-Methoxybenzyl thiol (4.5 mL, 33 mmol, 1.3 equiv) was added dropwise via syringe over 2 min, the solution was stirred for 5 min, then the ice-water bath was removed and the reaction mixture was allowed to stir and warm to 23° C. After 1 h, the light-gray suspension was cooled to 0° C., and carbon disulfide (2.0 mL, 33 mmol, 1.3 equiv) was added dropwise via syringe over 3.5 min. The ice-water bath was removed and the reaction mixture was allowed to stir and warm to 23° C. After 2 h, a yellow precipitate was collected by filtration of the yellow suspension through a 350-mL medium-porosity fritted-glass funnel. The yellow precipitate was washed with hexanes (2×50 mL) and was dried under reduced pressure to afford sodium p-methoxybenzyl trithiocarbonate 39 (5.76 g, 88.4%) as a yellow solid. Structural assignments were made with additional information from gCOSY, gHSQC, and gHMBC experiments. $^1$H NMR (500 MHz, DMSO-d$_6$, 25° C.): δ 7.20 (d, J=8.6 Hz, 2H, C$_4$H), 6.81 (d, J=8.6 Hz, 2H, C$_5$H), 4.29 (s, 2H, C$_2$H), 3.70 (s, 3H, OCH$_3$). $^{13}$C NMR (125 MHz, DMSO-d$_6$, 25° C.): δ 239.0 (C$_1$), 157.8 (C$_6$), 130.9 (C$_3$), 129.8 (C$_4$), 113.6 (C$_5$), 55.0 (OCH$_3$), 44.6 (C$_2$). FTIR (thin film) cm$^{-1}$: 1507 (w), 1248 (w), 1229 (w), 1177 (w), 1003 (s), 833 (m), 539 (m). HRMS (DART-TOF) (m/z): calc'd for $C_9H_9OS_3$ [M-Na]$^-$: 228.9821, found: 228.9813.

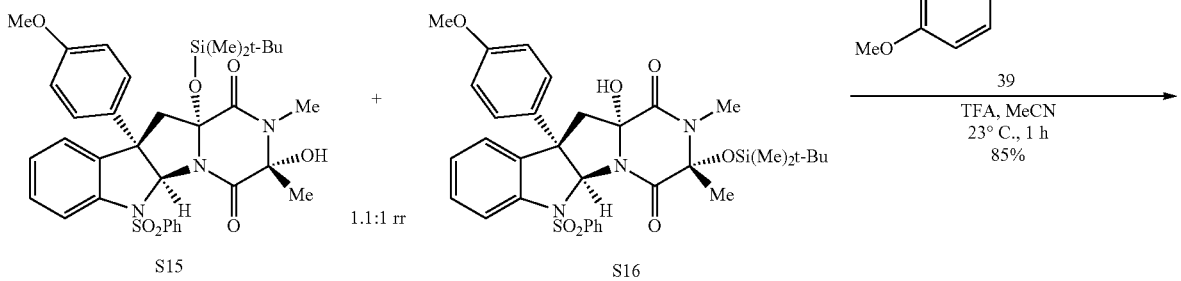

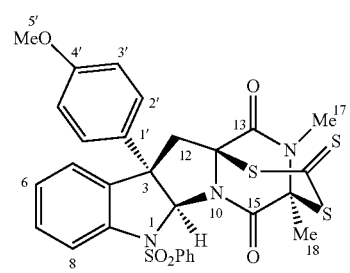

Example 37: Dithiepanethione (+)-41

A mixture of regioisomeric O-TBS protected monoalcohols $S_{15}$ and $S_{16}$ (1.1:1, 956 mg, 1.44 mmol, 1 equiv) was azeotropically dried by concentration from dichloromethane (5 mL) and anhydrous benzene (50 mL) under reduced pressure. The resulting white foam was dissolved in acetonitrile (100 mL) via cannula, and trithiocarbonate 39 (1.82 g, 7.21 mmol, 5.01 equiv) was added as a solid. Trifluoroacetic acid (TFA, 50 mL) was poured rapidly into the reaction mixture over 15 seconds, resulting in a homogeneous yellow solution. After 1 h, the dark orange solution was diluted with ethyl acetate-hexanes (9:1, 100 mL), was slowly poured into a saturated aqueous sodium bicarbonate solution (650 mL), and the biphasic mixture was stirred vigorously for 30 min. The aqueous layer was extracted with ethyl acetate-hexanes (9:1, 2×100 mL), and the combined organic extracts were washed sequentially with deionized water (200 mL) and with a saturated aqueous sodium chloride solution (150 mL). The combined aqueous layers were extracted with a single portion of ethyl acetate-hexanes (4:1, 100 mL), and the combined organic extracts were dried over anhydrous sodium sulfate, were filtered, and were concentrated under reduced pressure. The resulting residue was purified by flash column chromatography on silica gel (eluent: 0→7.5% diethyl ether in dichloromethane) to afford dithiepanethione (+)-41 (766 mg, 85.0%) as a yellow foam. Structural assignments were made with additional information from gCOSY, gHSQC, and gHMBC experiments. $^1$H NMR (400 MHz, CDCl$_3$, 25° C.): δ 7.55 (d, J=8.1 Hz, 1H, C$_8$H), 7.43 (app-d, J=7.6 Hz, 2H, SO$_2$Ph-o-H), 7.30-7.21 (m, 2H, C$_7$H, SO$_2$Ph-p-H), 7.30-7.21 (m, 2H, C$_5$H, C$_6$H), 7.13 (app-t, 2H, J=7.9 Hz, SO$_2$Ph-m-H), 6.87 (app-d, J=8.8 Hz, 2H, C$_{2'}$H), 6.68 (app-d, J=8.8 Hz, 2H, C$_{3'}$H), 6.59 (s, 1H, C$_2$H), 3.78 (s, 3H, C$_{5'}$H), 3.53 (d, J=15.3 Hz, 1H, C$_{12}$H$_a$), 3.06 (s, 3H, C$_{17}$H), 3.05 (d, J=15.2 Hz, 1H, C$_{12}$H$_b$), 1.92 (s, 3H, C$_{18}$). $^{13}$C NMR (100 MHz, CDCl$_3$, 25° C.): 215.7 (CS$_3$), 164.7 (C$_{13}$), 160.5 (C$_{16}$), 159.0 (C$_{4'}$), 141.5 (C$_9$), 138.9 (SO$_2$Ph-ipso-C), 134.9 (C$_4$), 133.1 (SO$_2$Ph-p-C), 131.4 (C$_{1'}$), 130.1 (C$_7$), 128.7 (SO$_2$Ph-m-C), 127.5 (C$_{2'}$), 126.8 (SO$_2$Ph-o-C), 126.4 (C$_6$), 125.5 (C$_5$), 118.7 (C$_8$), 114.6 (C$_{3'}$), 87.8 (C$_2$), 75.0 (C$_{11}$), 73.5 (C$_{15}$), 57.8 (C$_3$), 55.5 (C$_{5'}$), 48.7 (C$_{12}$), 28.4 (C$_{17}$), 19.8 (C$_{18}$). FTIR (thin film) cm$^{-1}$: 3002 (w), 1713 (s), 1685 (s), 1476 (w), 1362 (s), 1169 (s), 1034 (m), 999 (m), 895 (w), 737 (m), 599 (m). HRMS (ESI) (m/z): calc'd for C$_{29}$H$_{26}$N$_3$O$_5$S$_4$[M+H]$^+$: 624.0750, found: 624.0747. [α]$_D^{23}$: +148 (c=0.61, CHCl$_3$). TLC (5% diethyl ether in dichloromethane), Rf: 0.31 (UV, CAM).

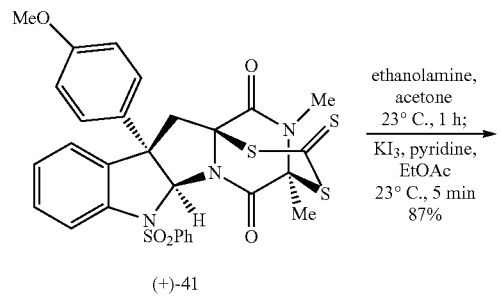

(+)-41

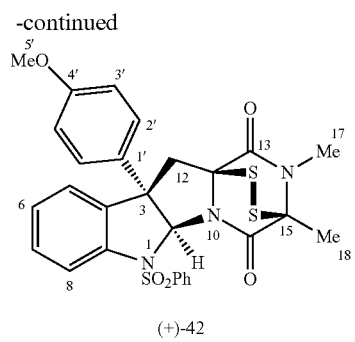

(+)-42

Example 38: Epidithiodiketopiperazine (+)-42

A yellow solution of dithiepanethione (+)-41 (374 mg, 0.600 mmol, 1 equiv) in acetone (15 mL) at 23° C. was sparged with argon for 10 min by discharge of a balloon equipped with a needle extending into the reaction mixture. Ethanolamine (3.75 mL) was added via syringe over 30 seconds, resulting in a nearly colorless solution. After 1 h, the reaction mixture was diluted with ethyl acetate-hexanes (9:1, 100 mL) and was washed with an aqueous hydrogen chloride solution (1 M, 150 mL). The aqueous layer was extracted with ethyl acetate-hexanes (9:1, 2×50 mL), and the combined organic extracts were washed with a saturated aqueous sodium chloride solution (100 mL). A stock solution of potassium triiodide in pyridine$^{43}$ was added dropwise into the organic layer containing crude bisthiol until a persistent yellow color was observed. The resulting mixture was washed sequentially with an aqueous hydrogen chloride solution (1 M, 2×75 mL), with a mixture of deionized water and a saturated aqueous sodium thiosulfate solution (3:1, 100 mL), with deionized water (100 mL), and with a saturated aqueous sodium chloride solution (100 mL). The aqueous layers were separately extracted with a single portion of ethyl acetate-hexanes (9:1, 100 mL). The combined organic extracts were dried over anhydrous sodium sulfate, were filtered, and were concentrated under reduced pressure. The resulting residue was purified by flash column chromatography on silica gel (eluent: 15% dichloromethane, 0→7.5% isopropanol in hexanes) to afford epidithiodiketopiperazine (+)-42 (304 mg, 87.0%) as a white solid. Structural assignments were made with additional information from gCOSY, gHSQC, and gHMBC experiments.$^{57}$ $^1$H NMR (500 MHz, CDCl$_3$, 25° C.): δ 7.65 (d, J=8.0 Hz, 1H, C$_8$H), 7.40 (app-t, d, J=7.1, 1.5 Hz, 1H, C$_7$H), 7.34 (dd, J=8.5, 1.2 Hz, 2H, SO$_2$Ph-o-H), 7.31-7.22 (m, 3H, SO$_2$Ph-p-H, Hs, H$_6$), 7.02 (app-t, J=7.5 Hz, 2H, SO$_2$-m-H), 6.74 (app-d, J=8.8 Hz, 2H, C$_{2'}$H), 6.62 (app-d, J=8.7 Hz, 2H, C$_{3'}$H), 6.42 (s, 1H, C$_2$H), 3.79 (s, 3H, C$_{5'}$H), 3.67 (d, J=15.6 Hz, 1H, C$_{12}$H$_a$), 3.05 (s, 3H, C$_{17}$H), 2.88 (d, J=15.5 Hz, 1H, C$_{12}$H$_b$), 1.97 (s, 3H, C$_{18}$H). $^{13}$C NMR (100 MHz, CDCl$_3$, 25° C.): δ 165.8 (C$_{13}$), 161.4 (C$_{16}$), 158.8 (C$_{4'}$), 141.2 (C$_9$), 138.3 (SO$_2$Ph-ipso-C), 135.8 (C$_4$), 132.9 (SO$_2$Ph-p-C), 131.4 (C$_{1'}$), 129.7 (C$_7$), 128.5 (SO$_2$Ph-m-C), 127.9 (C$_{2'}$), 127.2 (SO$_2$Ph-o-C), 126.1 (C$_6$), 125.6 (C$_5$), 119.0 (C$_8$), 114.5 (C$_{3'}$), 88.0 (C$_2$), 73.9 (C$_{11}$), 73.5 (C$_{15}$), 59.1 (C$_3$), 55.5 (C$_{5'}$), 46.1 (C$_{12}$), 27.6 (C$_{17}$), 18.2 (C$_{18}$). FTIR (thin film) cm$^{-1}$: 2951 (br), 2359 (w), 1679 (s), 1514 (s), 1457 (m), 1341 (m), 1249 (s), 1163 (s), 1028 (m), 905 (m), 730 (s). HRMS (ESI) (m/z): calc'd for C$_{28}$H$_{26}$N$_3$O$_5$S$_3$[M+H]$^+$: 580.1029, found: 580.1032. [α]$_D^{23}$: +293 (c=0.57, CHCl$_3$).

TLC (15% dichloromethane and 15% isopropanol in hexanes), Rf: 0.42 (UV, CAM).

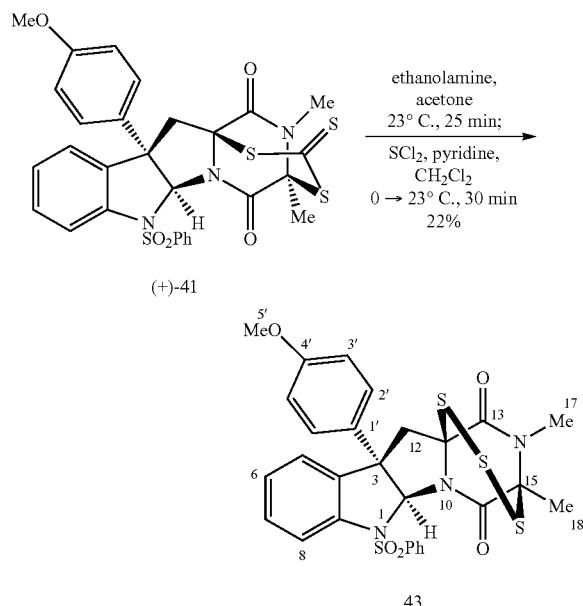

Example 39: Epitrithiodiketopiperazine 43

A yellow solution of dithiepanethione (+)-41 (30.2 mg, 48.4 µmol, 1 equiv) in acetone (1.6 mL) at 23° C. was sparged with argon for 10 min by discharge of a balloon equipped with a needle extending into the reaction mixture. Ethanolamine (0.4 mL) was added via syringe over 30 seconds, resulting in a nearly colorless solution. After 25 min, the reaction mixture was diluted with dichloromethane (30 mL) and was washed with an aqueous hydrogen chloride solution (1 M, 2×30 mL). The combined aqueous layers were extracted with dichloromethane (30 mL), and the combined organic extracts were washed with a saturated aqueous sodium chloride solution (30 mL). The aqueous layer was extracted with dichloromethane (15 mL). The combined organic extracts were dried over anhydrous sodium sulfate, were filtered, and were sparged with argon for 15 min by discharge of a balloon equipped with a needle extending into the stirring reaction mixture. The reaction mixture was then concentrated under reduced pressure to approximately 25 mL and was cooled to 0° C. Pyridine (25 µL, 310 µmol, 6.4 equiv) was added via syringe to the crude bisthiol solution, followed by the dropwise addition of a solution of monosulfur dichloride (0.39 M, 0.50 mL, 0.20 mmol, 4.1 equiv) in dichloromethane via syringe over 30 seconds. The reaction mixture was removed from the ice-water bath and allowed to stir and warm to 23° C. After 30 min, the reaction mixture was washed sequentially with a saturated aqueous sodium bicarbonate solution (2×30 mL) and with a saturated aqueous ammonium chloride solution (2×40 mL). The aqueous layers were separately extracted with a single portion of dichloromethane (20 mL). The combined organic extracts were dried over anhydrous sodium sulfate, were filtered, and were concentrated under reduced pressure. The resulting residue[58] was purified by flash column chromatography on silica gel (eluent: 0→20% ethyl acetate in dichloromethane) to afford epitrithiodiketopiperazine 43 (7.4 mg, 22%) as a white solid. Structural assignments were made with additional information from gCOSY, gHSQC, and gHMBC experiments. Based on $^1$H NMR analysis at 25° C. in CDCl$_3$, the product exists as a 3.5:1 mixture of major:minor conformers. $^1$H NMR (500 MHz, CDCl$_3$, 25° C.): Major conformer: δ 7.60 (m, 3H, SO$_2$Ph-o-H, C$_8$H), 7.48-7.36 (m, 2H, SO$_2$Ph-p-H, C$_7$H), 7.23-7.12 (m, 4H, SO$_2$Ph-m-H, C$_5$H, C$_6$H), 6.85 (app-d, J=8.8 Hz, 2H, C$_{2'}$H), 6.67 (app-d, J=8.8 Hz, 2H, C$_{3'}$H), 6.47 (s, 1H, C$_2$H), 3.77 (s, 3H, C$_{5'}$H), 3.41 (d, J=14.7 Hz, 1H, C$_{12}$H$_a$), 3.18 (s, 3H, C$_{17}$H), 3.12 (d, J=14.7 Hz, 1H, C$_{12}$H$_b$), 1.84 (s, 3H, C$_{18}$H). Minor conformer: δ 7.31 (m, 2H), 7.10-7.04 (m, 1H), 6.80 (app-d, J=8.8 Hz, 2H, C$_{2'}$H), 6.72 (s, 1H, C$_2$H), 6.64 (app-d, J=8.8 Hz, 2H, C$_{3'}$H), 3.78 (s, 3H, C$_{5'}$H), 3.28 (d, J=14.9 Hz, 1H, C$_{12}$H$_a$), 3.03-2.95 (m, 4H, C$_{17}$H, C$_{12}$H$_b$), 1.93 (s, 3H, C$_{18}$H). $^{13}$C NMR (150 MHz, CDCl$_3$, 25° C.): Major conformer: δ 168.8 (C$_{13}$), 163.8 (C$_{16}$), 159.0 (C$_{4'}$), 143.2 (C$_9$), 139.6 (SO$_2$Ph-ipso-C), 135.0 (C$_4$), 133.0 (SO$_2$Ph-p-C), 131.7 (C$_1$), 130.2 (C$_7$), 128.8 (SO$_2$Ph-m-C), 127.5 (C$_{2'}$), 127.1 (SO$_2$Ph-o-C), 125.8 (C$_5$), 125.8 (C$_6$), 118.9 (C$_8$), 114.6 (C$_{3'}$), 86.8 (C$_2$), 79.9 (C$_{11}$), 72.2 (C$_{15}$), 57.2 (C$_3$), 55.5 (C$_{5'}$), 51.7 (C$_{12}$), 28.5 (C$_{18}$), 21.8 (C$_{17}$). Minor conformer: δ 167.2 (C$_{13}$), 141.6 (C$_9$), 138.7 (SO$_2$Ph-ipso-C), 135.8 (C$_4$), 129.6, 129.2, 128.6, 127.8, 127.6, 126.3, 125.5, 118.8 (C$_8$), 88.8 (C$_2$), 75.7 (C$_{5/6}$), 75.5 (C$_{5/6}$), 57.5 (C$_3$), 49.8 (C$_{12}$), 29.2 (C$_{17}$), 24.1 (C$_{18}$). FTIR (thin film) cm$^{-1}$: 2936 (br-w), 1682 (s), 1513 (m), 1350 (s), 1167 (s), 1033 (m), 896 (w), 687 (w), 577 (m). HRMS (ESI) (m/z): calc'd for C$_{28}$H$_{26}$N$_3$O$_5$S$_4$[M+H]$^+$: 612.0750, found: 612.0748. TLC (10% ethyl acetate in dichloromethane), Rf: 0.42 (UV, CAM).

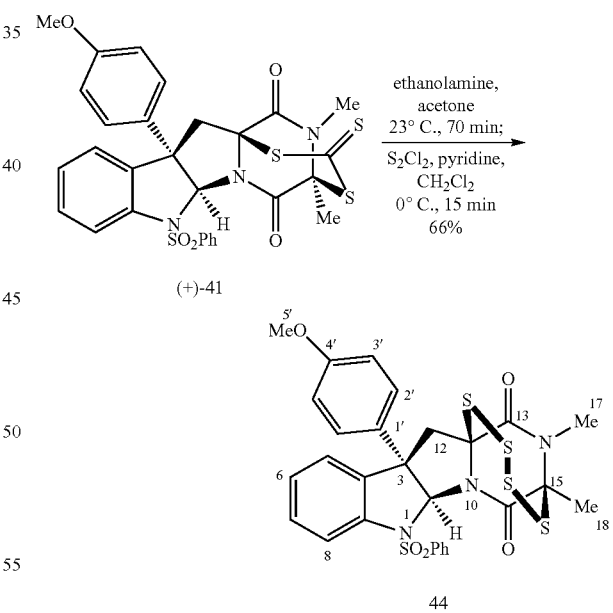

Example 40: Epitetrathiodiketopiperazine 44

A yellow solution of dithiepanethione (+)-41 (40.3 mg, 64.6 µmol, 1 equiv) in acetone (2.0 mL) at 23° C. was sparged with argon for 10 min by discharge of a balloon equipped with a needle extending into the reaction mixture. Ethanolamine (0.4 mL) was added via syringe over 30 seconds, resulting in a nearly colorless solution. After 70 min, the reaction mixture was diluted with dichloromethane (30 mL) and was washed with an aqueous hydrogen chloride solution (1 M, 2×30 mL). The combined aqueous layers were extracted with dichloromethane (30 mL), and the combined organic extracts were washed with a saturated aqueous sodium chloride solution (30 mL). The combined organic extracts were dried over anhydrous sodium sulfate, were filtered, and were sparged with argon for 15 min by discharge of a balloon equipped with a needle extending into the stirring reaction mixture. The reaction mixture was then concentrated under reduced pressure to approximately 30 mL and was cooled to 0° C. Pyridine (26 µL, 320 µmol, 5.0 equiv) was added via syringe to the stirring crude bisthiol solution, followed by the dropwise addition of a solution of disulfur dichloride (0.50 M, 0.50 mL, 250 µmol, 3.9 equiv) in dichloromethane via syringe over 30 seconds. After 15 min, the reaction mixture was washed with a saturated aqueous ammonium chloride solution (2×30 mL), and the combined aqueous layers were extracted with dichloromethane (25 mL). The combined organic extracts were washed with a saturated aqueous sodium chloride solution (45 mL), were dried over anhydrous sodium sulfate, were filtered, and were concentrated under reduced pressure. The resulting residue was purified by flash column chromatography on silica gel (eluent: 0→20% ethyl acetate in dichloromethane) to afford epitetrathiodiketopiperazine 44 (27.6 mg, 66.3%) as a white solid. Structural assignments were made with additional information from gCOSY, gHSQC, and gHMBC experiments. $^1$H NMR (500 MHz, CDCl$_3$, 25° C.): δ 7.96 (app-d, J=7.2 Hz, 2H, SO$_2$Ph-o-H), 7.54 (app-t, J=7.5 Hz, 1H, SO$_2$Ph-p-H), 7.48-7.39 (m, 3H, C$_8$H, SO$_2$Ph-m-H), 7.27-7.20 (m, 1H, C$_7$H), 7.05 (app-t, J=7.5, 1H, C$_6$H), 6.99 (d, J=7.6, 1H, C$_5$H), 6.89 (s, 1H, C$_2$H), 6.84 (app-d, J=8.8 Hz, 2H, C$_{2'}$H), 6.70 (app-d, J=8.8 Hz, 2H, C$_{3'}$H), 3.75 (s, 3H, C$_{5'}$H), 3.27 (d, J=14.4 Hz, 1H, C$_{12}$H$_a$), 3.10 (d, J=14.4 Hz, 1H, C$_{12}$H$_b$), 3.05 (s, 3H, C$_{17}$H), 1.98 (s, 3H, C$_{18}$H). $^{13}$C NMR (125 MHz, CDCl$_3$, 25° C.): δ 168.4 (C$_{13}$), 164.8 (C$_{16}$), 158.9 (C$_{4'}$), 141.7 (C$_9$), 139.1 (SO$_2$Ph-ipso-C), 136.8 (C$_4$), 133.8 (C$_{1'}$), 133.4 (SO$_2$Ph-p-C), 129.4 (C$_7$), 129.2 (SO$_2$Ph-m-C), 127.8 (SO$_2$Ph-o-C), 126.9 (C$_{2'}$), 125.5 (C$_6$), 124.6 (C$_5$), 116.5 (C$_8$), 114.5 (C$_{3'}$), 87.1 (C$_2$), 76.1 (C$_{11}$), 74.4 (C$_{15}$), 56.9 (C$_3$), 55.5 (C$_{5'}$), 49.9 (C$_{12}$), 29.6 (C$_{17}$), 22.8 (C$_{18}$). FTIR (thin film) cm$^{-1}$: 2930 (w), 1668 (s), 1610 (w), 1513 (m), 1354 (s), 1168 (s), 1032 (m), 899 (w), 738 (m), 565 (m). HRMS (ESI) (m/z): calc'd for C$_{28}$H$_{25}$N$_3$NaO$_5$S$_5$ [M+Na]$^+$: 666.0290, found: 666.0289. TLC (5% ethyl acetate in hexanes), Rf: 0.35 (UV, CAM).

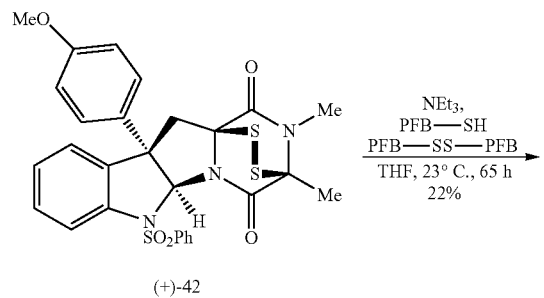

(+)-42

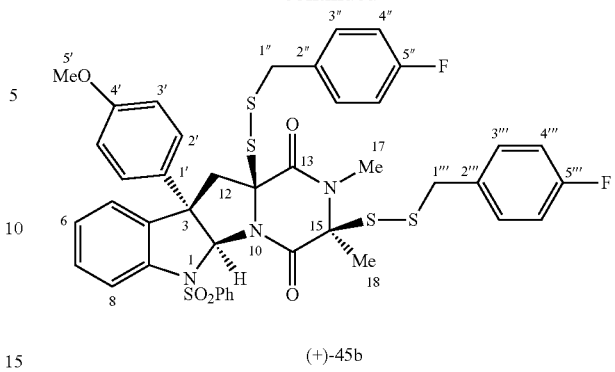

(+)-45b

Example 41: Bis(p-fluorobenzyl)disulfide (+)-45b

Triethylamine (70 µL, 0.50 mmol, 2.5 equiv) and (p-fluorophenyl)methanethiol (PFB-SH, 25 µL, 0.20 mmol, 1.0 equiv) were added via syringe to a solution of epidithiodiketopiperazine (+)-42 (116 mg, 0.200 mmol, 1 equiv) and 1,2-bis(p-fluorobenzyl)disulfane (PFB-SS-PFB, 552 mg, 1.95 mmol, 9.75 equiv) in tetrahydrofuran (0.5 mL) at 23° C. After 15 h, additional tetrahydrofuran (1.1 mL) was added via syringe to dissolve a white precipitate. After an additional 50 h, the reaction mixture was concentrated under reduced pressure and the resulting residue was purified by flash column chromatography on silica gel (eluent: 0→15% ethyl acetate in dichloromethane) to afford bisdisulfide (+)-45b (38.7 mg, 22.4%) as a white solid and unreacted epidithiodiketopiperazine (+)-42 (76.6 mg, 66.0%) as a white solid. Structural assignments were made with additional information from gCOSY, gHSQC, and gHMBC experiments. $^1$H NMR (400 MHz, CDCl$_3$, 25° C.): 7.67 (d, J=8.1 Hz, 1H, C$_8$H), 7.48 (app-d, J=7.6 Hz, 2H, SO$_2$Ph-o-H), 7.38-7.33 (m, 3H, C$_{3'''/3''''}$H, C$_7$H), 7.30 (app-t, J=7.7 Hz, 1H, SO$_2$Ph-p-H), 7.22-7.15 (m, 2H, C$_5$H, C$_6$H), 7.14-7.09 (m, 4H, C$_{3''/3'''}$H, SO$_2$Ph-m-H), 6.95 (app-t, J=8.7 Hz, 2H, C$_{4''/4'''}$), 6.90 (app-t, J=8.6 Hz, C$_{4''/4'''}$H), 6.67 (app-d, J=8.8 Hz, 2H, C$_{2'}$H), 6.59 (s, 1H, C$_2$H), 6.58 (app-d, J=9.1 Hz, 2H, C$_{3'}$H), 4.09 (d, J=12.9 Hz, 1H, C$_{1''/1'''}$H), 3.99 (d, J=12.9 Hz, 1H, C$_{1''/1'''}$H), 3.84 (d, J=14.7 Hz, 1H, C$_{12}$H$_a$), 3.83 (s, 2H, C$_{1''/1'''}$H), 3.76 (s, 3H, C$_{5'}$H), 3.10 (s, 3H, C$_{17}$H), 2.99 (d, J=14.8 Hz, 1H, C$_{12}$H$_b$), 2.09 (s, 3H, C$_{18}$H). $^{13}$C NMR (100 MHz, CDCl$_3$, 25° C.): δ 167.4 (C$_{13}$), 164.2 (C$_{16}$), 162.3 (d, J=245.6 Hz, C$_{5''/5'''}$), 162.3 (d, J=246.3 Hz, C$_{5''/5'''}$), 158.6 (C$_{4'}$), 142.2 (C$_9$), 137.9 (SO$_2$Ph-ipso-C), 135.5 (C$_4$), 133.2 (C$_1$/SO$_2$Ph-p-C), 133.1 (C$_1$/SO$_2$Ph-p-C), 132.9 (d, J=3.2 Hz, C$_{2''/2'''}$), 132.4 (d, J=3.3 Hz, C$_{2''/2'''}$), 131.7 (d, J=8.2 Hz, C$_{3''/3'''}$), 131.3 (d, J=8.2 Hz, C$_{3''/3'''}$), 129.4 (C$_7$), 128.7 (SO$_2$Ph-m-C), 127.5 (C$_{2'}$), 127.5 (SO$_2$Ph-o-C), 125.9 (C$_{5/6}$), 125.7 (C$_{5/6}$), 118.5 (C$_8$), 115.5 (d, J=21.5 Hz, C$_{4''/4'''}$), 115.4 (d, J=21.5 Hz, C$_{4''/4'''}$), 114.3 (C$_{3'}$), 88.3 (C$_2$), 73.7 (C$_{11}$), 71.1 (C$_{15}$), 57.1 (C$_3$), 55.5 (C$_{5'}$), 46.9 (C$_{12}$), 42.2 (C$_{1''/1'''}$), 41.7 (C$_{1''/1'''}$), 29.5 (C$_{17}$), 22.8 (C$_{18}$). FTIR (thin film) cm$^{-1}$: 3485 (br), 2927 (br), 2106 (w), 1663 (m), 1600 (w), 1509 (s), 1362 (s), 833 (m), 687 (w), 599 (m). HRMS (ESI) (m/z): calc'd for C$_{42}$H$_{38}$F$_2$N$_3$O$_5$S$_5$[M+H]$^+$: 862.1378, found: 862.1371. [α]$_D^{23}$: +9 (c=0.26, CHCl$_3$). TLC (5% ethyl acetate in dichloromethane), Rf: 0.35 (UV, CAM).

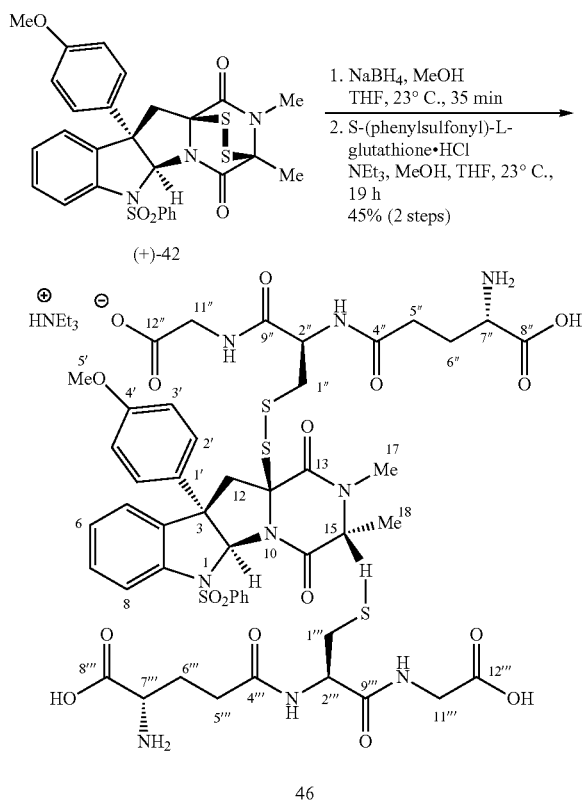

Example 42: Bis(L-glutathione)disulfide 46

Sodium borohydride (4.9 mg, 0.13 mmol, 4.3 equiv) was added as a solid in one portion to a solution of epidithiodiketopiperazine (+)-42 (17.3 mg, 29.8 µmol, 1 equiv) in tetrahydrofuran (4.0 mL) and methanol (30 µL). After 35 min, the reaction mixture was diluted with ethyl acetate-hexanes (9:1, 40 mL) and was washed sequentially with a saturated aqueous ammonium chloride solution (40 mL), with deionized water (30 mL), and with a saturated aqueous sodium chloride solution (20 mL). The aqueous layers were separately extracted with a single portion of ethyl acetate-hexanes (9:1, 25 mL). The combined organic extracts were dried over anhydrous sodium sulfate, were filtered, and were sparged with argon for 15 min by discharge of a balloon equipped with a needle extending into the stirring reaction mixture. The reaction mixture was then concentrated under reduced pressure, and the resulting residue containing bisthiol was dissolved in tetrahydrofuran (0.25 mL) and added dropwise via syringe to a solution of S-(phenylsulfonyl)-L-glutathione hydrogen chloride[59] (72.9 mg, 163 µmol, 5.45 equiv) and triethylamine (45 µL, 320 µmol, 11 equiv) in tetrahydrofuran (1.1 mL) and methanol (1.1 mL). The transfer was quantitated with additional tetrahydrofuran (2×0.25 mL). After 19 h, the reaction mixture was diluted with methanol and adsorbed onto Celite (0.4 g) by concentration under reduced pressure until a free-flowing powder was obtained. The Celite-absorbed crude mixture was purified by flash column chromatography on $C_{18}$-reversed phase silica gel (eluent: 10→80% acetonitrile in water) to afford the bisdisulfide 46 (17.2 mg, 44.6%) as a white solid and recovered epidithiodiketopiperazine (+)-42 (6.0 mg, 21%). Structural assignments were made with additional information from gCOSY, gHSQC, and gHMBC experiments. $^1$H NMR (500 MHz, 5:1 $D_2O:CD_3CN$,[60] 25° C.): δ 7.45 (d, J=8.2 Hz, 1H, $C_8H$), 7.42-7.34 (m, 3H, $SO_2Ph$-p-H, $SO_2Ph$-o-H), 7.32 (app-t, J=7.7 Hz, 1H, $C_7H$), 7.26 (d, J=7.6 Hz, 1H, $C_5H$), 7.16 (app-t, J=7.5 Hz, 1H, $C_6H$), 7.10 (app-t, J=7.8 Hz, 2H, $SO_2Ph$-m-H), 6.70 (app-d, J=8.4 Hz, 2H, $C_2H$), 6.59 (app-d, J=8.4 Hz, 2H, $C_3H$), 6.40 (s, 1H, $C_2H$), 4.66 (dd, J=8.6, 5.1 Hz, 1H, $C_{2''/2'''}H$), 4.42 (dd, J=10.0, 4.0 Hz, 1H, $C_{2''/2'''}H$), 3.80-3.57 (m, 9H, $C_5H$, $C_7''H$, $C_7'''H$, $C_{11''}H$, $C_{11'''}H$), 3.54 (d, J=14.6 Hz, $C_{12}H_a$), 3.26-3.03 (m, 9H, $HN^+(CH_2CH_3)_3$, $C_{1''}H_a$, $C_{1''}H_b$, $C_{1'''}H_a$), 3.03-2.93 (m, 4H, $C_{17}H$, $C_{12}H_b$), 2.65-2.54 (m, 1H, $C_{1'''}H_b$), 2.42 (app-t, J=7.6 Hz, 2H, $C_{5''/5'''}H$), 2.34 (app-t, J=7.7 Hz, 2H, $C_{5''/5'''}H$), 2.04 (app-q, J=7.2 Hz, 2H, $C_{6''/6'''}H$), 1.98 (app-q, J=7.5 Hz, 2H, $C_{6''/6'''}H$), 1.89 (s, 3H, $C_{18}H$), 1.17 (t, J=7.3 Hz, 9H, $HN^+(CH_2CH_3)_3$). $^{13}$C NMR (125 MHz, 5:1 $D_2O:CD_3CN$,[60] 25° C.): δ 174.5 (br, 2C, $C_{12''}$, $C_{12'''}$), 173.7 ($C_{4''/4'''}$), 173.6 ($C_{4''/4'''}$), 172.8 (br, 2C, $C_{8''}$, $C_{8'''}$), 170.5 ($C_{9''/9'''}$), 170.0 ($C_{9''/9'''}$), 166.6 ($C_{13}$), 163.9 ($C_{16}$), 157.0 ($C_{4'}$), 140.3 ($C_9$), 135.6 ($SO_2Ph$-ipso-C), 134.7 ($C_4$), 133.5 ($SO_2Ph$-p-C), 132.3 ($C_{1'}$), 128.8 ($C_7$), 128.4 ($SO_2Ph$-m-C), 126.7 ($C_{2'}$), 125.9 ($SO_2Ph$-o-C), 125.6 ($C_6$), 125.3 ($C_5$), 117.3 ($C_8$), 113.7 ($C_{3'}$), 87.1 ($C_2$), 73.1 ($C_{11}$), 71.5 ($C_{15}$), 56.1 ($C_3$), 54.6 ($C_{5'}$), 53.3 ($C_{7''/7'''}$), 53.2 ($C_{7''/7'''}$), 52.1 ($C_{2''/2'''}$), 51.7 ($C_{2''/2'''}$), 45.8 ($HN^+(CH_2CH_3)_3$), 44.4 ($C_{12}$), 42.3 ($C_{11''/11'''}$), 42.2 ($C_{11''/11'''}$), 40.4 ($C_{1''/1'''}$), 37.5 ($C_{1''/1'''}$), 30.8 ($C_{5''/5'''}$), 30.7 ($C_{5''/5'''}$), 29.2 ($C_{17}$), 25.5 ($C_{6''/6'''}$), 25.4 ($C_{6''/6'''}$), 20.8 ($C_{18}$), 7.4 ($HN^+(CH_2CH_3)_3$). FTIR (thin film) $cm^{-1}$: 3273 (br), 1645 (s), 1513 (s), 1253 (m), 1167 (m), 1109 (w), 1028 (w), 832 (w), 686 (m). HRMS (ESI) (m/z): calc'd for $C_{48}H_{57}N_9NaO_{17}S_5$ $[M+Na]^+$: 1214.2368, found: 1214.2359. TLC (30% acetonitrile in water, $C_{18}$-reversed phase), Rf: 0.25 (UV, CAM).

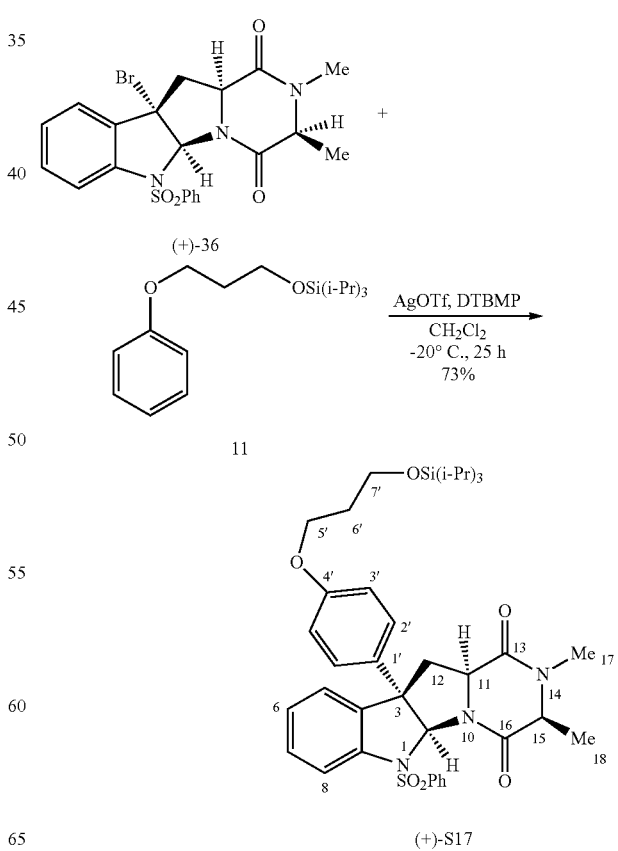

Example 43: C$_3$—Friedel-Crafts Adduct (+)—S$_{17}$

Endo-tetracyclic bromide[55] (+)-36 (1.03 g, 2.09 mmol, 1 equiv), 2,6-di-tert-butyl-4-methylpyridine (DTBMP, 1.11 g, 5.39 mmol, 2.58 equiv), and (3-phenoxypropoxy)triisopropylsilane 11 (1.35 g, 4.37 mmol, 2.09 equiv) were azeotropically dried by concentration from anhydrous benzene (5 mL) under reduced pressure. Dichloromethane (21 mL) was added via cannula, the resulting colorless solution was cooled to −20° C., and silver trifluoromethanesulfonate (1.09 g, 4.22 mmol, 2.02 equiv) was added as a solid in one portion. After 25 min, the reaction mixture was filtered through a pad of Celite, the filter cake was washed with dichloromethane (200 mL), and the filtrate was concentrated under reduced pressure. The resulting residue was dissolved in ethyl acetate (200 mL) and was washed sequentially with a mixture of saturated aqueous sodium chloride solution and deionized water (1:1, 2×50 mL) and with a saturated aqueous sodium chloride solution (50 mL). The organic layer was dried over anhydrous sodium sulfate, was filtered, and was concentrated under reduced pressure. The resulting residue was purified by flash column chromatography on silica gel (eluent: 0→20% acetone in dichloromethane) to afford Friedel-Crafts adduct (+)—S$_{17}$ (1.10 g, 73.2%) as a white foam. Structural assignments were made with additional information from gCOSY, gHSQC, and gHMBC experiments. $^1$H NMR (400 MHz, CDCl$_3$, 25° C.): δ 7.61 (d, J=8.1 Hz, 1H, C$_8$H), 7.45 (app-d, J=7.9 Hz, 2H, SO$_2$Ph-o-H), 7.35-7.23 (m, 2H, SO$_2$Ph-p-H, C$_7$H), 7.15-7.05 (m, 4H, SO$_2$Ph-m-H, C$_5$H, C$_6$H), 6.68-6.59 (m, 4H, C$_2$H, C$_3$H), 6.15 (s, 1H, C$_2$H), 4.39 (dd, J=9.0, 6.6 Hz, 1H, C$_{11}$H), 4.10-3.99 (m, 3H, C$_{15}$H, C$_{5'}$H), 3.88 (t, J=5.9 Hz, 2H, C$_{7'}$H), 3.13 (dd, J=14.1, 6.6 Hz, 1H, C$_{12}$H$_a$), 2.87 (dd, J=14.1, 19.2 Hz, 1H, C$_{12}$H$_b$), 2.86 (s, 3H, C$_{17}$H), 2.00 (p, J=6.1 Hz, 2H, C$_{6'}$H), 1.58 (d, J=7.0 Hz, 3H, C$_{18}$H), 1.15-0.99 (m, 21H, SiCH(CH$_3$)$_2$, SiCH(CH$_3$)$_2$). $^{13}$C NMR (100 MHz, CDCl$_3$, 25° C.): δ 168.4 (C$_{13}$), 167.8 (C$_{16}$), 158.2 (C$_{4'}$), 139.9 (C$_9$), 138.2 (SO$_2$Ph-ipso-C), 135.7 (C$_4$), 132.8 (SO$_2$Ph-p-C), 132.5 (C$_{1'}$), 129.1 (C$_7$), 128.6 (SO$_2$Ph-m-C), 128.0 (C$_{2'}$), 127.5 (SO$_2$Ph-o-C), 126.0 (C$_5$), 125.2 (C$_6$), 117.2 (C$_8$), 114.9 (C$_{3'}$), 87.3 (C$_2$), 64.8 (C$_{5'}$), 59.8 (C$_{7'}$), 59.3 (C$_3$), 58.7 (C$_{11}$), 57.1 (C$_{15}$), 39.0 (C$_{12}$), 32.6 (C$_{6'}$), 29.5 (C$_{17}$), 18.1 (SiCH(CH$_3$)$_2$), 14.5 (C$_{18}$), 12.0 (SiCH(CH$_3$)$_2$). FTIR (thin film) cm$^{-1}$: 2944 (m), 2866 (m), 2359 (w), 1679 (s), 1509 (s), 1457 (s), 1381 (s), 1249 (s), 1168 (s), 1092 (s), 877 (m), 754 (s). HRMS (ESI) (m/z): calc'd for C$_{39}$H$_{52}$N$_3$O$_6$SSi [M+H]$^+$: 719.3369, found: 719.3365. [α]$_D^{23}$: +34 (c=0.39, CHCl$_3$). TLC (10% acetone in dichloromethane), Rf: 0.45 (UV, CAM).

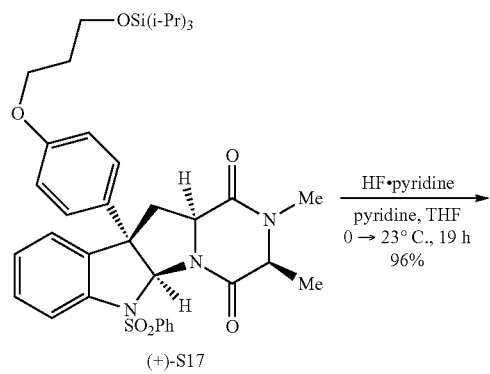

(+)-S17

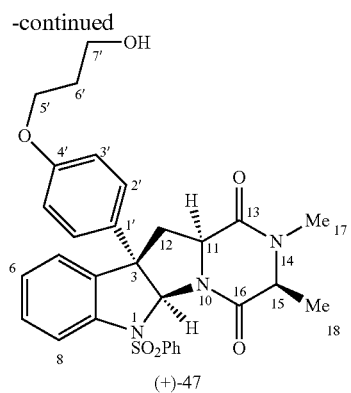

(+)-47

Example 44: Alcohol (+)-47

A freshly prepared stock solution of hydrogen fluoride-pyridine (70% HF, 4.8 mL), pyridine (9.6 mL), and tetrahydrofuran (38 mL) at 0° C. was poured a solution of Friedel-Crafts adduct (+)—S$_{17}$ (1.03 g, 1.44 mmol, 1 equiv) in tetrahydrofuran (48 mL) at 0° C. contained in a 1-L polypropylene vessel. After 20 min, the ice-water bath was removed and the solution was allowed to stir and to warm to 23° C. After 19 h, the reaction mixture was cooled to 0° C. and was diluted with a saturated aqueous sodium bicarbonate solution (350 mL) in portions (50 mL) over 15 min. The resulting mixture was extracted with ethyl acetate (2×100 mL), and the combined organic extracts were washed sequentially with a saturated aqueous copper(II) sulfate solution (4×50 mL) and with a saturated aqueous ammonium chloride solution (3×50 mL). The combined aqueous layers were extracted with a single portion of ethyl acetate (100 mL), and the organic extract was washed sequentially with a saturated aqueous copper(II) sulfate solution (2×25 mL) and with a saturated aqueous ammonium chloride solution (2×25 mL). The combined organic extracts were dried over anhydrous sodium sulfate, were filtered, and were concentrated under reduced pressure. The resulting residue was purified by flash column chromatography on silica gel (eluent: 20→50% acetone in dichloromethane) to afford alcohol (+)-47 (775 mg, 96.0%) as a white solid. Structural assignments were made with additional information from gCOSY, gHSQC, and gHMBC experiments. $^1$H NMR (400 MHz, CDCl$_3$, 25° C.): δ 7.60 (d, J=8.1 Hz, 1H, C$_8$H), 7.44 (app-d, J=7.6 Hz, 2H, SO$_2$Ph-o-H), 7.33 (app-t, J=7.5 Hz, 1H, SO$_2$Ph-p-H), 7.29-7.23 (m, 1H, C$_7$H), 7.16-7.05 (m, 4H, SO$_2$Ph-m-H, C$_5$H, C$_6$H), 6.64 (app-d, J=8.9 Hz, 2H, C$_{2'}$H), 6.59 (app-d, J=8.9 Hz, 2H, C$_{3'}$H), 6.14 (s, 1H, C$_2$H), 4.39 (dd, J=9.0, 6.5 Hz, 1H, C$_{11}$H), 4.11-4.00 (m, 3H, C$_{15}$H, C$_{5'}$H), 3.85 (t, J=5.9 Hz, 2H, C$_{7'}$H), 3.12 (dd, J=14.1, 6.5 Hz, 1H, C$_{12}$H$_a$), 2.91-2.80 (m, 4H, C$_{12}$H$_b$, C$_{17}$H), 2.15-1.99 (br-s, 1H, OH), 2.03 (p, J=6.0 Hz, 2H, C$_{7'}$H), 1.56 (d, J=7.0 Hz, 3H, C$_{18}$H). $^{13}$C NMR (100 MHz, CDCl$_3$, 25° C.): δ 168.4 (C$_{13}$), 167.9 (C$_{16}$), 157.9 (C$_{4'}$), 139.8 (C$_9$), 138.2 (SO$_2$Ph-ipso-C), 135.6 (C$_4$), 132.9 (C$_{1'}$/SO$_2$Ph-p-C), 132.8 (C$_{1'}$/SO$_2$Ph-p-C), 129.2 (C$_7$), 128.6 (SO$_2$Ph-m-C), 128.0 (C$_{2'}$), 127.4 (SO$_2$Ph-o-C), 126.0 (C$_5$), 125.3 (C$_6$), 117.2 (C$_8$), 114.9 (C$_{3'}$), 87.3 (C$_2$), 65.6 (C$_{5'}$), 60.1 (C$_{7'}$), 59.3 (C$_3$), 58.7 (C$_{11}$), 57.1 (C$_{15}$), 38.9 (C$_{12}$), 32.0 (C$_{6'}$), 29.5 (C$_{17}$), 14.4 (C$_{18}$). FTIR (thin film) cm$^{-1}$: 3455 (br-w), 2951 (w), 2361 (w), 1672 (s), 1511 (m), 1386 (s), 1253 (s), 1170 (s), 1690 (s), 981 (m), 751 (s). HRMS (ESI) (m/z): calc'd for $C_{30}H_{32}N_3O_6S$ [M+H]$^+$: 562.2006, found: 562.2007. $[\alpha]_D^{23}$: +52 (c=0.26, CHCl$_3$). TLC (40% acetone in dichloromethane), Rf: 0.35 (UV, CAM).

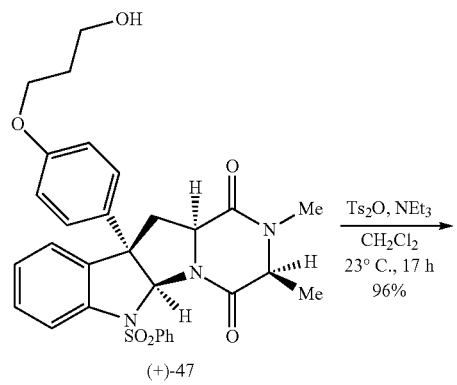

Example 45: Tosylate S18

Alcohol (+)-47 (277 mg, 0.494 mmol, 1 equiv) was azeotropically dried by concentration from anhydrous benzene (3 mL) under reduced pressure. Dichloromethane (4.9 mL) was added via syringe, followed by the addition of triethylamine (0.35 mL, 2.5 mmol, 5.1 equiv) via syringe and p-toluenesulfonic anhydride (655 mg, 1.99 mmol, 4.03 equiv) as a solid in one portion. After 17 h, the reaction mixture was diluted with dichloromethane (75 mL) and was washed with a saturated aqueous sodium bicarbonate solution (25 mL). The aqueous layer was extracted with dichloromethane (50 mL), and the combined organic extracts were dried over anhydrous sodium sulfate, were filtered, and were concentrated under reduced pressure. The resulting residue was purified by flash column chromatography on silica gel (eluent: 0→25% acetone in dichloromethane) to afford tosylate S18 (339 mg, 95.8%) as a white solid. Structural assignments were made with additional information from gCOSY, gHSQC, and gHMBC experiments. $^1$H NMR (400 MHz, CDCl$_3$, 25° C.): δ 7.77 (app-d, J=8.3 Hz, 2H, C$_{9'}$H), 7.61 (d, J=8.1 Hz, 1H, C$_8$H), 7.47 (app-d, J=7.6 Hz, 1H, SO$_2$Ph-o-H), 7.34 (app-t, J=7.4 Hz, 1H, SO$_2$Ph-p-H) 7.31-7.24 (m, 3H, C$_7$H, C$_{10'}$H), 7.15-7.06 (m, 3H, C$_5$H, C$_6$H, SO$_2$Ph-m-H), 6.66 (app-d, J=8.7 Hz, 1H, C$_{2'}$H), 6.54 (app-d, J=8.7 Hz, 1H, C$_{3'}$H), 6.15 (s, 1H, C$_2$H), 4.39 (app-t, J=7.3 Hz, 1H, C$_{11}$H), 4.25 (t, J=5.8 Hz, 1H, C$_{5'}$H), 4.04 (q, J=7.0 Hz, 1H, C$_{15}$H), 3.95 (t, J=5.9 Hz, 1H, C$_{7'}$H), 3.13 (dd, J=14.1, 6.6 Hz, 1H, C$_{12}$H$_a$), 2.93-2.83 (m, 4H, C$_{12}$H$_b$, C$_{17}$H), 2.40 (s, 3H, C$_{12'}$H), 2.13 (p, J=5.9 Hz, 2H, C$_{6'}$H), 1.58 (d, J=7.0 Hz, 3H, C$_{18}$H). $^{13}$C NMR (100 MHz, CDCl$_3$, 25° C.): δ 168.4 (C$_{13}$), 167.9 (C$_{16}$), 157.7 (C$_{4'}$), 145.0 (C$_{11'}$), 139.9 (C$_9$), 138.3 (SO$_2$Ph-ipso-C), 135.6 (C$_4$), 133.1 (C$_{1'}$), 133.0 (C$_{8'}$), 133.0 (SO$_2$Ph-p-C), 130.0 (C$_{10'}$), 129.2 (C$_7$), 128.7 (SO$_2$Ph-m-C), 128.1 (C$_{2'}$), 128.0 (C$_{9'}$), 127.5 (SO$_2$Ph-o-C), 126.0 (C$_5$), 125.3 (C$_6$), 117.2 (C$_8$), 114.9 (C$_3$), 87.2 (C$_2$), 67.0 (C$_{5'}$), 63.4 (C$_{7'}$), 59.3 (C$_3$), 58.7 (C$_{11}$), 57.1 (C$_{15}$), 39.0 (C$_{12}$), 29.6 (C$_{17}$), 29.0 (C$_{6'}$), 21.8 (C$_{12'}$), 14.5 (C$_{18}$). FTIR (thin film) cm$^{-1}$: 2918 (br-w), 2361 (m), 1672 (m), 1511 (m), 1357 (m), 1256 (m), 1173 (s), 1095 (m), 938 (w), 747 (s). HRMS (ESI) (m/z): calc'd for $C_{37}H_{38}N_3O_8S_2$[M+H]$^+$: 716.2095, found: 716.2092. TLC (10% acetone in dichloromethane), Rf: 0.30 (UV, CAM).

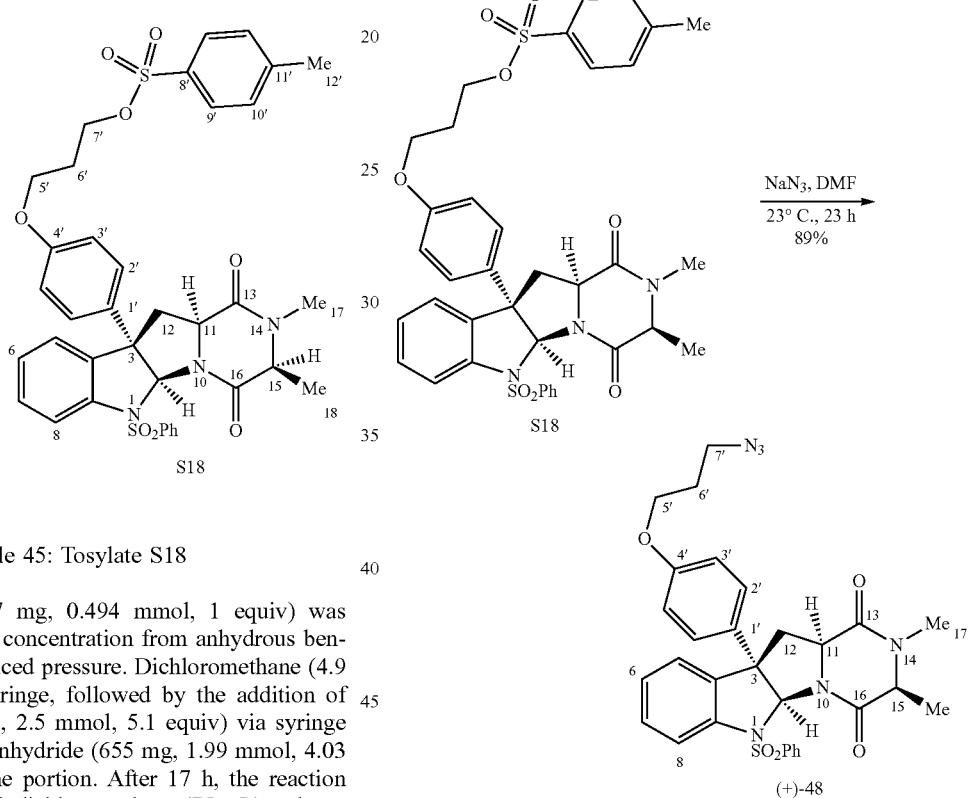

Example 46: Azide (+)-48

Sodium azide (145 mg, 2.24 mmol, 3.99 equiv) was added as a solid in one portion to a solution of tosylate S$_{18}$ (401 mg, 0.560 mmol, 1 equiv) in N,N-dimethylformamide (3.7 mL). After 23 h, the reaction mixture was diluted with ethyl acetate-hexanes (9:1, 150 mL) and was washed sequentially with a saturated aqueous sodium bicarbonate solution (2×50 mL), with deionized water (3×40 mL), and with a saturated aqueous sodium chloride solution (30 mL). The organic layer was dried over anhydrous sodium sulfate, was filtered, and was concentrated under reduced pressure. The resulting residue was purified by flash column chromatography on silica gel (eluent: 0→20% acetone in dichloromethane) to afford azide (+)-48 (292 mg, 89.0%) as a white solid. Structural assignments were made with additional information from gCOSY, gHSQC, and gHMBC experiments. $^1$H NMR (500 MHz, CDCl$_3$, 25° C.): δ 7.62 (d, J=8.1 Hz, 1H, C$_8$H), 7.48 (dd, J=8.5, 1.2 Hz, 2H, SO$_2$Ph-o-H), 7.34 (tt, J=7.4, 1.2 Hz, 1H, SO$_2$Ph-p-H), 7.31-7.25 (m, 1H, C$_7$H), 7.15-7.08 (m, 4H, SO$_2$Ph-m-H, C$_5$H, C$_6$H), 6.68 (app-d, J=8.9 Hz, 2H, C$_2$·H), 6.62 (app-d, J=8.9 Hz, 2H, C$_3$·H), 6.15 (s, 1H, C$_2$H), 4.38 (dd, J=8.9, 6.7 Hz, 1H, C$_{11}$H), 4.04 (q, J=7.1 Hz, 1H, C$_{15}$H), 4.00 (t, J=5.9 Hz, 2H, C$_5$·H), 3.53 (t, J=6.5 Hz, 2H, C$_7$·H), 3.13 (dd, J=14.1, 6.7 Hz, 1H, C$_{12}$H$_a$), 2.88 (dd, J=14.0, 9.0 Hz, 1H, C$_{12}$H$_b$), 2.86 (s, 3H, C$_{17}$H), 2.05 (p, J=6.2 Hz, 2H, C$_6$·H), 1.58 (d, J=7.1 Hz, 3H, C$_{18}$H). $^{13}$C NMR (125 MHz, CDCl$_3$, 25° C.): δ 168.4 (C$_{13}$), 167.9 (C$_{16}$), 157.8 (C$_{4'}$), 139.9 (C$_9$), 138.3 (SO$_2$Ph-ipso-C), 135.6 (C$_4$), 133.0 (C$_{1'}$), 132.9 (SO$_2$Ph-p-C), 129.2 (C$_7$), 128.6 (SO$_2$Ph-m-C), 128.1 (C$_{2'}$), 127.5 (SO$_2$Ph-o-C), 126.0 (C$_5$), 125.3 (C$_6$), 117.2 (C$_8$), 114.9 (C$_{3'}$), 87.2 (C$_2$), 64.6 (C$_{5'}$), 58.8 (C$_{11}$), 57.1 (C$_{15}$), 48.3 (C$_{7'}$), 39.0 (C$_{12}$), 29.6 (C$_{17}$), 28.8 (C$_{6'}$), 14.5 (C$_{18}$). FTIR (thin film) cm$^{-1}$: 2956 (br-w), 2096 (s), 1670 (s), 1611 (w), 1476 (m), 1360 (s), 1168 (s), 1090 (m), 971 (w), 829 (w), 758 (m). HRMS (ESI) (m/z): calc'd for C$_{30}$H$_{31}$N$_6$OSS [M+H]$^+$: 588.2100, found: 588.2101. [α]$_D^{23}$: +46 (c=0.25, CHCl$_3$). TLC (10% acetone in dichloromethane), Rf: 0.27 (UV, CAM).

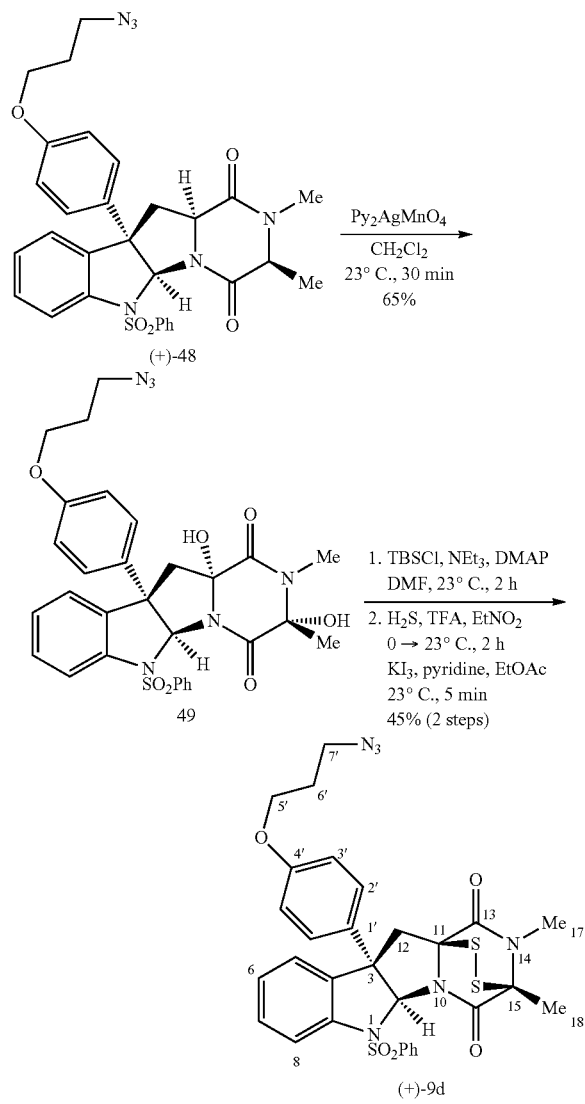

Example 47: Epidithiodiketopiperazine Azide (+)-9d

Bis(pyridine)silver(I) permanganate (178 mg, 0.464 mmol, 3.03 equiv) was added as a solid to a solution of azide (+)-48 (90 mg, 0.153 mmol, 1 equiv) in dichloromethane (3 mL). After 30 min, the reaction mixture was diluted with a saturated aqueous sodium bisulfite solution (10 mL) and was extracted with ethyl acetate-hexanes (9:1, 2×20 mL). The combined organic extracts were washed sequentially with deionized water (15 mL) and with a saturated aqueous ammonium chloride solution (3×30 mL). The combined aqueous layers were extracted with ethyl acetate-hexanes (4:1, 20 mL), and the organic extract was washed with a saturated aqueous ammonium chloride solution (2×20 mL). The combined organic layers were dried over anhydrous sodium sulfate, were filtered, and were concentrated under reduced pressure. The resulting residue was purified by flash column chromatography on silica gel (eluent: 5→15% acetone in dichloromethane) to afford diol 49 (61.3 mg, 64.6%) as a white foam.[61] Diol 49 (55.0 mg, 88.9 μmol, 1 equiv) was azeotropically dried by concentration from dichloromethane (0.5 mL) and anhydrous benzene (1.5 mL) under reduced pressure. The flask was charged with 4-dimethylaminopyridine (DMAP, 1.5 mg, 12 μmol, 0.14 equiv), and the solids were dissolved in N,N-dimethylformamide (0.9 mL). Triethylamine (40 μL, 290 μmol, 3.2 equiv) was then added via syringe followed by the dropwise addition of a solution of t-butyldimethylsilyl chloride (TBSCl, 2.05 M, 88 μL, 180 μmol, 2.0 equiv) in N,N-dimethylformamide. After 2 h, the reaction mixture was diluted with ethyl acetate-hexanes (4:1, 25 mL) and with a saturated aqueous ammonium chloride solution (15 mL). The aqueous layer was extracted with ethyl acetate-hexanes (4:1, 25 mL). The combined organic extracts were washed with deionized water (3×10 mL) and with a saturated aqueous sodium chloride solution (10 mL). The organic layer was dried over anhydrous sodium sulfate, was filtered, and was concentrated under reduced pressure. The resulting residue was purified by flash column chromatography on silica gel (eluent: 0→30% acetone in hexanes) to afford a mixture of O-TBS protected monoalcohols S22 and S23 (55.4 mg, 85.0%, 1.1:1) as a white foam.[62] A solution of O-TBS protected monoalcohols S22 and S23 (16.5 mg, 22.5 μmol, 1 equiv) in anhydrous nitroethane (1.0 mL) at 0° C. was sparged with hydrogen sulfide gas for 20 min by discharge of a balloon equipped with a needle extending into the reaction mixture, providing a saturated hydrogen sulfide solution. Trifluoroacetic acid (TFA, 0.75 mL) was added via syringe over 20 seconds, and the sparging with hydrogen sulfide was maintained for another 20 min. The ice-water bath was removed, and the solution was allowed to stir and warm to 23° C. under an atmosphere of hydrogen sulfide. After 2 h, the reaction mixture was diluted with a saturated aqueous sodium bicarbonate solution (20 mL) and the resulting mixture was extracted with ethyl acetate (2×10 mL). A stock solution of potassium triiodide in pyridine[43] was added dropwise into the organic layer containing crude bisthiol until a persistent yellow color was observed. The resulting mixture was washed with an aqueous hydrogen chloride solution (1 M, 2×15 mL) and with a saturated aqueous sodium chloride solution (10 mL). The combined aqueous layers were extracted with ethyl acetate (10 mL), and the combined organic layers were dried over anhydrous sodium sulfate, were filtered, and were concentrated under reduced pressure. The resulting residue was purified by flash column chromatography on silica gel (eluent: 0→10% ethyl acetate in dichloromethane) to afford the epidithiodiketopiperazine (+)-9d (7.8 mg, 53%) as a beige solid. Structural assignments were made with additional information from gCOSY, gHSQC, and gHMBC experiments.[63] 1H NMR (500 MHz, CDCl$_3$, 25° C.): 7.65 (d, J=8.5 Hz, 1H, C$_8$H), 7.40 (app-t, J=8.3 Hz, 1H, C$_7$H), 7.36 (app-d, J=8.1 Hz, 2H, SO$_2$Ph-o-H), 7.33-7.22 (m, 3H, C$_6$H, C$_5$H, SO$_2$Ph-p-H), 7.04 (app-t, J=7.9 Hz, 2H, SO$_2$Ph-m-H), 6.75 (app-d, J=8.8 Hz, 2H, C$_2$,H), 6.62 (app-d, J=8.9 Hz, 2H, C$_3$,H), 6.42 (s, 1H, C$_2$H), 4.01 (t, J=5.9 Hz, 2H, C$_5$,H), 3.67 (d, J=15.5 Hz, 1H, C$_{12}$H$_a$), 3.54 (t, J=6.5 Hz, 2H, C$_7$,H), 3.05 (s, 3H, C$_{17}$H), 2.88 (d, J=15.5 Hz, 1H, C$_{12}$H$_b$), 2.07 (p, J=6.2 Hz, 2H, C$_6$,H), 1.97 (s, 3H, C$_{18}$H). $^{13}$C NMR (100 MHz, CDCl$_3$, 25° C.): 165.8 (C$_{13}$), 161.4 (C$_{16}$), 158.0 (C$_4$,), 141.3 (C$_9$), 138.5 (SO$_2$Ph-ipso-C), 135.8 (C$_4$), 133.0 (SO$_2$Ph-p-C), 131.7 (C$_1$,), 129.8 (C$_7$), 128.6 (SO$_2$Ph-m-C), 128.0 (C$_2$,), 127.3 (SO$_2$Ph-o-C), 126.1 (C$_6$), 125.6 (C$_5$), 119.0 (C$_8$), 115.1 (C$_3$,), 88.0 (C$_2$), 74.0 (C$_{11}$), 73.5 (C$_{15}$), 64.7 (C$_5$,), 59.2 (C$_3$), 48.3 (C$_7$,), 46.1 (C$_{12}$), 28.9 (C$_{17}$), 27.6 (C$_6$,), 18.3 (C$_{18}$). FTIR (thin film) cm$^{-1}$: 2922 (w), 2097 (s), 1712 (s), 1686 (s), 1610 (w), 1512 (s), 1251 (s), 1169 (s), 1056 (m), 895 (w), 738 (m), 601 (s). HRMS (ESI) (m/z): calc'd for C$_{30}$H$_{29}$N$_6$O$_5$S$_3$ [M+H]$^+$: 649.1356, found: 649.1356. [α]$_D^{23}$: +231 (c=0.06, CHCl$_3$). TLC (15% ethyl acetate in dichloromethane), Rf: 0.38 (UV, CAM).

iodide (0.9 mg, 5 μmol, 0.5 equiv) was added as a solid, and the suspension was sparged with argon for 2 min by discharge of balloon equipped with a needle extending into the reaction mixture. After 17 h, the reaction mixture was diluted with dichloromethane (0.5 mL) and was purified by flash chromatography on silica gel (eluent: 5→40% acetone in dichloromethane) to afford triazole 51 as a yellow solid. The mixture was further purified by flash column chromatography on silica gel (eluent: 0→4% methanol in dichloromethane) to afford triazole 51 (9.0 mg, 91.7%) as a white solid. Structural assignments were made with additional information from gCOSY, gHSQC, and gHMBC experiments. $^1$H NMR (500 MHz, CDCl$_3$, 25° C.): δ 7.68-7.60 (m, 2H, C$_8$H, C$_8$,H), 7.40 (app-t, J=7.6 Hz, 1H, C$_7$H), 7.36 (app-d, J=7.9 Hz, 2H, SO$_2$Ph-o-H), 7.31 (app-t, J=7.5 Hz, 1H, SO$_2$Ph-p-H), 7.29-7.22 (m, 2H, C$_5$H, C$_6$H), 7.05 (app-t, J=7.7 Hz, 2H, SO$_2$Ph-m-H), 6.74 (app-d, J=8.2 Hz, 2H, C$_2$,H), 6.59 (br-s, 2H, C$_3$,H), 6.42 (s, 1H, C$_2$H), 5.04 (br-s, 1H, N$_{17}$,H), 4.70 (s, 2H, C$_{10}$,H), 4.60 (t, J=5.7 Hz, 2H, C$_7$,H), 3.97-3.88 (m, 2H, C$_5$,H), 3.73-3.57 (m, 9H, C$_{12}$H$_a$, C$_{11}$,H, C$_{12}$,H, C$_{13}$,H, C$_{14}$,H), 3.53 (t, J=5.0 Hz, 2H, C$_{15}$,H), 3.30 (app-q, J=5.5 Hz, 2H, C$_{16}$,H), 3.05 (s, 3H, C$_{17}$H), 2.88 (d, J=15.5 Hz, 1H, C$_{12}$H$_b$), 2.40 (p, J=6.4 Hz, 2H, C$_6$,H), 1.96 (s, 3H, C$_{18}$H), 1.43 (s, 9H, C$_{19}$,(CH$_3$)$_3$). $^{13}$C NMR (125 MHz, CDCl$_3$, 25° C.): δ 165.8 (C$_{13}$), 161.4 (C$_{16}$), 157.7

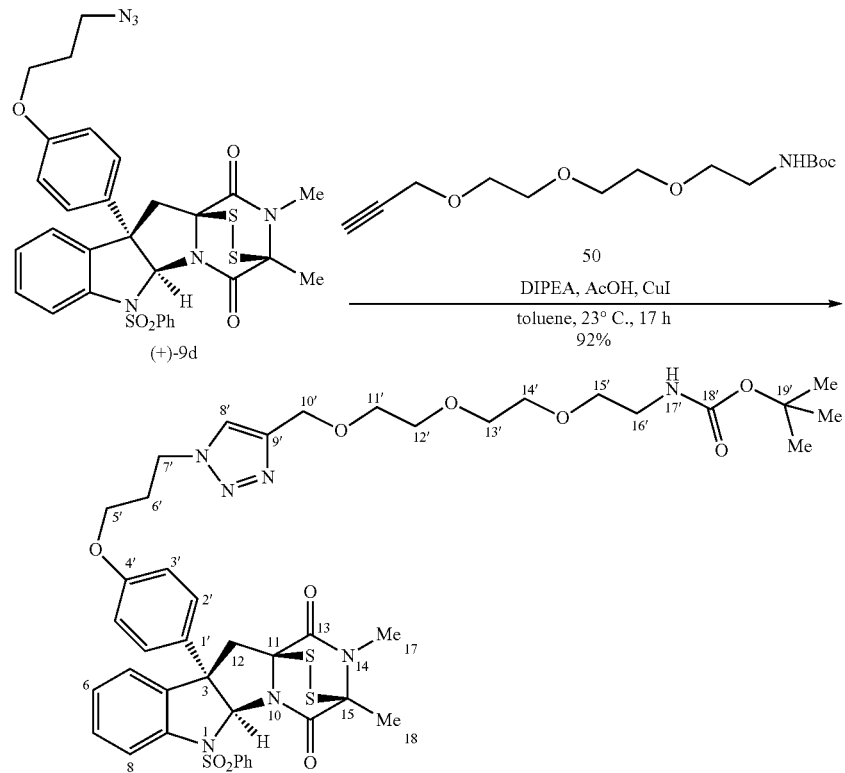

51

Example 48: Triazole 51

A solution of N,N-diisopropylethylamine (DIPEA, 2.7 μL, 16 μmol, 1.5 equiv) and acetic acid (AcOH, 0.90 μL, 16 μmol, 1.5 equiv) in toluene (0.2 mL) was added to a flask containing azide (+)-9d (6.8 mg, 11 μmol, 1 equiv) and alkyne[64] 50 (11.6 mg, 40.4 μmol, 3.67 equiv). Copper (I)

(C$_4$,), 156.1 (C$_{18}$,), 145.45 (C$_9$,), 141.3 (C$_9$), 138.5 (SO$_2$Ph-ipso-C), 135.8 (C$_4$), 133.1 (SO$_2$Ph-p-C), 132.0 (C$_1$,), 129.8 (C$_7$), 128.6 (SO$_2$Ph-m-C), 128.0 (C$_2$,), 127.2 (SO$_2$Ph-o-C), 126.1 (C$_6$), 125.5 (C$_5$), 123.0 (C$_8$,), 119.0 (C$_8$), 115.0 (C$_3$,), 87.9 (C$_2$), 79.3 (C$_{19}$,), 73.9 (C$_{11}$), 73.5 (C$_{15}$), 70.7 (3C, C$_{12}$,, C$_{13}$,, C$_{14}$,), 70.4 (C$_{15}$,), 69.9 (C$_{11}$,), 64.8 (C$_{10}$,), 64.2 (C$_5$,), 59.1 (C$_3$), 47.1 (C$_7$,), 46.0 (C$_{12}$), 40.5 (C$_{16}$,), 30.0 (C$_6$,), 28.6

($C_{19'}(CH_3)_3$), 27.7 ($C_{17}$), 18.2 ($C_{18}$). FTIR (thin film) cm$^{-1}$: 3360 (br-m), 2921 (s), 2851 (m), 1659 (m), 1632 (m), 1468 (w), 1411 (w), 1024 (w), 801 (w). HRMS (ESI) (m/z): calc'd for $C_{44}H_{53}N_7NaO_{10}S_3$ [M+Na]$^+$: 958.2908, found: 958.2902. TLC (40% acetone in dichloromethane), Rf: 0.39 (UV, CAM). TLC (5% methanol in dichloromethane), Rf: 0.26 (UV, CAM).

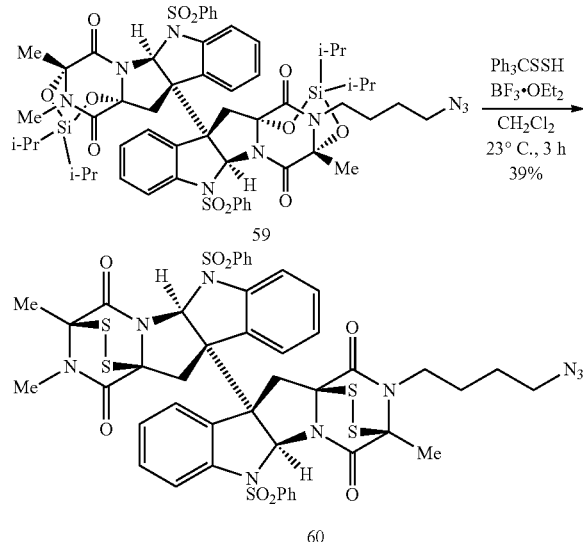

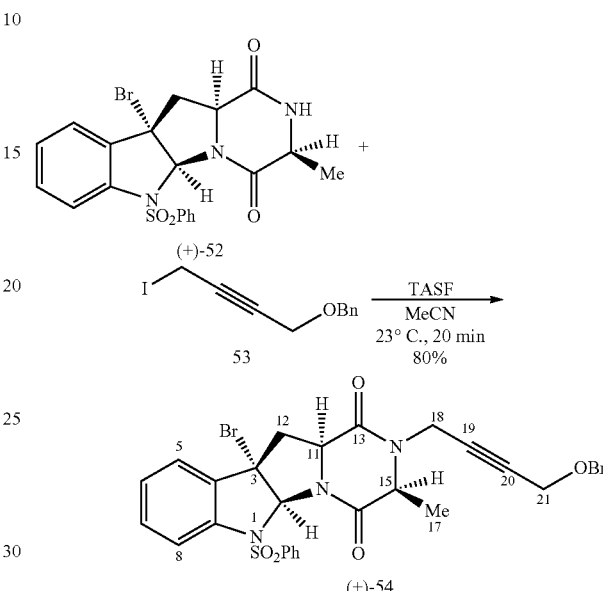

Example 49: Heterodimeric Epidithiodiketopiperazine Azide 60

A solution of heterodimeric dioxasilane 59 (14.5 mg, 12.0 μmol, 1 equiv) in dichloromethane (0.5 mL) was added via cannula to a solution of tritylhydrodisulfane (40.0 mg, 129 μmol, 10.8 equiv) in dichloromethane (1 mL). The transfer was quantitated with additional dichloromethane (0.5 mL). Boron trifluoride diethyl etherate (29 μL, 240 μmol, 20 equiv) was added via syringe, and the resulting bright yellow solution was stirred at 23° C. After 70 min, another portion of boron trifluoride etherate (29 μL, 240 μmol, 20 equiv) was added via syringe. After an additional 2 h, the reaction mixture was diluted with dichloromethane (10 mL) and was washed with a saturated aqueous sodium bicarbonate solution (10 mL). The layers were separated, and the aqueous layer was extracted with dichloromethane (2×10 mL). The combined organic layers were washed with a saturated aqueous sodium chloride solution (10 mL), were dried over anhydrous sodium sulfate, were filtered, and were concentrated under reduced pressure. The resulting residue was purified by flash column chromatography on silica gel (eluent: 0→10% ethyl acetate in dichloromethane). The resulting colorless residue was further purified by flash column chromatography on silica gel (eluent: 0→15% diethyl ether in dichloromethane) to afford heterodimeric epidithiodiketopiperazine azide 60 (4.9 mg, 39.3%) as a colorless solid. $^1$H NMR (600 MHz, CDCl$_3$, 25° C.): δ 7.90-7.88 (m, 4H), 7.70-7.66 (m, 2H), 7.58-7.54 (m, 2H), 7.50-7.46 (m, 4H), 7.26-7.21 (m, 2H), 7.21-7.17 (m, 2H), 7.10-7.06 (m, 2H), 6.84 (s, 1H), 6.83 (s, 1H), 3.82-3.74 (m, 1H), 3.60-3.53 (m, 2H), 3.33-3.21 (m, 3H), 2.99 (s, 3H), 2.97-2.91 (m, 2H), 1.74-1.63 (m, 8H), 1.62-1.56 (m, 2H). $^{13}$C NMR (150 MHz, CDCl$_3$, 25° C.): δ 164.8, 164.4, 160.7, 160.6, 142.5 (2C), 142.3 (2C), 132.5, 130.9 (2C), 128.9 (2C), 125.8, 125.7, 125.1, 124.8, 81.9, 73.8, 73.6, 73.4, 72.0, 60.4, 51.0, 42.3, 41.6 (2C), 27.7, 26.3, 25.3, 17.9, 17.4. FTIR (thin film) cm$^{-1}$: 2927 (w), 2162 (m), 2097 (w), 1716 (s), 1688 (s), 1480 (m), 1462 (m), 1348 (s), 1168 (s), 1096 (m), 1057 (m), 753 (m), 730 (m), 582 (s). HRMS (ESI) (m/z): calc'd for $C_{45}H_{41}N_9O_8S_6$[M+H]$^+$: 1027.1409, found: 1027.1402. TLC (15% ethyl acetate in dichloromethane), Rf: 0.34 (UV, CAM).

Alkyne (+)-54

Diketopiperazine bromide (+)-52 (966 mg, 2.04 mmol, 1 equiv) and propargylic iodide (Propargylic iodide was prepared using a procedure adapted from Yasuda, S.; Kawaguchi, Y.; Okamoto, Y.; Mukai, C. Chem. Eur. J. 2016, 22, 1218) 53 (11.6 g, 40.7 mmol, 20.0 equiv) were azeotropically dried by concentration from anhydrous benzene (20 mL). The resulting residue was dissolved in acetonitrile (14.8 mL). A sample of tris(dimethylamino) sulfonium difluorotrimethylsilicate (TASF, 2.00 g, 5.59 mmol, 2.75 equiv) was added at 23° C. After 20 min, the red solution was diluted with ethyl acetate (75 mL) and with a saturated aqueous sodium bicarbonate solution (75 mL). The aqueous layer was extracted with ethyl acetate (2×75 mL). The combined organic extracts were washed with a saturated aqueous sodium chloride solution (150 mL), were dried over anhydrous sodium sulfate, were filtered, and were concentrated under reduced pressure. The resulting residue was purified by flash column chromatography on silica gel (eluent: 10→50% ethyl acetate in hexanes) to afford alkyne (+)-54 (1.03 g, 80.4%) as a white foam. Structural assignments were made using additional information from gCOSY, gHSQC, and gHMBC experiments. $^1$H NMR (600 MHz, CDCl$_3$, 25° C.): δ 7.98 (d, J=8.5 Hz, 2H, SO$_2$Ph-o-H), 7.55 (d, J=8.2 Hz, 1H, C$_8$H), 7.54 (t, J=7.5 Hz, 1H, SO$_2$Ph-p-H), 7.44 (t, J=7.8 Hz, 2H, SO$_2$Ph-m-H), 7.39-7.29 (m, 7H, C$_5$H, C$_7$H, OCH$_2$Ph), 7.11 (t, J=7.6 Hz, 1H, C6H), 6.26 (s, 1H, C2H), 4.72 (dt, J=17.7, 2.0 Hz, 1H, C18H$_a$), 4.54 (s, 2H, OCH$_2$Ph), 4.41 (dd, J=8.7, 6.5 Hz, 1H, C11H), 4.20 (q, J=7.0 Hz, 1H, C15H), 4.13 (t, J=1.9 Hz, 2H, C21H), 3.70 (dt, J=17.6, 1.9 Hz, 1H, C18H$_b$), 3.34 (dd, J=14.4, 6.5 Hz, 1H, C12H$_a$). 3.05 (dd, J=14.4, 8.8 Hz, 1H, C12H$_b$), 1.69 (d, J=7.0 Hz, 3H, C17H). $^{13}$C NMR (150 MHz, CDCl$_3$, 25° C.): δ 167.9 (C16), 167.5 (C13), 138.9 (C9), 137.8 (SO$_2$Ph-ipso- C), 137.4 (OCH$_2$Ph-ipso-C), 133.6 (SO$_2$Ph-p-C), 133.5 (C4), 130.9 (C7), 129.0 (SO$_2$Ph-m-C), 128.6 (OCH$_2$Ph-m-C), 128.3 (SO$_2$Ph-o-C), 128.1 (2C, (OCH$_2$Ph-p-C, OCH$_2$Ph-o-C), 125.9 (C6), 125.0 (C5), 117.0 (C8), 87.1 (C2), 80.6 (C20), 80.0 (C19), 71.9 (OCH$_2$Ph), 61.1 (C3), 58.4 (C11), 58.0 (C21), 57.5 (C11), 55.8 (C15), 41.2 (C12), 31.9 (C18), 14.2 (C17). FTIR (thin film) cm$^{-1}$: 3065 (w), 2857 (w), 2252 (w), 1683 (s), 1496 (m), 1388 (s), 1290 (m), 1169 (s), 910 (w), 730 (s). HRMS (ESI) (m/z): calc'd for C$_{31}$H$_{28}$BrN$_3$NaO$_5$S [M+Na]$^+$: 656.0825, found: 656.0852. [α]$_D^{23}$: +53 (c=1.4, CHCl$_3$). TLC (20% ethyl acetate in dichloromethane), Rf: 0.60 (UV, CAM)

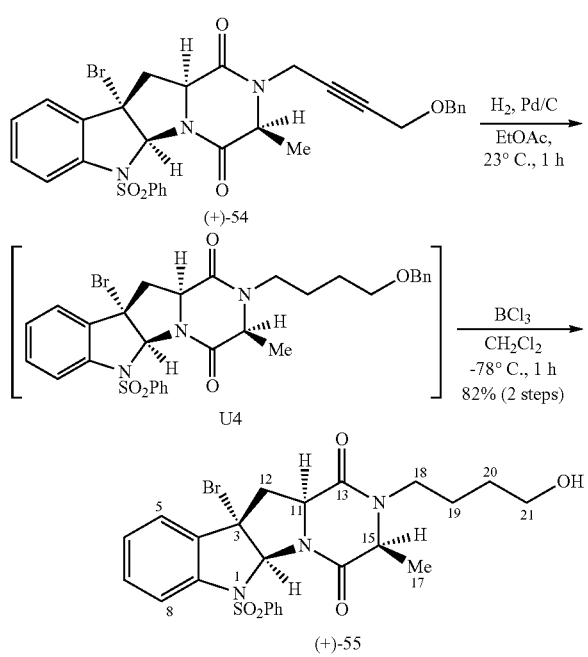

Alcohol (+)-55

A sample of palladium on activated charcoal (10% w/w, 744 mg, 664 μmol, 0.200 equiv) was added to a solution of alkyne (+)-54 (2.11 g, 3.32 mmol, 1 equiv) in ethyl acetate (296 mL). The suspension was sparged with hydrogen gas for 10 min by discharge of a balloon equipped with a needle extending into the reaction mixture. After stirring for 1 h under an atmosphere of dihydrogen, the suspension was filtered through a pad of celite. The filter cake was washed with ethyl acetate (750 mL). The filtrate was concentrated under reduced pressure to afford benzyl ether U4 as a white foam that was used in the next step without further purification.

The sample of crude benzyl ether U4 (1 equiv) was azeotropically dried by concentration from anhydrous benzene (3×8 mL). The residue was dissolved in dichloromethane (33 mL) and cooled to –78° C. Boron trichloride (1.0 M in dichloromethane, 25.6 mmol, 8.00 equiv) was added dropwise from a pressure-equalizing addition funnel over 5 min. After 1 h, the reaction mixture was diluted with methanol-chloroform (1:9, 50 mL) and the cooling bath was removed. After warming to 23° C., the reaction mixture was diluted with a saturated aqueous sodium bicarbonate solution (200 mL). The layers were separated and the aqueous layer was extracted with dichloromethane (2×200 mL). The combined organic layers were washed with a saturated aqueous sodium chloride solution (200 mL), were dried over anhydrous sodium sulfate, were filtered, and were concentrated under reduced pressure. The resulting residue was purified by flash column chromatography on silica gel (eluent: 10→30% acetone in dichloromethane) to afford alcohol (+)-55 (1.48 g, 81.5% over two steps) as a white foam. Structural assignments were made using additional information from gCOSY, gHSQC, and gHMBC experiments. $^1$H NMR (600 MHz, CDCl$_3$, 25° C.): δ 7.94 (d, J=7.4 Hz, 2H, SO$_2$Ph-o-H), 7.55 (d, J=8.2, 1H, C8H), 7.51 (t, J=7.1 Hz, 1H, SO$_2$Ph-p-H), 7.43 (t, J=8.0 Hz, 2H, SO$_2$Ph-m-H), 7.36 (d, J=7.9 Hz, 1H, C5H), 7.28 (td, J=8.3, 7.4 Hz, 1H, C7H) 7.12 (td, J=7.6, 1.0 Hz, 1H, C6H), 6.24 (s, 1H, C2H), 4.33 (dd, J=9.0, 5.3 Hz, 1H, C11H), 4.11 (q, J=7.1 Hz, 1H, C15H), 3.55 (t, J=5.8 Hz, 2H, C21H), 3.48 (dd, J=14.2, 5.3 Hz, 1H, C12H$_a$), 3.42-3.36 (m, 1H, C18H$_a$), 3.33-3.26 (m, 1H, C18H$_b$), 3.03 (dd, J=14.2, 9.0 Hz, 1H, C12H$_b$), 1.58 (d, J=6.8 Hz, 3H, C17H), 1.44-1.30 (m, 4H, C19H, C20H). $^{13}$C NMR (150 MHz, CDCl$_3$, 25° C.): δ 167.7 (2C, C16, C13), 139.0 (C9), 138.0 (SO$_2$Ph-ipso-C), 133.8 (C4), 133.5 (SO$_2$Ph-p-C), 130.9 (C7), 129.0 (SO$_2$Ph-m-C), 128.3 (SO$_2$Ph-p-C), 125.9 (C6), 125.3 (C5), 116.9 (C8), 87.1 (C2), 62.4 (C21), 61.1 (C3), 58.5 (C11), 56.1 (C15), 42.1 (C18), 40.3 (C12), 29.3 (C19), 25.3 (C20), 13.6 (C17). FTIR (thin film) cm$^{-1}$: 3399 (br-w), 2930 (w), 1713 (s), 1462 (m), 1349 (s), 1167 (s), 1096 (m), 730 (m), 582 (s). HRMS (ESI) (m/z): calc'd for C$_{24}$H$_{26}$BrN$_3$NaO$_5$S [M+Na]$^+$: 570.0669, found: 570.0689. [α]$_D^{23}$: +102 (c=0.17, CHCl$_3$). TLC (30% acetone in dichloromethane), Rf: 0.32 (UV, CAM).

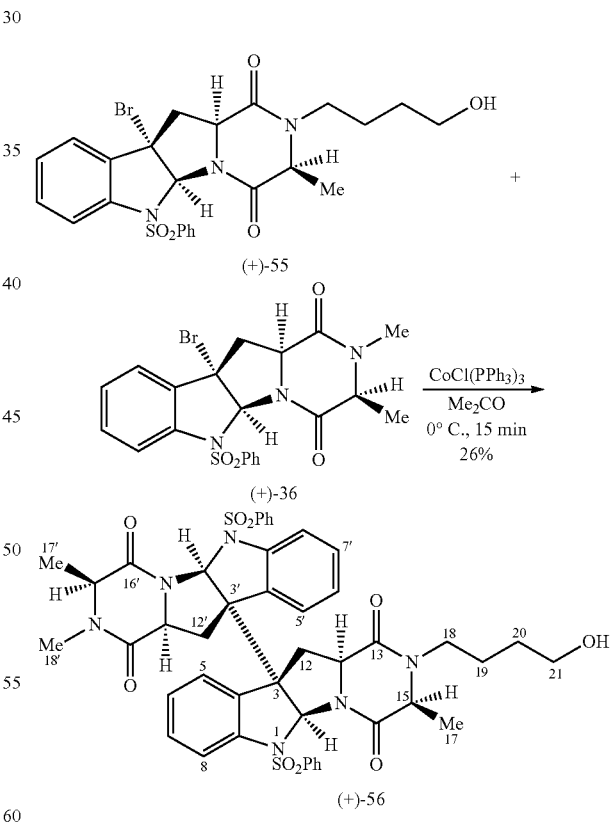

Heterodimeric Diketopiperazine Alcohol (+)-56

A sample of tris(triphenylphosphine)cobalt(I) chloride complex (4.17 g, 4.73 mmol, 3.00 equiv) was added as a solid to a solution of alcohol (+)-55 (862 mg, 1.58 mmol, 1 equiv) and N-methyl diketopiperazine bromide (Kim, J.; Ashenhurst, J. A.; Movassaghi, M. Science, 2009, 324, 238-241) (+)-36 (772 mg, 1.58 mmol, 1 equiv) in degassed (Ar stream, 20 min) acetone (30 mL) at 0° C. The ice-water bath was removed. After 15 min, the green suspension was diluted with ethyl acetate and was stirred vigorously for 10 min. The resulting blue solution was diluted with a saturated aqueous ammonium chloride solution (150 mL). The layers were separated and the aqueous layer was extracted with ethyl acetate (2×150 mL). The combined organic extracts were washed with a saturated aqueous sodium chloride solution (300 mL), were dried over anhydrous sodium sulfate, were filtered, and were concentrated under reduced pressure. The residue was purified by flash column chromatography on silica gel (eluent: 5→10% isopropanol, 50% dichloromethane 45→40% hexanes) to afford heterodimeric diketopiperazine alcohol (+)-56 (364 mg, 26.2%) as a white solid. Structural assignments were made using additional information from gCOSY, gHSQC, and gHMBC experiments. $^1$H NMR (600 MHz, CDCl$_3$, 25° C.): δ 8.11-8.01 (m, 4H, SO$_2$Ph-o-H, SO$_2$Ph'-o-H), 7.63-7.59 (m, 2H, SO$_2$Ph-p-H, SO$_2$Ph'-p-H), 7.56-7.52 (m, 4H, SO$_2$Ph-m-H, SO$_2$Ph'-m-H), 7.36 (dd, J=7.7, 1.3 Hz, 1H, C5H/C5'H), 7.33 (dd, J=7.8, 1.3 Hz, 1H, C5H/C5'H), 7.32-7.28 (m, 2H, C7H, C7'H), 7.24-7.18 (m, 2H, C6H, C6'H), 7.08 (d, J=8.4 Hz, 1H, C8H/C8'H), 7.04 (d, J=8.1 Hz, 1H, C8H/C8'H), 6.44 (s, 1H, C2H/C2'H), 6.43 (s, 1H, C2H/C2'H), 4.60 (t, J=9.0 Hz, 1H, C11H/C11'H), 4.51 (dd, J=9.5, 7.5 Hz, 1H, C11H/C11'H), 4.03 (q, J=7.0 Hz, 1H, C15/C15'H), 3.98 (q, J=7.0 Hz, 1H, C15/15'H), 3.55 (m, 3H, C18H$_a$, C20H), 3.09 (dt, J=14.3, 7.1 Hz, 1H, C18H$_b$), 2.84 (s, 3H, C18'H), 2.80-2.70 (m, 2H, C12H$_a$, C12H$_a$'), 2.62 (dd, J=15.0, 7.5 Hz, 1H, C12H$_b$/C12'H$_b$), 2.55 (dd, J=15.0, 8.6 Hz, 1H, C12H$_b$/C12'H$_b$), 1.46-1.34 (m, 4H, C19H, C20H), 1.37 (d, J=7.0 Hz, 3H, C17H/C17'H) 1.36 (d, J=7.0 Hz, 3H, C17H/C17'H). $^{13}$C NMR (150 MHz, CDCl$_3$, 25° C.): δ 169.2 (2C, C16, C16'), 168.4 (C13/C13'), 168.2 (C13/C13'), 142.2 (2C, C9, C9'), 141.7 (SO$_2$Ph-ipso-C/SO$_2$Ph'-ipso-C), 141.6 (SO$_2$Ph-ipso-C/SO$_2$Ph'-ipso-C), 135.5 (C4/C4'), 135.0 (C4/C4'), 133.1 (2C, SO$_2$Ph-p-C, SO$_2$Ph'-p-C), 129.8 (C7/C7'), 129.7 (C7/C7'), 129.0 (2C, SO$_2$Ph-m-C, SO$_2$Ph'-m-C), 127.5 (SO$_2$Ph-o-C/SO$_2$Ph'-o-C), 127.4 (SO$_2$Ph-o-C/SO$_2$Ph'-o-C), 127.3 (C5/C5'), 127.1 (C5/C5'), 125.1 (2C, C6, C6'), 117.4 (C8/C8'), 117.2 (C8/C8'), 81.9 (2C, C2/C2'), 62.3 (C21), 59.7 (C3/C3'), 59.4 (C3/C3'), 57.5 (C11/C11'), 57.4 (C11/C11'), 57.1 (C15/C15'), 55.9 (C15/C15'), 42.1 (C18), 34.1 (C12/C12'), 33.4 (C12/C12'), 29.9 (C18'), 29.4 (C19), 24.8 (C20), 15.1 (C17/C17'), 14.3 (C17/C17'). FTIR (thin film) cm$^{-1}$: 3408 (br-w), 3071 (w), 2249 (w), 1665 (s), 1391 (m), 1335 (m), 1159 (s), 909 (m), 727 (s), 589 (s). HRMS (ESI) (m/z): calc'd for C$_{45}$H$_{47}$N$_6$O$_9$S$_2$ [M+H]$^+$: 879.2840, found: 879.2878. [α]$_D^{23}$: +12 (c=1.2, CHCl$_3$). TLC (10% isopropanol, 50% dichloromethane, 40% hexanes), Rf: 0.35 (UV, CAM).

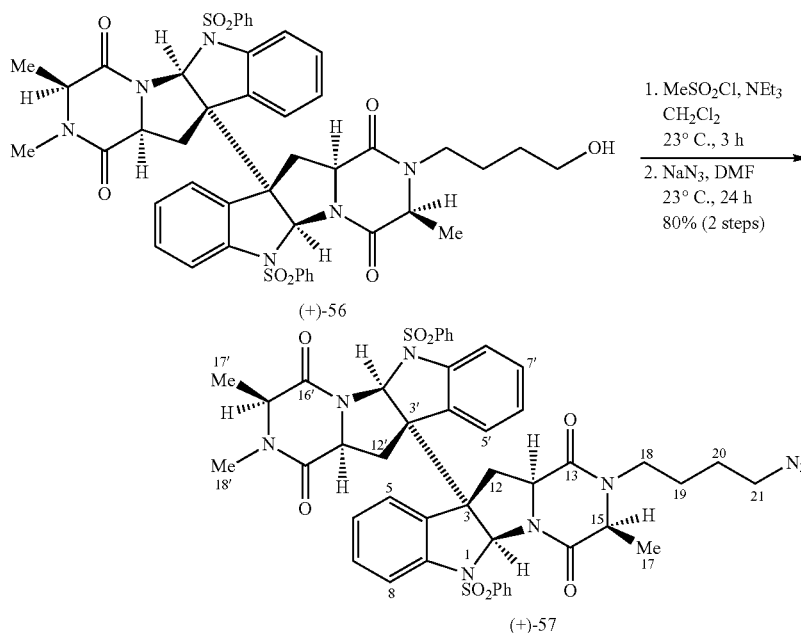

Heterodimeric Diketopiperazine Azide (+)-57

Methanesulfonyl chloride (130 μL, 1.55 mmol, 4.00 equiv) was added to a solution of heterodimeric alcohol (+)-56 (340 mg, 387 μmol, 1 equiv) and triethylamine (393 μL, 3.10 mmol, 8.00 equiv) at 23° C. After 3 h, the orange solution was diluted with dichloromethane (30 mL) and a saturated aqueous sodium bicarbonate solution (30 mL). The layers were separated and the aqueous layer was extracted with dichloromethane (2×30 mL). The combined organic extracts were washed with a saturated aqueous sodium chloride solution (45 mL), were dried over anhydrous sodium sulfate, were filtered, and were concentrated under reduced pressure to provide the crude mesylate as a yellow foam, which was used directly in the next step without further purification.

A sample of sodium azide (91.3 mg, 1.42 mmol, 4.00 equiv) was added as a solid to a solution of the crude mesylate in N,N-dimethylformamide (3.78 mL) at 23° C. After 24 h, the orange suspension was diluted with a saturated aqueous sodium bicarbonate solution (30 mL). The mixture was extracted with ethyl acetate (3×30 mL). The combined organic extracts were washed with a saturated aqueous sodium chloride solution (2×45 mL), were dried over anhydrous sodium sulfate, were filtered, and were concentrated under reduced pressure. The residue was purified by flash column chromatography on silica gel (eluent: 10→15% acetone in dichloromethane) to afford heterodimeric diketopiperazine azide (+)-57 (280 mg, 80.1%) as an off-white solid. Structural assignments were made using additional information from gCOSY, gHSQC, and gHMBC experiments. $^1$H NMR (600 MHz, CDCl$_3$, 25° C.): δ 8.14-8.04 (m, 4H, SO$_2$Ph-o-H, SO$_2$Ph'-o-H), 7.65-7.58 (m, 2H, SO$_2$Ph-p-H, SO$_2$Ph'-p-H), 7.57-7.50 (m, 4H, SO$_2$Ph-m-H, SO$_2$Ph'-m-H), 7.37 (d, J=6.7 Hz, 1H, C5H/C5'H), 7.34-7.28 (m, 3H, C5H/C5'H, C7H, C7'H), 7.22 (m, 2H, C6H, C6'H), 7.09 (d, J=8.3 Hz, 1H, C8H/C8'H), 7.04 (d, J=8.0 Hz, 1H, C8H/C8'H), 6.45 (s, 1H, C2H/C2'H), 6.43 (s, 1H, C2H/C2'H), 4.60 (t, J=9.0 Hz, 1H, C11H/C11'H), 4.55-4.45 (m, 1H, C11H/C11'H), 4.07-3.94 (m, 2H, C15H/C15'H), 3.55-3.46 (m, 1H, C18H$_a$), 3.23-3.16 (m, 2H, C21H), 3.14-3.05 (m, 1H, C18H$_b$), 2.84 (s, 3H, C18'H), 2.80-2.69 (m, 2H, C12H$_a$, C12'H$_a$), 2.63 (dd, J=15.0, 7.4 Hz, 1H, C12H$_b$/C12'H$_b$), 2.55 (dd, J=15.1, 8.6 Hz, 1H, C12H$_b$/C12'H$_b$), 1.48-1.31 (m, 10H, C19H, C20H, C17H, C17'H). $^{13}$C NMR (150 MHz, CDCl$_3$, 25° C.): δ 169.2 (C16/C16'), 169.0 (C16/C16'), 168.3 (C13/C13'), 168.2 (C13/C13'), 142.1 (2C, C9, C9'), 141.7 (SO$_2$Ph-ipso-C/SO$_2$Ph'-ipso-C), 141.6 (SO$_2$Ph-ipso-C/SO$_2$Ph'-ipso-C), 135.5 (C4/C4'), 134.9 (C4/C4'), 133.1 (2C, SO$_2$Ph-p-C, SO$_2$Ph'-p-C), 129.7 (2C, C7, C7') 129.0 (2C, SO$_2$Ph-m-C, SO$_2$Ph'-m-C), 127.5 (C5/C5'), 127.3 (2C, C5/C5', SO$_2$Ph-o-C/SO$_2$Ph'-o-C), 127.1 (SO$_2$Ph-o-C/SO$_2$Ph'-o-C), 125.1 (C6/C6'), 125.0 (C6/C6'), 117.4 (C8/C8'), 117.2 (C8/C8'), 81.9 (2C C2, C2'), 59.7 (C3/C3'), 59.4 (C3/C3'), 57.5 (C11/C11'), 57.4 (C11/C11'), 57.0 (C15/C15'), 55.8 (C15/C15'), 51.0 (C21), 41.7 (C18), 34.0 (C12/C12'), 33.3 (C12/C12'), 29.8 (C18'), 26.1 (C20), 25.6 (C19), 15.1 (C17/C17'), 14.3 (C17/C17'). FTIR (thin film) cm$^{-1}$: 3615 (br-w), 3067 (w), 2947 (w), 2097 (m), 1676 (s), 1477 (m), 1162 (s), 731 (s), 598 (s). HRMS (ESI) (m/z): calc'd for C$_{45}$H$_{46}$N$_9$O$_8$S$_2$[M+H]$^+$: 904.2905, found: 904.2920. [α]$_D^{23}$: +2.0 (c=1.2, CHCl$_3$). TLC (20% acetone in dichloromethane), Rf: 0.35 (UV, CAM).

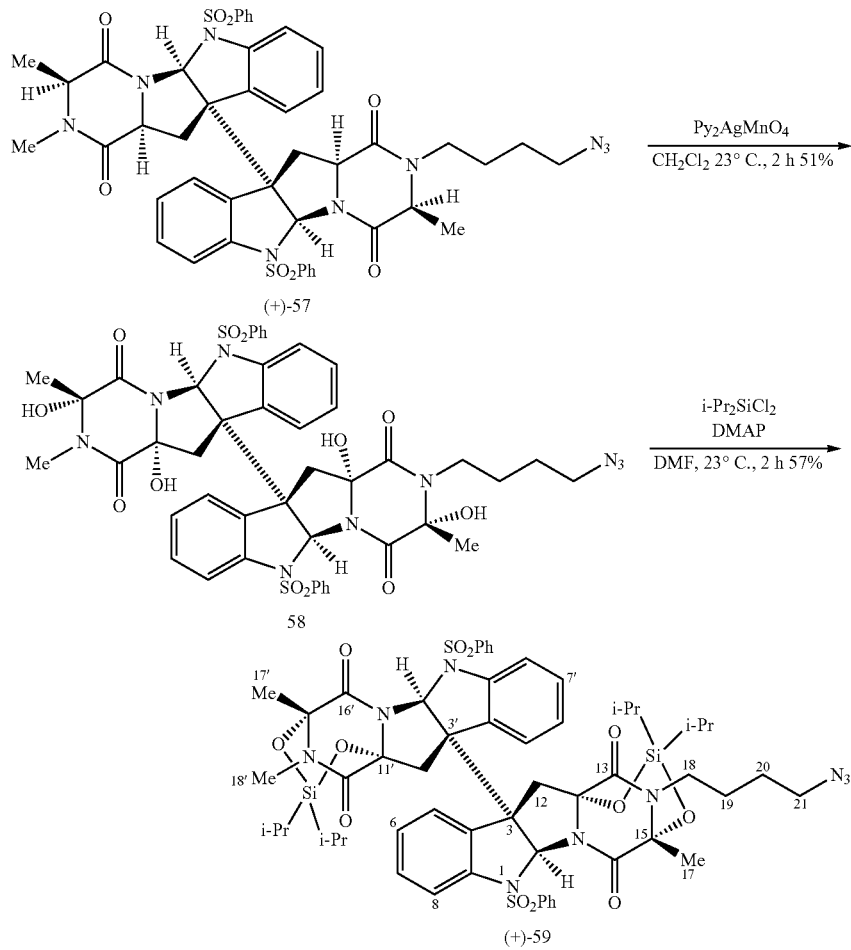

Heterodimeric Dioxasilane (+)-59:

A sample of bis(pyridine)silver(I) permanganate (102 mg, 264 μmol, 5.00 equiv) was added to a solution of heterodimeric azide (+)-57 (47.8 mg, 52.9 μmol, 1 equiv) in dichloromethane (530 μL) at 23° C. After 2 h, the thick purple suspension was diluted with a saturated aqueous sodium bisulfite solution (20 mL) and dichloromethane (20 mL). The layers were separated and the aqueous layer was extracted with dichloromethane (2×20 mL). The combined organic extracts were washed with a saturated aqueous copper sulfate solution (20 mL), were dried over anhydrous sodium sulfate, were filtered, and were concentrated under reduced pressure. The residue was purified by flash column chromatography on silica gel (eluent: 20% acetone in dichloromethane) to afford heterodimeric tetraol 58 (26.0 mg, 50.8%) as a white solid.

A sample of 4-(dimethylamino)pyridine (DMAP, 32.9 mg, 268 µmol, 10.0 equiv) and dichlorodiisopropylsilane (20.4 µL, 107 µmol, 4.00 equiv) were sequentially added to a solution of heterodimeric tetraol 58 (25.8 mg, 26.7 µmol, 1 equiv) in N,N-dimethylformamide (650 µL). After 2 h, the reaction mixture was diluted with ethyl acetate-hexanes (1:1, 10 mL) and a saturated aqueous sodium bicarbonate solution (10 mL). The layers were separated, and the aqueous layer was extracted with ethyl acetate-hexanes (1:1, 2×10 mL). The combined organic extracts were washed with a saturated aqueous sodium chloride solution (3×10 mL), were dried over anhydrous sodium sulfate, were filtered, and were concentrated under reduced pressure. The residue was purified by flash column chromatography on silica gel (eluent: 10→30% ethyl acetate in hexanes) to afford heterodimeric dioxasilane (+)-59 (18.1 mg, 57.0%) as a white solid. Structural assignments were made using additional information from gCOSY, gHSQC, and gHMBC experiments. $^1$H NMR (600 MHz, CDCl$_3$, 25° C.): δ 7.80-7.72 (m, 6H, SO$_2$Ph-o-H, SO$_2$Ph'-o-H, C5H, C5'H), 7.55-7.49 (m, 2H, SO$_2$Ph-p-H, SO$_2$Ph'-p-H), 7.49-7.39 (m, 4H, SO$_2$Ph-m-H, SO$_2$Ph'-m-H), 7.17-7.12 (m, 2H, C6H, C6'H), 7.13-7.03 (m, 2H, C7H, C7'H), 6.89 (m, 2H, C8H, C8'H), 6.82 (s, 1H, C2H/C2'H), 6.80 (s, 1H, C2H/C2'H), 3.84 (m, 2H, C12H$_a$, C12'H$_a$), 3.53 (dt, J=14.3, 8.0 Hz, 1H, C18H$_a$), 3.25-3.10 (m, 4H, C12H$_b$/C12'H$_b$, C18H$_b$ C21H), 3.07 (d, J=15.0 Hz, 1H, C12H$_b$/C12'H$_b$), 2.93 (s, 3H, C18'H), 1.48-1.28 (m, 4H, C19H, C20H), 1.37 (app-d, J=2.7 Hz, 6H, C17H, C17'H), 1.10-1.00 (m, 14H, SiCH(CH$_3$)$_2$, SiCH(CH$_3$)$_2$, SiCH(CH$_3$)$_2$, SiCH(CH$_3$)$_2$), 0.95-0.79 (m, 14H, SiCH(CH$_3$)$_2$, SiCH (CH$_3$)$_2$, SiCH(CH$_3$)$_2$, SiCH(CH$_3$)$_2$). $^{13}$C NMR (150 MHz, CDCl$_3$, 25° C.): δ 167.6 (C16/C16'), 167.2 (C16/C16'), 165.8 (C13/C13'), 165.7 (C13/C13'), 143.3 (SO$_2$Ph-ipso-C/SO$_2$Ph'-ipso-C), 143.1 (SO$_2$Ph-ipso-C/SO$_2$Ph'-ipso-C), 141.1 (2C, C9, C9'), 132.2 (2C, C4, C4') 132.0 (SO$_2$Ph-p-C/SO$_2$Ph'-p-C), 131.3 (SO$_2$Ph-p-C/SO$_2$Ph'-p-C), 129.7 (C7/C7'), 129.6 (C7/C7'), 128.7 (2C, SO$_2$Ph-m-C, SO$_2$Ph'-m-C), 126.3 (C5/C5'), 126.1 (C5/C5'), 125.7 (SO$_2$Ph-o-C/SO$_2$Ph'-o-C), 125.6 (SO$_2$Ph-o-C/SO$_2$Ph'-o-C), 125.2 (C6/C6'), 125.1 (C6/C6'), 115.4 (C8/C8'), 115.3 (C8/C8'), 88.9 (C11/C11'), 88.8 (C11/C11'), 87.1 (C15/C15'), 86.7 (C15/C15'), 82.4 (C2/C2'), 82.1 (C2/C2'), 60.3 (C3/C3'), 60.2 (C3/C3'), 51.1 (C21), 45.2 (C12/C12'), 44.7 (C12/C12'), 42.1 (C18), 28.3 (C18'), 26.8 (C20), 26.1 (C19), 22.6 (4C, SiCH(CH$_3$)$_2$), 16.6 (SiCH(CH$_3$)$_2$), 16.5 (2C, SiCH(CH$_3$)$_2$), 16.4 (SiCH (CH$_3$)$_2$), 16.3 (SiCH(CH$_3$)$_2$), 16.2 (SiCH(CH$_3$)$_2$), 13.7 (SiCH(CH$_3$)$_2$), 13.5 (SiCH(CH$_3$)$_2$). FTIR (thin film) cm$^{-1}$: 3418 (br-w), 2925 (s), 2868 (m), 2097 (m), 1721 (m), 1462 (m), 1355 (s), 1167 (s), 979 (m), 781 (m), 584 (s). HRMS (ESI) (m/z): calc'd for C$_{57}$H$_{69}$N$_9$NaO$_{12}$S$_2$Si$_2$ [M+Na]$^+$: 1214.3943, found: 1214.3921. [α]$_D^{23}$: +10 (c=1.38, CHCl$_3$). TLC (30% ethyl acetate in hexanes), Rf: 0.31 (UV, CAM). Hydrogen-bonding induced signal broadening and instability of tetraol 58 complicated its full characterization by NMR. The measured HRMS was consistent with the desired product; HRMS (ESI) (m/z): calc'd for C$_{45}$H$_{45}$N$_9$NaO$_{12}$S$_2$ [M+Na]$^+$: 990.2521, found: 990.2484.

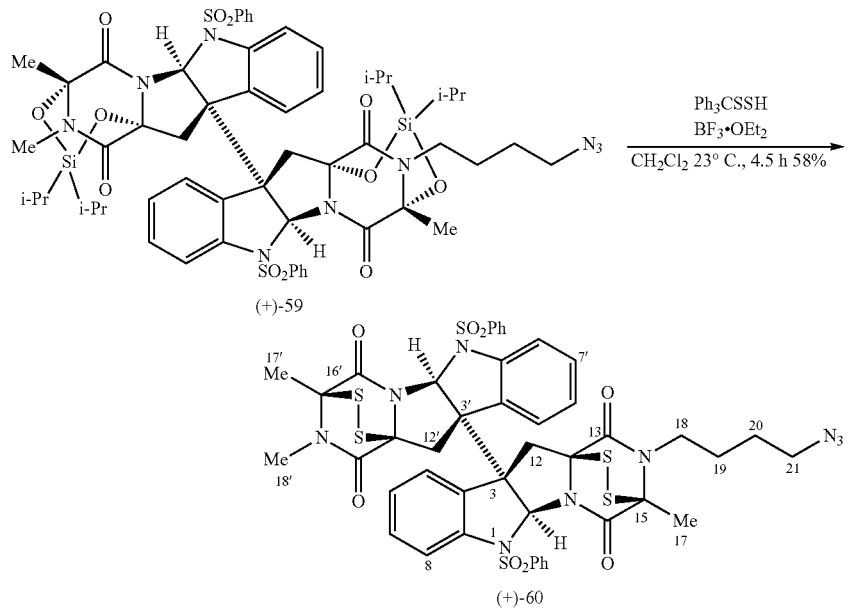

Alternative Synthesis of Heterodimeric Epidithiodiketopiperazine Azide 60

A solution of heterodimeric dioxasilane (+)-59 (20.8 mg, 17.4 µmol, 1 equiv) in dichloromethane (500 µL) was added via cannula to a solution of freshly prepared tritylhydrodisulfane (81.0 mg, 263 µmol, 15.1 equiv) in dichloromethane (500 µL). The transfer was quantitated with additional dichloromethane (750 µL). Boron trifluoride diethyl etherate (44.5 µL, 349 µmol, 20.0 equiv) was added at 23° C. After 4.5 h, the reaction mixture was diluted with dichloromethane (10 mL) and with a saturated aqueous sodium bicarbonate solution (30 mL). The layers were separated, and the aqueous layer was extracted with dichloromethane (2×30 mL). The combined organic layers were washed with a saturated aqueous sodium chloride solution (30 mL), were dried over anhydrous sodium sulfate, were filtered, and were concentrated under reduced pressure. The resulting residue was purified by flash column chromatography on silica gel (eluent: 0→15% ethyl acetate in dichloromethane) to afford heterodimeric epidithiodiketopiperazine azide (+)-60 (10.4 mg, 58.0%) as a white solid. Structural assignments were made using additional information from gCOSY, gHSQC, and gHMBC experiments. $^1$H NMR (600 MHz, CDCl$_3$, 25°

C.): δ 7.90-7.86 (m, 4H, SO₂Ph-o-H, SO₂Ph'-o-H), 7.70-7.65 (m, 2H, C8H, C8'H), 7.58-7.53 (m, 2H, SO₂Ph-p-H, SO₂Ph'-p-H), 7.51-7.45 (m, 4H, SO₂Ph-m-H, SO₂Ph'-m-H), 7.26-7.20 (m, 2H, C6H, C6'H), 7.19 (m, 2H, C7H, C7'H), 7.10-7.05 (m, 2H, C5H, C5'H), 6.84 (s, 1H, C2H/C2'H), 6.83 (s, 1H, C2H/C2'H), 3.78 (dt, J=15.1, 7.7 Hz, 1H, C18H$_a$), 3.57 (dd, J=15.1, 2.4 Hz, 2H, C12H$_a$/C12'H$_a$), 3.32-3.20 (m, 3H, C21H, C18H$_b$), 2.99 (s, 3H, C18'H), 2.94 (dd, J=15.2, 3.7 Hz, 2H, C12H$_b$/C12'H$_b$), 1.72-1.67 (m, 2H, C19H) 1.70 (s, 3H, C17H/C17'H), 1.65 (s, 3H, C17H/C17'H), 1.62-1.56 (m, 2H, C20H). ¹³C NMR (150 MHz, CDCl₃, 25° C.): δ 164.8 (C16/C16'), 164.4 (C16/C16'), 160.7 (C13/C13'), 160.6 (C13/C13'), 142.5 (2C, C9, C9'), 142.3 (2C, SO₂Ph-ipso-C, SO₂Ph'-ipso-C), 132.5 (2C, SO₂Ph-p-C, SO₂Ph'-p-C), 130.9 (2C, C4, C4'), 130.4 (2C, C6, C6'), 128.9 (2C, SO₂Ph-m-C, SO₂Ph'-m-C), 125.8 (SO₂Ph-o-C/SO₂Ph'-o-C), 125.7 (SO₂Ph-o-C/SO₂Ph'-o-C), 125.1 (2C, C7, C7'), 124.8 (2C, C8'C8'), 116.3 (2C, C5, C5'), 81.9 (2C, C3'C3'), 73.8 (C15/C15'), 73.6 (C11/C11'), 73.4 (C11/C11'), 72.0 (C15/C15'), 60.4 (2C, C3'C3'), 51.0 (C21), 42.3 (C18), 41.6 (2C, C12, C12'), 27.7 (C18'), 26.3 (C20), 25.3 (C19), 17.9 (C17/C17'), 17.4 (C17/C17'). FTIR (thin film) cm⁻¹: 2927 (w), 2162 (m), 2097 (w), 1716 (s), 1688 (s), 1480 (m), 1462 (m), 1348 (s), 1168 (s), 1096 (m), 1057 (m), 753 (m), 730 (m), 582 (s). HRMS (ESI) (m/z): calc'd for C₄₅H₄₂N₉O₈S₆[M+H]⁺: 1027.1475, found: 1027.1483. [α]$_D^{23}$: +329 (c=0.29, CHCl₃). TLC (15% ethyl acetate in dichloromethane), Rf: 0.34 (UV, CAM).

Epithiodiketopiperazine Triazole (+)-61

A solution of aqueous copper sulfate pentahydrate (46.1 μM, 12.5 μL, 576 nmol, 0.100 equiv), and a solution of aqueous sodium L-ascorbate (92.2 μM, 12.5 μL, 1.15 μmol, 0.200 equiv) were added sequentially via syringe to a solution of heterodimeric epithiodiketopiperazine azide (+)-60 (5.92 mg, 5.76 μmol, 1 equiv) and alkyne (Grimes, K. D.; Aldrich, C. C. *Analytical Biochemistry*, 2011, 417, 264-273) U12 (4.88 mg, 17.3 μmol, 3.00 equiv) in N,N-dimethylformamide-water (4:1, 250 μL) at 23° C. The reaction vessel was sealed with a Teflon-lined glass stopper. After 18 h, the reaction mixture was diluted with ethyl acetate (10 mL) and with water (10 mL). The layers were separated, and the aqueous layer was extracted with ethyl acetate (2×10 mL). The combined organic extracts were washed with a saturated aqueous sodium chloride solution (10 mL), were dried over anhydrous sodium sulfate, were filtered, and were concentrated under reduced pressure. The resulting residue was purified by flash column chromatography on silica gel (eluent: 20% acetone in dichloromethane→5% methanol in dichloromethane) to afford epithiodiketopiperzine triazole (+)-61 (5.61 mg, 74.3%) as a colorless solid. Structural assignments were made using additional information from gCOSY, gHSQC, and gHMBC experiments. ¹H NMR (600 MHz, CDCl₃, 25° C.): δ 7.93-7.82 (m, 4H, SO₂Ph-o-H, SO₂Ph'-o-H), 7.67-7.64 (m, 2H, C8H, C8'H), 7.60-7.54 (m, 2H, SO₂Ph-p-H, SO₂Ph'-p-H), 7.52 (s, 1H, C22H), 7.50-7.45 (m, 4H, SO₂Ph-m-H, SO₂Ph'-m-H), 7.27-7.23 (m, 2H, C6H, C6'H), 7.22-7.17 (m, 2H, C7H, C7'H), 7.12-7.06 (m, 2H, C5H, C5'H), 6.82 (m, 2H, C2H, C2'H), 5.05 (br-s, 1H, NHBoc), 4.65 (s, 2H, C24H), 4.35 (td, J=6.9, 2.6 Hz, 2H, C21H), 3.77 (dt, J=15.4, 7.7 Hz, 1H, C29H$_a$), 3.70-3.51 (m, 12H, C12H$_a$, C12'H$_a$, C18H, C25H, C26H, C27H, C28H),

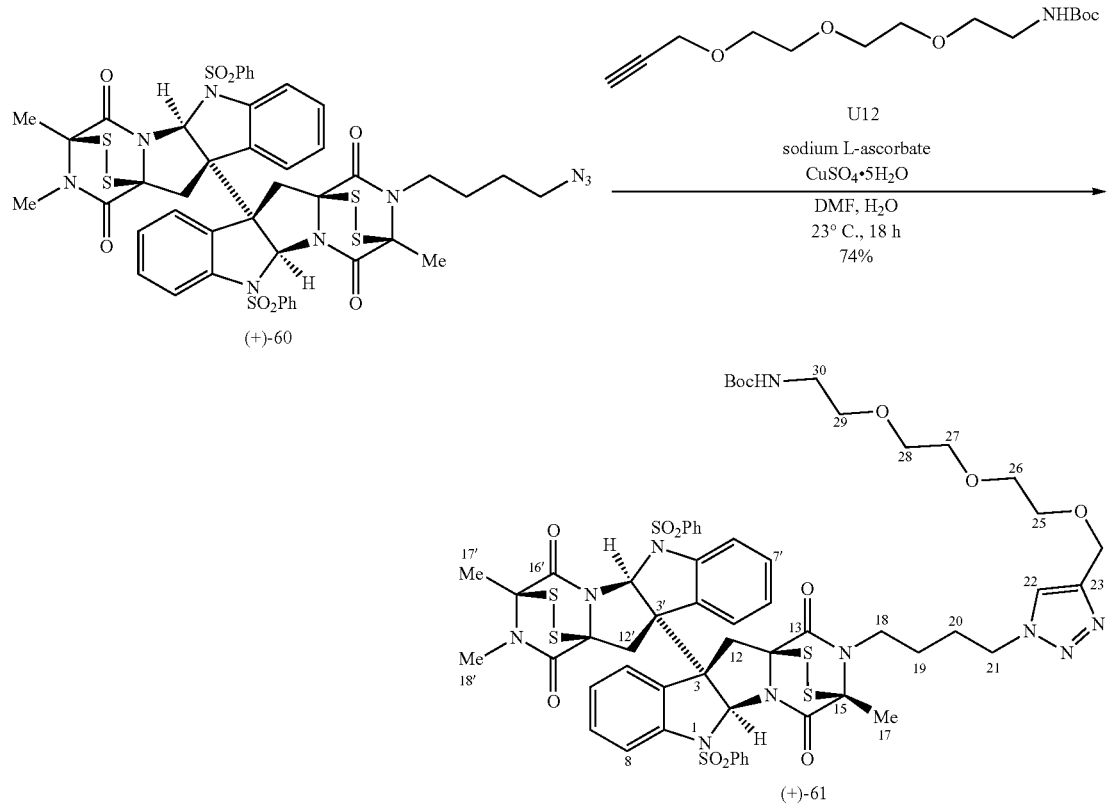

3.50-3.44 (m, 1H, C29H$_b$), 3.36-3.25 (m, 2H, C30H), 2.99 (s, 3H, C18'H), 2.95-2.85 (m, 2H, C12H$_b$, C12'H$_b$), 1.90 (p, J=7.2 Hz, 2H, C20H), 1.70-1.64 (m, 2H, C19H), 1.67 (s, 3H, C17H/C17'H), 1.65 (s, 3H, C17H/C17'H), 1.43 (s, 9H, NCO₂C(CH₃)₃). ¹³C NMR (150 MHz, CDCl₃, 25° C.): δ

164.8 (C16/C16'), 164.6 (C16/C16'), 160.8 (C13/C13'), 160.6 (C13/C13'), 156.2 (NCO$_2$C(CH$_3$)$_3$), 145.4 (C23), 142.6 (2C, C9, C9'), 142.2 (2C, SO$_2$Ph-ipso-C, SO$_2$Ph'-ipso-C), 132.6 (2C, SO$_2$Ph-p-C, SO$_2$Ph'-p-C), 131.0 (C4/C4'), 130.9 (C4/C4'), 130.6 (2C, C6, C6'), 129.0 (SO$_2$Ph-m-C/SO$_2$Ph'-m-C), 128.9 (SO$_2$Ph-m-C/SO$_2$Ph'-m-C), 125.8 (2C, SO$_2$Ph-o-C, SO$_2$Ph'-o-C), 125.1 (2C, C7, C7'), 124.9 (2C, C8'C8'), 122.7 (C22), 116.5 (2C, C5, C5'), 81.9 (2C, C2, C2'), 79.3 (NCO$_2$C(CH$_3$)$_3$), 73.8 (C15/C15'), 73.6 (C11/C11'), 73.4 (C11/C11'), 73.0 (C15/C15'), 70.7 (3C, C26, C27, C28), 70.4 (C29), 69.8 (C25), 64.8 (C24), 60.3 (2C, C3'C3'), 49.6 (C21), 41.8 (C18), 41.5 (2C, C12, C12'), 40.5 (C30), 28.6 (NCO$_2$C(CH$_3$)$_3$), 27.8 (C18'), 27.5 (C20), 25.2 (C19), 17.9 (C17/C17'), 17.4 (C17/C17'). FTIR (thin film) cm$^{-1}$: 3398 (br-w), 2930 (w), 1713 (s), 1684 (s), 1349 (s) 1167 (s), 1096 (m), 1056 (m), 753 (m), 582 (s). HRMS (ESI) (m/z): calc'd for C$_{59}$H$_{67}$N$_{10}$O$_{13}$S$_6$[M+H]$^+$: 1315.3208, found: 1315.3200. [α]$_D^{23}$: +231 (c 0.17, CHCl$_3$). TLC (5% methanol in dichloromethane), Rf: 0.18 (UV, CAM).

information from gCOSY, gHSQC, and gHMBC experiments. $^1$H NMR (600 MHz, CD$_3$OD, 25° C.): δ 7.95 (s, 1H, C22H), 7.92-7.86 (m, 4H, SO$_2$Ph-o-H, SO$_2$Ph'-o-H), 7.76-7.69 (m, 2H, C8H, C8'H), 7.69-7.60 (m, 2H, SO$_2$Ph-p-H, SO$_2$Ph'-p-H), 7.59-7.50 (m, 4H, SO$_2$Ph-m-H, SO$_2$Ph'-m-H), 7.32-7.23 (m, 2H, C6H, C6'H), 7.22-7.13 (m, 2H, C7H, C7'H), 7.13-7.06 (m, 2H, C5H, C5'H), 6.93-6.85 (m, 2H, C2H, C2'H), 4.60 (s, 2H, C24H), 4.43 (t, J=7.0 Hz, 2H, C21H), 3.72-3.62 (m, 14H, C12H$_a$, C12'H$_a$, C18H, C25H, C26H, C27H, C28H, C29H$_a$, C29H$_b$), 3.14-3.07 (m, 2H, C30H), 3.02-2.94 (m, 5H, C18'H, C12H$_b$, C12'H$_b$), 1.95-1.87 (m, 2H, C20H), 1.70-1.64 (m, 6H, C17H, C17'H), 1.61-1.56 (m, 2H, C19H). $^{13}$C NMR (150 MHz, CD$_3$OD, 25° C.): δ 166.6 (C16/C16'), 166.3 (C16/C16'), 162.4 (C13/C13'), 162.3 (C13/C13'), 145.7 (C23), 143.8 (2C, C9, C9'), 143.5 (2C, SO$_2$Ph-ipso-C, SO$_2$Ph'-ipso-C), 133.8 (2C, SO$_2$Ph-p-C, SO$_2$Ph'-p-C), 132.6 (C4/C4'), 131.1 (2C, C6, C6'), 130.0 (2C, SO$_2$Ph-m-C/SO$_2$Ph'-m-C), 126.94 (2C, SO$_2$Ph-o-C, SO$_2$Ph'-o-C), 126.5 (2C, C7, C7'), 126.0 (2C,

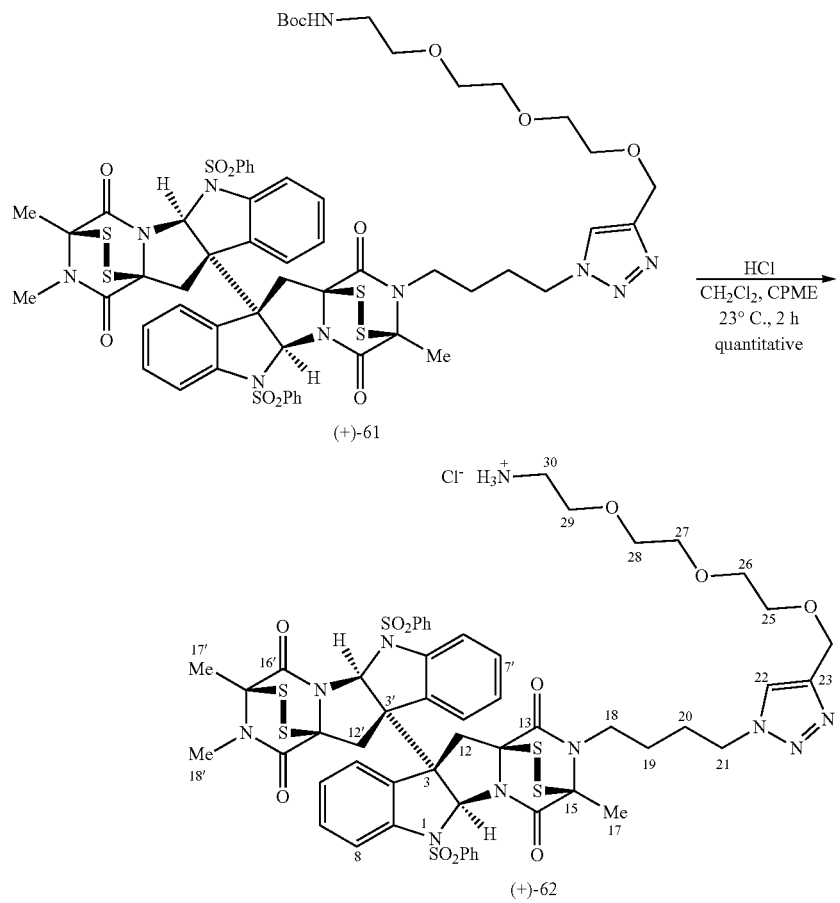

Epithiodiketopiperazine Ammonium Salt (+)-62

A solution of hydrogen chloride (3 M in CPME, 600 μL) was added via syringe to a solution of triazole (+)-61 (3.79 mg, 2.82 μmol, 1 equiv) in dichloromethane (200 μL) at 23° C. After 2 h, the heterogeneous reaction mixture was concentrated under reduced pressure. The resulting residue was filtered through a pad of silica gel (eluent: 10% methanol in dichloromethane) to afford epithiodiketopiperazine ammonium salt (+)-62 (3.48 mg, quantitative yield) as a white powder. Structural assignments were made using additional C8'C8'), 125.2 (C22), 117.4 (2C, C5, C5'), 83.2 (2C, C2, C2'), 75.0 (C15/C15'), 74.7 (2C, C11, C11'), 74.3 (C15/C15'), 71.6 (C26/C27/C28), 71.3 (C26/C27/C28), 71.1 (C26/C27/C28), 70.5 (C29), 67.9 (C25), 64.7 (C24), 61.4 (2C, C3'C3'), 50.7 (C21), 42.8 (C18), 41.9 (2C, C12, C12'), 40.7 (C30), 28.5 (C18'), 27.8 (C20), 26.0 (C19), 17.8 (C17/C17'), 17.4 (C17/C17'). FTIR (thin film) cm$^{-1}$: 2926 (w), 1717 (s), 1688 (m), 1349 (s), 1168 (s), 752 (s), 581 (m). HRMS (ESI) (m/z): calc'd for C$_{54}$H$_{59}$N$_{10}$O$_{11}$S$_6$[M]$^+$:

1215.2684, found: 1215.2691. $[\alpha]_D^{23}$: +171 (c=0.27, MeOH). TLC (20% methanol in dichloromethane), Rf: 0.43 (UV, CAM).

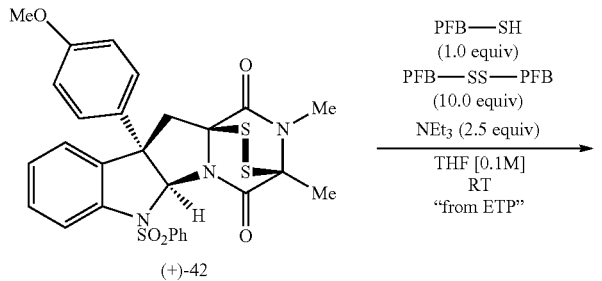

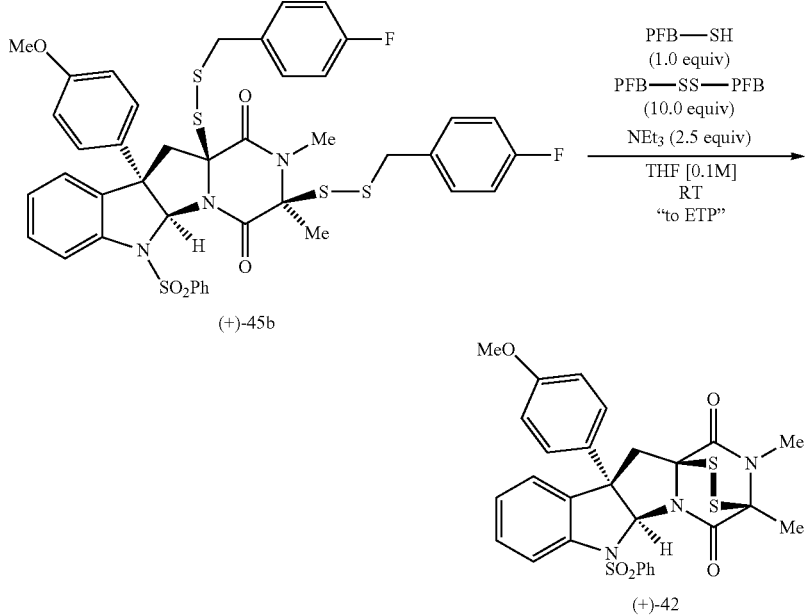

Equilibration of Epidisulfide (+)-42 and Bisdisulfide (+)-45b

Figure 3:
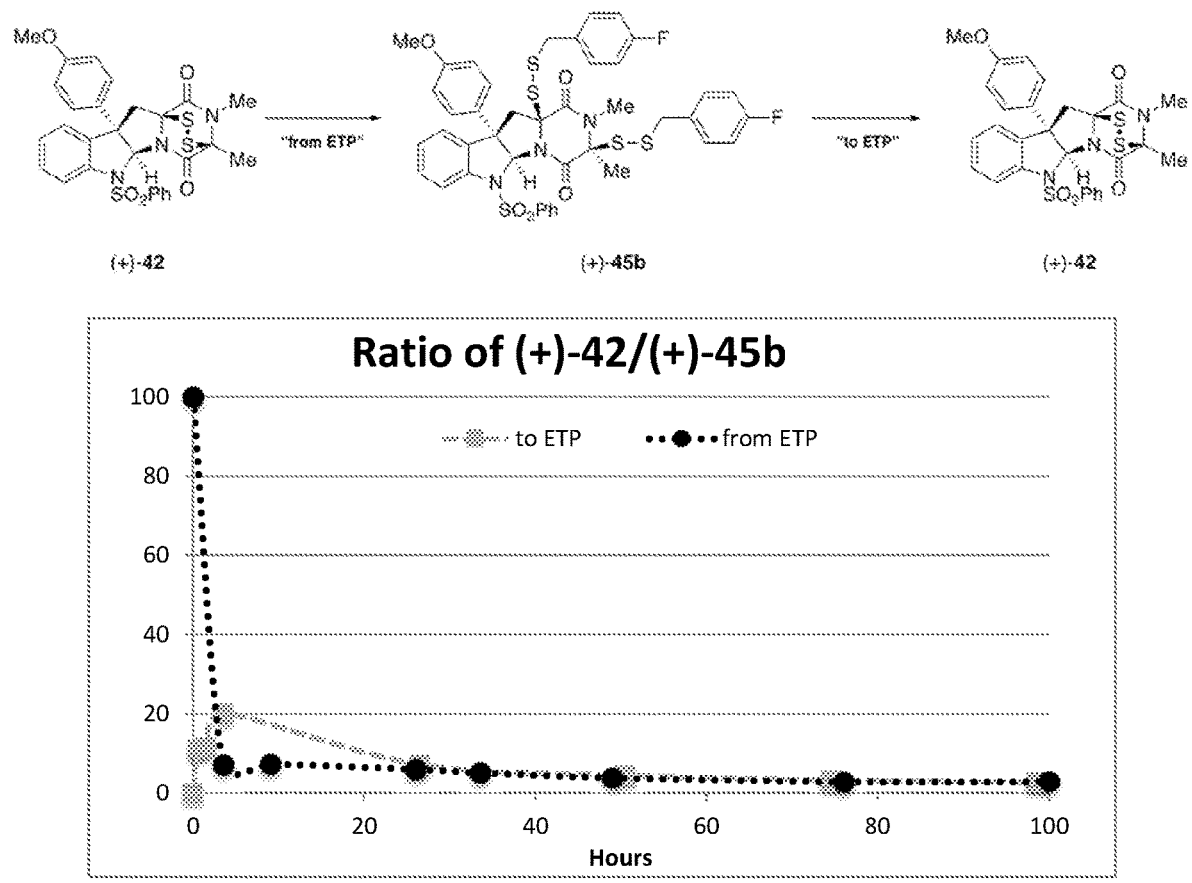
FIG. 3 shows the ratio of (+)-42 to (+)-45b.
Figure 4:
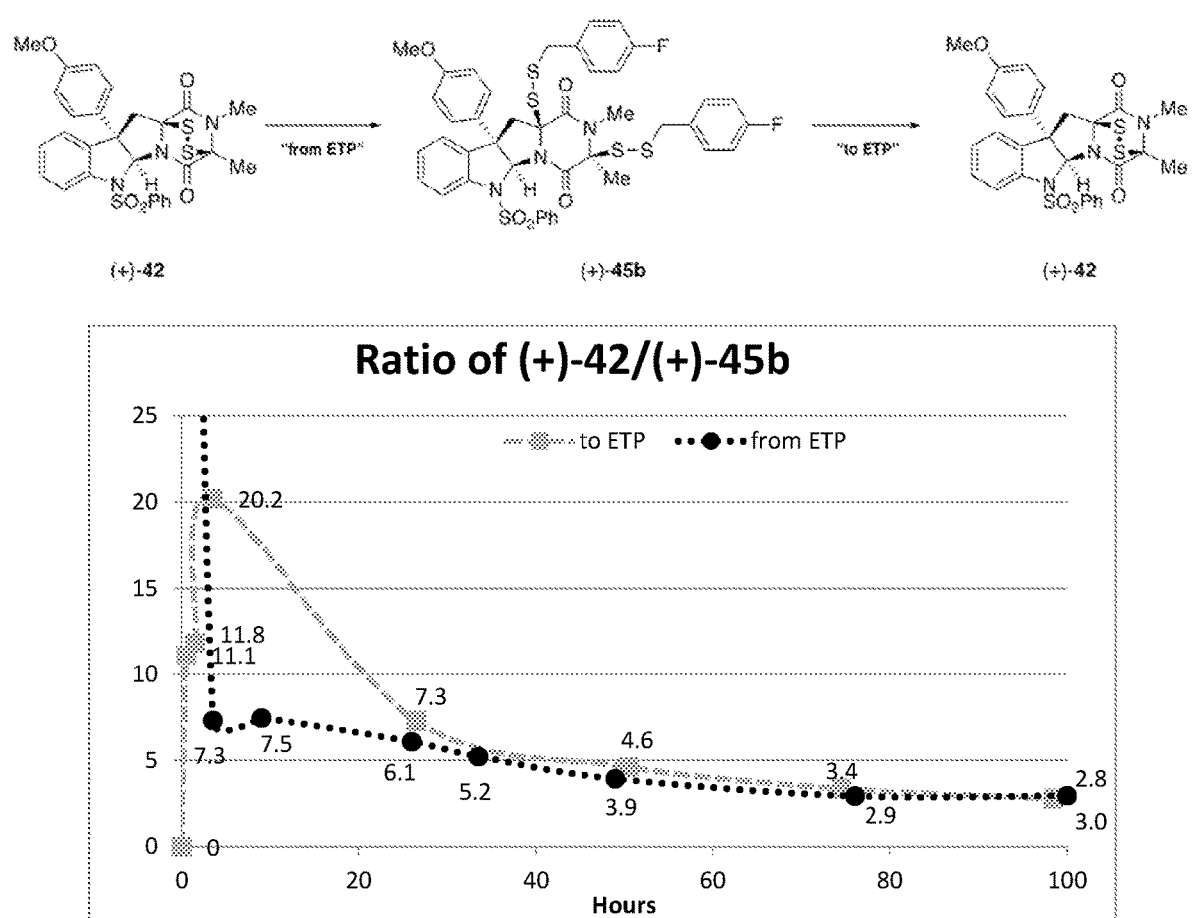
FIG. 4 shows the ratio of (+)-42 to (+)-45b.
Figure 5:
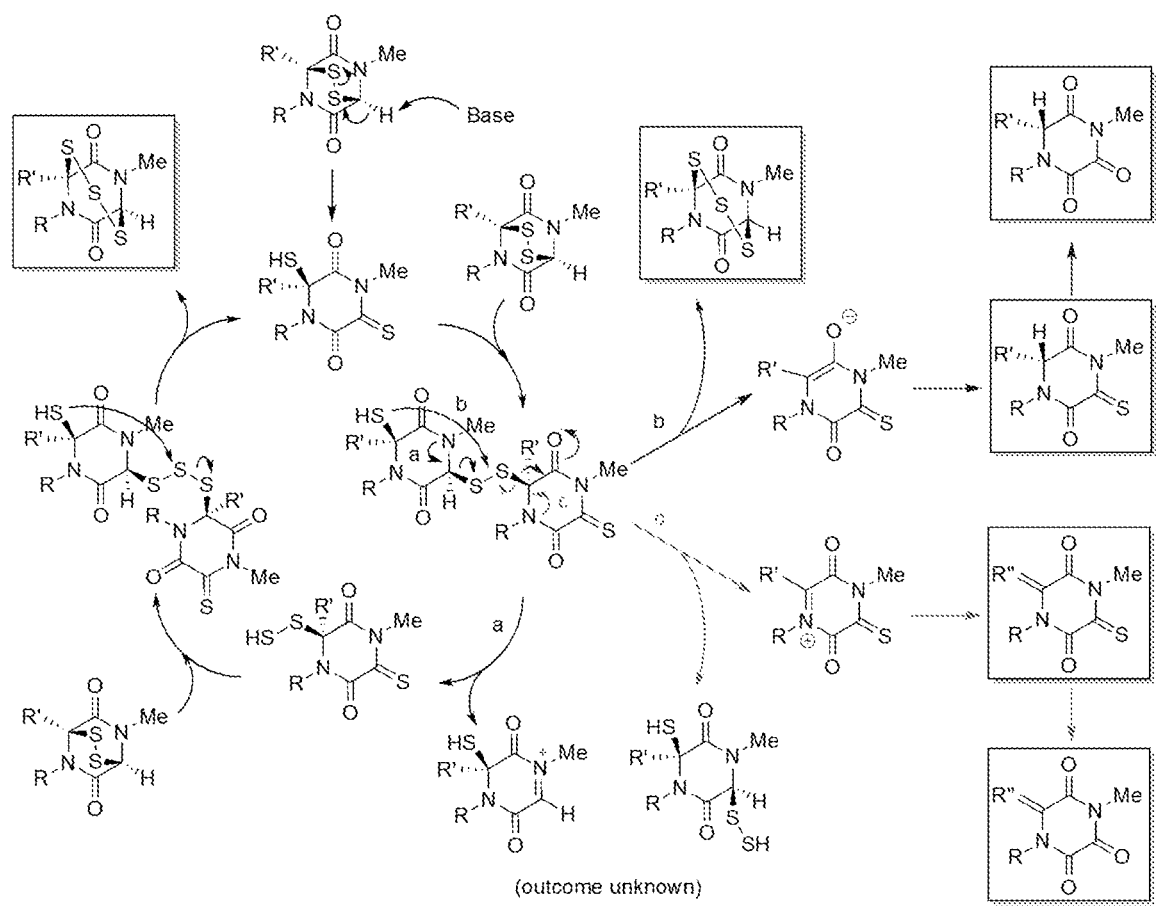
FIG. 5 shows the proposed mechanism of base-catalyzed decomposition of glycine-derived ETP.

As shown herein, the isolated quantities of epidisulfide (+)-42 and bisdisulfide (+)-45b suggested an equilibrium ratio of 3:1 favoring the ETP. To investigate this, aliquots of the reaction were diluted starting with epidisulfide (+)-42 ("from ETP") in CDCl$_3$ to analyze the composition versus an internal standard over a period of 100 h. Additionally, (+)-45b was resubjected to the same reaction conditions and monitored the reversion back to epidisulfide ("to ETP") in an analogous experiment. In both cases, equilibration approaching 3:1 was observed. See FIGS. 3-4.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All patent publications and non-patent publications are indicative of the level of skill of those skilled in the art to which this disclosure pertains. All these publications are herein incorporated by reference to the same extent as if each individual publication were specifically and individually indicated as being incorporated by reference.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

REFERENCES

1. U. Anthoni, C. Christophersen and P. H. Nielsen, in Alkaloids: Chemical and Biological Perspectives, ed. S. W. Pelletier, Pergamon Press, London, 1999, vol. 13, ch. 2, pp. 163-236; T. Hino and M. Nakagawa, in The Alkaloids: Chemistry and Pharmacology, ed. A. Brossi, Academic Press, New York, 1989, vol. 34, ch. 1, pp. 1-75.
2. (a) Gardiner, D. M.; Waring P.; Howlett, B. J. *Microbiology*, 2005, 151, 1021. (b) Patron, N. J.; Waller, R. F.; Cozijnsen, A. J.; Straney, D. C.; Gardiner, D. M.; Nierman W. C.; Howlett, B. J. *BMC Evol. Biol.*, 2007, 7, 174. (c) Steven, A.; Overman, L. E. *Angew. Chem., Int. Ed.* 2007, 46, 5488. (d) Huang, R.; Zhou, X.; Xu, T.; Yang, X.; Liu, Y. *Chem. Biodiversity*, 2010, 7, 2809. (e) Iwasa, E.; Hamashima Y.; Sodeoka, M. Isr. *J. Chem.*, 2011, 51, 420. (f) Kim, J.; Movassaghi, M. *Acc. Chem. Res.* 2015, 48, 1159. (g) Waring, P.; Beaver, J. *Gen. Pharmacol*, 1996, 27, 1311.
3. (a) Vigushin, D. M.; Mirsaidi, N.; Brooke, G.; Sun, C.; Pace, P.; Inman, L.; Moody, C. J.; Coombes, R. C. *Med. Oncol.* 2004, 21, 21. (b) Greiner, D.; Bonaldi, T.; Eskeland, R.; Roemer, E.; Imhof, A. *Nat. Chem. Biol.* 2005, 1, 143. (c) Yanagihara, M.; Sasaki-Takahashi, N.; Sugahara, T.; Yamamoto, S.; Shinomi, M.; Yamashita, I.; Hayashida, M.; Yamanoha, B.; Numata, A.; Yamori, T.; Andoh, T. *Cancer Sci.* 2005, 96, 816. (d) Zheng, C. J.; Kim, C. J.; Bae, K. S.; Kim, Y. H.; Kim, W. G. *J. Nat. Prod.* 2006, 69, 1816. (e) Isham, C. R.; Tibodeau, J. D.; Jin, W.; Xu, R.; Timm, M. M.; Bible, K. C. *Blood* 2007, 109, 2579. (f) Cherrier, T.; Suzanne, S.; Redel, L.; Calao, M.; Marban, C.; Samah, B.; Mukerjee, R.; Schwartz, C.; Gras, G.; Sawaya, B. E.; Zeichner, S. L.; Aunis, D.; Van Lint, C.; Rohr, O. *Oncogene* 2009, 28, 3380. (g) Chen, Y.; Guo, H.; Du, Z.; Liu, X. Z.; Che, Y.; Ye, X. *Cell Proliferation* 2009, 42, 838. (h) Cook, K. M.; Hilton, S. T.; Mecinovic, J.; Motherwell, W. B.; Figg, W. D.; Schofield, C. J. *J. Bio. Chem.* 2009, 39, 26831. (i) Isham, C. R.; Tibodeau, J. D.; Jin, W.; Timm, M. M.; Bible, K. C. *Blood* 2010, 109, 2579. (j) Jiana, C. S.; Guo, Y. W. *Mini-Rev. Med. Chem.* 2011, 9, 728. (k) Liu, F.; Liu, Q.; Yang, D.; Bollag, W. B.; Roberston, K.; Wu, P.; Liu, L. *Cancer Res.* 2011, 71, 6807. (l) Yano, K.; Horinaka, M.; Yoshida, T.; Yasuda, T.; Taniguchi, H.; Goda, A. E.; Wakada, M.; Yoshikawa, S.; Nakamura, T.; Kawauchi, A.; Miki, T.; Sakai, T. *Int. J. Oncol.* 2011, 38, 365. (m) Chaib, H.; Nebbioso, A.; Prebet, T.; Castellano, R.; Garbit, S.; Restouin, A.; Vey, N.; Altucci, L.; Collette, Y. *Leukemia* 2012, 26, 662. (n) Isham, C. R.; Tibodeau, J. D.; Bossou, A. R.; Merchan, J. R.; Bible, K. C. *Br. J. Cancer* 2012, 106, 314. (o) Takahashi, M.; Takemoto, Y.; Shimazu, T.; Kawasaki, H.; Tachibana, M.; Shinkai, Y.; Takagi, M.; Shin-ya, K.; Igarashi, Y.; Ito, A.; Yoshida, M. *J. Antibiot.* 2012, 65, 263. (p) Boyer, N.; Morrison K. C.; Kim, J.; Hergenrother, P. J.; Movassaghi M. *Chem. Sci.* 2013, 4, 1646. (q) Baumann, M.; Dieskau, A. P.; Loertscher, B. M.; Walton, M. C.; Nam, S.; Xie, J.; Home, D.; Overman, L. E. *J. Chem. Sci.* 2015, 6, 4451.
4. For representative syntheses of epipolythiodiketopiperazines, see: (a) Trown, P. W. *Biochem. Biophys. Res. Commun.* 1968, 33, 402. (b) Hino, T.; Sato, T. *Tetrahedron Lett.* 1971, 12, 3127. (c) Poisel, H.; Schmidt, U. *Chem. Ber.* 1971, 104, 1714. (d) Öhler, E.; Tataruch, F.; Schmidt, U. *Chem. Ber.* 1973, 106, 396. (e) Ottenheijm, H. C. J.; Herscheid, J. D. M.; Kerkhoff, G. P. C.; Spande, T. F. *J. Org. Chem.* 1976, 41, 3433. (f) Coffen, D. L.; Katonak, D. A.; Nelson, N. R.; Sancilio, F. D. *J. Org. Chem.* 1977, 42, 948. (g) Herscheid, J. D. M.; Nivard, R. J. F.; Tijhuis, M. W.; Scholten, H. P. H.; Ottenheijm, H. C. J. *J. Org. Chem.* 1980, 45, 1885. (h) Williams, R. M.; Rastetter, W. H. *J. Org. Chem.* 1980, 45, 2625. (i) Aliev, A. E.; Hilton, S. T.; Motherwell, W. B.; Selwood, D. L. *Tetrahedron Lett.* 2006, 47, 2387. (j) Overman, L. E.; Sato, T. *Org. Lett.* 2007, 9, 5267. (k) Polaske, N. W.; Dubey, R.; Nichol, G. S.; Olenyuk, B. *Tetrahedron: Asymmetry* 2009, 20, 2742. (l) Ruff, B. M.; Zhong, S.; Nieger, M.; Bräse, S. *Org. Biomol. Chem.* 2012, 10, 935. (m) Nicolaou, K. C.; Giguére, D.; Totokotsopoulos, S.; Sun, Y.-P. *Angew. Chem., Int. Ed.* 2012, 51, 728. (n) Codelli, J. A.; Puchlopek, A. L.; Reisman, S. E. *J. Am. Chem. Soc.* 2012, 134, 1930. (o) Takeuchi, R.; Shimokawa, J.; Fukuyama, T. *Chem. Sci.* 2014, 5, 2003.

5. For representative syntheses of epipolythiodiketopiperazines from our laboratory, see: (a) Kim, J.; Ashenhurst, J. A.; Movassaghi, M. *Science* 2009, 324, 238. (b) Kim, J.; Movassaghi, M. *J. Am. Chem. Soc.* 2010, 132, 14376. (c) Boyer, N.; Movassaghi, M. *Chem. Sci.,* 2012, 3, 1798. (d) Coste, A.; Kim, J.; Adams, T. C.; Movassaghi, M. *Chem. Sci.* 2013, 4, 3191. (e) Adams, T. C.; Payette, J. N.; Cheah, J. H.; Movassaghi, M. *Org. Lett.* 2015, 17, 4268.
6. (a) Hein, J. E.; Fokin, V. V. *Chem. Soc. Rev.* 2010, 39, 1302. (b) Berg, R.; Straub, B. F. *Beilstein J. Org. Chem.* 2013, 9, 2715.
7. Smith I.; Collins, I. *Future Med. Chem.* 2015, 7, 159.
8. Ghosh, B.; Jones, L. H. *Med. Chem. Commun.* 2014, 5, 247.
9. Larson, N.; Ghandehari, H. *Chem. Mater.* 2012, 24, 840.
10. (a) Flygare, J. A.; Pillow, T. H.; Aristoff, P. *Chem. Biol. Drug Des.* 2013, 81, 113. (b) Chari, R. V. J.; Miller, M. L.; Widdison, W. C. *Angew. Chem. Int. Ed.* 2014, 53, 3796.
11. Still, W. C.; Kahn, M.; Mitra, A. *J. Org. Chem.* 1978, 43, 2923.
12. Murdock, K. C. *J. Med. Chem.* 1974, 17(8), 827.
13. Pangborn, A. B.; Giardello, M. A.; Grubbs, R. H.; Rosen, R. K.; Timmers, F. *Organometallics* 1996, 15, 1518.
14. Fulmer, G. R.; Miller, A. J. M.; Sherden, N. H.; Gottlieb, H. E.; Nudelman, A.; Stoltz, B. M.; Bercaw, J. E.; Goldberg, K. I. *Organometallics* 2010, 29, 2176.
15. a) Yates, P.; MacLachlan, F. N.; Rae, I. D.; Rosenberger, M.; Szabo, A. G.; Willis, C. R.; Cava, M. P.; Behforouz, M.; Lakshmikantham, M. V.; Zeiger, W. *J. Am. Chem. Soc.* 1973, 95, 7842; b) Saxton, J. E. *The Alkaloids, Chem. and Biol.* 1998, 51, 1.
16. (a) Hein, J. E.; Fokin, V. V. *Chem. Soc. Rev.* 2010, 39, 1302. (b) Berg, R.; Straub, B. F. *Beilstein J. Org. Chem.* 2013, 9, 2715.
17. Smith I.; Collins, I. *Future Med. Chem.* 2015, 7, 159.
18. Ghosh, B.; Jones, L. H. *Med. Chem. Commun.* 2014, 5, 247.
19. Larson, N.; Ghandehari, H. *Chem. Mater.* 2012, 24, 840.
20. (a) Flygare, J. A.; Pillow, T. H.; Aristoff, P. *Chem. Biol. Drug Des.* 2013, 81, 113. (b) Chari, R. V. J.; Miller, M. L.; Widdison, W. C. *Angew. Chem. Int. Ed.* 2014, 53, 3796.
21. See the Examples section for details.
22. Lal, B.; Pramanik, B. N.; Manhas, M. S.; Bose, A. K. *Tetrahedron Lett.* 1977, 18, 1977.
23. Karaman, H.; Barton, R. J.; Robertson, B. E.; Lee, D. G. *J. Org. Chem.* 1984, 49, 4509.
24. For the preparation of bromide (+)-15 described in the Examples section.
25. Hulce, M.; Chapdelaine, M. C. Nucleophilic Addition-Electrophilic Coupling with a Carbanion Intermediate. In *Comprehensive Organic Synthesis*; Trost, B. M.; Fleming, I., Eds.; Pergamon: London, 1991; Vol. 4, pp 273-268.
26. (a) Okada, K.; Murakami, K.; Tanino, H.; Kakoi, H, Inoue, S. *Heterocycles* 1996, 43, 1735. (b) Fanning, K. N.; Sutherland, A. *Tetrahedron Lett.* 2007, 48, 8479.
27. Use of $CH_2Cl_2$ as solvent in the CuAAC reaction of ETP (+)-9b and 4-ethynylanisole X gave cycloadduct (+)-28b in 73% yield whereas use of toluene gave cycloadduct (+)-28b in 85% yield.
28. Shao, C.; Wang, X.; Zhang, Q.; Luo, S.; Zhao, J.; Hu, Y. *J. Org. Chem.* 2011, 76, 6832.
29. Firouzabadi, H.; Sardarian, A.; Naderi, M.; Vessal, B. *Synth. Commun.* 1984, 40(23), 5001.
30. For a procedure using potassium trithiocarbonate, see references 3p and 5a.
31. Chou, T.-H.; Hsu, Y-L.; Lo, L.-C. *J. Chinese Chem. Soc.* 2014, 61 (6), 707.
32. Christophersen, C.; Holm, A. *Acta Chim. Scandinavia,* 1971, 25, 2015.
33. (a) Bernardo, P. H.; Chai, C. L. L.; Deeble, G. J.; Liu, X.-M.; Waring, P. *Bioorg. & Med. Chem. Lett.,* 2001, 11, 483. (b) Bernardo, P. H.; Brasch, N.; Chai, C. L. L.; Waring, P.; *J. Biol. Chem.* 2003, 278(47), 46549.
34. (a) Bertling, A.; Niemann, S.; Uekotter, A.; Fegeler, W.; Lass-Flörl, C.; von Eiff, C.; Kehrel, B. E. *Thromb. Haemost.,* 2010, 104, 270. (b) Block, K. M.; Wang, H.; Szabó, L. Z.; Polaske, N. W.; Henchey, L. K.; Dubey, R.; Kushal, S.; László, C. F.; Makhoul, J.; Song, Z.; Meuillet, E. J.; Olenyuk, B. Z. *J. Am. Chem. Soc.,* 2009, 131, 18078; (c) Kushal, S.; Wang, H.; László, C. F.; Szábo, L. Z.; Olenyuk, B. *Z. Biopolymers,* 2011, 95, 8. (d) Srinivasan, U.; Bala, A.; Jao, S.-C.; Starke, D. W.; Jordan, T. W.; Mieyal, J. J. *Biochemistry,* 2006, 45 (29), 8978. (e) Chai, C. L. L.; Waring, P. *Redox Rep.,* 2000, 5, 257.
35. The sensitivity to concentration in the presence of base was confirmed by removing polymer-bound base from the reaction mixture by filtration prior to concentration. The reactivity upon exposure to silica is due to the presence of unidentified reactive intermediates. For example, when epidisulfide (+)-8 was exposed to PFB-SH (0.5 equiv) in $CDCl_3$ [0.02 M], after 18 h we observed only 48% remaining epidisulfide (+)-8 and 21% of an unknown intermediate by in situ 1H NMR spectroscopy. However, upon exposure we observed the appearance of 29% epitrisulfide 31.
36. See the Examples section for further details.
37. Hart, T. W. *Tet. Lett.* 1985, 26 (16), 2013.
38. (a) Jonas, C. R.; Ziegler, T. R.; Gu, L. H.; Jones, D. P. *Free Radical Bio. & Med.* 2002, 33 (11), 1499. (b) Ramirez, A.; Ramadan, B.; Ritzenthaler, J. D.; Rivera, H. N.; Jones, D. P.; Roman, J. *Am. J. Physiol. Lung Cell Mol. Physiol.* 2007, 293, 972. (c) Rubartelli A.; Lotze, M. T. *TRENDS in Immunology,* 2007, 28(10), 429-436. (d) Chaiswing, L.; Zhong, W.; Cullen, J. J.; Oberley, L. W.; Oberley, T. D. *Cancer Research,* 2008, 68 (14), 5820.
39. (a) Movassaghi, M.; Schmidt, M. A.; *Angew. Chem. Int. Ed.* 2007, 46, 3725. (b) Movassaghi, M.; Schmidt, M. A.; Ashenhurst, J. A.; *Angew. Chem. Int. Ed.* 2008, 47, 1485.
40. Muthyala, M. K.; Choudary, S.; Pandey, K.; Shelke, G. M.; Jha, M.; Kumar, A. *Eur. J. Org. Chem.* 2014, 2365.
41. Boyer, N.; Movassaghi, M. *Chem. Sci.* 2012, 3, 1798.
42. Karaman, H.; Barton, R. J.; Robertson, B. E.; Lee, D. G. *J. Org. Chem.* 1984, 49, 4509.
43. Prepared from potassium iodide (200 mg, 1.20 mmol) and iodine (305 mg, 1.20 mmol) in pyridine (5 mL).
44. The relative stereochemistry of the epidisulfide (+)-9a was confirmed by key NOESY cross-peaks on the corresponding bis(methylthioether). Our assignment is supported by key NOESY signals ($^1H$, $^1H$) in ppm: (3.12, 7.10-7.04), (3.12, 1.88), (2.97, 6.88). This derivative was prepared in one step using our chemistry developed to access (+)-gliocladin B (Boyer, N.; Movassaghi M. *Chem*

Sci. 2012, 3, 1798). The corresponding bis(methylthioether) of epidisulfide (+)-9a was characterized as follows: $^1$H NMR (400 MHz, CDCl$_3$, 25° C.): δ 7.86 (d, J=8.4 Hz, 2H, SO$_2$Ph-o-H), 7.51 (d, J=8.1 Hz, 1H, C$_8$H), 7.47 (t, J=7.5 Hz, 1H, SO$_2$Ph-p-H), 7.35 (t, J=8.1 Hz, 2H, SO$_2$Ph-m-H), 7.27 (ddd, J=2.4, 6.4, 8.6 Hz, 1H, C$_7$H), 7.10-7.04 (m, 2H, C$_5$H, C$_6$H), 6.88 (d, J=8.8 Hz, 2H, C$_2$H), 6.67 (d, J=8.8 Hz, 2H, C$_{3'}$H), 6.63 (s, 1H, C$_2$H), 4.46 (s, 1H, C$_{15}$H), 3.96 (t, J=6.0 Hz, 2H, C$_{5'}$H), 3.47 (t, J=6.6 Hz, 2H, C$_{7'}$H), 3.12 (d, J=14.3 Hz, 1H, C$_{12}$H$_a$), 3.03 (s, 3H, C$_{17}$H), 2.97 (d, J=14.3 Hz, 1H, C$_{12}$H$_b$), 2.17 (s, 3H, C$_{15}$SCH$_3$), 2.00 (p, J=6.2 Hz, 2H, C$_{6'}$H), 1.88 (s, 3H, C$_{11}$SCH$_3$). $^{13}$C NMR (100 MHz, CDCl$_3$, 25° C.): δ 165.1 (C$_{13}$), 162.3 (C$_{16}$), 158.0 (C$_{4'}$), 142.4 (C$_9$), 140.2 (SO$_2$Ph-ipso-C), 136.7 (C$_4$), 134.6 (C$_{1'}$), 132.9 (SO$_2$Ph-p-C), 129.1 (C$_7$), 129.1 (SO$_2$Ph-m-C), 127.1 (C$_{2'}$), 127.0 (SO$_2$Ph-o-C), 124.9 (C$_6$), 123.8 (C$_5$), 117.0 (C$_8$), 115.0 (C$_{3'}$), 85.7 (C$_2$), 69.8 (C$_{11}$), 67.6 (C$_{15}$), 64.7 (C$_{5'}$), 57.0 (C$_3$), 48.3 (C$_7$), 45.7 (C$_{12}$), 32.5 (C$_{17}$), 28.9 (C$_{6'}$), 17.1 (C$_{15}$SCH$_3$), 15.5 (C$_{11}$SCH$_3$). HRMS (ESI) (m/z): calc'd for C$_{31}$H$_{32}$N$_6$NaO$_5$S$_3$ [M+Na]$^+$: 687.1489, found 687.1501.

45. Movassaghi, M.; Schmidt M. A.; Ashenhurst, J. A.; *Angew. Chemie. Int. Ed.* 2008, 47 (18), 1485-1487.

46. An analytical sample of amide (−)—S$_5$ was obtained by flash column chromatography on silica gel (eluent: 50% ethyl acetate in hexanes). The amide (−)—S$_5$ was characterized as follows: $^1$H NMR (400 MHz, CDCl$_3$, 25° C.): δ 7.93 (d, J=8.3 Hz, 1H, C$_8$H), 7.82 (d, J=7.6 Hz, 2H, SO$_2$Ph-o-H), 7.52-7.46 (m, 2H, C$_5$H, SO$_2$Ph-p-H), 7.44 (s, 1H, C$_2$H), 7.38 (t, J=7.9 Hz, 2H, SO$_2$Ph-m-H), 7.27 (t, J=7.6 Hz, 1H, C$_7$H), 7.19 (J=7.6 Hz, 1H, C$_6$H), 6.62 (br-s, 1H, NH), 5.20 (d, J=8.2 Hz, 1H, NHCO$_2$C(CH$_3$)$_3$), 4.47 (br-s, 1H, C$_{11}$H), 3.97-3.84 (m, 2H, C$_{15}$H), 3.67 (s, 3H, OCH$_3$), 3.21-3.04 (m, 2H, C$_{12}$H), 1.36 (s, 9H, OCCH$_3$). $^{13}$C NMR (100 MHz, CDCl$_3$, 25° C.): δ 171.6 (C$_{13}$), 170.0 (C$_{16}$), 155.6 (NHCO$_2$C(CH$_3$)$_3$), 138.3 (SO$_2$Ph-ipso-C), 135.3 (C$_9$), 133.9 (SO$_2$Ph-p-C), 130.9 (C$_4$), 129.4 (SO$_2$Ph-m-C), 126.9 (SO$_2$Ph-o-C), 125.1 (C$_2$), 124.7 (C$_7$), 123.5 (C$_6$), 119.7 (C$_5$), 118.0 (C$_3$), 113.8 (C$_8$), 80.6 (OC(CH$_3$)$_3$), 54.3 (C$_{11}$), 52.5 (OCH$_3$), 41.3 (C$_{15}$), 28.4 (OC(CH$_3$)$_3$), 28.0 (C$_{12}$). FTIR (thin film) cm$^{-1}$: 3309 (m), 2977 (w), 1748 (m), 1662 (s), 1520 (s), 1447 (m), 1365 (s), 1278 (s), 746 (m). HRMS (ESI) (m/z): calc'd for C$_{25}$H$_{29}$N$_3$NaO$_7$S [M+Na]$^+$: 538.1618, found 538.1624. [α]$_D^{23}$: −5.0 (c=0.20, CHCl$_3$). TLC (100% ethyl acetate), Rf: 0.74 (UV, CAM).

47. Kern, N.; Blanc, A.; Weibel, J.-M.; Pale, P. *Chem Commun.*, 2011, 47, 6665.

48. The relative stereochemistry of the epidisulfide (+)-9b was confirmed by key NOESY cross-peaks on the corresponding bis(methylthioether). Our assignment is supported by key NOESY signals ($^1$H, $^1$H) in ppm: (3.12, 7.09-7.04), (3.12, 1.88), (2.96, 6.88). This derivatized compound was prepared in one step using our methodology developed to access (+)-gliocladin B (Boyer, N.; Movassaghi M. *Chem Sci.* 2012, 3, 1798). The corresponding bis(methylthioether) of epidisulfide (+)-9b was characterized as follows: $^1$H NMR (400 MHz, CDCl$_3$, 25° C.): δ 7.86 (d, J=8.0 Hz, 2H, SO$_2$Ph-o-H), 7.52 (d, J=8.2 Hz, 1H, C$_8$H), 7.47 (t, J=7.4 Hz, 1H, SO$_2$Ph-p-H,) 7.35 (t, J=8.0 Hz, 2H, SO$_2$Ph-m-H), 7.27 (ddd, J=2.2, 6.5, 8.6 Hz, 1H, C$_7$H), 7.09-7.04 (m, 2H, C$_5$H, C$_6$H), 6.88 (d, J=8.8 Hz, 2H, C$_2$H), 6.68 (d, J=8.9 Hz, 2H, C$_{3'}$H), 6.63 (s, 1H, C$_2$H), 4.49 (s, 1H, C$_{15}$H), 3.73 (s, 3H, C$_{5'}$H), 3.66-3.58 (m, 1H, C$_{17}$H$_a$), 3.34-3.28 (m, 1H, C$_{17}$H$_b$), 3.30 (t, J=6.7 Hz, 2H, C$_{20}$H), 3.12 (d, J=14.3 Hz, 1H, C$_{12}$H$_a$), 2.96 (J=14.3 Hz, 1H, C$_{12}$H$_b$), 2.16 (s, 3H, C$_{15}$SCH$_3$), 1.88 (s, 3H, C$_{11}$SCH$_3$), 1.75-1.68 (m, 2H, C$_{18}$H), 1.63-1.55 (m, 2H, C$_{19}$H). $^{13}$C NMR (100 MHz, CDCl$_3$, 25° C.): δ 165.3 (C$_{13}$), 162.3 (C$_{16}$), 158.9 (C$_{4'}$), 142.2 (C$_9$), 140.2 (SO$_2$Ph-ipso-C), 136.8 (C$_4$), 134.3 (C$_{1'}$), 132.9 (SO$_2$Ph-p-C), 129.2 (C$_7$, SO$_2$Ph-m-C), 127.0 (C$_{2'}$, SO$_2$Ph-o-C), 124.9 (C$_6$), 123.8 (C$_5$), 117.0 (C$_8$), 114.5 (C$_{3'}$), 85.7 (C$_2$), 69.8 (C$_{11}$), 65.7 (C$_{15}$), 57.0 (C$_3$), 55.5 (C$_{5'}$), 51.1 (C$_{20}$), 45.7 (C$_{12}$), 44.9 (C$_{17}$), 26.3 (C$_{19}$), 24.9 (C$_{18}$), 17.1 (C$_{15}$SCH$_3$), 15.4 (C$_{11}$SCH$_3$). HRMS (ESI) (m/z): calc'd for C$_{32}$H$_{34}$N$_6$NaO$_5$S$_3$ [M+Na]$^+$: 701.1645, found 701.1649.

49. Maury, J.; Feray, L.; Bertrand, M. P.; Kapat, A.; Renaud, P. *Tetrahedron,* 2012, 68, 9606.

50. To remove residual acetic acid, pooled fractions containing N-sulfonylated tryptophan (−)-22 were concentrated under reduced pressure to approximately 10% of the volume, then diluted with benzene (100 mL) and concentrated. This process was repeated two more times.

51. The relative stereochemistry of epidisulfide (+)-9c has been confirmed by key NOESY cross-peaks on the corresponding bis(methylthioether). Our assignment is supported by key NOESY signals ($^1$H, $^1$H) in ppm: (3.09-3.04, 7.10-7.06), (3.09-3.04, 1.86), (2.93, 6.82), (2.93, 6.55). This derivatized compound was prepared in one step using our methodology developed to access (+)-gliocladin B (Boyer, N.; Movassaghi M. *Chem Sci.* 2012, 3, 1798). The corresponding bis(methylthioether) of epidisulfide (+)-9c was characterized as follows: $^1$H NMR (400 MHz, CDCl$_3$, 25° C.): δ 7.67 (d, J=8.8 Hz, 2H, C$_2$H), 7.56 (d, J=8.1 Hz, 1H, C$_8$H), 7.29 (ddd, J=3.0, 5.8, 8.4, 1H, C$_7$H), 7.10-7.06 (m, 2H, C$_6$H, C$_5$H), 6.82 (d, J=8.8 Hz, 2H, C$_2$H), 6.70 (d, J=8.9 Hz, 2H, C$_{3'}$H), 6.65 (d, J=8.8 Hz, 2H, C$_{3'}$H), 6.55 (s, 1H, C$_2$H), 4.51 (s, 1H, C$_{15}$H), 4.00 (t, J=5.9 Hz, 2H, C$_{5''}$H), 3.73 (s, 3H, C$_{5'}$H), 3.49 (t, J=6.5 Hz, 2H, C$_{7''}$H), 3.09-3.04 (m, 4H, C$_{12}$H$_a$, C$_{17}$H) 2.93 (d, J=15.5 Hz, 1H, C$_{12}$H$_b$), 2.27 (s, 3H, C$_{15}$SCH$_3$), 2.03 (p, J=6.2 Hz, 2H, C$_{6''}$H) 1.86 (s, 3H, C$_{11}$SCH$_3$). $^{13}$C NMR (100 MHz, CDCl$_3$, 25° C.): δ 165.2 (C$_{13}$), 162.3 (C$_{4''}$H or C$_{16}$), 162.3 (C$_{4''}$H or C$_{16}$), 158.7 (C$_{4'}$), 142.6 (C$_9$), 136.6 (C$_4$), 134.2 (C$_{1'}$), 129.4 (C$_{1''}$H), 129.4 (C$_{2''}$H), 129.1 (C$_7$), 127.2 (C$_{2'}$), 125.0 (C$_6$), 124.1 (C$_5$), 117.6 (C$_8$), 114.5 (C$_{3'}$ or C$_{3''}$), 114.3 (C$_{3'}$ or C$_{3''}$), 86.2 (C$_2$), 69.9 (C$_{11}$), 67.8 (C$_{15}$), 65.0 (C$_{5''}$H), 57.1 (C$_3$), 55.5 (C$_{5'}$), 48.2 (C$_7$H), 46.4 (C$_{12}$), 32.5 (C$_{17}$), 28.7 (C$_{6''}$H), 17.2 (C$_{15}$SCH$_3$), 15.5 (C$_{11}$SCH$_3$). HRMS (ESI) (m/z): calc'd for C$_{32}$H$_{34}$N$_6$NaO$_6$S$_3$ [M+Na]$^+$: 717.1594, found 717.1588.

52. For the preparation of diol S$_{12}$ and the corresponding methodology, see Boyer, N.; Morrison, K. C.; Kim, J.; Hergenrother, P. J.; Movassaghi, M. *Chem. Sci.,* 2013, 4, 1646.

53. The C11-hemithioaminal has been characterized by NMR: $^1$H NMR (500 MHz, CDCl$_3$, 25° C.): δ 7.75 (d, J=8.1 Hz, 1H, C$_8$H), 7.47 (d, J=8.0 Hz, 2H, SO$_2$Ph-o-H), 7.42 (t, J=8.3, C$_7$H), 7.35 (t, J=7.4 Hz, SO$_2$Ph-p-H), 7.29-7.22 (m, 2H, C$_5$H, C$_6$H), 7.11 (t, J=7.8 Hz, 2H, SO$_2$Ph-m-H), 6.69 (d, J=8.6 Hz, 2H, C$_2$H), 6.60 (d, J=8.4 Hz, 2H, C$_{3'}$H), 6.44 (s, 1H, C$_2$H), 5.33 (d, J=4.7 Hz, 1H, C$_{15}$H), 4.64 (d, J=4.8 Hz, C$_{15}$OH), 3.76 (s, 3H, C$_{5'}$H), 3.39 (d, J=14.6 Hz, 1H, C$_{12}$H$_a$), 3.11 (d, J=14.7 Hz, 1H, C$_{12}$H$_b$), 3.08 (s, 3H, C$_{17}$H), 2.45 (s, 1H, C$_{11}$SH). $^{13}$C NMR (125 MHz, CDCl$_3$, 25° C.): δ 166.0 (C$_{13}$), 165.3 (C$_{16}$), 158.7 (C$_4$), 141.6 (C$_9$), 137.9 (SO$_2$Ph-ipso-C), 135.3 (C$_4$), 133.2 (SO$_2$Ph-p-C), 132.0 (C$_1$), 129.7 (C$_7$), 128.7 (SO$_2$Ph-m-C), 127.6 (C$_{2'}$), 127.3 (SO$_2$Ph-o-C), 126.2 (C$_5$), 126.1 (C$_6$), 118.5 (C$_8$), 114.4 (C$_{3'}$), 86.8 (C$_{2'}$), 76.9 ($C_{15}$), 69.3 ($C_{11}$), 57.6 ($C_3$), 55.4 ($C_{5'}$), 53.45 ($C_{12}$), 29.0 ($C_{17}$). TLC (25% acetone in dichloromethane), Rf: 0.23 (UV, CAM, AgNO$_3$).

54. The $C_{11}$-triphenylmethanetrisulfide $S_{13}$ has been characterized by NMR: $^1$H NMR (500 MHz, CDCl$_3$, 25° C.): δ 7.59 (d, J=8.1 Hz, 1H, $C_8$H), 7.48 (d, J=7.4 Hz, 2H, SO$_2$Ph-o-H), 7.35 (t, J=7.5 Hz, 1H, SO$_2$Ph-p-H), 7.30-7.22 (m, 9H, Ph-m-H, Ph-p-H), 7.18-7.13 (m, 6H, Ph-o-H), 7.11 (t, J=7.9 Hz, 2H, SO$_2$Ph-m-H), 7.05 (d, J=7.0 Hz, 1H, $C_5$H), 6.98 (t, J=7.4 Hz, 1H, $C_6$H), 6.62 (d, J=8.9 Hz, 2H, $C_2$H), 6.56 (d, J=8.9 Hz, 2H, $C_3$H), 6.44 (s, 1H, $C_2$H), 5.36 (d, J=4.0 Hz, 1H, $C_{15}$H), 4.23 (d, J=4.0 Hz, 1H, $C_{15}$OH), 3.75 (s, 3H, $C_{5'}$H), 3.21 (d, J=15.1 Hz, 1H, $C_{12}H_a$), 3.11 (d, J=15.1 Hz, 1H, $C_{12}H_b$), 3.02 (s, 3H, $C_{17}$H). $^{13}$C NMR (100 MHz, CDCl$_3$, 25° C.): δ 165.7 ($C_{16}$), 163.7 ($C_{13}$), 158.7 ($C_{4'}$), 143.0 (C(Ph-ipso-C)$_3$), 141.5 ($C_9$), 138.1 (SO$_2$Ph-ipso-C), 135.4 ($C_4$), 133.2 (SO$_2$Ph-p-C), 132.6 ($C_{1'}$), 130.3 (C(Ph-m-C)$_3$), 129.5 ($C_7$), 128.8 (SO$_2$Ph-m-C), 128.1 (C(Ph-o-C)$_3$), 127.5 ($C_{2'}$), 127.5 (C(Ph-p-C)$_3$), 127.3 (SO$_2$Ph-o-C), 125.9 ($C_5$), 125.9 ($C_6$), 118.1 ($C_8$), 114.4 ($C_{3'}$), 87.0 ($C_2$), 77.0 ($C_{15}$), 75.9 ($C_{11}$), 73.6 (C(Ph)$_3$), 57.5 ($C_3$), 55.5 ($C_{5'}$), 49.2 ($C_{12}$), 29.6 ($C_{17}$). TLC (10% acetone in dichloromethane), Rf: 0.38 (UV, CAM, AgNO$_3$, Ellman's Reagent).

55. Kim, J.; Ashenhurst, J. A.; Movassaghi, M. *Science*, 2009, 324, 238-241.

56. Firouzabadi, H.; Naderi, M.; Sardarian, A.; Vessal, B. *Synth. Commun.* 1983, 13, 611.

57. The relative stereochemistry of epidisulfide (+)-42 was confirmed by key NOESY cross-peaks on the corresponding bis(methylthioether). Our assignment is supported by key NOESY signals ($^1$H, $^1$H) in ppm: (2.07, 3.18), (3.18, 7.11-7.03), (2.95, 6.70), (2.95, 6.76). This derivatized compound was prepared in one step using our methodology developed to access (+)-gliocladin B (Boyer, N.; Movassaghi M. *Chem Sci.* 2012, 3, 1798). The corresponding bis(methylthioether) of epidisulfide (+)-42 was characterized as follows: $^1$H NMR (400 MHz, CDCl$_3$, 25° C.): δ 6 7.94 (d, J=7.3 Hz, 2H, SO$_2$Ph-o-H), 7.61 (d, J=8.2 Hz, 1H, $C_8$H), 7.52 (t, J=7.5 Hz, 1H, SO$_2$Ph-p-H), 7.40 (t, J=7.8 Hz, 2H, SO$_2$Ph-m-H), 7.33-7.25 (m, 2H, $C_7$H), 7.11-7.03 (m, 2H, $C_5$H, $C_6$H), 6.76 (d, J=8.9 Hz, 2H, $C_2$H), 6.70 (s, 1H, $C_2$H), 6.65 (d, J=8.9 Hz, 2H, $C_3$H), 3.74 (s, 2H, $C_5$H), 3.18 (d, J=14.1 Hz, 1H, $C_{12}H_a$), 3.07 (s, 3H, $C_{17}$H), 2.95 (d, J=14.2 Hz, 1H, $C_{12}H_b$), 2.07 (s, 3H, $C_{11}$SCH$_3$), 1.91 (s, 3H, $C_{15}$SCH$_3$), 1.84 (s, 3H, $C_{18}$H). $^{13}$C NMR (100 MHz, CDCl$_3$) δ 165.7 ($C_{13}$), 163.3 ($C_{16}$), 158.7 ($C_{4'}$), 142.6 ($C_9$), 139.7 (SO$_2$Ph-ipso-C), 136.7 ($C_4$), 134.8 ($C_{1'}$), 133.0 (SO$_2$Ph-p-C), 129.2 (SO$_2$Ph-m-C), 129.0 ($C_7$), 127.1 (SO$_2$Ph-o-C), 126.9 ($C_{2'}$), 124.7 ($C_{5/6}$), 123.8 ($C_{5/6}$), 116.7 ($C_8$), 114.4 ($C_{3'}$), 86.1 ($C_2$), 70.0 ($C_{11}$), 67.4 ($C_{15}$), 56.7 ($C_3$), 55.4 ($C_{5'}$), 46.2 ($C_{12}$), 29.3 ($C_{17}$), 23.7 ($C_{18}$), 15.8 ($C_{15}$SCH$_3$), 14.4 ($C_{11}$SCH$_3$). HRMS (ESI) (m/z): calc'd for $C_{30}H_{31}N_3NaO_5S_3$ [M+Na]$^+$: 632.1318, found 632.1315.

58. As measured by crude $^1$H NMR (CDCl$_3$) analysis, the ratio of tetrasulfide 44:trisulfide 43:disulfide (+)-42 epithiodiketopiperazines was 1:2:1.2 before chromatography.

59. Hart, T. *Tetrahedron Lett.* 1985, 26, 2013-2016.

60. When pure D$_2$O was used, signal broadening was observed.

61. Diol 49 has been characterized by $^1$H NMR (500 MHz, CDCl$_3$, 25° C.): δ 7.62 (d, J=8.1 Hz, 1H, $C_8$H), 7.36-7.27 (m, 4H), 7.22-7.14 (m, 2H), 7.02 (t, J=7.8 Hz, 2H, SO$_2$Ph-m-H), 6.78 (app-d, J=8.8 Hz, 2H, $C_2$H), 6.55 (app-d, J=8.9 Hz, 2H, $C_3$H), 6.35 (s, 1H, $C_2$H), 5.65-5.40 (br-s, OH), 3.99 (t, J=5.9 Hz, 2H, $C_5$H), 3.54 (t, J=6.5 Hz, 2H, $C_7$H), 3.37 (d, J=15.1 Hz, 1H, $C_{12}H_a$), 3.00 (s, 3H, $C_{17}$H), 2.92 (d, J=15.2 Hz, 1H, $C_{12}H_b$), 2.10-2.01 (m, 2H, $C_6$H), 1.82 (s, 3H, $C_{18}$H). TLC (20% acetone in dichloromethane), Rf: 0.34 (UV, CAM).

62. O-TBS protected monoalcohols S22 and S23 have been characterized by $^1$H NMR (500 MHz, CDCl$_3$, 25° C., 1.1:1 mixture of regioisomers): δ 7.63-7.57 (m), 7.34-7.29 (m), 7.31-7.24 (m), 7.22-7.13 (m), 7.05-6.96 (m), 6.77-6.69 (m), 6.57 (t, J=9.2 Hz), 6.42 (s), 6.30 (s), 4.01 (t, d, J=5.9, 2.4 Hz), 3.85 (s), 3.57-3.52 (m), 3.51 (s), 3.37 (dd, J=15.2, 1.5 Hz), 2.97 (s), 2.93 (s), 2.85 (d, J=14.6 Hz), 2.78 (d, J=15.1 Hz), 2.06 (p, J=6.1 Hz), 1.83 (s), 1.65 (s), 0.97 (s), 0.92 (s, 3H), 0.33 (s), 0.32 (s), 0.24 (s), 0.23 (s). TLC (40% acetone in hexanes), Rf: 0.51 and 0.58 (UV, CAM).

63. The relative stereochemistry of the epidithiodiketopiperazine (+)-9d was confirmed by key NOE correlations on the corresponding bis(methylthioether). Our assignment is supported by key NOE signals ($^1$H, $^1$H) in ppm: (7.34, 3.29), (3.29, 1.88), (6.94, 3.03). This derivatized compound was prepared in one step using our methodology developed to access (+)-gliocladin B (Boyer, N.; Movassaghi M. *Chem Sci.* 2012, 3, 1798). The corresponding bis(methylthioether) of epidithiodiketopiperazine (+)-9d was characterized as follows: $^1$H NMR (500 MHz, acetone-d$_6$) δ 8.00 (d, J=7.3 Hz, 2H, SO$_2$Ph-o-H), 7.69 (t, J=7.5 Hz, 1H, SO$_2$Ph-p-H), 7.56 (t, J=7.9 Hz, 2H, SO$_2$Ph-m-H), 7.52 (d, J=8.1 Hz, 1H, $C_8$H), 7.34 (d, J=7.6 Hz, 1H, $C_5$H), 7.30 (t, J=7.8 Hz, 1H, $C_7$H), 7.10 (t, J=7.9 Hz, 1H, $C_6$H), 6.94 (d, J=8.8 Hz, 2H, $C_2$H), 6.77 (d, J=8.8 Hz, 2H, $C_3$H), 6.75 (s, 1H, $C_2$H), 4.05 (t, J=6.0 Hz, 2H, $C_5$H), 3.54 (t, J=6.7 Hz, 2H, $C_7$H), 3.29 (d, J=14.1 Hz, 1H, $C_{12}H_\beta$), 3.03 (d, J=14.1 Hz, 1H, $C_{12}H_\alpha$), 2.99 (s, 3H, $C_{17}$H), 2.06-2.03 (m, 2H, $C_6$H), 2.02 (s, 3H, $C_{18}$H), 1.88 (s, 3H, $C_{11}$SCH$_3$), 1.80 (s, 3H, $C_{15}$SCH$_3$).

64. Grimes, K. D.; Aldrich, C. C. *Analytical Biochemistry*, 2011, 417 (2), 264-273.

What is claimed is:

1. A compound having the structure of Formula (X):

$$R^XS-\underset{SR^Y}{\overset{S}{C}}$$  (X)

or salt thereof, wherein $R^X$ is unsubstituted alkyl, -Si($R^S$)$_3$, -Sn($R^S$)$_3$, substituted or unsubstituted benzyl, or $M^X$;

$R^Y$ is unsubstituted alkyl, -Si($R^S$)$_3$, -Sn($R^S$)$_3$, substituted or unsubstituted benzyl, hydrogen, or $M^Y$;

each $R^S$ is independently hydrogen, halogen, hydroxyl, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl;

$M^X$ is a metal selected from the group consisting of sodium, potassium, lithium, rubidium, and cesium; and $M^Y$ is a metal selected from the group consisting of sodium, potassium, lithium, rubidium, and cesium.

2. The compound of claim 1, wherein the compound is not sodium benzhydryl trithiocarbonate.

3. The compound of claim 1, wherein the compound is not sodium benzhydryl trithiocarbonate or sodium p-methoxybenzhydryl trithiocarbonate.

4. The compound of claim 1, wherein the compound is of the formula:

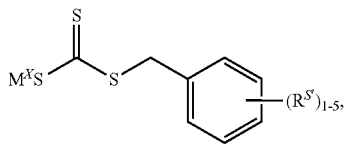

wherein each $R^{S'}$ is independently hydrogen, halogen, hydroxyl, substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

5. The compound of claim 1, wherein $R^X$ is $M^X$.

6. The compound of claim 5, wherein $M^X$ is sodium.

7. The compound of claim 1, wherein $R^Y$ is substituted or unsubstituted benzyl.

8. The compound of claim 1, wherein the compound is of the formula:

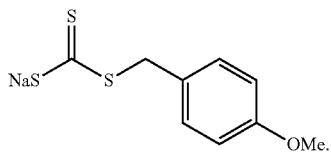

9. The compound of claim 4, wherein the compound is of the formula:

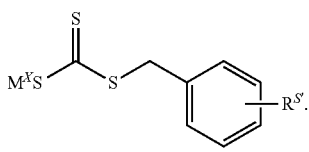

10. The compound of claim 4, wherein $M^X$ is sodium.

11. The compound of claim 9, wherein $M^X$ is sodium.

12. The compound of claim 4, wherein each $R^{S'}$ is hydrogen.

13. The compound of claim 10, wherein each $R^{S'}$ is hydrogen.

14. The compound of claim 9, wherein $R^{S'}$ is hydrogen.

15. The compound of claim 11, wherein $R^{S'}$ is hydrogen.

16. The compound of claim 4, wherein each $R^{S'}$ is independently halogen, hydroxyl, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

17. The compound of claim 10, wherein each $R^{S'}$ is independently halogen, hydroxyl, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

18. The compound of claim 9, wherein $R^{S'}$ is halogen, hydroxyl, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

19. The compound of claim 11, wherein $R^{S'}$ is halogen, hydroxyl, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, substituted or unsubstituted heterocyclyl, substituted or unsubstituted aryl, or substituted or unsubstituted heteroaryl.

20. The compound of claim 9, wherein $R^{S'}$ is substituted or unsubstituted $C_{1-6}$ heteroalkyl.

21. The compound of claim 11, wherein $R^{S'}$ is substituted or unsubstituted $C_{1-6}$ heteroalkyl.

* * * * *